US012466823B2

(12) United States Patent
Su et al.

(10) Patent No.: US 12,466,823 B2
(45) Date of Patent: Nov. 11, 2025

(54) INHIBITOR CONTAINING BICYCLIC DERIVATIVE, PREPARATION METHOD THEREFOR AND USE THEREOF

(71) Applicants: SHANGHAI HANSOH BIOMEDICAL CO., LTD., Shanghai (CN); JIANGSU HANSOH PHARMACEUTICAL GROUP CO., LTD., Lianyungang (CN)

(72) Inventors: Yidong Su, Shanghai (CN); Jun Wang, Shanghai (CN); Rudi Bao, Shanghai (CN)

(73) Assignees: SHANGHAI HANSOH BIOMEDICAL CO., LTD., Shanghai (CN); JIANGSU HANSOH PHARMACEUTICAL GROUP CO., LTD., Shanghai (CN)

( * ) Notice: Subject to any disclaimer, the term of this patent is extended or adjusted under 35 U.S.C. 154(b) by 1026 days.

(21) Appl. No.: 17/610,939

(22) PCT Filed: May 14, 2020

(86) PCT No.: PCT/CN2020/090142
§ 371 (c)(1),
(2) Date: Nov. 12, 2021

(87) PCT Pub. No.: WO2020/228756
PCT Pub. Date: Nov. 19, 2020

(65) Prior Publication Data

US 2022/0259201 A1 Aug. 18, 2022

(30) Foreign Application Priority Data

| | | |
|---|---|---|
| May 14, 2019 | (CN) | 201910400013.0 |
| Jul. 9, 2019 | (CN) | 201910615987.0 |
| Aug. 30, 2019 | (CN) | 201910816375.8 |
| Sep. 20, 2019 | (CN) | 201910895078.7 |
| Mar. 13, 2020 | (CN) | 202010177893.2 |

(51) Int. Cl.
*C07D 471/04* (2006.01)
*A61P 35/00* (2006.01)
*C07D 471/08* (2006.01)
*C07D 519/00* (2006.01)

(52) U.S. Cl.
CPC ............ *C07D 471/04* (2013.01); *A61P 35/00* (2018.01); *C07D 471/08* (2013.01); *C07D 519/00* (2013.01)

(58) Field of Classification Search
CPC .......................... C07D 471/04; A61K 31/5377
See application file for complete search history.

(56) References Cited

U.S. PATENT DOCUMENTS

| | | | | |
|---|---|---|---|---|
| 10,137,124 | B2 * | 11/2018 | Andrews | C07D 471/04 |
| 2017/0096425 | A1 | 4/2017 | Andrews et al. | |
| 2018/0133200 | A1 | 5/2018 | Andrews et al. | |
| 2018/0133207 | A1 * | 5/2018 | Andrews | A61K 31/5377 |
| 2022/0220104 | A1 | 7/2022 | Wang et al. | |

FOREIGN PATENT DOCUMENTS

| | | | |
|---|---|---|---|
| CN | 108349969 | A | 7/2018 |
| CN | 110964008 | A | 4/2020 |
| CN | 111635400 | A | 9/2020 |
| CN | 113474343 | A | 10/2021 |
| EP | 3845531 | A1 | 7/2021 |
| EP | 3936504 | A1 | 1/2022 |
| EP | 3950685 | A1 † | 2/2022 |
| WO | WO2017011776 | A1 † | 1/2017 |
| WO | WO2018071447 | A1 † | 4/2018 |
| WO | WO2018071454 | A1 † | 4/2018 |
| WO | WO2019075108 | A1 † | 4/2019 |

(Continued)

OTHER PUBLICATIONS

Office Action for Europe Application No. 20 806 520.1, mailed Apr. 17, 2024.

(Continued)

*Primary Examiner* — Paul V Ward

(74) *Attorney, Agent, or Firm* — Pilloff Passino & Cosenza LLP; Rachel Pilloff; Sean Passino

(57) ABSTRACT

Provided are an inhibitor containing a bicyclic derivative, a preparation method therefor and the use thereof. In particular, involved are a compound shown by general formula (I), a preparation method therefor, a pharmaceutical composition thereof, and the use thereof as an RET inhibitor in the treatment of cancers, inflammations, chronic liver diseases, diabetes, cardiovascular diseases, AIDS, and other related diseases, wherein each substituent in general formula (I) has the same definition as that given in the description.

(I)

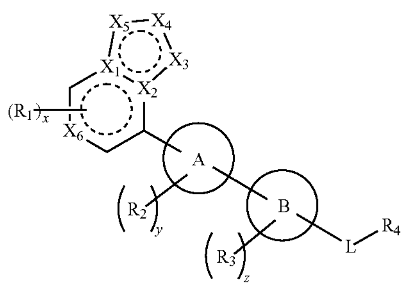

18 Claims, No Drawings

(56) References Cited

FOREIGN PATENT DOCUMENTS

| | | | | |
|---|---|---|---|---|
| WO | WO2020063751 | A1 | † | 4/2020 |
| WO | 2020177668 | A1 | | 9/2020 |
| WO | 2020200316 | A1 | | 10/2020 |

OTHER PUBLICATIONS

Office Action for Japan Application No. 2021-568429, mailed Apr. 9, 2024.
Office Action for Taiwan Application No. 109116032, mailed May 29, 2024.
First Office Action issued in Mexican Patent Application No. MX/a/2021/013846, mailed Jul. 24, 2024.
Second Office Action issued in Chinese Patent Application No. 202310081132.0, mailed Sep. 27, 2024.
Second Office Action issued in Chinese Patent Application No. 202310091956.6, mailed Sep. 28, 2024.
Richard J. Bastin, et al., Salt Selection and Optimisation Procedures for Pharmaceutical New ChemicalEntities, Organic Process Research & Development 2000, 4, 427-435.
Written Opinion of the International Searching Authority in PCT/CN2020/090142, dated Aug. 12, 2020 and its translation from WIPO.
Office action from EPO in EP20806520.1, dated Oct. 16, 2023.
Office action from India in IN 202147057306, dated Oct. 25, 2023.
Office action from Russia in RU 2021135532, dated Oct. 3, 2023.
Office action from Taiwan in TW109116032, dated Oct. 11, 2023.
Klaus Kuemmerer, Pharmaceuticals in the Environment, Annu. Rev. Environ. Resour. 2010. 35:57-75.
International Search Report and Written Opinion for PCT/CN2020/090142, mailed Aug. 12, 2020.
Office action for Canadian Application No. 3,137,887, mailed Mar. 21, 2024.
Notice of First Examination Opinion for China Application No. 202310081132.0, mailed Feb. 8, 2024.
First Search Report for China Application No. 202310081132.0, dated Feb. 6, 2024.
Notice of First Examination Opinion for China Application No. 202310091956.6, mailed Feb. 8, 2024.
First Search Report for China Application No. 202310091956.6, dated Feb. 7, 2024.
Dec. 13, 2022 Extended European Search Report issued in European U.S. Appl. No. 20/806,520.
Database PubChem Compound, NCBI; Dec. 15, 2010, Database accesion No. CID 49790026: "5-[6-(4-Methylpiperazin-1-yl)piridin-3-yl]imidazo[1,2-a]pyridine", XP093004872.
Chinese Office Action in Chinese Patent Application No. 2020800035466, mailed Jun. 8, 2022.
KIPO Request for the Submission of an Opinion dated Mar. 20, 2025 in KR application No. 10-2021-7040838.
Second Office Action of Mexican patent application dated Jan. 6, 2025 in MX application No. MX/a/2021/013846.
SIPO Rejection decision dated Jan. 23, 2025 in CN application No. 202310091956.6.
SIPO Rejection decision dated Jan. 23, 2025 in CN application No. 202310081132.0.
Examination report No. 1 dated Mar. 17, 2025 in AU application No. 2020276802.
Hearing Notice dated Apr. 9, 2025 in Indian patent application No. 202147057306.
Third Office Action of Mexican patent application dated Mar. 21, 2025 in MX application No. MX/a/2021/013846.

* cited by examiner
† cited by third party

INHIBITOR CONTAINING BICYCLIC DERIVATIVE, PREPARATION METHOD THEREFOR AND USE THEREOF

This application claims the priorities of the Chinese patent application CN201910400013.0 filed on May 14, 2019, the Chinese patent application CN201910615987.0 filed on Jul. 9, 2019, the Chinese patent application CN201910816375.8 filed on Aug. 30, 2019, the Chinese patent application CN 201910895078.7 filed on Sep. 20, 2019, the Chinese patent application CN202010177893.2 filed on Mar. 13, 2020. The present disclosure refers to the full text of the above Chinese patent disclosures.

TECHNICAL FIELD

The present disclosure belongs to the field of drug synthesis, specifically related to an inhibitor containing a bicyclic derivative, a preparation method therefor and a use thereof.

PRIOR ART

RET (rearranged during transfection) protein is encoded by the proto-oncogene RET located on chromosome 10, and is a receptor tyrosine kinase that consists of an extracellular domain, a transmembrane domain, and an intracellular kinase domain. RET ligands are glial-cell-line derived neurotrophic factor (GDNF) family ligands (GFLs) such as GDNF, neuroturin (NRTN), artemin (ARTN), persephin (PSPN), and the activation of the receptor also requires the combined effect of the co-receptor GFRα family, GFLs and GFRα form a dimer binding to RET and recruiting it to the cholesterol-rich membrane region, the RET protein undergoes dimerization and autophosphorylation, thereby activating downstream RAS-MAPK and PI3K-AKT, PKC and other signal pathways. RET plays an important role in the development of the kidney and enteric nervous system during embryonic development; it is also important for the homeostasis of neuroendocrine, hematopoietic and male germ cells and other tissues.

The disorder of RET protein function has led to the occurrence of many diseases. The lack of RET protein function during developmental processes can lead to a series of congenital diseases such as Hirschsprung disease (HSCR), congenital kidney and urinary tract malformations (CAKUT), etc. The activating mutations of RET protein, including point mutations and RET protein fusion caused by chromosome rearrangement, are also related to the occurrence of many diseases. RET fusion mainly occurs in 1 to 2% of non-small cell lung cancer (NSCLC) patients and 5 to 10% of papillary thyroid carcinoma, while RET mutations mainly occur in 60% of medullary thyroid carcinoma, and the activating mutations of RET protein are found in many other tumors such as breast cancer, gastric cancer, bowel cancer, and chronic bone marrow myelomonocytic leukemia.

Although there is a large clinical need, the current treatment for RET targets is still extremely limited, unlike ALK, EGFR and other targeted drugs that have achieved excellent efficacy in the clinic, there are still no approved targeted drugs for RET targets. At present, multi-kinase inhibitors (MKI) such as vandetinib and cabozantinib are mostly used in clinical drugs, these multi-kinase inhibitors have the disadvantages of high side effects and poor efficacy due to poor selectivity, and they cannot overcome the drug resistance problems that occur during treatment.

The demand for RET targeted drugs has attracted a large number of domestic and foreign pharmaceutical companies to develop RET specific targeted drugs, wherein the more prominent ones are Loxo Oncology's LOXO-292, which has entered clinical phase I/II, and Blueprint's BLU-667, which has also entered clinical phase I. Both of these targeted drugs have shown very good efficacy and safety in preclinical trials for patients with RET activating mutations, as well as overcoming possible drug resistance mutations in preclinical activity screening, which is expected to bring more treatment options for cancers with RET activating mutations in the future.

There are currently no specific targeted drugs for RET targets, and there is a large clinical demand. RET inhibitors with higher selectivity, better activity, better safety, and the ability to overcome drug-resistant mutations have the potential to treat a variety of cancers and have broad market prospects.

Content of the Present Invention

The object of the present disclosure is to provide a compound represented by general formula (I), a stereoisomer thereof or a pharmaceutically acceptable salt thereof, wherein the structure of the compound represented by general formula (I) is as follows:

(I)

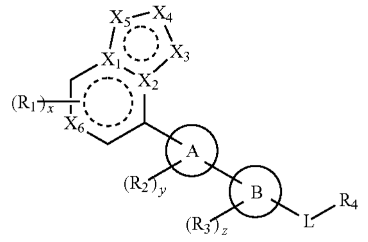

wherein:

$X_1$-$X_6$ are each independently selected from C, N, $CR_5$, $CR_{aa}R_{bb}$ or $NR_{aa}$;

L is selected from bond, $-(CH_2)_{n1}CR_{aa}R_{bb}-$, $-(CH_2)_{n1}NR_{aa}C(O)(CH_2)_{n2}-$, $-(CH_2)_{n1}C(O)(CH_2)_{n2}(CR_{aa}R_{bb})_m-$, $-(CH_2)_{n1}C(O)(CR_{aa}R_{bb})_m(CH_2)_{n2}-$, $-(CH_2)_{n1}C(O)NR_{cc}(CR_{aa}R_{bb})_{n2}-$, $-(CH_2)_{n1}(O)(CH_2)_{n2}-$ or $-(CH_2)_{n1}NR_{aa}(CH_2)_{n2}-$;

ring A is selected from heterocyclyl, aryl or heteroaryl;

ring B is selected from cycloalkyl, heterocyclyl, aryl or heteroaryl;

$R_1$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl, heteroaryl, $-(CH_2)_{n1}R_{aa}$, $-(C\equiv C)_{n1}(CR_{aa}R_{bb})_mR_{cc}$, $-(C=C)_n(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}R_{aa}$, $-(CH_2)_{n1}S(CH_2)_{n2}(CR_{aa}R_{bb})_mR_{cc}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}(CH_2)_{n2}R_{bb}$, $-(CH_2)_{n1}NR_{aa}C(O)R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, substituted or unsubstituted amino, nitro, hydroxyl, cyano, oxo, thio, imino, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}S(CH_2)_{n2}R_{dd}$, $-(CH_2)_{n1}C(O)R_{dd}$, $-(CH_2)_{n1}C(O)OR_{dd}$, $-(CH_2)_{n1}S(O)_mR_{dd}$, $-(CH_2)_{n1}S(O)(=NR_{dd})(CH_2)_{n2}R_{ee}$, $-(CH_2)_{n1}NR_{dd}R_{ee}$, $-(CH_2)_{n1}P(O)R_{dd}R_{ee}$, $-(CH_2)_{n1}C(O)NR_{dd}R_{ee}$, $-(CH_2)_{n1}NR_{dd}C(O)R_{ee}$ or $-(CH_2)_{n1}NR_{dd}S(O)_mR_{ee}$;

$R_2$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, halogen, amino, oxo, thio, nitro, cyano, hydroxyl, substituted or unsubstituted alkenyl, substituted or unsubstituted alkynyl, substituted or unsubstituted alkoxy, substituted or unsubstituted haloalkoxy, substituted or unsubstituted hydroxyalkyl, substituted or unsubstituted cycloalkyl, substituted or unsubstituted heterocyclyl, substituted or unsubstituted aryl or substituted or unsubstituted heteroaryl;

$R_3$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, halogen, amino, oxo, thio, nitro, cyano, hydroxyl, substituted or unsubstituted alkenyl, substituted or unsubstituted alkynyl, substituted or unsubstituted alkoxy, substituted or unsubstituted haloalkoxy, substituted or unsubstituted hydroxyalkyl, substituted or unsubstituted cycloalkyl, substituted or unsubstituted heterocyclyl, substituted or unsubstituted aryl or substituted or unsubstituted heteroaryl;

or, any two adjacent or non-adjacent $R_3$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted alkoxy, substituted or unsubstituted haloalkoxy, halogen, amino, nitro, hydroxyl, cyano, oxo, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

$R_4$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, amino, nitro, hydroxyl, cyano, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{cc}$, $-(CH_2)_{n1}OR_{cc}$, $-(CH_2)_{n1}S(CH_2)_{n2}R_{cc}$, $-(CH_2)_{n1}C(O)R_{cc}$, $-(CH_2)_{n1}C(O)OR_{cc}$, $-(CH_2)_{n1}S(O)_mR_{cc}$, $-(CH_2)_{n1}S(O)(=NR_{cc})(CH_2)_{n2}R_{dd}$, $-(CH_2)_{n1}NR_{cc}R_{dd}$, $-(CH_2)_{n1}P(O)R_{cc}R_{dd}$, $-(CH_2)_{n1}C(O)NR_{cc}R_{dd}$, $-(CH_2)_{n1}NR_{cc}C(O)R_{dd}$ or $-(CH_2)_{n1}NR_{cc}S(O)_mR_{dd}$;

$R_5$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

$R_{aa}$, $R_{bb}$, $R_{cc}$, $R_{dd}$ and $R_{ee}$ are each independently selected from hydrogen, deuterium, alkyl, deuterated alkyl, haloalkyl, alkoxy, haloalkoxy, halogen, cyano, nitro, hydroxyl, amino, alkenyl, alkynyl, cycloalkyl, heterocyclyl, aryl or heteroaryl, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted alkoxy, substituted or unsubstituted haloalkoxy, halogen, cyano, nitro, hydroxyl, amino, oxo, imino, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

or, any two of $R_{aa}$, $R_{bb}$, $R_{cc}$, $R_{dd}$ and $R_{ee}$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted alkoxy, substituted or unsubstituted haloalkoxy, halogen, cyano, nitro, hydroxyl, amino, oxo, imine, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

x is 0, 1, 2, 3, 4 or 5;

y is 0, 1, 2, 3, 4 or 5;

z is 0, 1, 2, 3, 4, 5 or 6;

m is 0, 1 or 2;

n1 is 0, 1, 2 or 3; and n2 is 0, 1, 2 or 3.

The present disclosure further provides a preferred embodiment, the compound represented by general formula (I), the stereoisomer thereof or the pharmaceutically acceptable salt thereof, and the general formula (I) is further represented by general formula (II):

(II)

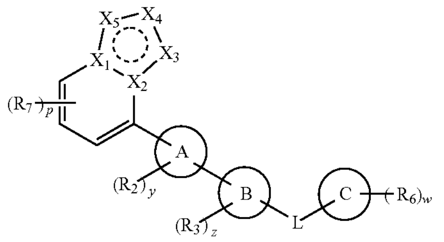

wherein:

ring C is selected from cycloalkyl, heterocyclyl, aryl or heteroaryl;

$R_6$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

$R_7$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(C\equiv C)_{n1}(CR_{aa}R_{bb})_mR_{cc}$, $-(C\equiv C)_n(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}R_{aa}$, $-(CH_2)_{n1}S(CH_2)_{n2}R_{aa}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$, $-(CH_2)_{n1}NR_{aa}(CH_2)_{n2}R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, substituted or unsubstituted amino, nitro, hydroxyl, cyano, oxo, thio, imino, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}S(CH_2)_{n2}R_{dd}$, $-(CH_2)_{n1}C(O)R_{dd}$, $-(CH_2)_{n1}C(O)OR_{dd}$, $-(CH_2)_{n1}S(O)_mR_{dd}$, $-(CH_2)_{n1}S(O)(=NR_{dd})(CH_2)_{n2}R_{ee}$, $-(CH_2)_{n1}NR_{dd}R_{ee}$, $-(CH_2)_{n1}P(O)R_{dd}R_{ee}$, $-(CH_2)_{n1}C(O)NR_{dd}R_{ee}$, $-(CH_2)_{n1}NR_{dd}C(O)R_{ee}$ or $-(CH_2)_{n1}NR_{dd}S(O)_mR_{ee}$;

p is 0, 1, 2 or 3;

w is 0, 1, 2, 3, 4, 5 or 6;

ring A, ring B, $X_1$-$X_5$, L, $R_2$-$R_3$, $R_{aa}$-$R_{ee}$, y, z, n1, n2 and m are as defined in general formula (I).

The present disclosure further provides a preferred embodiment, the compound represented by general formula (II), the stereoisomer thereof or the pharmaceutically acceptable salt thereof, and the general formula (II) is further represented by general formula (III):

(III)

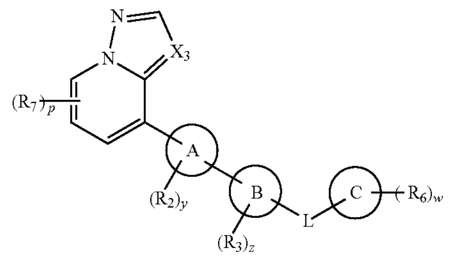

wherein:

$X_3$ is selected from N or $CR_5$;

$R_5$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

ring A, ring B, ring C, $X_3$, L, $R_2$, $R_3$, $R_6$-$R_7$, $R_{aa}$-$R_{bb}$, p, y, z, w, n1, n2 and m are as defined in general formula (II).

The present disclosure further provides a preferred embodiment, the compound represented by general formula (II), the stereoisomer thereof or the pharmaceutically acceptable salt thereof, and the general formula (II) is further represented by general formula (IV):

(IV)

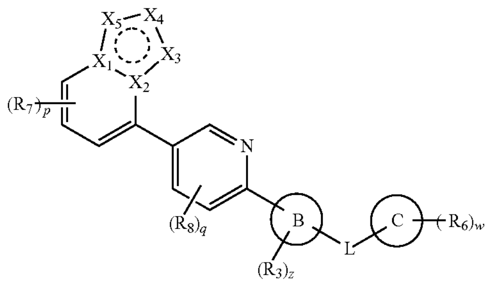

wherein:

$R_8$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl or heteroaryl;

q is 0, 1, 2, 3 or 4;

ring B, ring C, $X_1$-$X_5$, L, $R_3$, $R_6$-$R_7$, x, z and w are as defined in general formula (II).

The present disclosure further provides a preferred embodiment, the compound represented by general formula (II), the stereoisomer thereof or the pharmaceutically acceptable salt thereof, and the general formula (II) is further represented by general formula (V):

(V)

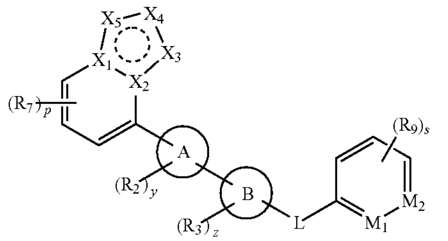

wherein:

$M_1$ and $M_2$ are each independently selected from $CR_{aa}$ or N;

$R_9$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

s is 0, 1, 2, 3, 4 or 5;

ring A, ring B, $X_1$-$X_5$, L, $R_2$, $R_3$, $R_7$, $R_{aa}$, $R_{bb}$, p, y, z, n1, n2 and m are as defined in general formula (II).

The present disclosure further provides a preferred embodiment, the compound represented by general formula (II), the stereoisomer thereof or the pharmaceutically acceptable salt thereof, and the general formula (II) is further represented by general formula (VI):

(VI)

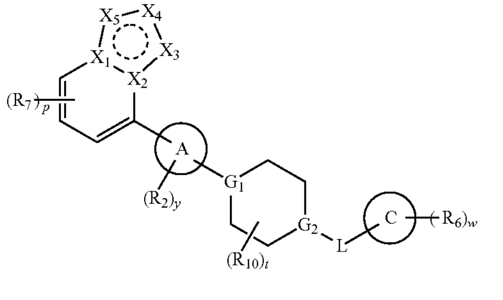

wherein:

$G_1$ and $G_2$ are each independently selected from $CR_{aa}$ or N;

$R_{10}$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl or heteroaryl;

or, any two adjacent or non-adjacent $R_{10}$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted alkoxy, substituted or unsubstituted haloalkoxy, halogen, amino, nitro, hydroxyl, cyano, oxo, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

t is 0, 1, 2, 3 or 4;

ring A, ring C, $X_1$-$X_5$, L, $R_1$, $R_2$, $R_6$-$R_7$, $R_{aa}$, p, y and w are as defined in general formula (II).

The present disclosure further provides a preferred embodiment, the compound represented by general formula (II), the stereoisomer thereof or the pharmaceutically acceptable salt thereof, and the general formula (II) is further represented by general formula (VII):

(VII)

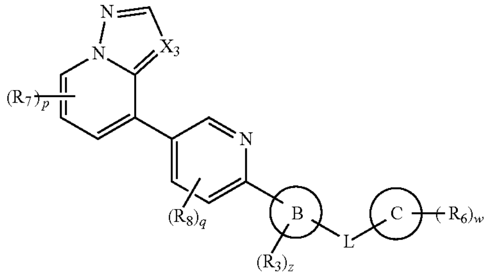

wherein:

ring B, ring C, $X_3$, L, $R_6$, $R_7$, p and w are as defined in general formula (III);

E, $R_3$, $R_8$, z and q are as described in general formula (IV).

The present disclosure further provides a preferred embodiment, the compound represented by general formula (II), the stereoisomer thereof or the pharmaceutically acceptable salt thereof, and the general formula (II) is further represented by general formula (VIII):

(VIII)

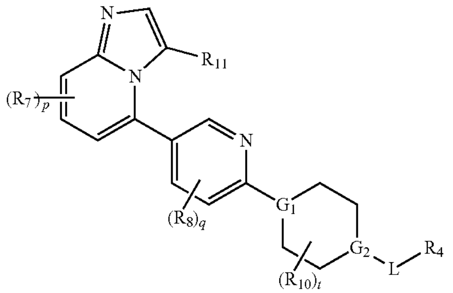

wherein:

L is selected from bond, $-(CH_2)_{n1}CR_{aa}R_{bb}-$, $-(CH_2)_{n1}NR_{aa}C(O)(CH_2)_{n2}$, $-(CH_2)_{n1}C(O)(CH_2)_{n2}(CR_{aa}R_{bb})_m-$, $-(CH_2)_{n1}C(O)(CR_{aa}R_{bb})_m(CH_2)_{n2}-$, $-(CH_2)_{n1}C(O)NR_{ee}(CR_{aa}R_{bb})_{n2}-$, $-(CH_2)_{n1}(O)(CH_2)_{n2}-$ or $-(CH_2)_{n1}NR_{aa}(CH_2)_{n2}-$;

$G_1$ and $G_2$ are each independently selected from $CR_{aa}$ or N;

$R_4$ is selected from hydrogen, deuterium, a deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, amino, nitro, hydroxyl, cyano, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{cc}$, $-(CH_2)_{n1}OR_{cc}$, $-(CH_2)_{n1}S(CH_2)_{n2}R_{cc}$, $-(CH_2)_{n1}C(O)R_{cc}$, $-(CH_2)_{n1}C(O)OR_{cc}$, $-(CH_2)_{n1}S(O)_mR_{cc}$, $-(CH_2)_{n1}S(O)(=NR_{cc})(CH_2)_{n2}R_{dd}$, $-(CH_2)_{n1}NR_{cc}R_{dd}$, $-(CH_2)_{n1}P(O)R_{cc}R_{dd}$, $-(CH_2)_{n1}C(O)NR_{cc}R_{dd}$, $-(CH_2)_{n1}NR_{cc}C(O)R_{dd}$ or $-(CH_2)_{n1}NR_{cc}S(O)_mR_{dd}$;

$R_7$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(C\equiv C)_{n1}(CR_{aa}R_{bb})_mR_{cc}$, $-(C\equiv C)_n(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}R_{aa}$, $-(CH_2)_{n1}S(CH_2)_{n2}R_{aa}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$, $-(CH_2)_{n1}NR_{aa}(CH_2)_{n2}R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, substituted or unsubstituted amino, nitro, hydroxyl, cyano, oxo, thio, imino, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}S(CH_2)_{n2}R_{dd}$, $-(CH_2)_{n1}C(O)R_{dd}$, $-(CH_2)_{n1}C(O)OR_{dd}$, $-(CH_2)_{n1}S(O)_mR_{dd}$, $-(CH_2)_{n1}S(O)(=NR_{dd})(CH_2)_{n2}R_{ee}$, $-(CH_2)_{n1}NR_{dd}R_{ee}$, $-(CH_2)_{n1}P(O)R_{dd}R_{ee}$, $-(CH_2)_{n1}C(O)NR_{dd}R_{ee}$, $-(CH_2)_{n1}NR_{dd}C(O)R_{ee}$ or $-(CH_2)_{n1}NR_{dd}S(O)_mR_{ee}$;

$R_9$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl or heteroaryl;

$R_9$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

$R_{10}$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl or heteroaryl;

or, any two adjacent or non-adjacent $R_{10}$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted alkoxy, substituted or unsubstituted haloalkoxy, halogen, amino, nitro, hydroxyl, cyano, oxo, substituted or unsubstituted alkenyl, substituted or unsubstituted alkynyl, substituted or unsubstituted cycloalkyl, substituted or unsubstituted heterocyclyl, substituted or unsubstituted aryl, and substituted or unsubstituted heteroaryl;

$R_{11}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}SR_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

t is 0, 1, 2 or 3;

z is 0, 1, 2, 3, 4, 5 or 6;

p is 0, 1, 2 or 3;

q is 0, 1, 2, 3 or 4; and s is 0, 1, 2, 3, 4 or 5.

The present disclosure further provides a preferred embodiment, the compound represented by general formula (II), the stereoisomer thereof or the pharmaceutically acceptable salt thereof, and the general formula (II) is further represented by general formula (IX):

(IX)

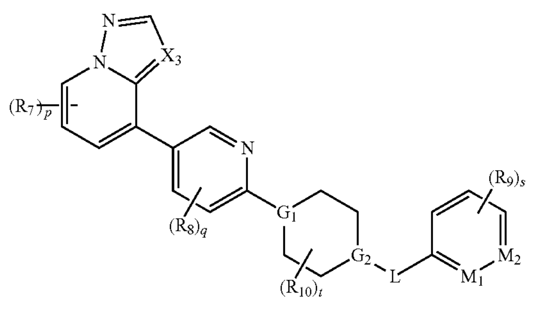

wherein:

$X_3$, L, $R_7$ and p are as defined in general formula (III);

$R_8$ and q are as described in general formula (IV);

$M_1$, $M_2$, $R_9$ and s are as defined in general formula (V);

$G_1$, $G_2$, $R_{10}$ and t are as defined in general formula (VI).

The present disclosure further provides a preferred embodiment, the compound represented by general formula (IX), the stereoisomer thereof or the pharmaceutically acceptable salt thereof, and the general formula (IX) is further represented by general formula (X):

(X)

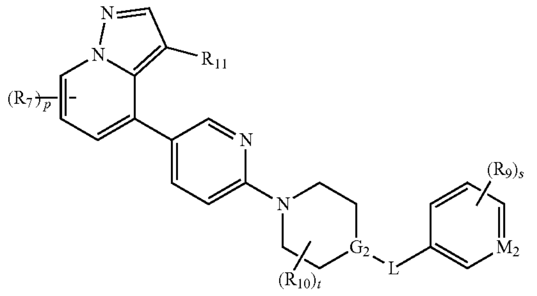

wherein:

$G_2$ is selected from $CR_{aa}$ or N;

$M_2$ is selected from $CR_{aa}$ or N;

L is selected from bond, $-(CH_2)_{n1}CR_{aa}R_{bb}-$, $-(CH_2)_{n1}NR_{aa}C(O)(CH_2)_{n2}-$, $-(CH_2)_{n1}C(O)(CH_2)_{n2}(CR_{aa}R_{bb})_m-$, $-(CH_2)_{n1}C(O)(CR_{aa}R_{bb})_m(CH_2)_{n2}-$, $-(CH_2)_{n1}C(O)NR_{cc}(CR_{aa}R_{bb})_{n2}-$, $-(CH_2)_{n1}(O)(CH_2)_{n2}-$ or $-(CH_2)_{n1}NR_{aa}(CH_2)_{n2}-$;

$R_7$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}(CR_{aa}R_{bb})_mR_{cc}$, $-(C\equiv C)_{n1}(CR_{aa}R_{bb})_mR_{cc}$, $-(C\equiv C)_{n1}(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}R_{aa}$, $-(CH_2)_{n1}S(CH_2)_{n2}(CR_{aa}R_{bb})_mR_{cc}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$, $-(CH_2)_{n1}NR_{aa}(CH_2)_{n2}R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, substituted or unsubstituted amino, nitro, hydroxyl, cyano, oxo, thio, imino, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}S(CH_2)_{n2}R_{dd}$, $-(CH_2)_{n1}C(O)R_{dd}$, $-(CH_2)_{n1}C(O)OR_{dd}$, $-(CH_2)_{n1}S(O)_mR_{dd}$, $-(CH_2)_{n1}S(O)(=NR_{dd})(CH_2)_{n2}R_{ee}$, $-(CH_2)_{n1}NR_{dd}R_{ee}$, $-(CH_2)_{n1}P(O)R_{dd}R_{ee}$, $-(CH_2)_{n1}C(O)NR_{dd}R_{ee}$, $-(CH_2)_{n1}NR_{dd}C(O)R_{ee}$ or $-(CH_2)_{n1}NR_{dd}S(O)_mR_{ee}$;

$R_9$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

$R_{10}$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl or heteroaryl;

or, any two adjacent or non-adjacent $R_{10}$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted alkoxy, substituted or unsubstituted haloalkoxy, halogen, amino, nitro, hydroxyl, cyano, oxo, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

$R_{11}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}SR_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$ or $-(CH_2)_{n1}NR_{aa}S(O)_mR_{bb}$;

$R_{aa}$, $R_{bb}$, $R_{cc}$, $R_{aa}$ and $R_{ee}$ are each independently selected from hydrogen, deuterium, alkyl, deuterated alkyl, haloalkyl, alkoxy, haloalkoxy, halogen, cyano, nitro, hydroxyl, amino, alkenyl, alkynyl, cycloalkyl, heterocyclyl, aryl and heteroaryl, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl substituted or unsubstituted, substituted or unsubstituted alkoxy, substituted or unsubstituted haloalkoxy, halogen, cyano, nitro, hydroxyl, amino, oxo, imino, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

or, any two of $R_{aa}$, $R_{bb}$, $R_{cc}$, $R_{dd}$ and $R_{ee}$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl substituted or unsubstituted, substituted or unsubstituted alkoxy, substituted or unsubstituted haloalkoxy, halogen, cyano, nitro, hydroxyl, amino, oxo, imine, substituted or unsubstituted alkenyl, substituted or unsubstituted alkynyl, substituted or unsubstituted cycloalkyl, substituted or unsubstituted heterocyclyl, substituted or unsubstituted aryl, or substituted or unsubstituted heteroaryl;

s is 0, 1, 2, 3, 4 or 5;

t is 0, 1, 2, 3 or 4; and p is 0, 1, 2, or 4.

The present disclosure further provides a preferred embodiment, the compound represented by general formula (X), the stereoisomer thereof or the pharmaceutically acceptable salt thereof, and the general formula (X) is further represented by general formula (XI) and (XI-A):

(XI)

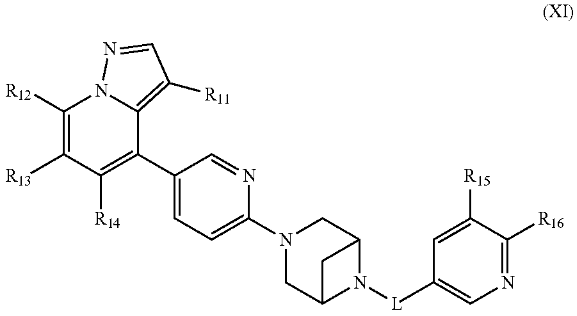

(XI-A)

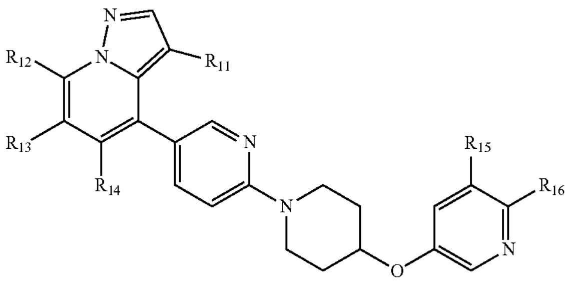

wherein:

$R_{12}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl or heteroaryl;

$R_{13}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}(CR_{aa}R_{bb})_mR_{cc}$, $-(C\equiv C)_{n1}(CR_{aa}R_{bb})_mR_{cc}$, $-(C=C)_n(CR_{aa}R_{bb})_mR_{cc}$, $-(CH_2)_{n1}O(CH_2)_{n2}(CR_{aa}R_{bb})_mR_{cc}$, $-(CH_2)_{n1}OR_{aa}$, $-(CH_2)_{n1}O(CH_2)_{n2}R_{aa}$, $-(CH_2)_{n1}S(CH_2)_{n2}(CR_{aa}R_{bb})_mR_{cc}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}NR_{aa}R_{bb}$, $-(CH_2)_{n1}P(O)R_{aa}R_{bb}$, $-(CH_2)_{n1}C(O)NR_{aa}R_{bb}$, $-(CH_2)_{n1}NR_{aa}C(O)R_{bb}$, $-(CH_2)_{n1}NR_{aa}(CH_2)_{n2}R_{bb}$ or $-(CH_2)_{n1}NR_{aa}S(O)_mR_{bb}$, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, substituted or unsubstituted amino, nitro, hydroxyl, cyano, oxo, thio, imino, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}S(CH_2)_{n2}R_{dd}$, $-(CH_2)_{n1}C(O)R_{dd}$, $-(CH_2)_{n1}C(O)OR_{dd}$, $-(CH_2)_{n1}S(O)_mR_{dd}$, $-(CH_2)_{n1}S(O)(=NR_{dd})(CH_2)_{n2}R_{ee}$, $-(CH_2)_{n1}NR_{dd}R_{ee}$, $-(CH_2)_{n1}P(O)R_{dd}R_{ee}$, $-(CH_2)_{n1}C(O)NR_{dd}R_{ee}$, $-(CH_2)_{n1}NR_{dd}C(O)R_{ee}$ or $-(CH_2)_{n1}NR_{dd}S(O)_mR_{ee}$;

$R_{12}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl or heteroaryl;

$R_{15}$ and $R_{16}$ are each independently selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl or $-(CH_2)_{n1}OR_{aa}$;

L, $R_{11}$, $R_{aa}$-$R_{ee}$, n1, n2 and m are as defined in general formula (X).

The present disclosure further provides a preferred embodiment, the compound represented by general formula (II), the stereoisomer thereof or the pharmaceutically acceptable salt thereof, and the general formula (II) is further represented by general formula (XII):

(XII)

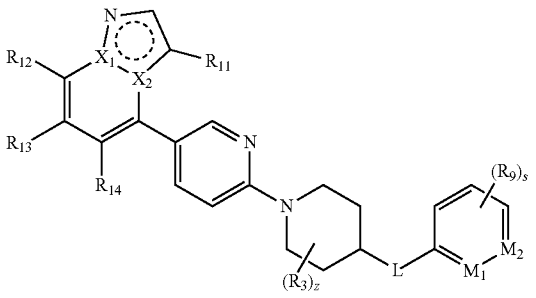

wherein:

L is selected from bond, $-(CH_2)_{n1}CR_{aa}R_{bb}-$, $-(CH_2)_{n1}NR_{aa}C(O)(CH_2)_{n2}-$, $-(CH_2)_{n1}C(O)(CH_2)_{n2}(CR_{aa}R_{bb})_m-$, $-(CH_2)_{n1}C(O)(CR_{aa}R_{bb})_m(CH_2)_{n2}-$, $-(CH_2)_{n1}C(O)NR_{cc}(CR_{aa}R_{bb})_{n2}-$, $-(CH_2)_{n1}(O)(CH_2)_{n2}-$ or $-(CH_2)_{n1}NR_{aa}(CH_2)_{n2}-$;

$M_1$ and $M_2$ are each independently selected from $CR_{aa}$ or N;

$X_1$ and $X_2$ are each independently selected from C, $CR_{aa}$ or N;

$R_3$ is selected from hydrogen, deuterium, alkyl, deuterated alkyl, haloalkyl, alkoxy, haloalkoxy, halogen, amino, nitro, hydroxyl, cyano, oxo, alkenyl, alkynyl, cycloalkyl, heterocyclyl, aryl or heteroaryl;

$R_9$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $-(CH_2)_{n1}R_{aa}$, $-(CH_2)_{n1}OR_{aa}$, $-(CH_2)_{n1}S(CH_2)_{n2}R_{aa}$, $-(CH_2)_{n1}C(O)R_{aa}$, $-(CH_2)_{n1}C(O)OR_{aa}$, $-(CH_2)_{n1}S(O)_mR_{aa}$, $-(CH_2)_{n1}S(O)(=NR_{aa})(CH_2)_{n2}R_{bb}$, $-(CH_2)_{n1}$ $NR_{aa}R_{bb}$, $—(CH_2)_{n1}P(O)R_{aa}R_{bb}$, $—(CH_2)_{n1}C(O)NR_{aa}R_{bb}$, $—(CH_2)_{n1}NR_{aa}C(O)R_{bb}$ or $—(CH_2)_{n1}NR_{aa}S(O)_mR_{bb}$;

Ru is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $—(CH_2)_{n1}R_{aa}$, $—(CH_2)_{n1}OR_{aa}$, $—(CH_2)_{n1}SR_{aa}$, $—(CH_2)_{n1}C(O)R_{aa}$, $—(CH_2)_{n1}C(O)OR_{aa}$, $—(CH_2)_{n1}S(O)_mR_{aa}$, $—(CH_2)_{n1}NR_{aa}R_{bb}$, $—(CH_2)_{n1}P(O)R_{aa}R_{bb}$, $—(CH_2)_{n1}C(O)NR_{aa}R_{bb}$, $—(CH_2)_{n1}NR_{aa}C(O)R_{bb}$ or $—(CH_2)_{n1}NR_{aa}S(O)_mR_{bb}$;

z is 0, 1, 2, 3, 4 or 5;

s is 0, 1, 2, 3, 4 or 5;

$R_{12}$-$R_{14}$, $R_{aa}$-$R_{ee}$, n1, n2 and m are as defined in general formula (XI).

The present disclosure further provides a preferred embodiment, the compound represented by general formula (I), the stereoisomer thereof or the pharmaceutically acceptable salt thereof, and the general formula (I) is further represented by general formula (IX-A):

(IX-A)

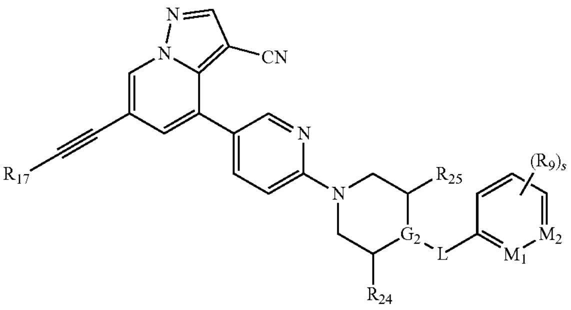

wherein:

L is selected from bond, $—(CH_2)_{n1}CR_{aa}R_{bb}—$, $—(CH_2)_{n1}NR_{aa}C(O)(CH_2)_{n2}—$, $—(CH_2)_{n1}C(O)(CH_2)_{n2}(CR_{aa}R_{bb})_m—$, $—(CH_2)_{n1}C(O)(CR_{aa}R_{bb})_m(CH_2)_{n2}—$, $—(CH_2)_{n1}C(O)NR_{cc}(CR_{aa}R_{bb})_{n2}—$, $—(CH_2)_{n1}(O)(CH_2)_{n2}—$ or $—(CH_2)_{n1}NR_{aa}(CH_2)_{n2}—$, preferably, $—CH_2—$, $—CD_2$-, —O— or —NHC(O)—;

$G_2$ is selected from N or $CR_{aa}$, preferably N, CH or $CCH_3$;

$M_1$ is selected from N or $CR_{aa}$, preferably N, CH or $CCH_3$;

$M_2$ is selected from N or $CR_{aa}$, preferably N or CH;

$R_9$ is selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or $—(CH_2)_{n1}OR_{aa}$;

preferably hydrogen, halogen, $C_{1-6}$ alkoxy, $C_{1-6}$ deuterated alkoxy or $—OR_{aa}$;

most preferably hydrogen, fluorine, chlorine, methyl, methoxy, deuterated methoxy or cyclopropoxy;

$R_{17}$ is selected from $C_{1-6}$ alkyl, $C_{1-6}$ haloalkyl, $C_{1-6}$ alkoxy, $C_{2-6}$ alkynyl, 3-12 membered heterocyclyl, 5-12 membered heteroaryl or $—(CH_2)_{n1}(CR_{aa}R_{bb})R_{cc}$, wherein the $C_{1-6}$ alkyl, $C_{1-6}$ haloalkyl, $C_{1-6}$ alkoxy, $C_{2-6}$ alkynyl, 3-12 membered heterocyclyl and 5-12 membered heteroaryl are optionally further substituted by one or more substituents selected from hydrogen, hydroxyl, cyano, oxo, thio, amino, imino, $C_{1-6}$ alkoxy, $C_{1-6}$ hydroxyalkyl, $C_{1-6}$ cyanoalkyl, $C_{3-8}$ cycloalkyl or 3-12 membered heterocyclyl;

$R_{24}$ and $R_{25}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or $—(CH_2)_{n1}OR_{aa}$, preferably hydrogen or methyl;

or, $R_{24}$ and $R_{25}$ together with the carbon atoms they are attached to and G2 form a $C_{3-8}$ cycloalkyl or 3-12 membered heterocyclyl, preferably azetidinyl;

$R_{aa}$, $R_{bb}$ and $R_{cc}$, are each independently selected from hydrogen, deuterium, cyano, amino, $C_{1-6}$ alkyl, $C_{1-6}$ alkoxy, $C_{1-6}$ hydroxyalkyl, hydroxyl, $C_{3-8}$ cycloalkyl, 3-12 membered heterocyclyl or $C_{6-14}$ aryl, wherein the $C_{1-6}$ alkyl, $C_{1-6}$ alkoxy, $C_{1-6}$ hydroxyalkyl, hydroxyl, $C_{3-8}$ cycloalkyl, 3-12 membered heterocylcyl and $C_{6-14}$ aryl are optionally further substituted by one or more substituents selected from hydrogen, halogen, cyano, hydroxyl, oxo, imino, $C_{1-6}$ alkyl or $C_{1-6}$ hydroxyalkyl;

or, any two of $R_{aa}$, $R_{bb}$ and $R_{cc}$ are optionally connected to form a $C_{3-8}$ cycloalkyl or a 3-12 membered heterocyclyl, wherein the $C_{3-8}$ cycloalkyl and 3-12 membered heterocyclyl are optionally further substituted by one or more substituents selected from hydrogen, amino, halogen, cyano, hydroxyl, oxo, imino, $C_{1-6}$ alkyl or $C_{1-6}$ hydroxyalkyl;

n1 is 0, 1 or 2;

n2 is 0, 1 or 2;

m is 0, 1 or 2; and s is 0, 1, 2 or 3.

The present disclosure further provides a preferred embodiment, the compound represented by general formula (I), the stereoisomer thereof or the pharmaceutically acceptable salt thereof, and the general formula (I) is further represented by general formula (IX-B):

(IX-B)

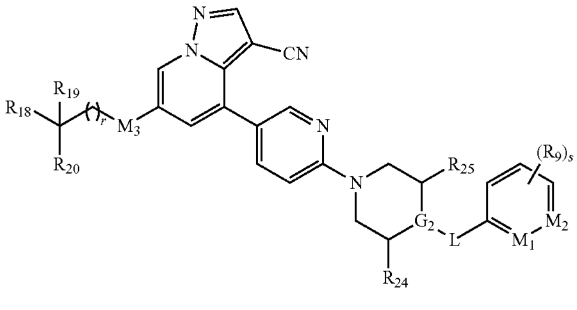

wherein:

$M_3$ is selected from bond, —O—, —S—, —NH— or $—NCH_3—$;

$R_{18}$ and $R_{19}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_6$-10 aryl or 5-12 membered heteroaryl, preferably hydrogen or methyl;

or, $R_{18}$ and $R_{19}$ together with the carbon atoms they are attached to form a $C_{3-8}$ cycloalkyl or a 3-12 membered heterocyclyl, preferably $C_{3-6}$ cycloalkyl or 3-7 membered heterocyclyl containing 1-2 oxygen atoms, nitrogen atoms or sulfur atoms, more preferably cyclopropyl, cyclobutyl, cyclopentyl, oxetanyl, azetidinyl, bicyclo[1,1,1]pentane or 1-imino-1-oxothiopyran, wherein the $C_{3-8}$ cycloalkyl or 3-12 membered heterocyclyl is optionally further substituted by one or more substituents selected from hydrogen, $C_{1-6}$ alkyl, hydroxyl, cyano or $C_{1-6}$ hydroxyalkyl;

$R_{20}$ is selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl or 5-12 membered heteroaryl;

preferably hydrogen, cyano or amino;

$R_{24}$ and $R_{25}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or $-(CH_2)_{n1}OR_{aa}$, preferably hydrogen or methyl;

or, $R_{24}$ and $R_{25}$ together with the carbon atoms they are attached to and G2 form a $C_3$-8 cycloalkyl or 3-12 membered heterocyclyl, preferably azetidinyl;

r is 0, 1 or 2;

L, $G_2$, $M_1$, $M_2$, $R_9$, and s are as defined in general formula (IX-A).

The present disclosure further provides a preferred embodiment, the compound represented by general formula (I), the stereoisomer thereof or the pharmaceutically acceptable salt thereof, $R_{18}$ and $R_{19}$ in general formula (IX-B) are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl or 5-12 membered heteroaryl, preferably hydrogen, methyl, ethynyl, amino, cyano or hydroxyl;

or, $R_{18}$ and $R_{19}$ together with the carbon atoms they are attached to form a $C_{3-8}$ cycloalkyl or a 3-12 membered heterocyclyl, preferably $C_{3-6}$ cycloalkyl or 3-7 membered heterocyclyl comprising 1-2 oxygen atoms, nitrogen atoms or sulfur atoms, more preferably cyclopropyl, cyclobutyl, cyclopentyl, oxetanyl, azetidinyl, tetrahydropyran, bicyclo[1,1,1]pentane or 1-imino-1-oxothiopyran, wherein the $C_{3-8}$ cycloalkyl or 3-12 membered heterocyclyl is optionally further substituted by one or more substituents selected from hydrogen, $C_{1-6}$ alkyl, halogen, hydroxyl, cyano, $C_{1-6}$ hydroxyalkyl and $-(CH_2)_{n1}C(O)NR_{aa}R_{bb}$;

$R_{20}$ is selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_6$-10 aryl or 5-12 membered heteroaryl, preferably hydrogen, methyl, ethynyl, amino, cyano or hydroxyl.

The present disclosure further provides a preferred embodiment, the compound, the stereoisomer thereof or the pharmaceutically acceptable salt thereof, the general formula (X) is further represented by general formula (XIII):

(XIII)

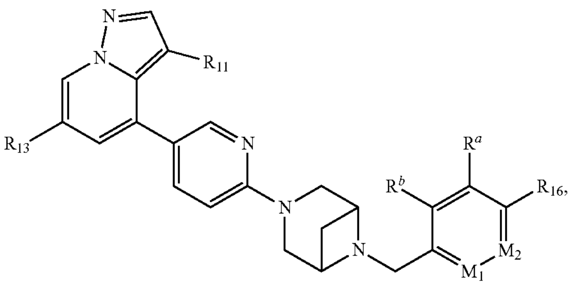

wherein:

$R_{11}$ is selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R_{13}$ is selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy,

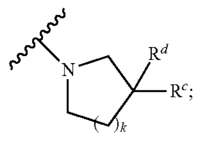

$R_{aa}$, $R_{bb}$ and $R_{cc}$, are each independently selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R^c$ and $R^d$ are each independently selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

or, R and $R^d$ together with the adjacent carbon atom form a $C_{3-8}$ cycloalkyl optionally substituted by one or more substituents selected from deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$M_1$ and $M_2$ are each independently selected from —N— or —CH—;

$R_{16}$ is selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R^a$ and $R^b$ are each independently selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

k is an integer of 0, 1 or 2;

n1 is an integer of 1, 2 or 3;

m is an integer of 1, 2 or 3.

The present disclosure further provides a preferred embodiment, the compound represented by general formula (XIII), the stereoisomer thereof or the pharmaceutically acceptable salt thereof, wherein:

$R_{11}$ is selected from hydrogen, deuterium, halogen, amino, nitro, hydroxyl, cyano or $C_{1-3}$ alkyl;

$R_{13}$ is selected from hydrogen, deuterium, halogen, amino, nitro, hydroxyl, cyano, $C_1$-3 alkyl, $C_{1-3}$ deuterated alkyl, $C_{1-3}$ haloalkyl, $C_{1-3}$ alkoxy, $C_{1-3}$ deuterium alkoxy, $C_{1-3}$ haloalkoxy, $C_{2-4}$ alkenyl, $C_{2-4}$ alkynyl, $—OCH_2CR_{aa}R_{bb}R_{cc}$ or;

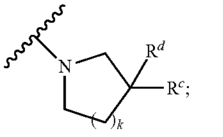

$R_{aa}$, $R_{bb}$ and $R_{cc}$ are each independently selected from hydrogen, deuterium, halogen, amino, nitro, hydroxyl, cyano, $C_{1-3}$ alkyl, $C_{1-3}$ deuterated alkyl, $C_{1-3}$ haloalkyl, $C_{1-3}$ alkoxy, $C_{1-3}$ deuterated alkoxy, $C_{1-3}$ haloalkoxy, $C_{2-4}$ alkenyl or $C_{2-4}$ alkynyl;

$R^c$ and $R^d$ are each independently selected from hydrogen, deuterium, halogen, amino, nitro, hydroxyl, cyano, $C_{1-3}$ alkyl, $C_{1-3}$ deuterated alkyl, $C_{1-3}$ haloalkyl, $C_{1-3}$ alkoxy, $C_{1-3}$ deuterated alkoxy or $C_{1-3}$ haloalkoxy;

or, $R^c$ and $R^d$ together with the adjacent carbon atom form a $C_{3-6}$ cycloalkyl optionally substituted by one or more substituents selected from deuterium, halogen, amino, nitro, hydroxyl, cyano, $C_{1-3}$ alkyl, $C_{1-3}$ deuterated alkyl, $C_{1-3}$ haloalkyl, $C_{1-3}$ alkoxy, $C_{1-3}$ deuterated alkoxy, $C_{1-3}$ haloalkoxy;

$M_1$ is —N—, $M_2$ is —CH—, or $M_1$ is —CH—, $M_2$ is —N—;

$R_{16}$ is selected from hydrogen, deuterium, halogen, amino, nitro, hydroxyl, cyano, $C_1$. 3 alkyl, $C_{1-3}$ deuterated alkyl, $C_{1-3}$ haloalkyl, $C_{1-3}$ alkoxy, $C_{1-3}$ deuterated alkoxy or $C_{1-3}$ haloalkoxy;

$R^a$ and $R^b$ are each independently selected from hydrogen, deuterium or halogen.

The present disclosure further provides a preferred embodiment, the compound represented by general formula (I), the stereoisomer thereof or the pharmaceutically acceptable salt thereof, and the general formula (I) is further represented by general formula (X):

(X)

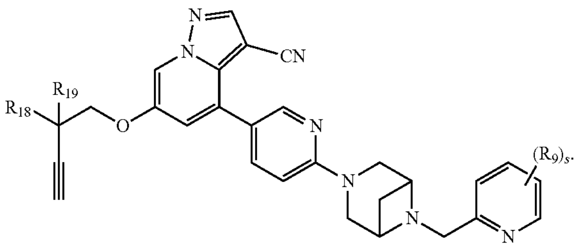

In a preferred embodiment of the present disclosure, $R_{18}$ and $R_{19}$ are each independently selected from hydrogen, deuterium, $C_{1-3}$ alkyl, $C_{1-3}$ deuterated alkyl, $C_{1-3}$ haloalkyl, $C_{1-3}$ alkoxy, $C_{1-3}$ deuterated alkoxy, $C_{1-3}$ haloalkoxy, halogen, amino, nitro, hydroxyl, cyano, $C_{2-4}$ alkenyl, $C_{2-4}$ alkynyl, $C_{3-6}$ cycloalkyl, 3-6 membered heterocyclyl, $C_{6-10}$ aryl or 5-6 membered heteroaryl, preferably hydroxyl or methyl;

$R_9$ is selected from hydrogen, deuterium, $C_{1-3}$ alkyl, $C_{1-3}$ deuterated alkyl, $C_{1-3}$ haloalkyl, $C_{1-3}$ alkoxy, $C_{1-3}$ deuterated alkoxy, $C_{1-3}$ haloalkoxy, halogen, amino, nitro, hydroxyl, cyano, $C_{2-4}$ alkenyl or $C_{2-4}$ alkynyl;

s is 0, 1, 2 or 3.

The present disclosure further provides a preferred embodiment, the compound represented by general formula (I), the stereoisomer thereof or the pharmaceutically acceptable

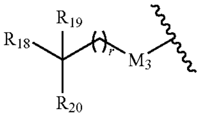

in general formula (IX-B) is selected from

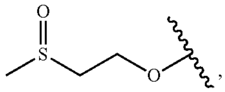,
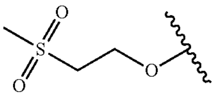,
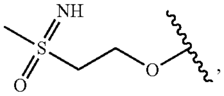,
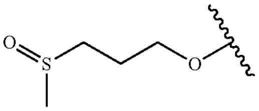,
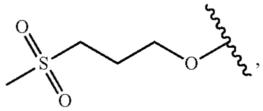,
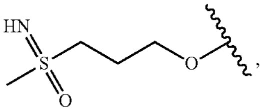,
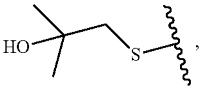,
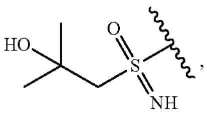,
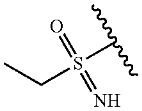,
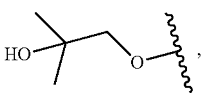,
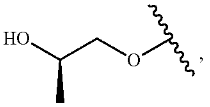,
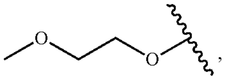,
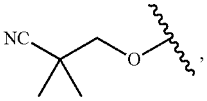,
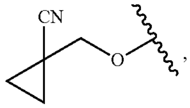,
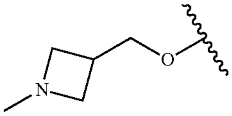,
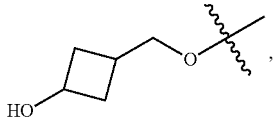,
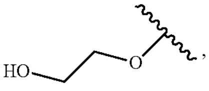,
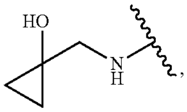,
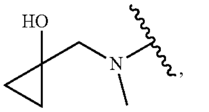,
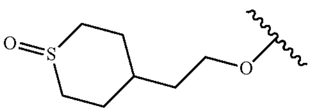,
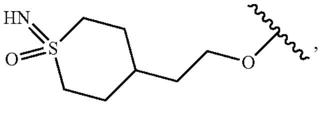, -continued

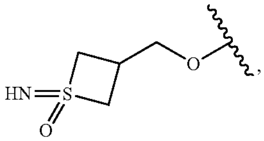,
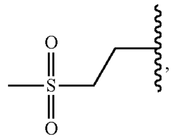,
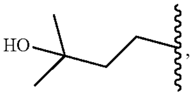,
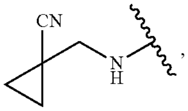,
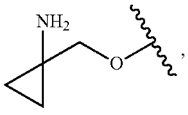,
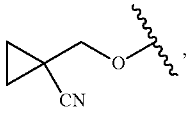,
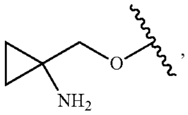,
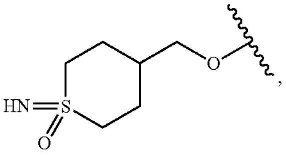,
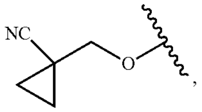,
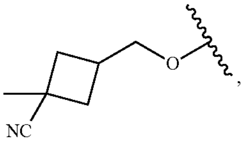,
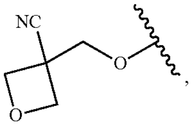,
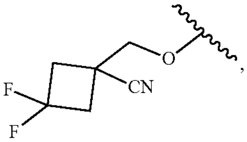,
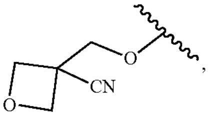,
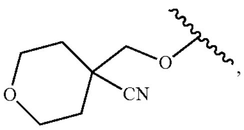,
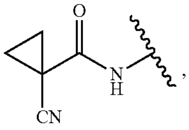,
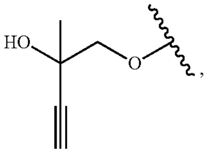,
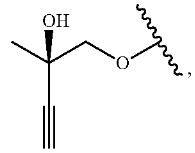,
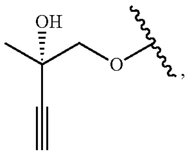,
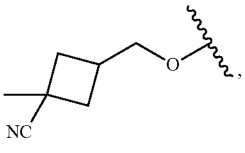,
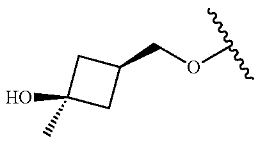,
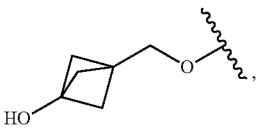,
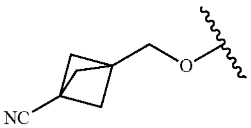,
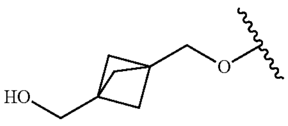 or -continued

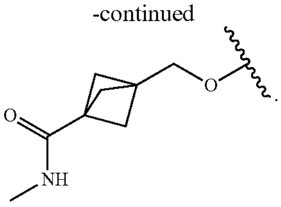.

The present disclosure further provides a preferred embodiment, the compound represented by general formula (I), the stereoisomer thereof or the pharmaceutically acceptable salt thereof is further represented by general formula (IX-C):

(IX-C)

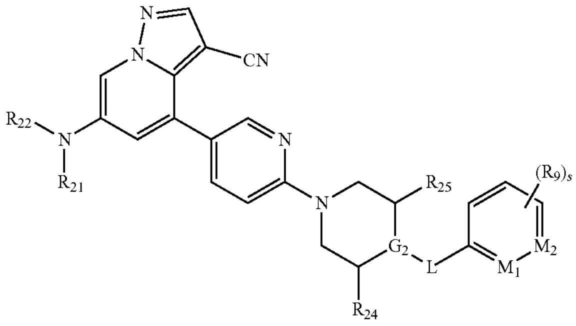

wherein:

$R_{21}$ and $R_{22}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl, $-(CH_2)_{n1}C(O)R_{aa}$ or $-(CH_2)_{n1}R_{aa}$;

or, $R_{21}$ and $R_{22}$ together with the carbon atoms they are attached to form a 3-12 membered heterocyclyl, wherein the 3-12 membered heterocyclyl is optionally further substituted by one or more substituents selected from hydrogen, amino, halogen, cyano, hydroxyl, oxo, $C_{1-6}$ alkyl or $C_{1-6}$ hydroxyalkyl;

preferably azetidinyl, pyrrolidinyl, 2-azaspiro[3.3]heptane or piperidinyl, wherein the azetidinyl, pyrrolidinyl, 2-azaspiro[3.3]heptane or piperidinyl is optionally further substituted by one or more substituents selected from of hydrogen, $C_{1-6}$ alkyl, hydroxyl or hydroxyalkyl;

$R_{24}$ and $R_{25}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or $-(CH_2)_{n1}OR_{aa}$, preferably hydrogen or methyl;

or, $R_{24}$ and $R_{25}$ together with the carbon atoms they are attached to and G2 form a $C_{3-8}$ cycloalkyl or 3-12 membered heterocyclyl, preferably azetidinyl;

L, $G_2$, $M_1$, $M_2$, $R_9$, $R_{aa}$, s and n1 are as defined in general formula (IX-A).

The present disclosure further provides a preferred embodiment, the compound represented by general formula (I), the stereoisomer thereof or the pharmaceutically acceptable salt thereof, $R_{21}$ and $R_{22}$ in general formula (IX-C) are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl, $-(CH_2)_{n1}C(O)R_{aa}$ or $-(CH_2)_{n1}R_{aa}$;

or, $R_{21}$ and $R_{22}$ together with the carbon atoms they are attached to form a 3-12 membered heterocyclyl, wherein the 3-12 membered heterocyclyl is optionally further substituted by one or more substituents selected from hydrogen, amino, halogen, cyano, hydroxyl, oxo, $C_{1-6}$ alkyl and $C_{1-6}$ hydroxyalkyl;

preferably azetidinyl, pyrrolidinyl, 2-azaspiro[3.3]heptane or piperidinyl, wherein the azetidinyl, pyrrolidinyl, 2-azaspiro[3.3]heptane or piperidinyl is optionally further substituted by one or more substituents selected from of hydrogen, $C_{1-3}$ alkyl, cyano, hydroxyl or hydroxyalkyl.

The present disclosure further provides a preferred embodiment, the compound represented by general formula (I), the stereoisomer thereof or the pharmaceutically acceptable salt thereof,

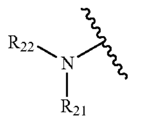

in general formula (IX-C) is selected from

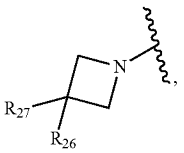,
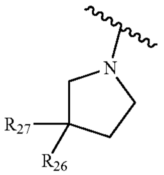,
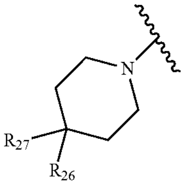
or
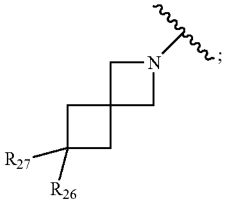;

wherein, $R_{26}$ and $R_{27}$ are each independently selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{1-6}$ hydroxyalkyl, $C_{2-6}$ alkenyl, $C_{2-6}$ alkynyl, $C_{3-8}$ cycloalkyl, 3-12 membered heterocyclyl, $C_{6-10}$ aryl or 5-12 membered heteroaryl;

preferably hydrogen, hydroxyl, cyano, $C_{1-3}$ alkyl or $C_{1-3}$ hydroxyalkyl;

more preferably hydrogen, hydroxyl, cyano, methyl or hydroxyisopropyl.

In a preferred embodiment of the present disclosure, L is selected from $-CH_2-$, $-CD_2-$, $-O-$, $-S-$, $-C(O)NH-$ or $-NHC(O)-$;

$G_2$ is selected from $-N-$, $-CH-$ or $-CCH_3-$;

$M_1$ is selected from $-N-$, $-CH-$ or $-CCH_3-$;

$M_2$ is selected from $-N$ or $-CH-$.

The present disclosure further provides a preferred embodiment, the compound represented by general formula (I), the stereoisomer thereof or the pharmaceutically acceptable salt thereof is further represented by general formula (IX-D):

(IX-D)

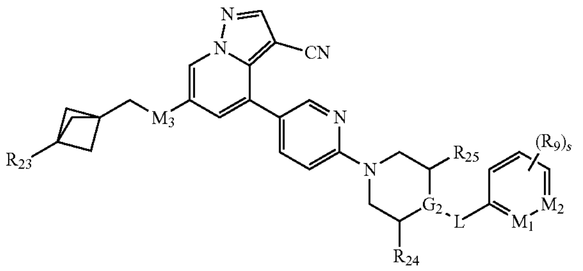

wherein:

$R_{23}$ is selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{1-6}$ hydroxyalkyl, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_6$-10 aryl, 5-12 membered heteroaryl, $-(CH_2)_{n1}C(O)R_{aa}$ or $-(CH_2)_{n1}R_{aa}$, preferably hydroxyl, cyano or $C_{1-6}$ hydroxyalkyl;

L, $G_2$, $M_1$, $M_2$, $M_3$, $R_9$, $R_{aa}$, s and n1 are as defined in general formula (IX-A).

The present disclosure further provides a preferred embodiment, the compound represented by general formula (I), the stereoisomer thereof or the pharmaceutically acceptable salt thereof, $R_{23}$ in general formula (IX-D) is selected from hydroxyl, cyano, $C_{1-6}$ hydroxyalkyl or $-(CH_2)_{n1}C(O)NR_{aa}R_{bb}$.

The present disclosure further provides a preferred embodiment, each of the compound represented by general formula, the stereoisomer thereof or the pharmaceutically acceptable salt thereof:

ring A is selected from the following groups:

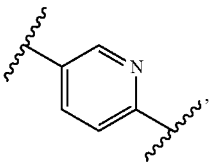,
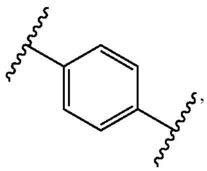,
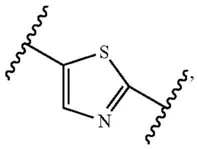,
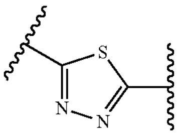
or
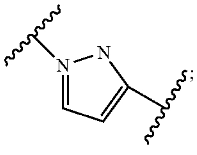;

ring B is selected from the following groups:

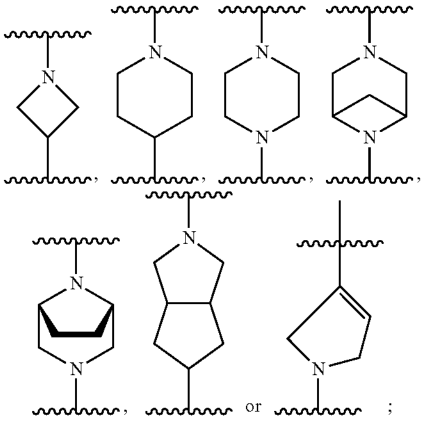

or ;

ring C is selected from the following groups:

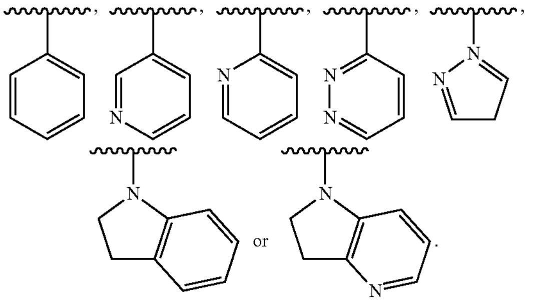

or .

The present disclosure further provides a preferred embodiment, each of the compound represented by general formula, the stereoisomer thereof or the pharmaceutically acceptable salt thereof:

L is selected from bond, $-(CH_2)_{n1}CR_{aa}R_{bb}-$, $-(CH_2)_{n1}NR_{aa}C(O)(CH_2)_{n2}-$, $-(CH_2)_{n1}C(O)(CR_{aa}R_{bb})_m(CH_2)_{n2}-$, $-(CH_2)_{n1}C(O)(CH_2)_m(CR_{aa}R_{bb})_{n2}-$, $-(CH_2)_{n1}C(O)NR_{cc}(CR_{aa}R_{bb})_{n2}-$, $-(CH_2)_{n1}(O)(CH_2)_{n2}-$ or $-(CH_2)_{n1}NR_{aa}(CH_2)_{n2}-$; preferably $-(CH_2)_2-$, $-(CD_2)_2$-, $-O-$, $-C(O)NH-$, $-C(O)N(CH_3)-$, $-NHC(O)-$ or $-O(CH_2)_2-$;

$R_1$ is selected from hydrogen, halogen, $C_{1-6}$ alkyl, $C_{1-6}$ alkoxy, $C_{1-6}$ hydroxyalkyl, oxo, $C_{2-6}$ alkynyl, 3-12 membered heterocyclyl, 5-12 membered heteroaryl, $-(C{\equiv}C)_{n1}(CR_{aa}R_{bb})_mR_{cc}$, $-(C{=}C)_n(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}(CR_{aa}R_{bb})_mC(O)NHR_{cc}$, $-(CH_2)_{n1}S(CH_2)_{n2}(CR_{aa}R_{bb})_mR_{cc}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}O(CH_2)_{n2}R_{aa}$, $-(CH_2)_{n1}NR_{aa}(CH_2)_{n2}CR_{bb}$, $-(CH_2)_{n1}NR_{aa}C(O)R_{bb}$ or $-(CH_2)_{n1}S(O)(=NR_{aa})(CH_2)_{n2}R_{bb}$, wherein the $C_{1-6}$ alkyl, $C_{1-6}$ alkoxy, $C_{2-6}$ alkynyl, 3-12 membered heterocyclyl and 5-12 membered heteroaryl are optionally further substituted by one or more substituents selected from hydrogen, deuterium, $C_{1-6}$ alkyl, $C_{1-6}$ haloalkyl, $C_{1-6}$ hydroxyalkyl, $C_{1-6}$ cyanoalkyl, $C_{1-6}$ alkoxy, halogen, hydroxyl, amino, cyano, oxo, thio, imino, $C_{3-8}$ cycloalkyl and 3-12 membered heterocyclyl;

$R_2$ is selected from hydrogen or halogen;

$R_3$ is selected from hydrogen, $C_{1-6}$ alkyl or amino; or, any two adjacent or non-adjacent $R_3$ are connected to form a $C_{3-8}$ cycloalkyl or 3-12 membered heterocyclyl;

$R_4$ is selected from $C_{1-6}$ alkyl, $C_{6-10}$ aryl or 5-12 membered heteroaryl, wherein the $C_{1-6}$ alkyl, $C_{6-10}$ aryl and 5-12 membered heteroaryl are optionally further substituted by one or more substituents selected from hydrogen, amino, $C_{1-6}$ alkyl, $C_{1-6}$ alkoxy, halogen, $-(CH_2)_{n1}OR_{aa}$, $-(CH_2)_{n1}C(O)NR_{aa}R_{bb}$ or $-(CH_2)_{n1}NR_{aa}C(O)R_{bb}$;

$R_5$ is selected form cyano, $-C(O)NR_{aa}R_{bb}$ or $-(CH_2)_{n1}P(O)R_{aa}R_{bb}$;

$R_6$ is selected from hydrogen, $C_{1-6}$ alkyl, $C_{1-6}$ alkoxy, halogen, amino, $-(CH_2)_{n1}OR_{aa}$, $-(CH_2)_{n1}C(O)NR_{aa}R_{bb}$ or $-(CH_2)_{n1}NR_{aa}C(O)R_{bb}$;

$R_7$ is selected from hydrogen, $C_{1-6}$ alkyl, $C_{1-6}$ alkoxy, oxo, $C_{2-6}$ alkynyl, 3-12 membered heterocyclyl, 5-12 membered heteroaryl, $-(C{\equiv}C)_{n1}(CR_{aa}R_{bb})_mR_{cc}$, $-(C{=}C)_{n1}(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}(CR_{aa}R_{bb})_mC(O)NHR_{cc}$, $-(CH_2)_{n1}S(CH_2)_{n2}(CR_{aa}R_{bb})_mR_{cc}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}O(CH_2)_{n2}R_{aa}$, $-(CH_2)_{n1}NR_{aa}(CH_2)_{n2}CR_{bb}$, $-(CH_2)_{n1}NR_{aa}C(O)R_{bb}$ or $-(CH_2)_{n1}S(O)(=NR_{aa})(CH_2)_{n2}R_{bb}$, wherein the $C_{1-6}$ alkyl, $C_{1-6}$ alkoxy, $C_{2-6}$ alkynyl, 3-12 membered heterocyclyl and 5-12 membered heteroaryl are optionally further substituted by one or more substituents selected from hydrogen, deuterium, $C_{1-6}$ alkyl, $C_{1-6}$ haloalkyl, $C_{1-6}$ hydroxyalkyl, $C_{1-6}$ cyanoalkyl, $C_{1-6}$ alkoxy, halogen, hydroxyl, amino, cyano, oxo, thio, imino, $C_{3-8}$ cycloalkyl or 3-12 membered heterocyclyl;

$R_8$ is selected from hydrogen or halogen;

$R_9$ is selected from hydrogen, $C_{1-6}$ alkyl, $C_{1-6}$ alkoxy, halogen or $-OR_{aa}$;

$R_{10}$ is selected from hydrogen, $C_{1-6}$ alkyl or amino;

or, any two adjacent or non-adjacent $R_{10}$ are connected to form a $C_{3-8}$ cycloalkyl or 3-12 membered heterocyclyl;

$R_{11}$ is selected form cyano, $-(CH_2)_{n1}P(O)R_{aa}R_{bb}$ or $-(CH_2)_{n1}C(O)NR_{aa}R_{bb}$;

$R_{12}$ is selected from hydrogen, $C_{1-6}$ alkyl or halogen;

$R_{13}$ is selected from $C_{1-6}$ alkyl, $C_{1-6}$ alkoxy, $C_{2-6}$ alkynyl, 3-12 membered heterocyclyl, 5-12 membered heteroaryl, $-(C{\equiv}C)_{n1}(CR_{aa}R_{bb})_mR_{cc}$, $-(C{=}C)_{n1}(CR_{aa}R_{bb})_mR_{cc}$, $-(CH_2)_{n1}O(CH_2)_{n2}(CR_{aa}R_{bb})_mR_{cc}$, $-(CH_2)_{n1}O(CH_2)_{n2}(CR_{aa}R_{bb})_mC(O)NHR_{cc}$, $-(CH_2)_{n1}S(CH_2)_{n2}(CR_{aa}R_{bb})_mR_{cc}$, $-(CH_2)_{n1}O(CH_2)_{n2}S(O)_mR_{aa}$, $-(CH_2)_{n1}O(CH_2)_{n2}S(O)(=NR_{aa})(CH_2)_mR_{bb}$, $-(CH_2)_{n1}O(CH_2)_{n2}R_{aa}$, $-(CH_2)_{n1}NR_{aa}(CH_2)_{n2}CR_{bb}$, $-(CH_2)_{n1}NR_{aa}C(O)R_{bb}$ or $-(CH_2)_{n1}S(O)(=NR_{aa})(CH_2)_{n2}R_{bb}$, wherein the $C_{1-6}$ alkyl, $C_{1-6}$ alkoxy, $C_{2-6}$ alkynyl, 3-12 membered heterocyclyl and 5-12 membered heteroaryl are optionally further substituted by one or more substituents selected from hydrogen, $C_{1-6}$ alkyl, hydroxyl, thio, imino, $C_{1-6}$ alkoxy, $C_{1-6}$ hydroxyalkyl, $C_{1-6}$ cyanoalkyl, $C_{3-8}$ cycloalkyl or 3-12 membered heterocyclyl;

$R_{14}$ is selected from hydrogen or halogen;

$R_{15}$ is selected from hydrogen or halogen;

$R_{16}$ is selected from hydrogen, alkoxy or $-OR_{aa}$;

$R_{aa}$, $R_{bb}$ and $R_{cc}$ are each independently selected from hydrogen, deuterium, cyano, amino, $C_{1-6}$ alkyl, $C_{1-6}$ alkoxy, $C_{1-6}$ hydroxyalkyl, hydroxyl, $C_{3-8}$ cycloalkyl, 3-12 membered heterocyclyl or $C_{6-14}$ aryl, wherein the $C_{1-6}$ alkyl, $C_{1-6}$ alkoxy, $C_{1-6}$ hydroxyalkyl, hydroxyl, $C_3$-8 cycloalkyl, 3-12 membered heterocyclyl and $C_{6-14}$ aryl are optionally further substituted by one or more substituents selected from hydrogen, halogen, cyano, hydroxyl, oxo, imino, $C_{1-6}$ alkyl or $C_{1-6}$ hydroxyalkyl;

or, any two of $R_{aa}$, $R_{bb}$ and $R_{cc}$ are optionally connected to form a $C_{3-8}$ cycloalkyl or a 3-12 membered heterocyclyl, wherein the $C_{3-8}$ cycloalkyl and 3-12 membered heterocyclyl are optionally further substituted by one or more substituents selected from hydrogen, halogen, cyano, hydroxyl, oxo, imino, $C_{1-6}$ alkyl or $C_{1-6}$ hydroxyalkyl;

The present disclosure also relates to a method for preparing the compound represented by general formula (IX-A), the stereoisomer thereof or the pharmaceutically acceptable salt thereof, comprising the following steps,

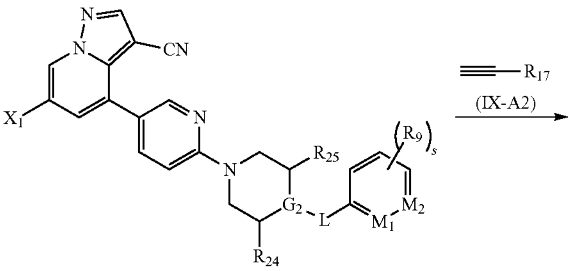

(IX-A1)

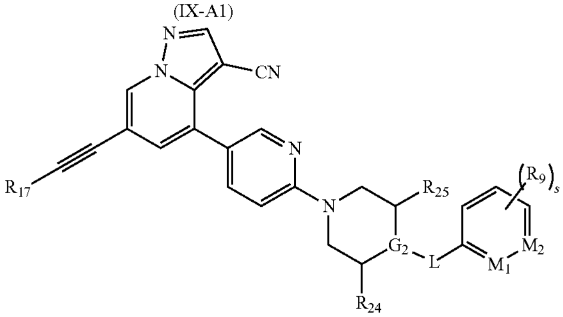

(IX-A)

a coupling reaction is carried out with general formula (IX-A1) and general formula (IX-A2) to obtain the compound represented by general formula (IX-A) or the stereoisomer thereof and the pharmaceutically acceptable salt thereof, wherein:

$X_1$ is selected from halogen; preferably fluorine, chlorine, bromine or iodine; more preferably bromine.

The present disclosure also relates to a method for preparing the compound represented by general formula (IX-B), the stereoisomer thereof or the pharmaceutically acceptable salt thereof, comprising the following steps,

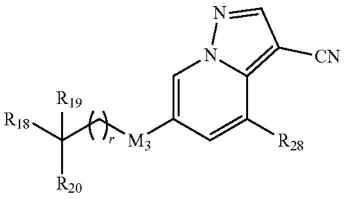

(IX-B1)

+

-continued

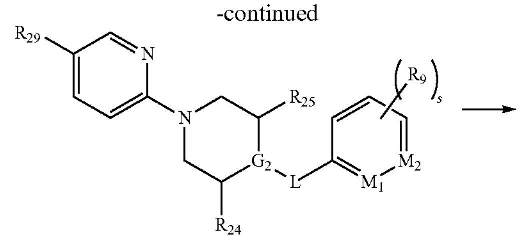

(IX-B2)

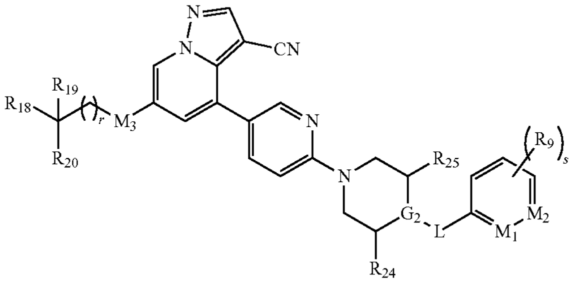

(IX-B)

a reaction is carried out with general formula (IX-B1) and general formula (IX-B2) to obtain the compound represented by general formula (IX-B) or the stereoisomer thereof and the pharmaceutically acceptable salt thereof;

wherein:

$R_{28}$ is selected from halogen, —$B(OH)_2$ or borate ester; preferably fluorine, chlorine, bromine, iodine, —$B(OH)_2$ or;

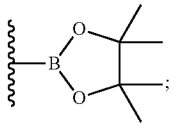 [SMILES: *B1OC(C)(C)C(C)(C)O1]

$R_{29}$ is selected from halogen, boric acid or borate ester; preferably fluorine, chlorine, bromine, iodine, —$B(OH)_2$ or;

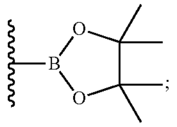 [SMILES: *B1OC(C)(C)C(C)(C)O1]

when $R_{28}$ is halogen, $R_{29}$ is selected from boric acid or borate ester;

when $R_{28}$ is selected from boric acid or borate ester, $R_{29}$ is halogen.

The present disclosure also relates to a method for preparing the compound represented by general formula (IX-B), the stereoisomer thereof or the pharmaceutically acceptable salt thereof, comprising the following steps,

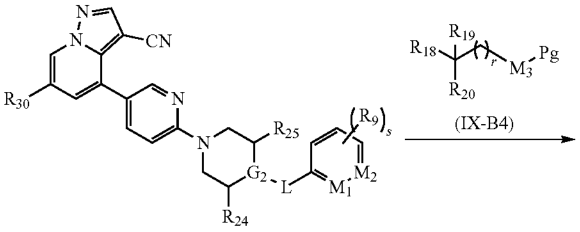

(IX-B3)

(IX-B4)

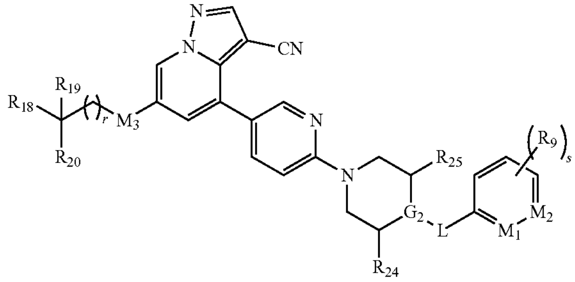

(IX-B)

a reaction is carried out with general formula (IX-B3) and general formula (IX-B4) to obtain the compound represented by general formula (IX-B) or the stereoisomer thereof and the pharmaceutically acceptable salt thereof;

wherein:

$M_3$ is selected from bond, —O—, —S—, —NH— or —$NCH_3$—;

$R_{30}$ is selected from halogen, hydroxyl; preferably fluorine, chlorine, bromine, iodine, or hydroxyl; more preferably bromine or hydroxyl;

Pg is selected from hydrogen, halogen or hydroxyl protecting group, and the halogen is preferably fluorine, chlorine, bromine or iodine;

when Pg is a hydroxyl protecting group, it is selected from methyl, tert-butyl, triphenyl, methyl sulfide methyl ether, 2-methoxyethoxymethyl ether, methoxymethyl ether, p-methoxybenzyl ether, pivaloyl, benzyl ether, methoxymethyl, trimethylsilyl, tetrahydrofuranyl, tert-butyldisilyl, acetyl, benzoyl or p-toluenesulfonyl; preferably p-toluenesulfonyl;

when $M_3$ is —O—, Pg is selected from hydrogen or hydroxyl protecting group.

The present disclosure also relates to a method for preparing the compound represented by general formula (IX-C), the stereoisomer thereof or the pharmaceutically acceptable salt thereof, comprising the following steps,

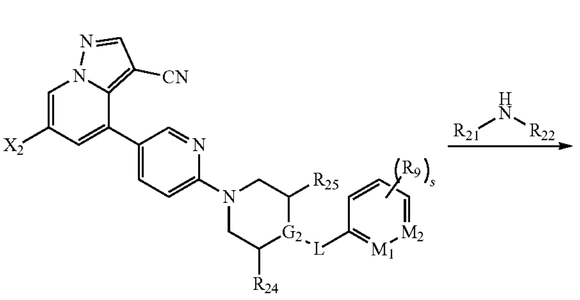

(IX-C1)

-continued

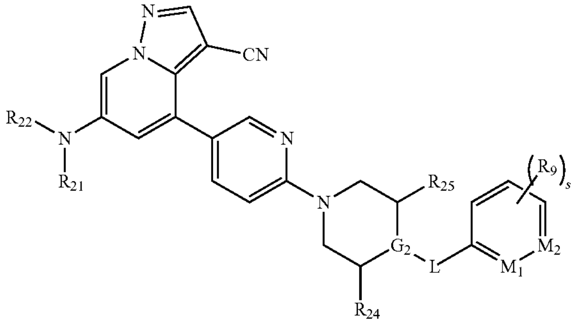

(IX-C)

a reaction is carried out with general formula (IX-C1) and general formula (IX-C2) to obtain the compound represented by general formula (IX-B) or the stereoisomer thereof and the pharmaceutically acceptable salt thereof;

wherein:

$X_2$ is selected from halogen; preferably fluorine, chlorine, bromine or iodine; more preferably bromine.

The present disclosure also relates to a method for preparing the compound represented by general formula (X), the stereoisomer thereof or the pharmaceutically acceptable salt thereof, wherein the method comprises the following steps,

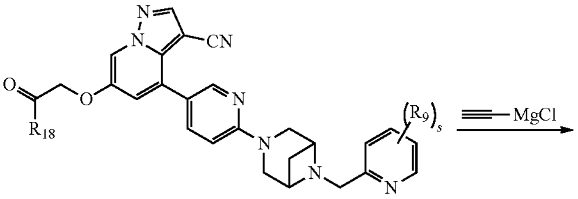

(X2)

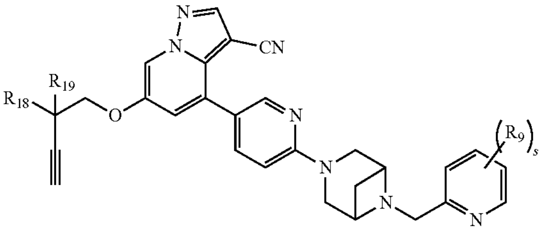

or (X)

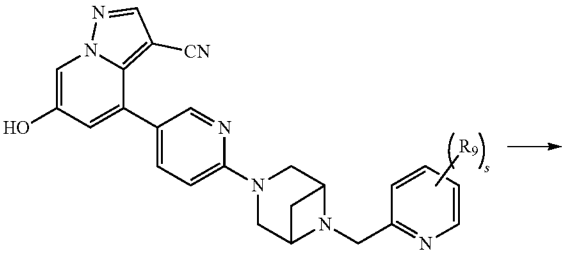

(X1)

-continued

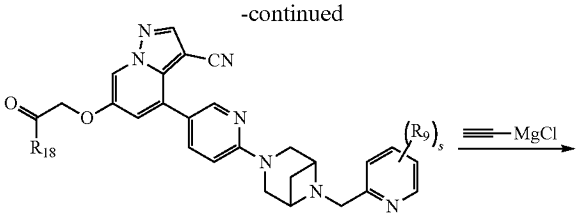

(X2)

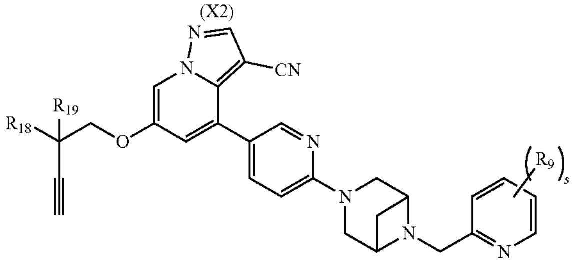

(X)

wherein:

$R_{18}$ and $R_{19}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl or 5-12 membered heteroaryl;

or, $R_{18}$ and $R_{19}$ together with the carbon atoms they are attached to form a $C_{3-8}$ cycloalkyl or a 3-12 membered heterocyclyl, preferably $C_{3-6}$ cycloalkyl or 3-7 membered heterocyclyl comprising 1-2 oxygen atoms, nitrogen atoms or sulfur atoms, more preferably cyclopropyl, cyclobutyl, cyclopentyl, oxetanyl, azetidinyl, bicyclo[1,1,1]pentane or 1-imino-1-oxothiopyran, wherein the $C_{3-8}$ cycloalkyl or 3-12 membered heterocyclyl is optionally further substituted by one or more substituents selected from hydrogen, $C_{1-6}$ alkyl, hydroxyl, cyano and $C_{1-6}$ hydroxyalkyl;

preferably, $R_{18}$ and $R_{19}$ are each independently selected from hydrogen, methyl or hydroxyl.

The present disclosure also provides a pharmaceutical composition comprising a therapeutically effective amount of the compound represented by each of the general formula and the stereoisomer thereof or the pharmaceutically acceptable salt thereof, and one or more pharmaceutically acceptable carriers, diluents or excipients.

The present disclosure further provides a preferred embodiment, related to a use of the compound represented by each of the general formula, the stereoisomer thereof or the pharmaceutically acceptable salt thereof, or the pharmaceutical composition in the preparation of medicaments related to RET inhibitor.

The present disclosure also provides a preferred embodiment, related to a use of the compound represented by general formula (I) and the stereoisomer thereof or the pharmaceutically acceptable salt thereof, or the pharmaceutical composition for the preparation of medicaments for the treatment and/or prevention of non-small cell lung cancer, fibrosarcoma, pancreatic tumor, medullary thyroid carcinoma, thyroid papillary tumor, soft tissue sarcoma, highly solid tumor, breast tumor and colon tumor and other related diseases.

The present disclosure further relates to a method of using the compound represented by general formula (I), the stereoisomer thereof or the pharmaceutically acceptable salt thereof, or the pharmaceutical composition for the preparation of medicaments for the treatment and/or prevention of non-small cell lung cancer, fibrosarcoma, pancreatic tumor, medullary thyroid carcinoma, thyroid papillary tumor, soft tissue sarcoma, highly solid tumor, breast tumor and colon tumor and other related diseases.

The present disclosure also relates to a method for the treatment and/or prevention of non-small cell lung cancer, fibrosarcoma, pancreatic tumor, medullary thyroid carcinoma, papillary thyroid tumor, soft tissue sarcoma, highly solid tumors, breast tumors, colon tumors and other related diseases, comprising administering a therapeutically effective amount of the compound of the present disclosure or the pharmaceutically acceptable salt, ester, prodrug, solvate, hydrate or derivative thereof to a mammal.

In some embodiments of the present disclosure, the method relates to, such as, the treatment and/or prevention of non-small cell lung cancer, fibrosarcoma, pancreatic tumor, medullary thyroid carcinoma, thyroid papillary tumor, soft tissue sarcoma, highly solid tumor, breast tumor and the treatment of colon tumor and other related diseases.

The methods for the treatment provided herein include administering a therapeutically effective amount of the compound of the disclosure to a subject. In an embodiment, the present disclosure provides a method for the treatment of diseases including menopausal hot flush related diseases in mammals. The method comprises administering a therapeutically effective amount of the compound of the present disclosure or the pharmaceutically acceptable salt, ester, prodrug, solvate, hydrate or derivative thereof to a mammal.

DETAILED DESCRIPTION OF THE INVENTION

Unless otherwise stated, the terms used in the description and claims have the following meanings.

The term "alkyl" refers to a saturated aliphatic hydrocarbon group, which is a straight or branched chain group comprising 1 to 20 carbon atoms, preferably alkyl comprising 1 to 8 carbon atoms, more preferably alkyl comprising 1 to 6 carbon atoms, the most preferably alkyl containing 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers. More preferrably lower alkyl comprising 1 to 6 carbon atoms, non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl may be substituted or unsubstituted, when substituted, the substituents may be substituted at any available attachment point, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl, or carboxylate; alkyl substituted by methyl, ethyl, isopropyl, tert-butyl, haloalkyl, deuterated alkyl, alkoxy-substituted alkyl and alkyl substituted by hydroxyl are preferred in the present disclosure.

The term "alkylidene" refers to that one hydrogen atom of an alkyl is further substituted, for example: "methylene" refers to $—CH_2—$, "ethylene" refers to $—(CH_2)_2—$, and "propylene" refers to $—(CH_2)_3—$, "butylene" refers to $—(CH_2)_4—$, etc. The term "alkenyl" refers to an alkyl as defined above comprising at least two carbon atoms and at least one carbon-carbon double bond, such as vinyl, 1-propenyl, 2-propenyl, 1-, 2-, or 3-butenyl etc. The alkenyl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio.

The term "cycloalkyl" refers to a saturated or partially unsaturated monocyclic or polycyclic cyclic hydrocarbon substituent, the cycloalkyl ring contains 3 to 20 carbon atoms, preferably 3 to 12 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctanyl, etc.; polycyclic cycloalkyl includes spiro, fused and bridged cycloalkyls, preferably cyclopropyl, cyclobutyl, cyclohexyl, cyclopentyl and cycloheptyl.

The term "spirocycloalkyl" refers to polycyclic group that shares one carbon atom (called a spiro atom) between 5- to 20-membered monocyclic rings, which may contain one or more double bonds, but none of the rings have complete conjugate π electron system. Preferably 6-14 membered, more preferably 7-10 membered. According to the number of shared spiro atoms between the rings, the spirocycloalkyl is classified into single spirocycloalkyl, bispirocycloalkyl or polyspirocycloalkyl, preferably single spirocycloalkyl and bispirocycloalkyl. More preferably, 4-membered/4-membered, 4-membered/5-membered, 4-membered/6-membered, 5-membered/5-membered, or 5-membered/6-membered monospirocycloalkyl. Non-limiting examples of spirocycloalkyls include:

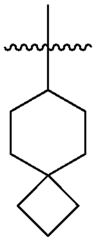
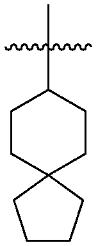
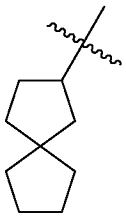
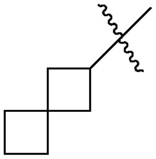
and

-continued

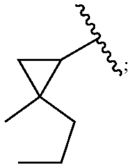
;

also include spirocycloalkyl in which single spirocycloalkyl and heterocycloalkyl share a spiro atom, non-limiting examples include:

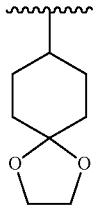
and
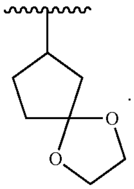
.

The term "fused cycloalkyl" refers to a 5-20 membered all-carbon polycyclic group in which each ring in the system shares an adjacent pair of carbon atoms with other rings in the system, wherein one or more of the rings may comprise one or multiple double bonds, but none of the ring has a fully conjugated 7r-electron system. Preferably 6-14 membered, more preferably 7-10 membered. According to the number of constituent rings, it can be classified into bicyclic, tricyclic, tetracyclic or polycyclic fused cycloalkyl, preferably bicyclic or tricyclic, and more preferably 5-membered/5-membered or 5-membered/6-membered bicyclic alkyl. Non-limiting examples of fused cycloalkyls include:

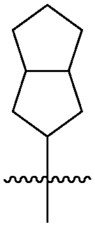
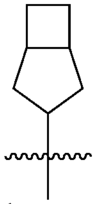
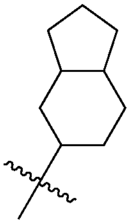
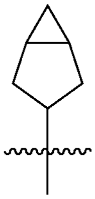
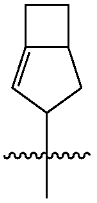
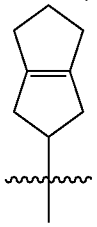
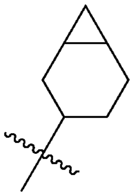
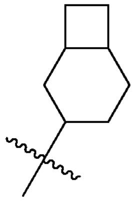
and
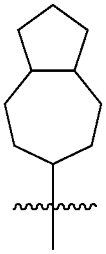
.

The term "bridged cycloalkyl" refers to 5-20 membered all-carbon polycyclic group, in which any two rings share two carbon atoms that are not directly connected, it may contain one or more double bonds, but none of the ring has a complete conjugated π electron system. Preferably 6-14 membered, more preferably 7-10 membered. According to the number of constituent rings, it can be classified into bicyclic, tricyclic, tetracyclic or polycyclic bridged cycloalkyl, preferably bicyclic, tricyclic, or tetracyclic, and more preferably bicyclic or tricyclic. Non-limiting examples of bridge ring alkyl include:

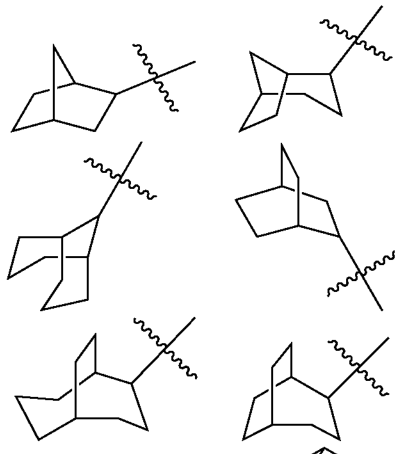

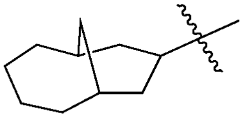

and

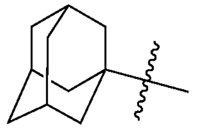

.

The cycloalkyl ring may be fused to an aryl, heteroaryl or heterocycloalkyl ring, wherein the ring connected to the parent structure is cycloalkyl, non-limiting examples include indanyl, tetrahydronaphthyl, benzocycloheptanyl, etc. The cycloalkyl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or carboylate.

The term "heterocyclyl" refers to saturated or partially unsaturated monocyclic or polycyclic hydrocarbon substituent comprising 3 to 20 ring atoms, wherein one or more of the ring atoms are heteroatoms selected from nitrogen, oxygen, C(O), S(O)(=NH) or $S(O)_m$ (wherein m is an integer of 0 to 2), but not including the ring part of —O—O—, —O—S— or —S—S—, and the remaining ring atoms are carbon. It preferably contains 3 to 12 ring atoms, wherein 1 to 4 ring atoms are heteroatoms; more preferably contains 3 to 8 ring atoms; most preferably contains 3 to 8 ring atoms. Non-limiting examples of monocyclic heterocyclic include oxetane, trimethylene sulfide, azetidine, tetrahydropyranyl, azepanyl, pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl, etc., preferably oxetane, trimethylene sulfide, azetidine, tetrahydrofuranyl, tetrahydropyranyl, 1-imino-1-oxothiopyran, azepanyl, piperidinyl and piperazinyl. Polycyclic heterocyclyl includes spiro, fused and bridged heterocyclyl; the spiro, fused and bridged heterocyclyl are optionally connected to other groups through a single bond, or connect to other cycloalkyl, heterocyclyl, aryl and heteroaryl through any two or more of ring atoms. The heterocyclyl may be substituted or unsubstituted, when substituted, the substituent is preferably one or more of the following groups independently selected from hydrogen, alkyl, hydroxyalkyl, amino, imino, cyano, oxo, cycloalkyl, heterocycloalkyl, aryl, heteroaryl.

The term "spiroheterocyclyl" refers to polycyclic heterocyclic group sharing one atom (called a spiro atom) between 5-20 membered monocyclic ring, wherein one or more ring atoms are selected from nitrogen, oxygen, S(O) (=NH) or $S(O)_m$ (wherein m is an integer of 0 to 2) heteroatoms, and the remaining ring atoms are carbon. It may contain one or more double bonds, but none of the ring have complete conjugate π electron system. Preferably 6-14 membered, more preferably 7-10 membered. According to the number of spiro atoms shared between the rings, the spiro heterocyclyl is classified into single spiro heterocyclyl, dispiro heterocyclyl or polyspiro heterocyclyl, preferably single spiro heterocyclyl and dispiro heterocyclyl. More preferably, 4-membered/4-membered, 4-membered/5-membered, 4-membered/6-membered, 5-membered/5-membered, or 5-membered/6-membered monospirocyclyl. Non-limiting examples of spiroheterocyclyl include:

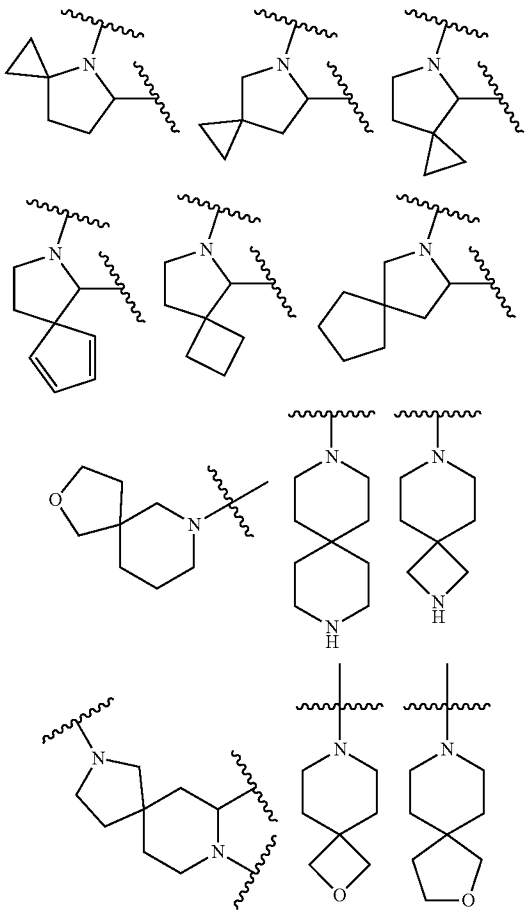

-continued

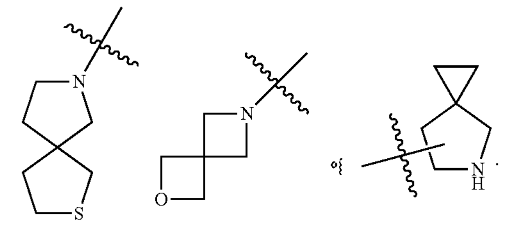

The term "fused heterocyclyl" refers to a 5-20 member and polycyclic heterocyclic group in which each ring in the system shares an adjacent pair of atoms with other rings in the system, one or more of the rings may comprise one or multiple double bonds, but none of the ring has a fully conjugated 7r-electron system, wherein one or more of the ring atoms are heteroatoms selected from nitrogen, oxygen or $S(O)_m$ (wherein m is an integer of 0 to 2), the rest of the ring atoms are carbon. Preferably 6-14 membered, more preferably 7-10 membered. According to the number of constituent rings, it can be classified into bicyclic, tricyclic, tetracyclic or polycyclic fused heterocyclyl, preferably bicyclic or tricyclic, and more preferably 5-membered/5-membered or 5-membered/6-membered bicyclic fused heterocylyl. Non-limiting examples of fused heterocylyl include:

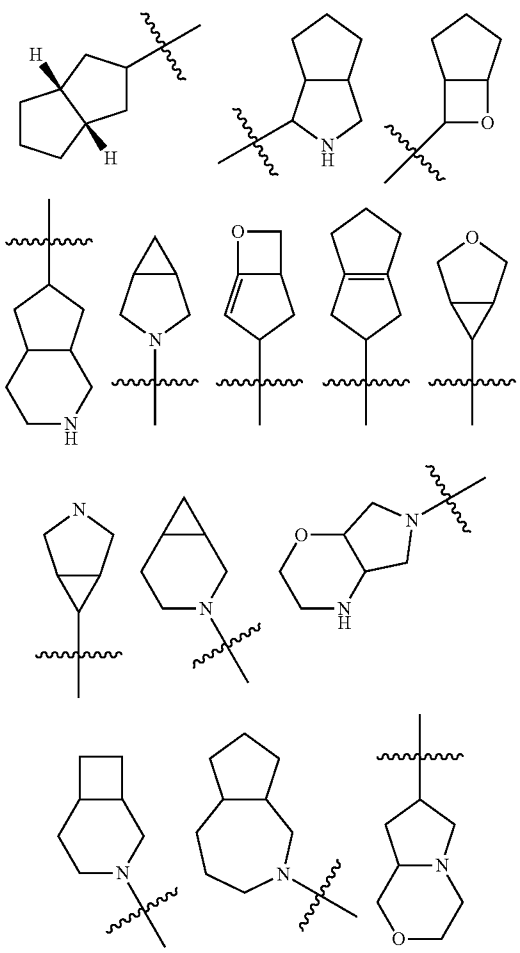

-continued

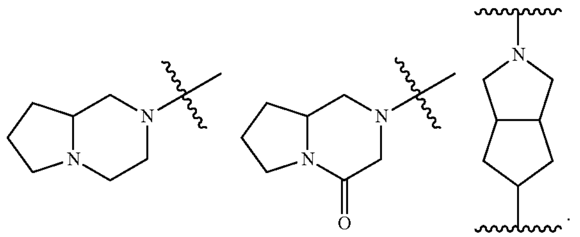

The term "bridged heterocyclyl" refers to a polycyclic heterocyclic group in which any two rings share two atoms that are not directly connected, it may contain one or multiple double bonds, but none of the ring has a fully conjugated 7r-electron system, wherein one or more of the ring atoms are heteroatoms selected from nitrogen, oxygen or $S(O)_m$ (wherein m is an integer of 0 to 2), the rest of the ring atoms are carbon. Preferably 6-14 membered, more preferably 7-10 membered. According to the number of constituent rings, it can be classified into bicyclic, tricyclic, tetracyclic or polycyclic bridged heterocyclyl, preferably bicyclic, tricyclic, or tetracyclic, and more preferably bicyclic or tricyclic. Non-limiting examples of bridged heterocyclyl include:

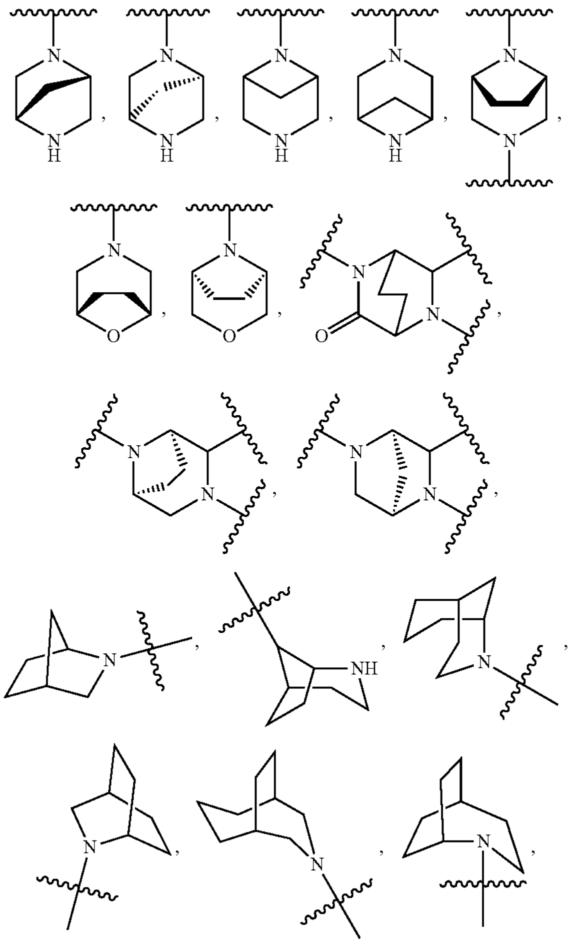

-continued

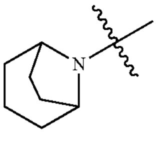

and

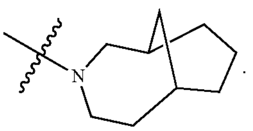

The heterocyclic ring may be fused to an aryl, heteroaryl or cycloalkyl ring, wherein the ring connected to the parent structure is heterocyclyl, non-limiting examples include:

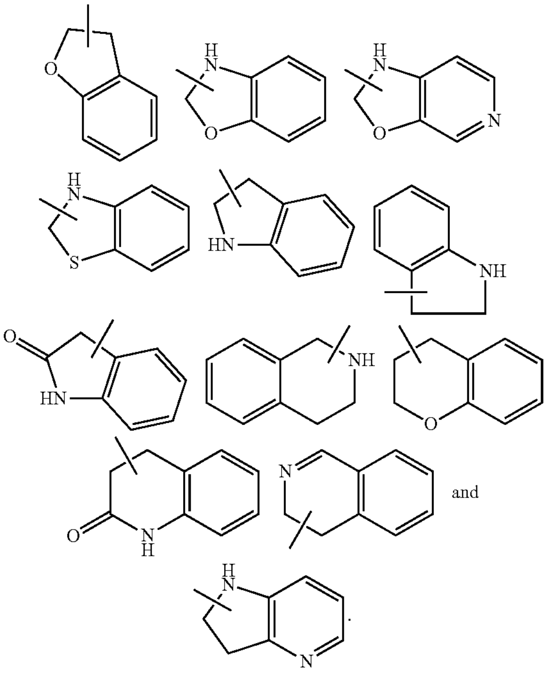

and

The heterocyclyl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or carboylate.

The term “aryl” refers to a 6-14 membered all-carbon monocyclic or fused polycyclic (that is, rings sharing adjacent pairs of carbon atoms) with conjugated 71-electron system, preferably 6-10 membered, such as phenyl and naphthyl. More preferably phenyl. The aryl ring may be fused to heteroaryl, heteroaryl or cycloalkyl ring, wherein the ring connected to the parent structure is aryl ring, non-limiting examples include:

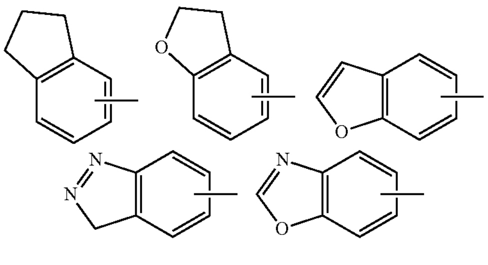

-continued

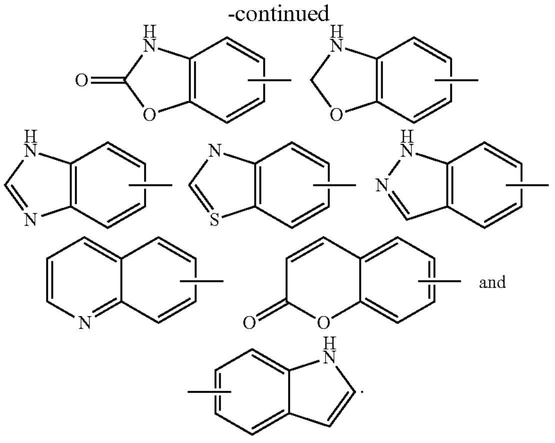

and

The aryl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

The term “heteroaryl” refers to heteroaromatic system comprising 1 to 4 heteroatoms and 5 to 14 ring atoms, wherein the heteroatoms are selected from oxygen, sulfur, and nitrogen. The heteroaryl is preferably 5-10 membered, more preferably 5- or 6-membered, such as imidazole, furanyl, thiophenyl, thiazolyl, pyrazolyl, oxazolyl, pyrrolyl, triazolyl, tetrazolyl, pyridyl, pyrimidinyl, thiadiazole, pyrazinyl, pyridazinyl and oxadiazole, preferably triazolyl, thiophenyl, imidazolyl, pyrazolyl, pyridazinyl and pyrimidinyl, thiazolyl; more preferably, triazolyl, pyrrolyl, thiophenyl, thiazolyl, pyrimidinyl, pyrazolyl, oxazolyl, thiazolyl, thiadiazole, pyridyl, pyridazinyl and oxadiazole. The heteroaryl ring may be fused to an aryl, heteroaryl or cycloalkyl ring, wherein the ring connected to the parent structure is heteroaryl ring, non-limiting examples include:

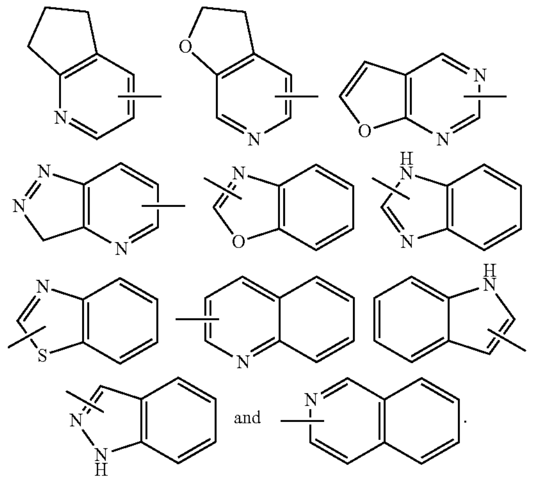

and

The heteroaryl may be optionally substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

The term "alkoxy" refers to —O-(alkyl) and —O-(unsubstituted cycloalkyl), wherein the definition of alkyl is as described above. Non-limiting examples of alkoxy include: methoxy, ethoxy, propoxy, butoxy, cyclopropoxy, cyclobutoxy, cyclopentyloxy, cyclohexyloxy. The alkoxy may be optionally substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

"Haloalkyl" refers to alkyl substituted by one or more halogens, wherein the alkyl is as defined above.

"Haloalkoxy" refers to alkoxy substituted by one or more halogens, wherein the alkoxy is as defined above.

"Hydroxyalkyl" refers to alkyl substituted by one or more hydroxyl, wherein the alkyl is as defined above.

"Alkenyl" refers to chain alkenyl, also known as olefinic group, wherein the alkenyl may be further substituted with other related groups, for example: alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboxylate.

"Alknyl" refers to (CH≡C— or —C≡C—), wherein the alknyl may be further substituted by other related groups, for example: alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

"Hydroxyl" refers to the —OH group.

"Halogen" refers to fluorine, chlorine, bromine or iodine.

"Amino" refers to $—NH_2$.

"Cyano" refers to —CN.

"Nitro" refers to $—NO_2$.

"Carboxyl" refers to —C(O)OH.

"THF" refers to tetrahydrofuran.

"EtOAc" refers to ethyl acetate.

"MeOH" refers to methanol.

"DMF" refers to N, N-dimethylformamide.

"DIPEA" refers to diisopropylethylamine.

"TFA" refers to trifluoroacetic acid.

"MeCN" refers to acetonitrile.

"DMA" refers to N,N-dimethylacetamide.

"$Et_2O$" refers to diethyl ether.

"DCE" refers to 1,2 dichloroethane.

"DIPEA" refers to N,N-diisopropylethylamine.

"NBS" refers to N-bromosuccinimide.

"NIS" refers to N-iodosuccinimide.

"Cbz-Cl" refers to benzyl chloroformate.

"$Pd_2(dba)_3$" refers to tris(dibenzylideneacetone)dipalladium.

"Dppf" refers to 1,1'-bis(diphenylphosphino)ferrocene.

"HATU" refers to 2-(7-aza-1H-benzotriazole-1-yl)-1,1,3,3-tetramethyluronium hexafluorophosphate.

"KHMDS" refers to potassium hexamethyldisilazide.

"LiHMDS" refers to lithium bistrimethylsilylamide.

"MeLi" refers to methyl lithium.

"n-BuLi" refers to n-butyl lithium.

"$NaBH(OAc)_3$" refers to sodium triacetoxyborohydride.

"X is selected from A, B, or C", "X is selected from A, B and C", "X is A, B or C", "X is A, B and C" and other terms all express the same meaning, which means that X can be any one or more of A, B, and C.

The hydrogen described in the present disclosure can be replaced by its isotope deuterium, and any hydrogen in the embodiment compounds of the present disclosure can also be replaced by a deuterium atom.

"Optional" or "optionally" refers to that the event or environment described later can but does not have to occur, and the description includes occasions where the event or environment occurs or does not occur. For example, "heterocyclic group optionally substituted by alkyl" refers to that alkyl may but does not have to be present, and the description includes the case where the heterocyclic group is substituted by alkyl and the case where the heterocyclic group is not substituted by alkyl.

"Substituted" refers to one or more hydrogen atoms in the group, preferably up to 5, more preferably 1 to 3 hydrogen atoms, independently substituted by a corresponding number of substituents. It goes without saying that the substituents are only in their possible chemical positions, and those skilled in the art can determine (by experiment or theory) possible or impossible substitutions without too much effort. For example, amino or hydroxyl having free hydrogen may be unstable when combined with a carbon atom having an unsaturated (e.g., olefinic) bond.

"Pharmaceutical composition" refers to a mixture comprising one or more of the compounds described herein or the physiologically/pharmaceutically acceptable salt or prodrug thereof and other chemical components, and the other component is, for example, physiological/pharmaceutically acceptable carrier and excipient. The purpose of the pharmaceutical composition is to promote the administration to the organism, facilitate the absorption of the active ingredient and then exert the biological activity.

"Pharmaceutically acceptable salt" refers to a salt of the compound of the present disclosure, which is safe and effective when used in mammals, and has due biological activity.

DETAILED DESCRIPTION OF THE PREFERRED EMBODIMENT

The following embodiments will further describe the present disclosure, but these embodiments do not limit the scope of the present disclosure.

Embodiment

The structures of the compounds of the present disclosure were determined by nuclear magnetic resonance (NMR) or/and liquid chromatography-mass spectrometry (LC-MS). NMR chemical shift (δ) was given in units of parts per million (ppm). NMR was determined using a Bruker AVANCE-400 NMR instrument with deuterated dimethyl sulfoxide (DMSO-$d_6$), deuterated methanol ($CD_3OD$) and deuterated chloroform ($CDCl_3$) as solvents and tetramethylsilane (TMS) as internal standard.

Liquid chromatography-mass spectrometry LC-MS was determined with an Agilent 1200 Infinity Series mass spectrometer. HPLC determinations were performed using an Agilent 1200DAD high pressure liquid chromatograph (Sunfire C18 150×4.6 mm column) and a Waters 2695-2996 high pressure liquid chromatograph (Gimini C18 150×4.6 mm column).

Yantai Huanghai HSGF254 or Qingdao GF254 silica gel plate was used as thin layer chromatography silica gel plate, the specification of TLC was 0.15 mm-0.20 mm, and the specification of thin layer chromatography separation and purification products was 0.4 mm-0.5 mm. Generally, Yantai Huanghai silica gel 200-300 mesh silica gel was used as carrier for column chromatography.

The starting materials in the embodiments of the present disclosure are known and commercially available, or can be synthesized by using or following methods known in the art.

Unless otherwise specified, all reactions of the present disclosure were carried out under continuous magnetic stirring under dry nitrogen or argon atmosphere, the solvent is a dry solvent, and the unit of the reaction temperature was degrees Celsius.

Embodiment 1

4-(6-(6-((6-Methoxypyridin-3-yl)methyl)-3,6-diazabicyclo[3.1.1]heptan-3-yl)pyridin-3-yl)-6-(2-(methylsulfinyl<sulfinyl>)ethoxy)pyrazolo[1,5-a]pyridine-3-carbonitrile

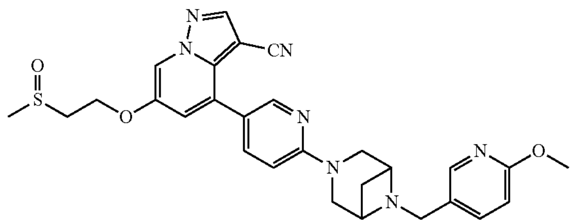

Step 1: 2-(methylthio)ethan-1-ol

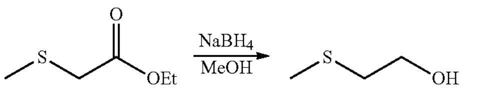

Ethyl 2-(methylthio)acetate (500 mg, 3.7 mmol) was dissolved in 20 mL of MeOH, and $NaBH_4$ (562 mg, 14.8 mmol) was added at 0° C., and the mixture was stirred at room temperature for 0.5 hours. 10 mL of $NH_4Cl$ solution was added thereto, and the mixture was extracted with ethyl acetate (20 mL*3). The organic phase was washed with saturated saline, dried over anhydrous sodium sulfate. The residue was filtered and evaporated to dryness to obtain 2-(methylthio)ethan-1-ol (240 mg, colorless liquid, the yield was 70%).

Step 2: 4-bromo-6-(2-(methylthio)ethoxy)pyrazolo[1,5-a]pyridine-3-carbonitrile

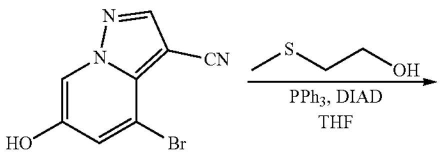

-continued

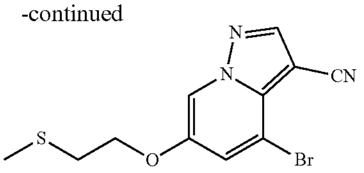

4-Bromo-6-hydroxypyrazolo[1,5-a]pyridine-3-carbonitrile (100 mg, 0.42 mmol) was dissolved in 10 mL of THF; 2-(methylthio)ethan-1-ol (16 mg, 0.5 mmol), triphenylphosphine (165 mg, 0.63 mmol) and DIAD (127 mg, 0.63 mmol) were added and stirred at room temperature overnight. 10 mL of water was added thereto, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 4-bromo-6-(2-(methylthio)ethoxy)pyrazolo[1,5-a]pyridine-3-carbonitrile (69 mg, white solid, the yield was 53%).

MS m/z (ESI): 311.9 $[M+H]^+$.

Step 3: 4-bromo-6-(2-(methylsulfinyl<sulfinyl>)ethoxy)pyrazolo[1,5-a]pyridine-3-carbonitrile

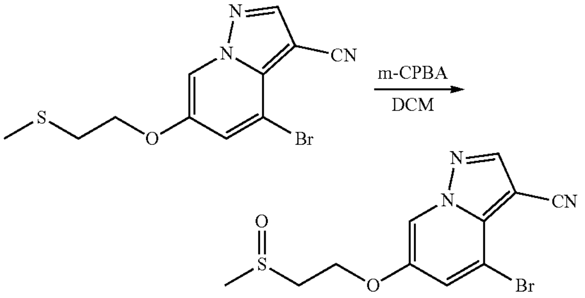

4-Bromo-6-(2-(methylthio)ethoxy)pyrazolo[1,5-a]pyridine-3-carbonitrile (200 mg, 0.64 mmol) was dissolved in 20 mL of DCM; m-chloroperoxybenzoic acid (110 mg, 0.64 mmol) was added thereto, and the mixture was stirred at room temperature for 4 hours, 10 mL of water was added thereto and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 4-bromo-6-(2-(methylsulfinyl<sulfinyl>)ethoxy)pyrazolo[1,5-a]pyridine-3-carbonitrile (189 mg, white solid, the yield was 90%).

MS m/z (ESI): 327.9 $[M+H]^+$.

Step 4: tert-butyl 3-(5-bromopyridin-2-yl)-3,6-diazabicyclo[3.1.1]heptane-6-carboxylate

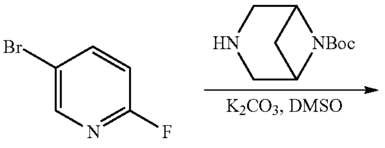

-continued

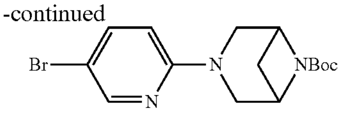

5-Bromo-2-fluoropyridine (500 mg, 2.5 mmol) was dissolved in 20 mL of DMSO; and tert-butyl 3,6-diazabicyclo [3.1.1]heptane-6-carboxylate (489 mg, 2.8 mmol), potassium carbonate (1.7 g, 12.5 mmol) were added thereto, and the mixture was stirred at 90° C. overnight. 10 mL of water was added thereto, and the mixture was extracted with ethyl acetate (20 mL*3). The organic phase was washed with water and saturated saline, dried over anhydrous sodium sulfate. The residue was filtered, evaporated to dryness; and the crude product was separated by column chromatography (eluted with petroleum ether/ethyl acetate=1/1) to obtain tert-butyl 3-(5-bromopyridin-2-yl)-3,6-diazabicyclo[3.1.1] heptane-6-carboxylate (650 mg, white solid, the yield was 3%).

MS m/z (ESI): 354.0 $[M+H]^+$.

Step 5: 3-(5-bromopyridin-2-yl)-3,6-diazabicyclo [3.1.1]heptane

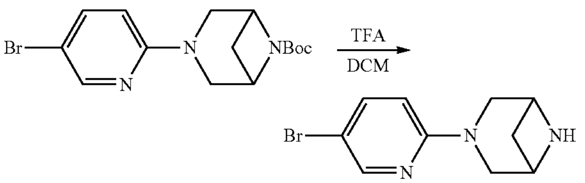

Tert-butyl 3-(5-bromopyridin-2-yl)-3,6-diazabicyclo [3.1.1]heptane-6-carboxylate (100 mg, 0.28 mmol) was dissolved in 3 mL of DCM; and 1 mL of TFA was added thereto, and the mixture was stirred at room temperature for 2 hours. The mixture was then evaporated to dryness, sodium bicarbonate aqueous solution was added to adjust the pH value to basic, and extracted with ethyl acetate (20 mL*3). The organic phase was washed with saturated saline, dried over anhydrous sodium sulfate. The residue was filtered, evaporated to dryness to obtain 3-(5-bromopyridin-2-yl)-3,6-diazabicyclo[3.1.1]heptane (70 mg, white solid, the yield was 99%).

MS m/z (ESI): 254.0 $[M+H]^+$.

Step 6: 3-(5-bromopyridin-2-yl)-6-((6-methoxypyridin-3-yl)methyl)-3,6-diazabicyclo[3.1.1]heptane

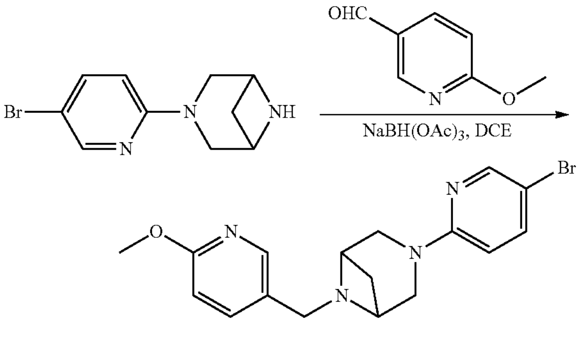

3-(5-Bromopyridin-2-yl)-3,6-diazabicyclo[3.1.1]heptane (70 mg, 0.28 mmol), 6-methoxynicotinaldehyde (113 mg, 0.83 mmol) were dissolved in 10 mL of DCE, $NaBH(OAc)_3$ (176 mg, 0.83 mmol) was added thereto, and the mixture was stirred at room temperature overnight. 10 mL of water was added, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 3-(5-bromopyridin-2-yl)-6-((6-methoxypyridin-3-yl)methyl)-3,6-diazabicyclo[3.1.1]heptane (60 mg, white solid, the yield was 57%).

MS m/z (ESI): 375.0 $[M+H]^+$.

Step 7: 6-(2-(methylsulfinyl<sulfinyl>)ethoxy)-4-(4,4,5,5-tetramethyl-1,3,2-dioxaborolan-2-yl) pyrazolo [1,5-a]pyridine-3-carbonitrile

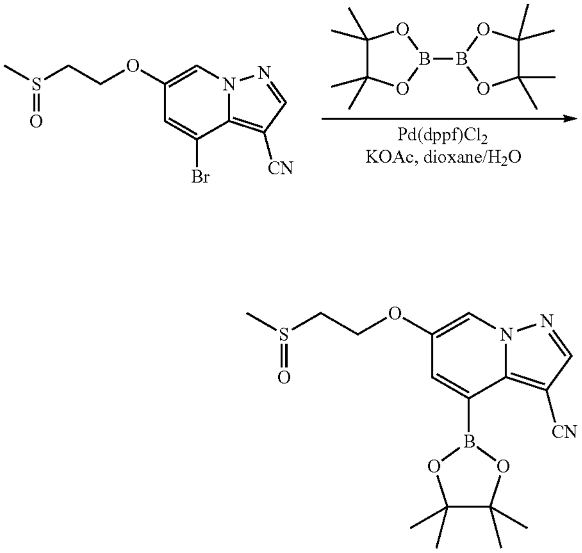

4-Bromo-6-(2-(methylsulfinyl<sulfinyl>)ethoxy)pyrazolo[1,5-a]pyridine-3-carbonitrile (200 mg, 0.6 mmol), bis (pinacolato)diboron (232 mg, 0.91 mmol), $Pd(dppf)Cl_2$ (44 mg, 0.06 mmol) and KOAc (176 mg, 1.8 mmol) were dissolved in dioxane/$H_2O$ (20 mL, v/v=10:1), and the mixture was stirred at 90° C. overnight under the protection of nitrogen. 10 mL of water was added thereto, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 6-(2-(methylsulfinyl<sulfinyl>) ethoxy)-4-(4,4,5,5-tetramethyl-1,3,2-dioxaborolan-2-yl) pyrazolo[1,5-a]pyridine-3-carbonitrile (117 mg, white solid, the yield was 52%).

MS m/z (ESI): 376.1 $[M+H]^+$.

Step 8: 4-(6-(6-((6-methoxypyridin-3-yl)methyl)-3,6-diazabicyclo[3.1.1]heptan-3-yl)pyridin-3-yl)-6-(2-(methylsulfinyl<sulfinyl>)ethoxy)pyrazolo[1,5-a]pyridine-3-carbonitrile

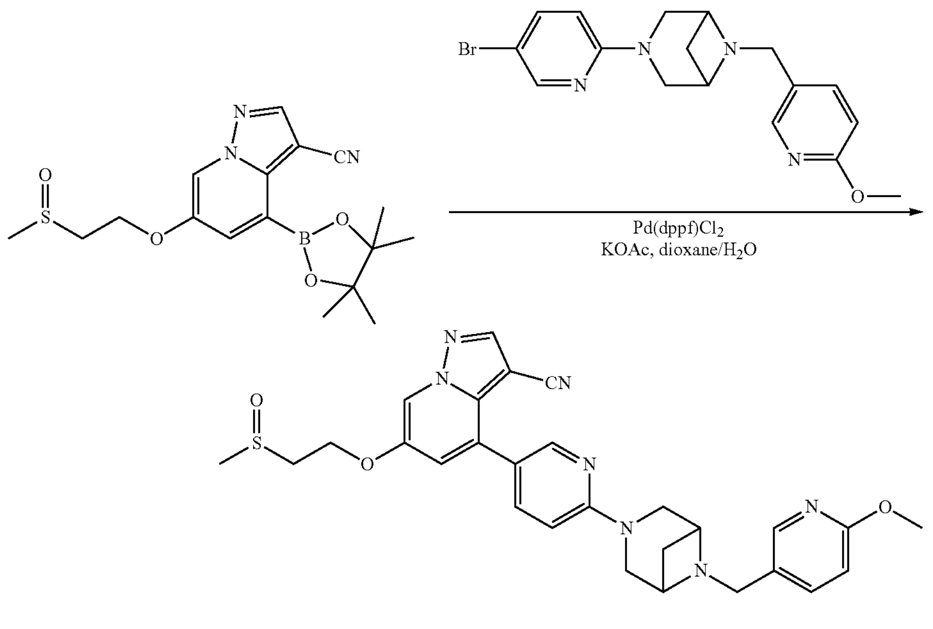

6-(2-(methylsulfinyl<sulfinyl>)ethoxy)-4-(4,4,5,5-tetramethyl-1,3,2-dioxaborolan-2-yl)pyrazolo[1,5-a]pyridine-3-carbonitrile (60 mg, 0.16 mmol), 3-(5-bromopyridin-2-yl)-6-((6-methoxypyridin-3-yl)methyl)-3,6-diazabicyclo[3.1.1]heptane (72 mg, 0.19 mmol), Pd(dppf)$Cl_2$ (15 mg, 0.02 mmol) and KOAc (44 mg, 0.5 mmol) were dissolved in dioxane/$H_2O$ (20 mL, v/v=10:1), and the mixture was stirred at 90° C. overnight under the protection of nitrogen. 10 mL of water was added thereto, and the mixture was extracted with ethyl acetate (20 mL*3). The organic phase was washed with saturated saline, dried over anhydrous sodium sulfate. The residue was filtered and evaporated to dryness, the crude product was prepared by prep-HPLC to obtain 4-(6-(6-((6-methoxypyridin-3-yl)methyl)-3,6-diazabicyclo[3.1.1]heptan-3-yl)pyridin-3-yl)-6-(2-(methylsulfinyl<sulfinyl>)ethoxy)pyrazolo[1,5-a]pyridine-3-carbonitrile (41 mg, white solid, the yield was 48%).

MS m/z (ESI): 544.2 $[M+H]^+$.

$^1$H NMR (400 MHz, DMSO) δ 8.82 (d, J=1.9 Hz, 1H), 8.62 (s, 1H), 8.41 (d, J=2.3 Hz, 1H), 8.07 (d, J=1.9 Hz, 1H), 7.85 (dd, J=8.8, 2.4 Hz, 1H), 7.68 (dd, J=8.5, 2.2 Hz, 1H), 7.32 (d, J=2.0 Hz, 1H), 6.78 (t, J=9.4 Hz, 2H), 4.62-4.44 (m, 2H), 3.82 (s, 3H), 3.73 (d, J=11.6 Hz, 2H), 3.67 (d, J=5.7 Hz, 2H), 3.58-3.52 (m, 2H), 3.50 (s, 2H), 3.13 (dt, J=13.6, 4.4 Hz, 1H), 2.67 (s, 3H), 2.59-2.52 (m, 2H), 1.59 (d, J=8.5 Hz, 1H).

Embodiment 2

4-(6-(6-((6-Methoxypyridin-3-yl)methyl)-3,6-diazabicyclo[3.1.1]heptan-3-yl)pyridin-3-yl)-6-(2-(methylsulfonyl)ethoxy)pyrazolo[1,5-a]pyridine-3-carbonitrile

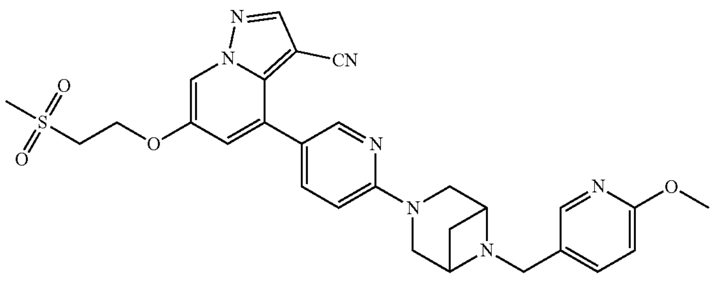

-continued

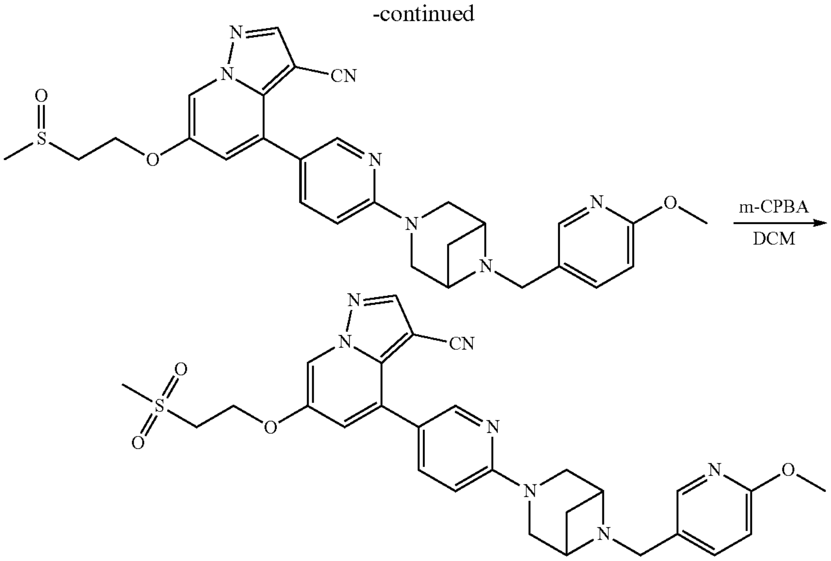

4-(6-(6-((6-Methoxypyridin-3-yl)methyl)-3,6-diazabicyclo[3.1.1]heptan-3-yl)pyridin-3-yl)-6-(2-(methylsulfinyl<sulfinyl>)ethoxy)pyrazolo[1,5-a]pyridine-3-carbonitrile was used as raw material, 4-(6-(6-((6-methoxypyridin-3-yl)methyl)-3,6-diazabicyclo[3.1.1]heptan-3-yl)pyridin-3-yl)-6-(2-(methylsulfonyl)ethoxy)pyrazolo[1,5-a]pyridine-3-carbonitrile (45 mg, white solid, the yield was 70%) was obtained with reference to step 3 of embodiment 1.

MS m/z (ESI): 560.2 $[M+H]^+$.

Embodiment 3

4-(6-(6-((6-Methoxypyridin-3-yl)methyl)-3,6-diazabicyclo[3.1.1]heptan-3-yl)pyridin-3-yl)-6-(2-(S-methylsulfonimidoyl)ethoxy)pyrazolo[1,5-a]pyridine-3-carbonitrile

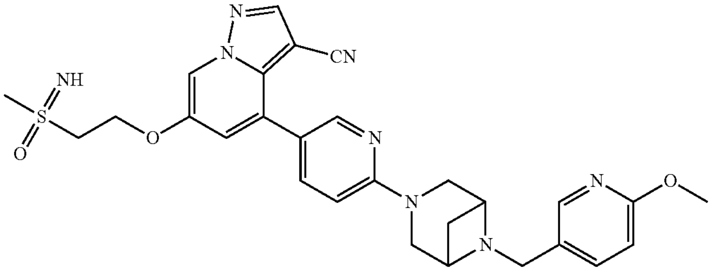

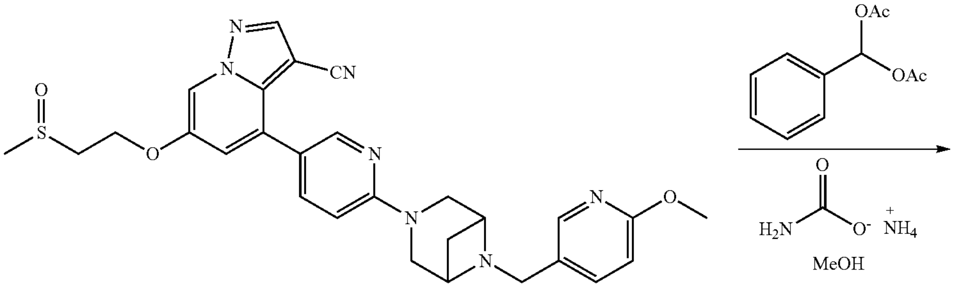

-continued

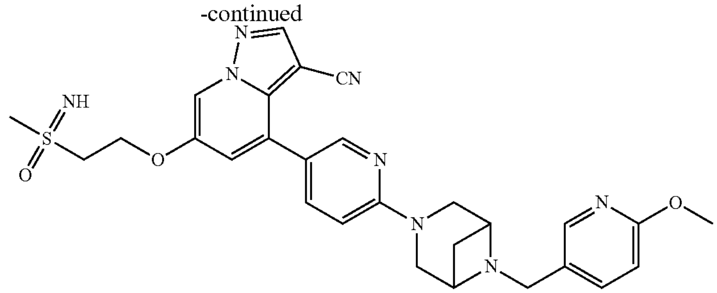

4-(6-(6-((6-Methoxypyridin-3-yl)methyl)-3,6-diazabicyclo[3.1.1]heptan-3-yl)pyridin-3-yl)-6-(2-(methylsulfonyl)ethoxy)pyrazolo[1,5-a]pyridine-3-carbonitrile (60 mg, 0.11 mmol) was dissolved in 5 mL of methanol; and ammonium carbamate (17 mg, 0.22 mmol), iodobenzene diacetate (70 mg, 0.22 mmol) were added thereto, and the reaction was carried out at room temperature for 2 hours. 10 mL of water was added thereto, and the mixture was extracted with ethyl acetate (10 mL*3). The organic phase was washed with saturated saline, dried over anhydrous sodium sulfate. The residue was filtered and evaporated to dryness, the crude product was prepared by prep-HPLC to obtain 4-(6-(6-((6-methoxypyridin-3-yl)methyl)-3,6-diazabicyclo[3.1.1]heptan-3-yl)pyridin-3-yl)-6-(2-(S-methylsulfonimidoyl)ethoxy)pyrazolo[1,5-a]pyridine-3-carbonitrile (25 mg, white solid, the yield was 45%).

MS m/z (ESI): 559.2 $[M+H]^+$.

Embodiment 4

4-(6-(6-((6-Methoxypyridin-3-yl)methyl)-3,6-diazabicyclo[3.1.1]heptan-3-yl)pyridin-3-yl)-6-(3-(methylsulfinyl<sulfinyl>)propoxy)pyrazolo[1,5-a]pyridine-3-carbonitrile

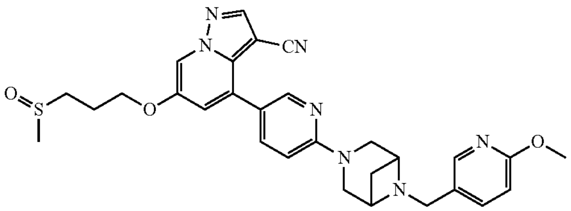 [SMILES: COc1ccc(CN2C3CC2CN(c2ccc(-c4cc(OCCCS(C)=O)cn5ncc(C#N)c45)cn2)C3)cn1]

The title compound (35 mg, white solid, 40%) was obtained by using ethyl 3-(methylthio)propionate as raw material with reference to embodiment 1.

MS m/z (ESI): 558.2 $[M+H]^+$.

Embodiment 5

4-(6-(6-((6-Methoxypyridin-3-yl)methyl)-3,6-diazabicyclo[3.1.1]heptan-3-yl)pyridin-3-yl)-6-(3-(methylsulfonyl)propoxy)pyrazolo[1,5-a]pyridine-3-carbonitrile

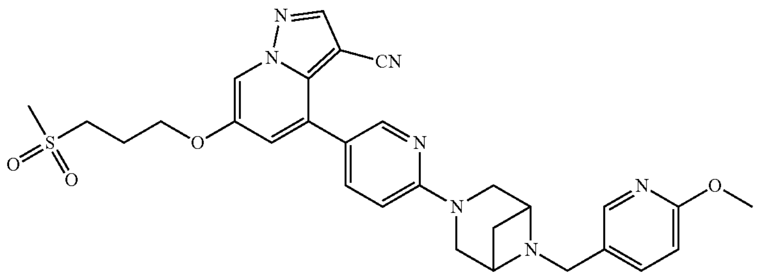

-continued

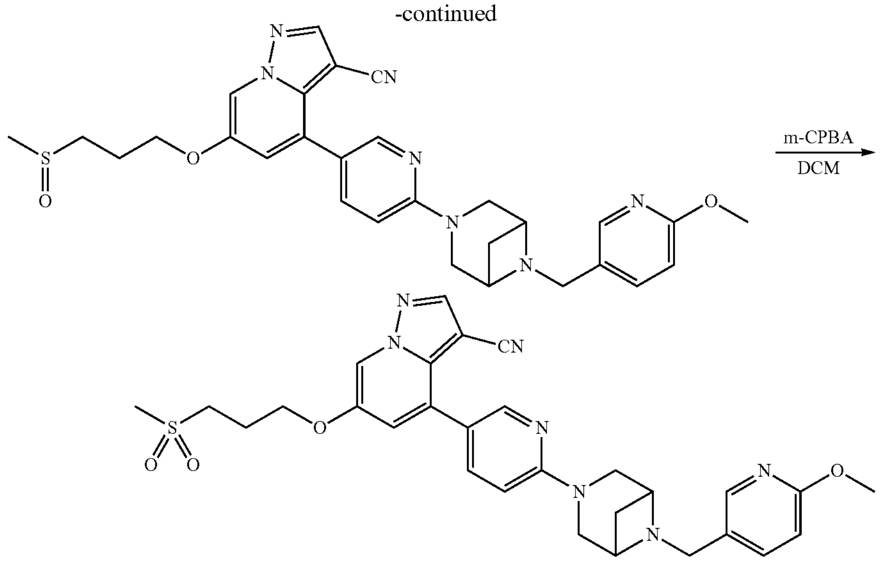

4-(6-(6-((6-Methoxypyridin-3-yl)methyl)-3,6-diazabicyclo[3.1.1]heptan-3-yl)pyridin-3-yl)-6-(3-(methylsulfinyl<sulfinyl>)propoxy)pyrazolo[1,5-a]pyridine-3-carbonitrile was used as raw material, 4-(6-(6-((6-methoxypyridin-3-yl)methyl)-3,6-diazabicyclo[3.1.1]heptan-3-yl)pyridin-3-yl)-6-(3-(methylsulfonyl)propoxy)pyrazolo[1,5-a]pyridine-3-carbonitrile was obtained with reference to embodiment 2 (32 mg, white solid, the yield was 56%).

MS m/z (ESI): 574.2 $[M+H]^+$.

Embodiment 6

4-(6-(6-((6-Methoxypyridin-3-yl)methyl)-3,6-diazabicyclo[3.1.1]heptan-3-yl)pyridin-3-yl)-6-(3-(S-methylsulfonimidoyl)propoxy)pyrazolo[1,5-a]pyridine-3-carbonitrile

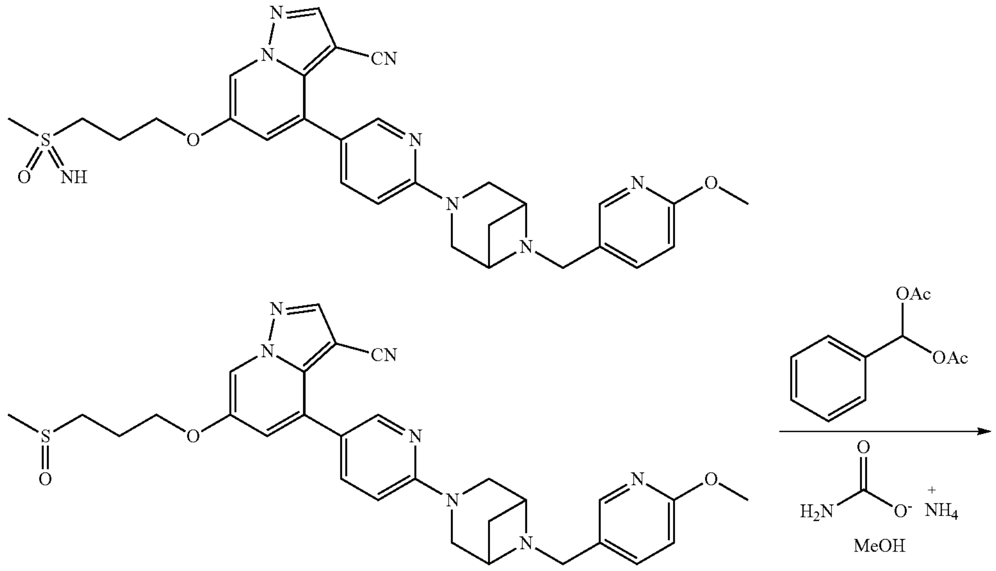

-continued

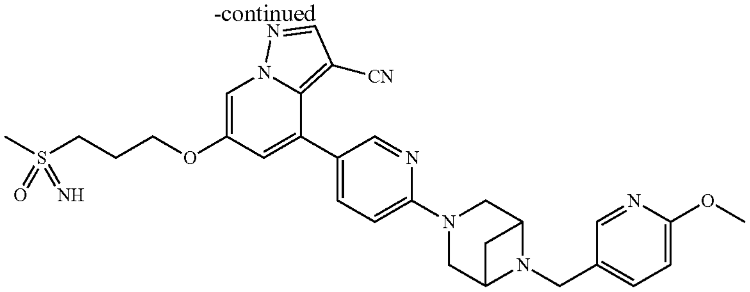

4-(6-(6-((6-Methoxypyridin-3-yl)methyl)-3,6-diazabicyclo[3.1.1]heptan-3-yl)pyridin-3-yl)-6-(3-(methylsulfinyl<sulfinyl>)propoxy)pyrazolo[1,5-a]pyridine-3-carbonitrile was used as raw material, 4-(6-(6-((6-methoxypyridin-3-yl)methyl)-3,6-diazabicyclo[3.1.1]heptan-3-yl)pyridin-3-yl)-6-(3-(S-methylsulfonimidoyl)propoxy)pyrazolo[1,5-a]pyridine-3-carbonitrile was obtained with reference to embodiment 3 (28 mg, white solid, the yield was 44%).

MS m/z (ESI): 573.2 $[M+H]^+$.

Embodiment 7

6-((2-Hydroxy-2-methylpropyl)thio)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

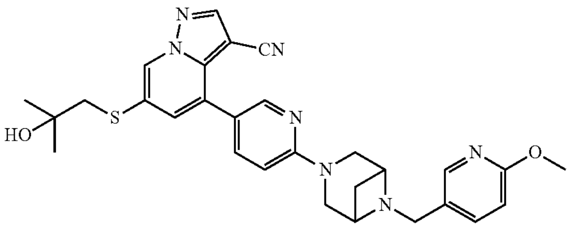 [SMILES: COc1ccc(CN2C3CC2CN(c2ccc(-c4cc(SCC(C)(C)O)cn5ncc(C#N)c45)cn2)C3)cn1]

Step 1: 4-bromo-3-cyanopyrazolo[1,5-a]pyridin-6-yl trifluoromethanesulfonate

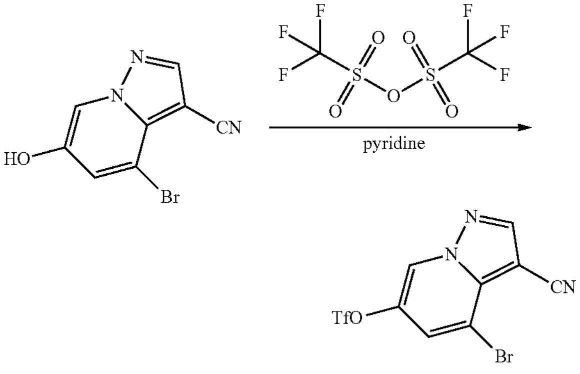

4-Bromo-6-hydroxypyrazolo[1,5-a]pyridine-3-carbonitrile (200 mg, 0.84 mmol), dichloromethane (5 mL) and pyridine (1 mL) were added to a 25 mL single-neck flask sequentially, after the reaction mixture was stirred for 2 minutes, trifluoromethanesulfonic anhydride (355 mg, 1.26 mmol) was slowly added thereto dropwise. The reaction mixture was stirred at room temperature for 12 hours, the reaction mixture was concentrated, dissolved in ethyl acetate (10 mL) and washed with saturated saline (5 mL×3), and the organic phase was dried over anhydrous sodium sulfate, filtered and evaporated to dryness. The crude product was purified by column chromatography (petroleum ether/ethyl acetate: 1/1) to obtain 4-bromo-3-cyanopyrazolo[1,5-a]pyridin-6-yl trifluoromethanesulfonate (280 mg, light yellow solid, yield: 90.0%).

MS m/z (ESI): 370.0$[M+H]^+$, 372.0$[M+H+2]^+$.

Step 2: 4-bromo-6-((2-hydroxy-2-methylpropyl)thio)pyrazolo[1,5-a]pyridine-3-carbonitrile

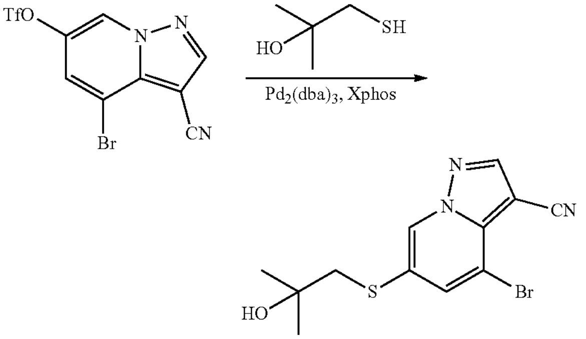

4-Bromo-3-cyanopyrazolo[1,5-a]pyridin-6-yl trifluoromethanesulfonate (280 mg, 0.75 mmol), 1-mercapto-2-methylpropan-2-ol (80 mg, 0.75 mmol), tris(dibenzylideneacetone)dipalladium (68 mg, 0.075 mmol), 2-dicyclohexylphosphino-2',4',6'-triisopropylbiphenyl (71 mg, 0.15 mmol), diisopropylethylamine (193 mg, 1.5 mmol) and dioxane (10 mL) were added to a 25 mL three-necked flask sequentially, and the reaction mixture was replaced with nitrogen 5 times. The reaction mixture was heated to 85° C. under the protection of nitrogen, and the mixture was stirred for 5 hours and then cooled to room temperature; the reaction mixture was concentrated, dissolved in ethyl acetate (10 mL) and washed with saturated saline (5 mL×3), and the organic phase was dried over anhydrous sodium sulfate, filtered and evaporated to dryness. The crude product was separated by column chromatography (dichloromethane/methanol: 30/1) and purified to obtain the product of 4-bromo-6-((2-hydroxy-2-methylpropyl)thio)pyrazolo[1,5-a]pyridine-3-carbonitrile (140 mg, white solid, the yield: 56.6%).

MS m/z (ESI): 326.0$[M+H]^+$, 328.0$[M+H+2]^+$.

Step 3: 6-((2-hydroxy-2-methylpropyl)thio)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

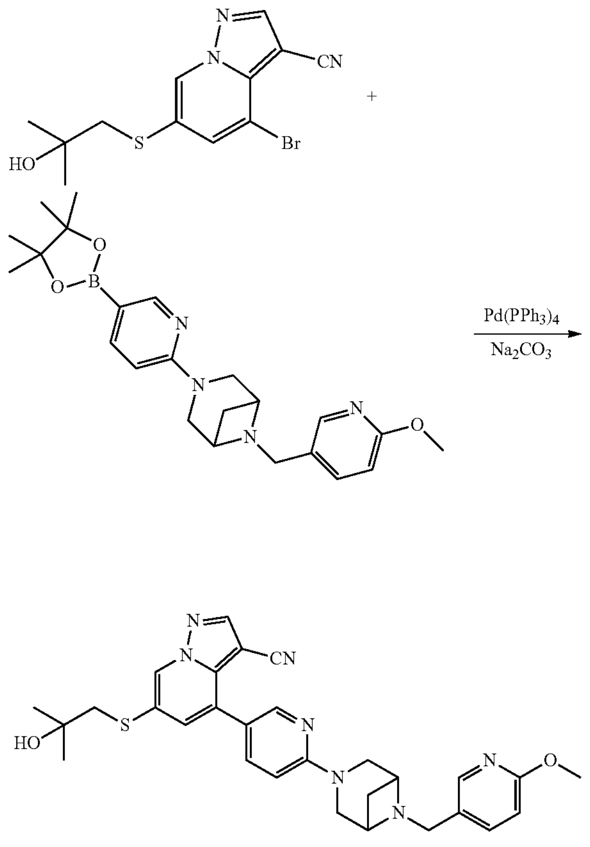

7

4-Bromo-6-((2-hydroxy-2-methylpropyl)thio)pyrazolo[1,5-a]pyridine-3-carbonitrile (50 mg, 0.15 mmol), 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane (64 mg, 0.15 mmol), tetrakis(triphenylphosphine)palladium (17 mg, 0.015 mmol), sodium carbonate (48 mg, 0.45 mmol), and dioxane (5 mL) and water (1 mL) were added to a 25 mL three-necked flask sequentially, and the reaction mixture was replaced with nitrogen 5 times. The reaction mixture was heated to 85° C. under the protection of nitrogen, and the mixture was stirred for 5 hours and then cooled to room temperature; the reaction mixture was concentrated, dissolved in ethyl acetate (10 mL) and washed with saturated saline (5 mL×3), and the organic phase was dried over anhydrous sodium sulfate, filtered and evaporated to dryness. The crude product was purified by prep-HPLC to obtain 6-((2-hydroxy-2-methylpropyl)thio)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (25 mg, white solid, yield: 30.1%).

MS m/z (ESI): 542.2[M+H]$^+$.

Embodiment 8

6-((2-Hydroxy-2-methylpropyl)thio)-4-(6-(4-((6-methoxypyridin-3-yl)oxo)piperidin-1-yl)pyridin-3-yl)pyrazolo[1,5-a]pyridine-3-carbonitrile

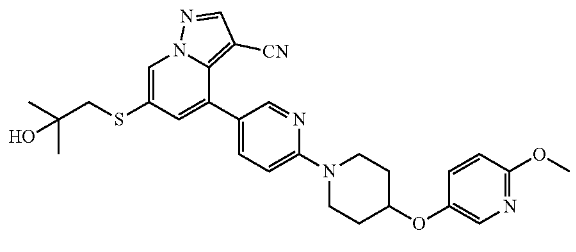 [SMILES: COc1ccc(OC2CCN(c3ccc(-c4cc(SCC(C)(C)O)cn5ncc(C#N)c45)cn3)CC2)cn1]

Step 1: 4-(6-fluoropyridin-3-yl)-6-((2-hydroxy-2-methylpropyl)thio)pyrazolo[1,5-a]pyridine-3-carbonitrile

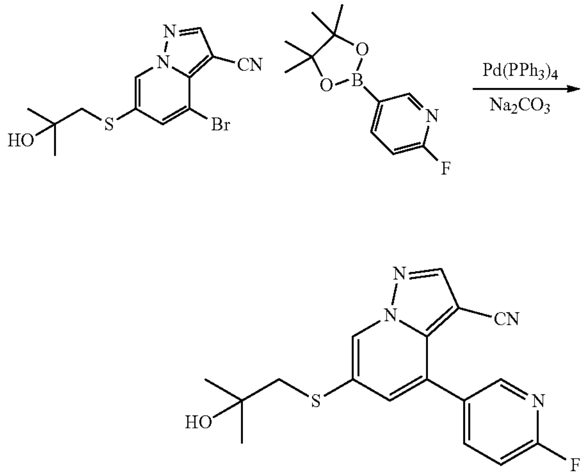

4-Bromo-6-((2-hydroxy-2-methylpropyl)thio)pyrazolo[1,5-a]pyridine-3-carbonitrile (100 mg, 0.30 mmol), 2-fluoro-5-(4,4,5,5-tetramethyl-1,3,2-dioxaborolan-2-yl)pyridine (68 mg, 0.30 mmol), tetrakis(triphenylphosphine)palladium (27 mg, 0.03 mmol), sodium carbonate (97 mg, 0.09 mmol), and dioxane (5 mL) and water (1 mL) were added to a 25 mL three-necked flask sequentially, and the reaction mixture was replaced with nitrogen 5 times. The reaction mixture was heated to 85° C. under the protection of nitrogen, and the mixture was stirred for 5 hours and then cooled to room temperature; the reaction mixture was concentrated, dissolved in ethyl acetate (10 mL) and washed with saturated saline (5 mL×3), and the organic phase was dried over anhydrous sodium sulfate, filtered and evaporated to dryness. The crude product was separated by column chromatography (dichloromethane/methanol: 30/1) and purified to obtain 4-(6-fluoropyridin-3-yl)-6-((2-hydroxy-2-methylpropyl)thio)pyrazolo[1,5-a]pyridine-3-carbonitrile (85 mg, light yellow solid, yield: 80.9%).

MS m/z (ESI): 343.1[M+H]$^+$.

Step 2: 6-((2-hydroxy-2-methylpropyl)thio)-4-(6-(4-((6-methoxypyridin-3-yl)oxo)piperidin-1-yl)pyridin-3-yl)pyrazolo[1,5-a]pyridine-3-carbonitrile

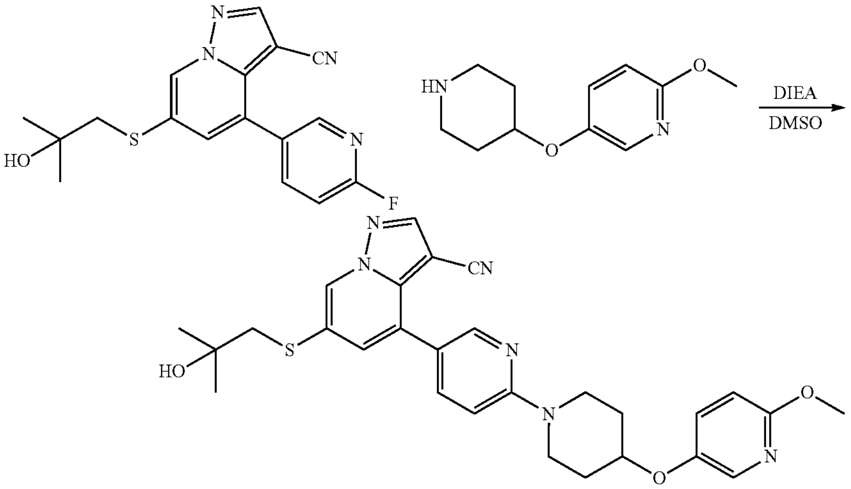

8

4-(6-Fluoropyridin-3-yl)-6-((2-hydroxy-2-methylpropyl)thio)pyrazolo[1,5-a]pyridine-3-carbonitrile (85 mg, 0.25 mmol), 2-methoxy-5-(piperidin-4-oxy)pyridine (52 mg, 0.25 mmol), diisopropylethylamine (65 mg, 0.50 mmol) and dimethyl sulfoxide (2 mL) were added to a 25 mL three-necked flask sequentially. The reaction mixture was heated to 90° C. under the protection of nitrogen, and the mixture was stirred for 48 hours and then cooled to room temperature; the reaction mixture was concentrated, dissolved in ethyl acetate (10 mL) and washed with saturated saline (5 mL×3), and the organic phase was dried over anhydrous sodium sulfate, filtered and evaporated to dryness. The crude product was purified by prep-HPLC to obtain product 6-((2-hydroxy-2-methylpropyl)thio)-4-(6-(4-((6-methoxypyridin-3-yl)oxo)piperidin-1-yl)pyridin-3-yl)pyrazolo[1,5-a]pyridine-3-carbonitrile (60 mg, white solid, yield: 45.5%).

MS m/z (ESI): 531.2[M+H]$^+$.

Embodiment 9

6-(2-Hydroxy-2-methylpropylsulfonimidoyl)-4-(6-(4-(pyridin-2-oxy)piperidin-1-yl)pyridin-3-yl)pyrazolo[1,5-a]pyridine-3-carbonitrile

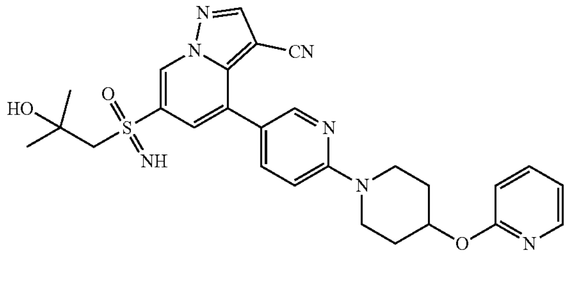 [SMILES: CC(C)(O)CS(=N)(=O)c1cc(-c2ccc(N3CCC(Oc4ccccn4)CC3)nc2)c2c(C#N)cnn2c1]

Step 1: 4-bromo-6-((2-hydroxy-2-methylpropyl)sulfinyl)pyrazolo[1,5-a]pyridine-3-carbonitrile

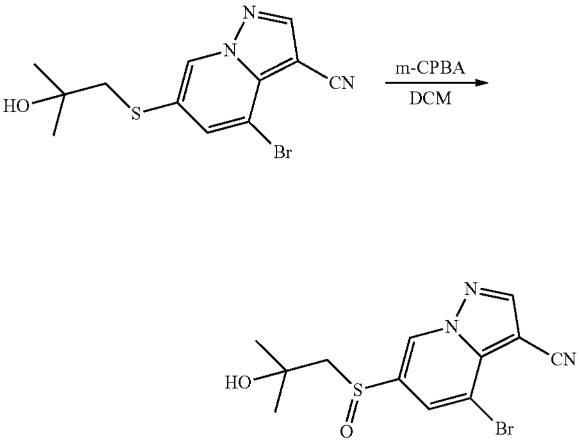

4-Bromo-6-((2-hydroxy-2-methylpropyl)thio)pyrazolo[1,5-a]pyridine-3-carbonitrile (100 mg, 0.30 mmol) was dissolved in dichloromethane (5 mL), cooled to −20° C. in a dry ice/ethyl acetate bath, and m-chloroperoxybenzoic acid (51 mg, 0.3 mmol) was added thereto in batches; after the addition was completed, the dry ice bath was removed, the mixture was warmed up to room temperature naturally and stirred for 30 minutes. Saturated sodium carbonate solution (5 mL) was added to the reaction mixture, the mixture was then extracted with ethyl acetate (5 mL×2); and the organic phases were mixed, washed with saturated sodium chloride solution (5 mL×2), dried over anhydrous sodium sulfate, and concentrated under reduced pressure to obtain 4-bromo-6-((2-hydroxy-2-methylpropyl)sulfinyl)pyrazolo[1,5-a]pyridine-3-carbonitrile (95 mg, 90.5%).

MS m/z (ESI): 342.0 [M+H]$^+$, 344.0[M+2+H]$^+$.

Step 2: 4-bromo-6-(2-hydroxy-2-methylpropylsulfonimidoyl)pyrazolo[1,5-a]pyridine-3-carbonitrile

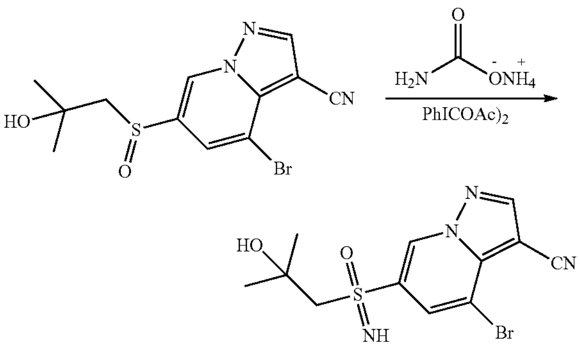

4-Bromo-6-((2-hydroxy-2-methylpropyl)thionyl)pyrazolo[1,5-a]pyridine-3-carbonitrile (95 mg, 0.28 mmol) was dissolved in methanol (5 mL); then ammonium carbamate (108 mg, 1.39 mmol) and iodobenzene diacetate (268 mg, 0.83 mmol) were added thereto sequentially, and the mixture was stirred at room temperature for 1 hour. The reaction was stopped, the reaction was quenched with water (5 mL), extracted with ethyl acetate (5 mL×2), and the organic phases were combined. The organic phase was washed with saturated sodium chloride (5 mL), dried over anhydrous sodium sulfate, filtered and concentrated under reduced pressure to obtain 4-bromo-6-(2-hydroxy-2-methylpropylsulfonimidoyl)pyrazolo[1,5-a]pyridine-3-carbonitrile (90 mg, 90.7%).

MS m/z (ESI): 357.0 $[M+H]^+$, 359.0$[M+2+H]^+$.

Step 3: 4-(6-fluoropyridin-3-yl)-6-(2-hydroxy-2-methylpropylsulfonimidoyl)pyrazolo[1,5-a]pyridine-3-carbonitrile

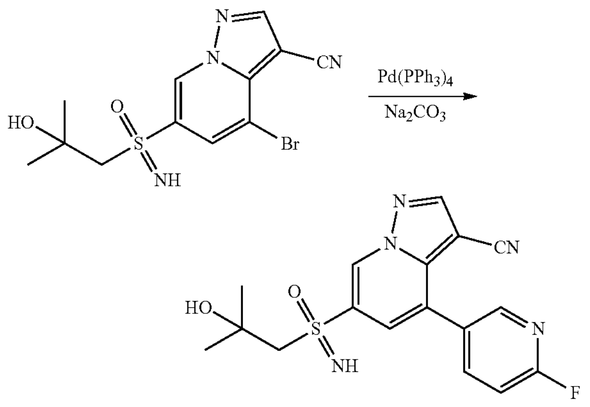

The product 4-(6-fluoropyridin-3-yl)-6-(2-hydroxy-2-methylpropylsulfonimidoyl)pyrazolo[1,5-a]pyridine-3-carbonitrile (95 mg, white solid, the yield was 95.6%) was obtained by using 4-bromo-6-(2-hydroxy-2-methylpropylsulfonimidoyl)pyrazolo[1,5-a]pyridine-3-carbonitrile as raw material with reference to step 1 of embodiment 8.

MS m/z (ESI): 374.1$[M+H]^+$.

Step 4: 6-(2-hydroxy-2-methylpropylsulfonimidoyl)-4-(6-(4-(pyridin-2-oxy)piperidin-1-yl)pyridin-3-yl)pyrazolo[1,5-a]pyridine-3-carbonitrile

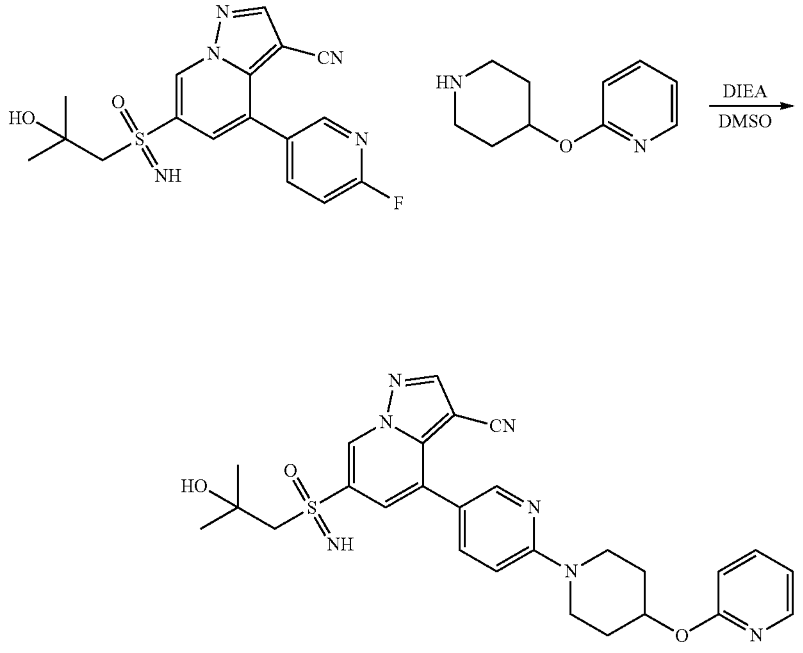

9

The product 6-(2-hydroxy-2-methylpropylsulfonimidyl)-4-(6-(4-(pyridin-2-oxy)piperidin-1-yl)pyridin-3-yl)pyrazolo[1,5-a]pyridine-3-carbonitrile (30 mg, white solid, yield was 22.0%) was obtained by using 4-(6-fluoropyridin-3-yl)-6-(2-hydroxy-2-methylpropylsulfonimidyl)pyrazolo[1,5-a]pyridine-3-carbonitrile as raw material with reference to step 2 of embodiment 8.

MS m/z (ESI): 532.2 [M+H]$^+$.

Embodiment 10

6-(Ethylsulfonimidoyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

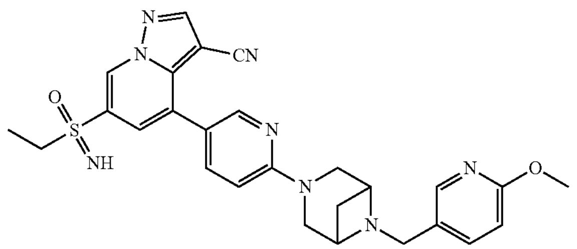 [SMILES: CCS(=N)(=O)c1cc(-c2ccc(N3CC4CC(C3)N4Cc3ccc(OC)nc3)nc2)c2c(C#N)cnn2c1]

Step 1: 4-bromo-6-(ethylthio)pyrazolo[1,5-a]pyridine-3-carbonitrile

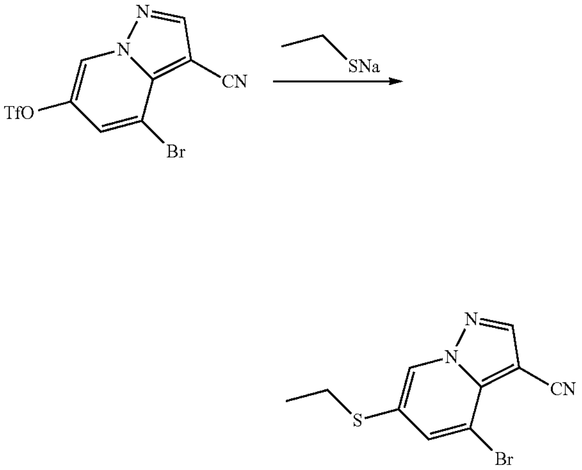

4-Bromo-3-cyanopyrazolo[1,5-a]pyridin-6-yl trifluoromethanesulfonate (200 mg, 0.54 mmol), sodium ethanethiolate (90 mg, 1.08 mmol) and dioxane (5 mL) were added to a 25 mL three-necked flask sequentially. The reaction mixture was heated to 85° C. under the protection of nitrogen, and the mixture was stirred for 5 hours and then cooled to room temperature; the reaction mixture was concentrated, dissolved in ethyl acetate (10 mL) and washed with saturated saline (5 mL×3), and the organic phase was dried over anhydrous sodium sulfate, filtered and evaporated to dryness. The crude product was separated by column chromatography (dichloromethane/methanol: 30/1) and purified to obtain 4-bromo-6-(ethylthio)pyrazolo[1,5-a]pyridine-3-carbonitrile (120 mg, white solid, yield: 78.7%).

MS m/z (ESI): 282.0[M+H]$^+$, 284.0[M+H+2]*.

Step 2: 4-bromo-6-(ethylsulfinyl<sulfinyl>)pyrazolo[1,5-a]pyridine-3-carbonitrile

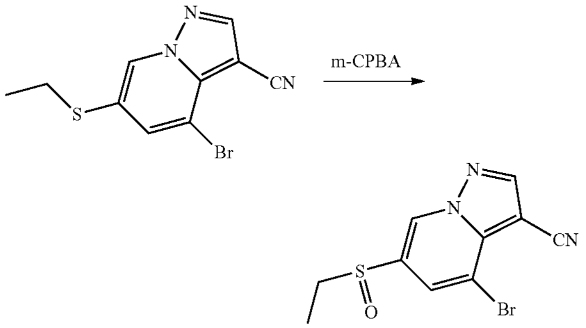

The product 4-bromo-6-(ethylsulfinyl<sulfinyl>)pyrazolo[1,5-a]pyridine-3-carbonitrile (120 mg, white solid, the yield was 96.6%) was obtained by using 4-bromo-6-(ethylthio)pyrazolo[1,5-a]pyridine-3-carbonitrile as raw material with reference to step 1 of embodiment 9.

MS m/z (ESI): 298.0[M+H]$^+$, 300.0[M+H+2]*.

Step 3: 4-bromo-6-(ethylsulfonimidoyl)pyrazolo[1,5-a]pyridine-3-carbonitrile

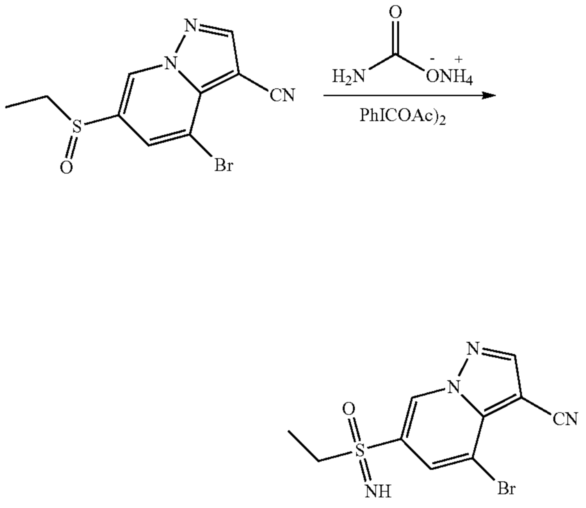

The product 4-bromo-6-(ethylsulfonimidoyl)pyrazolo[1,5-a]pyridine-3-carbonitrile (120 mg, white solid, the yield was 95.9%) was obtained by using 4-bromo-6-(ethylsulfinyl<sulfinyl>)pyrazolo[1,5-a]pyridine-3-carbonitrile as raw material with reference to step 2 of embodiment 9.

MS m/z (ESI): 313.0[M+H]$^+$, 315.0[M+H+2]$^+$.

Step 4: 6-(ethylsulfonimidoyl)-4-(6-(6-((6-methoxy-pyridin-3-yl)methyl)-3,6-diazabicyclo[3.1.1]heptan-3-yl)pyridin-3-yl)pyrazolo[1,5-a]pyridine-3-carbonitrile

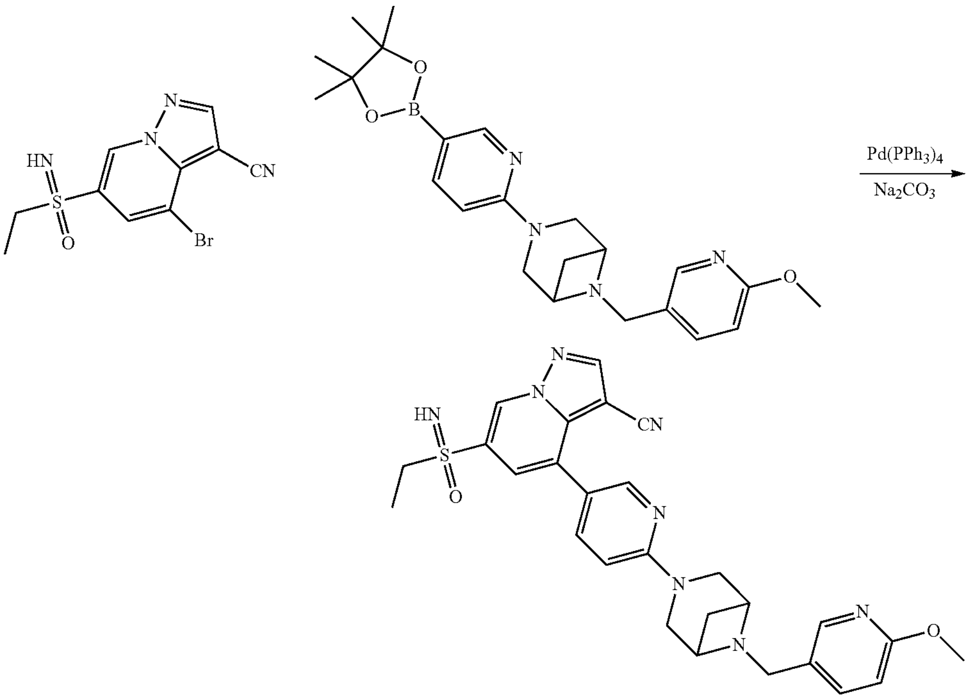

10

The product 6-(ethylsulfonimidoyl)-4-(6-(6-((6-methoxy-pyridin-3-yl)methyl)-3,6-diazabicyclo[3.1.1]heptan-3-yl)pyridin-3-yl)pyrazolo[1,5-a]pyridine-3-carbonitrile (45 mg, white solid, yield was 22.2%) was obtained by using 4-bromo-6-(ethylsulfonimidoyl)pyrazolo[1,5-a]pyridine-3-carbonitrile as raw material with reference to step 3 of embodiment 7.

MS m/z (ESI): 529.2[M+H]$^+$.

Embodiment 11

6-(2-Hydroxy-2-methylpropoxy)-4-(6-(6-((6-methoxypyridin-3-yl)methyl)-3,6-diazabicyclo[3.1.1]heptan-3-yl)pyridin-3-yl)-7-methylpyrazolo[1,5-a]pyridine-3-carbonitrile

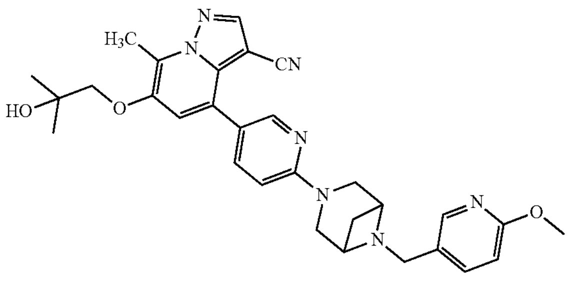 [SMILES: COc1ccc(CN2C3CC2CN(c2ccc(-c4cc(OCC(C)(C)O)c(C)n5ncc(C#N)c45)cn2)C3)cn1]

Step 1: 5-bromo-3-methoxy-2-methylpyridine

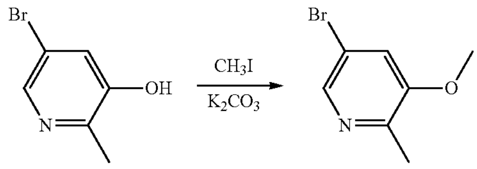

5-Bromo-2-methylpyridin-3-ol (10 g, 53.2 mmol) was dissolved in acetonitrile (50 mL), then potassium carbonate (14.7 g, 106.4 mmol) was added thereto and iodomethane (22.66 g, 160 mmol) was added dropwise, then the reaction mixture was stirred at 80° C. for 16 hours; the reaction mixture was cooled to room temperature, concentrated under reduced pressure to dryness, and purified by layer-by-layer separation (petroleum ether/ethyl acetate=15:1) to obtain light yellow solid 5-bromo-3-methoxy-2-methylpyridine (5 g, yield: 46.7%).

$^1$H NMR (400 MHz, $CDCl_3$) δ 8.14 (d, J=1.6 Hz, 1H), 7.22 (d, J=1.4 Hz, 1H), 3.84 (s, 3H), 2.42 (s, 3H).

MS m/z (ESI): 202.0 [M+H]$^+$.

Step 2: 2,4,6-trimethylbenzenesulfonic acid 1-amino-5-bromo-3-methoxy-2-methylpyridin-1-ium

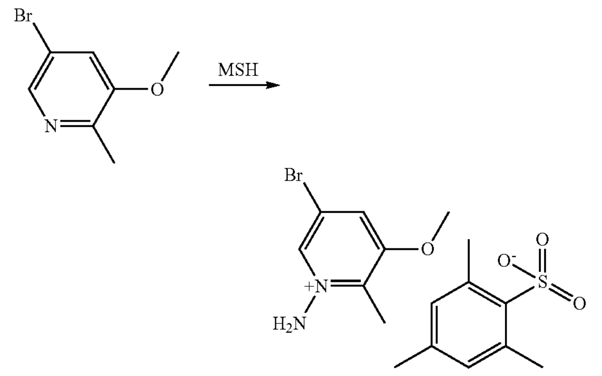

5-Bromo-3-methoxy-2-methylpyridine (5 g, 24.75 mmol) was added to a solution of 2-[(aminooxy)sulfonyl]-1,3,5-trimethylbenzene (5.32 g, 24.75 mmol) in dichloromethane (50 mL) at 0° C. in batches, then the mixture was stirred at 0° C. for 1.5 hours; methyl tert-butyl ether (30 mL) was added to the reaction mixture, and the mixture was slurried for 15 min, then filtered and the filter cake was dried to obtain white solid 2,4,6-trimethylbenzenesulfonic acid 1-amino-5-bromo-3-methoxy-2-methylpyridine-1-ium (9 g, yield: 87.3%).

Step 3: 4-bromo-6-methoxy-7-methylpyrazolo[1,5-a]pyridine-3-carbonitrile

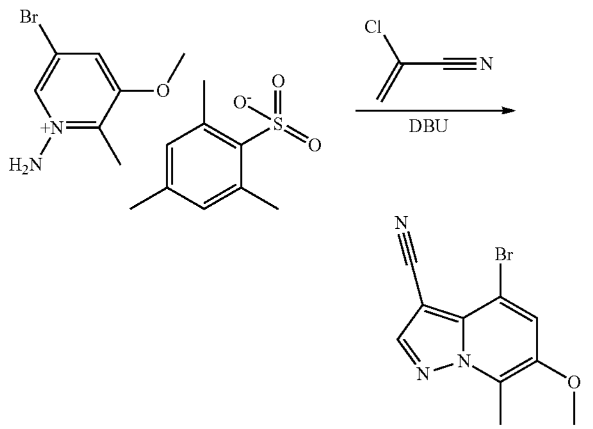

1.8-Diazabicyclo[5.4.0]undec-7-ene (6.6 g, 43.2 mmol) was added to a solution of 2,4,6-trimethylbenzenesulfonic acid 1-amino-5-bromo-3-methoxy-2-methylpyridine-1-ium (9 g, 21.6 mmol) and 2-chloroacrylonitrile (2.8 g, 32.37 mmol) in dichloromethane (100 mL) at 0° C. in batches, then the mixture was warmed up to room temperature and stirred for 24 hours, methyl tert-butyl ether (50 mL) was added to the reaction mixture, and the mixture was slurried at room temperature for 15 min, then filtered and the filter cake was dried to obtain light yellow solid 4-bromo-6-methoxy-7-methylpyrazolo[1,5-a]pyridine-3-carbonitrile (2 g, yield: 35%).

MS m/z (ESI): 266.0 $[M+H]^+$.

Step 4: 4-bromo-6-hydroxy-7-methylpyrazolo[1,5-a]pyridine-3-carbonitrile

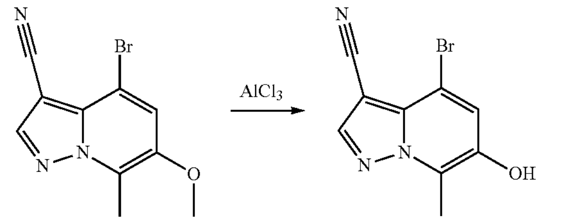

Aluminum trichloride (2 g, 15.1 mmol) was added to a solution of 4-bromo-6-methoxy-7-methylpyrazolo[1,5-a]pyridine-3-carbonitrile (2 g, 7.55 mmol) in 1.2-dichloroethane (20 mL) in batches, then the mixture was stirred at 80° C. for 2 hours, cooled to room temperature, quenched with sodium sulfate decahydrate, filtered, and the filter cake was washed with dichloromethane, the filtrate was washed with saturated saline; the organic phase was dried over anhydrous sodium sulfate, filtered, and the filtrate was concentrated under reduced pressure to dryness to obtain black solid 4-bromo-6-hydroxy-7-methylpyrazolo[1,5-a]pyridine-3-carbonitrile (1.5 g, yield: 79%).

MS m/z (ESI): 249.7 $[M-H]^+$.

Step 5: 4-bromo-6-(2-hydroxy-2-methylpropoxy)-7-methylpyrazolo[1,5-a]pyridine-3-carbonitril

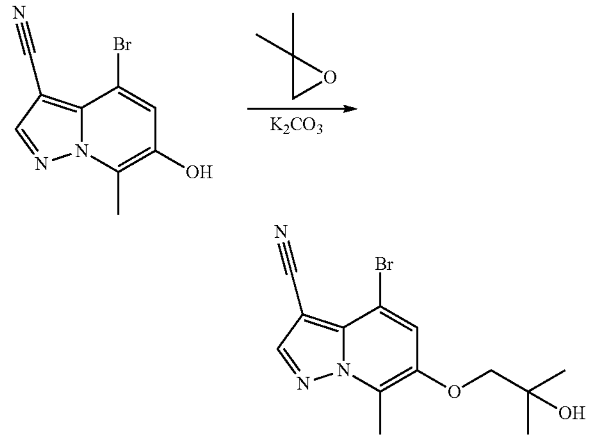

2,2-Dimethyloxirane (857 mg, 11.9 mmol) was added to a solution of 4-bromo-6-hydroxy-7-methylpyrazolo[1,5-a]pyridine-3-carbonitrile (1.5 g, 5.95 mmol), potassium carbonate (1.6 g, 11.9 mmol) and acetonitrile (10 mL), and then the reaction mixture was stirred at 80° C. for 16 hours; the reaction mixture was concentrated under reduced pressure to dryness, separated by column chromatography (dichloromethane/methanol=10:1) to obtain colorless oil 4-bromo-6-(2-hydroxy-2-methylpropoxy)-7-methylpyrazolo[1,5-a]pyridine-3-carbonitrile (1.4 g, yield: 74%).

MS m/z (ESI): 324.0 $[M+H]^+$.

Step 6: 4-(6-fluoropyridin-3-yl)-6-(2-hydroxy-2-methylpropoxy)-7-methylpyrazolo[1,5-a]pyridine-3-carbonitrile

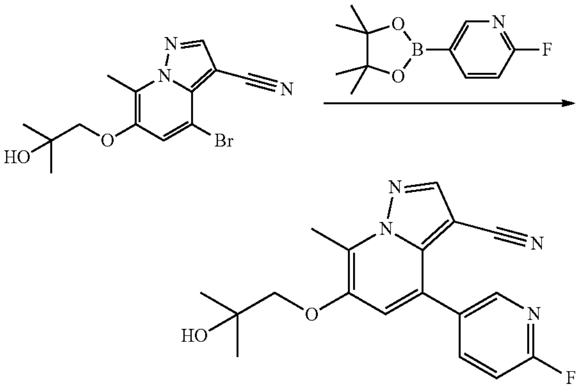

1,1'-Bis(diphenylphosphino)ferrocene-palladium(II)dichloride dichloromethane complex (178 mg, 0.22 mmol) was added to a mixed solution of 4-bromo-6-(2-hydroxy-2-methylpropoxy)-7-methylpyrazolo[1,5-a]pyridine-3-carbonitrile (1.4 g, 4.32 mmol), 2-fluoro-5-(4,4,5,5-tetramethyl-1,3,2-dioxaborolan-2-yl)pyridine (1.15 g, 5.18 mmol), potassium acetate (847 mg, 8.64 mmol) and dioxane (15 mL), the mixture was replaced with nitrogen three times and then stirred at 100° C. for 16 hours under the protection of the protection of nitrogen, after the reaction was complete, the mixture was cooled and filtered, the filtrate was concentrated under reduced pressure to dryness and separated by column chromatography (dichloromethane/methanol=10:1) to obtain colorless oil 4-(6-fluoropyridin-3-yl)-6-(2-hydroxy-2-methylpropoxy)-7-methylpyrazolo[1,5-a]pyridine-3-carbonitrile (1.2 g, yield: 82%).

MS m/z (ESI): 341.1 $[M+H]^+$.

Step 7: tert-butyl 3-(5-(3-cyano-6-(2-hydroxy-2-methylpropoxy)-7-methylpyrazolo[1,5-a]pyridin-4-yl)pyridin-2-yl)-3,6-diazabicyclo[3.1.1]heptane-6-carboxylate

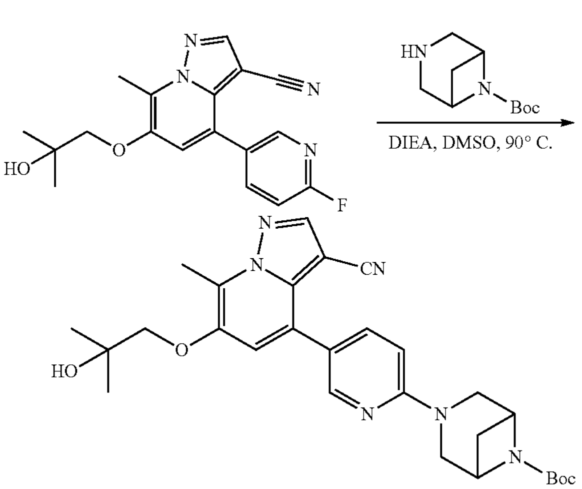

A mixed solution of 4-(6-fluoropyridin-3-yl)-6-(2-hydroxy-2-methylpropoxy)-7-methylpyrazolo[1,5-a]pyridine-3-carbonitrile (1.2 g, 3.52 mmol), tert-butyl 3,6-diazabicyclo[3.1.1]heptane-6-carboxylate (1.4 g, 7.04 mmol), N,N-diisopropylethylamine (1.36 g, 10.56 mmol) and dimethyl sulfoxide (10 mL) was stirred at 100° C. for 24 hours; the reaction was quenched with water and extracted with ethyl acetate (50 mL*3), the combined organic phase was washed with saturated saline, dried over anhydrous sodium sulfate, filtered, and the filtrate was concentrated under reduced pressure to dryness and separated by column chromatography (dichloromethane/methanol=10:1) to obtain colorless oil tert-butyl 3-(5-(3-cyano-6-(2-hydroxy-2-methylpropoxy)-7-methylpyrazolo[1,5-a]pyridin-4-yl)pyridin-2-yl)-3,6-diazabicyclo[3.1.1]heptane-6-carboxylate (800 mg, yield: 44%).

MS m/z (ESI): 519.2 $[M+H]^+$.

Step 8: 4-(6-(3,6-diazabicyclo[3.1.1]heptan-3-yl)pyridin-3-yl)-6-(2-hydroxy-2-methylpropoxy)-7-methylpyrazolo[1,5-a]pyridine-3-carbonitrile

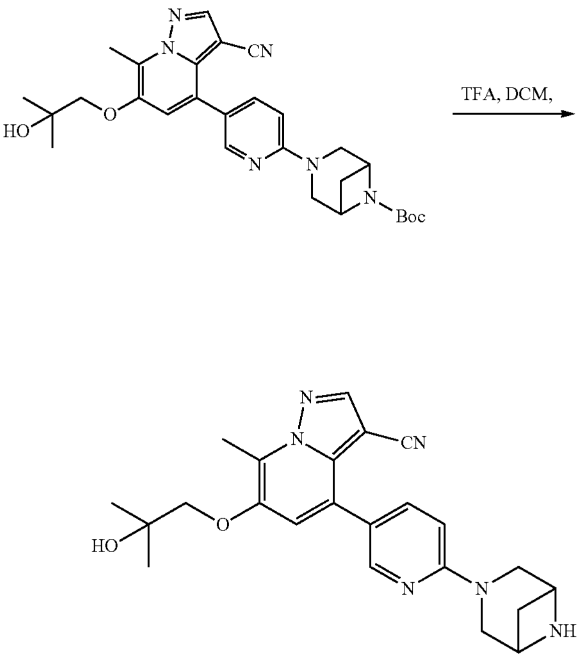

Tert-butyl 3-(5-(3-cyano-6-(2-hydroxy-2-methylpropoxy)-7-methylpyrazolo[1,5-a]pyridin-4-yl)pyridin-2-yl)-3,6-diazabicyclo[3.1.1]heptane-6-carboxylate (800 mg, 1.54 mmol) was dissolved in dichloromethane (9 mL), then trifluoroacetic acid (3 mL) was added, the mixture was stirred at room temperature for 1 hour; after the reaction was completed, the mixture was concentrated under reduced pressure to dryness and used directly in the next step without purification to obtain light yellow oil 4-(6-(3,6-diazabicyclo[3.1.1]heptan-3-yl)pyridin-3-yl)-6-(2-hydroxy-2-methylpropoxy)-7-methylpyrazolo[1,5-a]pyridine-3-carbonitrile (1 g, crude product).

MS m/z (ESI): 419.2 $[M+H]^+$.

Step 9: 6-(2-hydroxy-2-methylpropoxy)-4-(6-(6-((6-methoxypyridin-3-yl)methyl)-3,6-diazabicyclo[3.1.1]heptan-3-yl)pyridin-3-yl)-7-methylpyrazolo[1,5-a]pyridine-3-carbonitrile

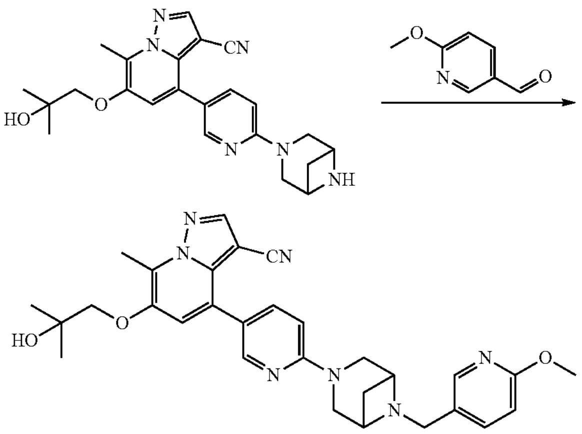

Sodium cyanoborohydride (45 mg, 0.72 mmol) was added to a solution of 4-(6-(3,6-diazabicyclo[3.1.1]heptan-3-yl)pyridin-3-yl)-6-(2-hydroxy-2-methylpropoxy)-7-methylpyrazolo[1,5-a]pyridine-3-carbonitrile (100 mg, 0.24 mmol), 6-methoxynicotinaldehyde (66 mg, 0.48 mmol) and 1,2-dichloroethane (3 mL), and then the mixture was stirred at room temperature for 24 hours, after the reaction was completed, the mixture was quenched with water and extracted with ethyl acetate (20 mL*3), and the combined organic phase was washed with saturated saline, dried over anhydrous sodium sulfate, filtered, and the filtrate was concentrated under reduced pressure to dryness and separated by preparative chromatography to obtain white solid 6-(2-hydroxy-2-methylpropoxy)-4-(6-(6-((6-methoxypyridin-3-yl)methyl)-3,6-diazabicyclo[3.1.1]heptan-3-yl)pyridin-3-yl)-7-methylpyrazolo[1,5-a]pyridine-3-carbonitrile (10 mg, yield: 8%).

MS m/z (ESI): 540.2 [M+H]$^+$.

Embodiment 12

3-(5-(3-Cyano-6-(2-hydroxy-2-methylpropoxy)-7-methylpyrazolo[1,5-a]pyridin-4-yl)pyridin-2-yl)-N-phenyl-3-diazabicyclo[3.1.1]heptane-6-carboxamide

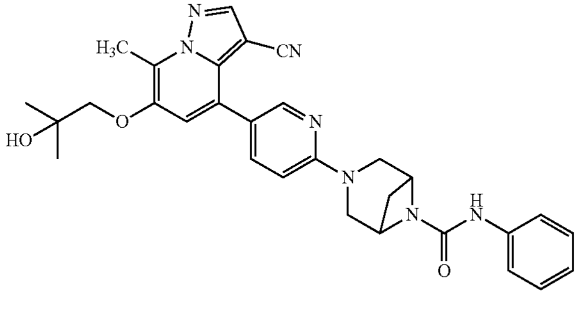

-continued

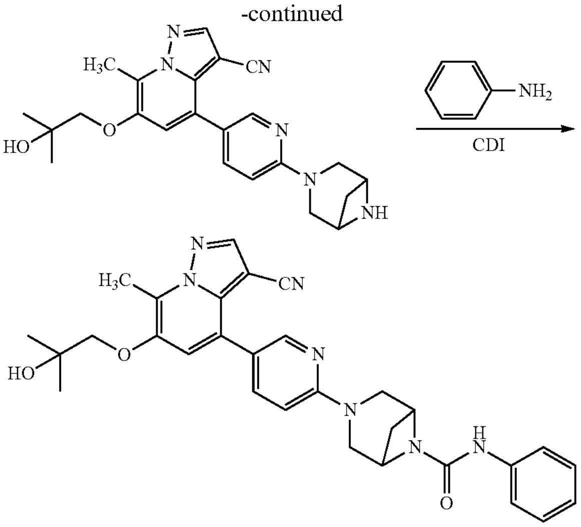

Carbonyldiimidazole (58 mg, 0.36 mmol) was added to a solution of 4-(6-(3,6-diazabicyclo[3.1.1]heptan-3-yl)pyridin-3-yl)-6-(2-hydroxy-2-methylpropoxy)-7-methylpyrazolo[1,5-a]pyridine-3-carbonitrile (100 mg, 0.24 mmol), triethylamine (48 mg, 0.48 mmol) and dichloromethane (3 mL), and the mixture was stirred at room temperature for 1 hour, then aniline was added (33 mg, 0.36 mmol) thereto, and the mixture was stirred at room temperature for 16 hours; after the reaction was completed, the mixture was quenched with water and extracted with ethyl acetate (20 ml*3); the combined organic phase was washed with saturated saline, dried over anhydrous sodium sulfate, filtered, concentrated and dried under reduced pressure to dryness, the residue was separated by preparative chromatography to obtain white solid 3-(5-(3-cyano-6-(2-hydroxyl-2-methylpropoxy)-7-methylpyrazolo[1,5-a]pyridin-4-yl)pyridin-2-yl)-N-phenyl-3-diazabicyclo[3.1.1]heptane-6-carboxamide (15 mg, yield: 12%).

MS m/z (ESI): 538.2 [M+H]$^+$.

Embodiment 13

6-(2-Hydroxy-2-methylpropoxy)-7-methyl-4-(6-(4-(pyridin-3-yloxy)piperidin-1-yl)pyridin-3-yl)pyrazolo[1,5-a]pyridine-3-carbonitrile

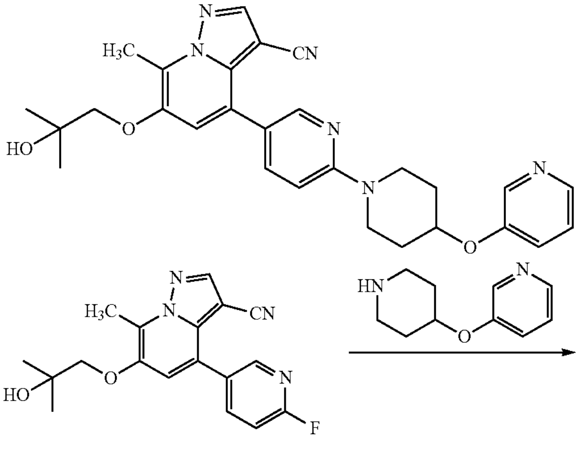

-continued

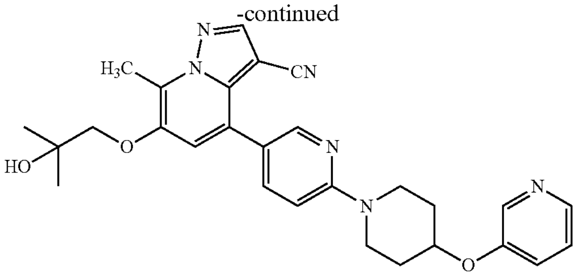

A mixture of 4-(6-fluoropyridin-3-yl)-6-(2-hydroxy-2-methylpropoxy)-7-methylpyrazolo[1,5-a]pyridine-3-carbonitrile (100 mg, 0.24 mmol), 3-(piperidin-4-yloxy)pyridine (85 mg, 0.48 mmol), potassium carbonate (99 mg, 0.72 mmol) and acetonitrile (3 mL) was stirred at 100° C. for 16 hours; after the reaction was completed, the mixture was quenched with water and extracted with ethyl acetate (20 mL*3); the combined organic phase was washed with saturated saline, dried over anhydrous sodium sulfate, filtered, and the filtrate was concentrated under reduced pressure to dryness and separated by preparative chromatography to obtain white solid 6-(2-hydroxy-2-methylpropoxy)-7-methyl-4-(6-(4-(pyridin-3-oxy)piperidin-1-yl)pyridin-3-yl) pyrazolo[1,5-a]pyridine-3-carbonitrile (15 mg, yield: 13%).

MS m/z (ESI): 499.2 [M+H]$^+$.

Embodiment 14

4-(6-(6-((6-Ethoxy-5-fluoropyridin-3-yl)methyl)-3,6-diazabicyclo[3.1.1]heptan-3-yl)pyridin-3-yl)-7-fluoro-6-(2-hydroxy-2-methylpropoxy)pyrazolo[1,5-a]pyridine-3-carbonitrile

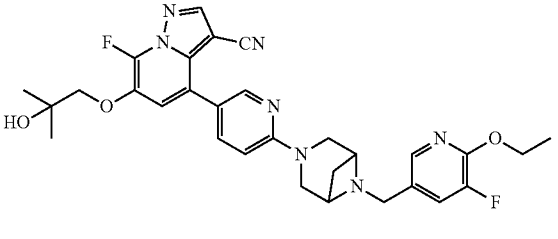 [SMILES: CCOc1ncc(CN2C3CC2CN(c2ccc(-c4cc(OCC(C)(C)O)c(F)n5ncc(C#N)c45)cn2)C3)cc1F]

Step 1: 5-bromo-2-fluoro-3-methoxypyridine

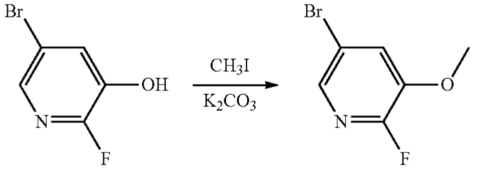

5-Bromo-2-fluoropyridin-3-ol (5 g, 26.18 mmol) was dissolved in acetonitrile (50 mL), then potassium carbonate (7.2 g, 52.36 mmol) was added and iodomethane (11.2 g, 78.54 mmol) was added dropwise, then the reaction mixture was stirred at 80° C. for 16 hours; the reaction mixture was cooled to room temperature, concentrated under reduced pressure to dryness, and separated and purified by column chromatography (petroleum ether/ethyl acetate=1:1) to obtain light yellow solid 5-bromo-2-fluoro-3-methoxypyridine (4.5 g, yield: 83%).

$^1$H NMR (400 MHz, $CDCl_3$) δ 7.80 (d, J=1.8 Hz, 1H), 7.38 (dd, J=8.8, 1.9 Hz, 1H), 3.91 (s, 3H).

MS m/z (ESI): 206.0 [M+H]$^+$.

Step 2: 2,4,6-trimethylbenzenesulfonic acid 1-amino-5-bromo-2-fluoro-3-methoxypyridine-1-ium

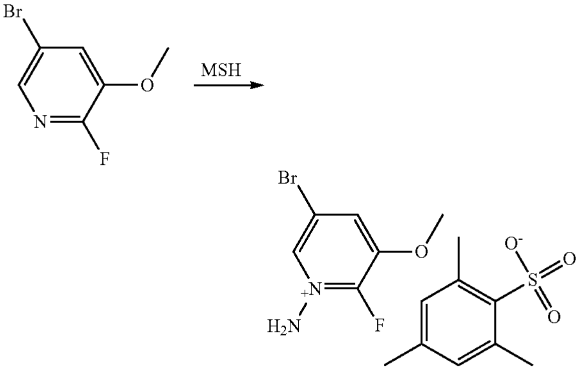

5-Bromo-2-fluoro-3-methoxypyridine (5 g, 21.84 mmol) was added to a solution of 2-[(aminooxy)sulfonyl]-1,3,5-trimethylbenzene (4.7 g, 21.84 mmol) in dichloromethane (50 mL) at 0° C. in batches, then the mixture was stirred at 0° C. for 1.5 hours; methyl tert-butyl ether (100 mL) was added to the reaction mixture, and the mixture was slurried for 15 min, then filtered and the filter cake was dried to obtain light yellow solid 2,4,6-trimethylbenzenesulfonic acid 1-amino-5-bromo-2-fluoro-3-methoxypyridine-1-ium (8 g, yield: 87%).

Step 3: 4-bromo-7-fluoro-6-methoxypyrazolo[1,5-a] pyridine-3-carbonitrile

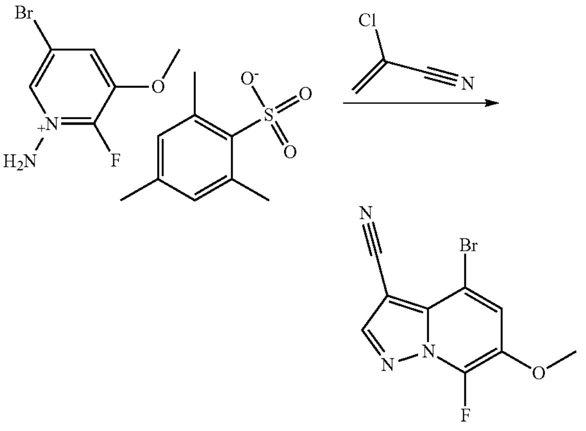

1.8-Diazabicyclo[5.4.0]undec-7-ene (5.8 g, 38 mmol) was added to a solution of 2,4,6-trimethylbenzenesulfonic acid 1-amino-5-bromo-2-fluoro-3-methoxypyridine-1-ium (8 g, 19 mmol) and 2-chloroacrylonitrile (2.5 g, 28.5 mmol) in dichloromethane (80 mL) at 0° C., then the mixture was warmed up to room temperature and stirred for 24 hours;

methyl tert-butyl ether (100 mL) was added to the reaction mixture, and the mixture was slurried at room temperature for 15 min, then filtered and the filter cake was dried to obtain light yellow solid 4-bromo-7-fluoro-6-methoxypyrazolo[1,5-a]pyridine-3-carbonitrile (3 g, yield: 58%).

MS m/z (ESI): 270.0 [M+H]$^+$.

Step 4: 4-bromo-7-fluoro-6-hydroxypyrazolo[1,5-a]pyridine-3-carbonitrile

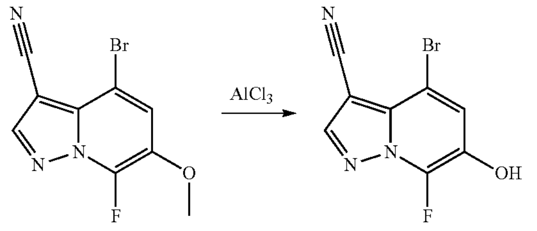

Aluminum trichloride (3 g, 22.22 mmol) was added to a solution of 4-bromo-7-fluoro-6-methoxypyrazolo[1,5-a]pyridine-3-carbonitrile (3 g, 11.11 mmol) in 1.2-dichloroethane (30 mL) in batches, then the mixture was stirred at 80° C. for 2 hours, cooled to room temperature, quenched with sodium sulfate decahydrate and filtered, the filter cake was washed with dichloromethane, the filtrate was washed with saturated saline; the organic phase was dried over anhydrous sodium sulfate, filtered, and the filtrate was concentrated under reduced pressure to dryness to obtain white solid 4-bromo-7-fluoro-6-hydroxypyrazolo[1,5-a]pyridine-3-carbonitrile (2.2 g, yield: 77%).

MS m/z (ESI): 255.0 [M−H]$^+$.

Step 5: 4-bromo-7-fluoro-6-(2-hydroxy-2-methylpropoxy)pyrazolo[1,5-a]pyridine-3-carbonitrile

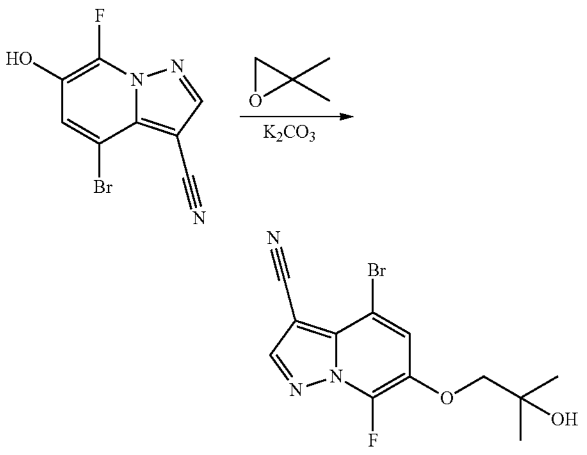

2,2-Dimethyloxirane (1.24 g, 17.2 mmol) was added to a solution of 4-bromo-7-fluoro-6-hydroxypyrazolo[1,5-a]pyridine-3-carbonitrile (2.2 g, 8.6 mmol), potassium carbonate (2.37 g, 17.2 mmol) and acetonitrile (25 mL), and then the reaction mixture was stirred at 80° C. for 16 hours; the reaction mixture was concentrated under reduced pressure to dryness, separated by column chromatography (dichloromethane/methanol=10:1) to obtain colorless oil 4-bromo-7-fluoro-6-(2-hydroxy-2-methylpropoxy)pyrazolo[1,5-a]pyridine-3-carbonitrile (2 g, yield: 71%).

MS m/z (ESI): 328.0 [M+H]$^+$.

Step 6: 7-fluoro-4-(6-fluoropyridin-3-yl)-6-(2-hydroxy-2-methylpropoxy)pyrazolo[1,5-a]pyridine-3-carbonitrile

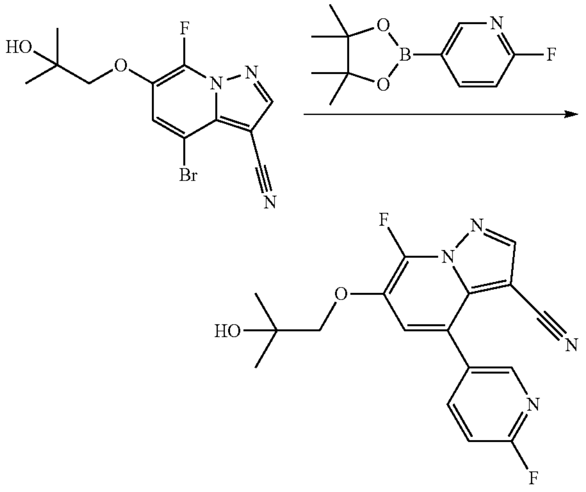

1,1'-Bis(diphenylphosphino)ferrocene-palladium(II)dichloride dichloromethane complex (50 mg, 0.061 mmol) was added to a mixed solution of 4-bromo-7-fluoro-6-(2-hydroxy-2-methylpropoxy)pyrazolo[1,5-a]pyridine-3-carbonitrile (2 g, 6.1 mmol), 2-fluoro-5-(4,4,5,5-tetramethyl-1,3,2-dioxaborolan-2-yl)pyridine (1.63 g, 7.32 mmol), potassium acetate (1.2 g, 12.2 mmol) and dioxane (30 mL), the mixture was replaced with nitrogen three times and then stirred at 100° C. under the protection of the protection of nitrogen for 16 hours; after the reaction was complete, the mixture was cooled and filtered, the filtrate was concentrated under reduced pressure to dryness and separated by column chromatography (dichloromethane/methanol=10:1) to obtain colorless oil 7-fluoro-4-(6-fluoropyridin-3-yl)-6-(2-hydroxy-2-methylpropoxy)pyrazolo[1,5-a]pyridine-3-carbonitrile (1.4 g, yield: 67%).

MS m/z (ESI): 345.1 [M+H]$^+$.

Step 7: tert-butyl 3-(5-(3-cyano-7-fluoro-6-(2-hydroxy-2-methylpropoxy)pyrazolo[1,5-a]pyridin-4-yl)pyridin-2-yl)-3,6-diazabicyclo[3.1.1]heptane-6-carboxylate

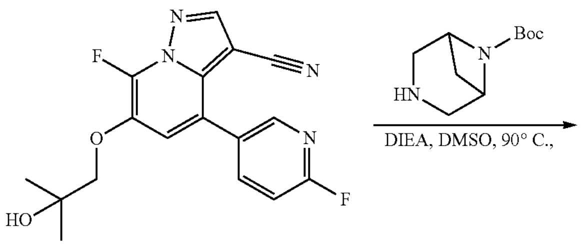

-continued

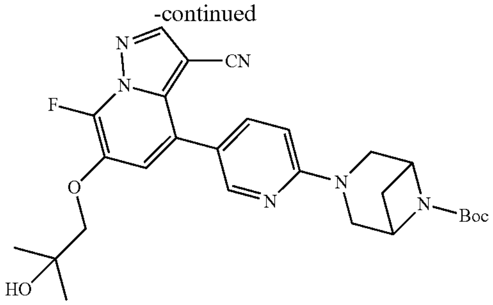

A mixed solution of 7-fluoro-4-(6-fluoropyridin-3-yl)-6-(2-hydroxy-2-methylpropoxy)pyrazolo[1,5-a]pyridine-3-carbonitrile (1.4 g, 4.06 mmol), tert-butyl 3,6-diazabicyclo[3.1.1]heptane-6-carboxylate (1.61 g, 8.12 mmol), N,N-diisopropylethylamine (1.57 g, 12.18 mmol) and dimethyl sulfoxide (15 mL) was stirred at 100° C. for 24 hours; after the reaction was complete, the mixture was quenched with water and extracted with ethyl acetate (50 mL*3), the combined organic phase was washed with saturated saline, the organic phase was dried over anhydrous sodium sulfate, filtered, and the filtrate was concentrated under reduced pressure to dryness and separated by column chromatography (dichloromethane/methanol=10:1) to obtain colorless oil tert-butyl 3-(5-(3-cyano-7-fluoro-6-(2-hydroxy-2-methylpropoxy)pyrazolo[1,5-a]pyridin-4-yl)pyridin-2-yl)-3,6-diazabicyclo[3.1.1]heptane-6-carboxylate (1.05 g, yield: 50%).

MS m/z (ESI): 523.2 [M+H]$^+$.

Step 8: 4-(6-(3,6-diazabicyclo[3.1.1]heptan-3-yl)pyridin-3-yl)-7-fluoro-6-(2-hydroxy-2-methylpropoxy)pyrazolo[1,5-a]pyridine-3-carbonitrile

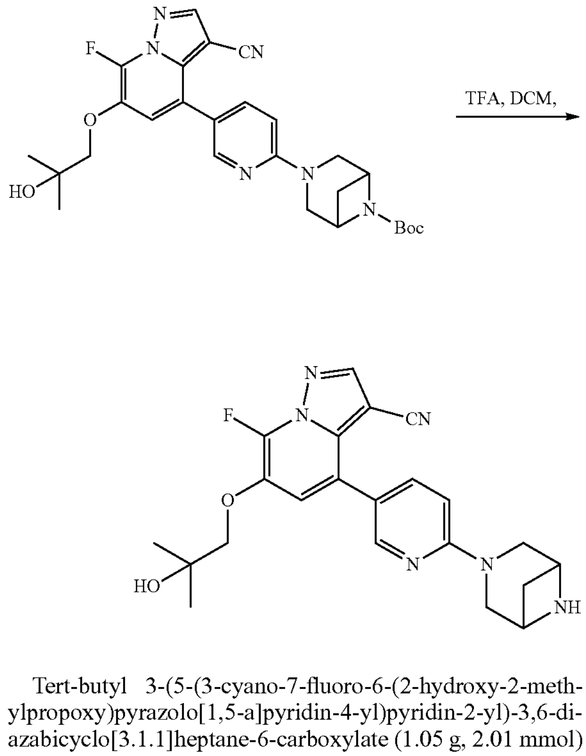

Tert-butyl 3-(5-(3-cyano-7-fluoro-6-(2-hydroxy-2-methylpropoxy)pyrazolo[1,5-a]pyridin-4-yl)pyridin-2-yl)-3,6-diazabicyclo[3.1.1]heptane-6-carboxylate (1.05 g, 2.01 mmol) was dissolved in dichloromethane (9 mL), then trifluoroacetic acid (3 mL) was added at room temperature for 1 hour; after the reaction was completed, the mixture was concentrated under reduced pressure to dryness and used directly in the next step without purification to obtain light yellow oil 4-(6-(3,6-diazabicyclo[3.1.1]heptan-3-yl)pyridin-3-yl)-7-fluoro-6-(2-hydroxy-2-methylpropoxy)pyrazolo[1,5-a]pyridine-3-carbonitrile (1.2 g, crude product).

MS m/z (ESI): 423.2 [M+H]$^+$.

Step 9: 4-(6-(6-((6-ethoxy-5-fluoropyridin-3-yl)methyl)-3,6-diazabicyclo[3.1.1]heptan-3-yl)pyridin-3-yl)-7-fluoro-6-(2-hydroxy-2-methylpropoxy)pyrazolo[1,5-a]pyridine-3-carbonitrile

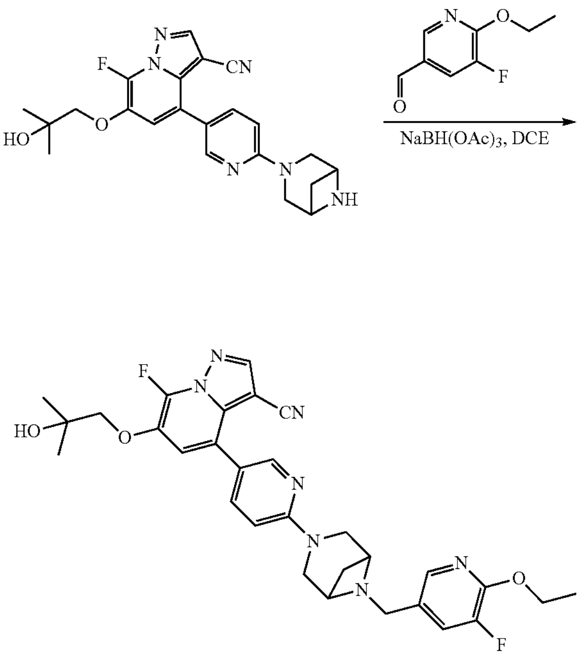

Sodium cyanoborohydride (54 mg, 0.85 mmol) was added to a solution of 4-(6-(3,6-diazabicyclo[3.1.1]heptan-3-yl)pyridin-3-yl)-7-fluoro-6-(2-hydroxy-2-methylpropoxy)-pyrazolo[1,5-a]pyridine-3-carbonitrile (120 mg, 0.28 mmol), 6-ethoxy-5-fluoronicotinaldehyde (73 g, 0.43 mmol) and 1,2-dichloroethane (5 mL), and then the mixture was stirred at room temperature for 24 hours; after the reaction was completed, the mixture was quenched with water and extracted with ethyl acetate (50 mL*3), and the combined organic phase was washed with saturated saline, dried over anhydrous sodium sulfate, filtered, and the filtrate was concentrated under reduced pressure to dryness and separated by preparative chromatography to obtain white solid 4-(6-(6-((6-ethoxy-5-fluoropyridin-3-yl)methyl)-3,6-diazabicyclo[3.1.1]heptan-3-yl)pyridin-3-yl)-7-fluoro-6-(2-hydroxy-2-methylpropoxy)pyrazolo[1,5-a]pyridine-3-carbonitrile (15 mg, yield: 9%).

MS m/z (ESI): 576.2 [M+H]$^+$.

Embodiment 15

7-Fluoro-6-(2-hydroxy-2-methylpropoxy)-4-(6-(4-(pyridin-2-oxy)piperidin-1-yl)pyridin-3-yl)pyrazolo[1,5-a]pyridine-3-carbonitrile

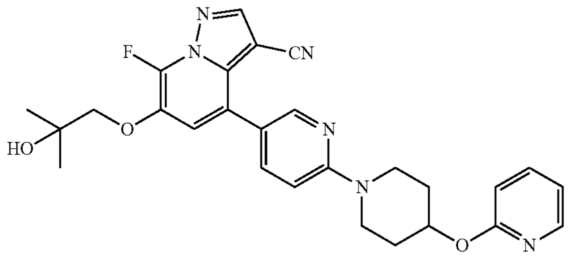 [SMILES: CC(C)(O)COc1cc(-c2ccc(N3CCC(Oc4ccccn4)CC3)nc2)c2c(C#N)cnn2c1F]

7-Fluoro-4-(6-fluoropyridin-3-yl)-6-(2-hydroxy-2-methylpropoxy)pyrazolo[1,5-a]pyridine-3-carbonitrile was used as raw material, the title compound was obtained by the synthetic method with reference to embodiment 13.

MS m/z (ESI): 503.2 $[M+H]^+$.

Embodiment 16

7-Fluoro-6-(2-hydroxy-2-methylpropoxy)-4-(6-(4-((6-methylpyridazin-3-yl)oxo)piperidin-1-yl)pyridin-3-yl)pyrazolo[1,5-a]pyridine-3-carbonitrile

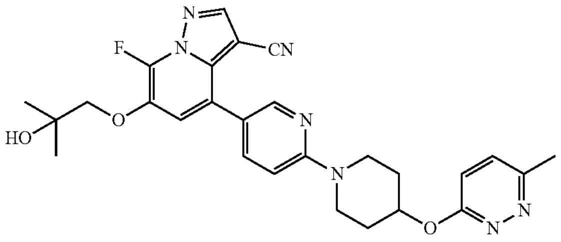 [SMILES: Cc1ccc(OC2CCN(c3ccc(-c4cc(OCC(C)(C)O)c(F)n5ncc(C#N)c45)cn3)CC2)nn1]

Step 1: tert-butyl 4-((6-methylpyridazin-3-yl)oxo)piperidine-1-carboxylate

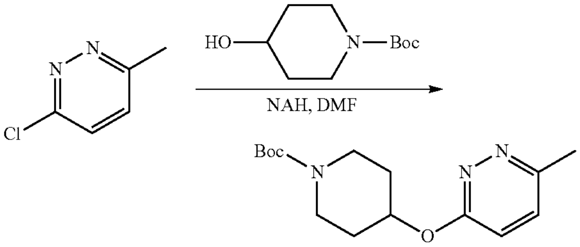

Tert-butyl 4-hydroxypiperidine-1-carboxylate (2 g, 9.95 mmol) was added to anhydrous N,N-dimethylformamide (20 mL) at 0° C., then sodium hydrogen (796 mg. 19.9 mmol) was added at 0° C. and the mixture was stirred at room temperature for 30 min, then 3-chloro-6-methylpyridazine (1.9 g, 14.93 mmol) was added; after the reaction was complete, the mixture was quenched with water, extracted with ethyl acetate (50 mL*3), and the combined organic phase was washed with saturated saline, dried over anhydrous sodium sulfate, filtered and the filtrate was concentrated under reduced pressure to dryness and separated by column chromatography to obtain white solid tert-butyl 4-((6-methylpyridazin-3-yl)oxo)piperidine-1-carboxylate (1.2 g, yield: 41%).

MS m/z (ESI): 294.1 $[M+H]^+$.

Step 2: 3-methyl-6-(piperidin-4-oxy)pyridazine

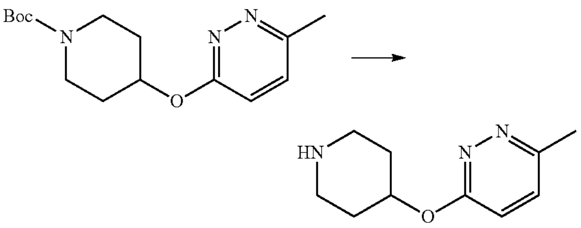

Trifluoroacetic acid (3 mL) was added dropwise to a solution of tert-butyl 4-((6-methylpyridazin-3-yl)oxo)piperidine-1-carboxylate (1.2 g, 4.1 mmol) in dichloromethane (9 mL), and then the mixture was stirred at room temperature for 1 hour; after the reaction was completed, the mixture was concentrated under reduced pressure to dryness to obtain light yellow solid 3-methyl-6-(piperidine-4-oxy)pyridazine (1.5 g, crude product).

MS m/z (ESI): 194.1 $[M+H]^+$.

Step 3: 7-fluoro-6-(2-hydroxy-2-methylpropoxy)-4-(6-(4-((6-methylpyridazin-3-yl)oxo)piperidin-1-yl)pyridin-3-yl)pyrazolo[1,5-a]pyridine-3-carbonitrile

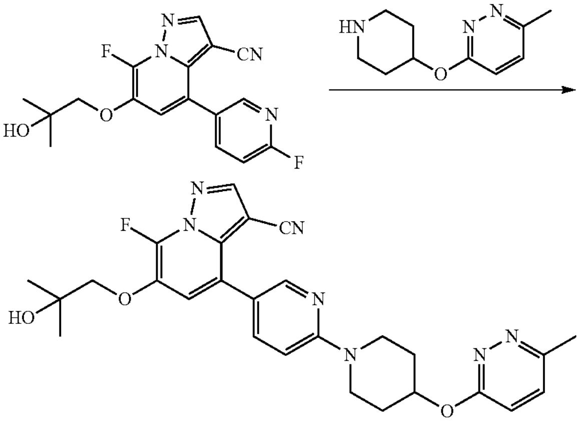

The title compound was obtained by using 4-(6-methylpyridin-3-yl)-6-(2-hydroxy-2-methylpropoxy)-7-methylpyrazolo[1,5-a]pyridine-3-carbonitrile and 3-methyl-6-(piperidin-4-oxy)pyridazine as raw material with reference to the method of embodiment 13.

MS m/z (ESI): 518.2 $[M+H]^+$.

Embodiment 17

3-(5-(3-Cyano-7-fluoro-6-(2-hydroxy-2-methylpropoxy)pyrazolo[1,5-a]pyridin-4-yl)pyridin-2-yl)-N-phenyl-3,6-diazabicyclo[3.1.1]heptane-6-carboxamide

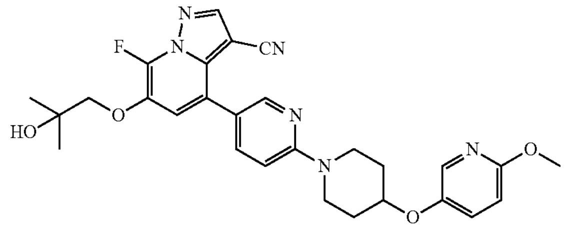 [SMILES: COc1ccc(OC2CCN(c3ccc(-c4cc(OCC(C)(C)O)c(F)n5ncc(C#N)c45)cn3)CC2)cn1]

The title compound was obtained by using 7-fluoro-4-(6-fluoropyridin-3-yl)-6-(2-hydroxy-2-methylpropoxy)pyrazolo[1,5-a]pyridine-3-carbonitrile as raw material with reference to embodiment 13.

MS m/z (ESI): 533.2 $[M+H]^+$.

Embodiment 18

3-(5-(3-Cyano-7-fluoro-6-(2-hydroxy-2-methylpropoxy)pyrazolo[1,5-a]pyridin-4-yl)pyridin-2-yl)-N-phenyl-3,6-diazabicyclo[3.1.1]heptane-6-carboxamide

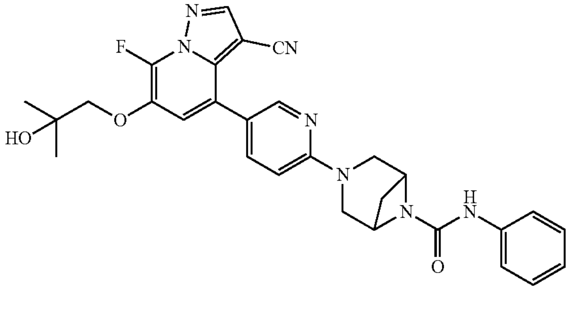 [SMILES: CC(C)(O)COc1cc(-c2ccc(N3CC4CC(C3)N4C(=O)Nc3ccccc3)nc2)c2c(C#N)cnn2c1F]

The title compound was obtained by using 7-fluoro-4-(6-fluoropyridin-3-yl)-6-(2-hydroxy-2-methylpropoxy)pyrazolo[1,5-a]pyridine-3-carbonitrile as raw material with reference to embodiment 12.

MS m/z (ESI): 542.2 $[M+H]^+$.

Embodiment 19

7-Chloro-6-((R)-2-hydroxypropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

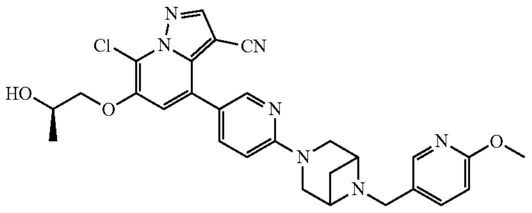 [SMILES: COc1ccc(CN2C3CC2CN(c2ccc(-c4cc(OC[C@@H](C)O)c(Cl)n5ncc(C#N)c45)cn2)C3)cn1]

The title compound was obtained with reference to embodiment 14, while 5-bromo-2-chloropyridine-3-ol was replaced with 5-bromo-2-fluoropyridine-3-ol in step 1 and (R)-2-methyloxirane was replaced with 2,2-dimethyloxirane in step 5.

MS m/z (ESI): 546.2 $[M+H]^+$.

Embodiment 20

5-Chloro-6-(2-hydroxy-2-methylpropoxy)-4-(6-(4-(pyridin-2-oxy)piperidin-1-yl)pyridin-3-yl)pyrazolo[1,5-a]pyridine-3-carbonitrile

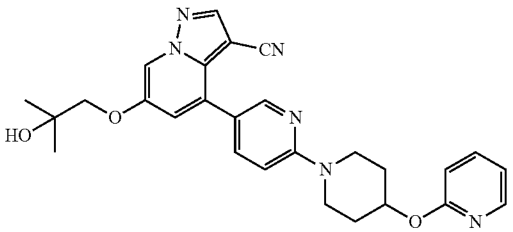 [SMILES: CC(C)(O)COc1cc(-c2ccc(N3CCC(Oc4ccccn4)CC3)nc2)c2c(C#N)cnn2c1]

Step 1: 2,4,6-trimethylbenzenesulfonic acid 1-amino-3-bromo-4-chloro-5-methoxypyridine-1-ium

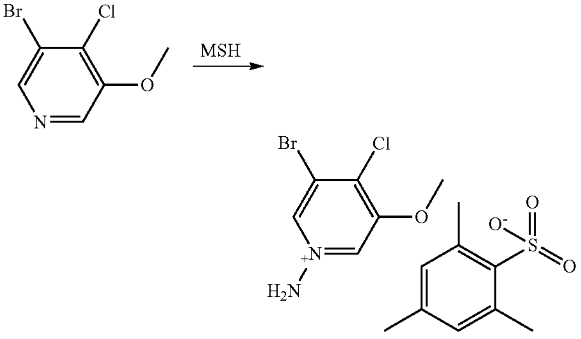

3-Bromo-4-chloro-5-methoxypyridine (5 g, 22.52 mmol) was added to a solution of 2-[(aminooxy)sulfonyl]-1,3,5-trimethylbenzene (4.8 g, 22.52 mmol) in dichloromethane (100 mL) at 0° C. in batches, then the mixture was stirred at 0° C. for 1.5 hours; methyl tert-butyl ether (30 mL) was added to the reaction mixture, and the mixture was slurried for 15 min, then filtered and the filter cake was dried to obtain light yellow solid 2,4,6-trimethylbenzenesulfonic acid 1-amino-3-bromo-4-chloro-5-methoxypyridine-1-ium (9 g, crude product).

Step 2: 4-bromo-5-chloro-6-methoxypyrazolo[1,5-a] pyridine-3-carbonitrile

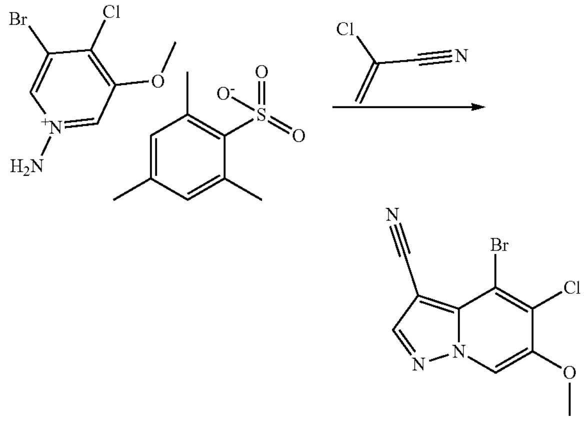

1.8-Diazabicyclo[5.4.0]undec-7-ene (6.3 g, 41.2 mmol) was added to a solution of 2,4,6-trimethylbenzenesulfonic acid 1-amino-3-bromo-4-chloro-5-methoxypyridine-1-ium (9 g, 20.6 mmol) and 2-chloroacrylonitrile (2.7 g, 30.9 mmol) in dichloromethane (100 mL) at 0° C., then the mixture was warmed up to room temperature and stirred for 24 hours; methyl tert-butyl ether (50 mL) was added to the reaction mixture, and the mixture was slurried at room temperature for 15 min, then filtered and the filter cake was dried to obtain light yellow solid 4-bromo-5-chloro-6-methoxypyrazolo[1,5-a]pyridine-3-carbonitrile (3 g, yield: 51%).

MS m/z (ESI): 286.0 $[M+H]^+$.

Step 3: 4-bromo-5-chloro-6-hydroxypyrazolo[1,5-a] pyridine-3-carbonitrile

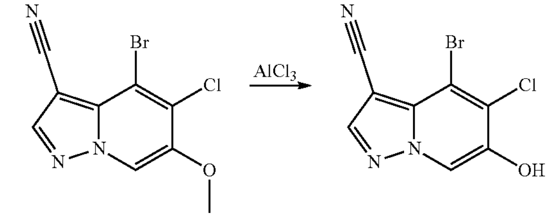

Aluminum trichloride (7 g, 52.63 mmol) was added to a solution of 4-bromo-5-chloro-6-methoxypyrazolo[1,5-a] pyridine-3-carbonitrile (3 g, 10.53 mmol) in 1.2-dichloroethane (30 mL) in batches, then the mixture was stirred at 80° C. for 2 hours, cooled to room temperature, quenched with sodium sulfate decahydrate and filtered, the filter cake was washed with dichloromethane, the filtrate was washed with saturated saline; the organic phase was dried over anhydrous sodium sulfate, filtered, and the filtrate was concentrated under reduced pressure to dryness to obtain white solid 4-bromo-5-chloro-6-hydroxypyrazolo[1,5-a] pyridine-3-carbonitrile (2.1 g, yield: 74%).

MS m/z (ESI): 269.9 $[M+H]^+$.

Step 4: 4-bromo-5-chloro-6-(2-hydroxy-2-methylpropoxy)pyrazolo[1,5-a]pyridine-3-carbonitrile

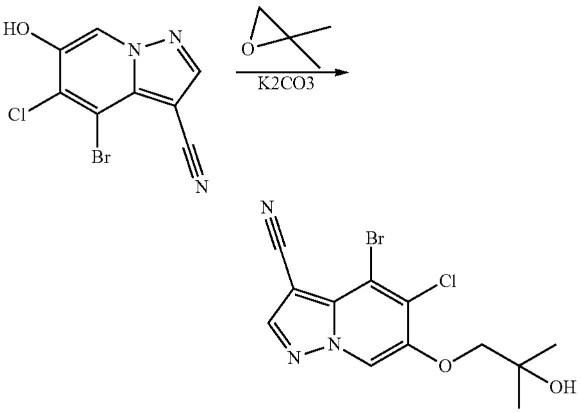

2,2-Dimethyloxirane (1.1 g, 15.5 mmol) was added to a solution of 4-bromo-5-chloro-6-hydroxypyrazolo[1,5-a] pyridine-3-carbonitrile (2.1 g, 7.75 mmol), potassium carbonate (2.14 g, 15.5 mmol) and acetonitrile (25 mL), and then the reaction mixture was stirred at 80° C. for 16 hours; the reaction mixture was concentrated under reduced pressure to dryness, separated by column chromatography (dichloromethane/methanol=10:1) to obtain colorless oil 4-bromo-5-chloro-6-(2-hydroxy-2-methylpropoxy)pyrazolo [1,5-a]pyridine-3-carbonitrile (1.4 g, yield: 53%).

MS m/z (ESI): 344.0 $[M+H]^+$.

Step 5: 5-chloro-4-(6-fluoropyridin-3-yl)-6-(2-hydroxy-2-methylpropoxy)pyrazolo[1,5-a]pyridine-3-carbonitrile

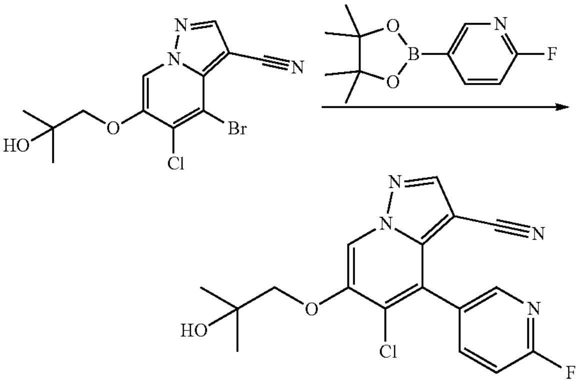

1,1'-Bis(diphenylphosphino)ferrocene-palladium(II)dichloride dichloromethane complex (330 mg, 0.4 mmol) was added to a mixed solution of 4-bromo-5-chloro-6-(2-hydroxy-2-methylpropoxy)pyrazolo[1,5-a]pyridine-3-carbonitrile (1.4 g, 4.08 mmol), 2-fluoro-5-(4,4,5,5-tetramethyl-1,3,2-dioxaborolan-2-yl)pyridine (1.1 g, 4.9 mmol), potassium acetate (800 mg, 8.16 mmol) and dioxane (20 mL), the mixture was replaced with nitrogen three times and then stirred at 100° C. under the protection of nitrogen for 16 hours; after the reaction was complete, the mixture was cooled and filtered, the filtrate was concentrated under reduced pressure to dryness and separated by column chromatography (dichloromethane/methanol=10:1) to obtain colorless oil 5-chloro-4-(6-fluoropyridin-3-yl)-6-(2-hydroxy-2-methylpropoxy)pyrazolo[1,5-a]pyridine-3-carbonitrile (1 g, yield: 68%).

MS m/z (ESI): 361.1 $[M+H]^+$.

Step 6: 5-chloro-6-(2-hydroxy-2-methylpropoxy)-4-(6-(4-(pyridin-2-yloxy)piperidin-1-yl)pyridin-3-yl)pyrazolo[1,5-a]pyridine-3-carbonitrile

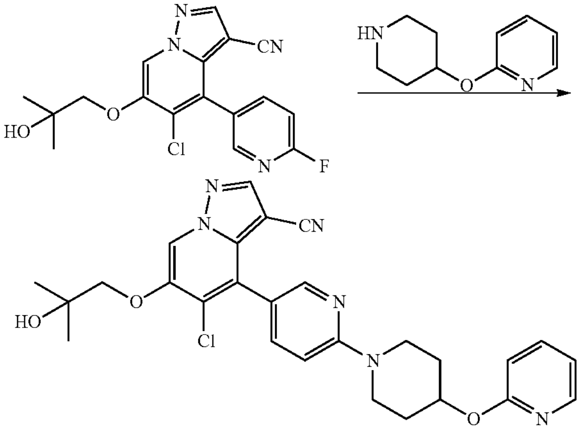

The synthesis of embodiment 22 was carried out with reference to embodiment 13.

MS m/z (ESI): 519.2 $[M+H]^+$.

Embodiment 21

5-Fluoro-6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

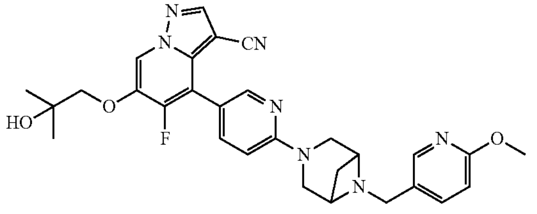 [SMILES: COc1ccc(CN2C3CC2CN(c2ccc(-c4c(F)c(OCC(C)(C)O)cn5ncc(C#N)c45)cn2)C3)cn1]

The title compound was obtained with reference to steps 1 to 5 of embodiment 20 by replacing 3-bromo-4-chloro-5-methoxypyridine with 3-bromo-4-fluoro-5-methoxypyridine, and then with reference to steps 7 to 9 of embodiment 14.

MS m/z (ESI): 544.2 $[M+H]^+$.

Embodiment 22

5-Fluoro-6-(2-hydroxy-2-methylpropoxy)-4-(6-(4-(pyridin-2-yloxy)piperidin-1-yl)pyridin-3-yl)pyrazolo[1,5-a]pyridine-3-carbonitrile

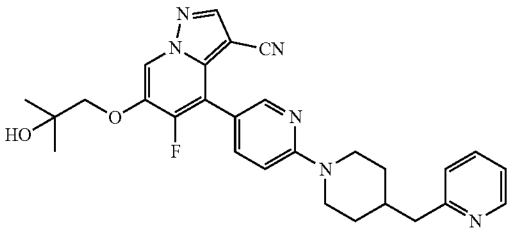 [SMILES: CC(C)(O)COc1cn2ncc(C#N)c2c(-c2ccc(N3CCC(Cc4ccccn4)CC3)nc2)c1F]

The title compound was obtained with reference to embodiment 20 by replacing 3-bromo-4-chloro-5-methoxypyridine with 3-bromo-4-fluoro-5-methoxypyridine.

MS m/z (ESI): 503.2 $[M+H]^+$.

Embodiment 23

6-(3-(2-Hydroxypropan-2-yl)azetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

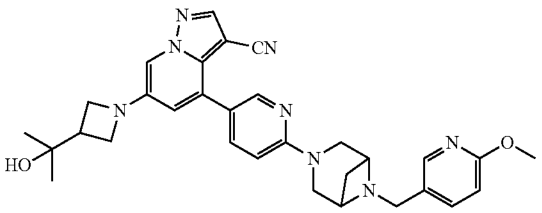 [SMILES: COc1ccc(CN2C3CC2CN(c2ccc(-c4cc(N5CC(C(C)(C)O)C5)cn5ncc(C#N)c45)cn2)C3)cn1]

Step 1: 6-bromo-3-cyanopyrazolo[1,5-a]pyridin-4-yl trifluoromethanesulfonate

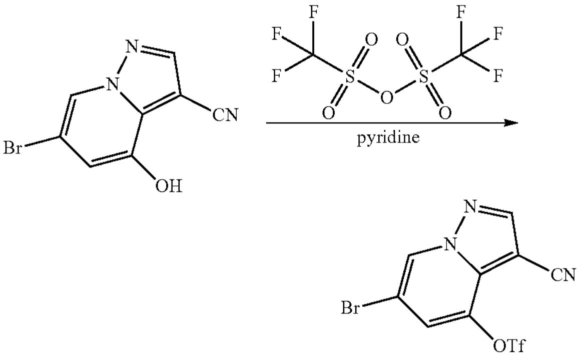

6-Bromo-4-hydroxypyrazolo[1,5-a]pyridine-3-carbonitrile was used as raw material to obtain product 6-bromo-3-cyanopyrazolo[1,5-a]pyridine-4-yl trifluoromethanesulfonate with reference to step 1 of embodiment 7.

MS m/z (ESI): 370.0$[M+H]^+$, 372.0$[M+H+2]^+$.

Step 2: 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

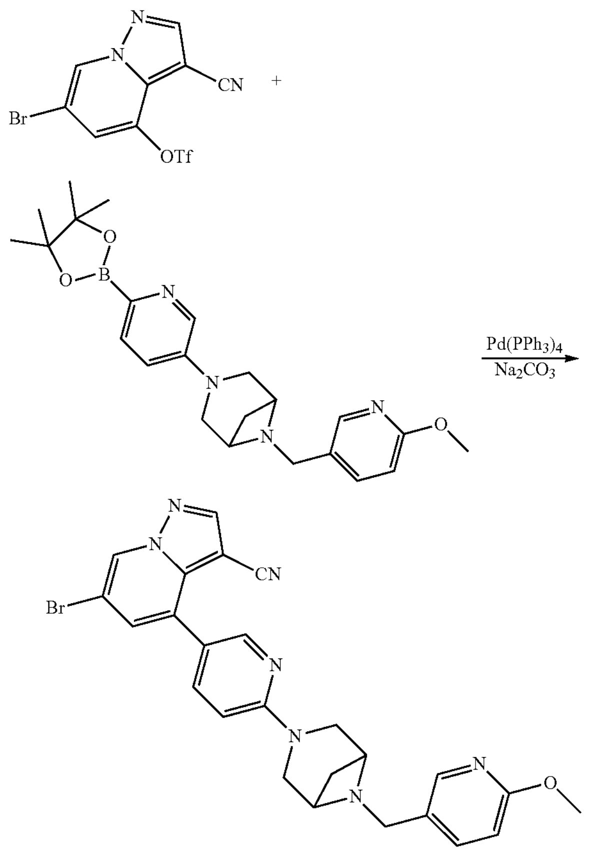

The product 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-bromo-3-cyanopyrazolo[1,5-a]pyridine-4-yl trifluoromethanesulfonate as raw material with reference to step 3 of embodiment 7.

MS m/z (ESI): 516.1[M+H]$^+$, 518.1[M+H+2]$^+$.

Step 3: 6-(3-(2-hydroxypropan-2-yl)azetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

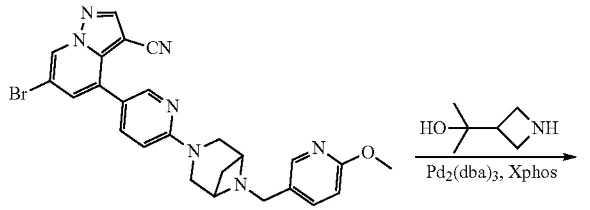

-continued

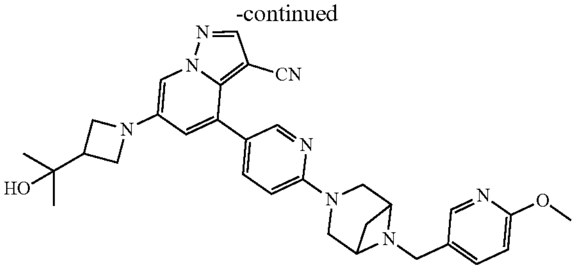

A mixture of 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (80 mg, 0.15 mmol), 2-(azetidin-3-yl)propan-2-ol (36 mg, 0.30 mmol), tris(dibenzylideneacetone)dipalladium (7 mg, 0.0075 mmol), 2-dicyclohexylphosphino-2',4',6'-triisopropylbiphenyl (4 mg, 0.0075 mmol), cesium carbonate (146 mg, 0.45 mmol) and toluene (4 mL) was replaced with nitrogen, then stirred at 130° C. for 2 hours under microwave conditions. After the reaction was complete, the mixture was cooled to room temperature, concentrated, dissolved in ethyl acetate (20 mL) and washed with saturated saline (15 mL); the organic phase was dried over anhydrous sodium sulfate, filtered, evaporated to dryness, and then purified by preparative chromatography (18 mg, white solid, yield: 21%).

MS m/z (ESI): 551.2[M+H]$^+$.

$^1$H NMR (400 MHz, MeOD) δ 8.32 (d, J=2.1 Hz, 1H), 8.24 (s, 1H), 8.08 (s, 1H), 7.85-7.79 (m, 2H), 7.71 (dd, J=8.5, 2.3 Hz, 1H), 6.92 (d, J=1.7 Hz, 1H), 6.86 (d, J=8.8 Hz, 1H), 6.78 (d, J=8.5 Hz, 1H), 3.97 (t, J=7.8 Hz, 2H), 3.92-3.84 (m, 7H), 3.78 (d, J=5.6 Hz, 2H), 3.65 (s, 1H), 3.62 (s, 3H), 2.95-2.81 (m, 1H), 2.70 (d, J=7.0 Hz, 1H), 1.70 (d, J=8.8 Hz, 1H), 1.21 (s, 6H).

Embodiment 24

6-(3-(2-Hydroxypropan-2-yl)azetidin-1-yl)-4-(6-(4-((6-methoxypyridazin-3-yl)oxo)piperidin-1-yl)pyridin-3-yl)pyrazolo[1,5-a]pyridine-3-carbonitrile

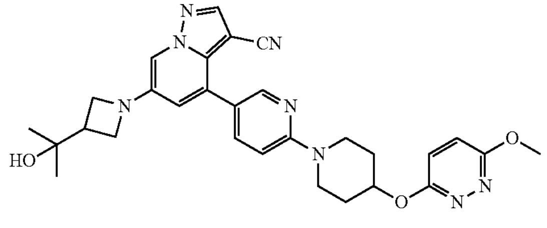 [SMILES: COc1ccc(OC2CCN(c3ccc(-c4cc(N5CC(C(C)(C)O)C5)cn5ncc(C#N)c45)cn3)CC2)nn1]

Step 1: 6-bromo-4-(6-fluoropyridin-3-yl)pyrazolo[1,5-a]pyridine-3-carbonitrile

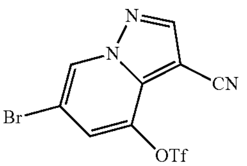
+

-continued

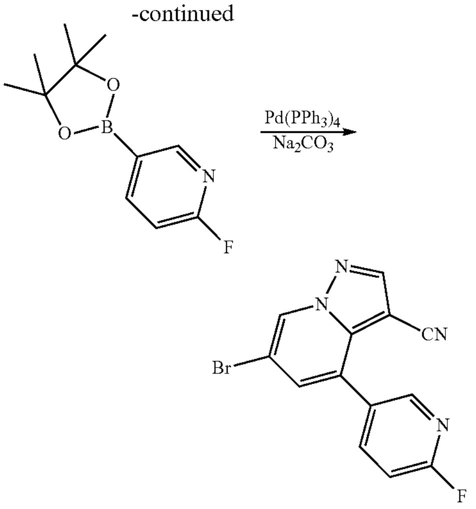

The product 6-bromo-4-(6-fluoropyridin-3-yl)pyrazolo[1,5-a]pyridine-3-carbonitrile was obtained by using 6-bromo-3-cyanopyrazolo[1,5-a]pyridin-4-yl trifluoromethanesulfonate as raw material with reference to step 3 of embodiment 7.

MS m/z (ESI): 317.0[M+H]$^+$, 319.0[M+H+2]$^+$.

Step 2: 6-bromo-4-(6-(4-((6-methoxypyridazin-3-yl)oxo)piperidin-1-yl)pyridin-3-yl)pyrazolo[1,5-a]pyridine-3-carbonitrile

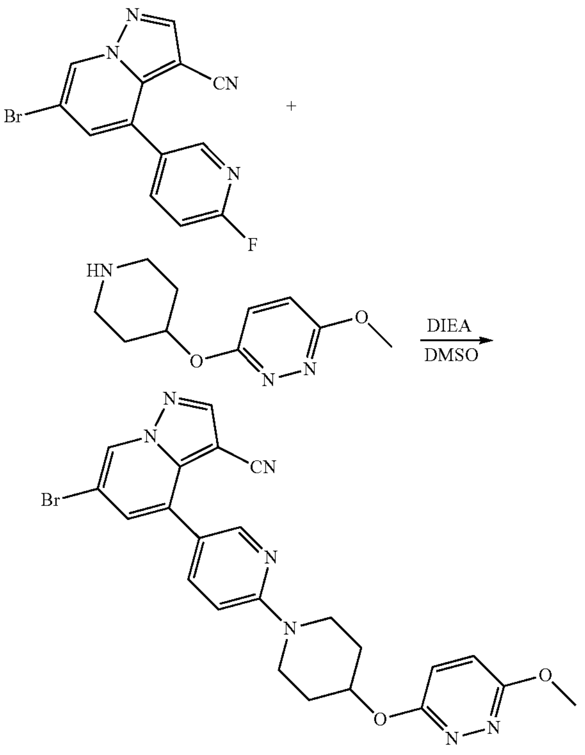

The product 6-bromo-4-(6-(4-((6-methoxypyridazin-3-yl)oxo)piperidin-1-yl)pyridin-3-yl)pyrazolo[1,5-a]pyridine-3-carbonitrile was obtained by using 6-bromo-4-(6-fluoropyridin-3-yl)pyrazolo[1,5-a]pyridine-3-carbonitrile as raw material with reference to step 2 of embodiment 8.

MS m/z (ESI): 506.1[M+H]$^+$, 508.1[M+H+2]$^+$.

Step 3: 6-(3-(2-hydroxypropan-2-yl)azetidin-1-yl)-4-(6-(4-((6-methoxypyridazin-3-yl)oxo)piperidin-1-yl)pyridin-3-yl)pyrazolo[1,5-a]pyridine-3-carbonitrile

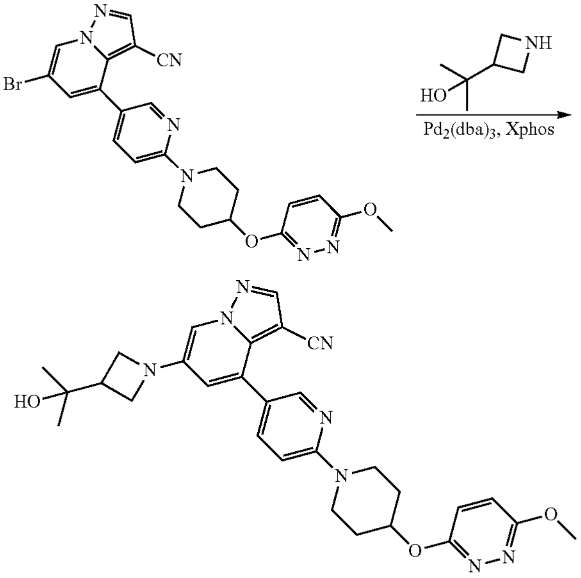

The product 6-(3-(2-hydroxypropan-2-yl)azetidin-1-yl)-4-(6-(4-((6-methoxypyridazin-3-yl)oxo)piperidin-1-yl)pyridin-3-yl)pyrazolo[1,5-a]pyridine-3-carbonitrile was obtained by using 6-bromo-4-(6-(4-((6-methoxypyridazin-3-yl)oxo)piperidin-1-yl)pyridine-3-yl)pyrazolo[1,5-a]pyridine-3-carbonitrile as raw material with reference to step 2 of embodiment 7.

MS m/z (ESI): 541.2[M+H]$^+$.

Embodiment 25

(6-(2-Hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridin-3-yl)dimethylphosphine oxide

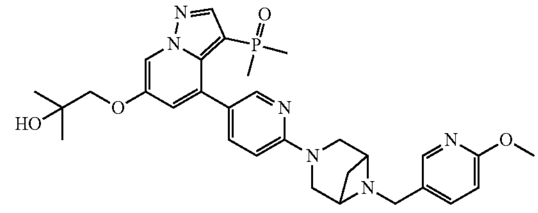 [SMILES: COc1ccc(CN2C3CC2CN(c2ccc(-c4cc(OCC(C)(C)O)cn5ncc(P(C)(C)=O)c45)cn2)C3)cn1]

Step 1: 4-bromo-3-iodopyrazolo[1,5-a]pyridin-6-ol

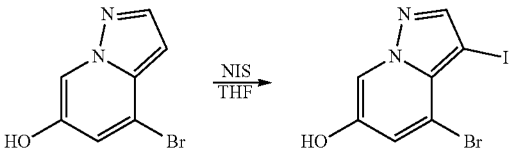

4-Bromopyrazolo[1,5-a]pyridin-6-ol (500 mg, 2.3 mmol) was dissolved in 20 mL of THF, and N-iodosuccinimide (792 mg, 3.5 mmol) was added, then the reaction was carried out at room temperature for 6 hours. 10 mL of ammonium chloride aqueous solution was added thereto, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 4-bromo-3-iodopyrazolo[1,5-a]pyridine-6-phenol (404 mg, white solid, the yield was 52%).

MS m/z (ESI): 338.8 [M+H]$^+$.

Step 2: 1-((4-bromo-3-iodopyrazolo[1,5-a]pyridin-6-yl)oxo)-2-methylpropan-2-ol

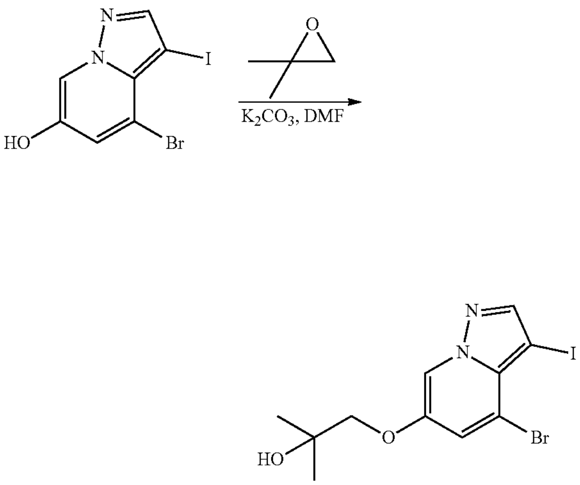

4-Bromo-3-iodopyrazolo[1,5-a]pyridin-6-ol (300 mg, 0.89 mmol) was dissolved in 20 mL of DMF, 2,2-dimethyloxirane (641 mg, 8.9 mmol) and $K_2CO_3$ (368 mg, 2.7 mmol) were added thereto, the reaction was carried out at 85° C. overnight. 10 mL of ammonium chloride aqueous solution was added thereto, and the mixture was extracted with ethyl acetate (20 mL*3). The organic phase was washed with saturated saline and dried over anhydrous sodium sulfate. The residue was filtered and evaporated to dryness, and the crude product was separated by column chromatography (eluted with dichloromethane/methanol=10/1) to obtain 1-((4-bromo-3-iodopyrazolo[1,5-a]pyridin-6-yl)oxo)-2-methylpropan-2-ol (262 mg, white solid, the yield was 72%).

MS m/z (ESI): 410.9 [M+H]$^+$.

Step 3: (4-bromo-6-(2-hydroxy-2-methylpropoxy)pyrazolo[1,5-a]pyridin-3-yl)dimethylphosphine oxide

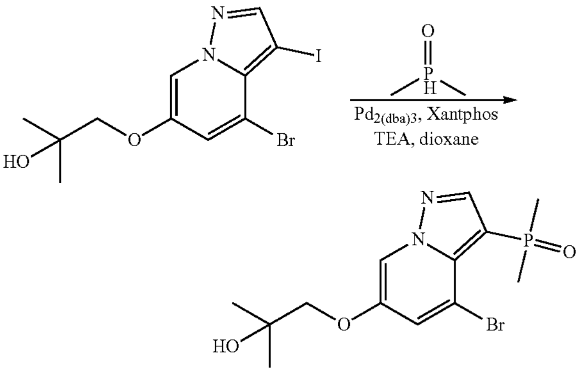

1-((4-Bromo-3-iodopyrazolo[1,5-a]pyridin-6-yl)oxo)-2-methylpropan-2-ol (300 mg, 0.89 mmol) was dissolved in 20 mL of dioxane, and dimethylphosphine oxide (104 mg, 1.3 mmol), $Pd_2(dba)_3$ (82 mg, 0.09 mmol), Xantphos (103 mg, 0.18 mmol) and TEA (270 mg, 2.7 mmol) were added, and the reaction was carried out at 85° C. overnight. 10 mL of ammonium chloride aqueous solution was added thereto, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain (4-bromo-6-(2-hydroxy-2-methylpropoxy)pyrazolo[1,5-a]pyridin-3-yl)dimethylphosphine oxide (180 mg, white solid, the yield was 56%).

MS m/z (ESI): 361.0 [M+H]$^+$.

Step 4: (6-(2-hydroxy-2-methylpropoxy)-4-(4,4,5,5-tetramethyl-1,3,2-dioxaborolan-2-yl)pyrazolo[1,5-a]pyridin-3-yl)dimethylphosphine oxide

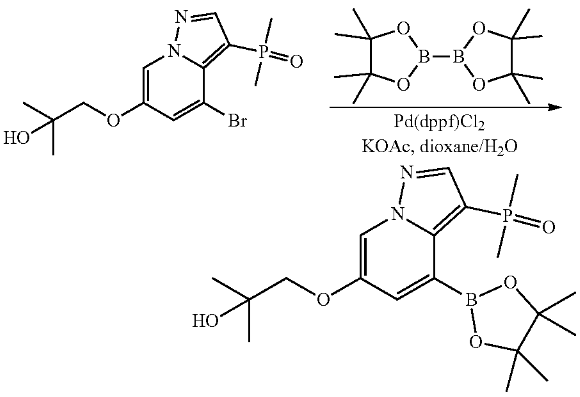

(6-(2-Hydroxy-2-methylpropoxy)-4-(4,4,5,5-tetramethyl-1,3,2-dioxaborolan-2-yl)pyrazolo[1,5-a]pyridin-3-yl)dimethylphosphine oxide (120 mg, white solid, yield was 65%) was obtained by using (4-bromo-6-(2-hydroxy-2-methylpropoxy)pyrazolo[1,5-a]pyridin-3-yl)dimethylphosphine oxide as raw material with reference to step 7 of embodiment 1.

MS m/z (ESI): 409.2 [M+H]$^+$.

Step 5: (6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridin-3-yl)dimethylphosphine oxide

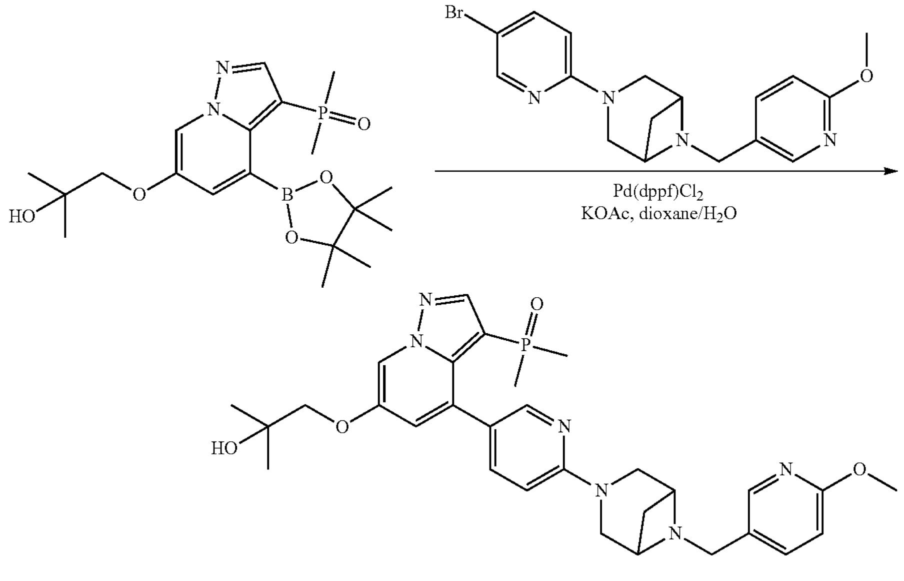

(6-(2-Hydroxy-2-methylpropoxy)-4-(4,4,5,5-tetramethyl-1,3,2-dioxaborolan-2-yl)pyrazolo[1,5-a]pyridin-3-yl)dimethylphosphine oxide and 3-(5-bromopyridin-2-yl)-6-((6-methoxypyridin-3-yl)methyl)-3,6-diazabicyclo[3.1.1]heptane were used as raw materials with reference to the step 8 of embodiment 1 to obtain (6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridin-3-yl)dimethylphosphine oxide (35 mg, white solid, 53%).

MS m/z (ESI): 577.2 $[M+H]^+$.

Embodiment 26

(4-(6-(6-((5-Fluoro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridin-3-yl)dimethylphosphine oxide

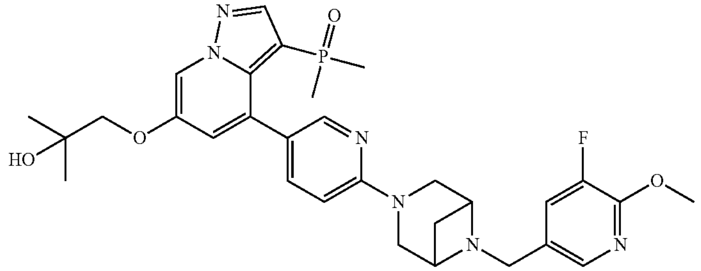

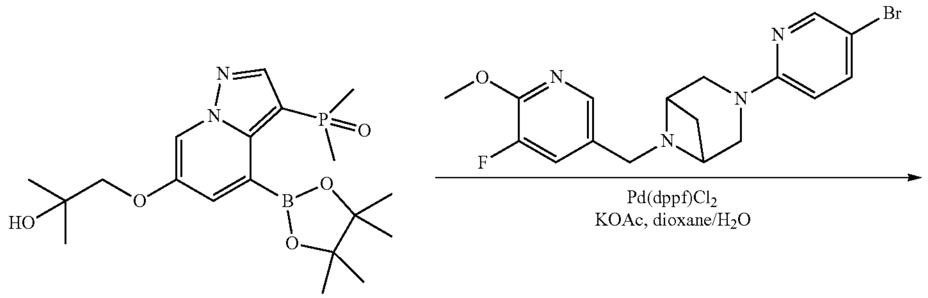

-continued

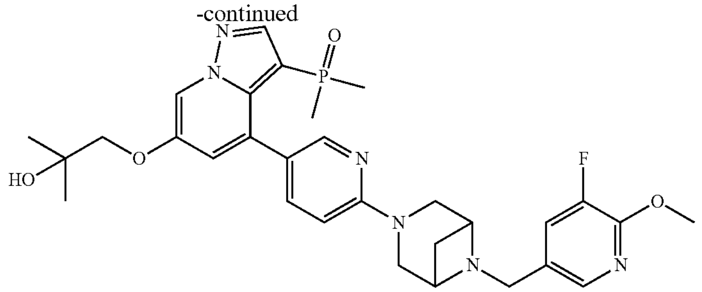

(6-(2-Hydroxy-2-methylpropoxy)-4-(4,4,5,5-tetramethyl-1,3,2-dioxaborolan-2-yl)pyrazolo[1,5-a]pyridin-3-yl)dimethylphosphine oxide and 3-(5-bromopyridin-2-yl)-6-((5-fluoro-6-methoxypyridin-3-yl)methyl)-3,6-diazabicyclo[3.1.1]heptane were used as raw materials with reference to the step 8 of embodiment 1 to obtain (4-(6-(6-((5-fluoro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridin-3-yl)dimethylphosphine oxide (28 mg, white solid, 49%).

MS m/z (ESI): 595.2 [M+H]$^+$.

Embodiment 27

3-(5-(3-(Dimethylphosphoryl)-6-(2-hydroxy-2-methylpropoxy)pyrazolo[1,5-a]pyridin-4-yl)pyridin-2-yl)-N-phenyl-3,6-diazabicyclo[3.1.1]heptane-6-carboxamide

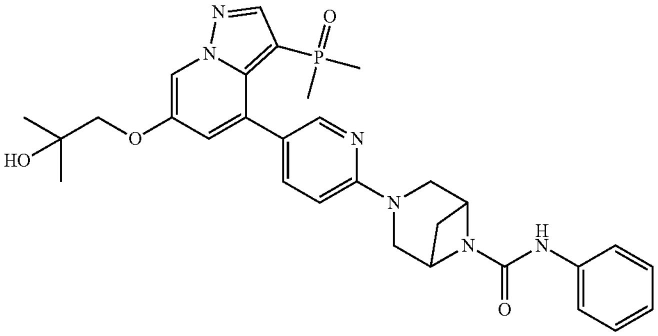

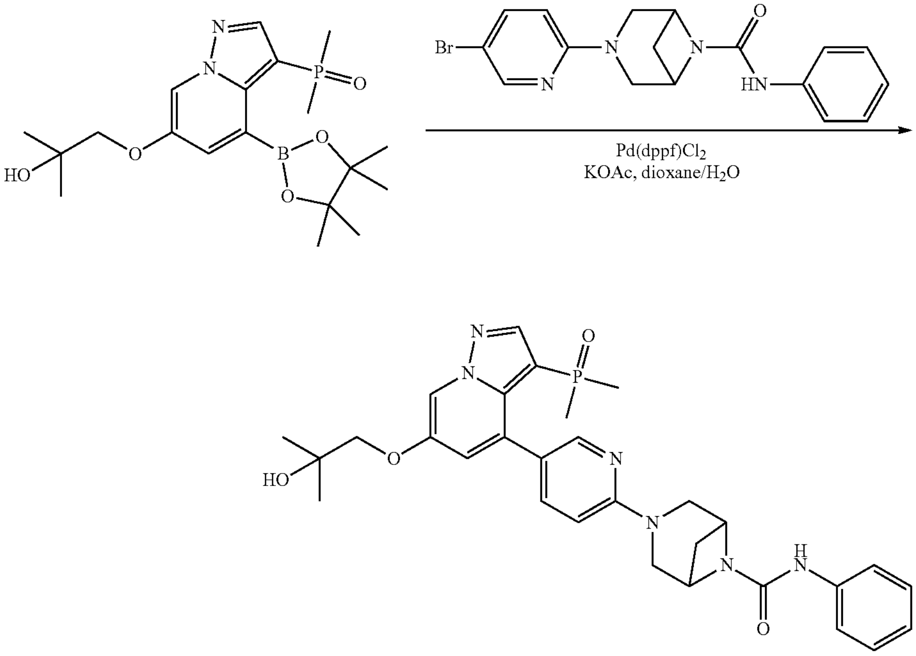

(6-(2-Hydroxy-2-methylpropoxy)-4-(4,4,5,5-tetramethyl-1,3,2-dioxaborolan-2-yl)pyrazolo[1,5-a]pyridin-3-yl)dimethylphosphine oxide and 3-(5-bromopyridin-2-yl)-N-phenyl-3,6-diazabicyclo[3.1.1]heptane-6-carboxamide were used as raw materials with reference to the step 8 of embodiment 1 to obtain 3-(5-(3-(dimethylphosphoryl)-6-(2-hydroxy-2-methylpropoxy)pyrazolo[1,5-a]pyridin-4-yl)pyridin-2-yl)-N-phenyl-3,6-diazabicyclo[3.1.1]heptane-6-carboxamide (38 mg, white solid, 56%).

MS m/z (ESI): 575.2 $[M+H]^+$.

Embodiment 28

4-(6-(6-((5-Fluoro-6-methoxypyridin-3-yl)methyl)-3,6-diazabicyclo[3.1.1]heptan-3-yl)pyridin-3-yl)-6-(2-hydroxy-2-methylpropoxy)-N,N-dimethylpyrazolo[1,5-a]pyridine-3-carboxamide

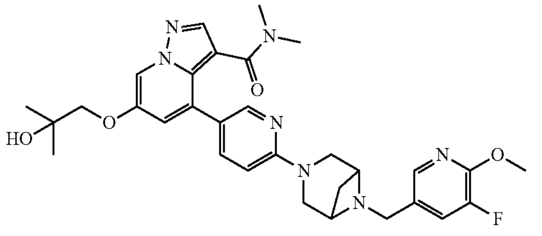 [SMILES: COc1ncc(CN2C3CC2CN(c2ccc(-c4cc(OCC(C)(C)O)cn5ncc(C(=O)N(C)C)c45)cn2)C3)cc1F]

Step 1: 2,4,6-trimethylbenzenesulfonic acid 1-amino-5-bromo-3-methoxy-2-methylpyridin-1-ium

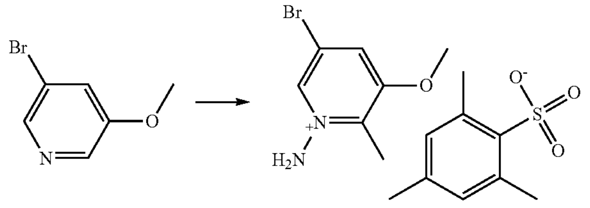

3-Bromo-5-methoxypyridine (10 g, 57.8 mmol) was added to a solution of 2-[(aminooxy)sulfonyl]-1,3,5-trimethylbenzene (12.4 g, 57.8 mmol) in dichloromethane (100 mL) at 0° C. in batches, then the mixture was stirred at 0° C. for 1.5 hours; methyl tert-butyl ether (150 mL) was added to the reaction mixture, and the mixture was slurried for 15 min, then filtered and the filter cake was dried to obtain crude white solid 2,4,6-trimethylbenzenesulfonic acid 1-amino-5-bromo-3-methoxy-2-methylpyridine-1-ium (15 g, yield: 62%).

Step 2: ethyl 4-bromo-6-methoxypyrazolo[1,5-a]pyridine-3-carboxylate

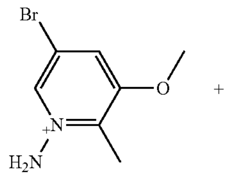

-continued

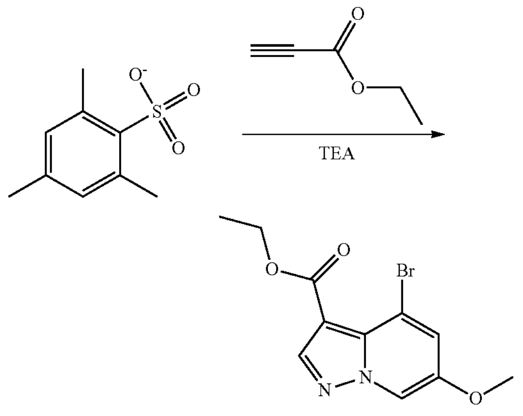

Ethyl propiolate (7.05 g, 71.94 mmol) was added to a solution of 2,4,6-trimethylbenzenesulfonic acid 1-amino-5-bromo-3-methoxy-2-methylpyridin-1-ium (15 g, 35.97 mmol), triethylamine (10.9 g, 107.91 mmol) and anhydrous N,N-dimethylformamide (100 mL) dropwise at 0° C.; then the reaction mixture was stirred at room temperature for 16 hours, added to ice water and slurried for 15 min, then filtered, the filter cake was dried, and then separated by column chromatography to obtain light yellow solid ethyl 4-bromo-6-methoxypyrazolo[1,5-a]pyridine-3-carboxylate (1 g, yield: 9%).

MS m/z (ESI): 299.0 $[M+H]^+$.

Step 3: 4-bromo-6-methoxypyrazolo[1,5-a]pyridine-3-carboxylic acid

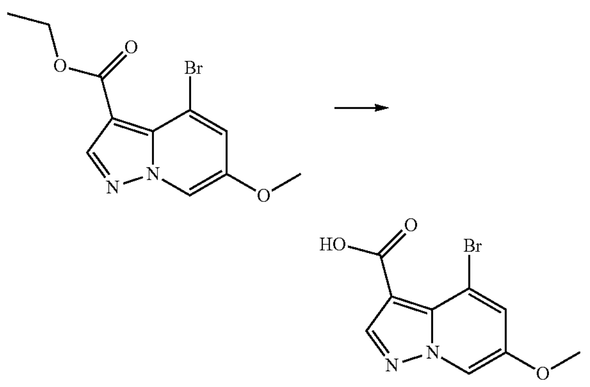

Lithium hydroxide monohydrate (281 mg, 6.68 mmol) was added to a solution of ethyl 4-bromo-6-methoxypyrazolo[1,5-a]pyridine-3-carboxylate (1 g, 3.34 mmol) in methanol (10 mL) and water (10 mL), then the mixture was stirred at room temperature for 16 hours; after the reaction was completed, the pH value was adjusted to 2 with dilute hydrochloric acid, and a white solid was precipitated; then the mixture was filtered, and the filter cake was washed with water and dried to obtain white solid 4-bromo-6-methoxypyrazolo[1,5-a]pyridine-3-carboxylic acid (800 mg, crude product).

MS m/z (ESI): 271.0 $[M+H]^+$.

Step 4: 4-bromo-6-methoxy-N,N-dimethylpyrazolo[1,5-a]pyridine-3-carboxamide

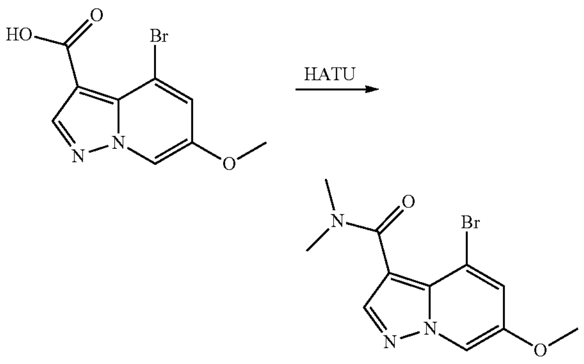

A mixture of 4-bromo-6-methoxypyrazolo[1,5-a]pyridine-3-carboxylic acid (800 mg, 2.96 mmol), 2-(7-azabenzotriazol-1-yl)-N,N,N',N'-tetramethyluronium hexafluorophosphate (1.35 g, 3.55 mmol), triethylamine (897 mg, 8.88 mmol), N,N-dimethylamine hydrochloride (485 mg, 5.92 mmol) and dichloromethane (15 mL) was stirred at room temperature for 16 hours; after the reaction was completed, the mixture was quenched with water, extracted with ethyl acetate, and the organic phase was washed with saturated saline, dried over anhydrous sodium sulfate, filtered, and the filtrate was concentrated under reduced pressure to dryness and separated by column chromatography (dichloromethane/methanol=10:1) to obtain colorless oil 4-bromo-6-methoxy-N,N-dimethylpyrazolo[1,5-a]pyridine-3-carboxamide (700 mg, yield: 80%).

MS m/z (ESI): 298.0 [M+H]$^+$.

Step 5: 4-bromo-6-hydroxy-N,N-dimethylpyrazolo[1,5-a]pyridine-3-carboxamide

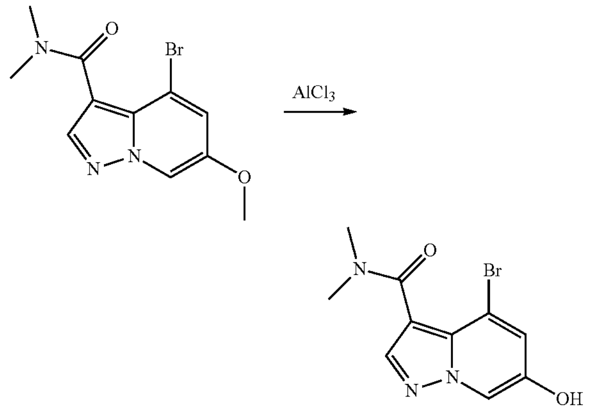

Aluminum trichloride (1.57 g, 11.8 mmol) was added to a solution of 4-bromo-6-methoxy-N,N-dimethylpyrazolo[1,5-a]pyridine-3-carbonitrile (700 mg, 2.36 mmol) in 1.2-dichloroethane (10 mL) in batches, then the mixture was stirred at 80° C. for 2 hours, cooled to room temperature, quenched with sodium sulfate decahydrate, filtered, the filter cake was washed with dichloromethane, the filtrate was washed with saturated saline; the organic phase was dried over anhydrous sodium sulfate, filtered, and the filtrate was concentrated under reduced pressure to dryness to obtain brown solid 4-bromo-6-hydroxy-N,N-dimethylpyrazolo[1,5-a]pyridine-3-carboxamide (620 mg, crude product).

MS m/z (ESI): 282.0 [M−H]$^+$.

Step 6: 4-bromo-6-(2-hydroxy-2-methylpropoxy)-N,N-dimethylpyrazolo[1,5-a]pyridine-3-carboxamide

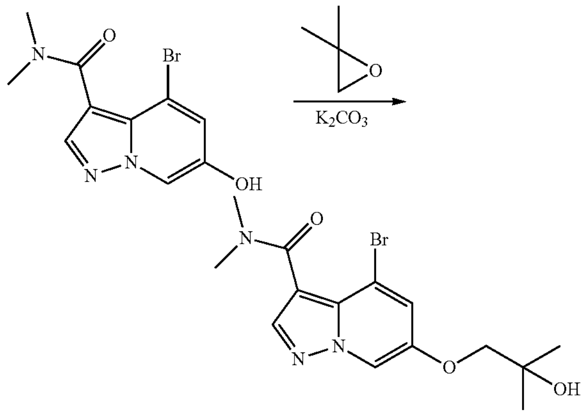

2,2-Dimethyloxirane (317 mg, 4.4 mmol) was added to solution of 4-bromo-6-methoxy-N,N-dimethylpyrazolo[1,5-a]pyridine-3-carboxamide (620 mg, 2.2 mmol), potassium carbonate (605 mg, 4.4 mmol) and acetonitrile (10 mL), and then the reaction mixture was stirred at 80° C. for 16 hours; the reaction mixture was concentrated under reduced pressure to dryness, separated by column chromatography (dichloromethane/methanol=10:1) to obtain colorless oil 4-bromo-6-(2-hydroxy-2-methylpropoxy)-N,N-dimethylpyrazolo[1,5-a]pyridine-3-carboxamide (520 mg, yield: 67%).

MS m/z (ESI): 356.2 [M+H]$^+$.

Step 7: 4-(6-fluoropyridin-3-yl)-6-(2-hydroxy-2-methylpropoxy)-N,N-dimethylpyrazolo[1,5-a]pyridine-3-carboxamide

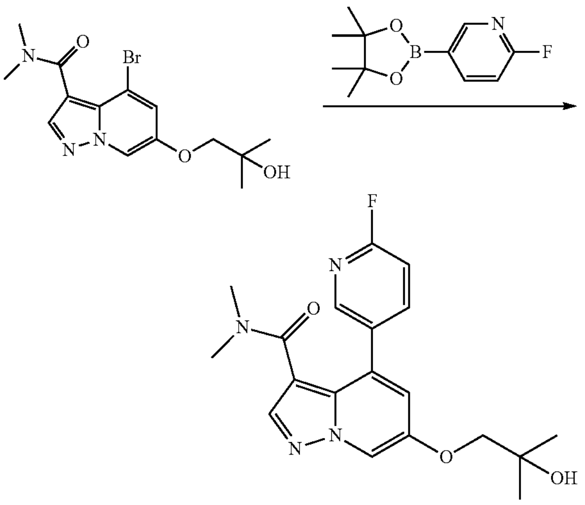

1,1'-Bis(diphenylphosphino)ferrocene-palladium(II)dichloride dichloromethane complex (60 mg, 0.07 mmol) was added to a mixed solution of 4-bromo-6-(2-hydroxy-2-methylpropoxy)-N,N-dimethylpyrazolo[1,5-a]pyridine-3-carboxamide (520 mg, 1.46 mmol), 2-fluoro-5-(4,4,5,5-tetramethyl-1,3,2-dioxaborolan-2-yl)pyridine (391 mg, 1.75 mmol), potassium acetate (286 mg, 2.92 mmol) and dioxane (10 mL), the mixture was replaced with nitrogen three times and then stirred at 100° C. for 16 hours under the protection of the protection of nitrogen; after the reaction was cooled and filtered, the filtrate was concentrated under reduced pressure to dryness and separated by column chromatography (dichloromethane/methanol=10:1) to obtain colorless oil 4-(6-fluoropyridin-3-yl)-6-(2-hydroxy-2-methylpropoxy)-N,N-dimethylpyrazolo[1,5-a]pyridine-3-carboxamide (405 mg, yield: 75%).

MS m/z (ESI): 373.2 [M+H]$^+$.

Step 8: tert-butyl 3-(5-(3-(dimethylcarbamoyl)-6-(2-hydroxy-2-methylpropoxy)pyrazolo[1,5-a]pyridin-4-yl)pyridin-2-yl)-3,6-diazabicyclo[3.1.1]heptane-6-carboxylate

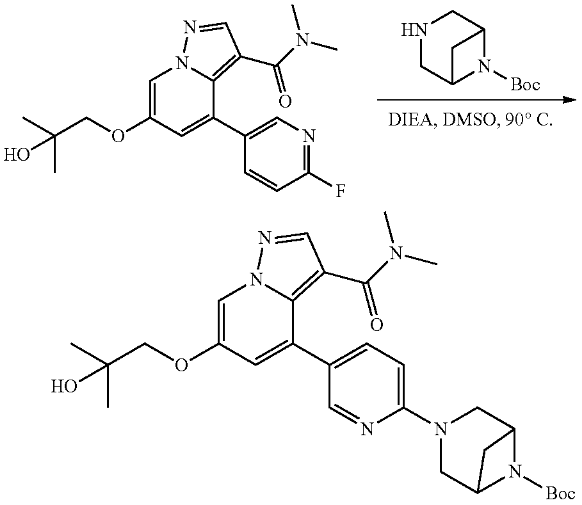

A mixed solution of 4-(6-fluoropyridin-3-yl)-6-(2-hydroxy-2-methylpropoxy)-N,N-dimethylpyrazolo[1,5-a]pyridine-3-carboxamide (405 mg, 1.09 mmol), tert-butyl 3,6-diazabicyclo[3.1.1]heptane-6-carboxylate (432 mg, 2.18 mmol), N,N-diisopropylethylamine (422 mg, 3.27 mmol) and dimethyl sulfoxide (8 mL) was stirred at 100° C. for 24 hours; the reaction mixture was quenched with water and extracted with ethyl acetate (50 mL*3), the combined organic phase was washed with saturated saline, the organic phase was dried over anhydrous sodium sulfate, filtered, and the filtrate was concentrated under reduced pressure to dryness and separated by column chromatography (dichloromethane/methanol=10:1) to obtain colorless oil tert-butyl 3-(5-(3-(dimethylcarbamoyl)-6-(2-hydroxy-2-methylpropoxy)pyrazolo[1,5-a]pyridin-4-yl)pyridin-2-yl)-3,6-diazabicyclo[3.1.1]heptane-6-carboxylate (280 mg, yield: 47%).

MS m/z (ESI): 551.2 [M+H]$^+$.

Step 9: 4-(6-fluoropyridin-3-yl)-6-(2-hydroxy-2-methylpropoxy)-N,N-dimethylpyrazolo[1,5-a]pyridine-3-carboxamide

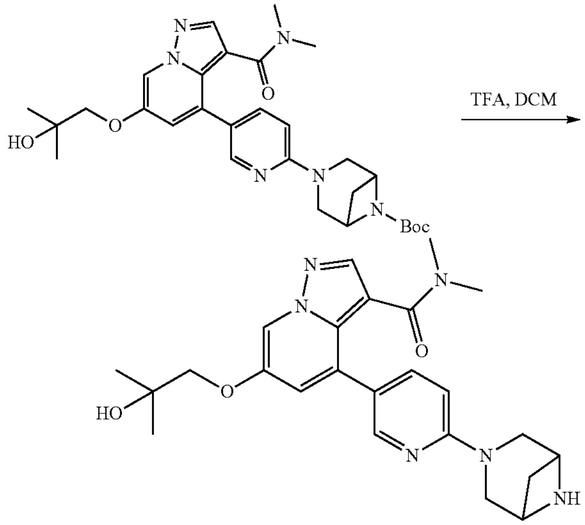

Tert-butyl 3-(5-(3-(dimethylcarbamoyl)-6-(2-hydroxy-2-methylpropoxy)pyrazolo[1,5-a]pyridin-4-yl)pyridin-2-yl)-3,6-diazabicyclo[3.1.1]heptane-6-carboxylate (280 mg, 0.51 mmol) was dissolved in dichloromethane (9 mL), then trifluoroacetic acid (3 mL) was added thereto at room temperature for 1 hour; after the reaction was completed, concentrated under reduced pressure to dryness and used directly in the next step without purification to obtain light yellow oil 4-(6-fluoropyridin-3-yl)-6-(2-hydroxy-2-methylpropoxy)-N,N-dimethylpyrazolo[1,5-a]pyridine-3-carboxamide (300 mg, crude product).

MS m/z (ESI): 451.2 [M+H]$^+$.

Step 10: 4-(6-(6-((5-fluoro-6-methoxypyridin-3-yl)methyl)-3,6-diazabicyclo[3.1.1]heptan-3-yl)pyridin-3-yl)-6-(2-hydroxy-2-methylpropoxy)-N,N-dimethylpyrazolo[1,5-a]pyridine-3-carboxamide

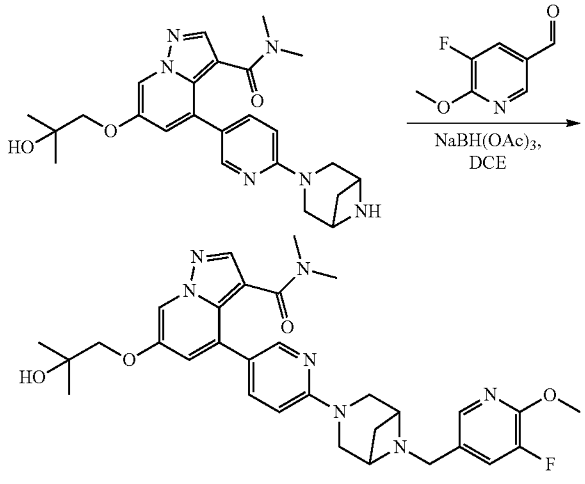

The title compound was obtained with reference to step 9 of embodiment 14 by using 4-(6-fluoropyridin-3-yl)-6-(2-hydroxy-2-methylpropoxy)-N,N-dimethylpyrazolo[1,5-a]pyridine-3-carboxamide as raw material.

MS m/z (ESI): 590.3 [M+H]$^+$.

Embodiment 29

6-(2-Methoxyethoxy)-4-(6-(6-((6-methoxypyridin-3-yl)methyl)-3,6-diazabicyclo[3.1.1]heptan-3-yl)pyridin-3-yl)-N,N-dimethylpyrazolo[1,5-a]pyridine-3-carboxamide

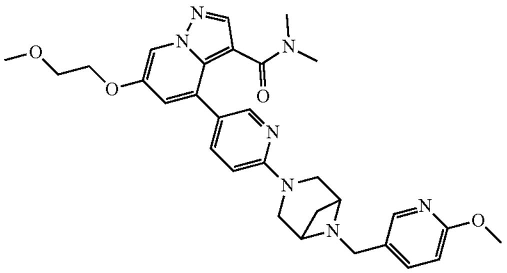

Step 1: 8-bromo-6-(2-methoxyethoxy)-N,N-dimethylindolizine-1-carboxamide

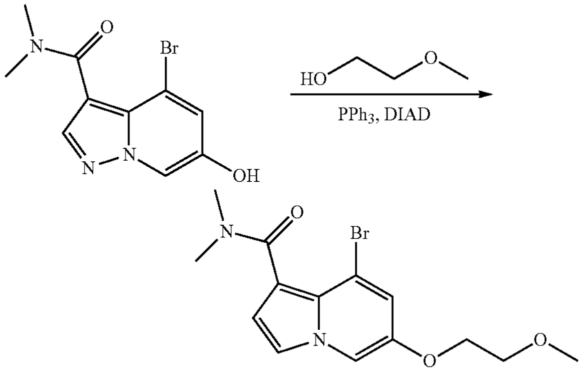

Diisopropyl azodicarboxylate (1.28 g, 6.36 mmol) was added dropwise to a mixed solution of 4-bromo-6-hydroxy-N,N-dimethylpyrazolo[1,5-a]pyridine-3-carboxamide (1.2 g, 4.24 mmol), 2-methoxyethan-1-ol (322 mg. 5.09 mmol), triphenylphosphine (1.67 g, 6.36 mmol) and tetrahydrofuran (15 mL), then the mixture was stirred at room temperature under the protection of nitrogen for 16 hours; after the reaction was completed, the mixture was cooled, concentrated under reduced pressure to dryness and separated by column chromatography to obtain colorless oil 8-bromo-6-(2-methoxyethoxy)-N,N-dimethylindolizine-1-carboxamide (1.3 g, yield: 90%).

MS m/z (ESI): 341.0 [M+H]$^+$ 6-(2-Methoxyethoxy)-4-(6-(6-((6-methoxypyridine-3-yl)methyl)-3,6-diazabicyclo[3.1.1]heptan-3-yl)pyridin-3-yl)-N,N-dimethylpyrazolo[1,5-a]pyridine-3-carboxamide was obtained by the reaction of step 2 to step 5 with reference to the synthesis of step 7 to step 10 of embodiment 28.

MS m/z (ESI): 558.3 [M+H]$^+$.

Embodiment 30

N-Cyclopropyl-6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carboxamide

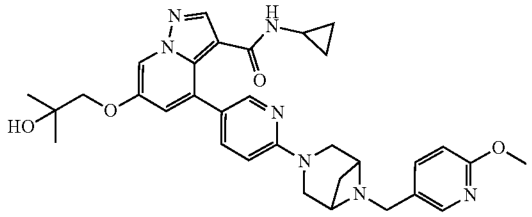 [SMILES: COc1ccc(CN2C3CC2CN(c2ccc(-c4cc(OCC(C)(C)O)cn5ncc(C(=O)NC6CC6)c45)cn2)C3)cn1]

With reference to the synthesis of embodiment 28, the title compound was obtained by replacing N, N-dimethylamine hydrochloride with cyclopropylamine hydrochloride in step 4.

MS m/z (ESI): 584.3 [M+H]$^+$.

Embodiment 31

6-(3-Hydroxy-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

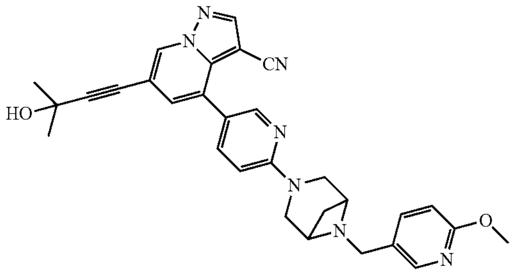 [SMILES: COc1ccc(CN2C3CC2CN(c2ccc(-c4cc(C#CC(C)(C)O)cn5ncc(C#N)c45)cn2)C3)cn1]

Step 1: 6-bromo-4-(4,4,5,5-tetramethyl-1,3,2-dioxaborolan-2-yl)pyrazolo[1,5-a]pyridine-3-carbonitrile

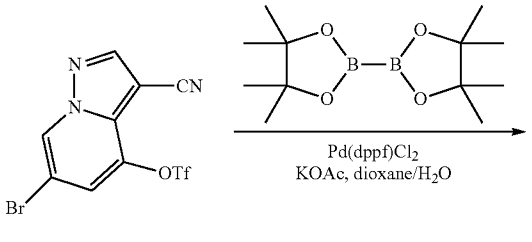

-continued

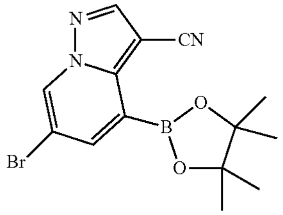

6-Bromo-4-(4,4,5,5-tetramethyl-1,3,2-dioxaborolan-2-yl) pyrazolo[1,5-a]pyridine-3-carbonitrile (620 mg, white solid, 56%) was obtained by using 6-bromo-3-cyanopyrazolo[1,5-a]pyridin-4-yl trifluoromethanesulfonate as raw material with reference to the step 7 of embodiment 1.

MS m/z (ESI): 348.0 $[M+H]^+$.

Step 2: 6-(3-hydroxy-3-methylbut-1-yn-1-yl)-4-(4,4,5,5-tetramethyl-1,3,2-dioxaborolan-2-yl)pyrazolo[1,5-a]pyridine-3-carbonitrile

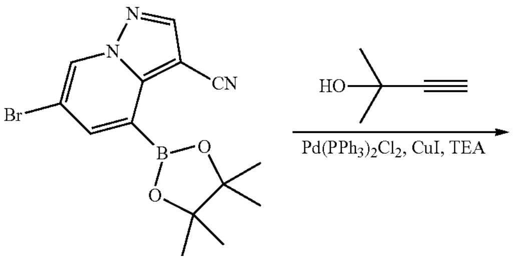

-continued

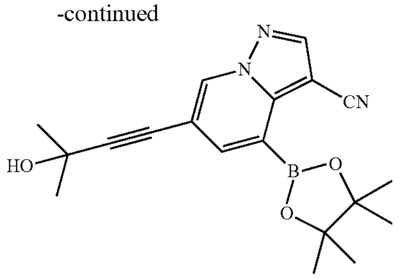

6-Bromo-4-(4,4,5,5-tetramethyl-1,3,2-dioxaborolan-2-yl) pyrazolo[1,5-a]pyridine-3-carbonitrile (300 mg, 0.86 mmol) was dissolved in 20 mL of triethylamine, and 2-methylbut-3-yn-2-ol (108 mg, 1.3 mmol), $Pd_2(PPh_3)_2Cl_2$ (120 mg, 0.17 mmol), CuI (17 mg, 0.09 mmol) were added thereto, and the reaction was carried out overnight at 65° C. under the protection of nitrogen. 10 mL of ammonium chloride aqueous solution was added, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 6-(3-hydroxy-3-methylbut-1-yn-1-yl)-4-(4,4,5,5-tetramethyl-1,3,2-dioxaborolan-2-yl)pyrazolo[1,5-a]pyridine-3-carbonitrile (197 mg, white solid, yield was 65%).

MS m/z (ESI): 352.1 $[M+H]^+$.

Step 3: 6-(3-hydroxy-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

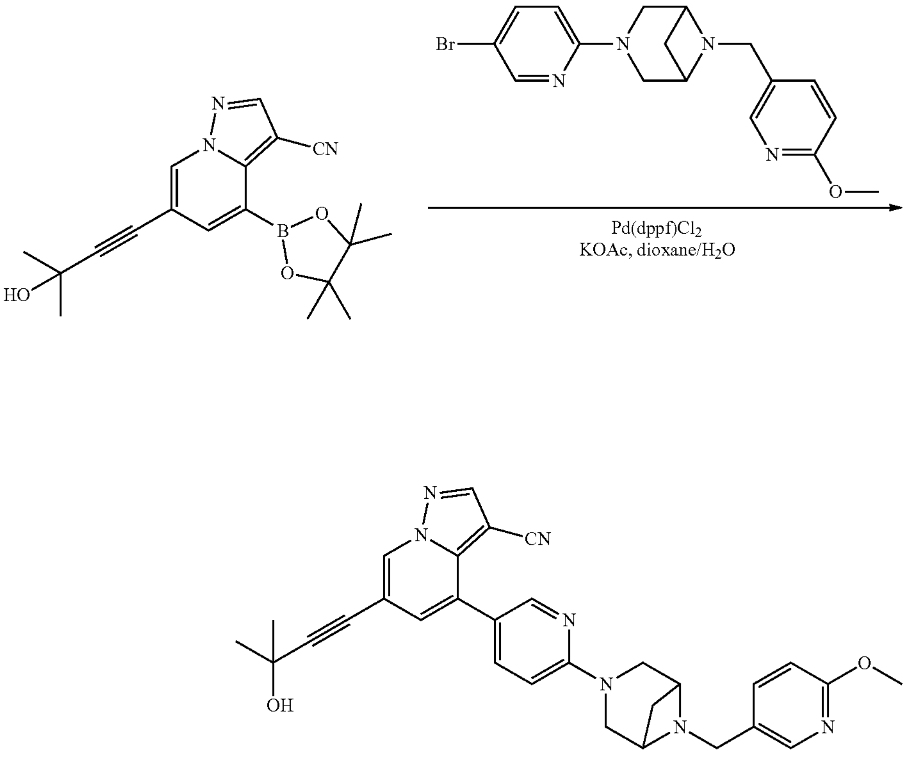

6-(3-Hydroxy-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (25 mg, white solid, 43%) was obtained by using 6-(3-hydroxy-3-methylbut-1-yn-1-yl)-4-(4,4,5,5-tetramethyl-1,3,2-dioxaborolan-2-yl)pyrazolo[1,5-a]pyridine-3-carbonitrile and 3-(5-bromopyridin-2-yl)-6-((6-methoxypyridin-3-yl)methyl)-3,6-diazabicyclo[3.1.1]heptane as raw materials with reference to the step 8 of embodiment 1.

MS m/z (ESI): 520.2 $[M+H]^+$.

$^1H$ NMR (400 MHz, MeOD) δ 8.83 (s, 1H), 8.47 (s, 1H), 8.35 (d, J=2.1 Hz, 1H), 8.09 (s, 1H), 7.84 (dd, J=8.8, 2.3 Hz, 1H), 7.72 (dd, J=8.4, 2.1 Hz, 1H), 7.41 (s, 1H), 6.88 (d, J=8.9 Hz, 1H), 6.78 (d, J=8.5 Hz, 1H), 3.91 (s, 1H), 3.88 (s, 4H), 3.79 (d, J=5.7 Hz, 2H), 3.66 (s, 1H), 3.63 (s, 3H), 2.74-2.62 (m, 1H), 1.70 (d, J=8.9 Hz, 1H), 1.59 (s, 6H).

Embodiment 32

6-(3-Hydroxy-3-methylbut-1-yn-1-yl)-4-(6-(4-((6-methoxypyridin-3-yl)oxo)piperidin-1-yl)pyridin-3-yl)pyrazolo[1,5-a]pyridine-3-carbonitrile

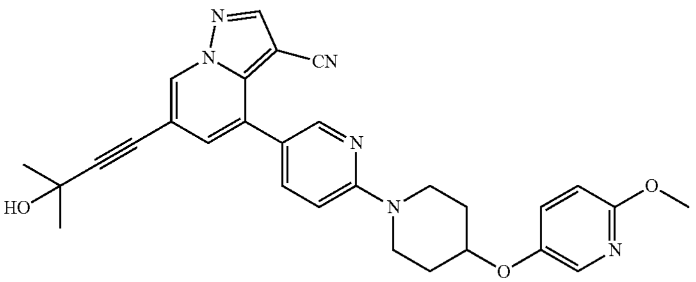

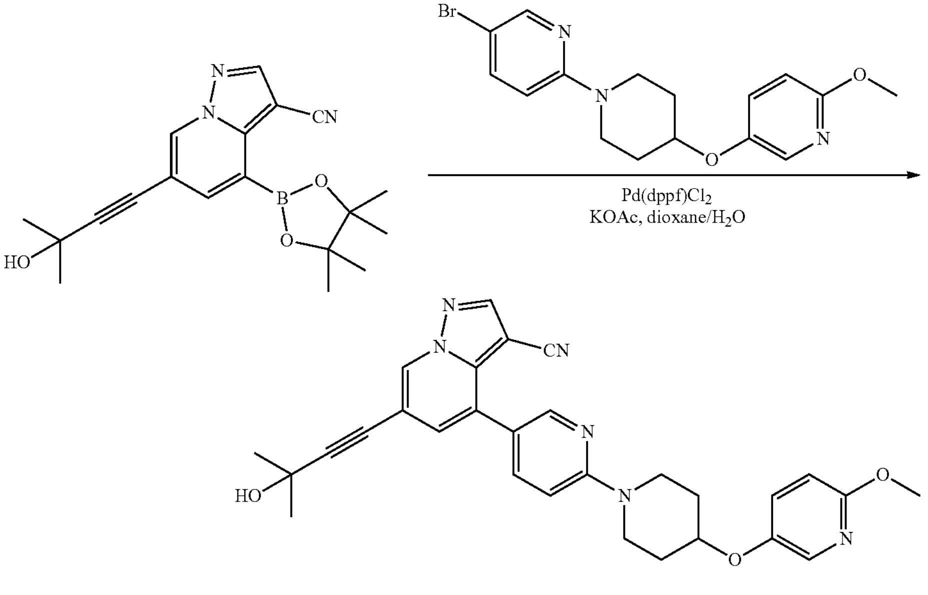

6-(3-Hydroxy-3-methylbut-1-yn-1-yl)-4-(6-(4-((6-methoxypyridin-3-yl)oxo)piperidin-1-yl)pyridin-3-yl)pyrazolo[1,5-a]pyridine-3-carbonitrile (33 mg, white solid, 49%) was obtained by using 6-(3-hydroxy-3-methylbut-1-yn-1-yl)-4-(4,4,5,5-tetramethyl-1,3,2-dioxaborolan-2-yl)pyrazolo[1,5-a]pyridine-3-carbonitrile and 5-bromo-2-(4-((6-methoxypyridin-3-yl)oxo)piperidin-1-yl)pyridine as raw materials with reference to the step 8 of embodiment 1.

MS m/z (ESI): 509.2 $[M+H]^+$.

$^1$H NMR (400 MHz, MeOD) δ 8.82 (s, 1H), 8.45 (s, 1H), 8.29 (d, J=2.2 Hz, 1H), 7.84 (d, J=2.9 Hz, 1H), 7.76 (dd, J=8.8, 2.4 Hz, 1H), 7.43 (dd, J=8.9, 3.0 Hz, 1H), 7.39 (s, 1H), 6.99 (d, J=9.0 Hz, 1H), 6.76 (d, J=8.9 Hz, 1H), 4.67-4.47 (m, 2H), 4.10-3.98 (m, 2H), 3.86 (s, 3H), 3.60-3.49 (m, 2H), 2.11-2.04 (m, 2H), 1.84-1.76 (m, 2H), 1.58 (s, 6H).

Embodiment 33

N-(1-(5-(3-cyano-6-(3-hydroxy-3-methylbut-1-yn-1-yl)pyrazolo[1,5-a]pyridin-4-yl)pyridin-2-yl)-4-methylpiperidin-4-yl)-5-fluoro-2-methylbenzamide

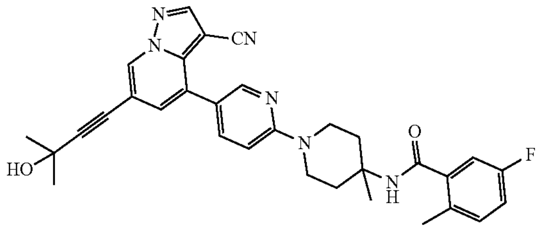 [SMILES: Cc1ccc(F)cc1C(=O)NC1(C)CCN(c2ccc(-c3cc(C#CC(C)(C)O)cn4ncc(C#N)c34)cn2)CC1]

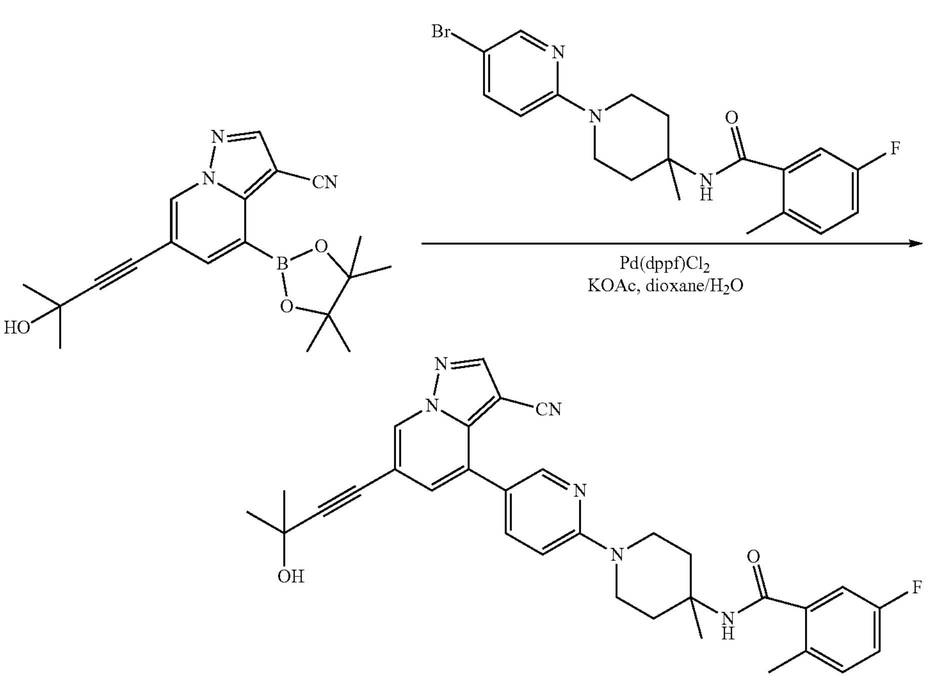

N-(1-(5-(3-cyano-6-(3-hydroxy-3-methylbut-1-yn-1-yl)pyrazolo[1,5-a]pyridin-4-yl)pyridin-2-yl)-4-methylpiperidin-4-yl)-5-fluoro-2-methylbenzamide (30 mg, white solid, 45%) was obtained by using 6-(3-hydroxy-3-methylbut-1-yn-1-yl)-4-(4,4,5,5-tetramethyl-1,3,2-dioxaborolan-2-yl)pyrazolo[1,5-a]pyridine-3-carbonitrile and N-(1-(5-bromopyridin-2-yl)-4-methylpiperidin-4-yl)-5-fluoro-2-methylbenzamide as raw materials with reference to step 8 of embodiment 1.

MS m/z (ESI): 551.2 $[M+H]^+$.

$^1$H NMR (400 MHz, Methanol-$d_4$) δ 8.82 (d, J=1.3 Hz, 1H), 8.46 (s, 1H), 8.29 (d, J=2.5 Hz, 1H), 7.76 (dd, J=9.0, 2.5 Hz, 1H), 7.41-7.36 (m, 1H), 7.28-7.21 (m, 1H), 7.09-7.02 (m, 2H), 6.98 (d, J=8.9 Hz, 1H), 4.10-4.00 (m, 2H), 3.44-3.39 (m, 2H), 2.44-2.38 (m, 2H), 2.38 (s, 3H), 1.77-1.69 (m, 2H), 1.58 (s, 6H), 1.54 (s, 3H).

Embodiment 34

6-(2-Cyano-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

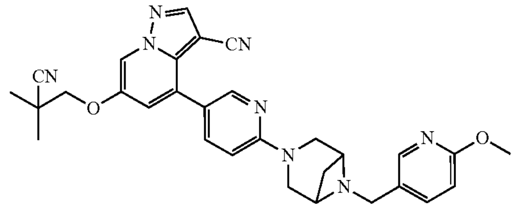 [SMILES: COc1ccc(CN2C3CC2CN(c2ccc(-c4cc(OCC(C)(C)C#N)cn5ncc(C#N)c45)cn2)C3)cn1]

Step 1: 4-bromo-6-(2-cyano-2-methylpropoxy)pyrazolo[1,5-a]pyridine-3-carbonitrile

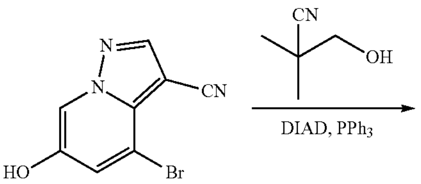

-continued

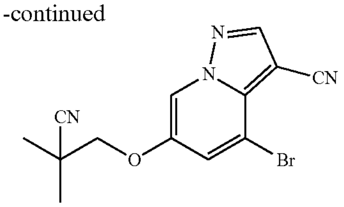

4-Bromo-6-hydroxypyrazolo[1,5-a]pyridine-3-carbonitrile (200 mg, 0.84 mmol) and 3-hydroxy-2,2-dimethylpropionitrile (83 mg, 0.84 mmol) were dissolved in 5 mL of anhydrous tetrahydrofuran solution, and then triphenylphosphine (330 mg, 1.26 mmol) and diisopropyl azodicarboxylate (202 mg, 1 mmol) were added thereto, and the reaction mixture was stirred at 0° C. for 12 hours under the protection of nitrogen. The reaction mixture was concentrated, dissolved in ethyl acetate (10 mL), washed three times with water (5 mL*3), and the organic phase was concentrated and separated by column chromatography (dichloromethane/methanol: 30/1) and purified to obtain product 4-bromo-6-(2-cyano-2-methylpropoxy)pyrazolo[1,5-a]pyridine-3-carbonitrile (180 mg, yellow solid, the yield was 67.1%).

MS m/z (ESI): 319.0 $[M+H]^+$. 321.0 $[M+H+2]^+$.

Step 2: 6-(2-cyano-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

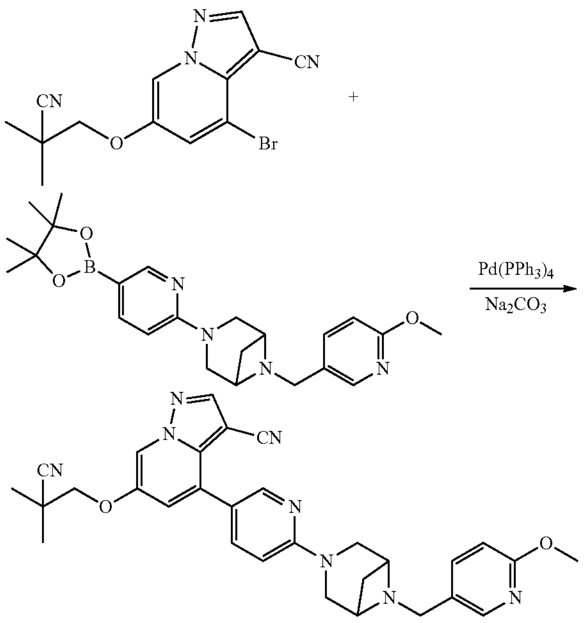

34

The product 6-(2-cyano-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 4-bromo-6-(2-cyano-2-methylpropoxy)pyrazolo[1,5-a]pyridine-3-carbonitrile as raw material with reference to step 3 of embodiment 7.

MS m/z (ESI): 535.2$[M+H]^+$.

$^1H$ NMR (400 MHz, Chloroform-d) δ 8.43 (d, J=2.5 Hz, 1H), 8.23 (s, 1H), 8.16 (d, J=2.1 Hz, 1H), 8.13 (d, J=2.4 Hz, 1H), 7.81-7.75 (m, 2H), 7.19 (d, J=2.1 Hz, 1H), 6.75 (d, J=8.5 Hz, 1H), 6.70 (d, J=8.8 Hz, 1H), 3.97 (s, 3H), 3.96-3.86 (m, 6H), 3.78-3.64 (m, 4H), 2.94-2.80 (m, 1H), 1.78-1.72 (m, 1H), 1.55 (s, 6H).

Embodiment 35

6-(2-Cyano-2-methylpropoxy)-4-(6-(4-((6-methylpyridazin-3-yl)oxo)piperidin-1-yl)pyridin-3-yl)pyrazolo[1,5-a]pyridine-3-carbonitrile

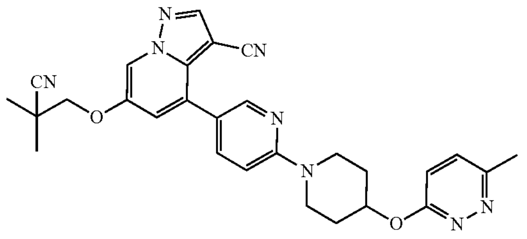 [SMILES: Cc1ccc(OC2CCN(c3ccc(-c4cc(OCC(C)(C)C#N)cn5ncc(C#N)c45)cn3)CC2)nn1]

Step 1: 6-(2-cyano-2-methylpropoxy)-4-(6-fluoropyridin-3-yl)pyrazolo[1,5-a]pyridine-3-carbonitrile

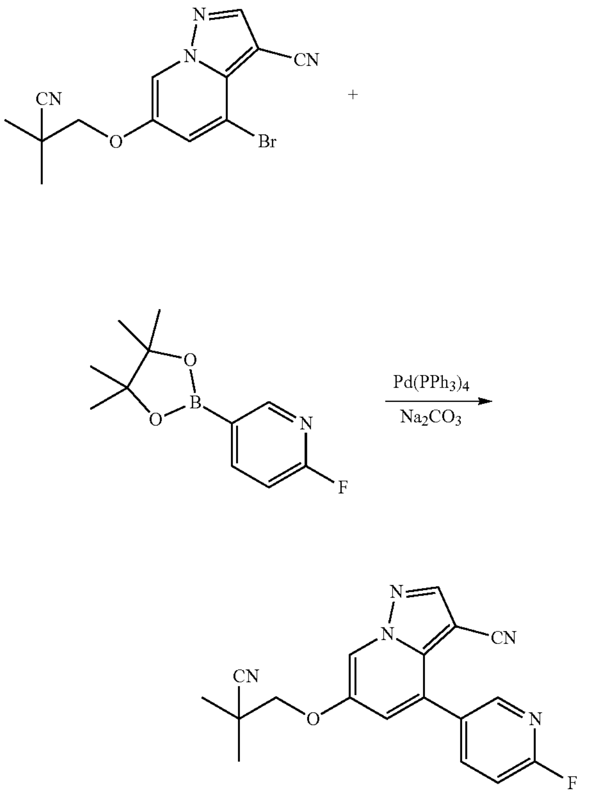

The product 6-(2-cyano-2-methylpropoxy)-4-(6-fluoropyridin-3-yl)pyrazolo[1,5-a]pyridine-3-carbonitrile was obtained by using 4-bromo-6-(2-cyano-2-methylpropoxy)pyrazolo[1,5-a]pyridine-3-carbonitrile as raw material with reference to step 3 of embodiment 7.

MS m/z (ESI): 336.1$[M+H]^+$.

Step 2: 6-(2-cyano-2-methylpropoxy)-4-(6-(4-((6-methylpyridazin-3-yl)oxo)piperidin-1-yl)pyridin-3-yl)pyrazolo[1,5-a]pyridine-3-carbonitrile

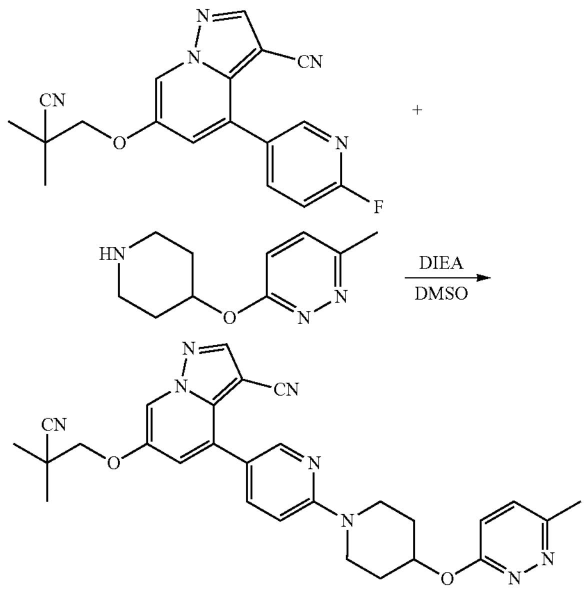

The product 6-(2-cyano-2-methylpropoxy)-4-(6-(4-((6-methylpyridazin-3-yl)oxo)piperidin-1-yl)pyridin-3-yl)pyrazolo[1,5-a]pyridine-3-carbonitrile was obtained by using 6-(2-cyano-2-methylpropoxy)-4-(6-fluoropyridin-3-yl)pyrazolo[1,5-a]pyridine-3-carbonitrile as raw material with reference to step 2 of embodiment 8.

MS m/z (ESI): 509.2$[M+H]^+$.

Embodiment 36

6-((1-Cyanocyclopropyl)methoxy)-4-(6-(4-(pyridin-2-oxy)piperidin-1-yl)pyridin-3-yl)pyrazolo[1,5-a]pyridine-3-carbonitrile

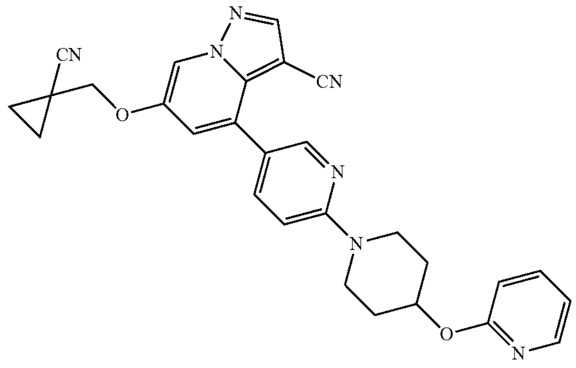 [SMILES: N#Cc1cnn2cc(OCC3(C#N)CC3)cc(-c3ccc(N4CCC(Oc5ccccn5)CC4)nc3)c12]

Step 1: 4-bromo-6-((1-cyanocyclopropyl)methoxy)pyrazolo[1,5-a]pyridine-3-carbonitrile

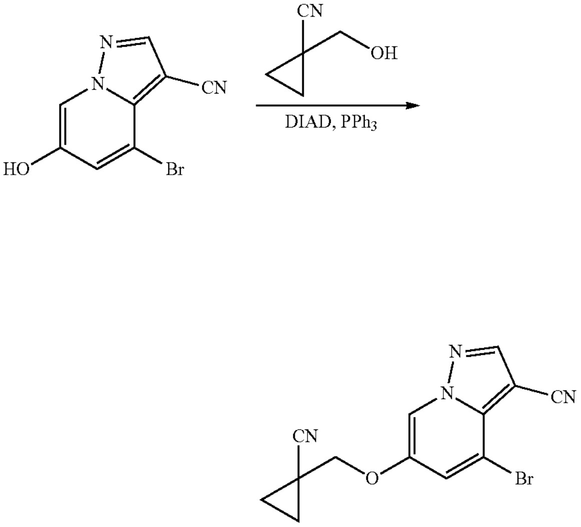

The product 4-bromo-6-((1-cyanocyclopropyl)methoxy)pyrazolo[1,5-a]pyridine-3-carbonitrile was obtained by using 4-bromo-6-hydroxypyrazolo[1,5-a]pyridine-3-carbonitrile as raw material with reference to step 1 of embodiment 34. MS m/z (ESI): 317.0$[M+H]^+$, 319.0$[M+H+2]^+$.

Step 2: 6-((1-cyanocyclopropyl)methoxy)-4-(6-fluoropyridin-3-yl)pyrazolo[1,5-a]pyridine-3-carbonitrile

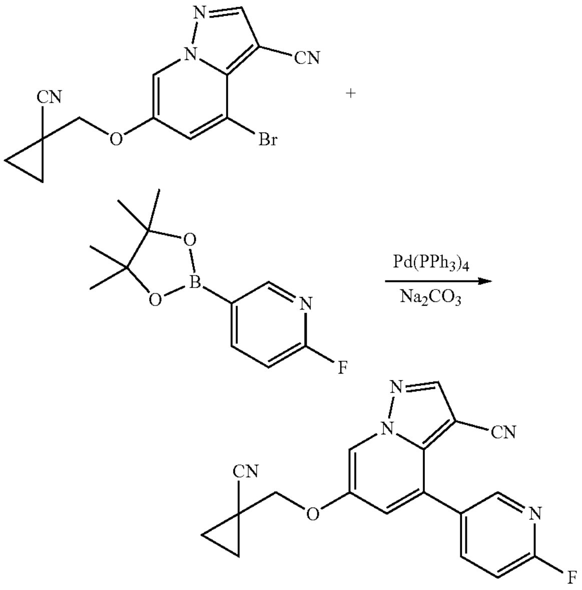

The product 6-((1-cyanocyclopropyl)methoxy)-4-(6-fluoropyridin-3-yl)pyrazolo[1,5-a]pyridine-3-carbonitrile was obtained by using 4-bromo-6-((1-cyanocyclopropyl)methoxy)pyrazolo[1,5-a]pyridine-3-carbonitrile as raw material with reference to step 3 of embodiment 7.

MS m/z (ESI): 334.1$[M+H]^+$.

Step 3: 6-((1-cyanocyclopropyl)methoxy)-4-(6-(4-(pyridin-2-oxy)piperidin-1-yl)pyridin-3-yl)pyrazolo[1,5-a]pyridine-3-carbonitrile

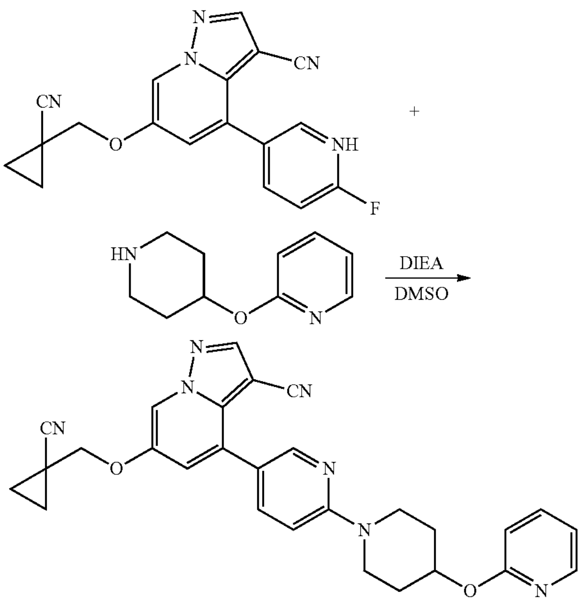

36

The product 6-((1-cyanocyclopropyl)methoxy)-4-(6-(4-(pyridin-2-oxy)piperidin-1-yl)pyridin-3-yl)pyrazolo[1,5-a]pyridine-3-carbonitrile was obtained by using 6-((1-cyano-cyclopropyl)methoxy)-4-(6-fluoropyridin-3-yl)pyrazolo[1,5-a]pyridine-3-carbonitrile as raw material with reference to step 2 of embodiment 8.

MS m/z (ESI): 492.2[M+H]$^+$.

Embodiment 37

6-((6-Methoxypyridin-3-yl)methyl)-3-(5-(6-((1-methylazetidin-3-yl)methoxy)-[1,2,4]triazolo[1,5-a]pyridin-8-yl)pyridin-2-yl)-3,6-diazabicyclo[3.1.1]heptane

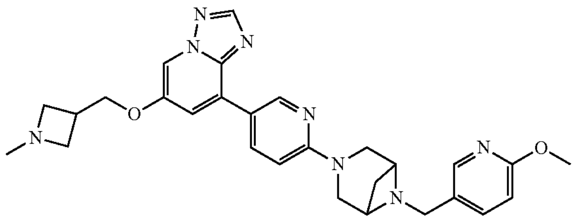

Step 1: Preparation of N-(3,5-dibromopyridin-2-yl)-N'-hydroxyformimidamide

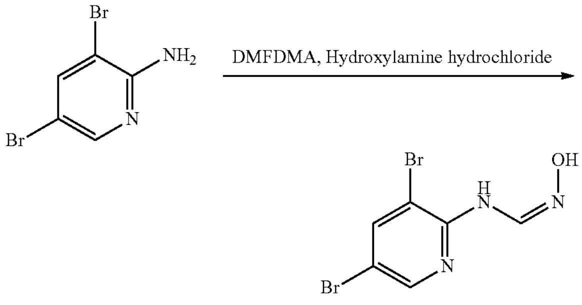

3,5-Dibromopyridin-2-amine (10 g, 39.7 mmol) was dissolved in isopropanol (100 mL), and DMFDMA (6.15 g, 51.6 mmol) was added thereto. The reaction mixture was stirred at 100° C. for 2 hours. The reaction mixture was cooled to 50° C., hydroxylamine hydrochloride (3.59 g, 51.6 mmol) was added thereto, and then stirred overnight. The reaction mixture was evaporated to dryness directly. The crude product was purified by column chromatography to obtain the target molecule N-(3,5-dibromopyridine-2-yl)-N'-hydroxyformamidine (11 g, yield: 94%).

MS m/z (ESI): 293.8[M+H]$^+$.

Step 2: Preparation of 6,8-dibromo-[1,2,4]triazolo[1,5-a]pyridine

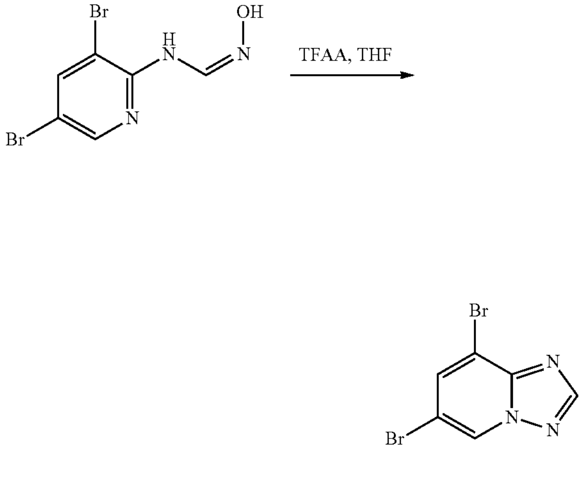

N-(3,5-dibromopyridin-2-yl)-N'-hydroxyformamidine (11 g, 37.3 mmol) was dissolved in anhydrous tetrahydrofuran (100 mL), and TFAA (8.62 g, 41.0 mmol) was slowly added thereto dropwise at 0° C. After the addition was completed, the reaction mixture was slowly raised to room temperature, and stirring was continued for 3 hours. $NaHCO_3$ aqueous solution was slowly added to the reaction mixture to quench the reaction, and then the mixture was extracted with methyl tert-butyl ether. The organic phase was dried and evaporated to dryness. The crude product was purified by column chromatography to obtain 6,8-dibromo-[1,2,4]triazolo[1,5-a]pyridine (8.2 g, yield: 79%).

MS m/z (ESI): 275.8[M+H]$^+$.

Step 3: Preparation of 3-(5-(6-bromo-[1,2,4]triazolo[1,5-a]pyridin-8-yl)pyridin-2-yl)-6-((6-methoxypyridin-3-yl)methyl)-3,6-diazabicyclo[3.1.1]heptane

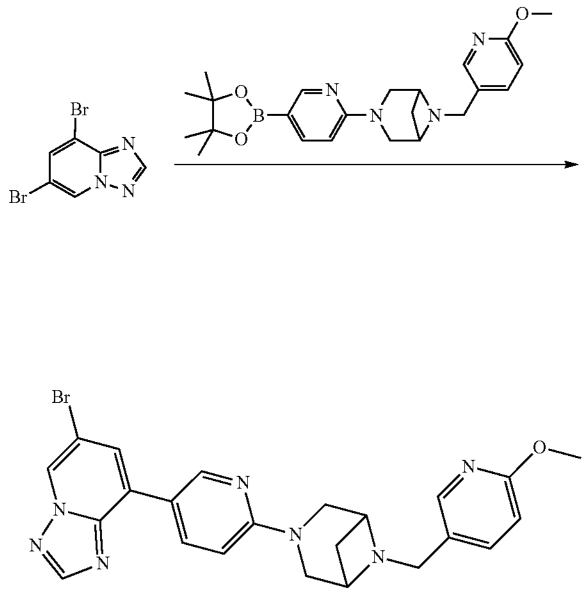

6,8-Dibromo-[1,2,4]triazolo[1,5-a]pyridine (4 g, 14.4 mmol) was dissolved in DMF (50 mL), and 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane (7.3 g, 17.3 mmol) and saturated sodium carbonate aqueous solution (15 mL) were added thereto. [1,1'-Bis(diphenylphosphino)ferrocene]palladium dichloride (1.05 g, 1.44 mmol) was added to the reaction mixture under the protection of nitrogen. The reaction mixture was stirred at 90° C. for 3 hours. Water (50 mL) was added thereto, and then the mixture was extracted with ethyl acetate (100 mL). The organic phase was dried and evaporated to dryness. The crude product was purified by column chromatography to obtain the target molecule 3-(5-(6-bromo-[1,2,4]triazolo[1,5-a]pyridin-8-yl)pyridin-2-yl)-6-((6-methoxypyridin-3-yl)methyl)-3,6-diazabicyclo[3.1.1]heptane (3.5 g, yield: 49%).

MS m/z (ESI): 492.1[M+H]$^+$.

Step 4: Preparation of 8-(6-(6-((6-methoxypyridin-3-yl)methyl)-3,6-diazabicyclo[3.1.1]heptan-3-yl)pyridin-3-yl)-[1,2,4]triazolo[1,5-a]pyridin-6-ol

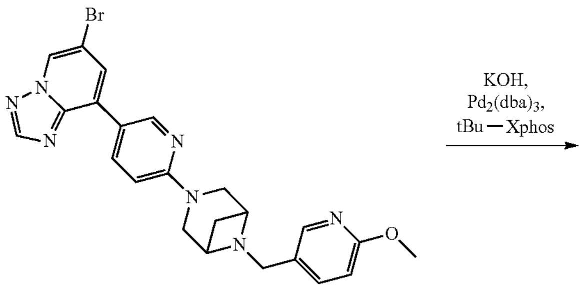

-continued

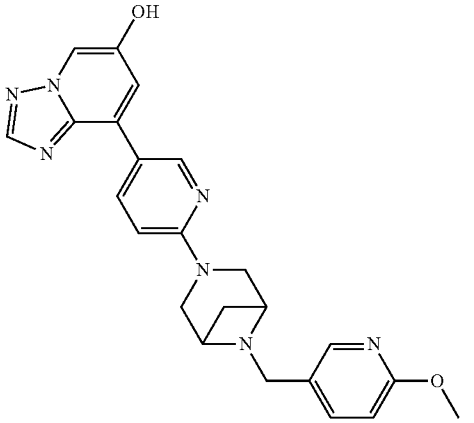

3-(5-(6-Bromo-[1,2,4]triazolo[1,5-a]pyridin-8-yl)pyridin-2-yl)-6-((6-methoxypyridin-3-yl)methyl)-3,6-diazabicyclo[3.1.1]heptane (3.5 g, 7.1 mmol) was dissolved in dioxane (40 mL), KOH (0.6 g, 10.7 mmol) and water (20 mL) were added thereto. Under the protection of nitrogen, tris (dibenzylideneacetone) dipalladium (0.65 g, 0.71 mmol) and tBu-Xphos (0.6 g, 1.42 mmol) were added thereto. The reaction mixture was stirred at 90° C. overnight. Water (50 mL) was added thereto, and then the reaction mixture was extracted with ethyl acetate (100 mL). The organic phase was dried and evaporated to dryness. The crude product was purified by column chromatography to obtain 8-(6-(6-((6-methoxypyridin-3-yl)methyl)-3,6-diazabicyclo[3.1.1]heptan-3-yl)pyridin-3-yl)-[1,2,4]triazolo[1,5-a]pyridin-6-ol) (2 g, yield: 65%).

MS m/z (ESI): 430.2[M+H]$^+$.

Step 5: Preparation of 6-((6-methoxypyridin-3-yl)methyl)-3-(5-(6-((1-methylazetidin-3-yl)methoxy)-[1,2,4]triazolo[1,5-a]pyridin-8-yl)pyridin-2-yl)-3,6-diazabicyclo[3.1.1]heptane

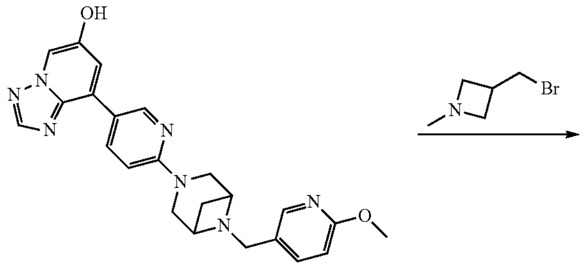

-continued

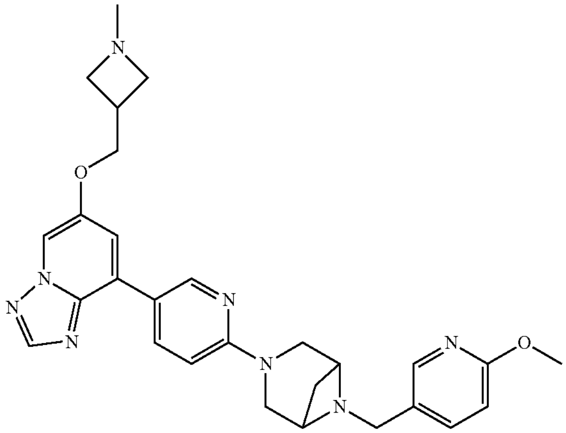

8-(6-(6-((6-Methoxypyridin-3-yl)methyl)-3,6-diazabicyclo[3.1.1]heptan-3-yl)pyridin-3-yl)-[1,2,4]triazolo[1,5-a]pyridin-6-ol (300 mg, 0.699 mmol) was dissolved in DMAc (10 mL), and 3-(bromomethyl)-1-methylazetidine (172 mg, 1.05 mmol) and cesium carbonate (569 mg, 1.75 mmol) were added thereto. The reaction mixture was stirred at 100° C. overnight. Water (20 mL) was added to the reaction mixture, and then ethyl acetate (50 mL) was added thereto for extraction. The organic phase was dried and evaporated to dryness. The crude product was purified by prep-HPLC to obtain 6-((6-methoxypyridin-3-yl)methyl)-3-(5-(6-((1-methylazetidin-3-yl)methoxy)-[1,2,4]triazolo[1,5-a]pyridin-8-yl)pyridin-2-yl)-3,6-diazabicyclo[3.1.1]heptane (50 mg, yield: 14%).

MS m/z (ESI): 513.2[M+H]$^+$.

Embodiment 38

3-(((8-(6-(6-((6-Methoxypyridin-3-yl)methyl)-3,6-diazabicyclo[3.1.1]heptan-3-yl)pyridin-3-yl)-[1,2,4]triazolo[1,5-a]pyridin-6-yl)oxo)methyl)cyclobutan-1-ol

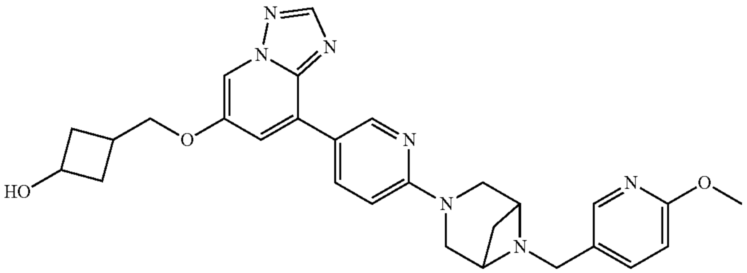

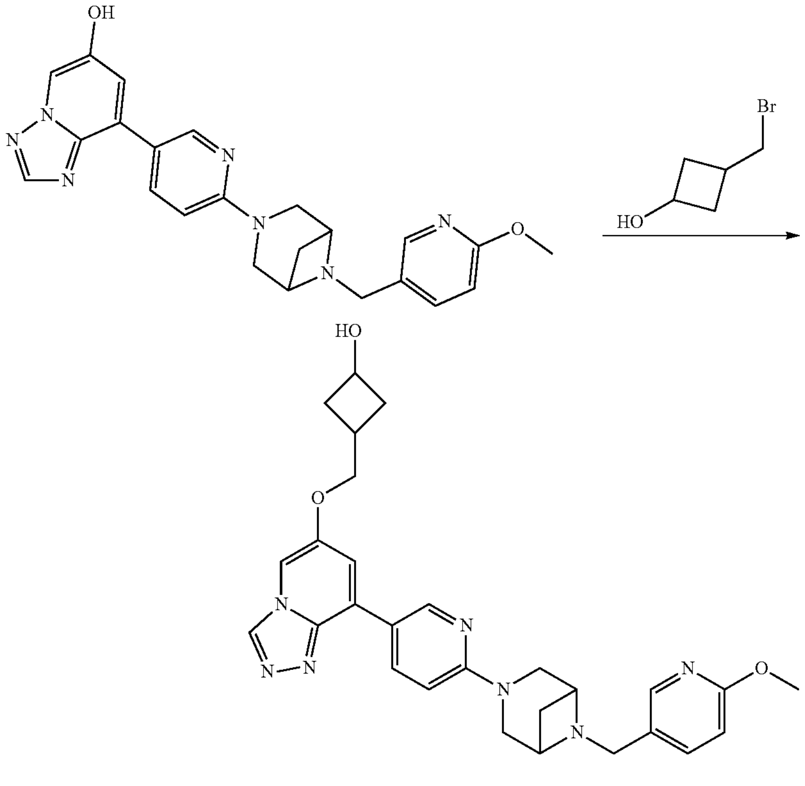

3-(((8-(6-(6-((6-Methoxypyridin-3-yl)methyl)-3,6-diazabicyclo[3.1.1]heptan-3-yl)pyridin-3-yl)-[1,2,4]triazolo[1,5-a]pyridin-6-yl)oxo)methyl)cyclobutan-1-ol (40 mg, yield: 11%) was obtained by using 8-(6-(6-((6-methoxypyridin-3-yl)methyl)-3,6-diazabicyclo[3.1.1]heptan-3-yl)pyridin-3-yl)-[1,2,4]triazolo[1,5-a]pyridin-6-ol and 3-(bromomethyl)cyclobutan-1-ol as raw materials with reference to step 5 of embodiment 37.

MS m/z (ESI): 514.2[M+H]$^+$.

Embodiment 39

(R)-1-((8-(6-(4-((6-methoxypyridin-3-yl)methyl)piperazin-1-yl)pyridin-3-yl)-[1,2,4]triazolo[1,5-a]pyridin-6-yl)oxo)propan-2-ol

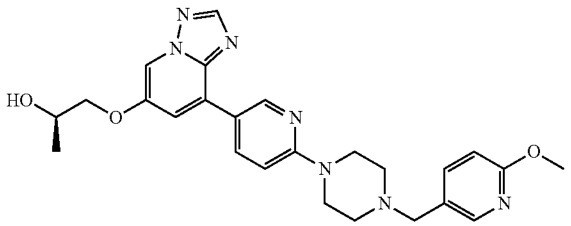 [SMILES: COc1ccc(CN2CCN(c3ccc(-c4cc(OC[C@@H](C)O)cn5ncnc45)cn3)CC2)cn1]

Step 1: Preparation of 6-bromo-8-(6-(4-((6-methoxypyridin-3-yl)methyl)piperazin-1-yl)pyridin-3-yl)-[1,2,4]triazolo[1,5-a]pyridine

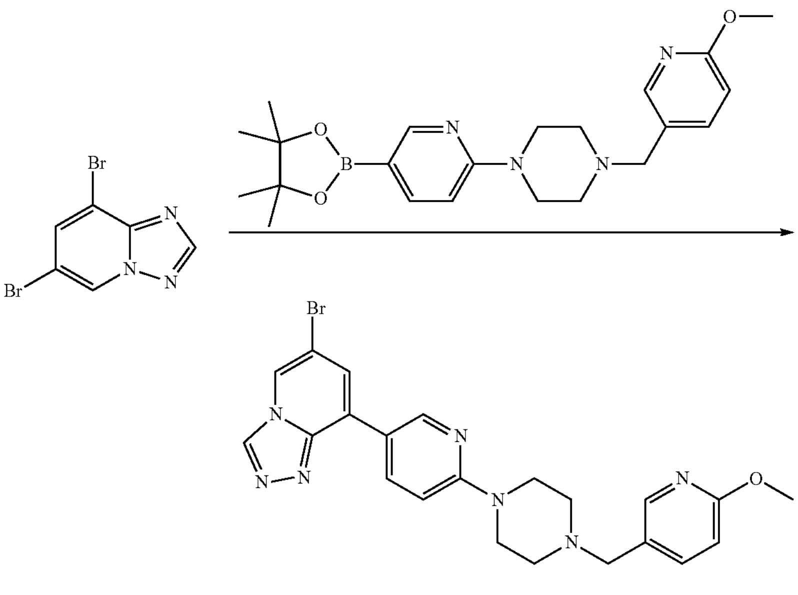

6-Bromo-8-(6-(4-((6-methoxypyridin-3-yl)methyl)piperazin-1-yl)pyridin-3-yl)-[1,2,4]triazolo[1,5-a]pyridine (1 g, yield: 70%) was obtained by using 6,8-dibromo-[1,2,4]triazolo[1,5-a]pyridine and 1-((6-methoxypyridin-3-yl)methyl)-4-(5-(4,4,5,5-tetramethyl-1,3,2-dioxaborolan-2-yl)pyridin-2-yl)piperazine with reference to step 3 of embodiment 37.

MS m/z (ESI): 480.2[M+H]$^+$.

Step 2: Preparation of 8-(6-(4-((6-methoxypyridin-3-yl)methyl)piperazin-1-yl)pyridin-3-yl)-[1,2,4]triazolo[1,5-a]pyridin-6-ol

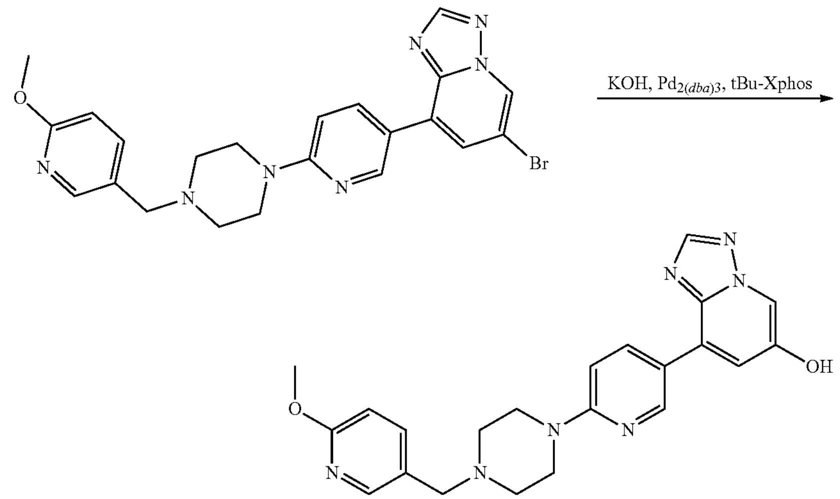

8-(6-(4-((6-Methoxypyridin-3-yl)methyl)piperazin-1-yl)pyridin-3-yl)-[1,2,4]triazolo[1,5-a]pyridin-6-ol (400 mg, yield: 57%) was obtained by using 6-bromo-8-(6-(4-((6-methoxypyridin-3-yl)methyl)piperazin-1-yl)pyridin-3-yl)-[1,2,4]triazolo[1,5-a]pyridine as raw material with reference to step 4 of embodiment 37.

MS m/z (ESI): 418.2[M+H]$^+$.

Step 3: Preparation of (R)-1-((8-(6-(4-((6-methoxypyridin-3-yl)methyl)piperazin-1-yl)pyridin-3-yl)-[1,2,4]triazolo[1,5-a]pyridin-6-yl)oxo)propan-2-ol

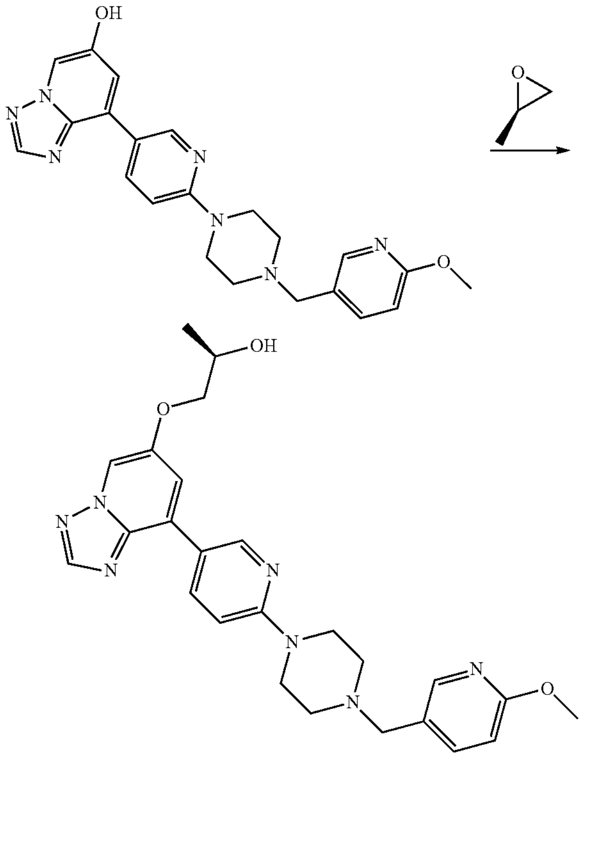

8-(6-(4-((6-Methoxypyridin-3-yl)methyl)piperazin-1-yl)pyridin-3-yl)-[1,2,4]triazolo[1,5-a]pyridin-6-ol (300 mg, 0.719 mmol) was dissolved in DMF (5 mL), (R)-2-methyloxirane (835 mg, 14.4 mmol) and potassium carbonate (497 mg, 3.59 mmol) were added thereto. The reaction mixture was stirred at 50° C. for 3 days. Water (10 mL) was added thereto, and the reaction mixture was then extracted with ethyl acetate (20 mL). The organic phase was dried and evaporated to dryness. The crude product was purified by prep-HPLC to obtain (R)-1-((8-(6-(4-((6-methoxypyridin-3-yl)methyl)piperazin-1-yl)pyridin-3-yl)-[1,2,4]triazolo[1,5-a]pyridin-6-yl)oxo)propan-2-ol (100 mg, yield: 29%).

MS m/z (ESI): 476.2[M+H]$^+$.

Embodiment 40

7-(2-Hydroxy-2-methylpropoxy)-5-(6-(6-((6-methoxypyridin-3-yl)methyl)-3,6-diazabicyclo[3.1.1]heptan-3-yl)pyridin-3-yl)imidazo[1,2-a]pyridine-3-carbonitrile

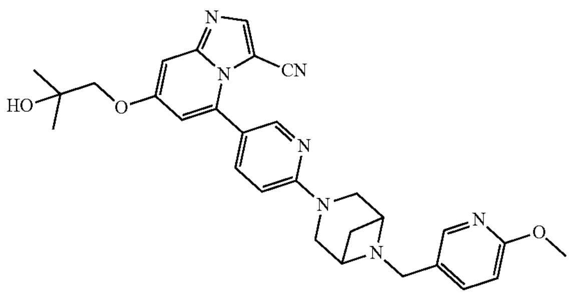 [SMILES: COc1ccc(CN2C3CC2CN(c2ccc(-c4cc(OCC(C)(C)O)cc5ncc(C#N)n45)cn2)C3)cn1]

Step 1: Preparation of ethyl 5-bromo-7-methoxy-imidazo[1,2-a]pyridine-3-carboxylate

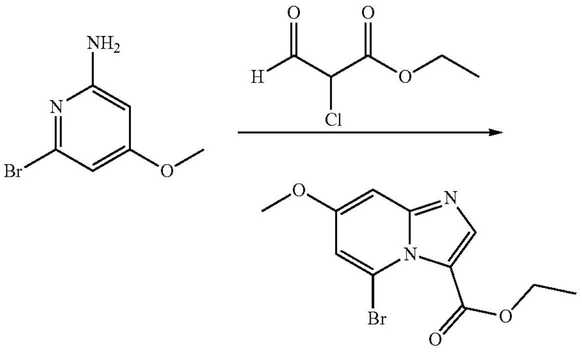

6-Bromo-4-methoxypyridin-2-amine (10 g, 49.2 mmol) was dissolved in ethanol (100 mL), and ethyl 2-chloro-3-carbonyl propionate (7.42 g, 49.2 mmol) was added thereto. The reaction was refluxed overnight. The reaction mixture was evaporated to dryness and directly purified by column chromatography to obtain target molecule ethyl 5-bromo-7-methoxyimidazo[1,2-a]pyridine-3-carboxylate (3.0 g, yield: 20%).

MS m/z (ESI): 299.2[M+H]$^+$.

Step 2: Preparation of 5-bromo-7-methoxyimidazo [1,2-a]pyridine-3-carboxylic acid

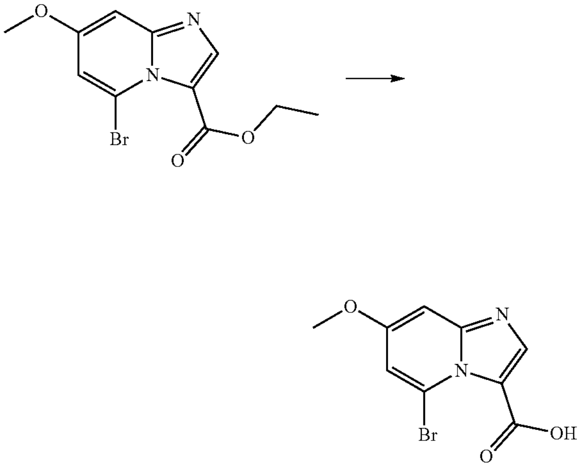 [SMILES: CCOC(=O)c1cnc2cc(OC)cc(Br)n12 ; COc1cc(Br)n2c(C(=O)O)cnc2c1]

Ethyl 5-bromo-7-methoxyimidazo[1,2-a]pyridine-3-carboxylate (3.0 g, 10.0 mmol) was dissolved in THF (20 mL), and 2N LiOH (10 mL) was added thereto. The reaction mixture was stirred at room temperature overnight. Ethyl acetate (20 mL) was added for extraction. The aqueous phase was collected, and the pH value was adjusted to 3-4 by 1 N HCl, then extracted with ethyl acetate (50 mL). The organic phase was collected, dried, and then evaporated to dryness to obtain 5-bromo-7-methoxyimidazo[1,2-a]pyridine-3-carboxylic acid (2.5 g, yield: 92%).

MS m/z (ESI): 270.8[M+H]$^+$.

Step 3: Preparation of 5-bromo-7-methoxyimidazo [1,2-a]pyridine-3-carboxamide

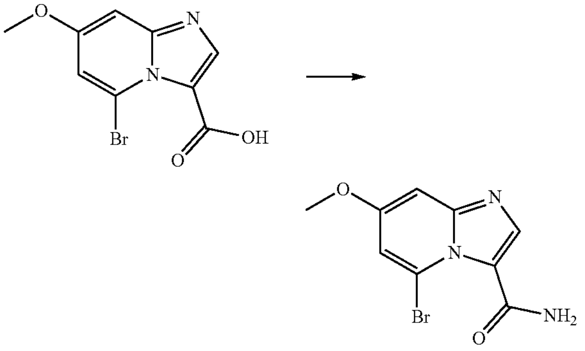

5-Bromo-7-methoxyimidazo[1,2-a]pyridine-3-carboxylic acid (2.5 g, 9.2 mmol) was dissolved in DMF (30 mL), and $NH_4Cl$ (0.99 g, 18.5 mmol), HATU (5.3 g, 13.8 mmol) and DIEA (3.6 g, 27.7 mmol) were added thereto. The reaction mixture was stirred at room temperature overnight. Water (50 mL) was added thereto, and then the reaction mixture was extracted with ethyl acetate (100 mL). The organic phase was washed with saturated sodium chloride and dried, then evaporated to dryness. The crude product was purified by column chromatography to obtain 5-bromo-7-methoxy-imidazo[1,2-a]pyridine-3-carboxamide (2 g, yield: 80%).

MS m/z (ESI): 269.8[M+H]$^+$.

Step 4: Preparation of 5-bromo-7-methoxyimidazo [1,2-a]pyridine-3-carbonitrile

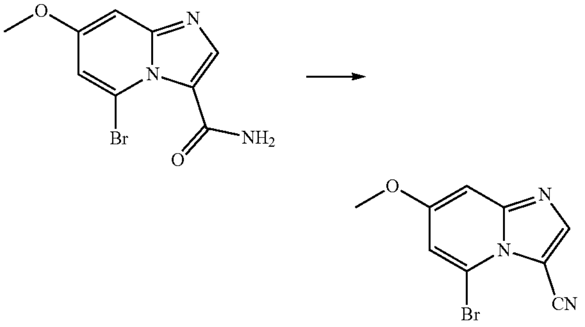

5-Bromo-7-methoxyimidazo[1,2-a]pyridine-3-carboxamide (2 g, 7.4 mmol) was dissolved in anhydrous tetrahydrofuran (30 mL), and pyridine (1.46 g, 18.5 mmol) was added thereto. TFAA (3.9 g, 18.5 mmol) was slowly added dropwise. After the addition was completed, the reaction was stirred at room temperature for 3 hours. Water (50 mL) was added thereto, and then the mixture was extracted with ethyl acetate (100 mL). The organic phase was dried and evaporated to dryness. The crude product was purified by column chromatography to obtain 5-bromo-7-methoxyimidazo[1,2-a]pyridine-3-carbonitrile (1.5 g, yield: 80%).

MS m/z (ESI): 251.8[M+H]$^+$.

Step 5: Preparation of 5-bromo-7-hydroxyimidazo[1,2-a]pyridine-3-carbonitrile

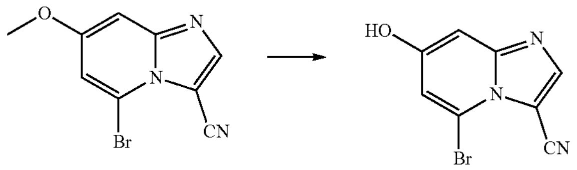

5-Bromo-7-methoxyimidazo[1,2-a]pyridine-3-carbonitrile (1.5 g, 6.0 mmol) was dissolved in DCE (20 mL). $AlCl_3$ (2.4 g, 17.9 mmol) was slowly added to the reaction mixture. After the addition was completed, the reaction was refluxed overnight under the protection of nitrogen. Tetrahydrofuran (100 mL) was added to the reaction mixture, and then an excess of sodium sulfate decahydrate (20 g) was added, and the mixture was stirred at room temperature overnight. The mixture was filtered, and the filtrate was evaporated to dryness. The crude product was subjected to column chromatography to obtain 5-bromo-7-hydroxyimidazo[1,2-a]pyridine-3-carbonitrile (1.2 g, yield: 85%).

MS m/z (ESI): 237.8$[M+H]^+$.

Step 6: Preparation of 5-bromo-7-(2-hydroxy-2-methylpropoxy)imidazo[1,2-a]pyridine-3-carbonitrile

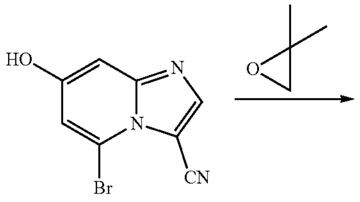

-continued

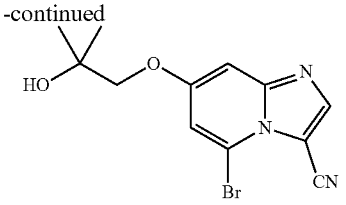

5-Bromo-7-hydroxyimidazo[1,2-a]pyridine-3-carbonitrile (1.2 g, 5.0 mmol) was dissolved in DMF (20 mL), and 2,2-dimethyloxirane (3.6 g, 50.4 mmol) and potassium carbonate (2.1 g, 15.1 mmol) were added thereto. The reaction mixture was stirred at 85° C. overnight. Water (30 mL) was added thereto, and then the reaction mixture was extracted with ethyl acetate (50 mL). The organic phase was washed with saturated sodium chloride aqueous solution, then dried and evaporated to dryness. The crude product was purified by column chromatography to obtain 5-bromo-7-(2-hydroxy-2-methylpropoxy)imidazo[1,2-a]pyridine-3-carbonitrile (1.3 g, yield: 83%).

MS m/z (ESI): 310.2$[M+H]^+$.

Step 7: Preparation of 7-(2-hydroxy-2-methylpropoxy)-5-(6-(6-((6-methoxypyridin-3-yl)methyl)-3,6-diazabicyclo[3.1.1]heptan-3-yl)pyridin-3-yl)imidazo[1,2-a]pyridine-3-carbonitrile

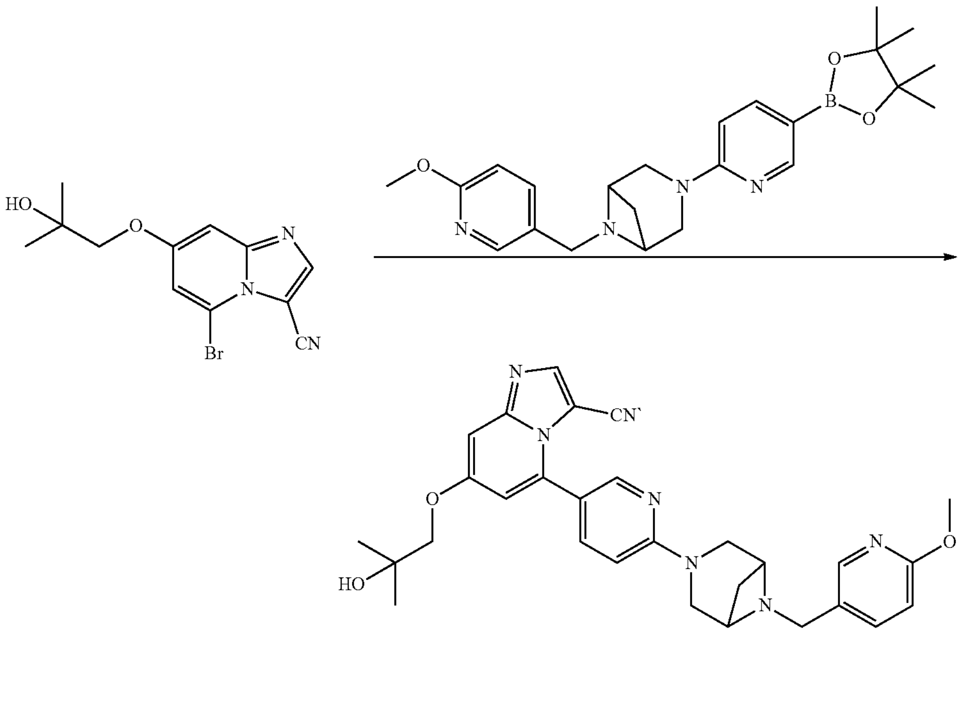

7-(2-Hydroxy-2-methylpropoxy)-5-(6-(6-((6-methoxypyridin-3-yl)methyl)-3,6-diazabicyclo[3.1.1]heptan-3-yl)pyridin-3-yl)imidazo[1,2-a]pyridine-3-carbonitrile (100 g, yield: 55%) was obtained by using 5-bromo-7-(2-hydroxy-2-methylpropoxy)imidazo[1,2-a]pyridine-3-carbonitrile and 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane as raw materials with reference to step 3 of embodiment 37.

MS m/z (ESI): 526.2[M+H]$^+$.

Embodiment 41

7-(2-Hydroxy-2-methylpropoxy)-5-(6-(4-(pyridin-2-oxy)piperidin-1-yl)pyridin-3-yl)imidazo[1,2-a]pyridine-3-carbonitrile

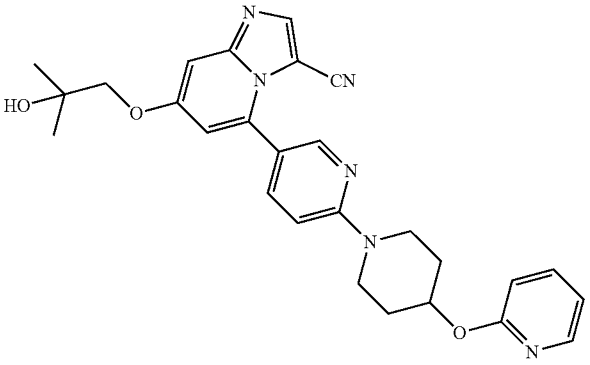

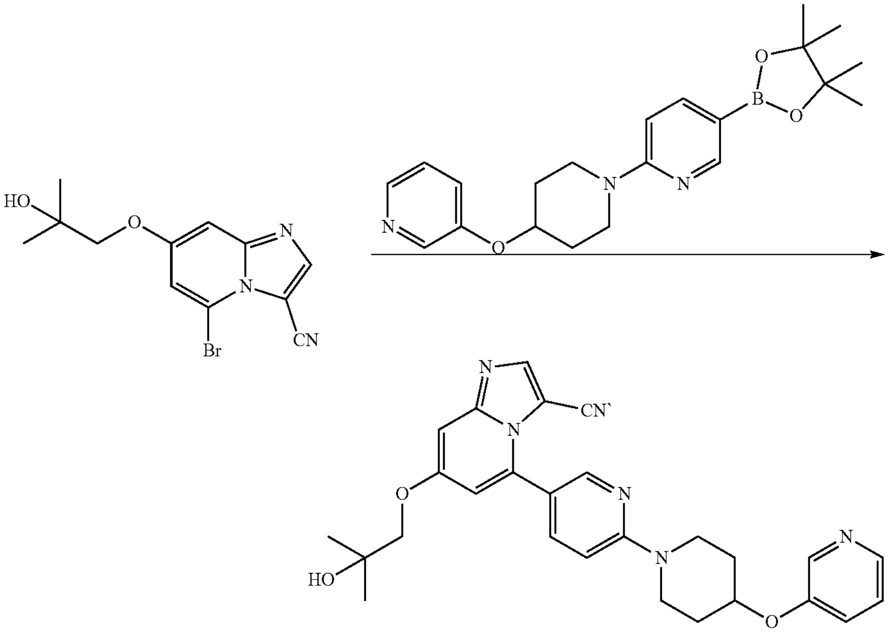

7-(2-Hydroxy-2-methylpropoxy)-5-(6-(4-(pyridin-2-oxy)piperidin-1-yl)pyridin-3-yl)imidazo[1,2-a]pyridine-3-carbonitrile (85 g, yield: 65%) was obtained by using 5-bromo-7-(2-hydroxy-2-methylpropoxy)imidazo[1,2-a]pyridine-3-carbonitrile and 2-(4-(pyridin-3-oxy)piperidin-1-yl)-5-(4,4,5,5-tetramethyl-1,3,2-dioxaborolan-2-yl)pyridine as raw material with reference to step 3 of embodiment 37.

MS m/z (ESI): 485.2[M+H]$^+$.

Embodiment 42

N-(1-(5-(3-cyano-7-(2-hydroxy-2-methylpropoxy) imidazo[1,2-a]pyridin-5-yl)pyridin-2-yl)-4-methylpiperidin-4-yl)-2,6-difluorobenzamide

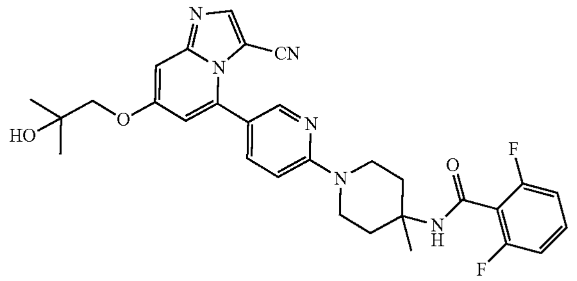 [SMILES: CC(C)(O)COc1cc(-c2ccc(N3CCC(C)(NC(=O)c4c(F)cccc4F)CC3)nc2)n2c(C#N)cnc2c1]

Step 1: Preparation of benzyl 4-((tert-butylsulfinyl<sulfinyl>)amino)-4-methylpiperidine-1-carboxylate

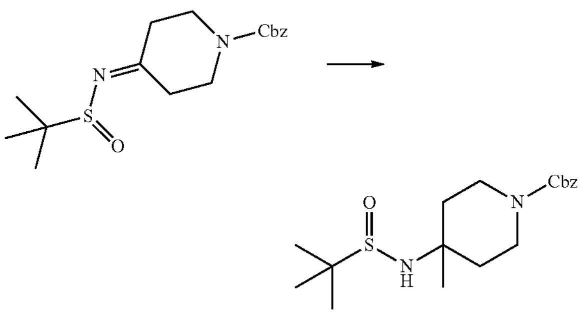

Benzyl 4-((tert-butylsulfinyl<sulfinyl>)imino)piperidine-1-carboxylate (5 g, 14.9 mmol) was dissolved in anhydrous tetrahydrofuran (50 mL), and the mixture was cooled to 0° C. Methylmagnesium bromide (17.9 mL, 17.9 mmol) was added slowly dropwise to the reaction mixture. After the addition was completed, the reaction was slowly warmed to room temperature, and stirring was continued for 3 hours. Ammonium chloride aqueous solution (10 mL) was slowly added dropwise to quench the reaction, and then the mixture was extracted with ethyl acetate (100 mL). The organic phase was dried and evaporated to dryness. The crude product was purified by column chromatography to obtain benzyl 4-((tert-butyl sulfinyl<sulfinyl>)amino)-4-methylpiperidine-1-carboxylate (4.2 g, yield: 80%).

MS m/z (ESI): 353.2[M+H]$^+$.

Step 2: Preparation of benzyl 4-amino-4-methylpiperidine-1-carboxylate

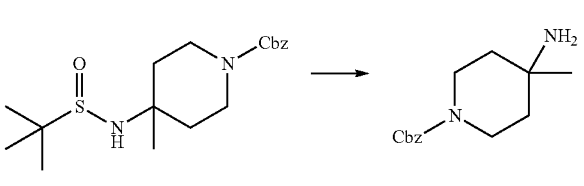 [SMILES: CC1(NS(=O)C(C)(C)C)CCN(C(=O)OCc2ccccc2)CC1 ; CC1(N)CCN(C(=O)OCc2ccccc2)CC1]

Benzyl 4-((tert-butylsulfinyl<sulfinyl>)amino)-4-methylpiperidine-1-carboxylate (4.2 g, 11.9 mmol) was dissolved in 25% trifluoroacetic acid/dichloromethane solution (50 mL). The reaction mixture was stirred at room temperature for 2 hours. The reaction mixture was evaporated to dryness, and dichloromethane (100 mL) was added thereto. $NaHCO_3$ aqueous solution was added slowly to adjust the pH value to 7-8. The organic phase was dried and then evaporated to dryness to obtain benzyl 4-amino-4-methylpiperidine-1-carboxylate (2.8 g, yield: 95%).

MS m/z (ESI): 249.2[M+H]$^+$.

Step 3: Preparation of benzyl 4-(2,6-difluorobenzamido)-4-methylpiperidine-1-carboxylate

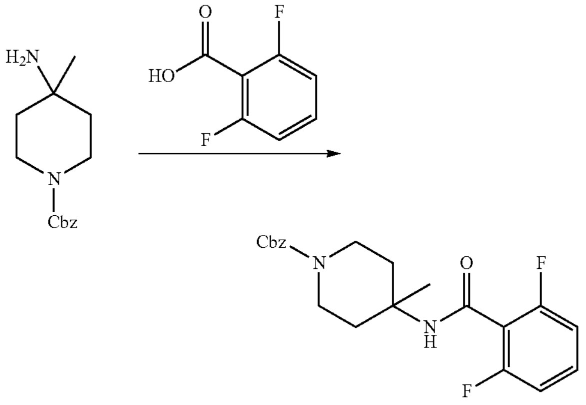

Benzyl 4-(2,6-difluorobenzamido)-4-methylpiperidine-1-carboxylate (1.5 g, yield: 84%) was obtained by using benzyl 4-amino-4-methylpiperidine-1-carboxylate and 2,6-difluorobenzoic acid as raw materials with reference to step 3 of example 40.

MS m/z (ESI): 389.2[M+H]$^+$.

Step 4: Preparation of 2,6-difluoro-N-(4-methylpiperidin-4-yl)benzamide

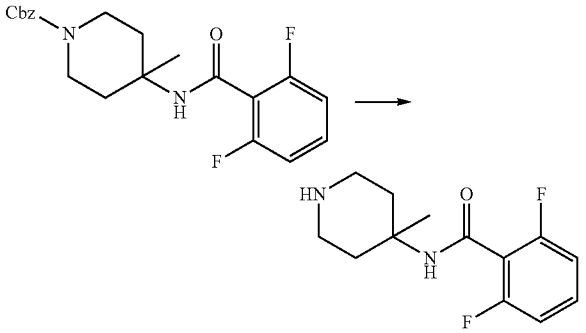

Methyl 4-(2,6-difluorobenzamido)-4-methylpiperidine-1-carboxylate (1.5 g, 3.9 mmol) was dissolved in methanol (50 mL), and palladium/carbon (200 mg) was added thereto. The reaction was stirred for 6 hours under hydrogen conditions. The reaction mixture was filtered. The filtrate was evaporated to dryness to obtain 2,6-difluoro-N-(4-methylpiperidin-4-yl)benzenamide (900 mg, yield: 92%).

MS m/z (ESI): 255.2[M+H]$^+$.

Step 5: Preparation of 5-(6-fluoropyridin-3-yl)-7-(2-hydroxy-2-methylpropoxy)imidazo[1,2-a]pyridine-3-carbonitrile

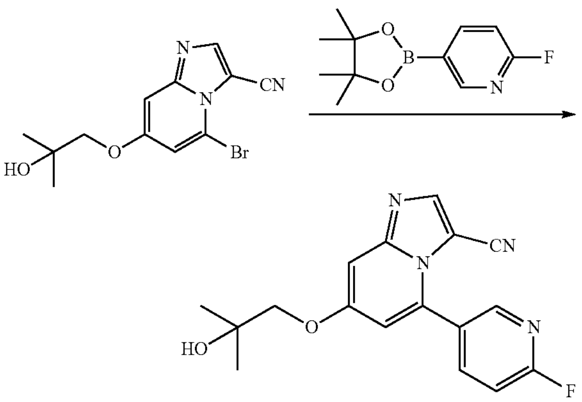

5-(6-Fluoropyridin-3-yl)-7-(2-hydroxy-2-methylpropoxy)imidazo[1,2-a]pyridine-3-carbonitrile (200 mg, yield was 72%) was obtained by using 5-bromo-7-(2-hydroxy-2-methylpropoxy)imidazo[1,2-a]pyridine-3-carbonitrile and 2-fluoro-5-(4,4,5,5-tetramethyl-1,3,2-dioxaborolan-2-yl)pyridine as raw materials with reference to step 3 of embodiment 37.

MS m/z (ESI): 327.2[M+H]$^+$.

Step 6: Preparation of N-(1-(5-(3-cyano-7-(2-hydroxy-2-methylpropoxy)imidazo[1,2-a]pyridin-5-yl)pyridin-2-yl)-4-methylpiperidin-4-yl)-2,6-difluorobenzamide

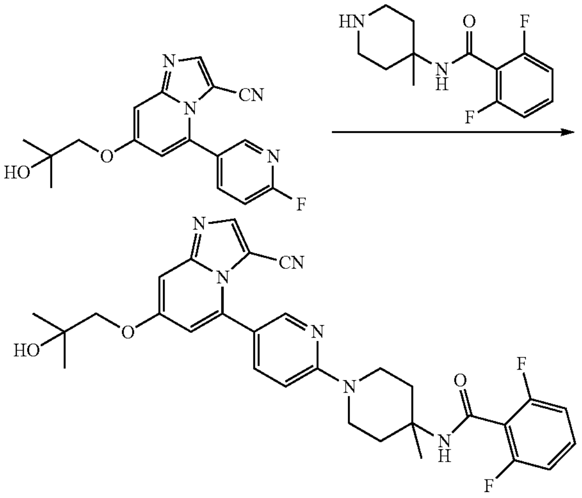

5-(6-Fluoropyridin-3-yl)-7-(2-hydroxy-2-methylpropoxy)imidazo[1,2-a]pyridine-3-carbonitrile (100 mg, 0.306 mmol) was dissolved in DMSO (10 mL), and 2,6-difluoro-N-(4-methylpiperidin-4-yl)benzamide (78 mg, 0.306 mmol) and DIEA (119 mg, 0.92 mmol) were added thereto. The reaction mixture was stirred at 90° C. for 2 days. Water (20 mL) was added thereto, and then the reaction mixture was extracted with ethyl acetate (30 mL). The organic phase was washed with saturated sodium chloride aqueous solution, then dried and evaporated to dryness. The crude product was purified by prep-HPLC to obtain N-(1-(5-(3-cyano-7-(2-hydroxy-2-methylpropoxy)imidazo[1,2-a]pyridin-5-yl)pyridin-2-yl)-4-methylpiperidin-4-yl)-2,6-difluorobenzamide (70 mg, yield: 41%).

MS m/z (ESI): 561.2[M+H]$^+$.

Embodiment 43

(R)-5-(6-(4-(3-hydroxy-3-phenylpropanoyl)piperazin-1-yl)pyridin-3-yl)-7-(1-methyl-1H-pyrazol-4-yl)imidazo[1,2-a]pyridine-3-carbonitrile

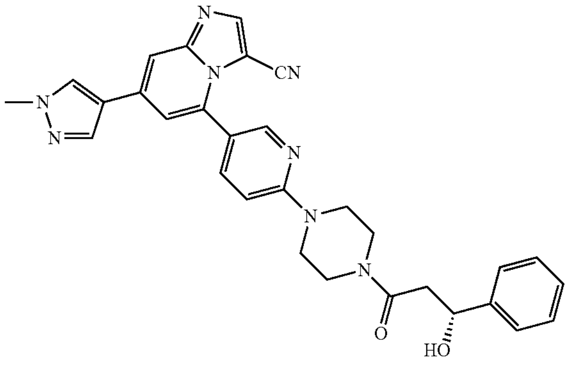 [SMILES: Cn1cc(-c2cc(-c3ccc(N4CCN(C(=O)C[C@@H](O)c5ccccc5)CC4)nc3)n3c(C#N)cnc3c2)cn1]

Step 1: Preparation of tert-butyl 4-(5-(3-cyano-7-hydroxyimidazo[1,2-a]pyridin-5-yl)pyridin-2-yl)piperazine-1-carboxylate

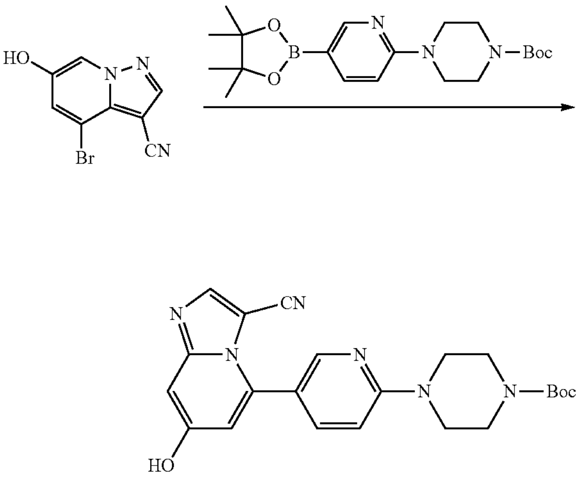

Tert-butyl 4-(5-(3-cyano-7-hydroxyimidazo[1,2-a]pyridin-5-yl)pyridin-2-yl)piperazine-1-carboxylate (1 g, yield: 72%) was obtained by using 5-bromo-7-hydroxyimidazo[1,2-a]pyridine-3-carbonitrile and tert-butyl 4-(5-(4,4,5,5-tetramethyl-1,3,2-dioxaborolan-2-yl)pyridin-2-yl)piperazine-1-carboxylate as raw materials with reference to step 3 of embodiment 37.

MS m/z (ESI): 421.2[M+H]$^+$.

Step 2: Preparation of tert-butyl 4-(5-(3-cyano-7-(((trifluoromethyl)sulfonyl)oxy)imidazo[1,2-a]pyridin-5-yl)pyridin-2-yl)piperazine-1-carboxylate

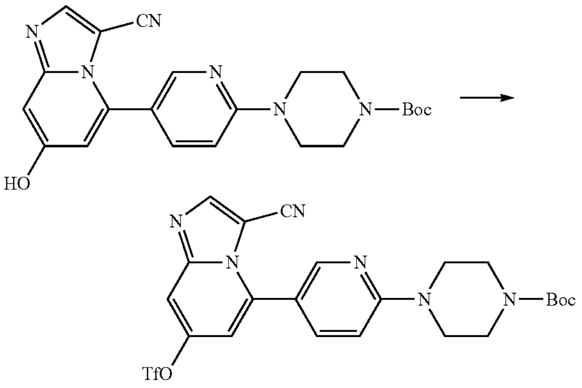

Tert-butyl 4-(5-(3-cyano-7-hydroxyimidazo[1,2-a]pyridin-5-yl)pyridin-2-yl)piperazine-1-carboxylate (1 g, 2.4 mmol) was dissolved in anhydrous dichloromethane (20 mL), and the mixture was cooled to 0° C. DIEA (0.46 g, 3.6 mmol) was added to the reaction mixture. Trifluoromethanesulfonic anhydride (0.74 g, 2.6 mmol) was slowly added thereto. After the addition was completed, the reaction mixture was slowly warmed to room temperature, and stirring was continued for 3 hours. Water (20 mL) was added thereto, and then the reaction mixture was extracted with dichloromethane (20 mL). The organic phase was dried and evaporated to dryness to obtain tert-butyl 4-(5-(3-cyano-7-(((trifluoromethyl)sulfonyl)oxo)imidazo[1,2-a]pyridin-5-yl)pyridin-2-yl)piperazine-1-carboxylate (1.2 g, yield: 91%).

MS m/z (ESI): 553.2$[M+H]^+$.

Step 3: Preparation of tert-butyl 4-(5-(3-cyano-7-(1-methyl-1H-pyrazol-4-yl)imidazo[1,2-a]pyridin-5-yl)pyridin-2-yl)piperazine-1-carboxylate

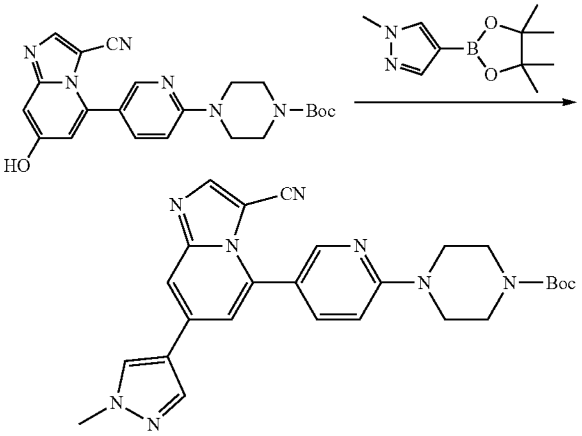

Tert-butyl 4-(5-(3-cyano-7-(1-methyl-1H-pyrazol-4-yl)imidazo[1,2-a]pyridin-5-yl)pyridin-2-yl)piperazine-1-carboxylate (0.8 g, yield: 76%) was obtained by using tert-butyl 4-(5-(3-cyano-7-(((trifluoromethyl)sulfonyl)oxo)imidazo[1,2-a]pyridin-5-yl)pyridin-2-yl)piperazine-1-carboxylate and 1-methyl-4-(4,4,5,5-tetramethyl-1,3,2-dioxaborolan-2-yl)-1H-pyrazole as raw material with reference to step 3 of embodiment 37.

MS m/z (ESI): 485.2$[M+H]^+$.

Step 4: Preparation of 7-(1-methyl-1H-pyrazol-4-yl)-5-(6-(piperazin-1-yl)pyridin-3-yl)imidazo[1,2-a]pyridine-3-carbonitrile

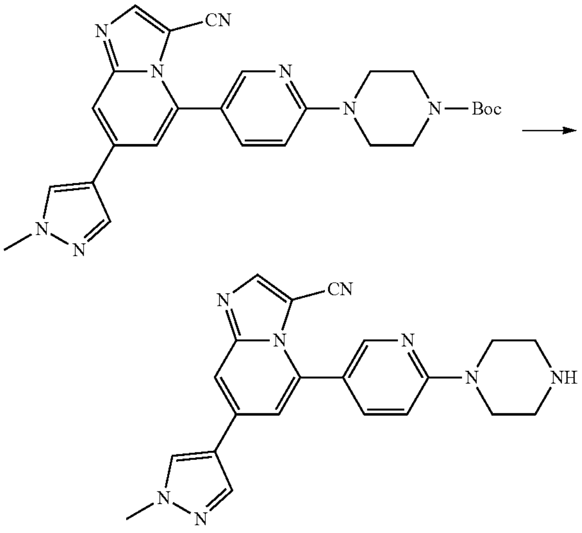

Tert-butyl 4-(5-(3-cyano-7-(1-methyl-1H-pyrazol-4-yl)imidazo[1,2-a]pyridin-5-yl)pyridin-2-yl)piperazine-1-carboxylate (0.8 g, 1.7 mmol) was dissolved in 25% trifluoroacetic acid/dichloromethane solution (20 mL). The reaction mixture was stirred at room temperature for 2 hours. The reaction mixture was evaporated to dryness and dichloromethane (30 mL) was added thereto. $NaHCO_3$ aqueous solution was added slowly to adjust the pH value to 7-8. The organic phase was dried and evaporated to dryness to obtain 7-(1-methyl-1H-pyrazol-4-yl)-5-(6-(piperazin-1-yl)pyridin-3-yl)imidazo[1,2-a]pyridine-3-carbonitrile (0.6 g, yield: 95%).

MS m/z (ESI): 385.2$[M+H]^+$.

Step 5: Preparation of (R)-5-(6-(4-(3-hydroxy-3-phenylpropanoyl)piperazin-1-yl)pyridin-3-yl)-7-(1-methyl-1H-pyrazol-4-yl)imidazo[1,2-a]pyridine-3-carbonitrile

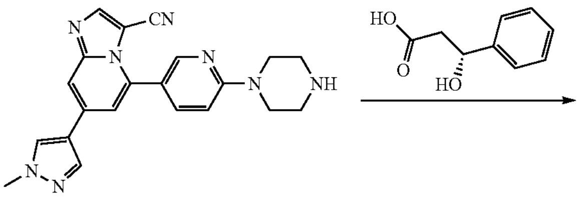

-continued

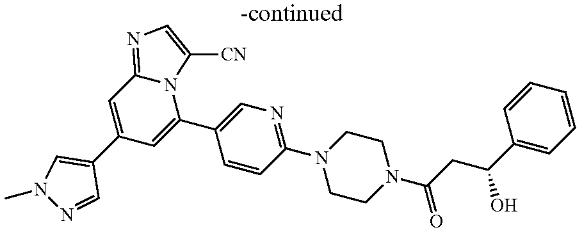

(R)-5-(6-(4-(3-hydroxy-3-phenylpropanoyl)piperazin-1-yl)pyridin-3-yl)-7-(1-methyl-1H-pyrazol-4-yl)imidazo[1,2-a]pyridine-3-carbonitrile (70 mg, yield: 62%) was obtained by using 7-(1-methyl-1H-pyrazol-4-yl)-5-(6-(piperazin-1-yl)pyridin-3-yl)imidazo[1,2-a]pyridine-3-carbonitrile and (R)-3-hydroxy-3-phenylpropanoic acid as raw materials with reference to step 3 of embodiment 40.

MS m/z (ESI): 533.2[M+H]$^+$.

Embodiment 44

(R)-5-(6-(4-(2-hydroxy-3-phenylpropanoyl)piperazin-1-yl)pyridin-3-yl)-7-(1-methyl-1H-pyrazol-4-yl)imidazo[1,2-a]pyridine-3-carbonitrile

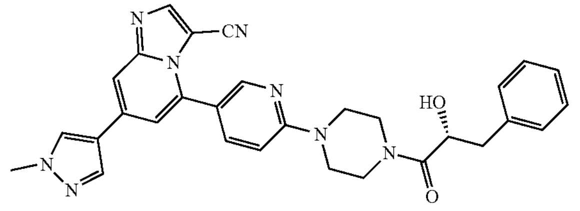 [SMILES: Cn1cc(-c2cc(-c3ccc(N4CCN(C(=O)[C@H](O)Cc5ccccc5)CC4)nc3)n3c(C#N)cnc3c2)cn1]

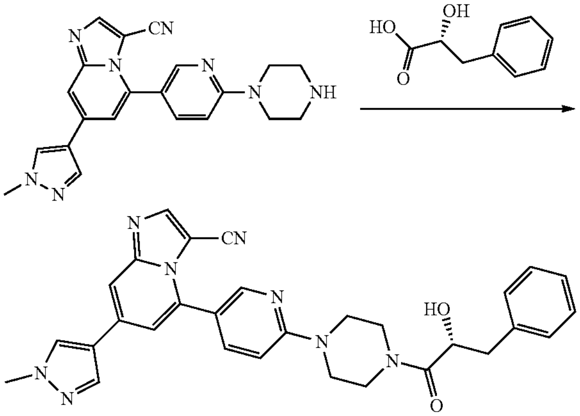

(R)-5-(6-(4-(2-hydroxy-3-phenylpropanoyl)piperazin-1-yl)pyridin-3-yl)-7-(1-methyl-1H-pyrazol-4-yl)imidazo[1,2-a]pyridine-3-carbonitrile (65 mg, yield: 66%) was obtained by using 7-(1-methyl-1H-pyrazol-4-yl)-5-(6-(piperazin-1-yl)pyridin-3-yl)imidazo[1,2-a]pyridine-3-carbonitrile and (R)-2-hydroxy-3-phenylpropanoic acid as raw materials with reference to step 3 of embodiment 40.

MS m/z (ESI): 533.2[M+H]$^+$.

Embodiment 45

4-(5-(3-Cyano-7-(1-methyl-1H-pyrazol-4-yl)imidazo[1,2-a]pyridin-5-yl)pyridin-2-yl)-N-isobutylpiperazine-1-carboxamide

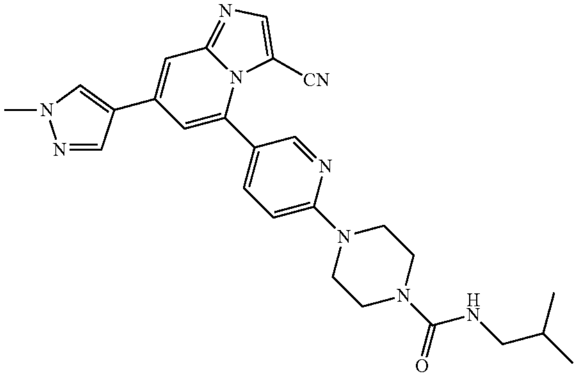

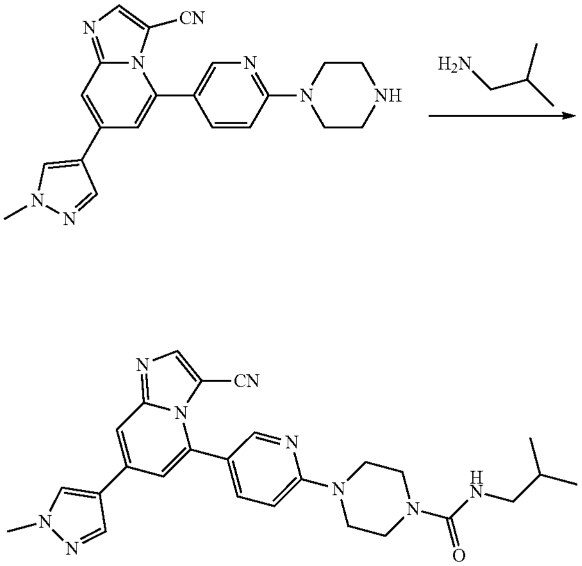

7-(1-Methyl-1H-pyrazol-4-yl)-5-(6-(piperazin-1-yl)pyridin-3-yl)imidazo[1,2-a]pyridine-3-carbonitrile (0.1 g, 0.26 mmol) was dissolved in dichloromethane (5 mL), and DIEA (168 mg, 1.3 mmol) and CDI (84 mg, 0.52 mmol) were added thereto. The reaction mixture was stirred at room temperature for 2 hours, and then 2-methylpropan-1-amine (38 mg, 0.52 mmol) was added thereto. The reaction mixture was stirred for 2 days. Water (10 mL) was added thereto, and then the reaction mixture was extracted with dichloromethane (20 mL). The organic phase was dried and evaporated to dryness. The crude product was purified by prep-HPLC to obtain 4-(5-(3-cyano-7-(1-methyl-1H-pyrazol-4-yl)imidazo[1,2-a]pyridin-5-yl)pyridin-2-yl)-N-isobutylpiperazine-1-carboxamide (30 mg, yield: 24%).

MS m/z (ESI): 484.2[M+H]$^+$.

Embodiment 46

6-((R)-2-hydroxypropoxy)-4-(6-(6-((6-methoxypyridin-3-yl)methyl)-3,6-diazabicyclo[3.1.1]heptan-3-yl)pyridin-3-yl)-1-methyl-1H-indazole-3-carbonitrile

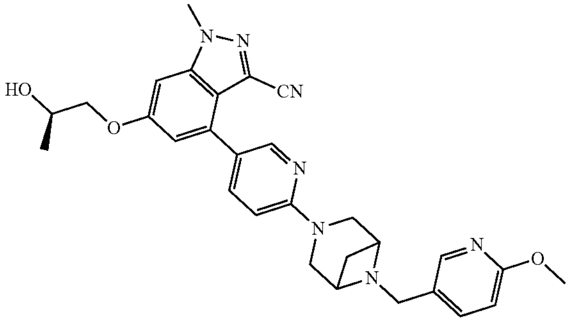 [SMILES: COc1ccc(CN2C3CC2CN(c2ccc(-c4cc(OC[C@@H](C)O)cc5c4c(C#N)nn5C)cn2)C3)cn1]

Step 1: 2-bromo-6-fluoro-4-methoxybenzaldehyde

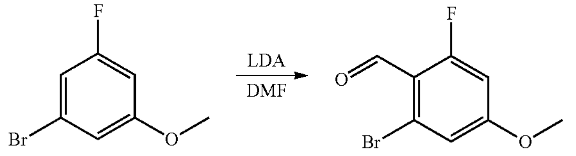

Lithium diisopropylamine (73.17 mmol, 36.6 mL, 2 M tetrahydrofuran) was added dropwise to a solution of 1-bromo-3-fluoro-5-methoxybenzene (10 g, 48.78 mmol) in tetrahydrofuran (100 mL) at −78° C., then the mixture was stirred at −78° C. for 1 hour, then anhydrous N,N-dimethylformamide (7.12 g, 97.56 mmol) was added dropwise, the mixture was stirred at −78° C. for 2 hours, quenched with saturated ammonium chloride solution, extracted with dichloromethane; the organic phase was washed with saturated saline, dried over anhydrous sodium sulfate, filtered, and the filtrate was concentrated under reduced pressure to dryness to obtain crude product 2-bromo-6-fluoro-4-methoxybenz(methyl)aldehyde (6.2 g, yield: 55%).

MS m/z (ESI): 232.9 $[M+H]^+$.

Step 2: 4-bromo-6-methoxy-1H-indazole

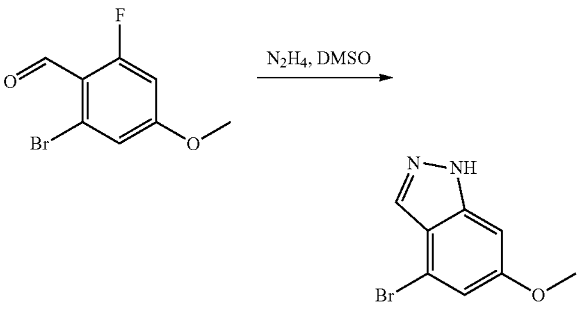

A mixed solution of 2-bromo-6-fluoro-4-methoxybenzene(methyl)aldehyde (6.2 g, 26.84 mmol), hydrazine hydrate (2.7 g, 53.68 mmol, 98%) and dimethyl sulfoxide (50 mL) was stirred at 130° C. for 2 hours, the mixture was cooled to room temperature and slurried with water, a solid precipitated and was filtered; the filter cake was washed with water, and dried to obtain light yellow solid 4-bromo-6-methoxy-1H-indazole (5.3 g, yield: 87%).

MS m/z (ESI): 227.0 $[M+H]^+$.

Step 3: 4-bromo-6-methoxy-1-methyl-1H-indazole

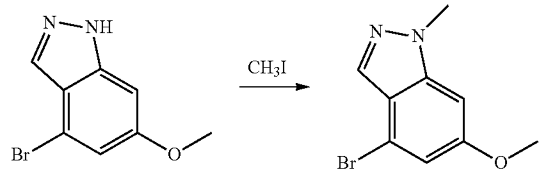

Sodium hydrogen (1.8 g, 46.9 mmol) was added to a solution of 4-bromo-6-methoxy-1H-indazole (5.3 g, 23.45 mmol) in tetrahydrofuran (50 mL) at 0° C., then the mixture was stirred for 30 min, and iodomethane (5 g, 35.17 mmol) was added dropwise, then stirred at room temperature for 2 hours, quenched with water and extracted with dichloromethane; the organic phase was washed with saturated saline, dried over anhydrous sodium sulfate, filtered, and the filtrate was concentrated under reduced pressure to dryness and separated by column chromatography (dichloromethane/methanol=10:1) to obtain colorless oil 4-bromo-6-methoxy-1-methyl-1H-indazole (2.8 g, yield: 50%).

MS m/z (ESI): 241.0 $[M+H]^+$.

Step 4: 4-bromo-3-iodo-6-methoxy-1-methyl-1H-indazole

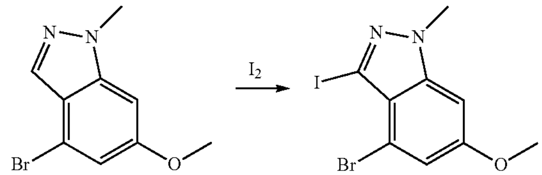

Iodine monomer (4.4 g, 17.5 mmol) was added to a mixed solution of 4-bromo-6-methoxy-1-methyl-1H-indazole (2.8 g, 11.67 mmol), potassium hydroxide (1.3 g, 23.34 mmol) and N,N-dimethylformamide (30 mL), then the mixture was stirred at room temperature for 3 hours; after the reaction was completed, saturated sodium bisulfite solution was added thereto, a solid precipitated and was filtered, the filter cake was washed with water and dried to obtain light yellow solid 4-bromo-3-iodo-6-methoxy-1-methyl-1H-indazole (3.1 g, yield: 73%).

MS m/z (ESI): 366.8 $[M+H]^+$.

Step 5: 4-bromo-6-methoxy-1-methyl-1H-indazole-3-carbonitrile

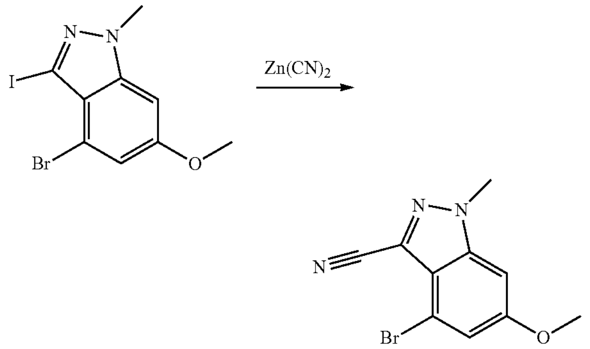

Tris(dibenzylideneacetone)dipalladium (388 mg, 0.42 mmol) was added to a mixture of 4-bromo-3-iodo-6-methoxy-1-methyl-1H-indazole (3.1 g, 8.47 mmol), zinc cyanide (2 g, 16.94 mmol) and anhydrous N,N-dimethylformamide (50 mL), then the mixture was replaced with nitrogen three times, and stirred at 100° C. for 16 hours under the protection of nitrogen, after the reaction was completed, the mixture was cooled to room temperature, filtered, water and dichloromethane was added to the filtrate, the mixture was then extracted with dichloromethane; the organic phase was washed with saturated saline, dried over anhydrous sodium sulfate, filtered, the filtrate was concentrated under reduced pressure to dryness to obtain black solid 4-bromo-6-methoxy-1-methyl-1H-indazole-3-carbonitrile (3.5 g, crude product), the crude product was directly for the next step.

MS m/z (ESI): 266.0 $[M+H]^+$.

Step 5: 4-bromo-6-hydroxy-1-methyl-1H-indazole-3-carbonitrile

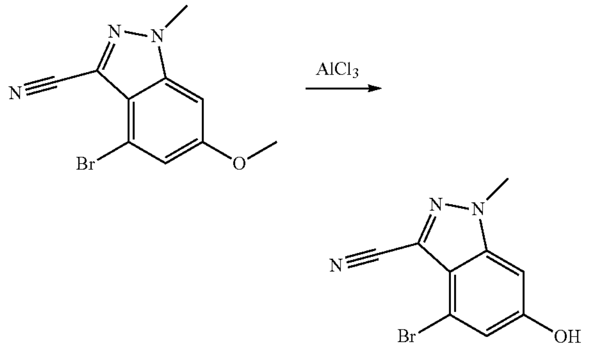

Aluminum trichloride (8.8 g, 66.05 mmol) was added to a solution of 4-bromo-6-methoxy-1-methyl-1H-indazole-3-carbonitrile (3.5 g, 13.21 mmol) in 1.2-dichloroethane (40 mL) in batches, then the mixture was stirred at 80° C. for 2 hours, cooled to room temperature, quenched with sodium sulfate decahydrate and filtered, the filter cake was washed with dichloromethane, the filtrate was washed with saturated saline; the organic phase was dried over anhydrous sodium sulfate, filtered, and the filtrate was concentrated under reduced pressure to dryness to obtain brown solid 4-bromo-6-hydroxy-1-methyl-1H-indazole-3-carbonitrile (3.2 g, crude product).

MS m/z (ESI): 250.9 [M−H].

Step 7: 4-bromo-6-(2-hydroxypropoxy)-1-methyl-1H-indazole-3-carbonitrile

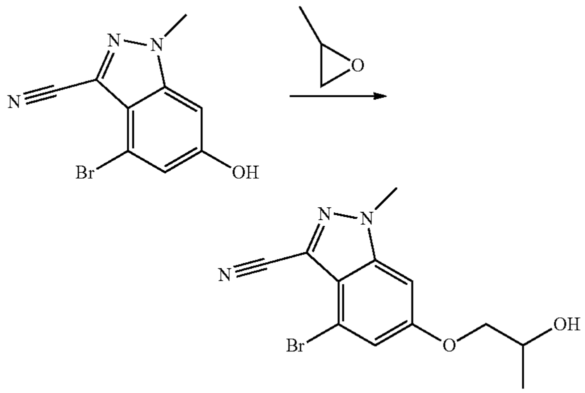

2-Methyloxirane (835 mg, 14.16 mmol) was added to a solution of 4-bromo-6-hydroxy-1-methyl-1H-indazole-3-carbonitrile (1.5 g, 7.08 mmol), potassium carbonate (2.93 g, 21.23 mmol) and acetonitrile (15 mL), and then the reaction mixture was stirred at 80° C. for 16 hours; the reaction mixture was concentrated under reduced pressure to dryness, separated by column chromatography (dichloromethane/methanol=10:1) to obtain colorless oil 4-bromo-6-(2-hydroxypropoxy)-1-methyl-1H-indazole-3-carbonitrile (900 mg, yield: 41%).

MS m/z (ESI): 310.0 $[M+H]^+$.

Step 8: (R)-4-(6-fluoropyridin-3-yl)-6-(2-hydroxypropoxy)-1-methyl-1H-indazole-3-carbonitrile

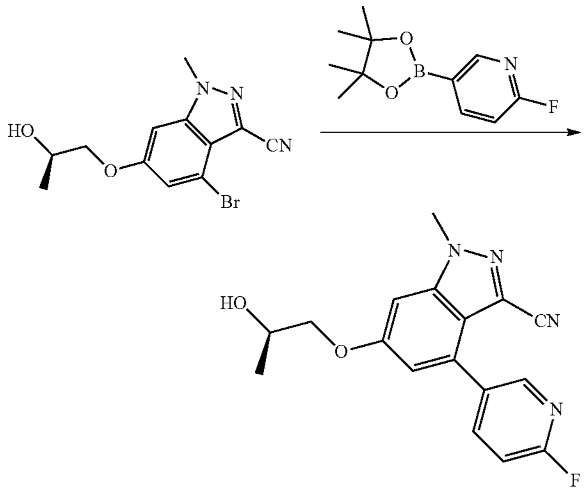

1,1'-Bis(diphenylphosphino)ferrocene-palladium(II)dichloride dichloromethane complex (120 mg, 0.15 mmol) was added to a mixed solution of 4-bromo-6-(2-hydroxypropoxy)-1-methyl-1H-indazole-3-carbonitrile (900 mg, 2.91 mmol), 2-fluoro-5-(4,4,5,5-tetramethyl-1,3,2-dioxaborolan-2-yl)pyridine (778 mg, 3.49 mmol), potassium acetate (570 mg, 5.82 mmol) and dioxane (10 mL), the mixture was replaced with nitrogen three times and then stirred at 100° C. under the protection of nitrogen for 16 hours; the reaction was cooled and filtered, the filtrate was concentrated under reduced pressure to dryness and separated by column chromatography (dichloromethane/methanol=10:1) to obtain colorless oil (R)-4-(6-fluoropyridin-3-yl)-6-(2-hydroxypropoxy)-1-methyl-1H-indazole-3-carbonitrile (650 mg, yield: 69%).

MS m/z (ESI): 327.1 [M+H]$^+$.

Step 9: ethyl 3-(5-(3-cyano-6-((R)-2-hydroxypropoxy)-1-methyl-1H-indazol-4-yl)pyridin-2-yl)-3,6-diazabicyclo[3.1.1]heptane-6-carboxylate

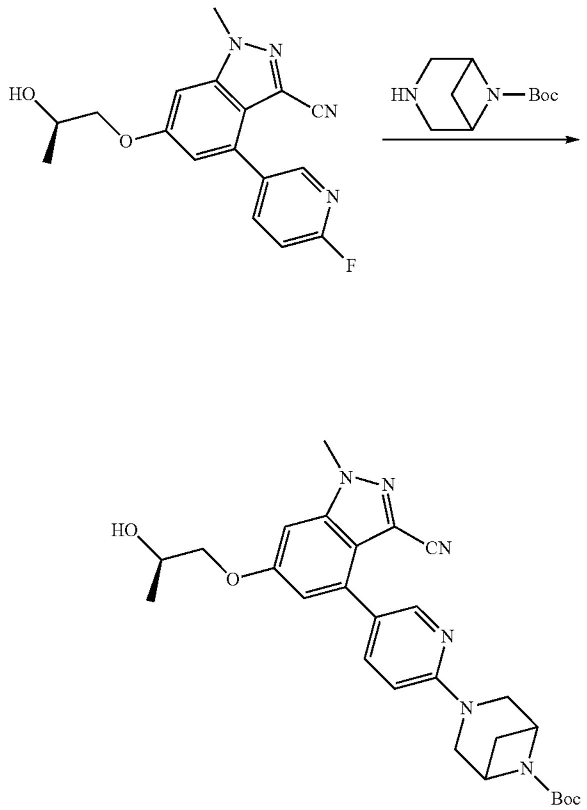

A mixed solution of (R)-4-(6-fluoropyridin-3-yl)-6-(2-hydroxypropoxy)-1-methyl-1H-indazole-3-carbonitrile (650 mg, 1.99 mmol), tert-butyl 3,6-diazabicyclo[3.1.1]heptane-6-carboxylate (788 mg, 3.98 mmol), N,N-diisopropylethylamine (770 mg, 5.97 mmol) and dimethyl sulfoxide (8 mL) was stirred at 100° C. for 24 hours; the reaction was quenched with water and extracted with ethyl acetate (50 mL*3), the combined organic phase was washed with saturated saline, the organic phase was dried over anhydrous sodium sulfate, filtered, and the filtrate was concentrated under reduced pressure to dryness and separated by column chromatography (dichloromethane/methanol=10:1) to obtain colorless oil ethyl 3-(5-(3-cyano-6-((R)-2-hydroxypropoxy)-1-methyl-1H-indazol-4-yl)pyridin-2-yl)-3,6-diazabicyclo[3.1.1]heptane-6-carboxylate (410 mg, yield: 41%).

MS m/z (ESI): 505.2 [M+H]$^+$.

Step 10: 4-(6-(3,6-diazabicyclo[3.1.1]heptan-3-yl)pyridin-3-yl)-6-((R)-2-hydroxypropoxy)-1-methyl-1H-indazole-3-carbonitrile

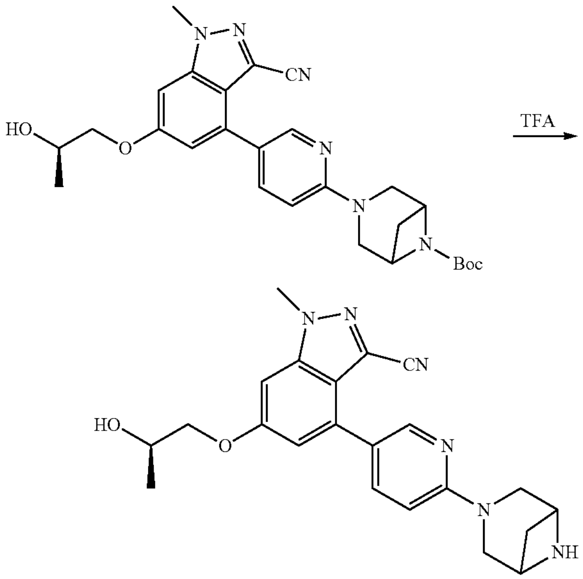

Ethyl 3-(5-(3-cyano-6-((R)-2-hydroxypropoxy)-1-methyl-1H-indazol-4-yl)pyridin-2-yl)-3,6-diazabicyclo[3.1.1]heptane-6-carboxylate (410 mg, 0.81 mmol) was dissolved in dichloromethane (6 mL), then trifluoroacetic acid (2 mL) was added at room temperature for 1 hour; after the reaction was completed, the mixture was concentrated under reduced pressure to dryness and used directly in the next step without purification to obtain light yellow oil 4-(6-(3,6-diazabicyclo[3.1.1]heptan-3-yl)pyridin-3-yl)-6-((R)-2-hydroxypropoxy)-1-methyl-1H-indazole-3-carbonitrile (520 mg, crude product).

MS m/z (ESI): 405.2 [M+H]$^+$.

Step 11: 6-((R)-2-hydroxypropoxy)-4-(6-(6-((6-methoxypyridin-3-yl)methyl)-3,6-diazabicyclo[3.1.1]heptan-3-yl)pyridin-3-yl)-1-methyl-1H-indazole-3-carbonitrile

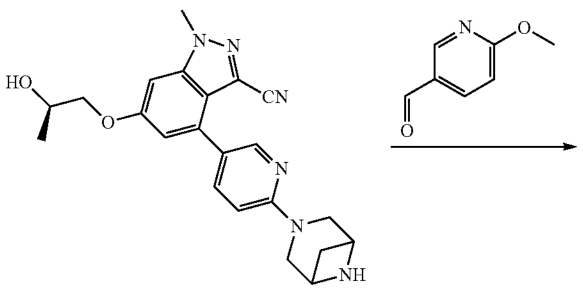

-continued

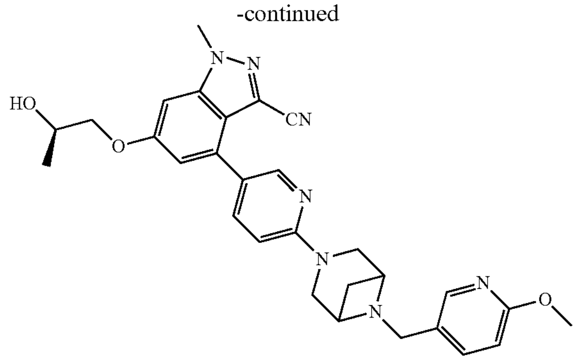

Sodium cyanoborohydride (47 mg, 0.75 mmol) was added to a solution of 4-(6-(3,6-diazabicyclo[3.1.1]heptan-3-yl)pyridin-3-yl)-6-((R)-2-hydroxypropoxy)-1-methyl-1H-indazole-3-carbonitrile (100 mg, 0.25 mmol), 6-methoxynicotinaldehyde (51 mg, 0.37 mmol) and 1,2-dichloroethane (3 mL), and then the mixture was stirred at room temperature for 24 hours; after the reaction was completed, the mixture was quenched with water and extracted with ethyl acetate (20 mL*3), and the combined organic phase was washed with saturated saline, dried over anhydrous sodium sulfate, filtered, and the filtrate was concentrated under reduced pressure to dryness and separated by preparative chromatography to obtain white solid 6-((R)-2-hydroxypropoxy)-4-(6-(6-((6-methoxypyridin-3-yl)methyl)-3,6-diazabicyclo[3.1.1]heptan-3-yl)pyridin-3-yl)-1-methyl-1H-indazole-3-carbonitrile (12 mg, yield: 9%).

MS m/z (ESI): 526.2 [M+H]$^+$.

Embodiment 47

4-(6-(6-((5-Fluoro-6-methoxypyridin-3-yl)-3,6-diazabicyclo[3.1.1]heptan-3-yl)pyridin-3-yl)-6-(2-hydroxyethoxy)-1-methyl-1H-indazole-3-carbonitrile

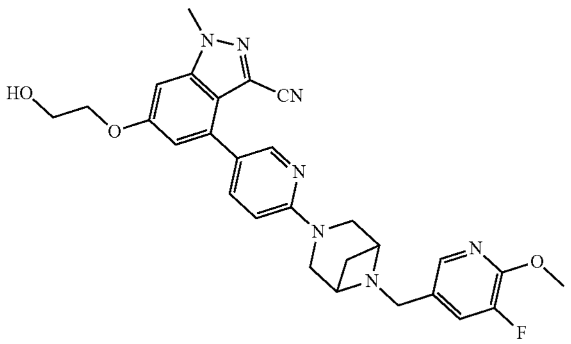 [SMILES: COc1ncc(CN2C3CC2CN(c2ccc(-c4cc(OCCO)cc5c4c(C#N)nn5C)cn2)C3)cc1F]

The title compound was obtained with reference to steps 1 to 8 of embodiment 46, wherein 2-methyloxirane in step 7 was replaced with ethylene oxide.

MS m/z (ESI): 530.2 [M+H]$^+$.

Embodiment 48

6-(2-Hydroxy-2-methylpropoxy)-4-(6-(4-((6-methoxypyridin-3-yl)oxy)piperidin-1-yl)pyridin-3-yl)-1-methyl-1H-indazole-3-carbonitrile

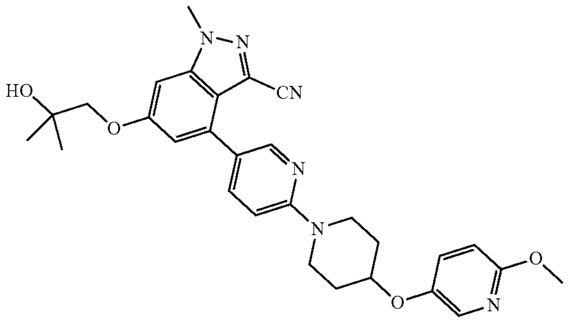 [SMILES: COc1ccc(OC2CCN(c3ccc(-c4cc(OCC(C)(C)O)cc5c4c(C#N)nn5C)cn3)CC2)cn1]

The title compound was obtained with reference to embodiment 46, wherein 2-methyloxirane in step 7 was replaced with 2,2-dimethyloxirane, and then with reference to embodiment 13.

MS m/z (ESI): 529.2 [M+H]$^+$.

Embodiment 49

6-(2-Hydroxy-2-methylpropoxy)-4-(2-(6-((6-methoxypyridin-3-yl)methyl)-3,6-diazabicyclo[3.1.1]heptan-3-yl)thiazol-5-yl)pyrazolo[1,5-a]pyridine-3-carbonitrile

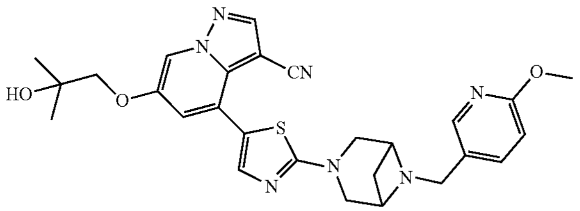 [SMILES: COc1ccc(CN2C3CC2CN(c2ncc(-c4cc(OCC(C)(C)O)cn5ncc(C#N)c45)s2)C3)cn1]

Step 1: tert-butyl 3-(5-bromothiazol-2-yl)-3,6-diazabicyclo[3.1.1]heptane-6-carboxylate

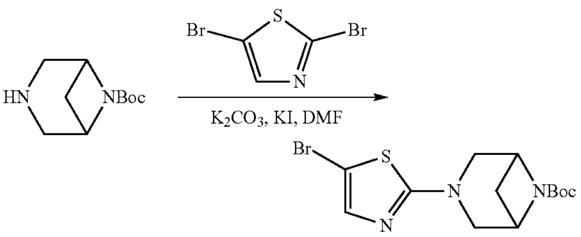

Tert-butyl 3,6-diazabicyclo[3.1.1]heptane-6-carboxylate (300 mg, 1.5 mmol) was dissolved in 20 mL of DMF; and 2,5-dibromothiazole (547 mg, 2.2 mmol), $K_2CO_3$ (621 mg, 4.5 mmol), KI (25 mg, 0.15 mmol) were added, and the reaction was carried out overnight at 90° C. under the protection of nitrogen. 10 mL of ammonium chloride aqueous solution was added, and the mixture was extracted with ethyl acetate (20 mL*3). The organic phase was washed with saturated saline, dried over anhydrous sodium sulfate. The residue was filtered, evaporated to dryness; and the crude product was separated by column chromatography (eluted with dichloromethane/methanol=10/1) to obtain tert-butyl 3-(5-bromothiazol-2-yl)-3,6-diazabicyclo[3.1.1]heptane-6-carboxylate (230 mg, white solid, the yield was 42%).

MS m/z (ESI): 360.0 [M+H]+.

Step 2: 2-(3,6-diazabicyclo[3.1.1]heptan-3-yl)-5-bromothiazole

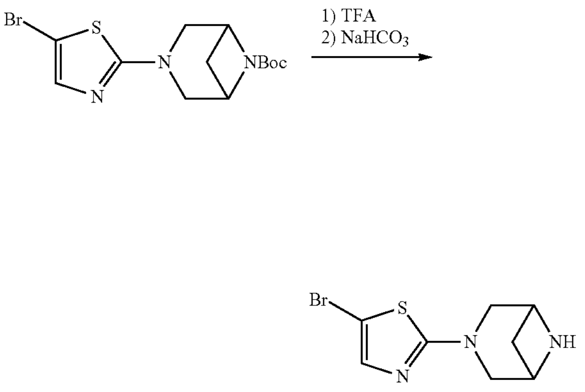

2-(3,6-diazabicyclo[3.1.1]heptan-3-yl)-5-bromothiazole (210 mg, white solid, 99%) was obtained by using tert-butyl 3-(5-bromothiazol-2-yl)-3,6-diazabicyclo[3.1.1]heptane-6-carboxylate as raw material with reference to step 5 of embodiment 1.

MS m/z (ESI): 259.9 [M+H]+.

Step 3: 5-bromo-2-(6-((6-methoxypyridin-3-yl)methyl)-3,6-diazabicyclo[3.1.1]heptan-3-yl)thiazole

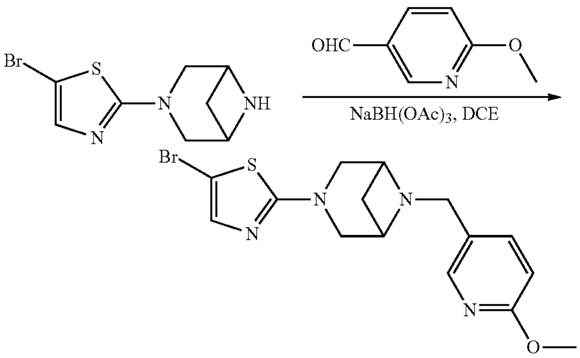

5-Bromo-2-(6-((6-methoxypyridin-3-yl)methyl)-3,6-diazabicyclo[3.1.1]heptan-3-yl)thiazole (100 mg, white solid, 52%) was obtained by using 2-(3,6-diazabicyclo[3.1.1]heptan-3-yl)-5-bromothiazole as raw material with reference to step 6 of embodiment 1.

MS m/z (ESI): 381.0 [M+H]+.

Step 4: 6-(2-hydroxy-2-methylpropoxy)-4-(4,4,5,5-tetramethyl-1,3,2-dioxaborolan-2-yl)pyrazolo[1,5-a]pyridine-3-carbonitrile

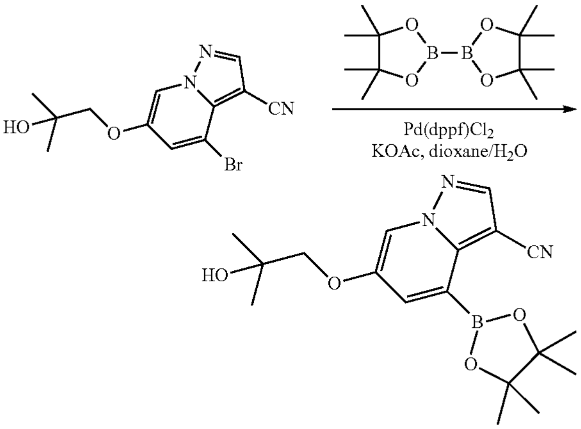

6-(2-Hydroxy-2-methylpropoxy)-4-(4,4,5,5-tetramethyl-1,3,2-dioxaborolan-2-yl)pyrazolo[1,5-a]pyridine-3-carbonitrile (130 mg, white solid, yield was 61%) was obtained by using 4-bromo-6-(2-hydroxy-2-methylpropoxy)pyrazolo[1,5-a]pyridine-3-carbonitrile as raw material with reference to step 7 of embodiment 1.

MS m/z (ESI): 358.1 [M+H]+.

Step 5: 6-(2-hydroxy-2-methylpropoxy)-4-(2-(6-((6-methoxypyridin-3-yl)methyl)-3,6-diazabicyclo[3.1.1]heptan-3-yl)thiazol-5-yl)pyrazolo[1,5-a]pyridine-3-carbonitrile

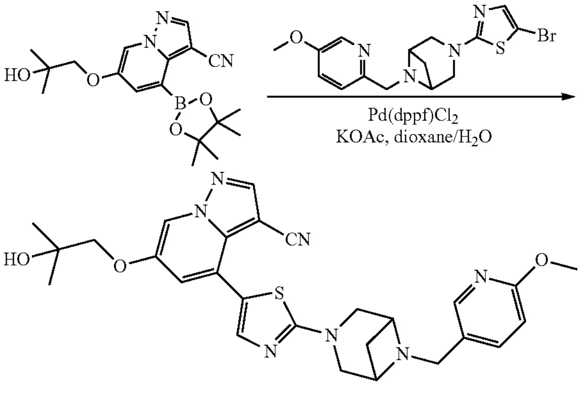

6-(2-Hydroxy-2-methylpropoxy)-4-(2-(6-((6-methoxypyridin-3-yl)methyl)-3,6-diazabicyclo[3.1.1]heptan-3-yl)thiazol-5-yl)pyrazolo[1,5-a]pyridine-3-carbonitrile (33 mg, white solid, 47%) was obtained by using 6-(2-hydroxy-2-methylpropoxy)-4-(4,4,5,5-tetramethyl-1,3,2-dioxaborolan-2-yl)pyrazolo[1,5-a]pyridine-3-carbonitrile and 5-bromo-2-(6-((6-methoxypyridin-3-yl)methyl)-3,6-diazabicyclo[3.1.1]heptan-3-yl)thiazole as raw materials with reference to step 8 of embodiment 1.

MS m/z (ESI): 532.2 [M+H]+.

Embodiment 50

4-(2-(6-((5-Fluoro-6-methoxypyridin-3-yl)methyl)-3,6-diazabicyclo[3.1.1]heptan-3-yl)thiazol-5-yl)-6-(2-hydroxy-2-methylpropoxy)pyrazolo[1,5-a]pyridine-3-carbonitrile

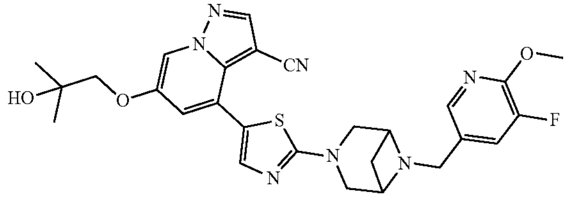 [SMILES: COc1ncc(CN2C3CC2CN(c2ncc(-c4cc(OCC(C)(C)O)cn5ncc(C#N)c45)s2)C3)cc1F]

Step 1: 5-bromo-2-(6-((5-fluoro-6-methoxypyridin-3-yl)methyl)-3,6-diazabicyclo[3.1.1]heptan-3-yl)thiazole

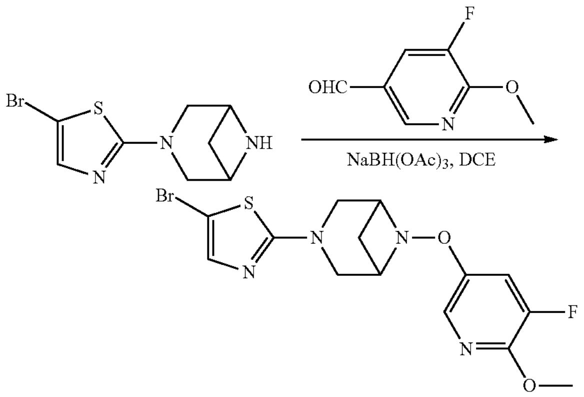

5-Bromo-2-(6-((5-fluoro-6-methoxypyridin-3-yl)methyl)-3,6-diazabicyclo[3.1.1]heptan-3-yl)thiazole (220 mg, white solid, 62%) was obtained by using 2-(3,6-diazabicyclo[3.1.1]heptan-3-yl)-5-bromothiazole and 5-fluoro-6-methoxynicotinaldehyde as raw material with reference to step 6 of embodiment 1.

MS m/z (ESI): 399.0 $[M+H]^+$.

Step 2: 4-(2-(6-((5-fluoro-6-methoxypyridin-3-yl)methyl)-3,6-diazabicyclo[3.1.1]heptan-3-yl)thiazol-5-yl)-6-(2-hydroxy-2-methylpropoxy)pyrazolo[1,5-a]pyridine-3-carbonitrile

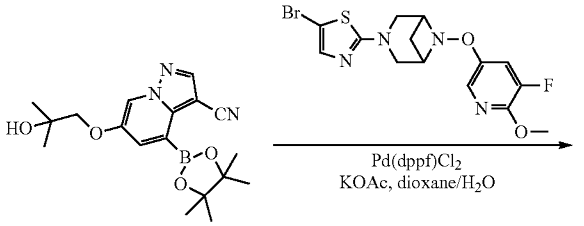

-continued

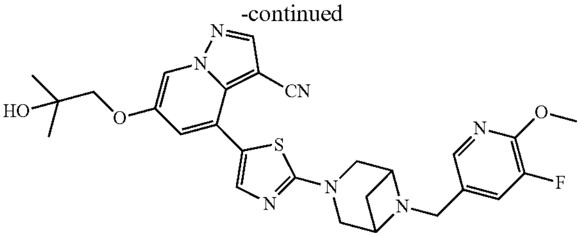

4-(2-(6-((5-Fluoro-6-methoxypyridin-3-yl)methyl)-3,6-diazabicyclo[3.1.1]heptan-3-yl)thiazol-5-yl)-6-(2-hydroxy-2-methylpropoxy)pyrazolo[1,5-a]pyridine-3-carbonitrile (35 mg, white solid, 48%) was obtained by using 6-(2-hydroxy-2-methylpropoxy)-4-(4,4,5,5-tetramethyl-1,3,2-dioxaborolan-2-yl)pyrazolo[1,5-a]pyridine-3-carbonitrile and 5-bromo-2-(6-((5-fluoro-6-methoxypyridin-3-yl)methyl)-3,6-diazabicyclo[3.1.1]heptan-3-yl)thiazole as raw materials with reference to step 8 of embodiment 1.

MS m/z (ESI): 550.2 $[M+H]^+$.

Embodiment 51

3-(5-(3-Cyano-6-(2-hydroxy-2-methylpropoxy)pyrazolo[1,5-a]pyridin-4-yl)thiazol-2-yl)-N-phenyl-3,6-diazabicyclo[3.1.1]heptane-6-carboxamide

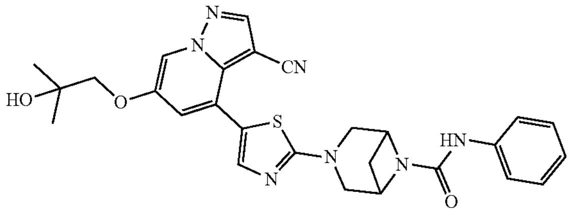 [SMILES: CC(C)(O)COc1cc(-c2cnc(N3CC4CC(C3)N4C(=O)Nc3ccccc3)s2)c2c(C#N)cnn2c1]

Step 1: 3-(5-bromothiazol-2-yl)-N-phenyl-3,6-diazabicyclo[3.1.1]heptane-6-carboxamide

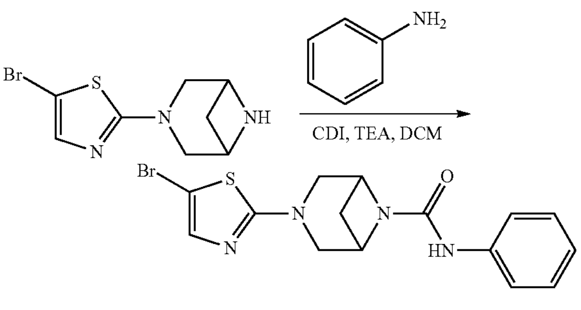

2-(3,6-Diazabicyclo[3.1.1]heptan-3-yl)-5-bromothiazole (300 mg, 1.2 mmol) was dissolved in 20 mL of DCM, and CDI (280 mg, 1.7 mmol) and TEA (245 mg, 2.4 mmol) were added, the reaction was carried out at room temperature for 2 hours. Aniline (223 mg, 2.4 mmol) was added thereto, and the reaction was carried out overnight at room temperature, 10 mL of ammonium chloride aqueous solution was added, and the mixture was extracted with ethyl acetate (20 mL*3). The organic phase was washed with saturated saline, dried over anhydrous sodium sulfate. The residue was filtered, evaporated to dryness; and the crude product was separated by column chromatography (eluted with dichloromethane/methanol=10/1) to obtain 3-(5-bromothiazol-2-yl)-N-phenyl-3,6-diazabicyclo[3.1.1]heptane-6-carboxamide (223 mg, white solid, the yield was 49%).

MS m/z (ESI): 379.0 $[M+H]^+$.

Step 2: 3-(5-(3-cyano-6-(2-hydroxy-2-methylpropoxy)pyrazolo[1,5-a]pyridin-4-yl)thiazol-2-yl)-N-phenyl-3,6-diazabicyclo[3.1.1]heptane-6-carboxamide

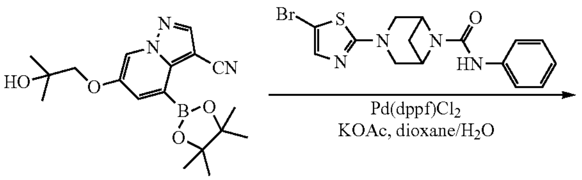

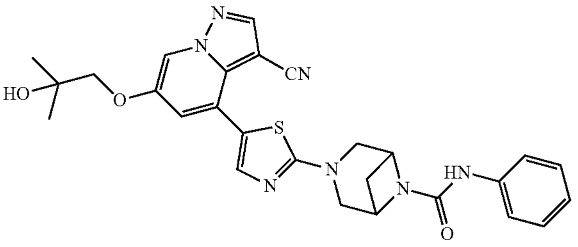

3-(5-(3-Cyano-6-(2-hydroxy-2-methylpropoxy)pyrazolo[1,5-a]pyridin-4-yl)thiazol-2-yl)-N-phenyl-3,6-diazabicyclo[3.1.1]heptane-6-carboxamide (29 mg, white solid, 39%) was obtained by using 6-(2-hydroxy-2-methylpropoxy)-4-(4,4,5,5-tetramethyl-1,3,2-dioxaborolan-2-yl)pyrazolo[1,5-a]pyridine-3-carbonitrile and 3-(5-bromothiazol-2-yl)-N-phenyl-3,6-diazabicyclo[3.1.1]heptane-6-carboxamide as raw materials with reference to step 8 of embodiment 1.

MS m/z (ESI): 530.1 $[M+H]^+$.

Embodiment 52

6-(2-Hydroxyethoxy)-4-(5-(6-((6-methoxypyridin-3-yl)methyl)-3,6-diazabicyclo[3.1.1]heptan-3-yl)-1,3,4-thiadiazol-2-yl)pyrazolo[1,5-a]pyridine-3-carbonitrile

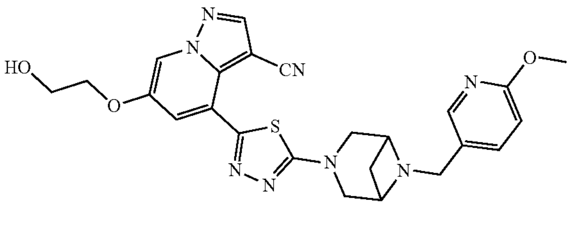 [SMILES: COc1ccc(CN2C3CC2CN(c2nnc(-c4cc(OCCO)cn5ncc(C#N)c45)s2)C3)cn1]

Step 1: tert-butyl 3-(5-bromo-1,3,4-thiadiazol-2-yl)-3,6-diazabicyclo[3.1.1]heptane-6-carboxylate

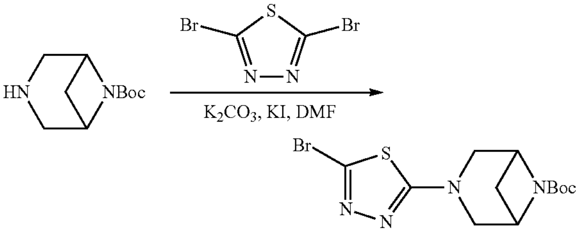

Tert-butyl 3-(5-bromo-1,3,4-thiadiazol-2-yl)-3,6-diazabicyclo[3.1.1]heptane-6-carboxylate (530 mg, white solid, 67%) was obtained by using 2,5-dibromo-1,3,4-thiadiazole as raw material with reference to step 1 of embodiment 49.

MS m/z (ESI): 361.0 $[M+H]^+$.

Step 2: 2-(3,6-diazabicyclo[3.1.1]heptan-3-yl)-5-bromo-1,3,4-thiadiazole

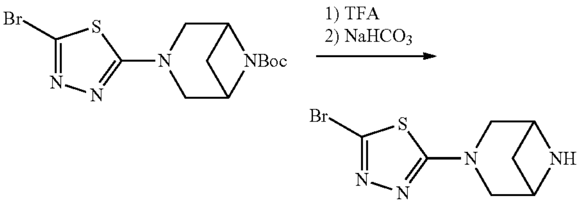

2-(3,6-Diazabicyclo[3.1.1]heptan-3-yl)-5-bromo-1,3,4-thiadiazole (350 mg, white solid, 99%) was obtained by using tert-butyl 3-(5-bromo-1,3,4-thiadiazol-2-yl)-3,6-diazabicyclo[3.1.1]heptane-6-carboxylate as raw material with reference to step 5 of embodiment 1.

MS m/z (ESI): 260.9 $[M+H]^+$.

Step 3: 2-bromo-5-(6-((6-methoxypyridin-3-yl)methyl)-3,6-diazabicyclo[3.1.1]heptan-3-yl)-1,3,4-thiadiazole

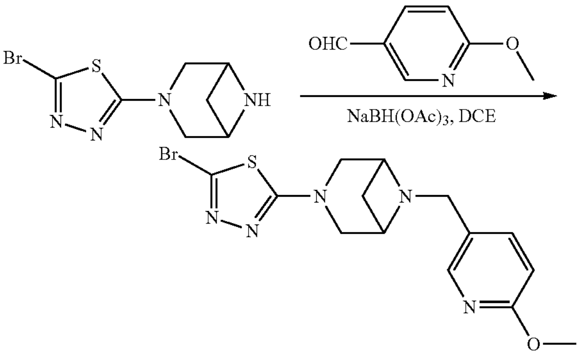

2-Bromo-5-(6-((6-methoxypyridin-3-yl)methyl)-3,6-diazabicyclo[3.1.1]heptan-3-yl)-1,3,4-thiadiazole (120 mg, white solid, 56%) was obtained by using 2-(3,6-diazabicyclo[3.1.1]heptan-3-yl)-5-bromo-1,3,4-thiadiazole as raw material with reference to step 6 of embodiment 1.

MS m/z (ESI): 382.0 $[M+H]^+$.

Step 4: 6-(2-hydroxyethoxy)-4-(5-(6-((6-methoxypyridin-3-yl)methyl)-3,6-diazabicyclo[3.1.1]heptan-3-yl)-1,3,4-thiadiazol-2-yl)pyrazolo[1,5-a]pyridine-3-carbonitrile

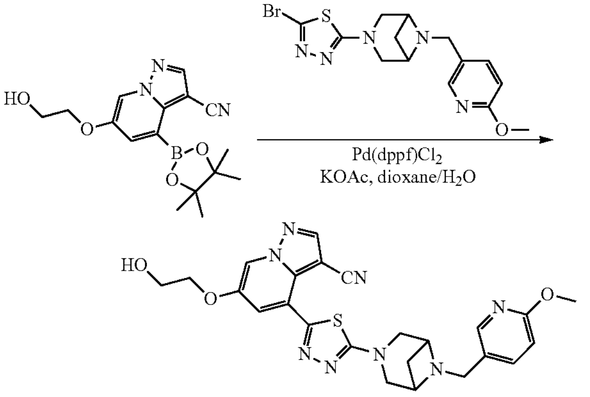

6-(2-Hydroxyethoxy)-4-(5-(6-((6-methoxypyridin-3-yl)methyl)-3,6-diazabicyclo[3.1.1]heptan-3-yl)-1,3,4-thiadiazol-2-yl)pyrazolo[1,5-a]pyridine-3-carbonitrile (25 mg, white solid, 38%) was obtained by using 6-(2-hydroxyethoxy)-4-(4,4,5,5-tetramethyl-1,3,2-dioxaborolan-2-yl)pyrazolo[1,5-a]pyridine-3-carbonitrile and 2-bromo-5-(6-((6-methoxypyridin-3-yl)methyl)-3,6-diazabicyclo[3.1.1]heptan-3-yl)-1,3,4-thiadiazole as raw materials with reference to step 8 of embodiment 1.

MS m/z (ESI): 505.1 $[M+H]^+$.

Embodiment 53

4-(5-(6-((5-Fluoro-6-methoxypyridin-3-yl)methyl)-3,6-diazabicyclo[3.1.1]heptan-3-yl)-1,3,4-thiadiazol-2-yl)-6-(2-hydroxyethoxy)pyrazolo[1,5-a]pyridine-3-carbonitrile

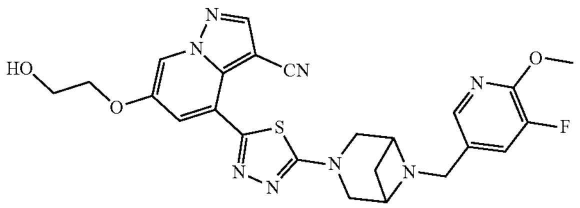 [SMILES: COc1ncc(CN2C3CC2CN(c2nnc(-c4cc(OCCO)cn5ncc(C#N)c45)s2)C3)cc1F]

Step 1: 2-bromo-5-(6-((5-fluoro-6-methoxypyridin-3-yl)methyl)-3,6-diazabicyclo[3.1.1]heptan-3-yl)-1,3,4-thiadiazole

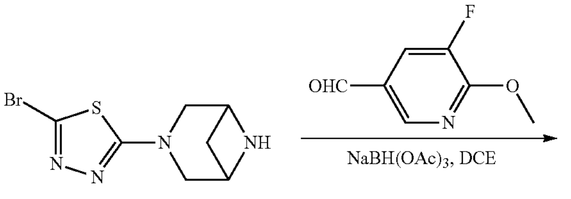

-continued

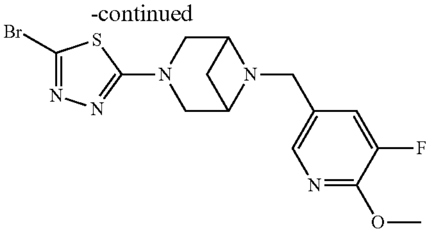

2-Bromo-5-(6-((5-fluoro-6-methoxypyridin-3-yl)methyl)-3,6-diazabicyclo[3.1.1]heptan-3-yl)-1,3,4-thiadiazole (150 mg, white solid, 59%) was obtained by using 2-(3,6-diazabicyclo[3.1.1]heptan-3-yl)-5-bromo-1,3,4-thiadiazole as raw material with reference to step 6 of embodiment 1.

MS m/z (ESI): 400.0 $[M+H]^+$.

Step 2: 4-(5-(6-((5-fluoro-6-methoxypyridin-3-yl)methyl)-3,6-diazabicyclo[3.1.1]heptan-3-yl)-1,3,4-thiadiazol-2-yl)-6-(2-hydroxyethoxy)pyrazolo[1,5-a]pyridine-3-carbonitrile

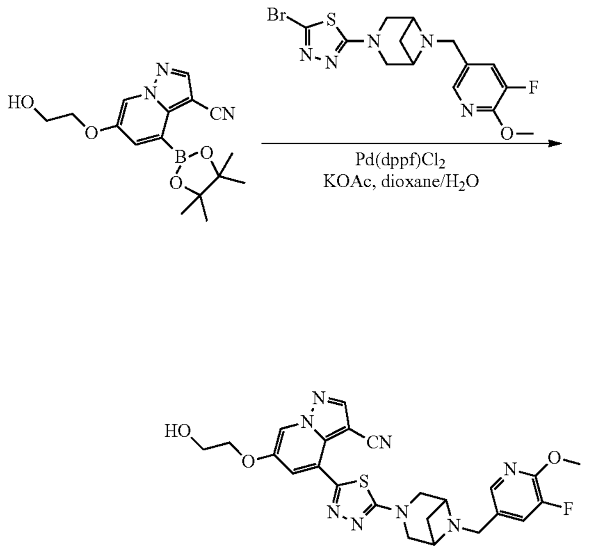

4-(5-(6-((5-Fluoro-6-methoxypyridin-3-yl)methyl)-3,6-diazabicyclo[3.1.1]heptan-3-yl)-1,3,4-thiadiazol-2-yl)-6-(2-hydroxyethoxy)pyrazolo[1,5-a]pyridine-3-carbonitrile (32 mg, white solid, 41%) was obtained by using 6-(2-hydroxyethoxy)-4-(4,4,5,5-tetramethyl-1,3,2-dioxaborolan-2-yl)pyrazolo[1,5-a]pyridine-3-carbonitrile and 2-bromo-5-(6-((5-fluoro-6-methoxypyridin-3-yl)methyl)-3,6-diazabicyclo[3.1.1]heptan-3-yl)-1,3,4-thiadiazole as raw materials with reference to step 8 of embodiment 1.

MS m/z (ESI): 523.1 $[M+H]^+$.

Embodiment 54

6-(2-Hydroxy-2-methylpropoxy)-4-(3-(6-((6-methoxypyridin-3-yl)methyl)-3,6-diazabicyclo[3.1.1]heptan-3-yl)-1H-pyrazol-1-yl)pyrazolo[1,5-a]pyridine-3-carbonitrile

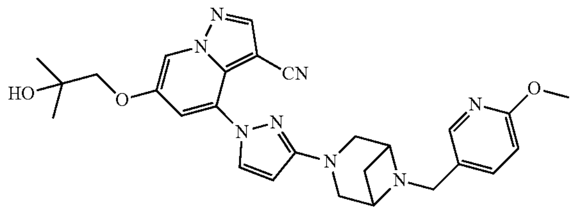 [SMILES: COc1ccc(CN2C3CC2CN(c2ccn(-c4cc(OCC(C)(C)O)cn5ncc(C#N)c45)n2)C3)cn1]

Step 1: Preparation of tert-butyl 3-(1-(4-methoxybenzyl)-1H-pyrazol-3-yl)-3,6-diazabicyclo[3.1.1]heptane-6-carboxylate

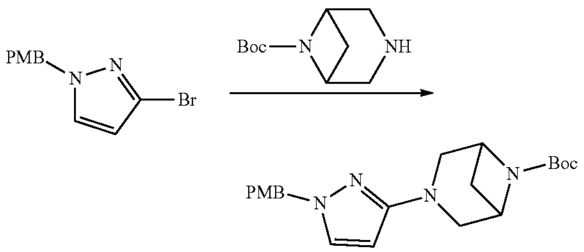

3-Bromo-1-(4-methoxybenzyl)-1H-pyrazole (5 g, 18.7 mmol) was dissolved in DMF (30 mL), tert-butyl 3,6-diazabicyclo[3.1.1]heptane-6-carboxylate (4.45 g, 22.5 mmol) and tert-butanol sodium (2.7 g, 28.1 mmol) were added thereto. Then $Pd_2(dba)_3$ (1.7 g, 1.87 mmol) and RuPhos (1.75 g, 3.74 mmol) were added thereto under the protection of nitrogen. The reaction was stirred at 90° C. overnight. Water (50 mL) was added to the reaction mixture, and then ethyl acetate (100 mL) was added thereto for extraction. The organic phase was dried and evaporated to dryness. The crude product was purified by column chromatography to obtain tert-butyl 3-(1-(4-methoxybenzyl)-1H-pyrazol-3-yl)-3,6-diazabicyclo[3.1.1]heptane-6-carboxylate (5 g, yield: 69%).

MS m/z (ESI): 385.2[M+H]$^+$.

Step 2: Preparation of 3-(1-(4-methoxybenzyl)-1H-pyrazol-3-yl)-3,6-diazabicyclo[3.1.1]heptane

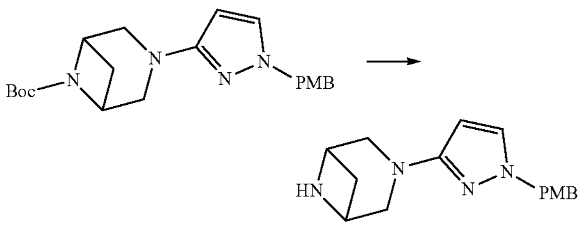

3-(1-(4-Methoxybenzyl)-1H-pyrazol-3-yl)-3,6-diazabicyclo[3.1.1]heptane was obtained by using tert-butyl 3-(1-(4-methoxybenzyl)-1H-pyrazol-3-yl)-3,6-diazabicyclo[3.1.1]heptane-6-carboxylate as raw material with reference to step 4 of embodiment 43.

MS m/z (ESI): 285.2[M+H]$^+$.

Step 3: 3-(1-(4-methoxybenzyl)-1H-pyrazol-3-yl)-6-((6-methoxypyridin-3-yl)methyl)-3,6-diazabicyclo[3.1.1]heptane

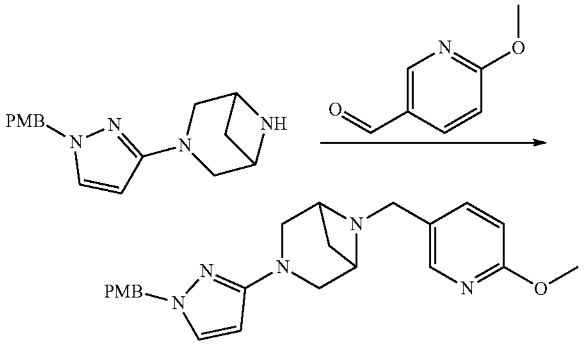

3-(1-(4-Methoxybenzyl)-1H-pyrazol-3-yl)-3,6-diazabicyclo[3.1.1]heptane (2 g, 7.0 mmol) was dissolved in DCE (30 mL), and 6-methoxynicotinaldehyde (1.9 g, 14.1 mmol) and sodium triacetoxyborohydride (4.5 g, 21.0 mmol) were added. The reaction mixture was stirred at room temperature overnight. Water (60 mL) was added thereto, and then the mixture was extracted with dichloromethane (50 mL). The organic phase was dried and evaporated to dryness. The crude product was purified by column chromatography to obtain 3-(1-(4-methoxybenzyl)-1H-pyrazol-3-yl)-6-((6-methoxypyridin-3-yl)methyl)-3,6-diazabicyclo[3.1.1]heptane (2.1 g, yield: 75%).

MS m/z (ESI): 406.2[M+H]$^+$.

Step 4: 6-((6-methoxypyridin-3-yl)methyl)-3-(1H-pyrazol-3-yl)-3,6-diazabicyclo[3.1.1]heptane

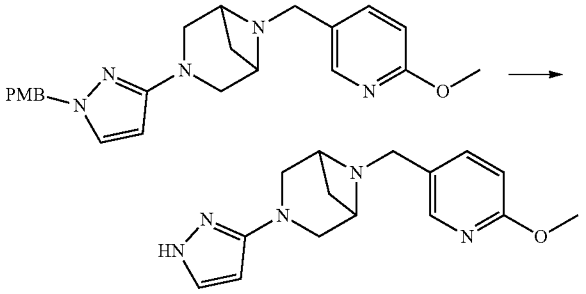

6-((6-Methoxypyridin-3-yl)methyl)-3-(1H-pyrazol-3-yl)-3,6-diazabicyclo[3.1.1]heptane (yield: 80%) was obtained by using 3-(1-(4-methoxybenzyl)-1H-pyrazol-3-yl)-6-((6-methoxypyridin-3-yl)methyl)-3,6-diazabicyclo[3.1.1]heptane as raw material with reference to step 4 of embodiment 42.

MS m/z (ESI): 286.2[M+H]$^+$.

Step 5: 6-(2-hydroxy-2-methylpropoxy)-4-(3-(6-((6-methoxypyridin-3-yl)methyl)-3,6-diazabicyclo[3.1.1]heptan-3-yl)-1H-pyrazol-1-yl)pyrazolo[1,5-a]pyridine-3-carbonitrile

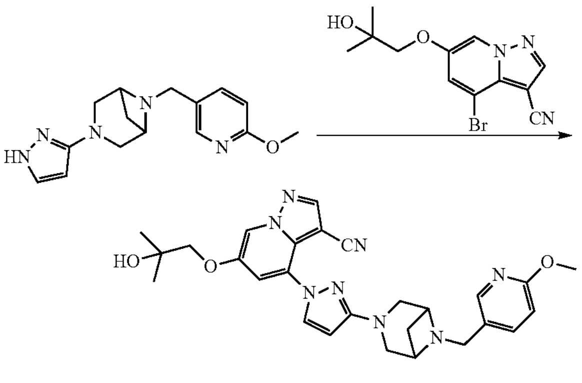

6-(2-Hydroxy-2-methylpropoxy)-4-(3-(6-((6-methoxypyridin-3-yl)methyl)-3,6-diazabicyclo[3.1.1]heptan-3-yl)-1H-pyrazol-1-yl)pyrazolo[1,5-a]pyridine-3-carbonitrile was obtained by using 6-((6-methoxypyridin-3-yl)methyl)-3-(1H-pyrazol-3-yl)-3,6-diazabicyclo[3.1.1]heptane and 4-bromo-6-(2-hydroxy-2-methylpropoxy)pyrazolo[1,5-a]pyridine-3-carbonitrile as raw material with reference to step 4 of embodiment 42.

MS m/z (ESI): 515.2[M+H]$^+$.

Embodiment 55

4-(3-(6-((6-Ethoxy-5-fluoropyridin-3-yl)methyl)-3,6-diazabicyclo[3.1.1]heptan-3-yl)-1H-pyrazol-1-yl)-6-(2-hydroxy-2-methylpropoxy)pyrazolo[1,5-a]pyridine-3-carbonitrile

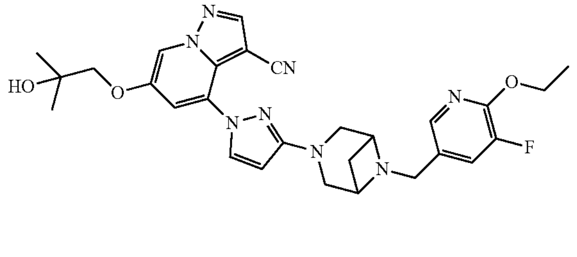 [SMILES: CCOc1ncc(CN2C3CC2CN(c2ccn(-c4cc(OCC(C)(C)O)cn5ncc(C#N)c45)n2)C3)cc1F]

Step 1: Preparation of tert-butyl 3-(1-(4-methoxybenzyl)-1H-pyrazol-3-yl)-3,6-diazabicyclo[3.1.1]heptane-6-carboxylate

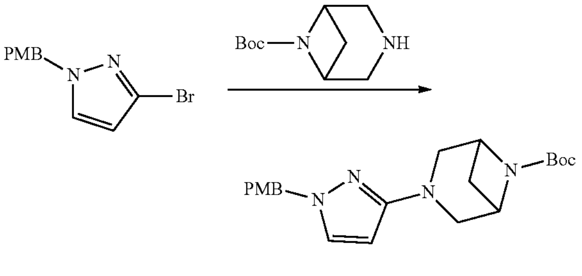

3-Bromo-1-(4-methoxybenzyl)-1H-pyrazole (5 g, 18.7 mmol) was dissolved in DMF (30 mL), and tert-butyl 3,6-diazabicyclo[3.1.1]heptane-6-carboxylate (4.45 g, 22.5 mmol) and tert-butanol sodium (2.7 g, 28.1 mmol) were added thereto. $Pd_2(dba)_3$ (1.7 g, 1.87 mmol) and RuPhos (1.75 g, 3.74 mmol) were added thereto under the protection of nitrogen. The reaction was stirred at 90° C. overnight. Water (50 mL) was added thereto, and then the mixture was extracted with ethyl acetate (100 mL). The organic phase was dried and evaporated to dryness. The crude product was purified by column chromatography to obtain tert-butyl 3-(1-(4-methoxybenzyl)-1H-pyrazol-3-yl)-3,6-diazabicyclo[3.1.1]heptane-6-carboxylate (5 g, yield: 69%).

MS m/z (ESI): 385.2[M+H]$^+$.

Step 2: Preparation of 3-(1-(4-methoxybenzyl)-1H-pyrazol-3-yl)-3,6-diazabicyclo[3.1.1]heptane

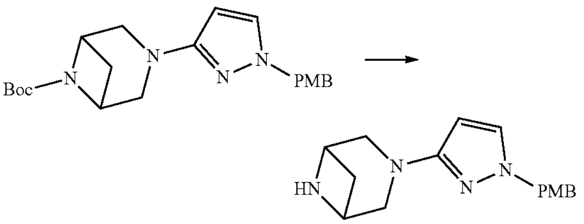

3-(1-(4-Methoxybenzyl)-1H-pyrazol-3-yl)-3,6-diazabicyclo[3.1.1]heptane was obtained by using tert-butyl 3-(1-(4-methoxybenzyl)-1H-pyrazol-3-yl)-3,6-diazabicyclo[3.1.1]heptane-6-carboxylate as raw material with reference to step 4 of embodiment 43 (3.5 g, yield: 95%).

MS m/z (ESI): 285.2[M+H]$^+$.

Step 3: Preparation of 6-((6-ethoxy-5-fluoropyridin-3-yl)methyl)-3-(1-(4-methoxybenzyl)-1H-pyrazol-3-yl)-3,6-diazabicyclo[3.1.1]heptane

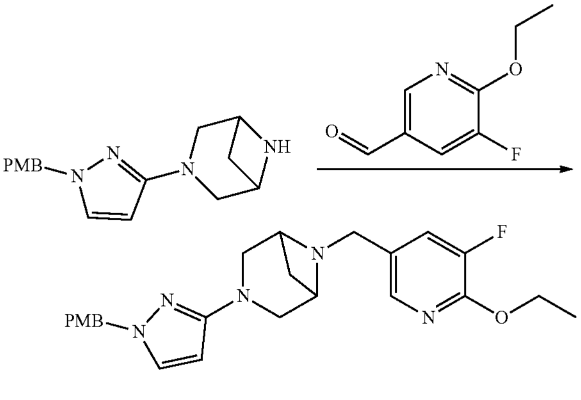

3-(1-(4-Methoxybenzyl)-1H-pyrazol-3-yl)-3,6-diazabicyclo[3.1.1]heptane (2 g, 7.0 mmol) was dissolved in DCE (30 mL), and 6-ethoxy-5-fluoronicotinaldehyde (2.4 g, 14.1 mmol) and sodium triacetoxyborohydride (4.5 g, 21.0 mmol) were added thereto. The reaction mixture was stirred at room temperature overnight. Water (60 mL) was added thereto and then the mixture was extracted with dichloromethane (50 mL). The organic phase was dried and evaporated to dryness. The crude product was purified by column chromatography to obtain 6-((6-ethoxy-5-fluoropyridin-3-yl)methyl)-3-(1-(4-methoxybenzyl)-1H-pyrazol-3-yl)-3,6-diazabicyclo[3.1.1]heptane (2.5 g, yield: 81%).

MS m/z (ESI): 438.2[M+H]+.

Step 4: Preparation of 6-((6-ethoxy-5-fluoropyridin-3-yl)methyl)-3-(1H-pyrazol-3-yl)-3,6-diazabicyclo[3.1.1]heptane

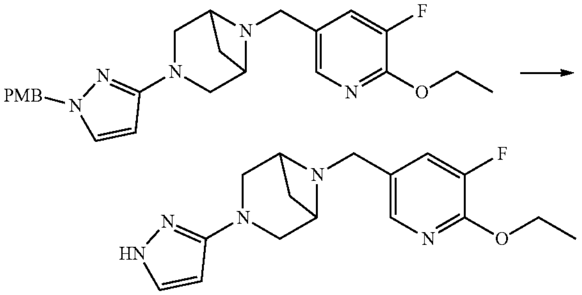

6-((6-Ethoxy-5-fluoropyridin-3-yl)methyl)-3-(1H-pyrazol-3-yl)-3,6-diazabicyclo[3.1.1]heptane was obtained by using 6-((6-ethoxy-5-fluoropyridin-3-yl)methyl)-3-(1-(4-methoxybenzyl)-1H-pyrazol-3-yl)-3,6-diazabicyclo[3.1.1]heptane as raw material with reference to step 4 of embodiment 42.

MS m/z (ESI): 318.2[M+H]+.

Step 5: 4-(3-(6-((6-ethoxy-5-fluoropyridin-3-yl)methyl)-3,6-diazabicyclo[3.1.1]heptan-3-yl)-1H-pyrazol-1-yl)-6-(2-hydroxy-2-methylpropoxy)pyrazolo[1,5-a]pyridine-3-carbonitrile

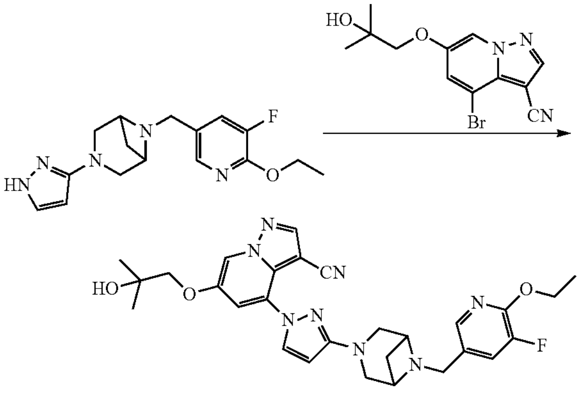

4-(3-(6-((6-Ethoxy-5-fluoropyridin-3-yl)methyl)-3,6-diazabicyclo[3.1.1]heptan-3-yl)-1H-pyrazol-1-yl)-6-(2-hydroxy-2-methylpropoxy)pyrazolo[1,5-a]pyridine-3-carbonitrile (80 mg, yield: 32%) was obtained by using 6-((6-ethoxy-5-fluoropyridin-3-yl)methyl)-3-(1H-pyrazol-3-yl)-3,6-diazabicyclo[3.1.1]heptane and 4-bromo-6-(2-hydroxy-2-methylpropoxy)pyrazolo[1,5-a]pyridine-3-carbonitrile as raw material with reference to step 4 of embodiment 42.

MS m/z (ESI): 547.2[M+H]+.

Embodiment 56

6-(2-Hydroxy-2-methylpropoxy)-4-(3-(4-((6-methoxypyridin-3-yl)oxo)piperidin-1-yl)-1H-pyrazol-1-yl)pyrazolo[1,5-a]pyridine-3-carbonitrile

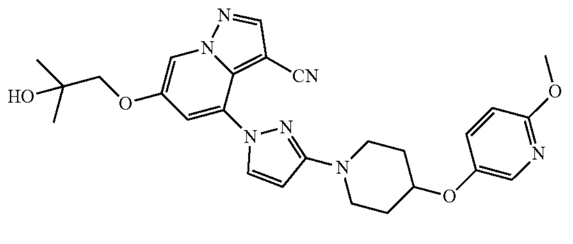 [SMILES: COc1ccc(OC2CCN(c3ccn(-c4cc(OCC(C)(C)O)cn5ncc(C#N)c45)n3)CC2)cn1]

Step 1: Preparation of 2-methoxy-5-(piperidin-4-oxy)pyridine

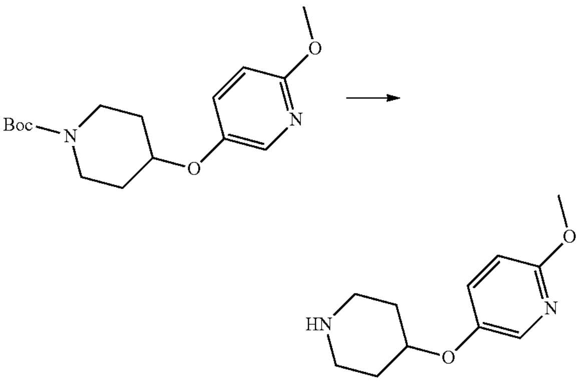

2-Methoxy-5-(piperidin-4-oxy)pyridine (2 g, yield: 90%) was obtained by using tert-butyl 4-((6-methoxypyridin-3-yl)oxy)piperidine-1-carboxylate as raw material with reference to step 4 of embodiment 43.

MS m/z (ESI): 209.2[M+H]+.

Step 2: tert-butyl 3-(4-((6-methoxypyridin-3-yl)oxo)piperidin-1-yl)-1H-pyrazole-1-carboxylate

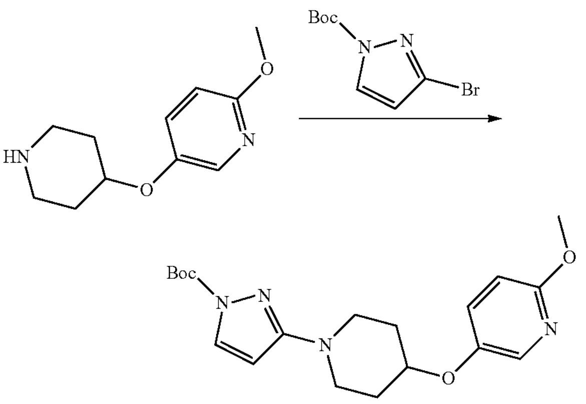

Tert-butyl 3-(4-((6-methoxypyridin-3-yl)oxo)piperidin-1-yl)-1H-pyrazole-1-carboxylate (yield: 68%) was obtained by using 2-methoxy-5-(piperidin-4-oxy)pyridine and tert-butyl 3-bromo-1H-pyrazole-1-carboxylate as raw material with reference to step 1 of embodiment 55.

MS m/z (ESI): 375.2[M+H]$^+$.

Step 3: Preparation of 5-((1-(1H-pyrazol-3-yl)piperidin-4-yl)oxo)-2-methoxypyridine

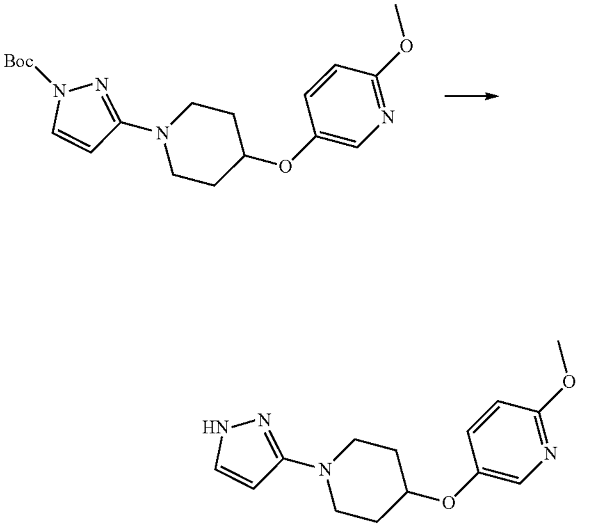

5-((1-(1H-pyrazol-3-yl)piperidin-4-yl)oxo)-2-methoxypyridine (yield: 88%) was obtained by using tert-butyl 3-(4-((6-methoxypyridin-3-yl)oxo)piperidin-1-yl)-1H-pyrazole-1-carboxylate as raw material with reference to step 4 of embodiment 43.

MS m/z (ESI): 275.2[M+H]$^+$.

Step 4: 6-(2-hydroxy-2-methylpropoxy)-4-(3-(4-((6-methoxypyridin-3-yl)oxo)piperidin-1-yl)-1H-pyrazol-1-yl)pyrazolo[1,5-a]pyridine-3-carbonitrile 6-(2-Hydroxy-2-methylpropoxy)-4-(3-(4-((6-methoxypyridin-3-yl)oxo)piperidin-1-yl)-1H-pyrazol-1-yl)pyrazolo[1,5-a]pyridine-3-carbonitrile (75 mg, yield: 30%) was obtained by using 5-((1-(1H-pyrazol-3-yl)piperidin-4-yl)oxo)-2-methoxypyridine and 4-bromo-6-(2-hydroxy-2-methylpropoxy)pyrazolo[1,5-a]pyridine-3-carbonitrile as raw material with reference to step 4 of embodiment 42.

MS m/z (ESI): 504.2[M+H]$^+$.

Embodiment 57

4-(4-Chloro-6-(6-((5-fluoro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile

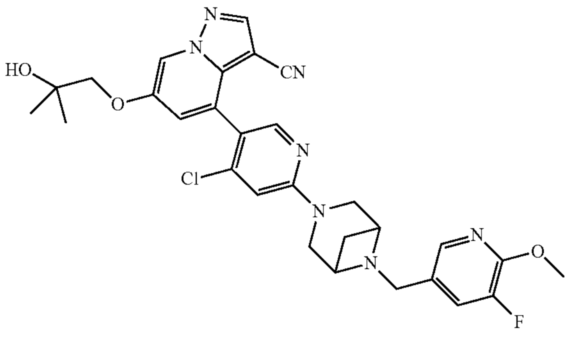 [SMILES: COc1ncc(CN2C3CC2CN(c2cc(Cl)c(-c4cc(OCC(C)(C)O)cn5ncc(C#N)c45)cn2)C3)cc1F]

Step 1: tert-butyl 3-(5-bromo-4-chloropyridin-2-yl)-3,6-diazabicyclo[3.1.1]heptane-6-carboxylate

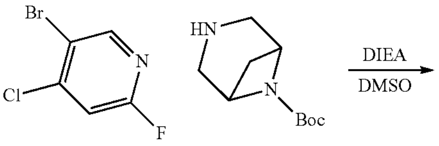

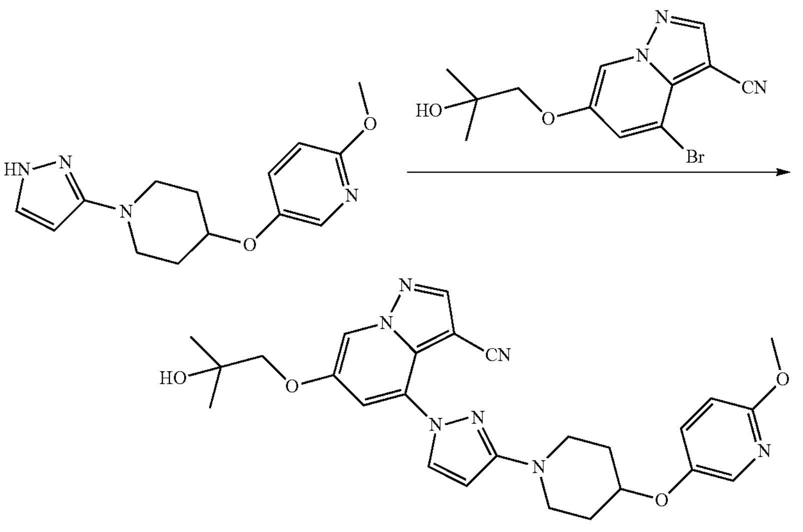

-continued

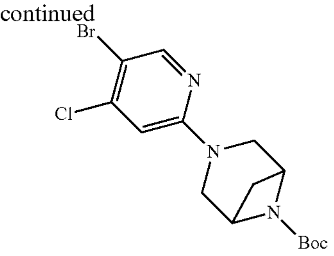

The product tert-butyl 3-(5-bromo-4-chloropyridin-2-yl)-3,6-diazabicyclo[3.1.1]heptane-6-carboxylate was obtained by using 5-bromo-4-chloro-2-fluoropyridine as raw material with reference to step 2 of embodiment 8.

MS m/z (ESI): 388.0[M+H]$^+$, 390.0[M+H+2]*.

Step 2: 3-(5-bromo-4-chloropyridin-2-yl)-3,6-diazabicyclo[3.1.1]heptane

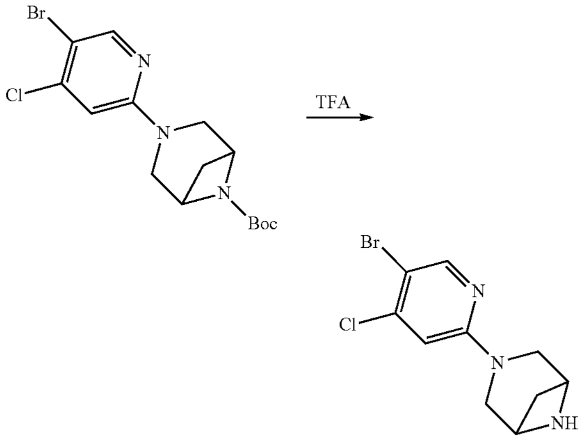

Tert-butyl 3-(5-bromo-4-chloropyridin-2-yl)-3,6-diazabicyclo[3.1.1]heptane-6-carboxylate (300 mg, 0.78 mmol) was dissolved in dichloromethane (5 mL), and trifluoroacetic acid (3 mL) was slowly added thereto dropwise, and the mixture was stirred at room temperature for 3 hours. The reaction mixture was concentrated, dissolved in ethyl acetate (10 mL), saturated sodium carbonate solution (5 mL) was added thereto, and the mixture was washed with saturated sodium chloride solution (5 mL×2); then the organic phase was dried over anhydrous sodium sulfate and concentrated under reduced pressure to obtain 3-(5-bromo-4-chloropyridin-2-yl)-3,6-diazabicyclo[3.1.1]heptane (230 mg).

MS m/z (ESI): 288.0 [M+H]$^+$, 290.0[M+2+H]$^+$.

Step 3: 3-(5-bromo-4-chloropyridin-2-yl)-6-((5-fluoro-6-methoxypyridin-3-yl)methyl)-3,6-diazabicyclo[3.1.1]heptane

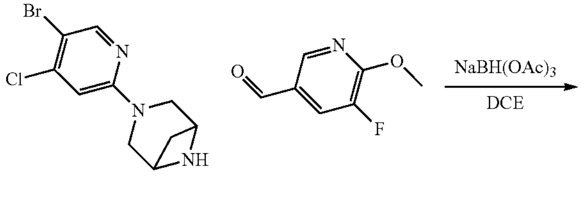

-continued

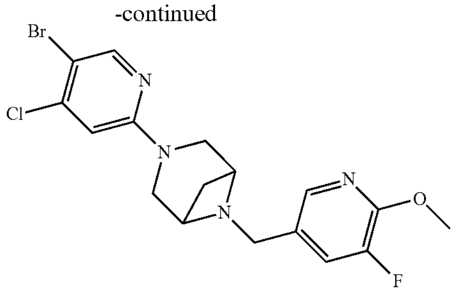

3-(5-Bromo-4-chloropyridin-2-yl)-3,6-diazabicyclo[3.1.1]heptane (230 mg, 0.78 mmol), 5-fluoro-6-methoxynicotinaldehyde (120 mg, 0.78 mmol) were dissolved in dichloroethane (5 mL), and sodium borohydride acetate (248 mg, 1.17 mmol) was added thereto under stirring, then the reaction mixture was stirred at room temperature for 12 hours. Saturated sodium carbonate solution (5 mL) thereto, then the reaction mixture was extracted with ethyl acetate (10 mL), washed with saturated sodium chloride solution (5 mL×2); and the organic phase was dried over anhydrous sodium sulfate and purified by column chromatography under reduced pressure (dichloromethane/methanol: 30/1) to obtain 3-(5-bromo-4-chloropyridin-2-yl)-6-((5-fluoro-6-methoxypyridin-3-yl) methyl)-3,6-diazabicyclo[3.1.1]heptane (200 mg, white solid, 58.1%).

MS m/z (ESI): 427.0 [M+H]$^+$, 429.0[M+2+H]$^+$.

Step 4: 3-(4-chloro-5-(4,4,5,5-tetramethyl-1,3,2-dioxaborolan-2-yl)pyridin-2-yl)-6-((5-fluoro-6-methoxypyridin-3-yl)methyl)-3,6-diazabicyclo[3.1.1]heptane

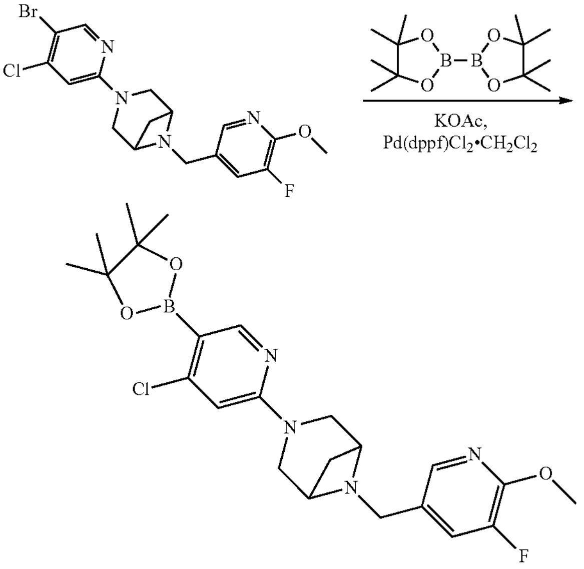

3-(5-Bromo-4-chloropyridin-2-yl)-6-((5-fluoro-6-methoxypyridin-3-yl)methyl)-3,6-diazabicyclo[3.1.1]heptane (200 mg, 0.47 mmol), bis(pinacolato)diboron (142 mg, 0.56 mmol), 1,1'-bis(diphenylphosphino)ferrocene-palladium(II)dichloride dichloromethane complex (19 mg, 0.023 mmol), potassium acetate (91 mg, 0.93 mmol), and dioxane (5 mL) were added sequentially in a 25 mL three-necked flask; and the reaction mixture was replaced with nitrogen five times. The reaction mixture was heated to 85° C. under the protection of nitrogen, and the mixture was stirred for 5 hours and then cooled to room temperature; the reaction mixture was concentrated, dissolved in ethyl acetate (10 mL) and washed with saturated saline (5 mL×3), and the organic phase was dried over anhydrous sodium sulfate, filtered and evaporated to dryness. The crude product was purified by prep-HPLC to obtain 3-(4-chloro-5-(4,4,5,5-tetramethyl-1,3,2-dioxaborolan-2-yl)pyridin-2-yl)-6-((5-fluoro-6-methoxypyridin-3-yl)methyl)-3,6-diazabicyclo[3.1.1]heptane (160 mg, yield: 72.2%).

MS m/z (ESI): 475.2[M+H]$^+$.

Step 5: 4-(4-chloro-6-(6-((5-fluoro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile

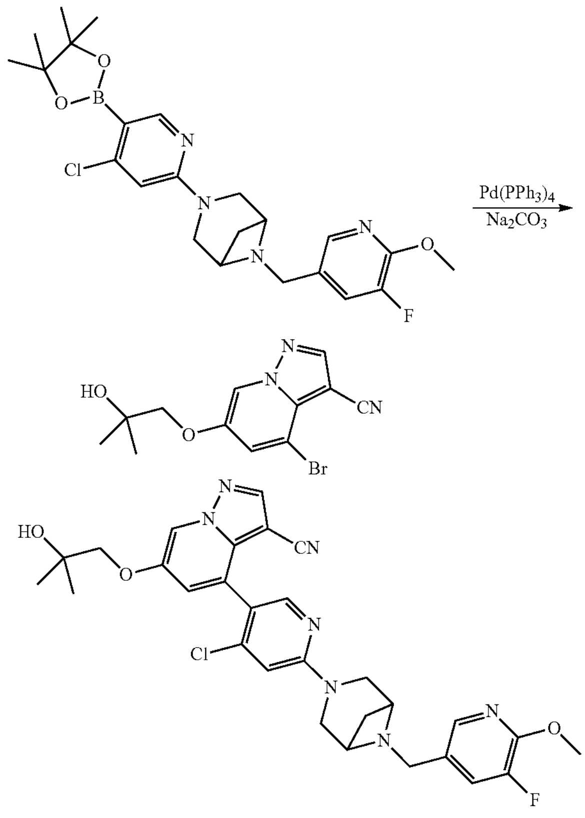

4-(4-Chloro-6-(6-((5-fluoro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile was obtained by using 3-(4-chloro-5-(4,4,5,5-tetramethyl-1,3,2-dioxaborolan-2-yl)pyridin-2-yl)-6-((5-fluoro-6-methoxypyridin-3-yl)methyl)-3,6-diazabicyclo[3.1.1]heptane as raw materials with reference to step 3 of embodiment 7.

MS m/z (ESI): 578.2[M+H]$^+$.

Embodiment 58

4-(4-Chloro-6-(4-(pyridin-2-oxy)piperidin-1-yl)pyridin-3-yl)-6-(2-hydroxy-2-methylpropoxy)pyrazolo[1,5-a]pyridine-3-carbonitrile

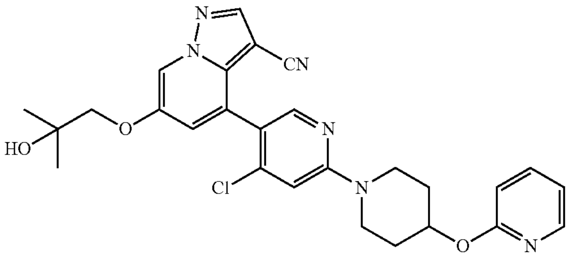 [SMILES: CC(C)(O)COc1cc(-c2cnc(N3CCC(Oc4ccccn4)CC3)cc2Cl)c2c(C#N)cnn2c1]

Step 1: 5-bromo-4-chloro-2-(4-(pyridin-2-oxy)piperidin-1-yl)pyridine

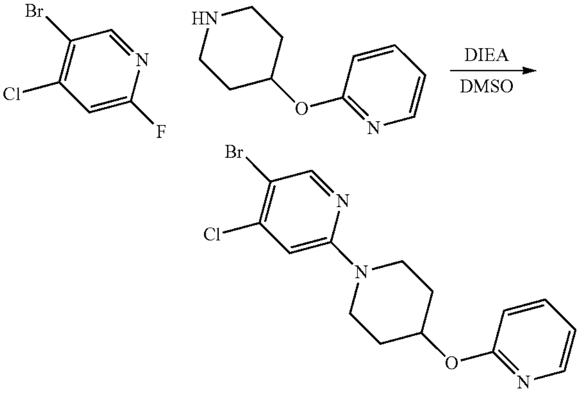

5-Bromo-4-chloro-2-(4-(pyridin-2-oxy)piperidin-1-yl)pyridine was obtained by using 5-bromo-4-chloro-2-fluoropyridine as raw material with reference to step 2 of embodiment 8.

MS m/z (ESI): 368.0[M+H]$^+$, 370.0[M+H+2]$^+$.

Step 2: 4-chloro-2-(4-(pyridin-2-oxy)piperidin-1-yl)-5-(4,4,5,5-tetramethyl-1,3,2-dioxaborolan-2-yl)pyridine

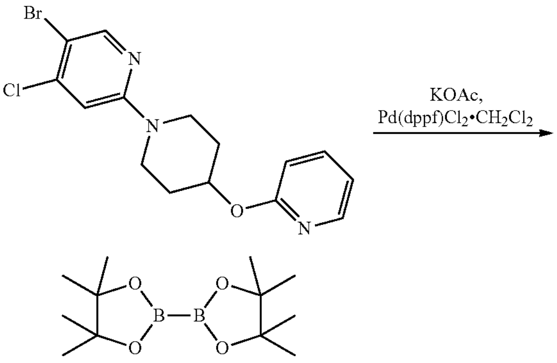

-continued

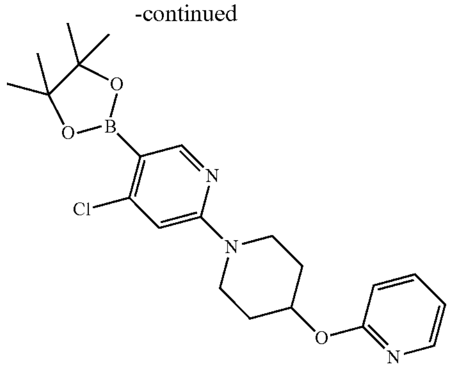

4-Chloro-2-(4-(pyridin-2-oxy)piperidin-1-yl)-5-(4,4,5,5-tetramethyl-1,3,2-dioxaborolan-2-yl)pyridine was obtained by using 5-bromo-4-chloro-2-(4-(pyridin-2-oxy)piperidin-1-yl)pyridine as raw material with reference to step 4 of embodiment 57.

MS m/z (ESI): 416.2[M+H]$^+$.

Step 3: 4-(4-chloro-6-(4-(pyridin-2-oxy)piperidin-1-yl)pyridin-3-yl)-6-(2-hydroxy-2-methylpropoxy)pyrazolo[1,5-a]pyridine-3-carbonitrile

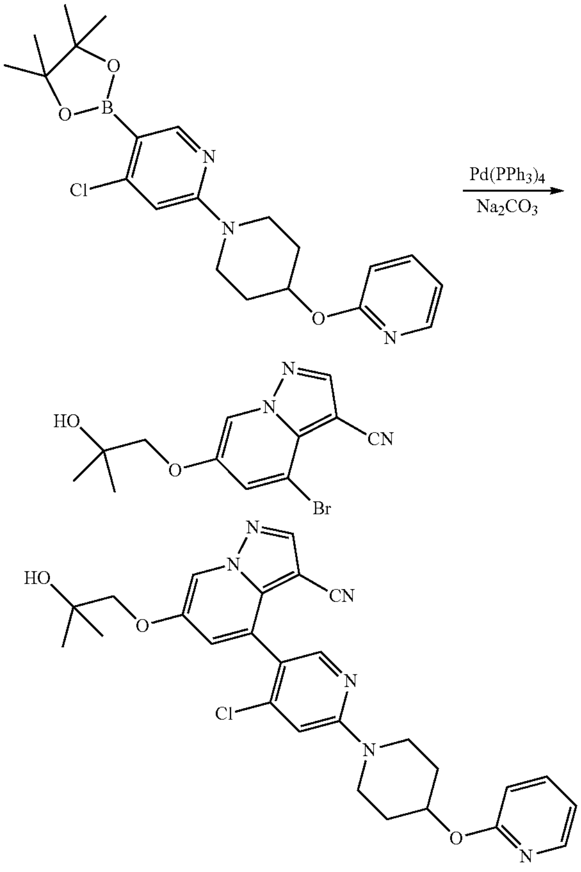

4-(4-Chloro-6-(4-(pyridin-2-oxy)piperidin-1-yl)pyridin-3-yl)-6-(2-hydroxy-2-methylpropoxy)pyrazolo[1,5-a]pyridine-3-carbonitrile was obtained by using 4-chloro-2-(4-(pyridin-2-oxy)piperidin-1-yl)-5-(4,4,5,5-tetramethyl-1,3,2-dioxaborolan-2-yl)pyridine as raw material with reference to step 3 of embodiment 7.

MS m/z (ESI): 519.1[M+H]$^+$.

Embodiment 59

4-(6-(4-Amino-4-((6-methoxypyridin-3-yl)methyl)piperidin-1-yl)pyridin-3-yl)-6-(2-hydroxy-2-methylpropoxy)pyrazolo[1,5-a]pyridine-3-carbonitrile

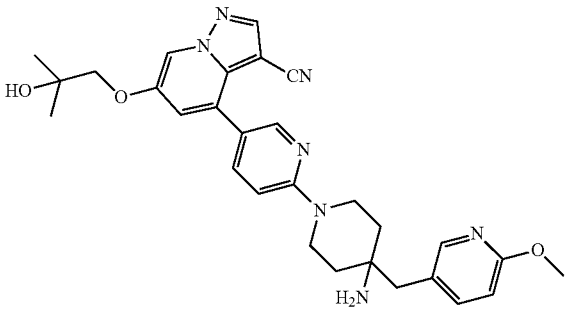 [SMILES: COc1ccc(CC2(N)CCN(c3ccc(-c4cc(OCC(C)(C)O)cn5ncc(C#N)c45)cn3)CC2)cn1]

Step 1: Preparation of 1-(tert-butyl) 4-ethyl 4-((6-methoxypyridin-3-yl)methyl)piperidine-1,4-dicarboxylate

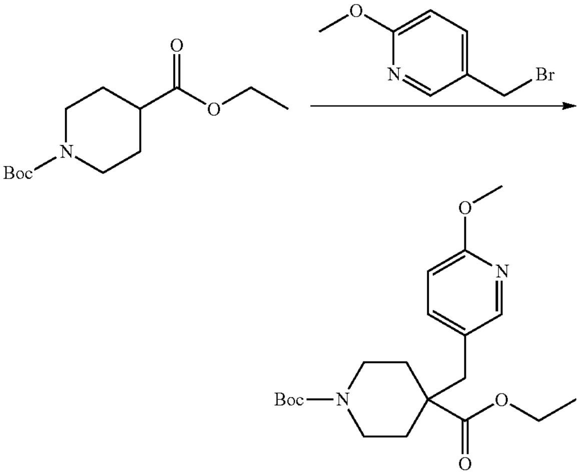

1-(Tert-butyl) 4-ethyl piperidine-1,4-dicarboxylate (10 g, 38.9 mmol) was dissolved in anhydrous tetrahydrofuran (100 mL), and the mixture was cooled to −76° C. under the protection of nitrogen. LDA (29.2 mL, 58.4 mmol) was slowly added dropwise to the reaction mixture, and the temperature was controlled not to be higher than −70° C. After the addition was completed, the reaction was slowly warmed to 0° C., stirred for half an hour and cooled to −76° C. 5-(Bromomethyl)-2-methoxypyridine (9.4 g, 46.6 mmol) was slowly added to the reaction mixture. After the addition was completed, the reaction mixture was slowly warmed to room temperature, and stirred for 4 hours. Saturated ammonium chloride aqueous solution was added to quench the reaction, and then the mixture was extracted with ethyl acetate. The organic phase was dried and evaporated to dryness. The crude product was purified by column chromatography to obtain 1-(tert-butyl) 4-ethyl 4-((6-methoxypyridin-3-yl)methyl)piperidine-1,4-dicarboxylate (3.5 g, yield: 24%).

MS m/z (ESI): 379.2[M+H]$^+$.

Step 2: Preparation of 1-(tert-butoxycarbonyl)-4-((6-methoxypyridin-3-yl)methyl)piperidine-4-carboxylic acid

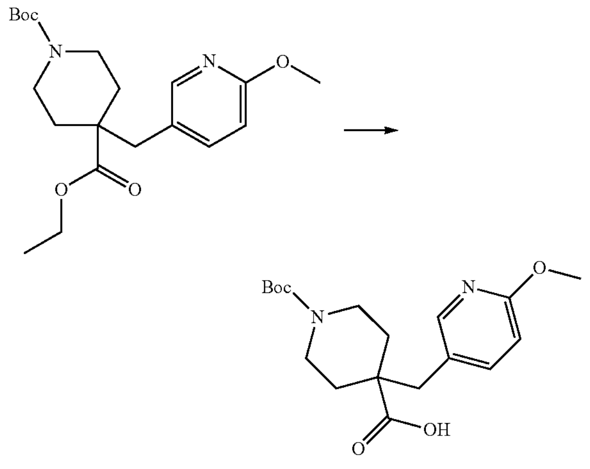

1-(Tert-butoxycarbonyl)-4-((6-methoxypyridin-3-yl)methyl)piperidine-4-carboxylic acid (2 g, yield: 80%) was obtained by using 51-(tert-butyl) 4-ethyl 4-((6-methoxypyridin-3-yl)methyl)piperidine-1,4-dicarboxylate as raw material with reference to step 2 of embodiment 40.

MS m/z (ESI): 351.2[M+H]$^+$.

Step 3: Preparation of tert-butyl 4-((tert-butoxycarbonyl)amino)-4-((6-methoxypyridin-3-yl)methyl)piperidine-1-carboxylate

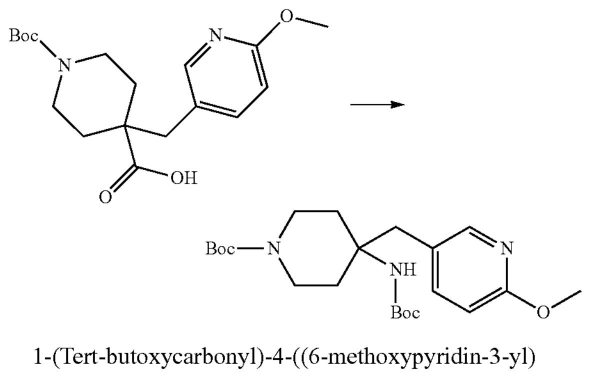

1-(Tert-butoxycarbonyl)-4-((6-methoxypyridin-3-yl)methyl)piperidine-4-carboxylic acid (2 g, 5.7 mmol) was dissolved in tert-butanol (50 mL), and DIEA (1.1 g, 8.6 mmol) and diphenyl azidophosphate (1.7 g, 6.3 mmol) were added thereto. The reaction mixture was stirred at 80° C. for 6 hours. The reaction mixture was evaporated to dryness. The crude product was purified by column chromatography to obtain tert-butyl 4-((tert-butoxycarbonyl)amino)-4-((6-methoxypyridin-3-yl)methyl)piperidine-1-carboxylate (1.6 g, yield: 67%).

MS m/z (ESI): 422.2[M+H]$^+$.

Step 3: Preparation of 4-((6-methoxypyridin-3-yl)methyl)piperidin-4-amine

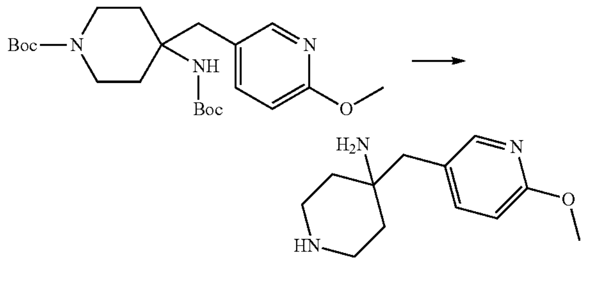

4-((6-Methoxypyridin-3-yl)methyl)piperidin-4-amine (0.8 g, yield: 70%) was obtained by using tert-butyl 4-((tert-butoxycarbonyl)amino)-4-((6-methoxypyridin-3-yl)methyl)piperidine-1-carboxylate as raw material with reference to step 4 of embodiment 43.

MS m/z (ESI): 222.2[M+H]$^+$.

Step 4: Preparation of 4-(6-(4-amino-4-((6-methoxypyridin-3-yl)methyl)piperidin-1-yl)pyridin-3-yl)-6-(2-hydroxy-2-methylpropoxy)pyrazolo[1,5-a]pyridine-3-carbonitrile

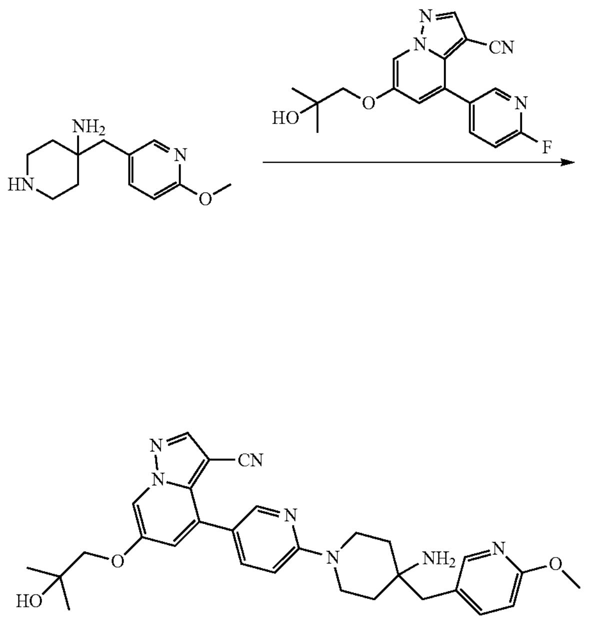 [SMILES: COc1ccc(CC2(N)CCNCC2)cn1 ; CC(C)(O)COc1cc(-c2ccc(F)nc2)c2c(C#N)cnn2c1 ; COc1ccc(CC2(N)CCN(c3ccc(-c4cc(OCC(C)(C)O)cn5ncc(C#N)c45)cn3)CC2)cn1]

4-(6-(4-Amino-4-((6-methoxypyridin-3-yl)methyl)piperidin-1-yl)pyridin-3-yl)-6-(2-hydroxy-2-methylpropoxy)pyrazolo[1,5-a]pyridine-3-carbonitrile (55 mg, yield: 46%) was obtained by using 4-((6-methoxypyridin-3-yl)methyl)piperidin-4-amine and 4-(6-fluoropyridin-3-yl)-6-(2-hydroxy-2-methylpropoxy)pyrazolo[1,5-a]pyridine-3-carbonitrile as raw material with reference to step 6 of embodiment 42.

MS m/z (ESI): 528.2[M+H]$^+$.

Embodiment 60

4-(6-(4-Amino-4-(pyridin-3-ylmethyl)piperidin-1-yl)pyridin-3-yl)-6-(2-hydroxy-2-methylpropoxy)pyrazolo[1,5-a]pyridine-3-carbonitrile

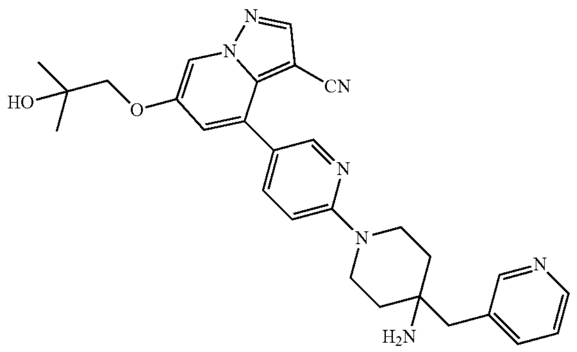 [SMILES: CC(C)(O)COc1cc(-c2ccc(N3CCC(N)(Cc4cccnc4)CC3)nc2)c2c(C#N)cnn2c1]

Step 1: 1-(tert-butyl) 4-ethyl 4-(pyridin-3-ylmethyl)piperidine-1,4-dicarboxylate

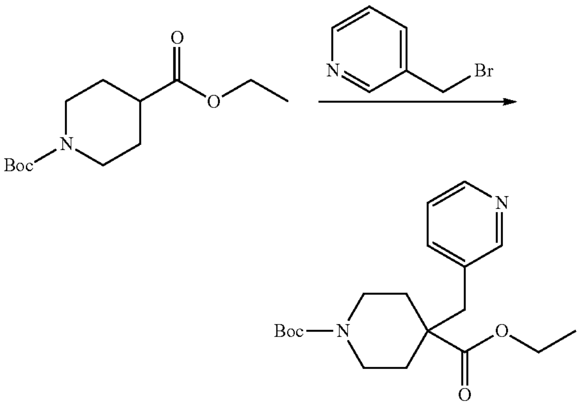

1-(Tert-butyl) 4-ethyl 4-(pyridin-3-ylmethyl)piperidine-1,4-dicarboxylate (3 g, yield: 68%) was obtained by using 1-(tert-butyl) 4-ethyl piperidine-1,4-dicarboxylate and 3-(bromomethyl)pyridine as raw material with reference to step 1 of embodiment 59.

MS m/z (ESI): 349.2[M+H]$^+$.

Step 2: Preparation of 1-(tert-butoxycarbonyl)-4-(pyridin-3-ylmethyl)piperidine-4-carboxylic acid

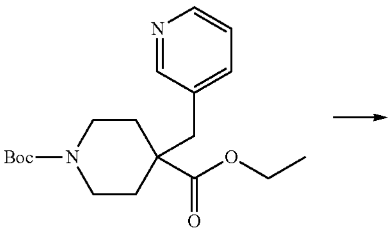

-continued

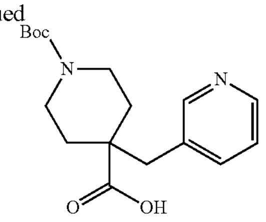

1-(Tert-butoxycarbonyl)-4-(pyridin-3-ylmethyl)piperidine-4-carboxylic acid (2.2 g, yield: 78%) was obtained by using 1-(tert-butyl) 4-ethyl 4-(pyridin-3-ylmethyl)piperidine-1,4-dicarboxylate as raw material with reference to step 2 of embodiment 40.

MS m/z (ESI): 321.2[M+H]$^+$.

Step 3: Preparation of tert-butyl 4-((tert-butoxycarbonyl)amino)-4-(pyridin-3-ylmethyl)piperidine-1-carboxylate

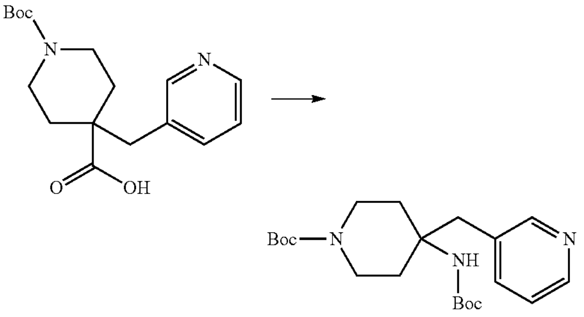

Tert-butyl 4-((tert-butoxycarbonyl)amino)-4-(pyridin-3-ylmethyl)piperidine-1-carboxylate (1.2 g, yield: 48%) was obtained by using 1-(tert-butoxycarbonyl)-4-(pyridin-3-ylmethyl)piperidine-4-carboxylic acid as raw material with reference to step 3 of embodiment 59.

MS m/z (ESI): 392.2[M+H]$^+$.

Step 4: Preparation of 4-(pyridin-3-ylmethyl)piperidin-4-amine

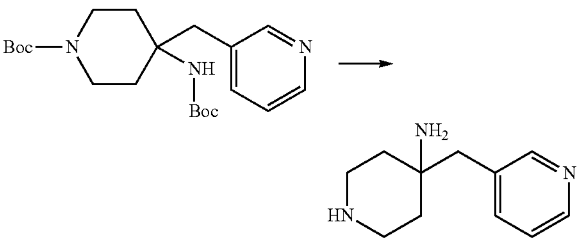

4-(Pyridin-3-ylmethyl)piperidin-4-amine (0.6 g, yield: 73%) was obtained by using tert-butyl 4-((tert-butoxycarbonyl)amino)-4-(pyridin-3-ylmethyl)piperidine-1-carboxylate as raw material with reference to step 4 of embodiment 43.

MS m/z (ESI): 192.2[M+H]$^+$.

Step 5: 4-(6-(4-amino-4-(pyridin-3-ylmethyl)piperidin-1-yl)pyridin-3-yl)-6-(2-hydroxy-2-methylpropoxy)pyrazolo[1,5-a]pyridine-3-carbonitrile

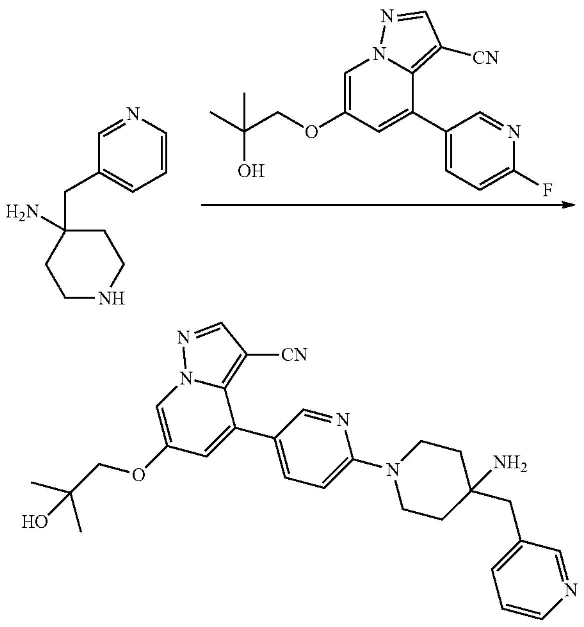

4-(6-(4-Amino-4-(pyridin-3-ylmethyl)piperidin-1-yl)pyridin-3-yl)-6-(2-hydroxy-2-methylpropoxy)pyrazolo[1,5-a]pyridine-3-carbonitrile (65 mg, yield: 44%) was obtained by using 4-(pyridin-3-ylmethyl)piperidin-4-amine and 4-(6-fluoropyridin-3-yl)-6-(2-hydroxy-2-methylpropoxy)pyrazolo[1,5-a]pyridine-3-carbonitrile as raw materials with reference to step 6 of embodiment 42.

MS m/z (ESI): 498.2[M+H]$^+$.

Embodiment 61

4-(4-(4-Amino-1-((6-methoxypyridin-3-yl)methyl)piperidin-4-yl)phenyl)-6-(2-hydroxy-2-methylpropoxy)pyrazolo[1,5-a]pyridine-3-carbonitrile

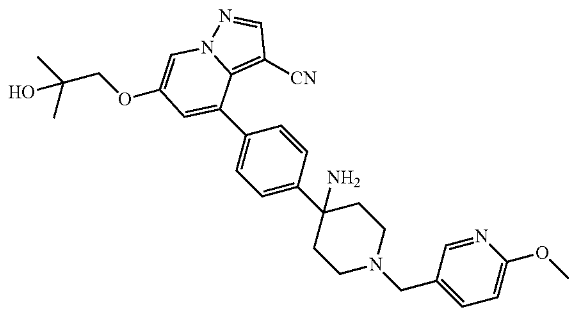 [SMILES: COc1ccc(CN2CCC(N)(c3ccc(-c4cc(OCC(C)(C)O)cn5ncc(C#N)c45)cc3)CC2)cn1]

Step 1: Preparation of benzyl 4-((tert-butylsulfinyl<sulfinyl>)amino)-4-(4-chlorophenyl)piperidine-1-carboxylate

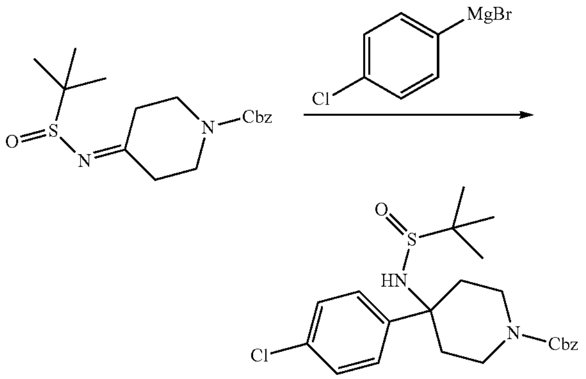

Benzyl 4-((tert-butyl sulfinyl<sulfinyl>)amino)-4-(4-chlorophenyl)piperidine-1-carboxylate (2 g, yield: 33%) was obtained by using benzyl 4-((tert-butylsulfinyl<sulfinyl>)imino)piperidine-1-carboxylate and (4-chlorophenyl)magnesium bromide as raw materials with reference to step 1 of embodiment 42.

MS m/z (ESI): 449.2[M+H]$^+$.

Step 2: Preparation of benzyl 4-((tert-butylsulfinyl<sulfinyl>)amino)-4-(4-(3-cyano-6-(2-hydroxy-2-methylpropoxy)pyrazolo[1,5-a]pyridin-4-yl)phenyl)piperidine-1-carboxylate

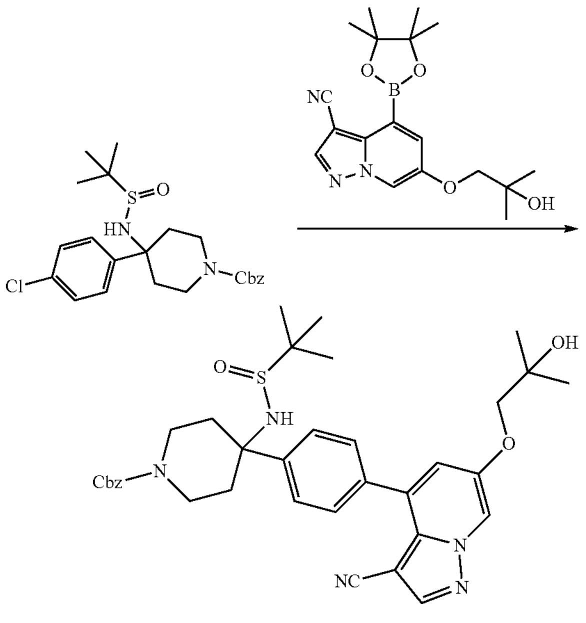

Benzyl 4-((tert-butylsulfinyl<sulfinyl>)amino)-4-(4-(3-cyano-6-(2-hydroxy-2-methylpropoxy)pyrazolo[1,5-a]pyridin-4-yl)phenyl)piperidine-1-carboxylate (1.2 g, yield: 66%) was obtained by using benzyl 4-((tert-butylsulfinyl<sulfinyl>)amino)-4-(4-chlorophenyl)piperidine–1-carboxylate and 6-(2-hydroxy-2-methylpropoxy)-4-

(4,4,5,5-tetramethyl-1,3,2-dioxaborolan-2-yl)pyrazolo[1,5-a]pyridine-3-carbonitrile as raw materials with reference to step 3 of embodiment 37.

MS m/z (ESI): 644.2[M+H]$^+$.

Step 3: Preparation of N-(4-(4-(3-cyano-6-(2-hydroxy-2-methylpropoxy)pyrazolo[1,5-a]pyridin-4-yl)phenyl)piperidin-4-yl)-2-methylpropane-2-sulfinamide

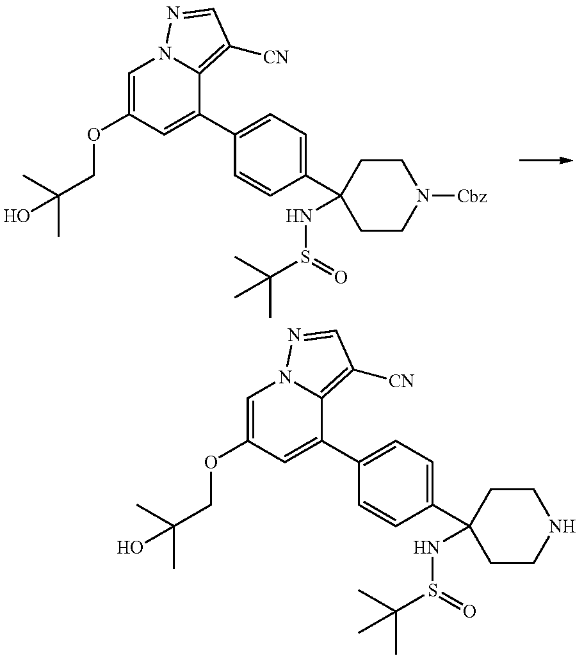

N-(4-(4-(3-cyano-6-(2-hydroxy-2-methylpropoxy)pyrazolo[1,5-a]pyridin-4-yl)phenyl)piperidin-4-yl)-2-methylpropane-2-sulfinamide was obtained by using benzyl 4-((tert-butylsulfinyl<sulfinyl>)amino)-4-(4-(3-cyano-6-(2-hydroxy-2-methylpropoxy)pyrazolo[1,5-a]pyridin-4-yl)phenyl)piperidine-1-carboxylate as raw material with reference to step 4 of embodiment 42.

MS m/z (ESI): 510.2[M+H]$^+$.

Step 4: Preparation of N-(4-(4-(3-cyano-6-(2-hydroxy-2-methylpropoxy)pyrazolo[1,5-a]pyridin-4-yl)phenyl)-1-((6-methoxypyridin-3-yl)methyl)piperidin-4-yl)-2-methylpropane-2-sulfinamide

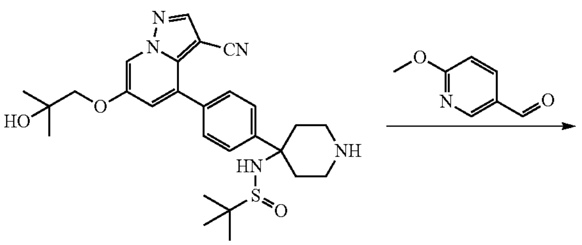

-continued

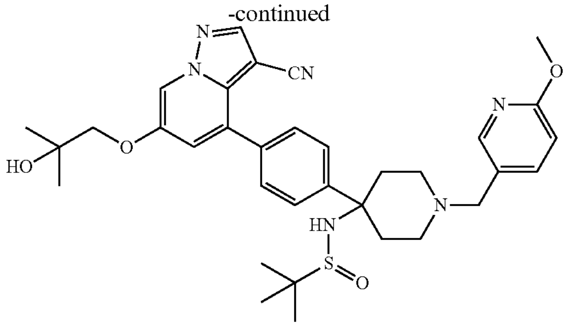

N-(4-(4-(3-cyano-6-(2-hydroxy-2-methylpropoxy)pyrazolo[1,5-a]pyridin-4-yl)phenyl)-1-((6-methoxypyridin-3-yl)methyl)piperidin-4-yl)-2-methylpropane-2-sulfinamide (0.3 g, yield: 56%) was obtained by using N-(4-(4-(3-cyano-6-(2-hydroxy-2-methylpropoxy)pyrazolo[1,5-a]pyridin-4-yl)phenyl)piperidin-4-yl)-2-methylpropane-2-sulfinamide and 6-methoxynicotinaldehyde as raw materials with reference to step 3 of embodiment 55.

MS m/z (ESI): 631.3[M+H]$^+$.

Step 5: 4-(4-(4-amino-1-((6-methoxypyridin-3-yl)methyl)piperidin-4-yl)phenyl)-6-(2-hydroxy-2-methylpropoxy)pyrazolo[1,5-a]pyridine-3-carbonitrile

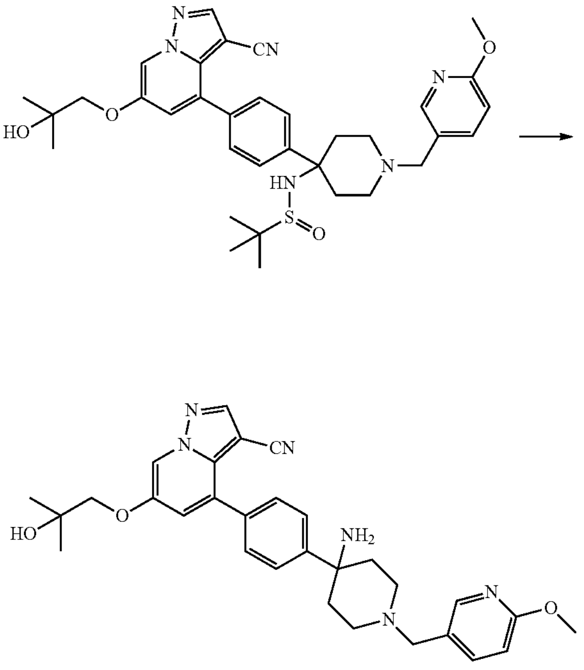

4-(4-(4-Amino-1-((6-methoxypyridin-3-yl)methyl)piperidin-4-yl)phenyl)-6-(2-hydroxy-2-methylpropoxy)pyrazolo[1,5-a]pyridine-3-carbonitrile (yield: 85%) was obtained by using N-(4-(4-(3-cyano-6-(2-hydroxy-2-methylpropoxy)pyrazolo[1,5-a]pyridin-4-yl)phenyl)-1-((6-methoxypyridin-3-yl)methyl)piperidin-4-yl)-2-methylpropane-2-sulfinamide as raw material with reference to step 2 of embodiment 42.

MS m/z (ESI): 527.3[M+H]$^+$.

Embodiment 62

4-(6-(4-Amino-4-(indoline-1-carbonyl)piperidin-1-yl)pyridin-3-yl)-6-(2-hydroxy-2-methylpropoxy) pyrazolo[1,5-a]pyridine-3-carbonitrile

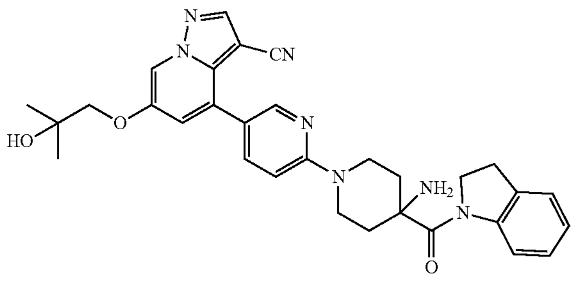 [SMILES: CC(C)(O)COc1cc(-c2ccc(N3CCC(N)(C(=O)N4CCc5ccccc54)CC3)nc2)c2c(C#N)cnn2c1]

Step 1: ethyl 4-((tert-butoxycarbonyl)amino)-1-(5-(3-cyano-6-(2-hydroxy-2-methylpropoxy)pyrazolo [1,5-a]pyridin-4-yl)pyridin-2-yl)piperidine-4-carboxylate

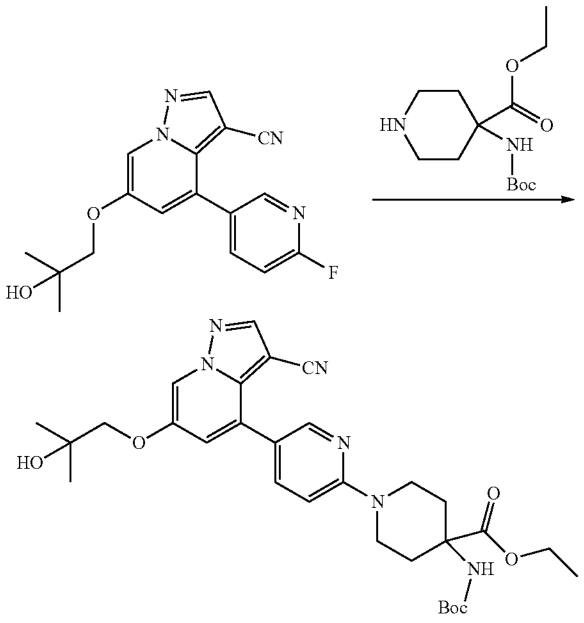

A mixture of 4-(6-fluoropyridin-3-yl)-6-(2-hydroxy-2-methylpropoxy)pyrazolo[1,5-a]pyridine-3-carbonitrile (3 g, 9.2 mmol), ethyl 4-((tert-butoxycarbonyl)amino)piperidine-4-carboxylate (3.0 g, 11.04 mmol), N,N-diisopropylethylamine (3.6 g, 27.6 mmol) and acetonitrile (30 mL) was stirred at 80° C. for 16 hours, and the mixture was stirred at 80° C. for 16 hours; after the reaction was completed, the mixture was mixed with silica gel and concentrated under reduced pressure to dryness, then separated by column chromatography (dichloromethane/methanol=10:1) to obtain colorless oil ethyl 4-((tert-butoxycarbonyl)amino)-1-(5-(3-cyano-6-(2-hydroxy-2-methylpropoxy)pyrazolo[1,5-a]pyridin-4-yl)pyridin-2-yl)piperidine-4-carboxylate (800 mg, yield: 15%).

MS m/z (ESI): 579.3 [M+H]+.

Step 2: 4-((tert-butoxycarbonyl)amino)-1-(5-(3-cyano-6-(2-hydroxy-2-methylpropoxy)pyrazolo[1,5-a]pyridin-4-yl)pyridin-2-yl)piperidine-4-carboxylic acid

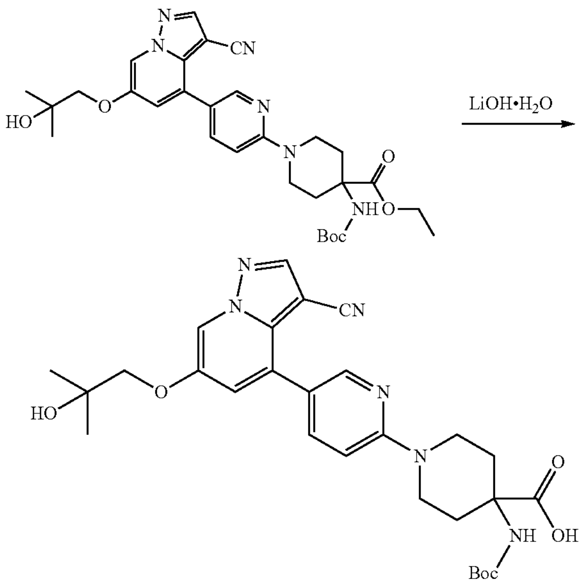

Lithium hydroxide monohydrate (116 mg, 2.76 mmol) was added to a solution of ethyl 4-((tert-butoxycarbonyl) amino)-1-(5-(3-cyano-6-(2-hydroxy-2-methylpropoxy) pyrazolo[1,5-a]pyridin-4-yl)pyridin-2-yl)piperidine-4-carboxylate (800 mg, 1.38 mmol) in methanol (10 mL) and water (10 mL); and the mixture was stirred at room temperature for 16 hours; after the reaction was completed, with the pH value was adjusted to 2 with dilute hydrochloric acid, a white solid precipitated and was filtered; and the filter cake was washed with water and dried to obtain white solid 4-((tert-butoxycarbonyl)amino)-1-(5-(3-cyano-6-(2-hydroxy-2-methylpropoxy)pyrazolo[1,5-a]pyridin-4-yl)pyridin-2-yl)piperidine-4-carboxylic acid (600 mg, yield: 79%).

MS m/z (ESI): 551.2 [M+H]+.

Step 3: tert-butyl (1-(5-(3-cyano-6-(2-hydroxy-2-methylpropoxy)pyrazolo[1,5-a]pyridin-4-yl)pyridin-2-yl)-4-(indoline-1-carbonyl)piperidin-4-yl)carbamate

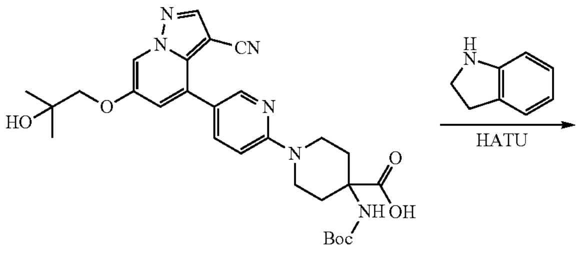

-continued

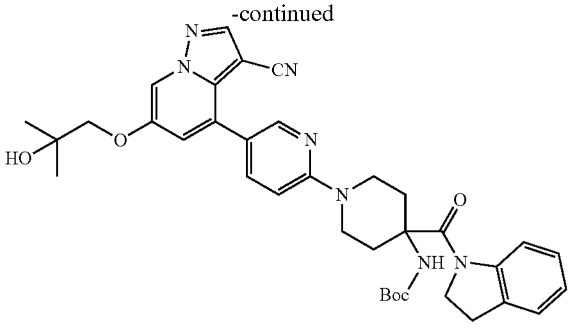

A mixture of 4-((tert-butoxycarbonyl)amino)-1-(5-(3-cyano-6-(2-hydroxy-2-methylpropoxy)pyrazolo[1,5-a]pyridin-4-yl)pyridin-2-yl)piperidine-4-carboxylic acid (100 mg, 0.18 mmol), 2-(7-azabenzotriazol-1-yl)-N,N,N',N'-tetramethyluronium hexafluorophosphate (82.91 mg, 0.22 mmol), triethylamine (36 mg, 0.36 mmol), dihydroindole (32 mg, 0.27 mmol) and dichloromethane (5 mL) was stirred at room temperature for 16 hours; after the reaction was completed, the mixture was quenched with water, extracted with ethyl acetate, the organic phase was washed with saturated saline, dried over anhydrous sodium sulfate, filtered, and the filtrate was concentrated under reduced pressure to dryness and separated by column chromatography (dichloromethane/methanol=10:1) to obtain colorless oil tert-butyl (1-(5-(3-cyano-6-(2-hydroxy-2-methylpropoxy)pyrazolo[1,5-a]pyridin-4-yl)pyridin-2-yl)-4-(indoline-1-carbonyl)piperidin-4-yl)carbamate (30 mg, yield: 26%).

MS m/z (ESI): 652.3 $[M+H]^+$.

Step 4: 4-(6-(4-amino-4-(indoline-1-carbonyl)piperidin-1-yl)pyridin-3-yl)-6-(2-hydroxy-2-methylpropoxy)pyrazolo[1,5-a]pyridine-3-carbonitrile

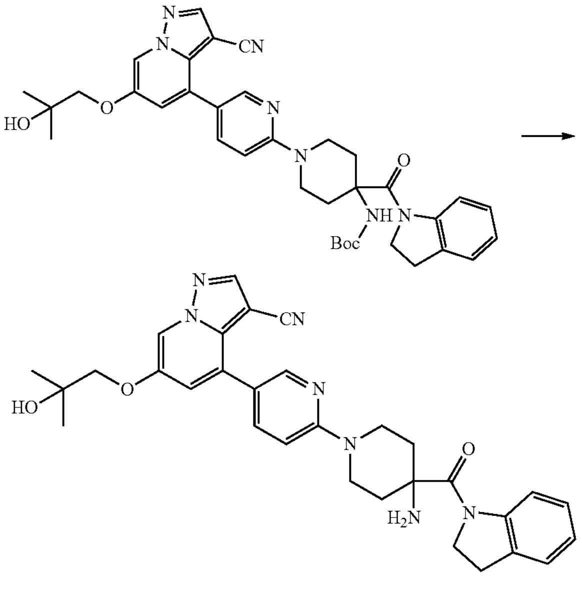

Tert-butyl (1-(5-(3-cyano-6-(2-hydroxy-2-methylpropoxy)pyrazolo[1,5-a]pyridin-4-yl)pyridin-2-yl)-4-(indoline)-1-carbonyl)piperidin-4-yl)carbamate (30 mg, 0.046 mmol) was dissolved in dichloromethane (3 mL), then trifluoroacetic acid (1 mL) was added thereto, and the mixture was stirred at room temperature for 1 hour; after the reaction was completed, the mixture was concentrated under reduced pressure to dryness and separated by preparative chromatography to obtain light yellow oil 4-(6-(4-amino-4-(indoline-1-carbonyl)piperidin-1-yl)pyridin-3-yl)-6-(2-hydroxy-2-methylpropoxy)[1,5-a]pyridine-3-carbonitrile (12 mg, yield: 47%).

$^1H$ NMR (400 MHz, $CDCl_3$) δ 8.34 (s, 1H), 8.26-8.18 (m, 2H), 8.16 (s, 1H), 7.70 (d, J=6.6 Hz, 1H), 7.18 (m, 3H), 7.07-7.03 (m, 1H), 6.83 (d, J=8.7 Hz, 1H), 4.42-4.39 (m, 2H), 4.11-4.07 (m, 2H), 3.85-3.81 (m, 4H), 3.13-3.09 (t, J=7.7 Hz, 2H), 2.51-2.47 (m, 2H), 1.92-1.89 (m, 4H), 1.40 (s, 6H).

MS m/z (ESI): 552.3 $[M+H]^+$.

Embodiment 63

4-Amino-1-(5-(3-cyano-6-(2-hydroxy-2-methylpropoxy)pyrazolo[1,5-a]pyridin-4-yl)pyridin-2-yl)-N-(6-methoxypyridin-3-yl)piperidine-4-carboxamide

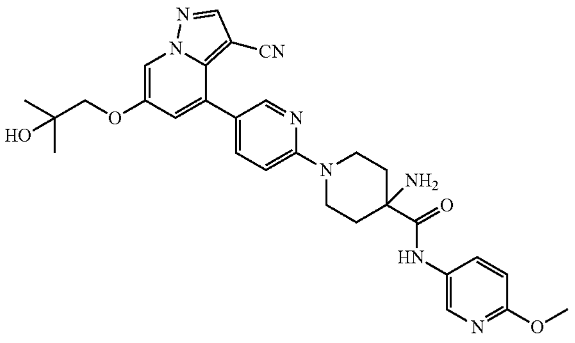 [SMILES: COc1ccc(NC(=O)C2(N)CCN(c3ccc(-c4cc(OCC(C)(C)O)cn5ncc(C#N)c45)cn3)CC2)cn1]

The synthesis of embodiment 63 was referred to embodiment 62.

MS m/z (ESI): 557.2 $[M+H]^+$.

Embodiment 64

4-Amino-1-(5-(3-cyano-6-(2-hydroxy-2-methylpropoxy)pyrazolo[1,5-a]pyridin-4-yl)pyridin-2-yl)-N-methyl-N-phenylpiperidine-4-carboxamide

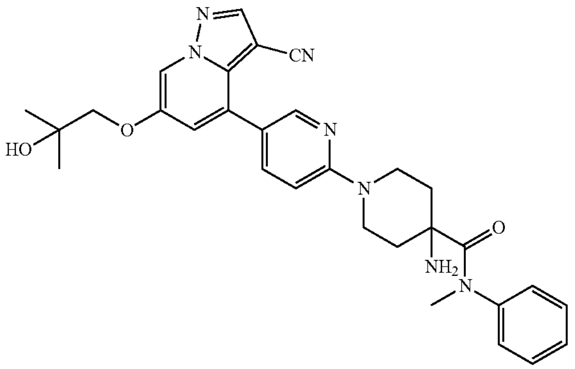 [SMILES: CN(C(=O)C1(N)CCN(c2ccc(-c3cc(OCC(C)(C)O)cn4ncc(C#N)c34)cn2)CC1)c1ccccc1]

The synthesis of embodiment 64 was referred to embodiment 62.

MS m/z (ESI): 540.2 $[M+H]^+$.

Embodiment 65

4-(6-(4-Amino-4-(2,3-dihydro-1H-pyrrolo[3,2-b]pyridine-1-carbonyl)piperidin-1-yl)pyridin-3-yl)-6-(2-hydroxy-2-methylpropoxy)pyrazolo[1,5-a]pyridine-3-carbonitrile

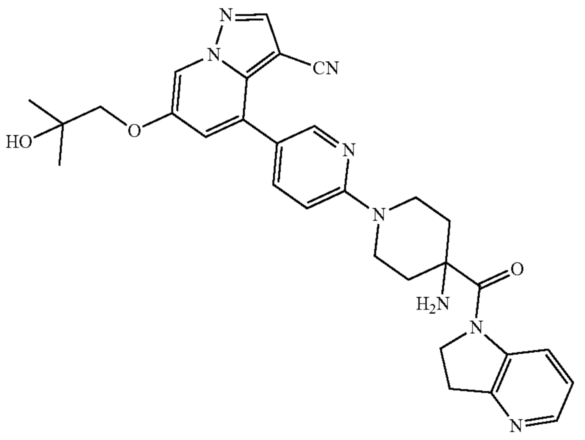 [SMILES: CC(C)(O)COc1cc(-c2ccc(N3CCC(N)(C(=O)N4CCc5ncccc54)CC3)nc2)c2c(C#N)cnn2c1]

The synthesis of embodiment 65 was referred to embodiment 62.

MS m/z (ESI): 553.2 $[M+H]^+$

Embodiment 66

4-(6-(3-((1H-pyrazol-1-yl)methyl)-3-aminoazetidin-1-yl)pyridin-3-yl)-6-(2-hydroxy-2-methylpropoxy)pyrazolo[1,5-a]pyridine-3-carbonitrile

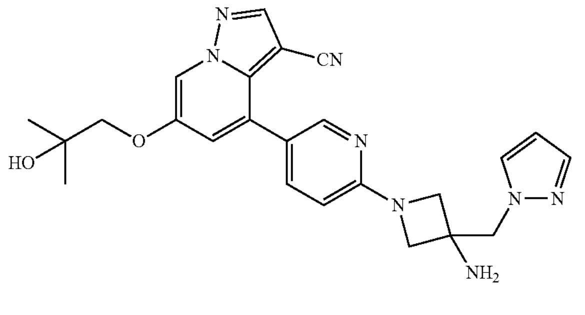 [SMILES: CC(C)(O)COc1cc(-c2ccc(N3CC(N)(Cn4cccn4)C3)nc2)c2c(C#N)cnn2c1]

Step 1: Preparation of 1-(tert-butyl) 3-methyl 3-((tert-butoxycarbonyl)amino azetidine-1,3-dicarboxylate

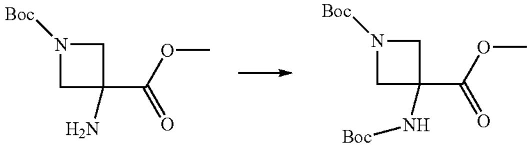 [SMILES: COC(=O)C1(N)CN(C(=O)OC(C)(C)C)C1 ; COC(=O)C1(NC(=O)OC(C)(C)C)CN(C(=O)OC(C)(C)C)C1]

1-(Tert-butyl) 3-methyl 3-aminoazetidine-1,3-dicarboxylate (10 g, 43.4 mmol) was dissolved in dichloromethane (100 mL); and di-tert-butyl dicarbonate (10 g, 45.6 mmol) and DIEA (8.4 g, 65.1 mmol) were added thereto. The reaction mixture was stirred at room temperature overnight. Water was added thereto, and then the mixture was extracted with dichloromethane. The organic phase was dried and evaporated to dryness. The crude product was purified by column chromatography to obtain 1-(tert-butyl) 3-methyl 3-((tert-butoxycarbonyl)amino)azetidine-1,3-dicarboxylate (13 g, yield: 91%).

MS m/z (ESI): 331.2$[M+H]^+$.

Step 2: Preparation of tert-butyl 3-((tert-butoxycarbonyl)amino)-3-(hydroxymethyl)azetidine-1-carboxylate

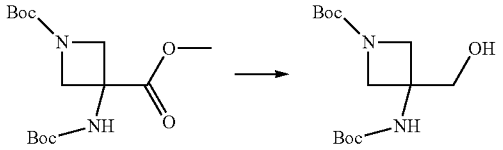 [SMILES: COC(=O)C1(NC(=O)OC(C)(C)C)CN(C(=O)OC(C)(C)C)C1 ; CC(C)(C)OC(=O)NC1(CO)CN(C(=O)OC(C)(C)C)C1]

1-(Tert-butyl) 3-methyl 3-((tert-butoxycarbonyl)amino)azetidine-1,3-dicarboxylate (5 g, 15.1 mmol) was dissolved in anhydrous tetrahydrofuran (50 mL), and lithium tetrahydroaluminum (0.86 g, 22.7 mmol) was added thereto. The reaction mixture was stirred at 70° C. overnight. Water was added to quench the reaction, and then the mixture was extracted with ethyl acetate. The mixture was filtered. The filtrate was dried and evaporated to dryness. The crude product was purified by column chromatography to obtain tert-butyl 3-((tert-butoxycarbonyl)amino)-3-(hydroxymethyl)azetidine-1-carboxylate (2.3 g, yield: 50%).

MS m/z (ESI): 303.2$[M+H]^+$.

Step 3: Preparation of tert-butyl 3-((tert-butoxycarbonyl)amino)-3-(((methylsulfonyl)oxo)methyl)azetidine-1-carboxylate

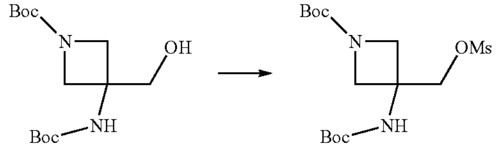 [SMILES: CC(C)(C)OC(=O)NC1(CO)CN(C(=O)OC(C)(C)C)C1 ; CC(C)(C)OC(=O)NC1(COS(C)(=O)=O)CN(C(=O)OC(C)(C)C)C1]

Tert-butyl 3-((tert-butoxycarbonyl)amino)-3-(hydroxymethyl)azetidine-1-carboxylate (2.3 g, 7.6 mmol) was dissolved in anhydrous dichloromethane (30 mL) and, DIEA (2 g, 15.2 mmol) was added thereto. MsCl (1.1 g, 9.1 mmol) was slowly added dropwise to the reaction mixture at 0° C. After the addition was completed, the reaction mixture was slowly warmed to room temperature, and stirred for 4 hours. Water was added to the reaction, and then the mixture was extracted with dichloromethane. The organic phase was evaporated to dryness to obtain tert-butyl 3-((tert-butoxycarbonyl)amino)-3-(((methylsulfonyl)oxo)methyl)azetidine-1-carboxylate (2.8 g, yield: 97%).

MS m/z (ESI): 381.2$[M+H]^+$.

Step 4: Preparation of tert-butyl 3-((1H-pyrazol-1-yl)methyl)-3-((tert-butoxycarbonyl)amino)azetidine-1-carboxylate

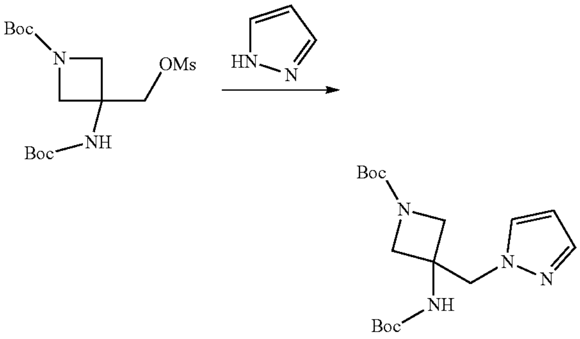

Tert-butyl 3-((1H-pyrazol-1-yl)methyl)-3-((tert-butoxycarbonyl)amino)azetidine-1-carboxylate was obtained by using tert-butyl 3-((tert-butoxycarbonyl)amino)-3-(((methylsulfonyl)oxy)methyl)azetidine-1-carboxylate and 1H-pyrazole as raw materials with reference to step 5 of embodiment 37.

MS m/z (ESI): 353.2[M+H]$^+$.

Step 5: Preparation of 3-((1H-pyrazol-1-yl)methyl)azetidin-3-amine

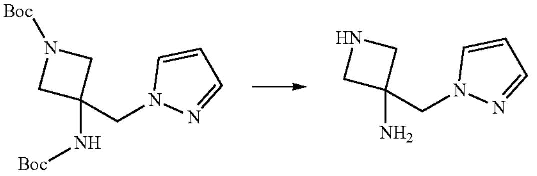 [SMILES: CC(C)(C)OC(=O)NC1(Cn2cccn2)CN(C(=O)OC(C)(C)C)C1 ; NC1(Cn2cccn2)CNC1]

3-((1H-pyrazol-1-yl)methyl)azetidin-3-amine (0.7 g, yield: 90%) was obtained by using tert-butyl 3-((1H-pyrazol-1-yl)methyl)-3-((tert-butoxycarbonyl)amino)azetidine-1-carboxylate as raw material with reference to step 4 of embodiment 43.

MS m/z (ESI): 153.1[M+H]$^+$.

Step 5: Preparation of 4-(6-(3-((1H-pyrazol-1-yl)methyl)-3-aminoazetidin-1-yl)pyridin-3-yl)-6-(2-hydroxy-2-methylpropoxy)pyrazolo[1,5-a]pyridine-3-carbonitrile

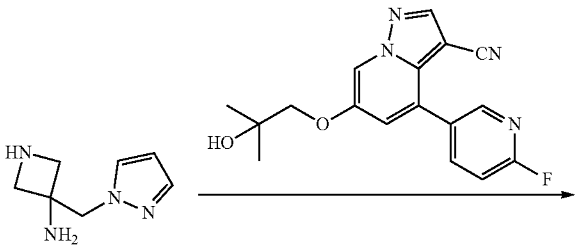

-continued

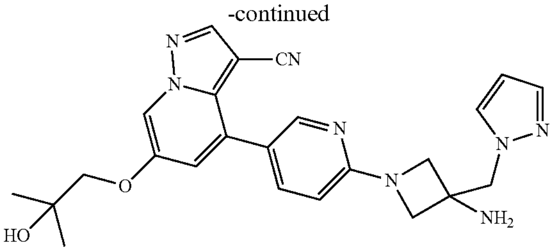

4-(6-(3-((1H-pyrazol-1-yl)methyl)-3-aminoazetidin-1-yl)pyridin-3-yl)-6-(2-hydroxy-2-methylpropoxy)pyrazolo[1,5-a]pyridine-3-carbonitrile (63 mg, yield: 69%) was obtained by using 3-((1H-pyrazol-1-yl)methyl)azetidin-3-amine and 4-(6-fluoropyridin-3-yl)-6-(2-hydroxy-2-methylpropoxy)pyrazolo[1,5-a]pyridine-3-carbonitrile as raw materials with reference to step 6 of embodiment 42.

MS m/z (ESI): 459.2[M+H]$^+$.

Embodiment 67

4-(6-(3-Amino-3-((6-methoxypyridin-3-yl)methyl)azetidin-1-yl)pyridin-3-yl)-6-(2-hydroxy-2-methylpropoxy)pyrazolo[1,5-a]pyridine-3-carbonitrile

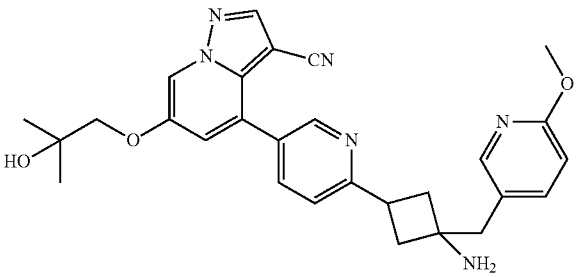 [SMILES: COc1ccc(CC2(N)CC(c3ccc(-c4cc(OCC(C)(C)O)cn5ncc(C#N)c45)cn3)C2)cn1]

Step 1: Preparation of 1-(tert-butyl) 3-methyl 3-((6-methoxypyridin-3-yl)methyl)azetidine-1,3-dicarboxylate

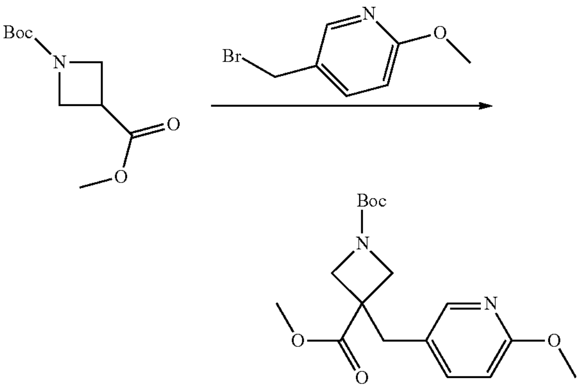

1-(tert-butyl) 3-methyl 3-((6-methoxypyridin-3-yl)methyl)azetidine-1,3-dicarboxylate (5 g, yield: 63%) was obtained by using 1-(tert-butyl) 3-methyl azetidine-1,3-dicarboxylate and 5-(bromomethyl)-2-methoxypyridine as raw material with reference to step 1 of embodiment 59.

MS m/z (ESI): 337.2[M+H]$^+$.

Step 2: Preparation of 1-(tert-butoxycarbonyl)-3-((6-methoxypyridin-3-yl)methyl)azetidine-3-carboxylic acid

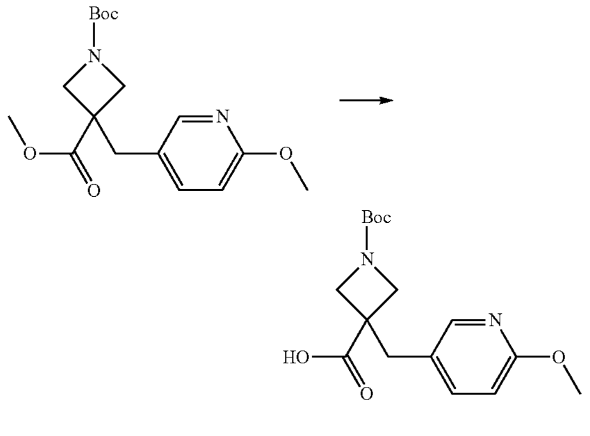

1-(Tert-butoxycarbonyl)-3-((6-methoxypyridin-3-yl)methyl)azetidine-3-carboxylic acid (2.5 g, yield: 76%) was obtained by using 1-(tert-butyl) 3-methyl 3-((6-methoxypyridin-3-yl)methyl)azetidine-1,3-dicarboxylate as raw material with reference to step 2 of embodiment 40.

MS m/z (ESI): 323.2[M+H]$^+$.

Step 3: Preparation of tert-butyl 3-((tert-butoxycarbonyl)amino)-3-((6-methoxypyridin-3-yl)methyl)azetidine-1-carboxylate

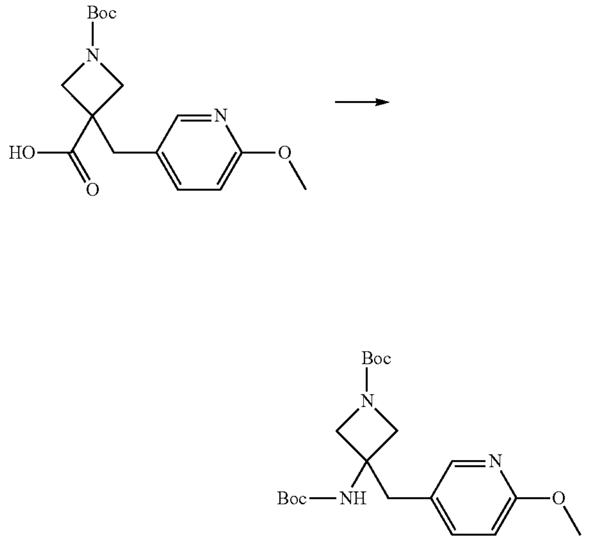

Tert-butyl 3-((tert-butoxycarbonyl)amino)-3-((6-methoxypyridin-3-yl)methyl)azetidine-1-carboxylate (1.5 g, yield: 67%) was obtained by using 1-(tert-butoxycarbonyl)-3-((6-methoxypyridin-3-yl)methyl)azetidine-3-carboxylic acid as raw material with reference to step 3 of embodiment 59.

MS m/z (ESI): 394.2[M+H]$^+$.

Step 4: Preparation of 3-((6-methoxypyridin-3-yl)methyl)azetidin-3-amine

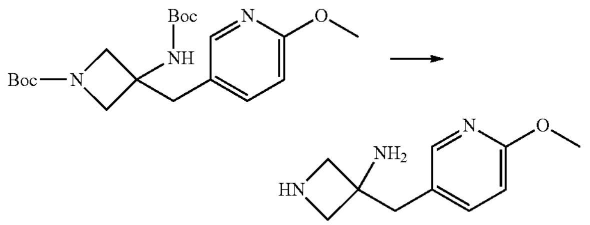

3-((6-Methoxypyridin-3-yl)methyl)azetidin-3-amine (0.7 g, yield: 91%) was obtained by using tert-butyl 3-((tert-butoxycarbonyl)amino)-3-((6-methoxypyridin-3-yl)methyl)azetidine-1-carboxylate as raw material with reference to step 4 of embodiment 43.

MS m/z (ESI): 194.1[M+H]$^+$.

Step 5: Preparation of 4-(6-(3-amino-3-((6-methoxypyridin-3-yl)methyl)azetidin-1-yl)pyridin-3-yl)-6-(2-hydroxy-2-methylpropoxy)pyrazolo[1,5-a]pyridine-3-carbonitrile

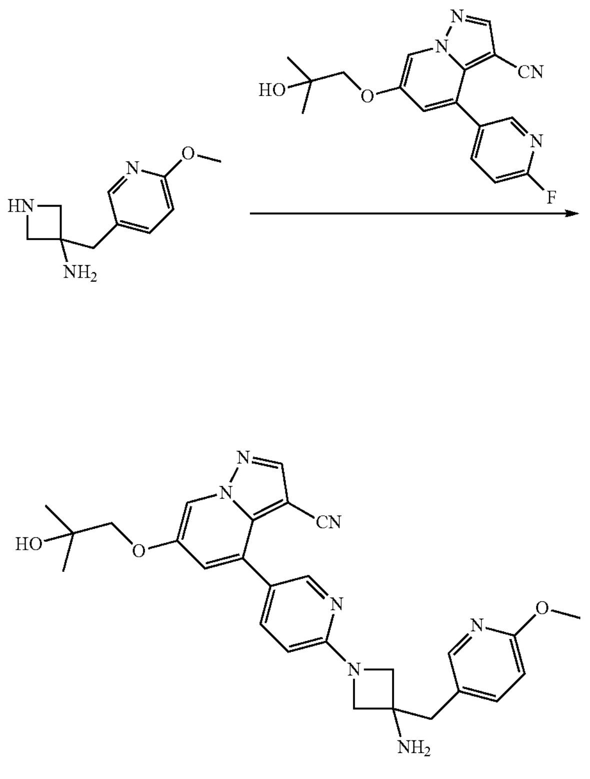

4-(6-(3-Amino-3-((6-methoxypyridin-3-yl)methyl)azetidin-1-yl)pyridin-3-yl)-6-(2-hydroxy-2-methylpropoxy)pyrazolo[1,5-a]pyridine-3-carbonitrile (53 mg, yield: 59%) was obtained by using 3-((6-methoxypyridin-3-yl)methyl)azetidin-3-amine and 4-(6-fluoropyridin-3-yl)-6-(2-hydroxy-2-methylpropoxy)pyrazolo[1,5-a]pyridine-3-carbonitrile as raw material with reference to step 6 of embodiment 42.

MS m/z (ESI): 500.2[M+H]$^+$.

Embodiment 68

4-(4-(3-Amino-1-((6-methoxypyridin-3-yl)methyl)azetidin-3-yl)phenyl)-6-(2-hydroxy-2-methylpropoxy)pyrazolo[1,5-a]pyridine-3-carbonitrile

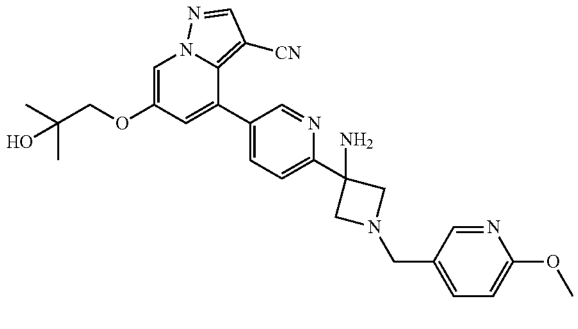 [SMILES: COc1ccc(CN2CC(N)(c3ccc(-c4cc(OCC(C)(C)O)cn5ncc(C#N)c45)cn3)C2)cn1]

Step 1: Preparation of benzyl 3-((tert-butylsulfinyl<sulfinyl>)amino)-3-(4-chlorophenyl)azetidin-1-carboxylate

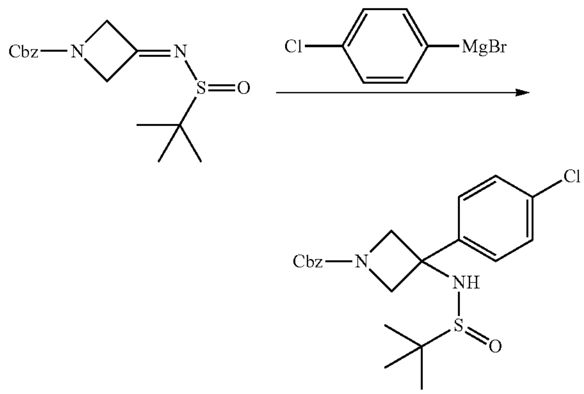

Benzyl 3-((tert-butylsulfinyl<sulfinyl>)amino)-3-(4-chlorophenyl)azetidin-1-carboxylate (2.2 g, yield: 35%) was obtained by using benzyl 3-((tert-butylsulfinyl<sulfinyl>)imino)azetidin-1-carboxylate and (4-chlorophenyl)magnesium bromide as raw materials with reference to step 1 of embodiment 42.

MS m/z (ESI): 421.2[M+H]$^+$.

Step 2: Preparation of benzyl 3-((tert-butylsulfinyl<sulfinyl>)amino)-3-(4-(3-cyano-6-(2-hydroxy-2-methylpropoxy)pyrazolo[1,5-a]pyridin-4-yl)phenyl)azetidin-1-carboxylate

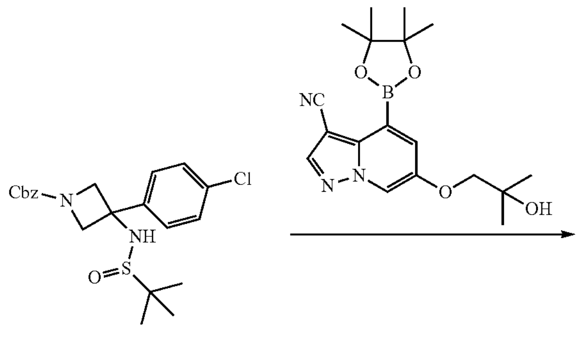

-continued

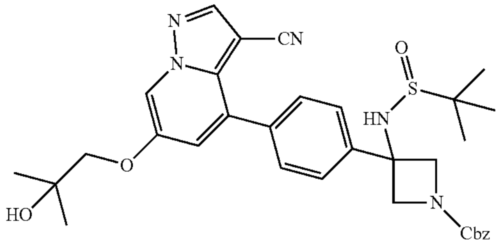

Benzyl 3-((tert-butylsulfinyl<sulfinyl>)amino)-3-(4-(3-cyano-6-(2-hydroxy-2-methylpropoxy)pyrazolo[1,5-a]pyridin-4-yl)phenyl)azetidine-1-carboxylate (1.3 g, yield: 68%) was obtained by using benzyl 3-((tert-butylsulfinyl<sulfinyl>)amino)-3-(4-chlorophenyl)azetidine-1-carboxylate and 6-(2-hydroxy-2-methylpropoxy)-4-(4,4,5,5-tetramethyl-1,3,2-dioxaborolan-2-yl)pyrazolo[1,5-a]pyridine-3-carbonitrile as raw materials with reference to step 3 of embodiment 37.

MS m/z (ESI): 616.2[M+H]$^+$.

Step 3: Preparation of N-(3-(4-(3-cyano-6-(2-hydroxy-2-methylpropoxy)pyrazolo[1,5-a]pyridin-4-yl)phenyl)azetidin-3-yl)-2-methylpropane-2-sulfinamide

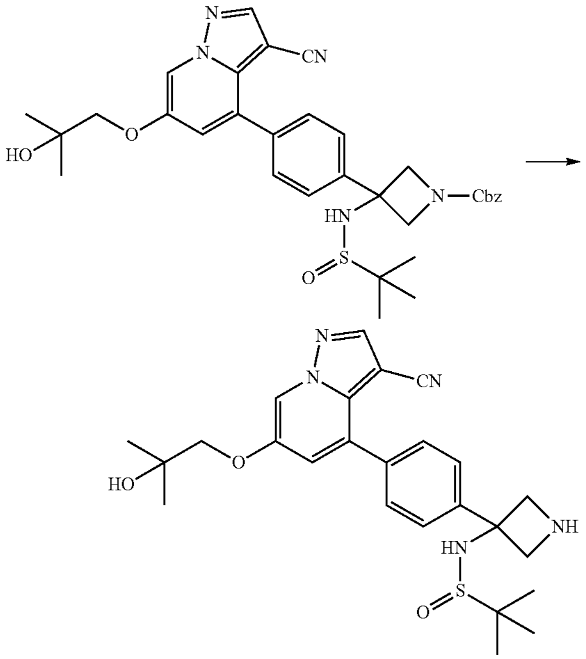

N-(3-(4-(3-cyano-6-(2-hydroxy-2-methylpropoxy)pyrazolo[1,5-a]pyridin-4-yl)phenyl)azetidin-3-yl)-2-methylpropane-2-sulfinamide (0.9 g, yield: 82%) was obtained by using benzyl 3-((tert-butylsulfinyl<sulfinyl>)amino)-3-(4-(3-cyano-6-(2-hydroxy-2-methylpropoxy)pyrazolo[1,5-a]pyridin-4-yl)phenyl)azetidine-1-carboxylate as raw materials with reference to step 4 of embodiment 42.

MS m/z (ESI): 482.2[M+H]$^+$.

Step 4: Preparation of N-(3-(4-(3-cyano-6-(2-hydroxy-2-methylpropoxy)pyrazolo[1,5-a]pyridin-4-yl)phenyl)-1-((6-methoxypyridin-3-yl)methyl)azetidin-3-yl)-2-methylpropane-2-sulfinamide

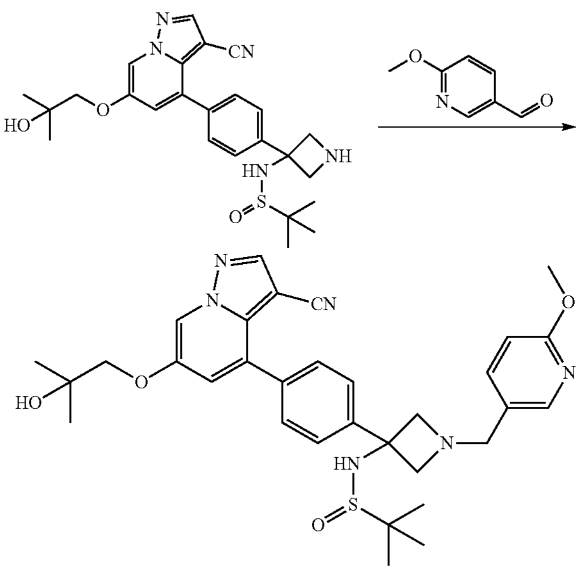

N-(3-(4-(3-cyano-6-(2-hydroxy-2-methylpropoxy)pyrazolo[1,5-a]pyridin-4-yl)phenyl)-1-((6-methoxypyridin-3-yl)methyl)azetidin-3-yl)-2-methylpropane-2-sulfinamide (0.4 g, yield: 62%) was obtained by using N-(3-(4-(3-cyano-6-(2-hydroxy-2-methylpropoxy)pyrazolo[1,5-a]pyridin-4-yl)phenyl)azetidin-3-yl)-2-methylpropane-2-sulfinamide and 6-methoxynicotinaldehyde as raw materials with reference to step 3 of embodiment 55.

MS m/z (ESI): 603.3[M+H]$^+$.

Step 5: 4-(4-(3-amino-1-((6-methoxypyridin-3-yl)methyl)azetidin-3-yl)phenyl)-6-(2-hydroxy-2-methylpropoxy)pyrazolo[1,5-a]pyridine-3-carbonitrile

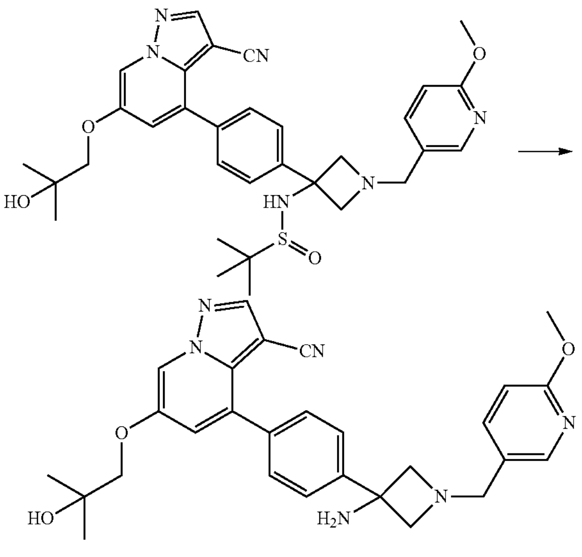

4-(4-(3-Amino-1-((6-methoxypyridin-3-yl)methyl)azetidin-3-yl)phenyl)-6-(2-hydroxy-2-methylpropoxy)pyrazolo[1,5-a]pyridine-3-carbonitrile (150 mg, yield: 84%) was obtained by using N-(3-(4-(3-cyano-6-(2-hydroxy-2-methylpropoxy)pyrazolo[1,5-a]pyridin-4-yl)phenyl)-1-((6-methoxypyridin-3-yl)methyl)azetidin-3-yl)-2-methylpropane-2-sulfinamide as raw material with reference to step 2 of embodiment 42.

MS m/z (ESI): 499.2[M+H]$^+$.

Embodiment 69

4-(6-(3-(3-Amino-1H-pyrazol-1-yl)azetidin-1-yl)pyridin-3-yl)-6-(2-hydroxy-2-methylpropoxy)pyrazolo[1,5-a]pyridine-3-carbonitrile

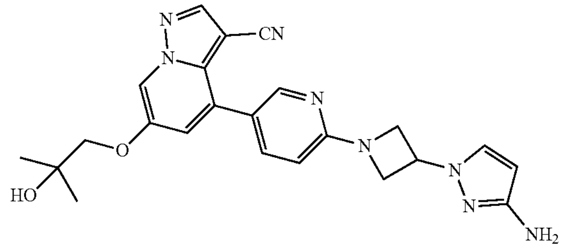 [SMILES: CC(C)(O)COc1cc(-c2ccc(N3CC(n4ccc(N)n4)C3)nc2)c2c(C#N)cnn2c1]

Step 1: tert-butyl 3-(3-nitro-1H-pyrazol-1-yl)azetidine-1-carboxylate

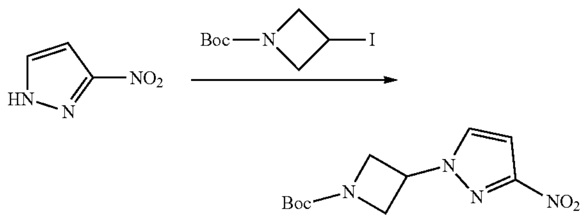

3-Nitro-1H-pyrazole (10 g, 88.4 mmol) was dissolved in anhydrous DMF (120 mL), and tert-butyl 3-iodoazetidine-1-carboxylate (30 g, 106.1 mmol) and potassium carbonate (24.4 g, 176.9 mmol) were added thereto. The reaction mixture was stirred at 60° C. overnight. Water was added thereto, and then the mixture was extracted with ethyl acetate. The organic phase was dried and evaporated to dryness. The crude product was purified by column chromatography to obtain tert-butyl 3-(3-nitro-1H-pyrazol-1-yl)azetidine-1-carboxylate (20 g, yield: 84%).

MS m/z (ESI): 269.1[M+H]$^+$.

Step 2: Preparation of 1-(azetidin-3-yl)-3-nitro-1H-pyrazole

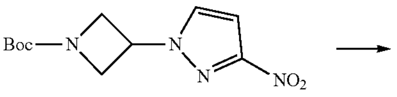

-continued

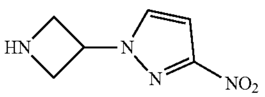

1-(Azetidin-3-yl)-3-nitro-1H-pyrazole (5 g, yield: 93%) was obtained by using tert-butyl 3-(3-nitro-1H-pyrazol-1-yl)azetidine-1-carboxylate as raw material with reference to step 4 of embodiment 43. MS m/z (ESI): 169.1[M+H]+.

Step 3: Preparation of 6-(2-hydroxy-2-methylpropoxy)-4-(6-(3-(3-nitro-1H-pyrazol-1-yl)azetidin-1-yl)pyridin-3-yl)pyrazolo[1,5-a]pyridine-3-carbonitrile

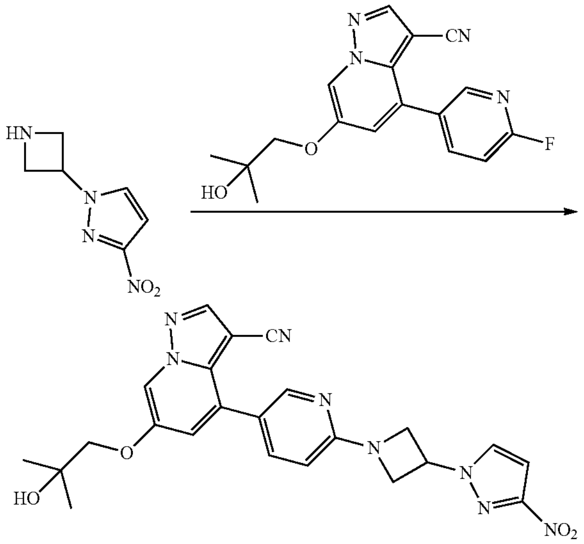

6-(2-Hydroxy-2-methylpropoxy)-4-(6-(3-(3-nitro-1H-pyrazol-1-yl)azetidin-1-yl)pyridin-3-yl)pyrazolo[1,5-a]pyridine-3-carbonitrile (500 mg, yield: 68%) was obtained by using 1-(azetidin-3-yl)-3-nitro-1H-pyrazole and 4-(6-fluoropyridin-3-yl)-6-(2-hydroxy-2-methylpropoxy)pyrazolo[1,5-a]pyridine-3-carbonitrile as raw materials with reference to step 6 of embodiment 42.

MS m/z (ESI): 475.2[M+H]+.

Step 4: Preparation of 4-(6-(3-(3-amino-1H-pyrazol-1-yl)azetidin-1-yl)pyridin-3-yl)-6-(2-hydroxy-2-methylpropoxy)pyrazolo[1,5-a]pyridine-3-carbonitrile

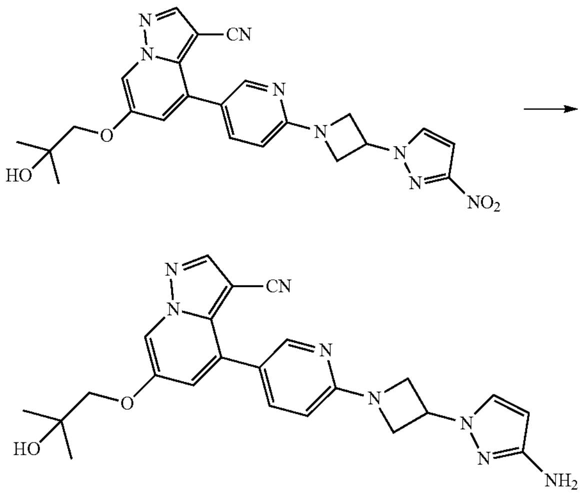

6-(2-Hydroxy-2-methylpropoxy)-4-(6-(3-(3-nitro-1H-pyrazol-1-yl)azetidin-1-yl)pyridin-3-yl)pyrazolo[1,5-a]pyridine-3-carbonitrile (200 mg, 0.42 mmol) was dissolved in tetrahydrofuran (20 mL); and iron powder (235 mg, 4.22 mmol), ammonium chloride (225 mg, 4.22 mmol) and water (10 mL) were added thereto. The reaction mixture was stirred at 80° C. for 1 hour. Then ethyl acetate was added to the reaction mixture and filtered. The filtrate was dried and evaporated to dryness. The crude product was purified by prep-HPLC to obtain 4-(6-(3-(3-amino-1H-pyrazol-1-yl)azetidin-1-yl)pyridin-3-yl)-6-(2-hydroxy-2-methylpropoxy)pyrazolo[1,5-a]pyridine-3-carbonitrile (75 mg, yield: 40%). MS m/z (ESI): 445.2[M+H]+.

Embodiment 70

N-(1-(1-(5-(3-cyano-6-(2-hydroxy-2-methylpropoxy)pyrazolo[1,5-a]pyridin-4-yl)pyridin-2-yl)azetidin-3-yl)-1H-pyrazol-3-yl)cyclopropanecarboxamide

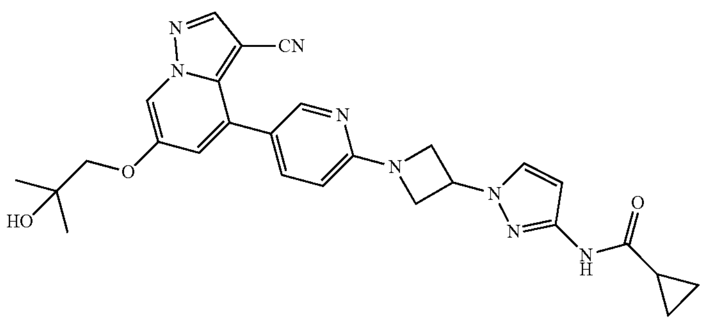

-continued

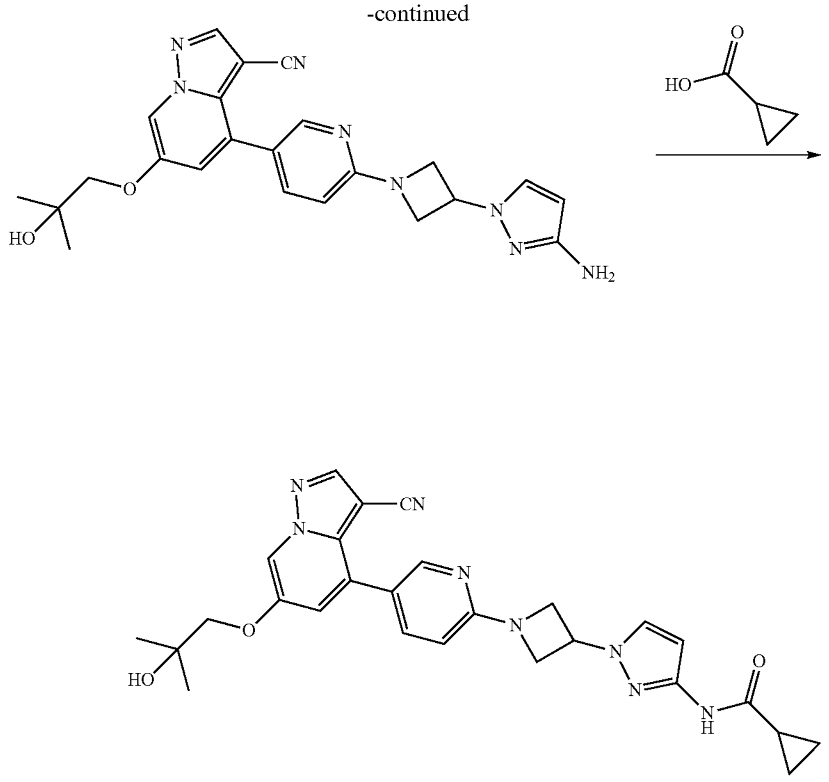

N-(1-(1-(5-(3-cyano-6-(2-hydroxy-2-methylpropoxy)pyrazolo[1,5-a]pyridin-4-yl)pyridin-2-yl)azetidin-3-yl)-1H-pyrazol-3-yl)cyclopropanecarboxamide (85 mg, 72%) was obtained by using 4-(6-(3-(3-amino-1H-pyrazol-1-yl)azetidin-1-yl)pyridin-3-yl)-6-(2-hydroxy-2-methylpropoxy)pyrazolo[1,5-a]pyridine-3-carbonitrile and cyclopropanecarboxylic acid as raw materials with reference to step 3 of embodiment 40.

MS m/z (ESI): 513.2[M+H]$^+$.

Embodiment 71

1-(1-(5-(3-Cyano-6-(2-hydroxy-2-methylpropoxy)pyrazolo[1,5-a]pyridin-4-yl)pyridin-2-yl)azetidin-3-yl)-N-cyclopropyl-1H-pyrazole-3-carboxamide

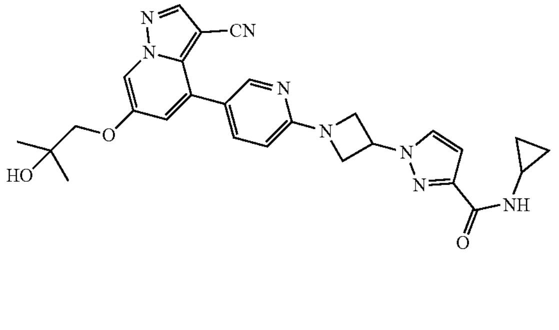 [SMILES: CC(C)(O)COc1cc(-c2ccc(N3CC(n4ccc(C(=O)NC5CC5)n4)C3)nc2)c2c(C#N)cnn2c1]

Step 1: Preparation of 1-diphenylmethylazetidin-3-yl methanesulfonate

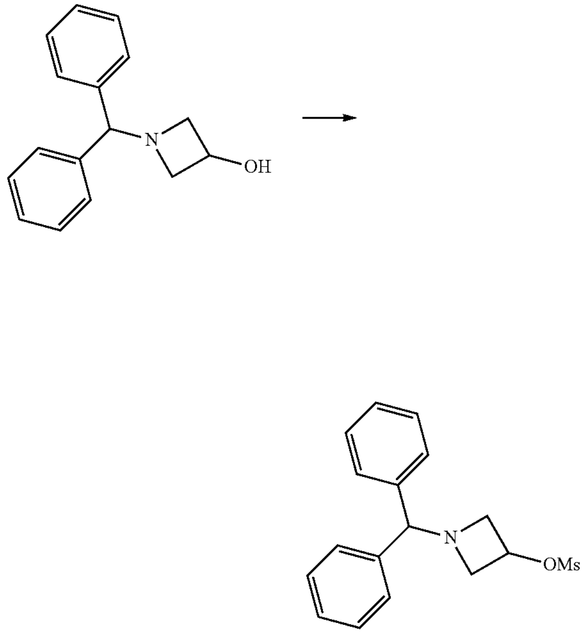

1-Diphenylmethylazetidin-3-yl methanesulfonate (10 g, yield: 95%) was obtained by using 1-diphenylmethylazetidin-3-ol as raw material with reference to step 3 of embodiment 66.

MS m/z (ESI): 318.2[M+H]$^+$.

Step 2: Preparation of methyl 1-(1-diphenylmethyl-azetidin-3-yl)-1H-pyrazole-3-carboxylate

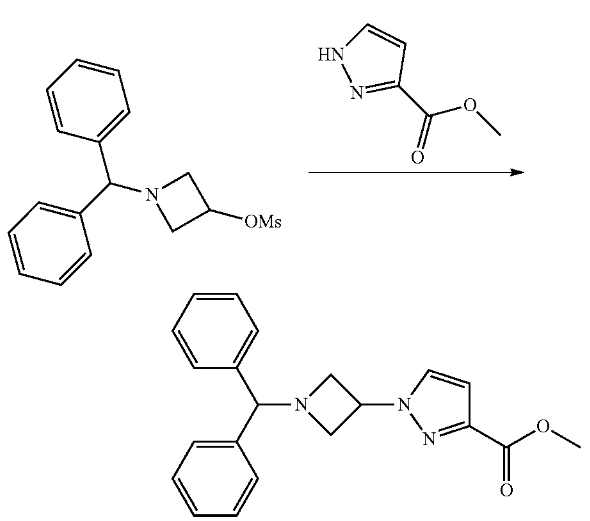

Methyl 1-(1-diphenylmethylazetidin-3-yl)-1H-pyrazole-3-carboxylate (3.5 g, yield: 40%) was obtained by using 1-diphenylmethylazetidin-3-yl methanesulfonate and methyl 1H-pyrazole-3-carboxylate as raw materials with reference to step 5 of embodiment 37.

MS m/z (ESI): 348.2[M+H]+.

Step 3: Preparation of 1-(1-diphenylmethylazetidin-3-yl)-1H-pyrazole-3-carboxylic acid

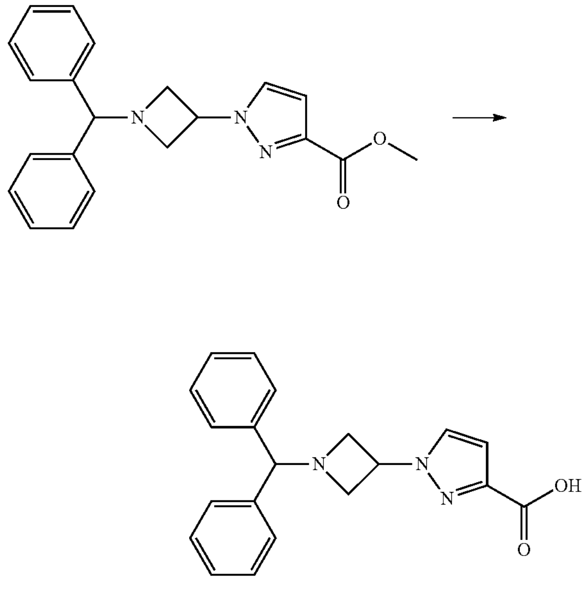

1-(1-Diphenylmethylazetidin-3-yl)-1H-pyrazole-3-carboxylic acid (2.0 g, yield: 75%) was obtained by using methyl 1-(1-diphenylmethylazetidin-3-yl)-1H-pyrazole-3-carboxylate as raw material with reference to step 2 of embodiment 40.

MS m/z (ESI): 334.2[M+H]+.

Step 4: Preparation of 1-(1-diphenylmethylazetidin-3-yl)-N-cyclopropyl-1H-pyrazole-3-carboxamide

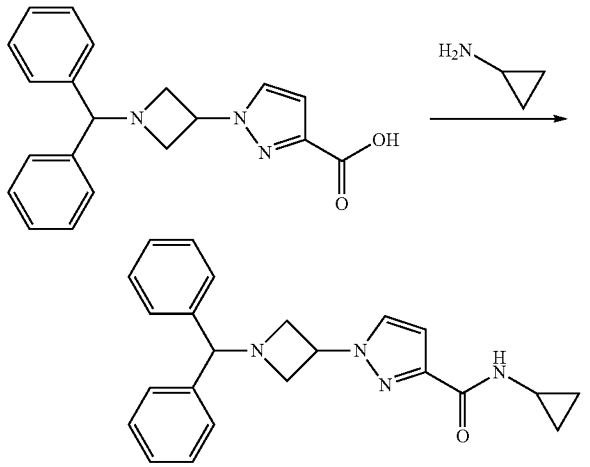

1-(1-Diphenylmethylazetidin-3-yl)-N-cyclopropyl-1H-pyrazole-3-carboxamide (500 mg, yield: 71%) was obtained by using 1-(1-diphenylmethylazetidin-3-yl)-1H-pyrazole-3-carboxylic acid as raw material with reference to step 3 of embodiment 40.

MS m/z (ESI): 373.2[M+H]+.

Step 5: Preparation of 1-(azetidin-3-yl)-N-cyclopropyl-1H-pyrazole-3-carboxamide

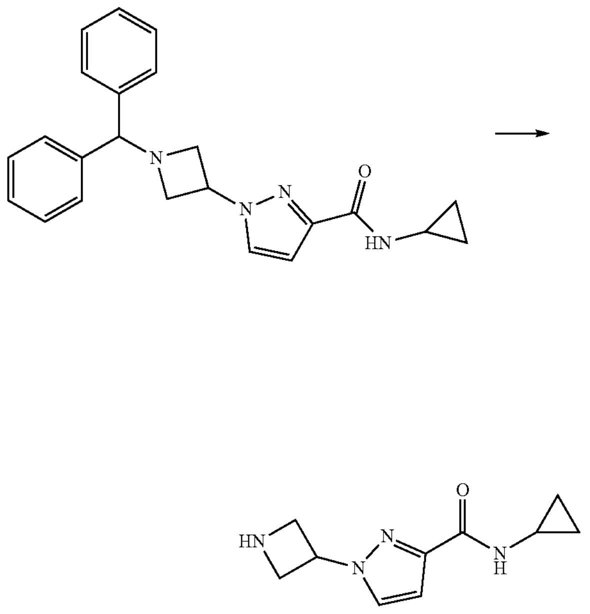 [SMILES: O=C(NC1CC1)c1ccn(C2CN(C(c3ccccc3)c3ccccc3)C2)n1 ; O=C(NC1CC1)c1ccn(C2CNC2)n1]

1-(azetidin-3-yl)-N-cyclopropyl-1H-pyrazole-3-carboxamide (250 mg, yield: 72%) was obtained by using 1-(1-diphenylmethylazetidin-3-yl)-N-cyclopropyl-1H-pyrazole-3-carboxamide as raw material with reference to step 4 of embodiment 42.

MS m/z (ESI): 207.2[M+H]+.

Step 6: Preparation of 1-(1-(5-(3-cyano-6-(2-hydroxy-2-methylpropoxy)pyrazolo[1,5-a]pyridin-4-yl) pyridin-2-yl)azetidin-3-yl)-N-cyclopropyl-1H-pyrazole-3-carboxamide

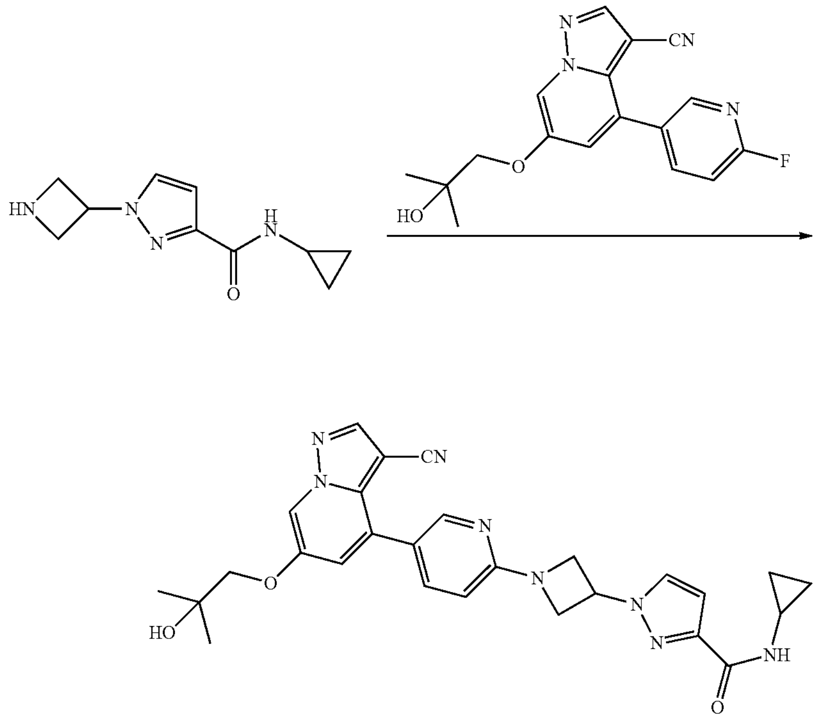

1-(1-(5-(3-Cyano-6-(2-hydroxy-2-methylpropoxy)pyrazolo[1,5-a]pyridin-4-yl)pyridin-2-yl)azetidin-3-yl)-N-cyclopropyl-1H-pyrazole-3-carboxamide was obtained by using 1-(azetidin-3-yl)-N-cyclopropyl-1H-pyrazole-3-carboxamide and 4-(6-fluoropyridin-3-yl)-6-(2-hydroxy-2-methylpropoxy)pyrazolo[1,5-a]pyridine-3-carbonitrile as raw materials with reference to step 6 of embodiment 42.

MS m/z (ESI): 513.2[M+H]$^+$.

Embodiment 72

6-(2-Hydroxy-2-methylpropoxy)-4-(6-(5-((6-methoxypyridin-3-yl)oxy)hexahydrocyclopenta[c] pyrrol-2(1H)-yl)pyridin-3-yl)pyrazolo[1,5-a]pyridine-3-carbonitrile

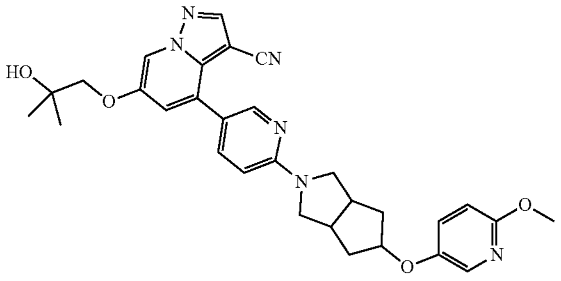 [SMILES: COc1ccc(OC2CC3CN(c4ccc(-c5cc(OCC(C)(C)O)cn6ncc(C#N)c56)cn4)CC3C2)cn1]

Step 1: tert-butyl 5-((6-methoxypyridin-3-yl)oxy) hexahydrocyclopenta[c]pyrrole-2(1H)-carboxylate

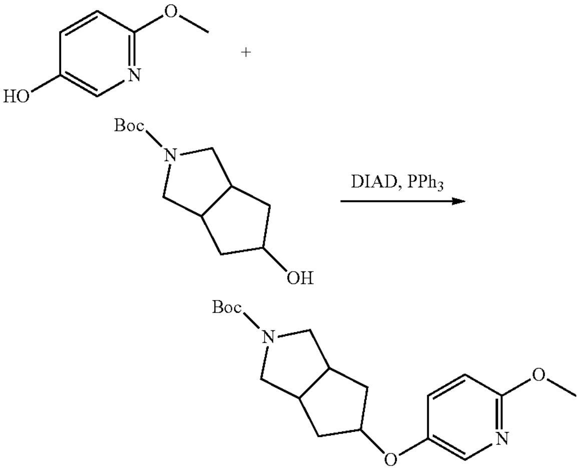

Tert-butyl 5-((6-methoxypyridin-3-yl)oxy)hexahydrocyclopenta[c]pyrrole-2(1H)-carboxylate was obtained by using 6-methoxypyridin-3-ol and tert-butyl 5-hydroxyhexahydrocyclopenta[c]pyrrole-2(1H)-carboxylate as raw material with reference to step 1 of embodiment 34.

MS m/z (ESI): 335.2[M+H]$^+$.

Step 2: 5-((6-methoxypyridin-3-yl)oxy)octahydrocyclopenta[c]pyrrole

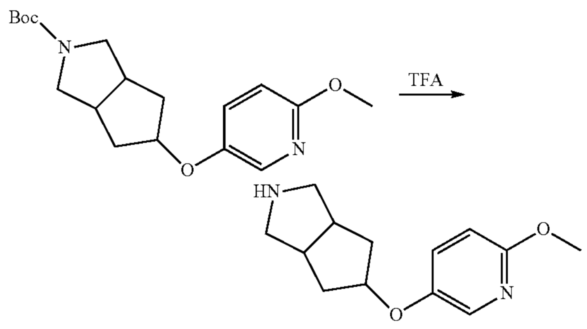

5-((6-Methoxypyridin-3-yl)oxo)octahydrocyclopenta[c]pyrrole was obtained by using tert-butyl 5-((6-methoxypyridin-3-yl)oxo)hexahydrocyclopenta[c]pyrrole-2(1H)-carboxylate as raw material with reference to step 2 of embodiment 57.

MS m/z (ESI): 235.1[M+H]$^+$.

Step 3: 6-(2-hydroxy-2-methylpropoxy)-4-(6-(5-((6-methoxypyridin-3-yl)oxo)hexahydrocyclopenta[c]pyrrol-2(1H)-yl)pyridin-3-yl)pyrazolo[1,5-a]pyridine-3-carbonitrile

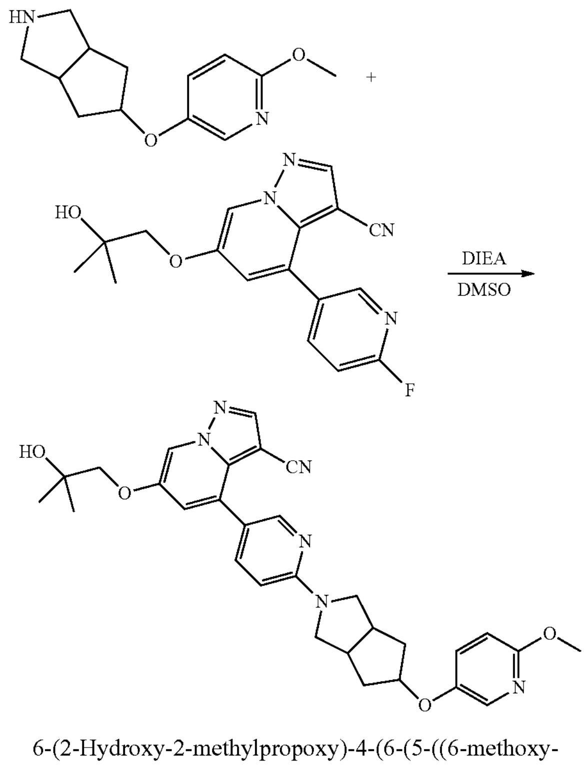

6-(2-Hydroxy-2-methylpropoxy)-4-(6-(5-((6-methoxypyridin-3-yl)oxo)hexahydrocyclopenta[c]pyrrol-2(1H)-yl)pyridin-3-yl)pyrazolo[1,5-a]pyridine-3-carbonitrile was obtained by using 5-((6-methoxypyridin-3-yl)oxo)octahydrocyclopenta[c]pyrrole as raw material with reference to step 2 of embodiment 8.

MS m/z (ESI) 541.2[M+H]$^+$.

Embodiment 73

6-(2-Hydroxy-2-methylpropoxy)-4-(6-(5-(pyridin-3-ylmethoxy)hexahydrocyclopenta[c]pyrrol-2(1H)-yl)pyridin-3-yl)pyrazolo[1,5-a]pyridine-3-carbonitrile

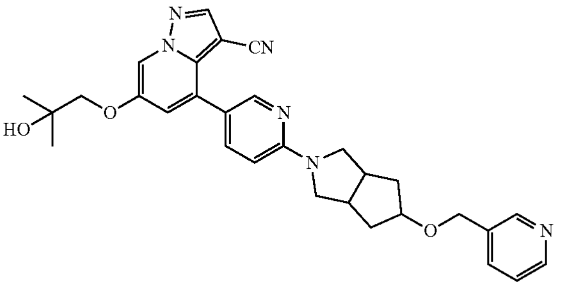 [SMILES: CC(C)(O)COc1cc(-c2ccc(N3CC4CC(OCc5cccnc5)CC4C3)nc2)c2c(C#N)cnn2c1]

Step 1: tert-butyl 5-(pyridin-3-ylmethoxy)hexahydrocyclopenta[c]pyrrole-2(1H)-carboxylate

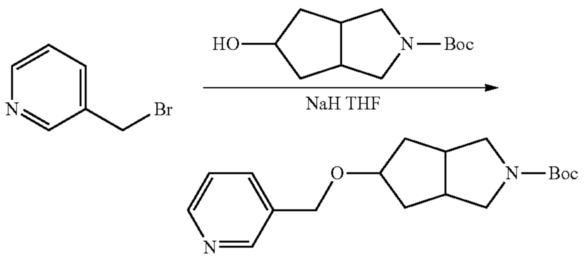

Tert-butyl 5-hydroxyhexahydrocyclopenta[c]pyrrole-2(1H)-carboxylate (660 mg, 2.9 mmol) was dissolved in tetrahydrofuran (10 mL), and sodium hydride (140 mg, 3.5 mmol, 60%) was added under stirring, then the reaction mixture was stirred at room temperature for 1 hour. Then, 3-(bromomethyl)pyridine (500 mg, 2.9 mmol) was added to the reaction mixture, and the stirring was continued for 12 hours. Water (5 mL) was added thereto, and the reaction mixture was extracted with ethyl acetate (10 mL) and washed with saturated sodium chloride solution (5 mL×2); the organic phase was dried over anhydrous sodium sulfate, concentrated under reduced pressure and purified by column chromatography (dichloromethane/methanol: 30/1) to obtain tert-butyl 5-(pyridin-3-ylmethoxy)hexahydrocyclopenta[c]pyrrole-2(1H)-carboxylate (550 mg, white solid, 59.5%).

MS m/z (ESI): 319.2 [M+H]$^+$.

Step 2: 5-(pyridin-3-ylmethoxy)octahydrocyclopenta[c]pyrrole

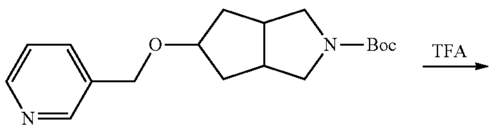

-continued

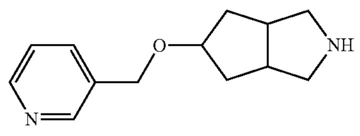

5-(Pyridin-3-ylmethoxy)octahydrocyclopenta[c]pyrrole was obtained by using tert-butyl 5-(pyridin-3-ylmethoxy) hexahydrocyclopenta[c]pyrrole-2(1H)-carboxylate as raw material with reference to step 2 of embodiment 57.

MS m/z (ESI) 219.2[M+H]$^+$.

Step 3: 6-(2-hydroxy-2-methylpropoxy)-4-(6-(5-(pyridin-3-ylmethoxy)hexahydrocyclopenta[c]pyrrol-2(1H)-yl)pyridin-3-yl)pyrazolo[1,5-a]pyridine-3-carbonitrile

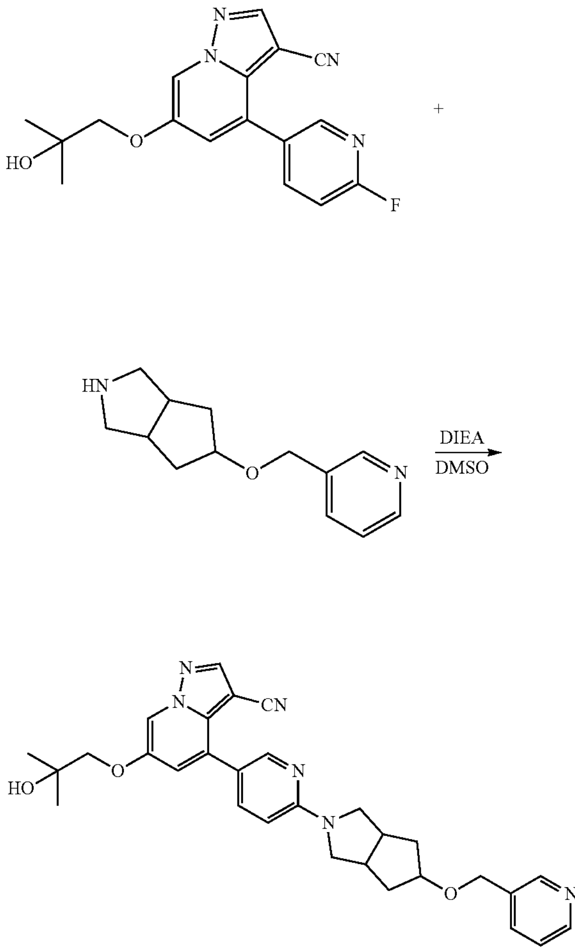

6-(2-Hydroxy-2-methylpropoxy)-4-(6-(5-(pyridin-3-ylmethoxy)hexahydrocyclopenta[c]pyrrol-2(1H)-yl)pyridin-3-yl)pyrazolo[1,5-a]pyridine-3-carbonitrile was obtained by using 5-(pyridin-3-ylmethoxy)octahydrocyclopenta[c]pyrrole as raw material with reference to step 2 of embodiment 8.

MS m/z (ESI) 525.2[M+H]$^+$.

Embodiment 74

6-(2-Hydroxy-2-methylpropoxy)-4-(6-(5-(((6-methoxypyridin-3-yl)methyl)amino)-5-methylhexahydrocyclopenta[c]pyrrol-2(1H)-yl)pyridin-3-yl) pyrazolo[1,5-a]pyridine-3-carbonitrile

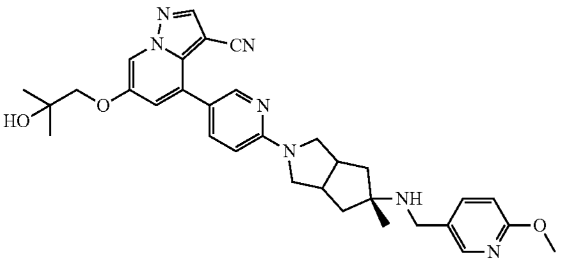

Step 1: 2-(5-bromopyridin-2-yl)hexahydrocyclopenta[c]pyrrol-5(1H)-one

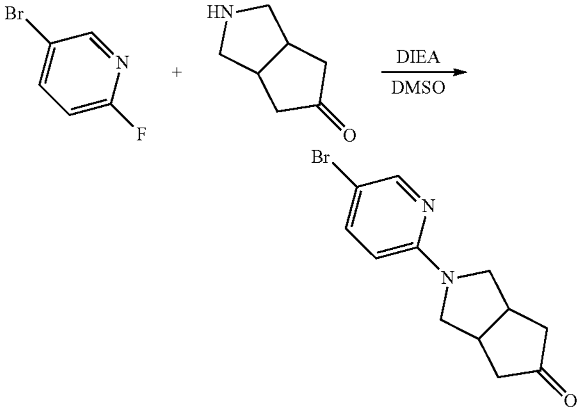

2-(5-Bromopyridin-2-yl)hexahydrocyclopenta[c]pyrrol-5 (1H)-one was obtained by using 5-bromo-2-fluoropyridine and hexahydrocyclopenta[c]pyrrol-5(1H)-one as raw material with reference to step 2 of embodiment 8.

MS m/z (ESI) 281.0[M+H]$^+$.

Step 2: 2-(5-bromopyridin-2-yl)-5-methyleneoctahydrocyclopenta[c]pyrrole

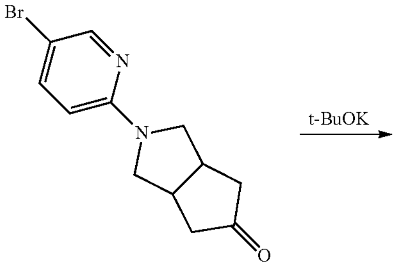

-continued

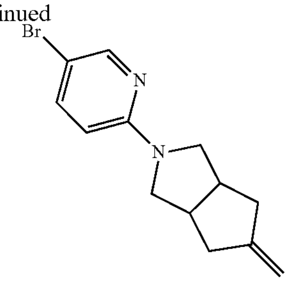

Methyltriphenylphosphine bromide (870 mg, 2.45 mmol) was dissolved in tetrahydrofuran (10 mL), the mixture was replaced with $N_2$, cooled to 0° C.; and potassium tert-butoxide (330 mg, 2.93 mmol) was added thereto, the reaction was stirred at room temperature for 2 hours. The mixture was cooled to 0° C., a solution of 2-(5-bromopyridin-2-yl)hexahydrocyclopenta[c]pyrrol-5(1H)-one (450 mg, 1.60 mmol) in tetrahydrofuran (10 mL) was added thereto. The reaction was stirred at room temperature for 2 hours, and then stirred at 50° C. overnight. The reaction was quenched with water (10 mL), the aqueous phase was extracted with ethyl acetate (10 mL); the organic phases were combined, dried over anhydrous sodium sulfate, filtered, concentrated, and the crude product was purified by column chromatography (petroleum ether/ethyl acetate: 1/1) to obtain 2-(5-bromopyridin-2-yl)-5-methyleneoctahydrocyclopenta[c]pyrrole (300 mg, yield: 67%).

MS m/z (ESI) 279.0[M+H]$^+$.

Step 3: N-(2-(5-bromopyridin-2-yl)-5-methyloctahydrocyclopenta[c]pyrrol-5-yl)formamide

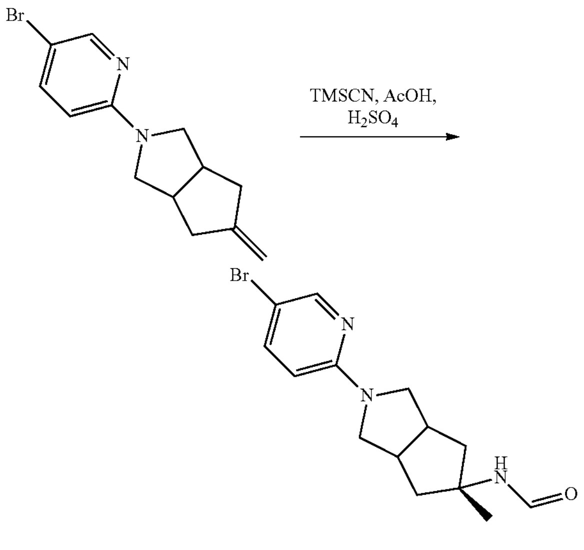

2-(5-Bromopyridin-2-yl)-5-methyleneoctahydrocyclopenta[c]pyrrole (300 mg, 1.07 mmol) was dissolved in dichloromethane (30 mL), acetic acid (180 mg, 3.0 mmol) was added thereto, and the mixture was cooled to 0° C., trimethylcyanosilane (200 mg, 2.0 mmol) was added thereto dropwise, and the reaction was stirred at 0° C. for half an hour. Then a mixed solution of acetic acid (180 mg, 3.0 mmol) and concentrated sulfuric acid (400 mg, 4.0 mmol) was added slowly dropwise and the reaction was stirred overnight at 0° C. to room temperature. At 0° C., 3 M sodium hydroxide aqueous solution was added until Ph>12. The mixture was separated, the aqueous phase was extracted with ethyl acetate (20 mL); and the organic phases were combined, dried over anhydrous sodium sulfate, filtered and concentrated to obtain N-(2-(5-bromopyridin-2-yl)-5-methyloctahydrocyclopenta[c]pyrrol-5-yl)formamide (230 mg, yield: 66.0%).

MS m/z (ESI): 324.0 [M+H]$^+$.

Step 4: 2-(5-bromopyridin-2-yl)-5-methyloctahydrocyclopenta[c]pyrrol-5-amine

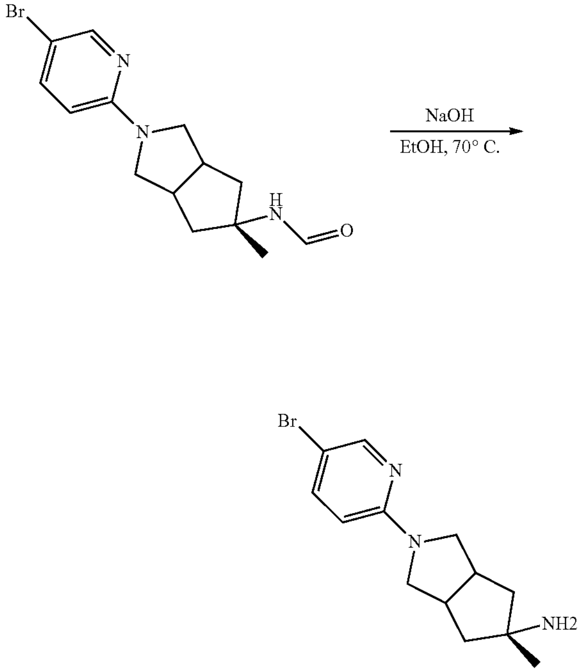

N-(2-(5-bromopyridin-2-yl)-5-methyloctahydrocyclopenta[c]pyrrol-5-yl)formamide (230 mg, 0.7 mmol) was dissolved in ethanol (5 mL); sodium hydroxide (80 mg, 2.1 mmol) and water (2 mL) were added thereto, and the reaction was stirred at 70° C. overnight. The mixture was evaporated to dryness to remove the solvent, water (5 mL) was added thereto; and the aqueous phase was extracted with ethyl acetate (5 mL×2), the organic phase was washed with 1 M hydrochloric acid aqueous solution (5 mL), the aqueous phase was adjusted to pH>12 with 3 M sodium hydroxide aqueous solution, then the aqueous phase was extracted with ethyl acetate (5 mL×2); and the organic phases were combined, dried over anhydrous sodium sulfate, filtered and concentrated to obtain 2-(5-bromopyridin-2-yl)-5-methyloctahydrocyclopenta[c]pyrrol-5-amine (150 mg, yield: 71%).

MS m/z (ESI): 296.0 [M+H]$^+$.

Step 5: 2-(5-bromopyridin-2-yl)-N-((6-methoxypyridin-3-yl)methyl)-5-methyloctahydrocyclopenta[c]pyrrol-5-amine

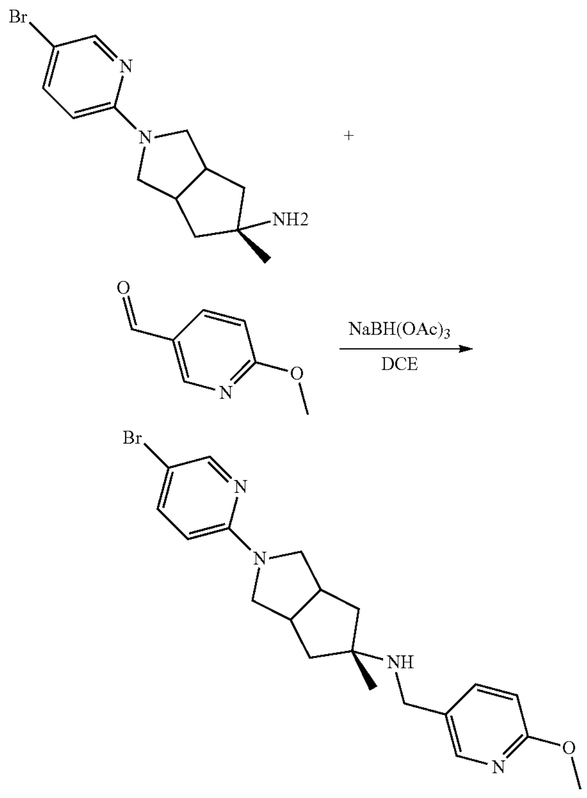

2-(5-Bromopyridin-2-yl)-N-((6-methoxypyridin-3-yl)methyl)-5-methyloctahydrocyclopenta[c]pyrrol-5-amine was obtained by using 2-(5-bromopyridin-2-yl)-5-methyloctahydrocyclopenta[c]pyrrol-5-amine as raw material with reference to step 3 of embodiment 57.

MS m/z (ESI): 417.1 $[M+H]^+$.

Step 6: N-((6-methoxypyridin-3-yl)methyl)-5-methyl-2-(5-(4,4,5,5-tetramethyl-1,3,2-dioxaborolan-2-yl)pyridin-2-yl)octahydrocyclopenta[c]pyrrol-5-amine

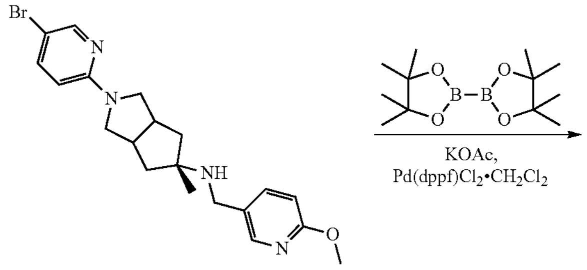

-continued

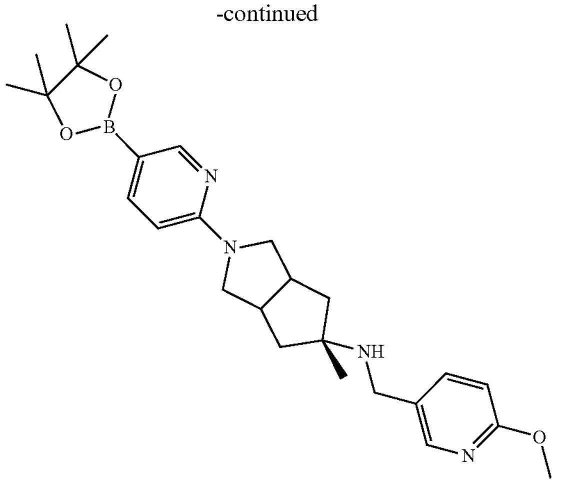

N-((6-methoxypyridin-3-yl)methyl)-5-methyl-2-(5-(4,4,5,5-tetramethyl-1,3,2-dioxaborolan-2-yl)pyridin-2-yl)octahydrocyclopenta[c]pyrrol-5-amine was obtained by using 2-(5-bromopyridin-2-yl)-N-((6-methoxypyridin-3-yl)methyl)-5-methyloctahydrocyclopenta[c]pyrrol-5-amine as raw material with reference to step 4 of embodiment 57.

MS m/z (ESI): 465.3 $[M+H]^+$.

Step 7: 6-(2-hydroxy-2-methylpropoxy)-4-(6-(5-(((6-methoxypyridin-3-yl)methyl)amino)-5-methylhexahydrocyclopenta[c]pyrrol-2(1H)-yl)pyridin-3-yl)pyrazolo[1,5-a]pyridine-3-carbonitrile

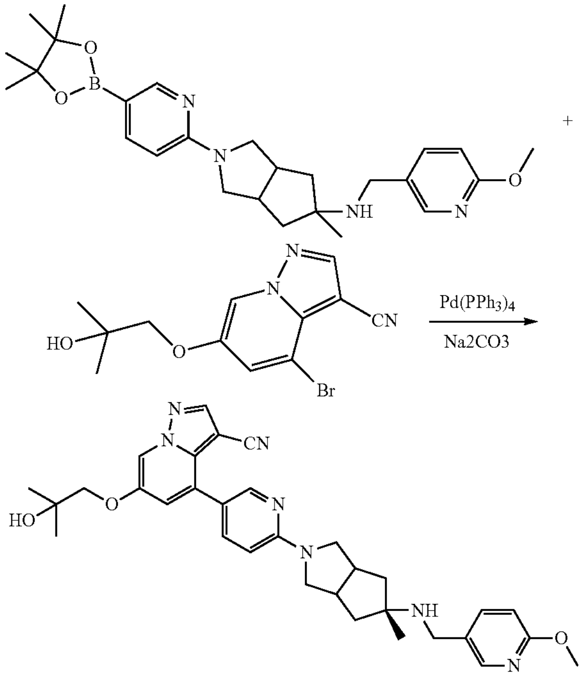

74

6-(2-Hydroxy-2-methylpropoxy)-4-(6-(5-(((6-methoxypyridin-3-yl)methyl)amino)-5-methylhexahydrocyclopenta[c]pyrrol-2(1H)-yl)pyridin-3-yl)pyrazolo[1,5-a]pyridine-3-carbonitrile was obtained by using N-((6-methoxypyridin- 3-yl)methyl)-5-methyl-2-(5-(4,4,5,5-tetramethyl-1,3,2-dioxaborolan-2-yl)pyridin-2-yl)octahydrocyclopenta[c]pyrrol-5-amine as raw material with reference to step 3 of embodiment 7.

MS m/z (ESI): 568.3[M+H]+.

Embodiment 75

N-(2-(5-(3-cyano-6-(2-hydroxy-2-methylpropoxy)pyrazolo[1,5-a]pyridin-4-yl)pyridin-2-yl)-5-methyl-octahydrocyclopenta[c]pyrrol-5-yl)-5-fluoro-2-methylbenzamide

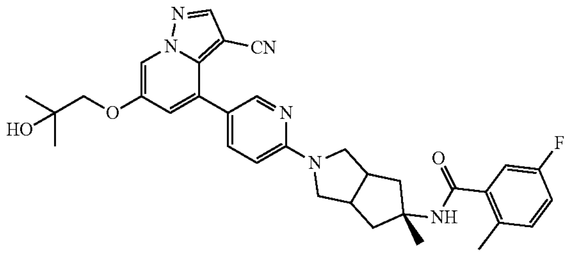

Step 1: N-(2-(5-bromopyridin-2-yl)-5-methyloctahydrocyclopenta[c]pyrrol-5-yl)-5-fluoro-2-methylbenzamide

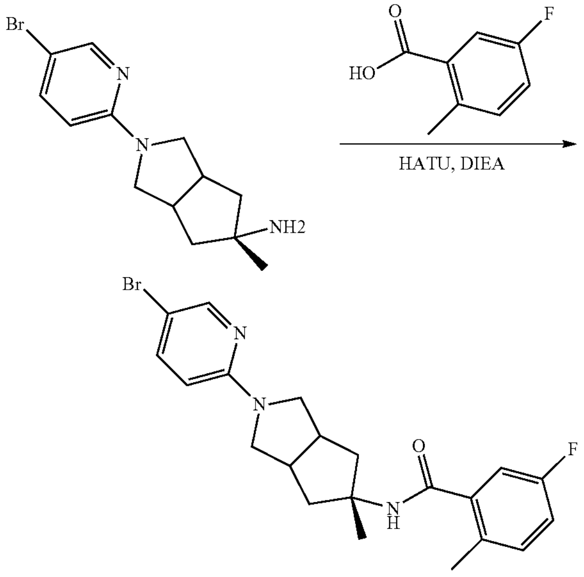

2-(5-Bromopyridin-2-yl)-5-methyloctahydrocyclopenta[c]pyrrol-5-amine (300 mg, 1.0 mmol), 5-fluoro-2-methylbenzoic acid (156 mg, 1.0 mmol), 2-(7-azabenzotriazol-1-yl)-N,N,N',N'-tetramethyluronium hexafluorophosphate (380 mg, 1.0 mmol), diisopropylethylamine (390 mg, 3 mmol), and dimethylformamide (5 mL) were added to a 25 mL three-necked flask sequentially. The reaction mixture was stirred at room temperature for 5 hours, then dissolved in ethyl acetate (10 mL) and washed with saturated saline (5 mL×3), and the organic phase was dried over anhydrous sodium sulfate, filtered and evaporated to dryness. The crude product was purified by column chromatography to obtain N-(2-(5-bromopyridin-2-yl)-5-methyloctahydrocyclopenta[c]pyrrol-5-yl)-5-fluoro-2-methylbenzamide (260 mg, yield: 59.3%).

MS m/z (ESI): 432.1[M+H]+.

Step 2: 5-fluoro-2-methyl-N-(5-methyl-2-(5-(4,4,5,5-tetramethyl-1,3,2-dioxaborolan-2-yl)pyridin-2-yl)octahydrocyclopenta[c]pyrrol-5-yl)benzamide

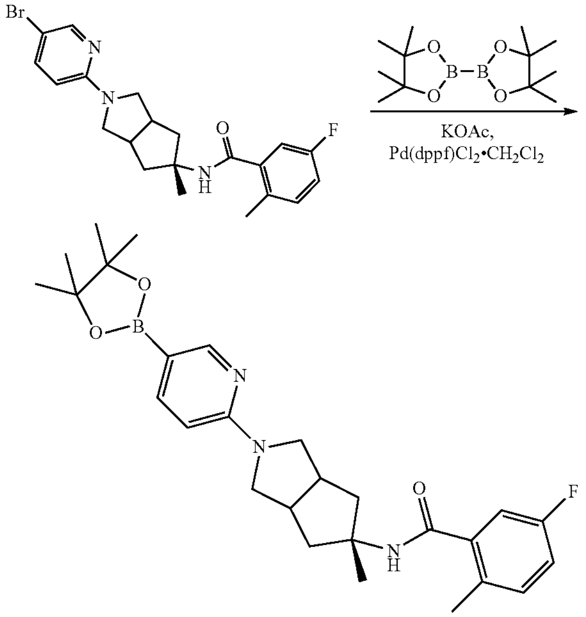

5-Fluoro-2-methyl-N-(5-methyl-2-(5-(4,4,5,5-tetramethyl-1,3,2-dioxaborolan-2-yl)pyridin-2-yl)octahydrocyclopenta[c]pyrrol-5-yl)benzamide was obtained by using N-(2-(5-bromopyridin-2-yl)-5-methyloctahydrocyclopenta[c]pyrrol-5-yl)-5-fluoro-2-methylbenzamide as raw material with reference to step 4 of embodiment 57.

MS m/z (ESI): 480.2 [M+H]+.

Step 3: N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)-5-fluoro-2-methylbenzamide

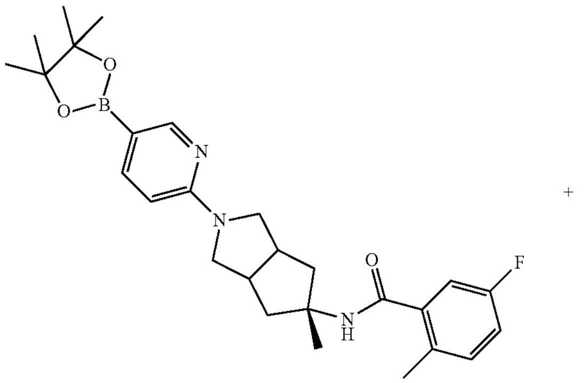

-continued

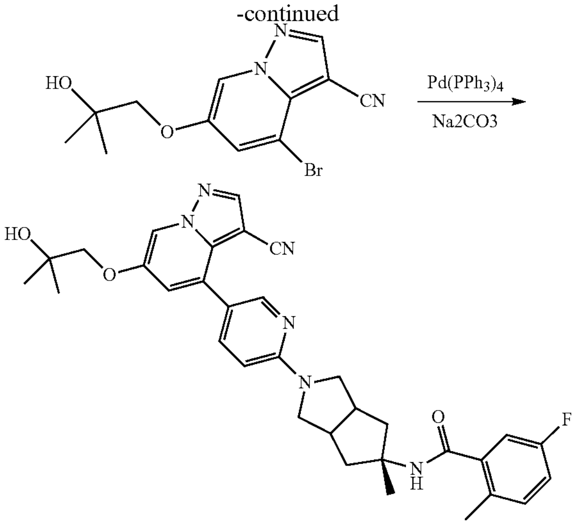

75

N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)-5-fluoro-2-methylbenzamide was obtained by using 5-fluoro-2-methyl-N-(5-methyl-2-(5-(4,4,5,5-tetramethyl-1,3,2-dioxaborolan-2-yl)pyridin-2-yl)octahydrocyclopenta[c]pyrrol-5-yl)benzamide as raw material with reference to step 3 of embodiment 7.

MS m/z (ESI): 583.2[M+H]$^+$.

Embodiment 76

2-Chloro-N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)benzamide

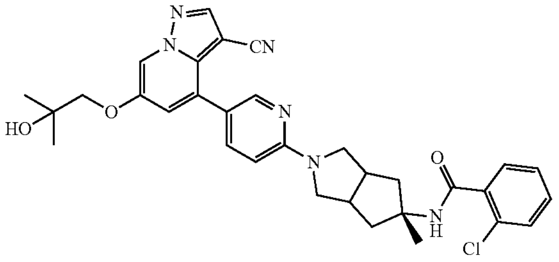

Step 1: N-(2-(5-bromopyridin-2-yl)-5-methyloctahydrocyclopenta[c]pyrrol-5-yl)-2-chlorobenzamide

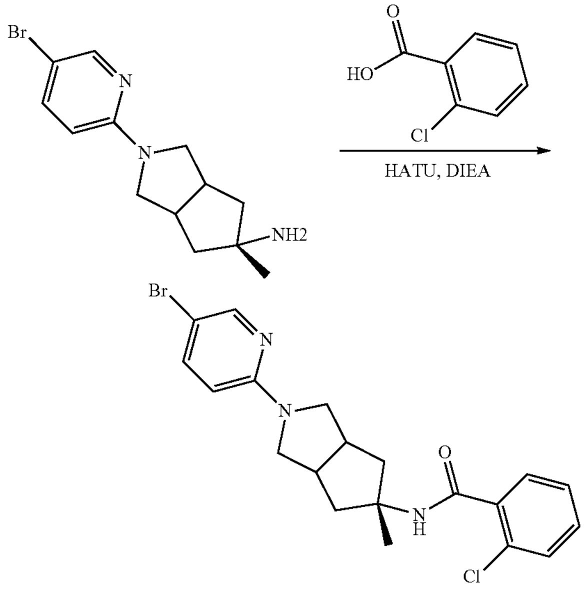

N-(2-(5-bromopyridin-2-yl)-5-methyloctahydrocyclopenta[c]pyrrol-5-yl)-2-chlorobenzamide was obtained by using 2-(5-bromopyridin-2-yl)-5-methyloctahydrocyclopenta[c]pyrrol-5-amine and 2-chlorobenzoic acid as raw materials with reference to step 1 of embodiment 75.

MS m/z (ESI): 434.0[M+H]$^+$.

Step 2: 2-chloro-N-(5-methyl-2-(5-(4,4,5,5-tetramethyl-1,3,2-dioxaborolan-2-yl)pyridin-2-yl octahydrocyclopenta[c]pyrrol-5-yl)benzamide

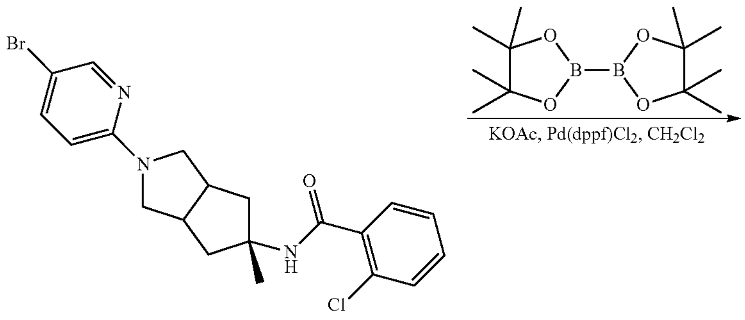

-continued

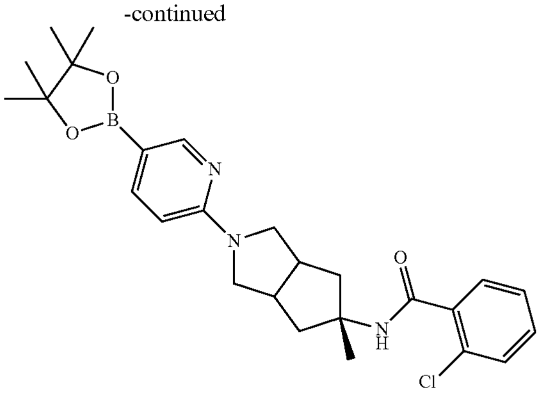

2-Chloro-N-(5-methyl-2-(5-(4,4,5,5-tetramethyl-1,3,2-dioxaborolan-2-yl)pyridin-2-yl)octahydrocyclopenta[c]pyrrol-5-yl)benzamide was obtained by using N-(2-(5-bromopyridin-2-yl)-5-methyloctahydrocyclopenta[c]pyrrol-5-yl)-2-chlorobenzamide as raw material with reference to step 4 of embodiment 57.

MS m/z (ESI): 482.2 $[M+H]^+$.

Step 3: 2-chloro-N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)benzamide

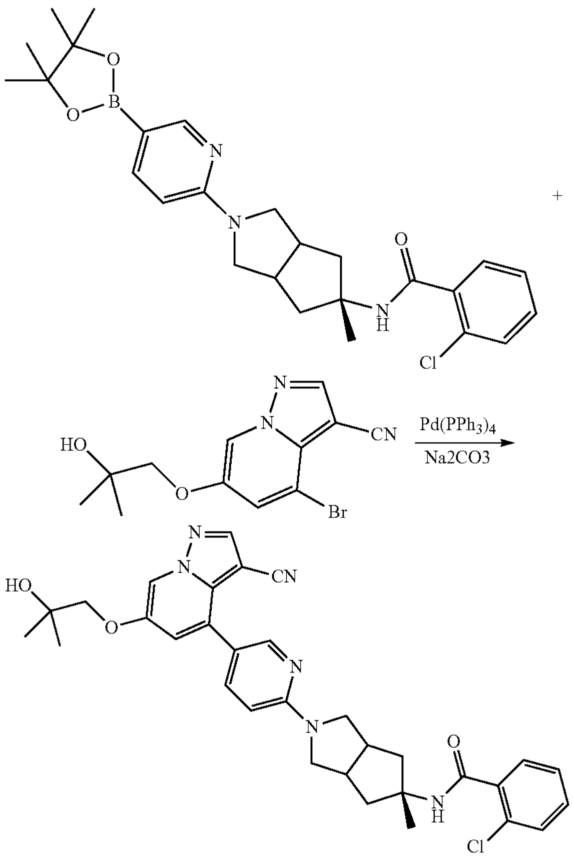

76

2-Chloro-N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)benzamide was obtained by using 2-chloro-N-(5-methyl-2-(5-(4,4,5,5-tetramethyl-1,3,2-dioxaborolan-2-yl)pyridin-2-yl)octahydrocyclopenta[c]pyrrol-5-yl)benzamide as raw material with reference to step 3 of embodiment 7.

MS m/z (ESI): 585.2$[M+H]^+$.

Embodiment 77

N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)-3-fluoro-6-methylpicolinamide

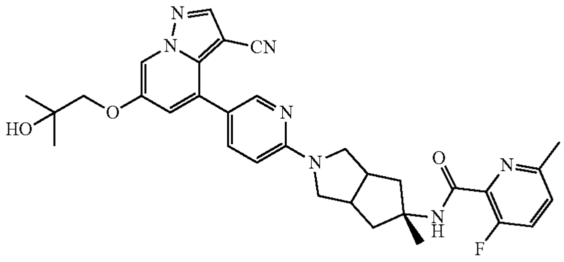

Step 1: N-(2-(5-bromopyridin-2-yl)-5-methyloctahydrocyclopenta[c]pyrrol-5-yl)-3-fluoro-6-methylpicolinamide

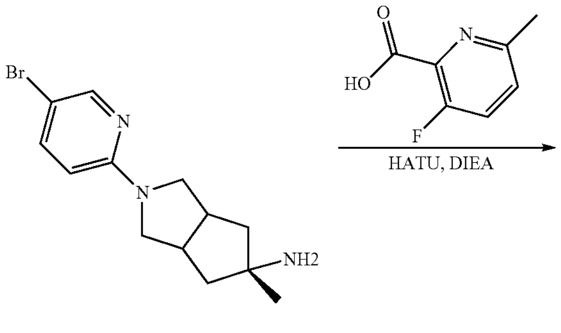

-continued

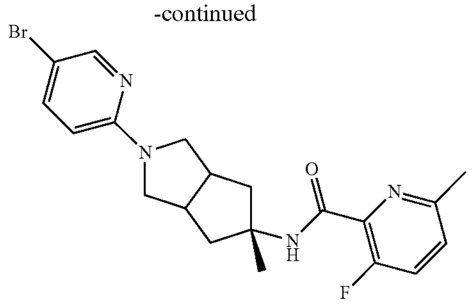

N-(2-(5-bromopyridin-2-yl)-5-methyloctahydrocyclopenta[c]pyrrol-5-yl)-3-fluoro-6-methylpicolinamide was obtained by using 2-(5-bromopyridin-2-yl)-5-methyloctahydrocyclopenta[c]pyrrol-5-amine and 3-fluoro-6-methylpicolinic acid as raw material with reference to step 1 of embodiment 75.

MS m/z (ESI): 433.0[M+H]$^+$.

Step 2: 3-fluoro-6-methyl-N-(5-methyl-2-(5-(4,4,5,5-tetramethyl-1,3,2-dioxaborolan-2-yl)pyridin-2-yl)octahydrocyclopenta[c]pyrrol-5-yl)picolinamide

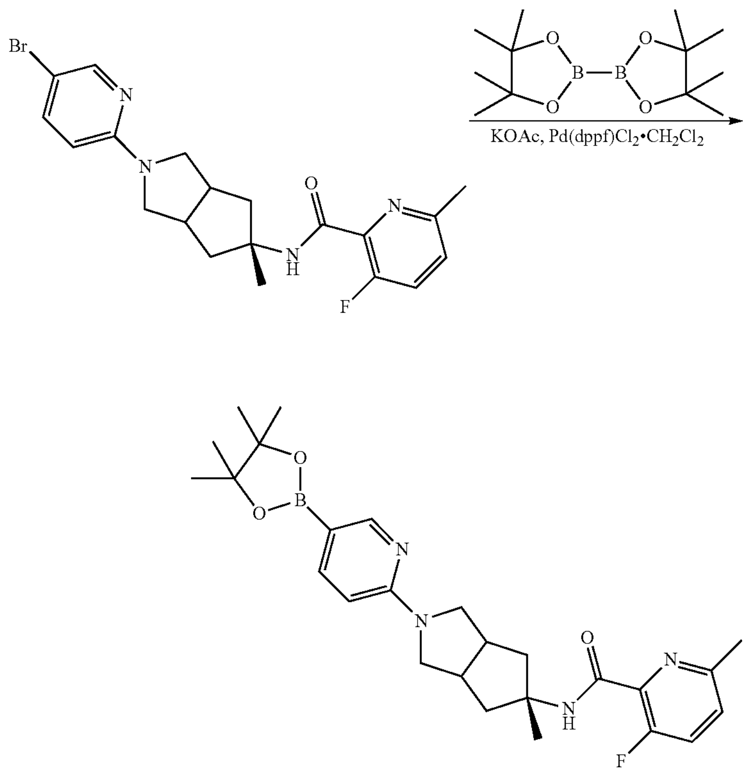

3-Fluoro-6-methyl-N-(5-methyl-2-(5-(4,4,5,5-tetramethyl-1,3,2-dioxaborolan-2-yl)pyridin-2-yl)octahydrocyclopenta[c]pyrrol-5-yl)picolinamide was obtained by using N-(2-(5-bromopyridin-2-yl)-5-methyloctahydrocyclopenta[c]pyrrol-5-yl)-3-fluoro-6-methylpicolinamide as raw material with reference to step 4 of embodiment 57.

MS m/z (ESI): 481.2 [M+H]$^+$.-

Step 3: N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)-3-fluoro-6-methylpicolinamide

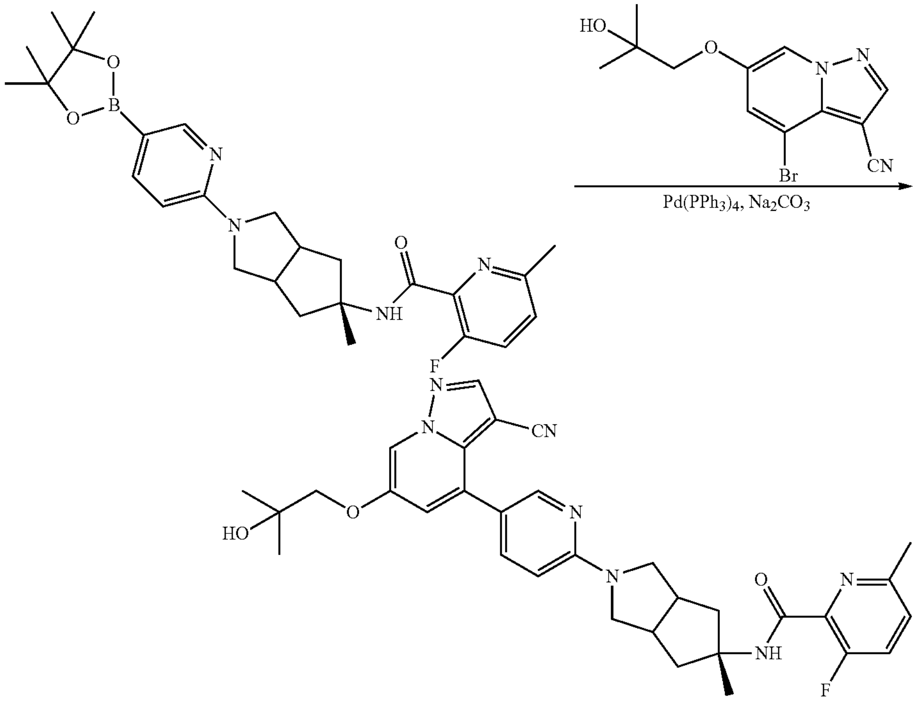

N-(2-(5-(3-cyano-6-(2-hydroxy-2-methylpropoxy)pyrazolo[1,5-a]pyridin-4-yl)pyridin-2-yl)-5-methyloctahydrocyclopenta[c]pyrrol-5-yl)-3-fluoro-6-methylpicolinamide was obtained by using 3-fluoro-6-methyl-N-(5-methyl-2-(5-(4,4,5,5-tetramethyl-1,3,2-dioxaborolan-2-yl)pyridin-2-yl)octahydrocyclopenta[c]pyrrol-5-yl)picolinamide as raw material with reference to step 3 of embodiment 7.

MS m/z (ESI): 584.2$[M+H]^+$.

Embodiment 78

6-(2-Hydroxy-2-methylpropoxy)-4-(6-((1R,5S)-3-((6-methoxypyridin-3-yl)oxo)-8-azabicyclo[3.2.1]octan-8-yl)pyridin-3-yl)pyrazolo[1,5-a]pyridine-3-carbonitrile

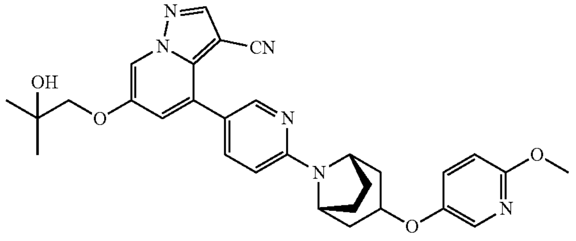

Step 1: tert-butyl (1R,5S)-3-((6-methoxypyridin-3-yl)oxo)-8-azabicyclo[3.2.1]octane-8-carboxylate

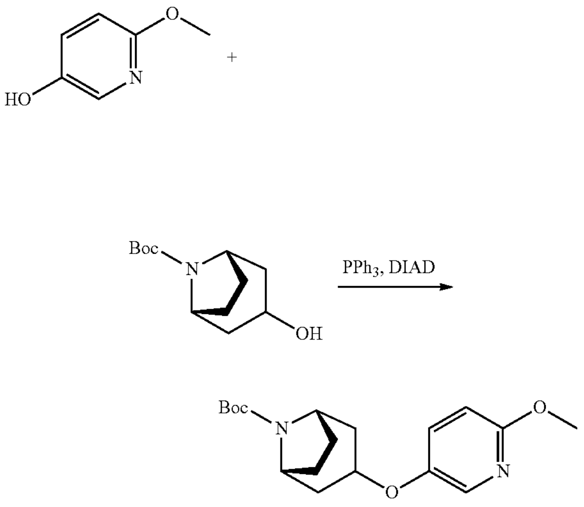

Tert-butyl (1R,5S)-3-((6-methoxypyridin-3-yl)oxo)-8-azabicyclo[3.2.1]octane-8-carboxylate was obtained by using 6-methoxypyridin-3-ol and tert-butyl (1R,5S)-3-hydroxy-8-azabicyclo[3.2.1]octane-8-carboxylate as raw materials with reference to step 1 of embodiment 34.

MS m/z (ESI): 335.1$[M+H]^+$.

Step 2: (1R,5S)-3-((6-methoxypyridin-3-yl)oxo)-8-azabicyclo[3.2.1]octane

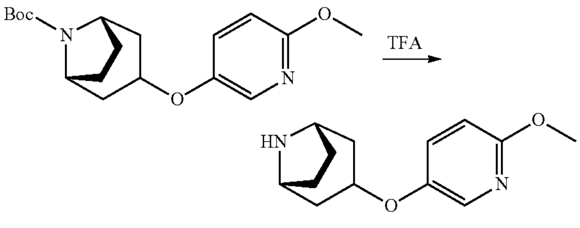

(1R,5S)-3-((6-methoxypyridin-3-yl)oxo)-8-azabicyclo[3.2.1]octane was obtained by using tert-butyl (1R,5S)-3-((6-methoxypyridin-3-yl)oxo)-8-azabicyclo[3.2.1]octane-8-carboxylate as raw material with reference to step 2 of embodiment 57.

MS m/z (ESI): 235.1[M+H]$^+$.

Step 3: 6-(2-hydroxy-2-methylpropoxy)-4-(6-((1R,5S)-3-((6-methoxypyridin-3-yl)oxo)-8-azabicyclo[3.2.1]octan-8-yl)pyridin-3-yl)pyrazolo[1,5-a]pyridine-3-carbonitrile

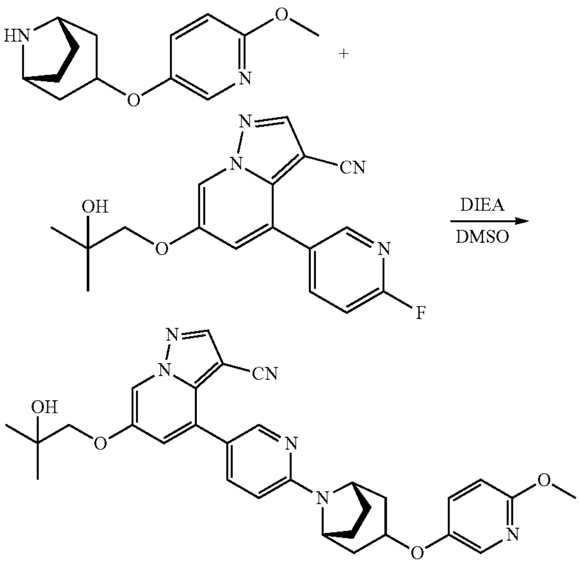

78

The product 6-(2-hydroxy-2-methylpropoxy)-4-(6-((1R,5S)-3-((6-methoxypyridin-3-yl)oxo)-8-azabicyclo[3.2.1]octan-8-yl)pyridin-3-yl)pyrazolo[1,5-a]pyridine-3-carbonitrile was obtained by using (1R,5S)-3-((6-methoxypyridin-3-yl)oxo)-8-azabicyclo[3.2.1]octane and 4-(6-fluoropyridin-3-yl)-6-(2-hydroxy-2-methylpropoxy)pyrazolo[1,5-a]pyridine-3-carbonitrile as raw materials with reference to step 2 of embodiment 8.

MS m/z (ESI): 541.2[M+H]$^+$.

Embodiment 79

4-(6-(1-((5-Fluoro-6-methoxypyridin-3-yl)methyl)-2,5-dihydro-1H-pyrrol-3-yl)pyridin-3-yl)-6-(2-hydroxyethoxy)pyrazolo[1,5-a]pyridine-3-carbonitrile

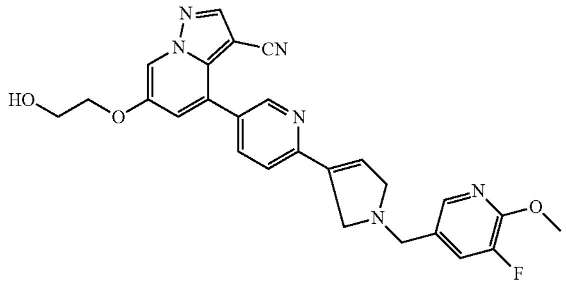 [SMILES: COc1ncc(CN2CC=C(c3ccc(-c4cc(OCCO)cn5ncc(C#N)c45)cn3)C2)cc1F]

Step 1: tert-butyl 3-hydroxy-3-(5-(4,4,5,5-tetramethyl-1,3,2-dioxaborolan-2-yl)pyridin-2-yl)pyrrolidine-1-carboxylate

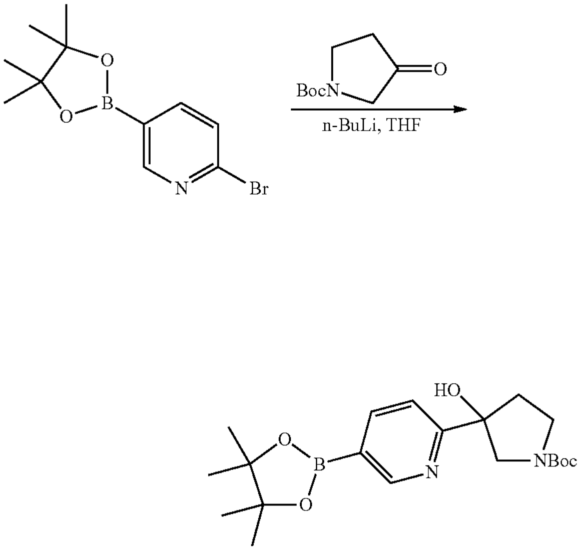

2-Bromo-5-(4,4,5,5-tetramethyl-1,3,2-dioxaborolan-2-yl)pyridine (500 mg, 1.7 mmol) was dissolved in 20 mL of THF, n-BuLi (1 mL, 2.6 mmol) was added thereto at −78° C., the mixture was stirred at −78° C. for half an hour; and tert-butyl 3-oxopyrrolidine-1-carboxylate was added thereto at −78° C., the mixture was stirred from −78° C. to room temperature for 2 hours, 10 mL of ammonium chloride aqueous solution was added, and the mixture was extracted with ethyl acetate (20 mL*3). The organic phase was washed with saturated saline, dried over anhydrous sodium sulfate. The residue was filtered, evaporated to dryness; and the crude product was separated by column chromatography (eluted with petroleum ether/ethyl acetate=2/1) to obtain tert-butyl 3-hydroxy-3-(5-(4,4,5,5-tetramethyl-1,3,2-dioxaborolan-2-yl)pyridin-2-yl)pyrrolidine-1-carboxylate (379 mg, white solid, yield was 57%).

MS m/z (ESI): 391.2 [M+H]$^+$.

Step 2: tert-butyl 3-(5-(4,4,5,5-tetramethyl-1,3,2-dioxaborolan-2-yl)pyridin-2-yl)-2,5-dihydro-1H-pyrrole-1-carboxylate

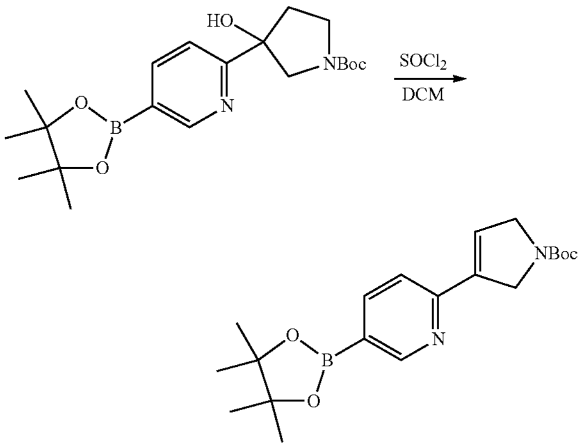

Tert-butyl 3-hydroxy-3-(5-(4,4,5,5-tetramethyl-1,3,2-dioxaborolan-2-yl)pyridin-2-yl)pyrrolidine-1-carboxylate (300 mg, 0.76 mmol) was dissolved in 20 mL of DCM, and $SOCl_2$ (1 mL) was added thereto at room temperature, and the mixture was stirred at room temperature for 2 hours, 10 mL of ammonium chloride aqueous solution was added thereto, and the mixture was extracted with ethyl acetate (20 mL*3). The organic phase was washed with saturated saline, dried over anhydrous sodium sulfate. The residue was filtered, evaporated to dryness; and the crude product was separated by column chromatography (eluted with petroleum ether/ethyl acetate=3/1) to obtain tert-butyl 3-(5-(4,4,5,5-tetramethyl-1,3,2-dioxaborolan-2-yl)pyridin-2-yl)-2,5-dihydro-1H-pyrrole-1-carboxylate (197 mg, white solid, yield was 70%).

MS m/z (ESI): 373.2 $[M+H]^+$.

Step 3: tert-butyl 3-(5-(3-cyano-6-(2-hydroxyethoxy)pyrazolo[1,5-a]pyridin-4-yl)pyridin-2-yl)-2,5-dihydro-1H-pyrrole-1-carboxylate

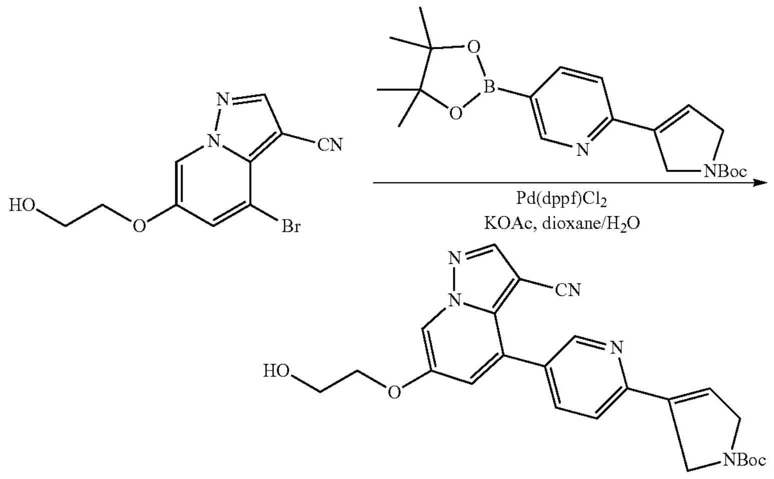

Tert-butyl 3-(5-(3-cyano-6-(2-hydroxyethoxy)pyrazolo[1,5-a]pyridin-4-yl)pyridin-2-yl)-2,5-dihydro-1H-pyrrole-1-carboxylate (180 mg, white solid, yield: 72%) was obtained by using 4-bromo-6-(2-hydroxyethoxy)pyrazolo[1,5-a]pyridine-3-carbonitrile and tert-butyl 3-(5-(4,4,5,5-tetramethyl-1,3,2-dioxaborolan-2-yl)pyridin-2-yl)-2,5-dihydro-1H-pyrrole-1-carboxylate as raw material with reference to step 8 of embodiment 1.

MS m/z (ESI): 448.1 $[M+H]^+$.

Step 4: 4-(6-(2,5-dihydro-1H-pyrrol-3-yl)pyridin-3-yl)-6-(2-hydroxyethoxy)pyrazolo[1,5-a]pyridine-3-carbonitrile

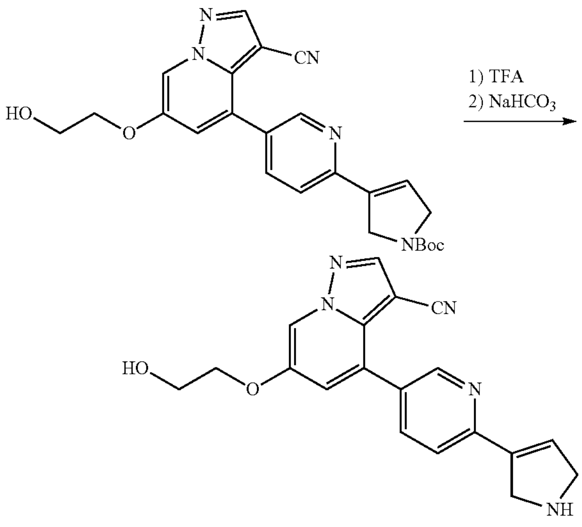

4-(6-(2,5-Dihydro-1H-pyrrol-3-yl)pyridin-3-yl)-6-(2-hydroxyethoxy)pyrazolo[1,5-a]pyridine-3-carbonitrile (120 mg, white solid, 99%) was obtained by using tert-butyl 3-(5-(3-cyano-6-(2-hydroxyethoxy)pyrazolo[1,5-a]pyridin-4-yl)pyridin-2-yl)-2,5-dihydro-1H-pyrrole-1-carboxylate as raw material with reference to the step 5 of embodiment 1.

MS m/z (ESI): 348.1 $[M+H]^+$.

Step 5: 4-(6-(1-((5-fluoro-6-methoxypyridin-3-yl)methyl)-2,5-dihydro-1H-pyrrol-3-yl)pyridin-3-yl)-6-(2-hydroxyethoxy)pyrazolo[1,5-a]pyridine-3-carbonitrile

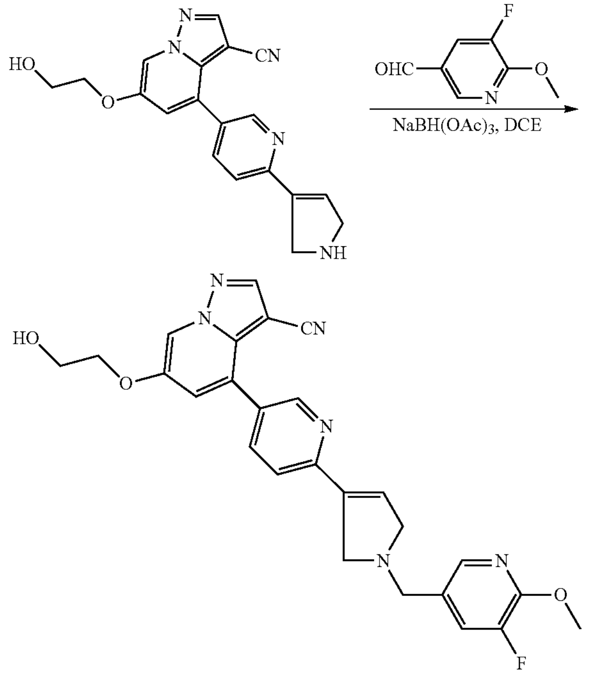

4-(6-(1-((5-Fluoro-6-methoxypyridin-3-yl)methyl)-2,5-dihydro-1H-pyrrol-3-yl)pyridin-3-yl)-6-(2-hydroxyethoxy)pyrazolo[1,5-a]pyridine-3-carbonitrile (34 mg, white solid, 62%) was obtained by using 4-(6-(2,5-dihydro-1H-pyrrol-3-yl)pyridin-3-yl)-6-(2-hydroxyethoxy)pyrazolo[1,5-a]pyridine-3-carbonitrile as raw material with reference to step 6 of embodiment 1.

MS m/z (ESI): 487.1 $[M+H]^+$.

Embodiment 80

6-(2-Hydroxy-2-methylpropoxy)-4-(6-(1-((6-methoxypyridin-3-yl)methyl)-2,5-dihydro-1H-pyrrol-3-yl)pyridin-3-yl)pyrazolo[1,5-a]pyridine-3-carbonitrile

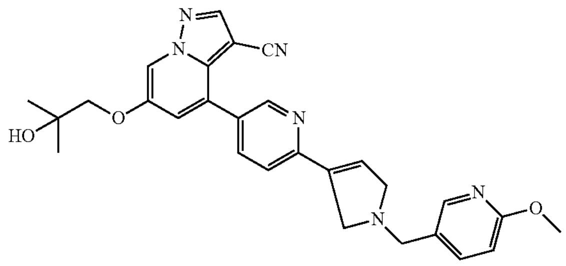 [SMILES: COc1ccc(CN2CC=C(c3ccc(-c4cc(OCC(C)(C)O)cn5ncc(C#N)c45)cn3)C2)cn1]

Step 1: tert-butyl 3-(5-(3-cyano-6-(2-hydroxy-2-methylpropoxy)pyrazolo[1,5-a]pyridin-4-yl)pyridin-2-yl)-2,5-dihydro-1H-pyrrole-1-carboxylate

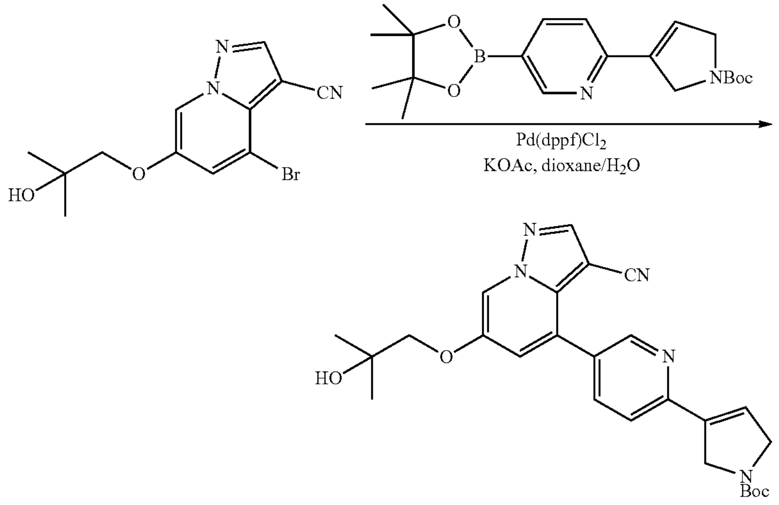

Tert-butyl 3-(5-(3-cyano-6-(2-hydroxy-2-methylpropoxy)pyrazolo[1,5-a]pyridin-4-yl)pyridin-2-yl)-2,5-dihydro-1H-pyrrole-1-carboxylate (165 mg, white solid, yield: 65%) was obtained by using 4-bromo-6-(2-hydroxy-2-methylpropoxy)pyrazolo[1,5-a]pyridine-3-carbonitrile and tert-butyl 3-(5-(4,4,5,5-tetramethyl-1,3,2-dioxaborolan-2-yl)pyridin-2-yl)-2,5-dihydro-1H-pyrrole-1-carboxylate as raw materials with reference to step 8 of embodiment 1.

MS m/z (ESI): 476.2 $[M+H]^+$.

Step 2: 4-(6-(2,5-dihydro-1H-pyrrol-3-yl)pyridin-3-yl)-6-(2-hydroxy-2-methylpropoxy)pyrazolo[1,5-a]pyridine-3-carbonitrile

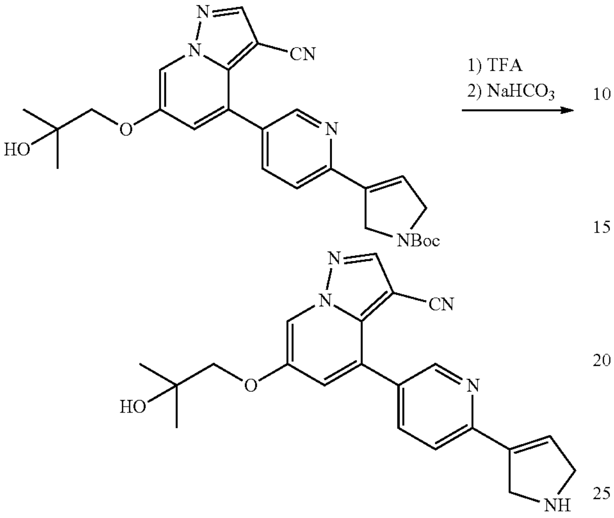

4-(6-(2,5-Dihydro-1H-pyrrol-3-yl)pyridin-3-yl)-6-(2-hydroxy-2-methylpropoxy)pyrazolo[1,5-a]pyridine-3-carbonitrile (82 mg, white solid, 67%) was obtained by using tert-butyl 3-(5-(3-cyano-6-(2-hydroxy-2-methylpropoxy)pyrazolo[1,5-a]pyridin-4-yl)pyridin-2-yl)-2,5-dihydro-1H-pyrrole-1-carboxylate as raw material with reference to the step 5 of embodiment 1.

MS m/z (ESI): 376.1 $[M+H]^+$.

Step 3: 6-(2-hydroxy-2-methylpropoxy)-4-(6-(1-((6-methoxypyridin-3-yl)methyl)-2,5-dihydro-1H-pyrrol-3-yl)pyridin-3-yl)pyrazolo[1,5-a]pyridine-3-carbonitrile

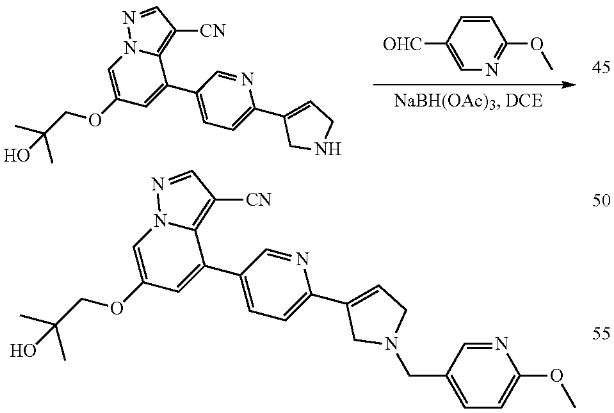

6-(2-Hydroxy-2-methylpropoxy)-4-(6-(1-((6-methoxypyridin-3-yl)methyl)-2,5-dihydro-1H-pyrrol-3-yl)pyridin-3-yl)pyrazolo[1,5-a]pyridine-3-carbonitrile (23 mg, white solid, 42%) was obtained by using 4-(6-(2,5-dihydro-1H-pyrrol-3-yl)pyridin-3-yl)-6-(2-hydroxy-2-methylpropoxy)pyrazolo[1,5-a]pyridine-3-carbonitrile as raw material with reference to step 6 of embodiment 1.

MS m/z (ESI): 497.2 $[M+H]^+$.

Embodiment 81

6-(3-Hydroxy-3-methylbutyl)-4-(6-(6-((6-methoxypyridin-3-yl)methyl)-3,6-diazabicyclo[3.1.1]heptan-3-yl)pyridin-3-yl)-7-carbonyl-6,7-dihydropyrazolo[1,5a]pyrimidine-3-carbonitrile

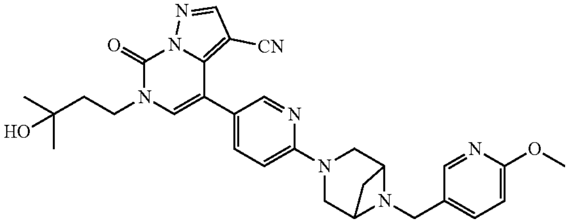 [SMILES: COc1ccc(CN2C3CC2CN(c2ccc(-c4cn(CCC(C)(C)O)c(=O)n5ncc(C#N)c45)cn2)C3)cn1]

MS m/z (ESI): 541.2 $[M+H]^+$.

Embodiment 82

4-(6-(6-((6-Methoxypyridin-3-yl)methyl)-3,6-diazabicyclo[3.1.1]heptan-3-yl)pyridin-3-yl)-6-(2-(methylsulfonyl)ethyl)pyrazolo[1,5-a]pyridine-3-carbonitrile

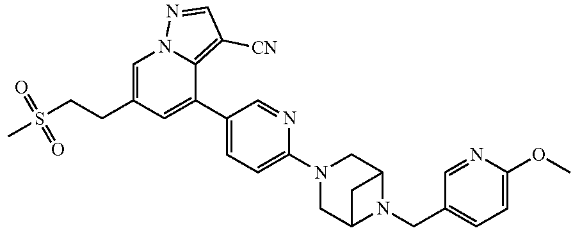

Step 1: 3-bromo-5-(2-(methylsulfonyl)ethyl)pyridine

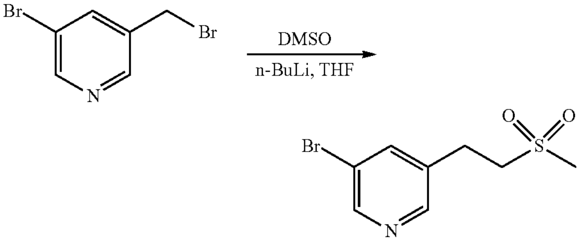

DMSO (780 mg, 10 mmol) was dissolved in 10 mL of THF, n-BuLi (4 mL, 10 mmol) was added thereto at −78° C., and the mixture was stirred at −78° C. for 0.5 hours; 3-bromo-5-(bromomethyl)pyridine (500 mg, 2 mmol) was added at −78° C., then the mixture was slowly warmed up to room temperature and stirred for 2 hours, 10 mL of ammonium chloride aqueous solution was added, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 3-bromo-5-(2-(methylsulfonyl)ethyl)pyridine (252 mg, the yield was 48%).

MS m/z (ESI): 263.9 $[M+H]^+$.

Step 2: 4-bromo-6-(2-(methylsulfonyl)ethyl)pyrazolo[1,5-a]pyridine-3-carbonitrile

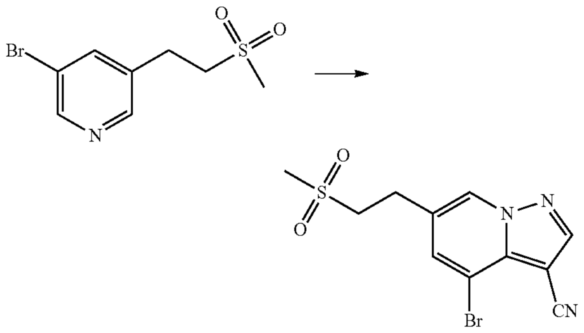

4-Bromo-6-(2-(methylsulfonyl)ethyl)pyrazolo[1,5-a]pyridine-3-carbonitrile (350 mg, white solid) was obtained by using 3-bromo-5-(2-(methylsulfonyl)ethyl)pyridine as raw material with reference to the embodiment 11.

MS m/z (ESI): 327.9 $[M+H]^+$.

Step 3: 6-(2-(methylsulfonyl)ethyl)-4-(4,4,5,5-tetramethyl-1,3,2-dioxaborolan-2-yl)pyrazolo[1,5-a]pyridine-3-carbonitrile

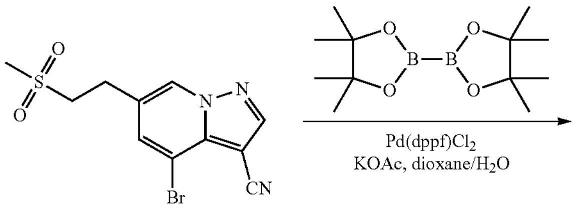

-continued

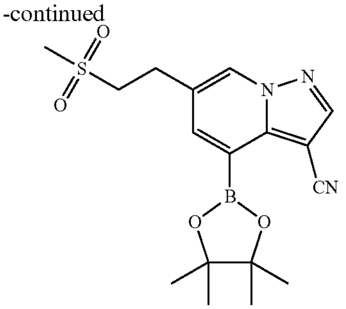

6-(2-(Methylsulfonyl)ethyl)-4-(4,4,5,5-tetramethyl-1,3,2-dioxaborolan-2-yl)pyrazolo[1,5-a]pyridine-3-carbonitrile (230 mg, white solid, 68%) was obtained by using 4-bromo-6-(2-(methylsulfonyl)ethyl)pyrazolo[1,5-a]pyridine-3-carbonitrile as raw material with reference to step 7 of embodiment 1.

MS m/z (ESI): 376.1 $[M+H]^+$.

Step 4: 4-(6-(6-((6-methoxypyridin-3-yl)methyl)-3,6-diazabicyclo[3.1.1]heptan-3-yl)pyridin-3-yl)-6-(2-(methylsulfonyl)ethyl)pyrazolo[1,5-a]pyridine-3-carbonitrile

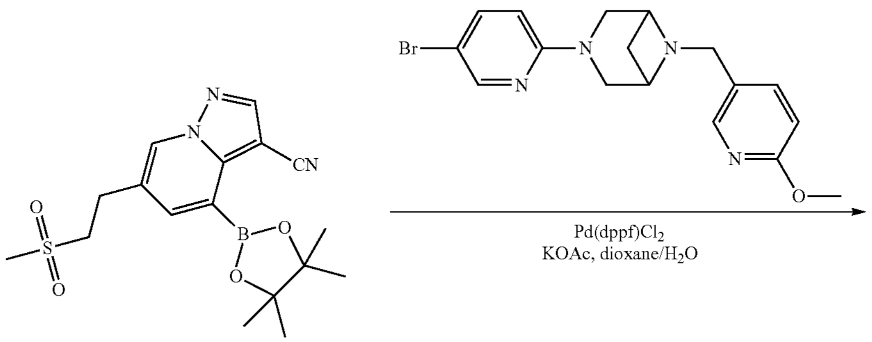

-continued

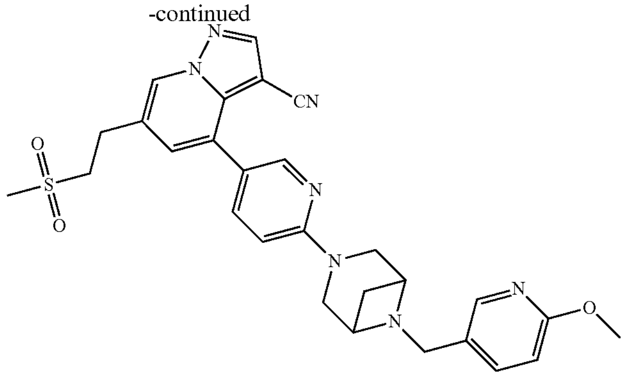

4-(6-(6-((6-Methoxypyridin-3-yl)methyl)-3,6-diazabicyclo[3.1.1]heptan-3-yl)pyridin-3-yl)-6-(2-(methylsulfonyl)ethyl)pyrazolo[1,5-a]pyridine-3-carbonitrile (30 mg, white solid, 48%) was obtained by using 6-(2-(methylsulfonyl)ethyl)-4-(4,4,5,5-tetramethyl-1,3,2-dioxaborolan-2-yl)pyrazolo[1,5-a]pyridine-3-carbonitrile as raw materials with reference to step 8 of embodiment 1.

MS m/z (ESI): 544.2 [M+H]+.

Embodiment 83

6-(3-Hydroxy-3-methylbutyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

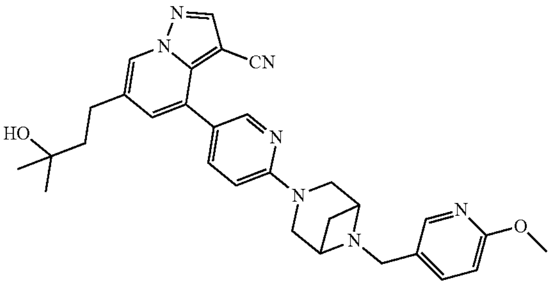 [SMILES: COc1ccc(CN2C3CC2CN(c2ccc(-c4cc(CCC(C)(C)O)cn5ncc(C#N)c45)cn2)C3)cn1]

The product 6-(3-hydroxy-3-methylbutyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (30 mg, white solid) was obtained with reference to embodiment 82.

MS m/z (ESI): 524.2 [M+H]+.

Embodiment 84

6-(3-Hydroxy-3-methylbutyl)-4-(6-(4-(pyridin-2-oxy)piperidin-1-yl)pyridin-3-yl)pyrazolo[1,5-a]pyridine-3-carbonitrile

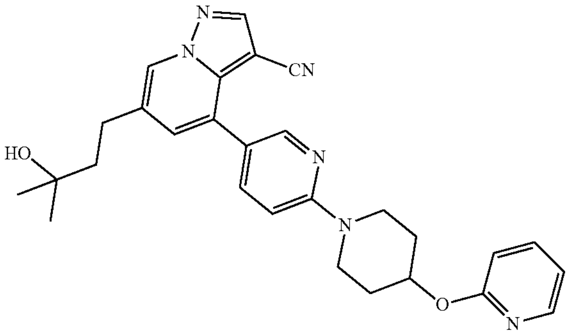 [SMILES: CC(C)(O)CCc1cc(-c2ccc(N3CCC(Oc4ccccn4)CC3)nc2)c2c(C#N)cnn2c1]

6-(3-Hydroxy-3-methylbutyl)-4-(6-(4-(pyridin-2-oxy)piperidin-1-yl)pyridin-3-yl)pyrazolo[1,5-a]pyridine-3-carbonitrile (38 mg, white solid) was obtained with reference to embodiment 82.

MS m/z (ESI): 483.2 [M+H]+.

Embodiment 85

6-((1-Imino-1-hydroxy-l16-thietan-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

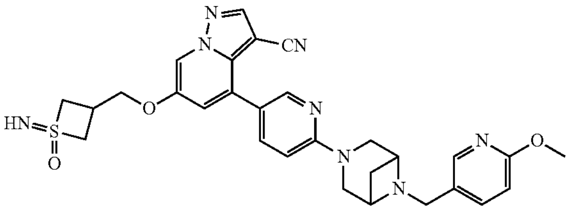 [SMILES: COc1ccc(CN2C3CC2CN(c2ccc(-c4cc(OCC5CS(=N)(=O)C5)cn5ncc(C#N)c45)cn2)C3)cn1]

Step 1: thietan-3-ylmethanol

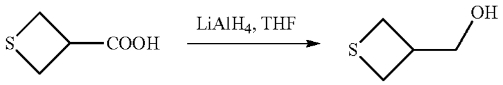

Thietane-3-carboxylic acid (500 mg, 4.2 mmol) was dissolved in 10 mL of THF, $LiAlH_4$(8.4 mL, 8.4 mmol) was added thereto at −78° C.; and the mixture was stirred at −78° C. for 2 hours, the temperature was slowly raised to room temperature and the mixture was stirred for 2 hours, then 10 mL of ammonium chloride aqueous solution was added, and the mixture was extracted with ethyl acetate (20 mL*3). The organic phase was washed with saturated saline and dried over anhydrous sodium sulfate. The residue was filtered and evaporated to dryness to obtain crude product thietan-3-ylmethanol (314 mg, the yield was 72%).

Step 2: 4-bromo-6-(thietan-3-ylmethoxy)pyrazolo[1,5-a]pyridine-3-carbonitrile

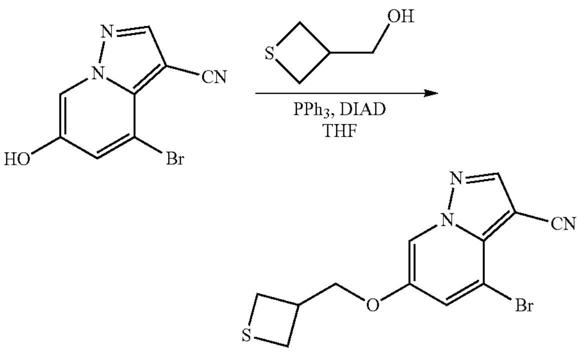

4-Bromo-6-(thietan-3-ylmethoxy)pyrazolo[1,5-a]pyridine-3-carbonitrile (210 mg, white solid, 67%) was obtained by using 4-bromo-6-hydroxypyrazolo[1,5-a]pyridine-3-carbonitrile and thietan-3-ylmethanol as raw materials with reference to step 2 of embodiment 1.

MS m/z (ESI): 323.9 $[M+H]^+$.

Step 3: 4-bromo-6-((1-hydroxythietan-3-yl)methoxy)pyrazolo[1,5-a]pyridine-3-carbonitrile

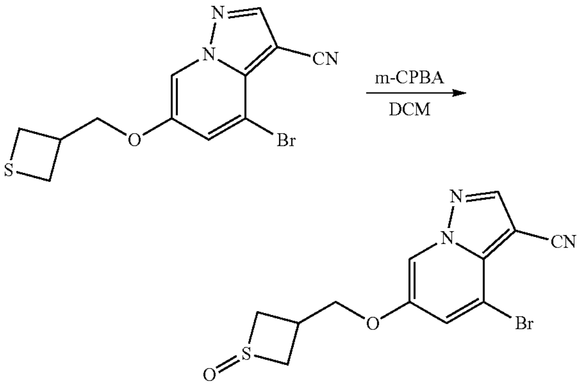

4-Bromo-6-((1-hydroxythietan-3-yl)methoxy)pyrazolo[1,5-a]pyridine-3-carbonitrile (180 mg, white solid, 85%) was obtained by using 4-bromo-6-(thietan-3-ylmethoxy)pyrazolo[1,5-a]pyridine-3-carbonitrile as raw material with reference to step 3 of embodiment 1.

MS m/z (ESI): 339.9 $[M+H]^+$.

Step 4: 4-bromo-6-((1-imino-1-hydroxy-l16-thietan-3-yl)methoxy)pyrazolo[1,5-a]pyridine-3-carbonitrile

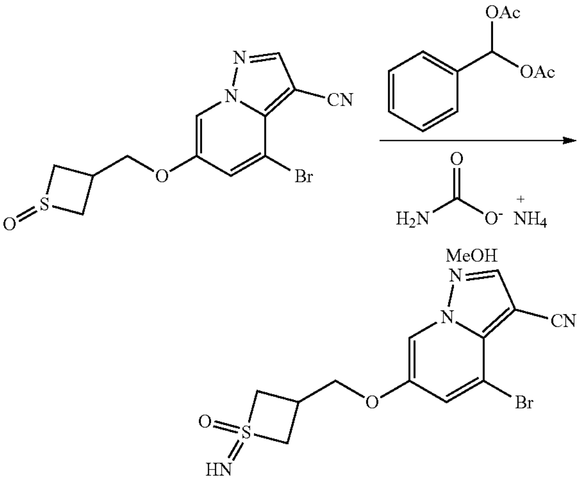

4-Bromo-6-((1-imino-1-hydroxy-l16-thietan-3-yl)methoxy)pyrazolo[1,5-a]pyridine-3-carbonitrile (150 mg, white solid, 79%) was obtained by using 4-bromo-6-((1-hydroxythietan-3-yl)methoxy)pyrazolo[1,5-a]pyridine-3-carbonitrile as raw material with reference to embodiment 3.

MS m/z (ESI): 354.9 $[M+H]^+$.

Step 5: 6-((1-imino-1-hydroxy-l16-thietan-3-yl)methoxy)-4-(4,4,5,5-tetramethyl-1,3,2-dioxaborolan-2-yl)pyrazolo[1,5-a]pyridine-3-carbonitrile

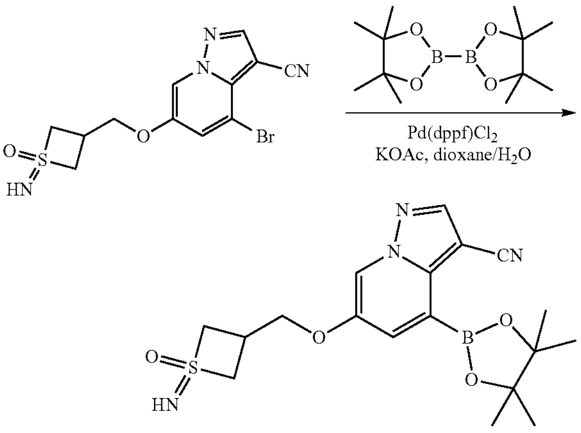

6-((1-Imino-1-hydroxy-l16-thietan-3-yl)methoxy)-4-(4,4,5,5-tetramethyl-1,3,2-dioxaborolan-2-yl)pyrazolo[1,5-a]pyridine-3-carbonitrile (96 mg, white solid, 64%) was obtained by using 4-bromo-6-((1-imino-1-hydroxy-l16-thietan-3-yl)methoxy)pyrazolo[1,5-a]pyridine-3-carbonitrile as raw material with reference to step 7 of embodiment 1.

MS m/z (ESI): 403.1 $[M+H]^+$.

Step 6: 6-((1-imino-1-hydroxy-l16-thietan-3-yl) methoxy)-4-(6-(6-((6-methoxypyridin-3-yl)methyl)-3,6-diazabicyclo[3.1.1]heptan-3-yl)pyridin-3-yl) pyrazolo[1,5-a]pyridine-3-carbonitrile

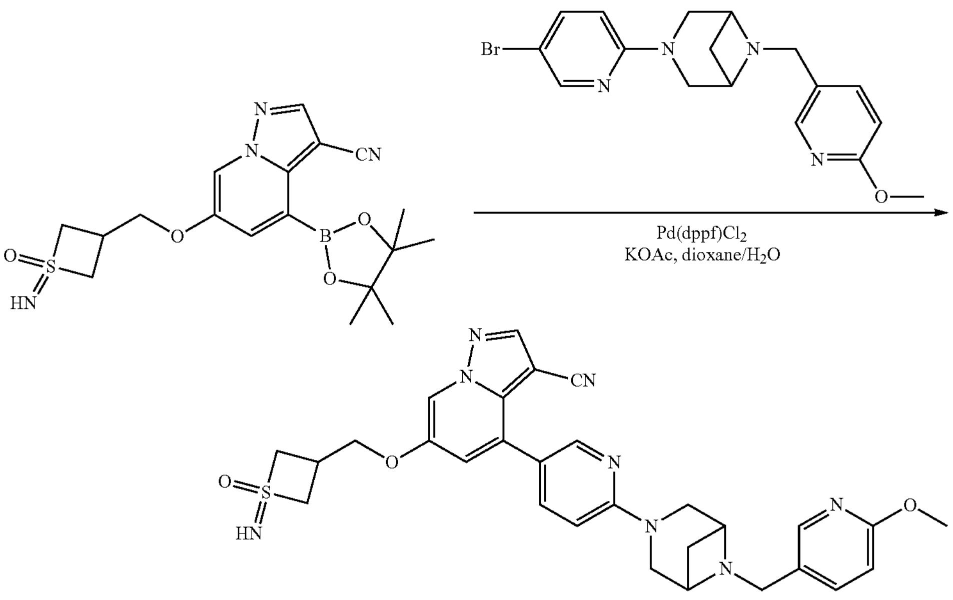

6-((1-Imino-1-hydroxy-l16-thietan-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (30 mg, white solid, 34%) was obtained by using 6-((1-imino-1-hydroxy-l16-thietan-3-yl)methoxy)-4-(4,4,5,5-tetramethyl-1,3,2-dioxaborolan-2-yl)pyrazolo[1,5-a]pyridine-3-carbonitrile as raw materials with reference to step 8 of embodiment 1.

MS m/z (ESI): 571.2 $[M+H]^+$.

$^1$H NMR (400 MHz, MeOD) δ 8.53 (s, 1H), 8.38 (s, 1H), 8.36 (s, 1H), 8.19 (s, 1H), 7.87 (d, J=8.8 Hz, 1H), 7.77 (d, J=8.7 Hz, 1H), 7.32 (s, 1H), 6.90 (d, J=8.7 Hz, 1H), 6.83 (d, J=8.7 Hz, 1H), 4.43-4.22 (m, 4H), 4.21-4.05 (m, 4H), 4.06-3.94 (m, 5H), 3.91 (s, 3H), 3.67-3.59 (m, 1H), 3.22-3.11 (m, 1H), 2.25-1.88 (m, 2H).

Embodiment 86

6-((1-Imino-1-hydroxy-l16-thietan-3-yl)methoxy)-4-(6-(4-((6-methoxypyridin-3-yl)oxo)piperidin-1-yl) pyridin-3-yl)pyrazolo[1,5-a]pyridine-3-carbonitrile

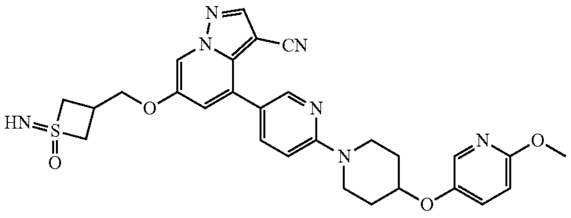 [SMILES: COc1ccc(OC2CCN(c3ccc(-c4cc(OCC5CS(=N)(=O)C5)cn5ncc(C#N)c45)cn3)CC2)cn1]

6-((1-Imino-1-hydroxy-l16-thietan-3-yl)methoxy)-4-(6-(4-((6-methoxypyridin-3-yl)oxo)piperidin-1-yl)pyridin-3-yl)pyrazolo[1,5-a]pyridine-3-carbonitrile (34 mg, white solid, 36%) was obtained by using 6-((1-imino-1-hydroxy-l16-thietan-3-yl)methoxy)-4-(4,4,5,5-tetramethyl-1,3,2-dioxaborolan-2-yl)pyrazolo[1,5-a]pyridine-3-carbonitrile as raw material with reference to step 8 of embodiment 1.

MS m/z (ESI): 560.2 $[M+H]^+$.

Embodiment 87

6-(2-(1-Imino-1-hydroxyl-l16-thietan-3-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

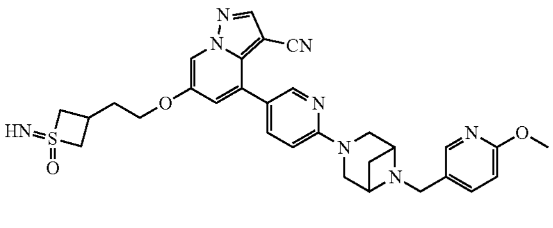 [SMILES: COc1ccc(CN2C3CC2CN(c2ccc(-c4cc(OCCC5CS(=N)(=O)C5)cn5ncc(C#N)c45)cn2)C3)cn1]

6-(2-(1-Imino-1-hydroxyl-l16-thietan-3-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (35 mg, white solid) was obtained by using 2-(thietan-3-yl)ethan-1-ol as raw material with reference to embodiment 85.

MS m/z (ESI): 585.2 $[M+H]^+$.

Embodiment 88

4-(6-(6-((6-Methoxypyridin-3-yl)methyl)-3,6-diazabicyclo[3.1.1]heptan-3-yl)pyridin-3-yl)-6-(2-(1-hydroxyltetrahydro-2H-thiopyran-4-yl)ethoxy)pyrazolo[1,5-a]pyridine-3-carbonitrile

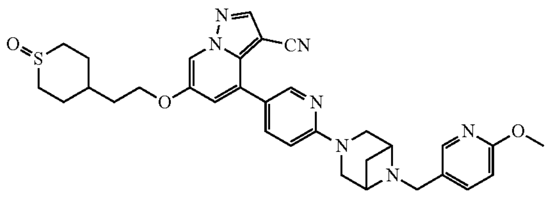 [SMILES: COc1ccc(CN2C3CC2CN(c2ccc(-c4cc(OCCC5CCS(=O)CC5)cn5ncc(C#N)c45)cn2)C3)cn1]

4-(6-(6-((6-Methoxypyridin-3-yl)methyl)-3,6-diazabicyclo[3.1.1]heptan-3-yl)pyridin-3-yl)-6-(2-(1-hydroxyltetrahydro-2H-thiopyran-4-yl)ethoxy)pyrazolo[1,5-a]pyridine-3-carbonitrile (29 mg, white solid) was obtained by using 2-(tetrahydro-2H-thiopyran-4-yl)ethan-1-ol as raw materials with reference to embodiment 85.

MS m/z (ESI): 598.2 $[M+H]^+$.

Embodiment 89

6-(2-(1-Imino-1-hydroxyhexahydro-l16-thiopyran-4-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

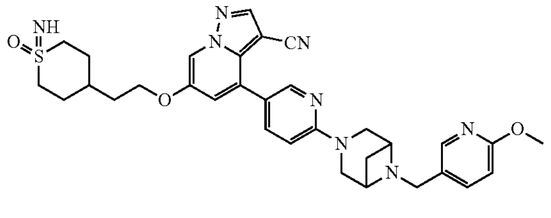 [SMILES: COc1ccc(CN2C3CC2CN(c2ccc(-c4cc(OCCC5CCS(=N)(=O)CC5)cn5ncc(C#N)c45)cn2)C3)cn1]

6-(2-(1-Imino-1-hydroxyhexahydro-l16-thiopyran-4-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (18 mg, white solid) was obtained by using 4-(6-(6-((6-methoxypyridin-3-yl)methyl)-3,6-diazabicyclo[3.1.1]heptan-3-yl)pyridin-3-yl)-6-(2-(1-hydroxytetrahydro-2H-thiopyran-4-yl)ethoxy)pyrazolo[1,5-a]pyridine-3-carbonitrile as raw material with reference to embodiment 3.

MS m/z (ESI): 613.2 $[M+H]^+$.

Embodiment 90

6-((1-Imino-1-hydroxyhexahydro-l16-thiopyran-4-yl)oxo)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

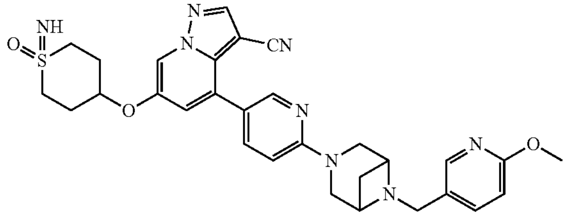 [SMILES: COc1ccc(CN2C3CC2CN(c2ccc(-c4cc(OC5CCS(=N)(=O)CC5)cn5ncc(C#N)c45)cn2)C3)cn1]

Step 1: 4-bromo-6-((tetrahydro-2H-thiopyran-4-yl)oxo)pyrazolo[1,5-a]pyridine-3-carbonitrile

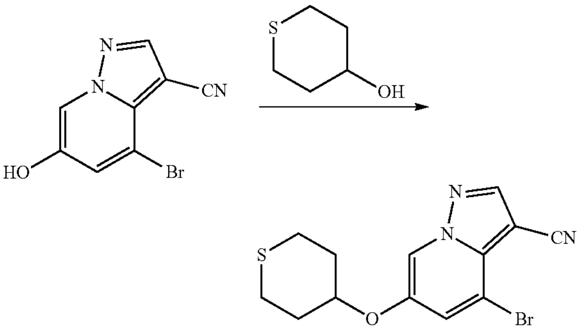

4-Bromo-6-hydroxypyrazolo[1,5-a]pyridine-3-carbonitrile (10 g, 42.0 mmol) was dissolved in tetrahydrofuran (100 mL), and tetrahydro-2H-thiopyran-4-ol (6 g, 50.4 mmol) and triphenylphosphine (22 g, 84.0 mmol) were added thereto. DEAD (14.6 g, 84.0 mmol) was slowly added dropwise to the reaction mixture. The reaction was stirred at room temperature overnight. Water was added to quench the reaction, and then the mixture was extracted with ethyl acetate. The organic phase was dried and evaporated to dryness. The crude product was purified by column chromatography to obtain 4-bromo-6-((tetrahydro-2H-thiopyran-4-yl)oxo)pyrazolo[1,5-a]pyridine-3-carbonitrile (7 g, yield: 49%).

MS m/z (ESI): 337.9$[M+H]^+$.

Step 2: Preparation of 4-bromo-6-((1-imino-1-hydroxyhexahydro-l16-thiopyran-4-yl)oxo)pyrazolo[1,5-a]pyridine-3-carbonitrile

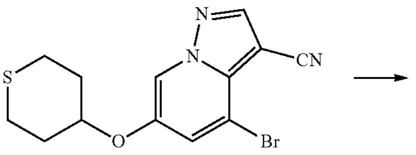

-continued

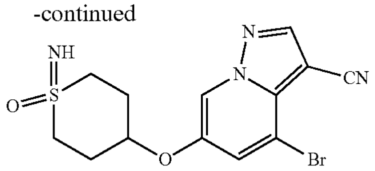

4-Bromo-6-((tetrahydro-2H-thiopyran-4-yl)oxo)pyrazolo[1,5-a]pyridine-3-carbonitrile (3 g, 8.9 mmol) was dissolved in methanol (40 mL), and ammonium carbonate (1.6 g, 16.9 mmol) and (diacetoxyiodo)benzene (5.7 g, 17.8 mmol) were added thereto. The reaction was stirred at room temperature overnight. The reaction mixture was evaporated to dryness. The crude product was purified by column chromatography to obtain 4-bromo-6-((1-imino-1-hydroxyhexahydro-l16-thiopyran-4-yl)oxo)pyrazolo[1,5-a]pyridine-3-carbonitrile (350 mg, yield: 11%).

MS m/z (ESI): 368.9[M+H]$^+$.

Step 3: Preparation of 6-((1-imino-1-hydroxyhexahydro-l16-thiopyran-4-yl)oxo)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

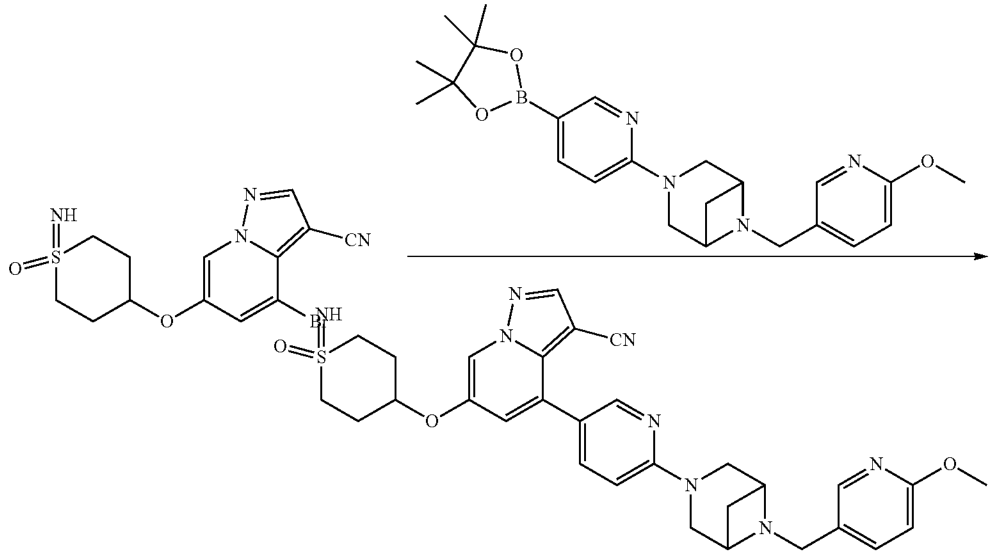

6-((1-Imino-1-hydroxyhexahydro-l16-thiopyran-4-yl)oxo)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (35 mg, yield: 36%) was obtained by using 4-bromo-6-((1-imino-1-hydroxyhexahydro-l16-thiopyran-4-yl)oxo)pyrazolo[1,5-a]pyridine-3-carbonitrile and 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane as raw materials with reference to step 3 of embodiment 37.

MS m/z (ESI): 585.2[M+H]$^+$.

$^1$H NMR (400 MHz, DMSO-d6) δ 8.89 (dd, J=7.6, 2.0 Hz, 1H), 8.62 (s, 1H), 8.42 (t, J=2.4 Hz, 1H), 8.07 (s, 1H), 7.85 (d, J=8.6 Hz, 1H), 7.72-7.60 (m, 1H), 7.51-7.40 (m, 1H), 6.78 (t, J=9.4 Hz, 2H), 4.90-4.78 (m, 1H), 3.82 (s, 3H), 3.79-3.61 (m, 4H), 3.60-3.45 (m, 4H), 3.27-3.13 (m, 2H), 3.13-2.98 (m, 2H), 2.65-2.53 (m, 1H), 2.31-2.14 (m, 3H), 2.13-1.92 (m, 1H), 1.59 (d, J=8.4 Hz, 1H), 0.84-0.69 (m, 1H).

Embodiment 91

6-((1-Imino-1-hydroxylhexahydro-l16-thiopyran-4-yl)oxo)-4-(6-(4-(pyridin-2-oxy)piperidin-1-yl)pyridin-3-yl)pyrazolo[1,5-a]pyridine-3-carbonitrile

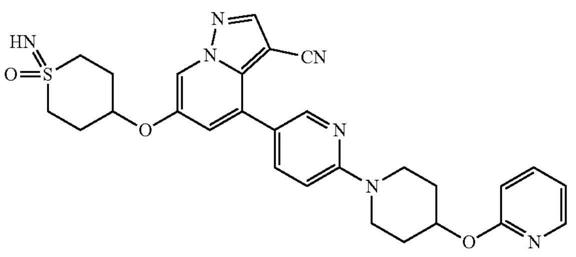 [SMILES: N#Cc1cnn2cc(OC3CCS(=N)(=O)CC3)cc(-c3ccc(N4CCC(Oc5ccccn5)CC4)nc3)c12]

Step 1: Preparation of 6-((1-imino-1-hydroxylhexahydro-l16-thiopyran-4-yl)oxo)-4-(6-(4-(pyridin-2-oxy)piperidin-1-yl)pyridin-3-yl)pyrazolo[1,5-a]pyridine-3-carbonitrile

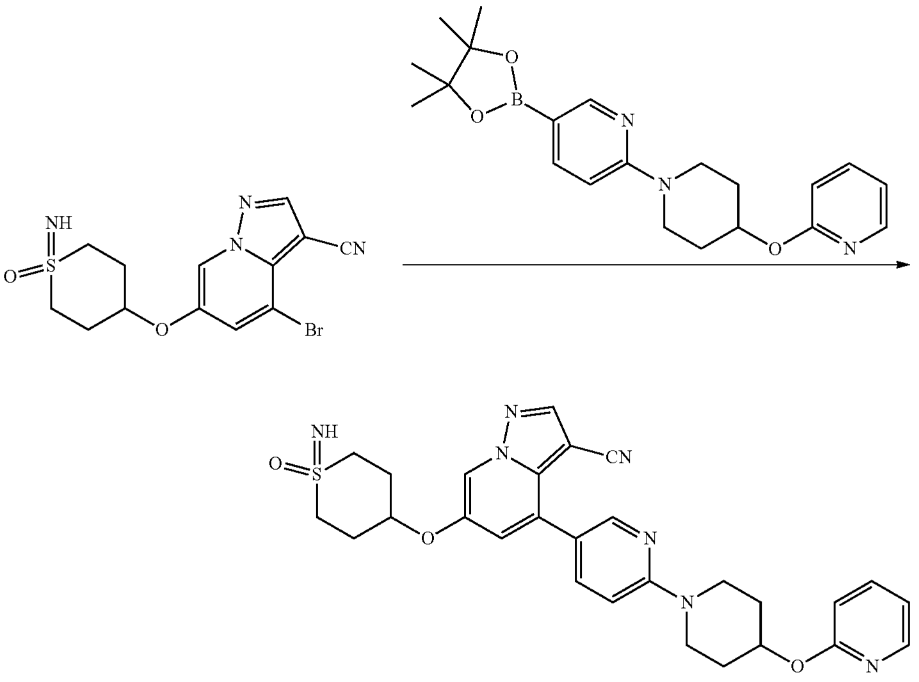

6-((1-Imino-1-hydroxylhexahydro-l16-thiopyran-4-yl) oxo)-4-(6-(4-(pyridin-2-oxy)piperidin-1-yl)pyridin-3-yl) pyrazolo[1,5-a]pyridine-3-carbonitrile (45 mg, yield: 38%) was obtained by using 4-bromo-6-((1-imino-1-hydroxy-hexahydro-l16-thiopyran-4-yl)oxo)pyrazolo[1,5-a]pyridine-3-carbonitrile and 2-(4-(pyridin-2-oxy)piperidin-1-yl)-5-(4,4,5,5-tetramethyl-1,3,2-dioxaborolan-2-yl)pyridine as raw materials with reference to step 3 of embodiment 37.

MS m/z (ESI): 544.2[M+H]$^+$.

Embodiment 92

6-(3-Amino-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

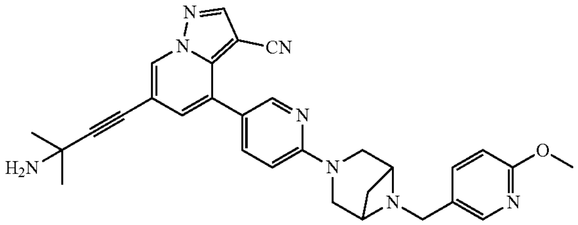 [SMILES: COc1ccc(CN2C3CC2CN(c2ccc(-c4cc(C#CC(C)(C)N)cn5ncc(C#N)c45)cn2)C3)cn1]

6-(3-Amino-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 2-methylbut-3-yn-2-amine as raw material with reference to embodiment 31.

MS m/z (ESI): 519.2 [M+H]$^+$.

$^1$H NMR (400 MHz, Methanol-$d_4$) δ8.82 (d, J=1.3 Hz, 1H), 8.46 (s, 1H), 8.34 (d, J=2.4 Hz, 1H), 8.09 (d, J=2.3 Hz, 1H), 7.84 (dd, J=8.9, 2.5 Hz, 1H), 7.72 (dd, J=8.5, 2.5 Hz, 1H), 7.41 (d, J=1.4 Hz, 1H), 6.88 (d, J=8.9 Hz, 1H), 6.78 (d, J=8.5 Hz, 1H), 4.01-3.83 (m, 5H), 3.84-3.73 (m, 2H), 3.72-3.56 (m, 4H), 2.78-2.65 (m, 1H), 1.71 (d, J=9.0 Hz, 1H), 1.52 (s, 6H).

Embodiment 93

6-(3-Amino-3-methylbut-1-yn-1-yl)-4-(6-(4-((6-methoxypyridin-3-yl)oxo)piperidin-1-yl)pyridin-3-yl)pyrazolo[1,5-a]pyridine-3-carbonitrile

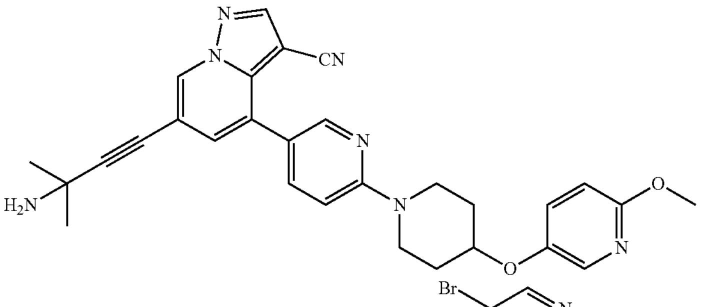

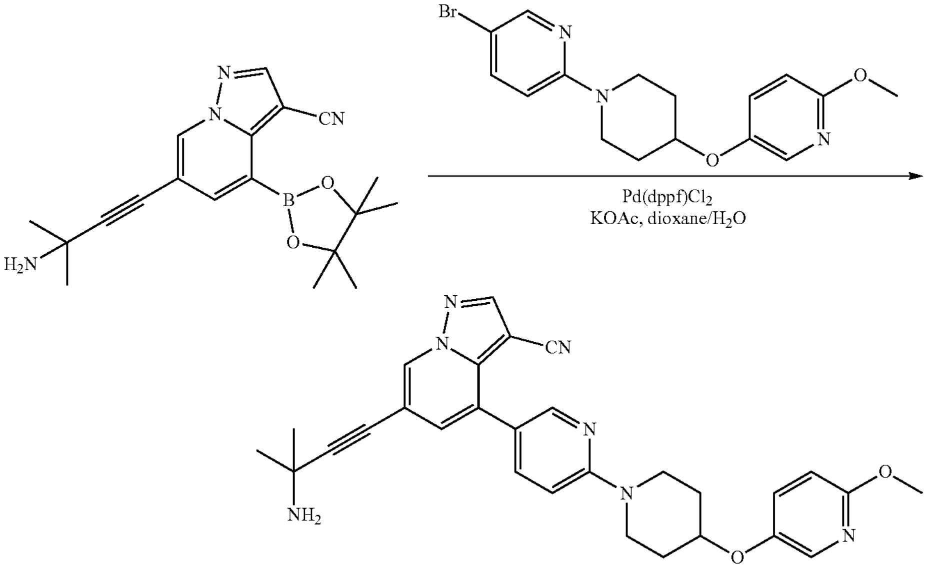

6-(3-Amino-3-methylbut-1-yn-1-yl)-4-(6-(4-((6-methoxypyridin-3-yl)oxo)piperidin-1-yl)pyridin-3-yl)pyrazolo[1,5-a]pyridine-3-carbonitrile was obtained by using 6-(3-amino-3-methylbut-1-yn-1-yl)-4-(4,4,5,5-tetramethyl-1,3,2-dioxaborolan-2-yl)pyrazolo[1,5-a]pyridine-3-carbonitrile and 5-bromo-2-(4-((6-methoxypyridin-3-yl)oxo)piperidin-1-yl)pyridine as raw materials with reference to the step 8 of embodiment 1.

MS m/z (ESI): 508.2 $[M+H]^+$.

Embodiment 94

4-(6-(6-((5-Fluoro-6-methoxypyridin-3-yl)methyl)-3,6-diazabicyclo[3.1.1]heptan-3-yl)pyridin-3-yl)-6-(3-hydroxy-3-methylbut-1-yn-1-yl)pyrazolo[1,5-a]pyridine-3-carbonitrile

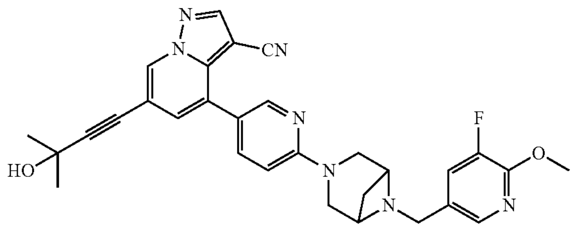 [SMILES: COc1ncc(CN2C3CC2CN(c2ccc(-c4cc(C#CC(C)(C)O)cn5ncc(C#N)c45)cn2)C3)cc1F]

Step 1: 6-bromo-3-cyanopyrazolo[1,5-a]pyridin-4-yl trifluoromethanesulfonate

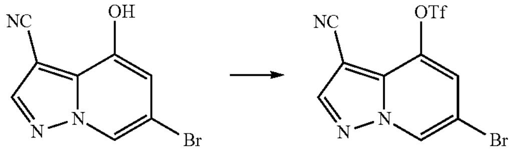 [SMILES: N#Cc1cnn2cc(Br)cc(O)c12 ; N#Cc1cnn2cc(Br)cc(OS(=O)(=O)C(F)(F)F)c12]

6-Bromo-4-hydroxypyrazolo[1,5-a]pyridine-3-carbonitrile (5 g, 21 mmol) and triethylamine (4.2 g, 42 mmol) were dissolved in dichloromethane (500 mL), and trifluoromethanesulfonic anhydride (8.9 g, 31.5 mmol) was added under ice bath; then the mixture was stirred at room temperature for 12 hours, 100 mL of water was added, and the mixture was extracted with ethyl acetate (80 mL*3). The organic phase was washed with saturated saline, dried over anhydrous sodium sulfate, filtered and evaporated to dryness, the crude product was separated by column chromatography (petroleum ether/ethyl acetate=1/1) to obtain 6-bromo-3-cyanopyrazolo[1,5-a]pyridin-4-yl trifluoromethanesulfonate (5 g, white solid, yield was 64%).

$^1H$ NMR (400 MHz, DMSO) δ 9.60 (d, J=0.9 Hz, 1H), 8.85 (s, 1H), 8.23 (s, 1H).

Step 2: 6-bromo-4-(6-fluoropyridin-3-yl)pyrazolo[1,5-a]pyridine-3-carbonitrile

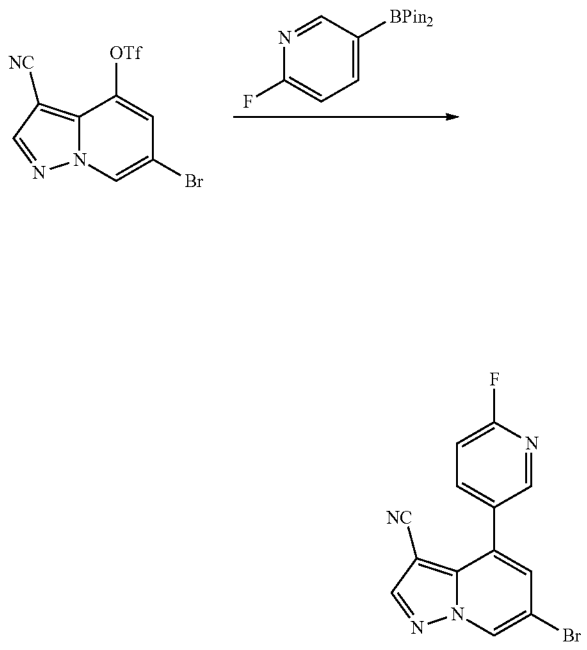

1,1'-Bis(diphenylphosphino)ferrocene-palladium(II)dichloride dichloromethane complex (494 mg, 0.68 mmol) was added to a mixed solution of 6-bromo-3-cyanopyrazolo[1,5-a]pyridin-4-yl trifluoromethanesulfonate (5 g, 13.51 mmol), 2-fluoro-5-(4,4,5,5-tetramethyl-1,3,2-dioxaborolan-2-yl)pyridine (3.3 g, 14.86 mmol), potassium carbonate (3.7 g, 27 mmol) and dioxane (100 mL), the mixture was replaced with nitrogen three times and then stirred at 70° C. under the protection of the protection of nitrogen for 16 hours; the reaction was cooled and filtered, the filtrate was concentrated under reduced pressure to dryness and separated by column chromatography (dichloromethane/methanol=10:1) to obtain white solid 6-bromo-4-(6-fluoropyridin-3-yl)pyrazolo[1,5-a]pyridine-3-carbonitrile (3 g, yield: 70%).

$^1$H NMR (400 MHz, DMSO) δ 9.49 (d, J=1.3 Hz, 1H), 8.73 (s, 1H), 8.51 (d, J=2.0 Hz, 1H), 8.27 (td, J=8.2, 2.5 Hz, 1H), 7.86 (d, J=1.2 Hz, 1H), 7.40 (dd, J=8.5, 2.5 Hz, 1H).

MS m/z (ESI): 317.0 [M+H]$^+$.

Step 3: tert-butyl 3-(5-(6-bromo-3-cyanopyrazolo[1,5-a]pyridin-4-yl)pyridin-2-yl)-3,6-diazabicyclo[3.1.1]heptane-6-carboxylate

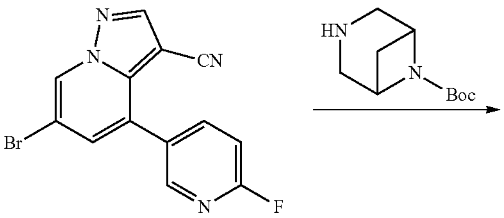

-continued

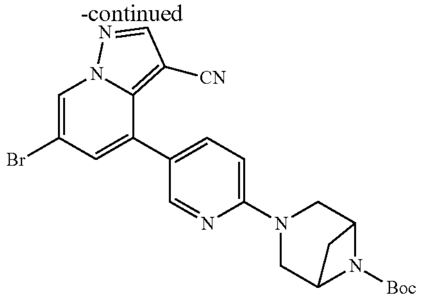

Tert-butyl 3-(5-(6-bromo-3-cyanopyrazolo[1,5-a]pyridin-4-yl)pyridin-2-yl)-3,6-diazabicyclo[3.1.1]heptane-6-carboxylate was obtained by using 6-bromo-4-(6-fluoropyridin-3-yl)pyrazolo[1,5-a]pyridine-3-carbonitrile as raw material with reference to step 7 of embodiment 11.

MS m/z (ESI): 495.1 [M+H]$^+$.

Step 4: 4-(6-(3,6-diazabicyclo[3.1.1]heptan-3-yl)pyridin-3-yl)-6-bromopyrazolo[1,5-a]pyridine-3-carbonitrile

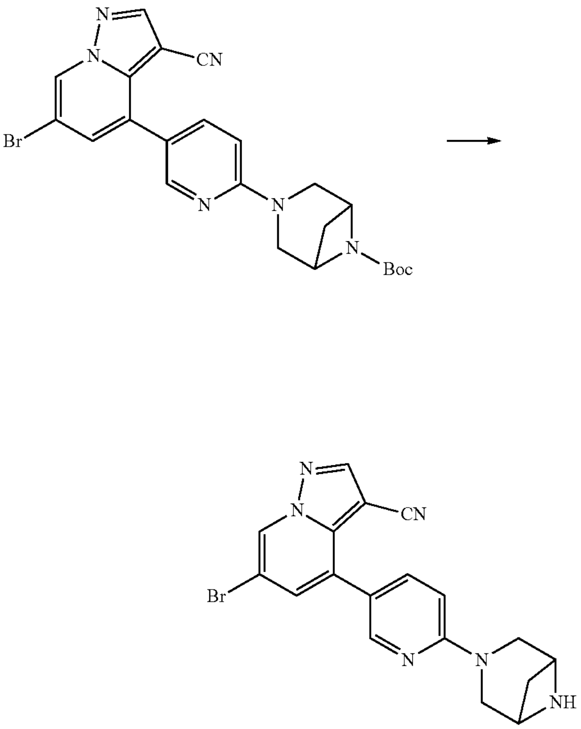

4-(6-(3,6-Diazabicyclo[3.1.1]heptan-3-yl)pyridin-3-yl)-6-bromopyrazolo[1,5-a]pyridine-3-carbonitrile was obtained by using tert-butyl 3-(5-(6-bromo-3-cyanopyrazolo[1,5-a]pyridin-4-yl)pyridin-2-yl)-3,6-diazabicyclo[3.1.1]heptane-6-carboxylate as raw material with reference to step 8 of embodiment 11.

MS m/z (ESI): 395.1 [M+H]$^+$.

Step 5: 6-bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

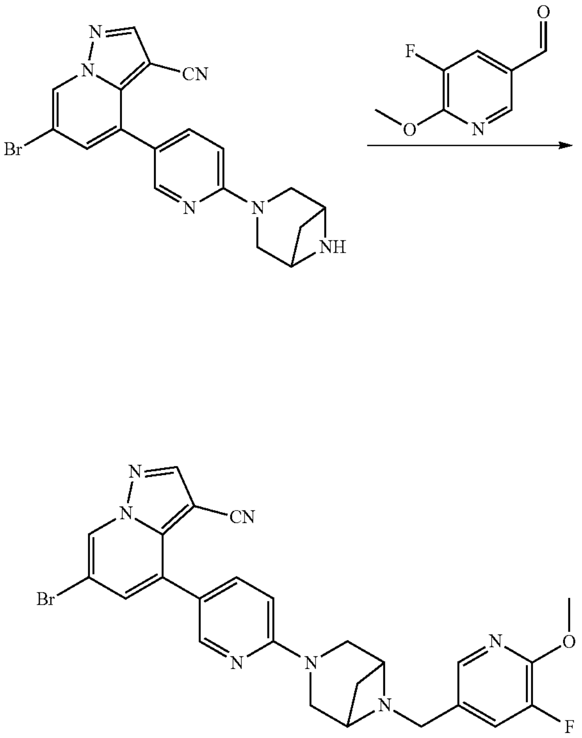

6-Bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 4-(6-(3,6-diazabicyclo[3.1.1]heptan-3-yl)pyridin-3-yl)-6-bromopyrazolo[1,5-a]pyridine-3-carbonitrile and 5-fluoro-6-methoxynicotinaldehyde as raw material with reference to step 9 of embodiment 11.

MS m/z (ESI): 534.1 [M+H]+.

Step 6: 4-(6-(6-((5-fluoro-6-methoxypyridin-3-yl)methyl)-3,6-diazabicyclo[3.1.1]heptan-3-yl)pyridin-3-yl)-6-(3-hydroxy-3-methylbut-1-yn-1-yl)pyrazolo[1,5-a]pyridine-3-carbonitrile

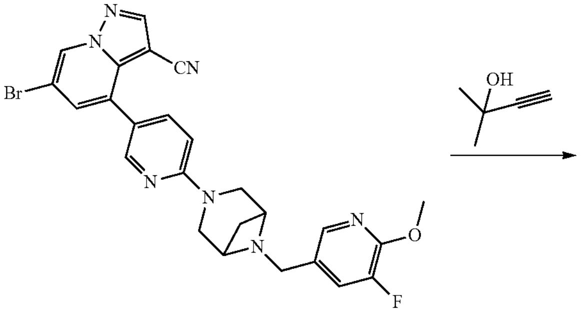

-continued

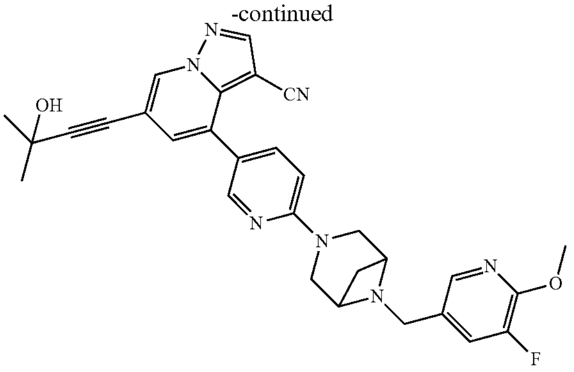

4-(6-(6-((5-Fluoro-6-methoxypyridin-3-yl)methyl)-3,6-diazabicyclo[3.1.1]heptan-3-yl)pyridin-3-yl)-6-(3-hydroxy-3-methylbut-1-yn-1-yl)pyrazolo[1,5-a]pyridine-3-carbonitrile was obtained by using 2-methylbut-3-yn-2-ol and 6-bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile as raw materials with reference to step 2 of embodiment 31.

MS m/z (ESI): 538.2 [M+H]+.

$^1$H NMR (400 MHz, CDCl3) δ 8.61 (s, 1H), 8.40 (d, J=2.2 Hz, 1H), 8.31 (s, 1H), 7.86 (s, 1H), 7.76 (dd, J=8.8, 2.4 Hz, 1H), 7.47 (d, J=11.1 Hz, 1H), 7.30 (s, 1H), 6.68 (d, J=8.7 Hz, 1H), 4.01 (s, 3H), 3.80 (s, 4H), 3.59 (s, 4H), 2.78-2.53 (m, 2H), 1.65 (s, 6H).

Embodiment 95

6-(3-Cyclopropyl-3-hydroxyprop-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

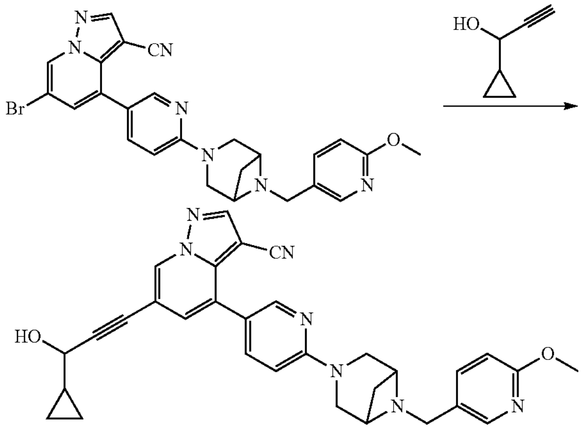

6-Bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (50 mg, 0.1 mmol) was dissolved in N,N-dimethylformamide (2 mL), and 1-cyclopropylprop-2-yn-1-ol (47 mg, 0.5 mmol), triethylamine (50 mg, 0.5 mmol), $Pd_2(PPh_3)_2Cl_2$ (7 mg, 0.01 mmol), CuI (1 mg, 0.01 mmol) were added thereto, the reaction was carried out at 65° C. overnight under the protection of nitrogen. 5 mL of ammonium chloride aqueous solution was added, and the mixture was extracted with ethyl acetate (3 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 6-(3-cyclopropyl-3-hydroxyprop-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (15 mg, white solid, yield was 29%).

MS m/z (ESI): 532.2 $[M+H]^+$.

Embodiment 96

6-((1-Cyanocyclopentyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

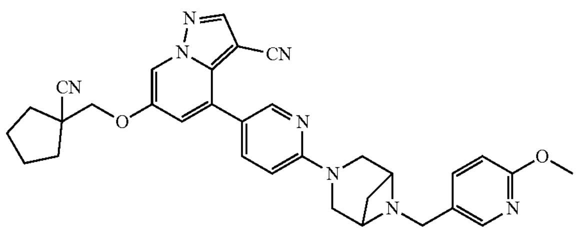 [SMILES: COc1ccc(CN2C3CC2CN(c2ccc(-c4cc(OCC5(C#N)CCCC5)cn5ncc(C#N)c45)cn2)C3)cn1]

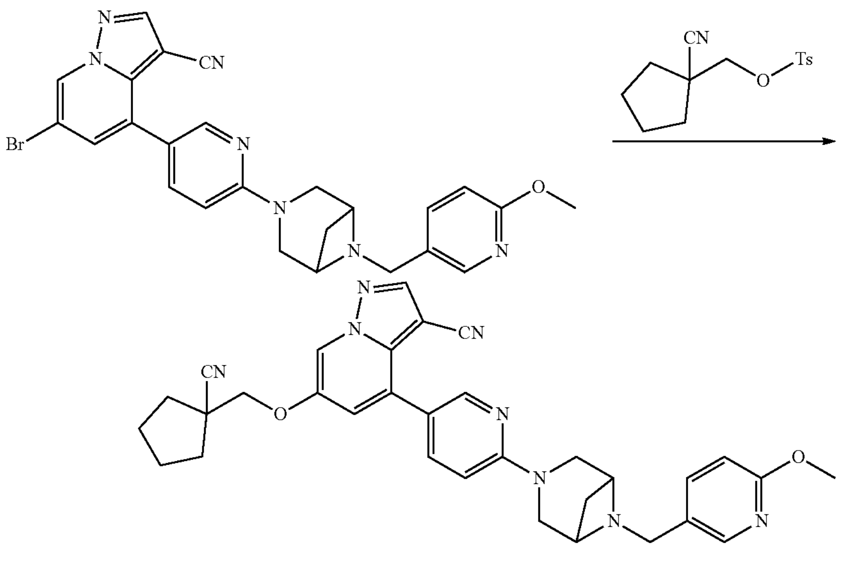

6-((1-Cyanocyclopentyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (1-cyanocyclopentyl)methyl 4-methylbenzenesulfonate as raw materials with reference to step 2 of embodiment 106.

MS m/z (ESI): 561.2 $[M+H]^+$.

Embodiment 97

3-Chloro-N-(1-(5-(3-cyano-6-(3-hydroxy-3-methylbut-1-yn-1-yl)pyrazolo[1,5-a]pyridin-4-yl)pyridin-2-yl)-4-methylpiperidin-4-yl)picolinamide

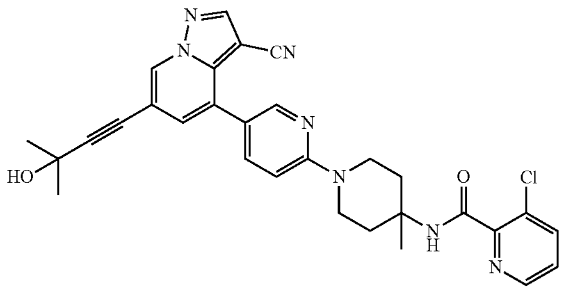 [SMILES: CC(C)(O)C#Cc1cc(-c2ccc(N3CCC(C)(NC(=O)c4ncccc4Cl)CC3)nc2)c2c(C#N)cnn2c1]

Step 1: tert-butyl (1-(5-(6-bromo-3-cyanopyrazolo[1,5-a]pyridin-4-yl)pyridin-2-yl)-4-methylpiperidin-4-yl)carbamate

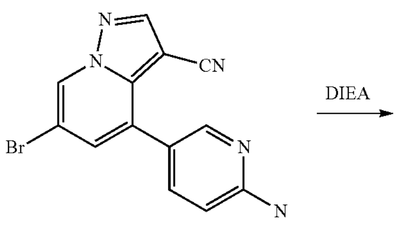

-continued

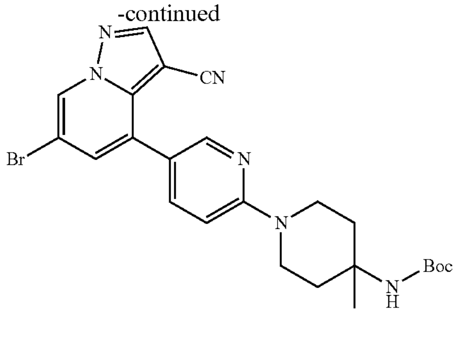

Tert-butyl (1-(5-(6-bromo-3-cyanopyrazolo[1,5-a]pyridin-4-yl)pyridin-2-yl)-4-methylpiperidin-4-yl)carbamate (white solid) was obtained by using 6-bromo-4-(6-fluoropyridin-3-yl)pyrazolo[1,5-a]pyridine-3-carbonitrile as raw material with reference to step 4 of embodiment 1.

MS m/z (ESI): 511.1 [M+H]$^+$.

Step 2: 4-(6-(4-amino-4-methylpiperidin-1-yl)pyridin-3-yl)-6-bromopyrazolo[1,5-a]pyridine-3-carbonitrile

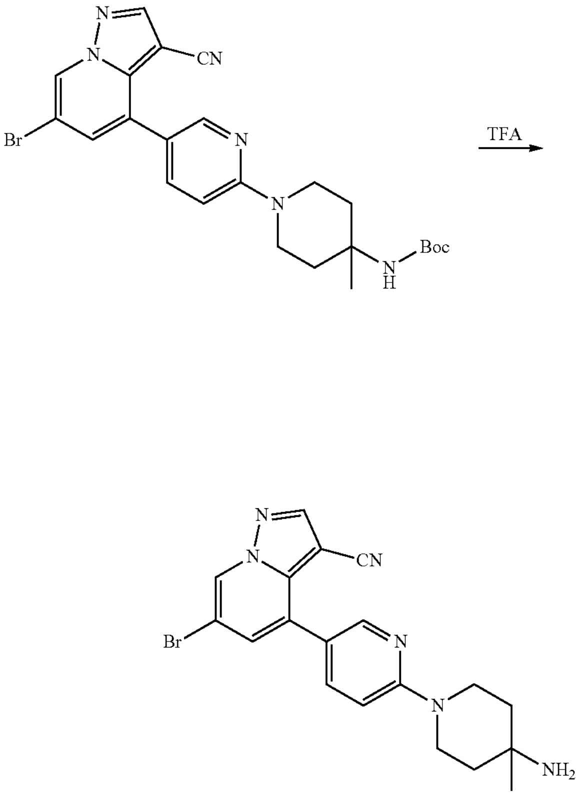

4-(6-(4-Amino-4-methylpiperidin-1-yl)pyridin-3-yl)-6-bromopyrazolo[1,5-a]pyridine-3-carbonitrile (white solid) was obtained by using tert-butyl (1-(5-(6-bromo-3-cyanopyrazolo[1,5-a]pyridin-4-yl)pyridin-2-yl)-4-methylpiperidin-4-yl)carbamate as raw material with reference to the step 5 of embodiment 1.

MS m/z (ESI): 411.1 [M+H]$^+$.

Step 3: N-(1-(5-(6-bromo-3-cyanopyrazolo[1,5-a]pyridin-4-yl)pyridin-2-yl)-4-methylpiperidin-4-yl)-3-chloropicolinamide

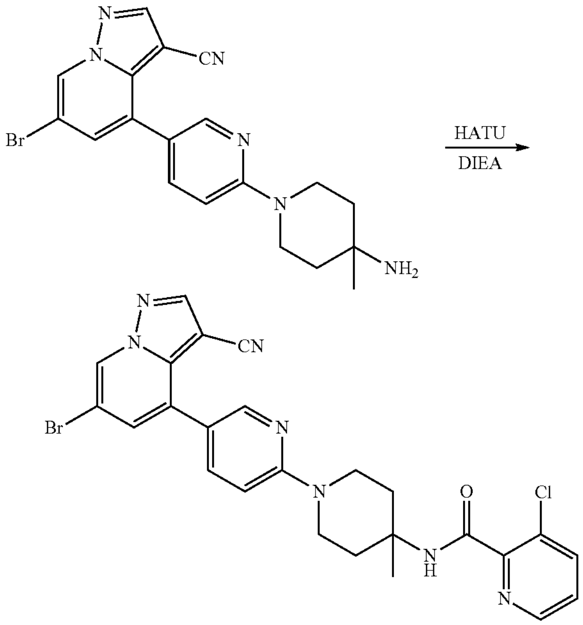

N-(1-(5-(6-bromo-3-cyanopyrazolo[1,5-a]pyridin-4-yl)pyridin-2-yl)-4-methylpiperidin-4-yl)-3-chloropicolinamide (white solid) was obtained by using 4-(6-(4-amino-4-methylpiperidin-1-yl)pyridin-3-yl)-6-bromopyrazolo[1,5-a]pyridine-3-carbonitrile as raw material with reference to step 1 of embodiment 96.

MS m/z (ESI): 550.0 [M+H]$^+$.

Step 4: 3-chloro-N-(1-(5-(3-cyano-6-(3-hydroxy-3-methylbut-1-yn-1-yl)pyrazolo[1,5-a]pyridin-4-yl)pyridin-2-yl)-4-methylpiperidin-4-yl)picolinamide

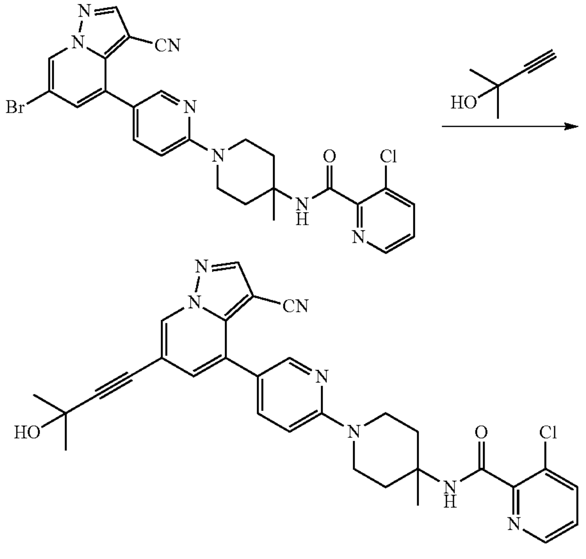

3-Chloro-N-(1-(5-(3-cyano-6-(3-hydroxy-3-methylbut-1-yn-1-yl)pyrazolo[1,5-a]pyridin-4-yl)pyridin-2-yl)-4-methylpiperidin-4-yl)picolinamide (white solid) was obtained by using N-(1-(5-(6-bromo-3-cyanopyrazolo[1,5-a]pyridin-4-yl)pyridin-2-yl)-4-methylpiperidin-4-yl)-3-chloropicolinamide as raw materials with reference to step 2 of embodiment 96.

MS m/z (ESI): 554.2 $[M+H]^+$.

$^1$H NMR (400 MHz, Methanol-d4) δ 8.81 (d, J=1.3 Hz, 1H), 8.50 (dd, J=4.7, 1.3 Hz, 1H), 8.45 (s, 1H), 8.28 (d, J=2.6 Hz, 1H), 7.96 (dd, J=8.2, 1.4 Hz, 1H), 7.75 (dd, J=8.8, 2.6 Hz, 1H), 7.48 (dd, J=8.2, 4.7 Hz, 1H), 7.38 (d, J=1.3 Hz, 1H), 6.97 (d, J=8.9 Hz, 1H), 4.18-4.03 (m, 2H), 3.48-3.37 (m, 2H), 2.54-2.34 (m, 2H), 1.80-1.68 (m, 2H), 1.58 (s, 6H), 1.56 (s, 3H).

Embodiment 98

6-((S)-3-hydroxybut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

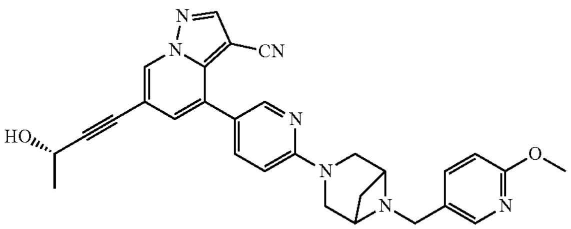 [SMILES: COc1ccc(CN2C3CC2CN(c2ccc(-c4cc(C#C[C@H](C)O)cn5ncc(C#N)c45)cn2)C3)cn1]

6-((S)-3-hydroxybut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (S)-but-3-yn-2-ol as raw materials with reference to step 2 of embodiment 96.

MS m/z (ESI): 506.2 $[M+H]^+$.

$^1$H NMR (400 MHz, Methanol-d4) δ 8.85 (s, 1H), 8.47 (s, 1H), 8.35 (d, J=2.5 Hz, 1H), 8.08 (d, J=2.5 Hz, 1H), 7.84 (dd, J=8.9, 2.6 Hz, 1H), 7.72 (dd, J=8.5, 2.5 Hz, 1H), 7.42 (s, 1H), 6.88 (d, J=8.9 Hz, 1H), 6.78 (d, J=8.6 Hz, 1H), 4.72 (q, J=6.6 Hz, 1H), 3.96-3.84 (m, 5H), 3.83-3.74 (m, 2H), 3.69-3.56 (m, 4H), 2.76-2.64 (m, 1H), 1.70 (d, J=8.9 Hz, 1H), 1.51 (d, J=6.6 Hz, 3H).

Embodiment 99

6-((R)-3-hydroxybut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

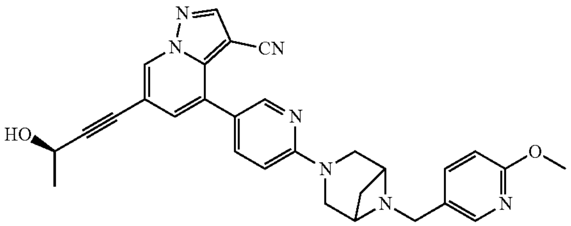 [SMILES: COc1ccc(CN2C3CC2CN(c2ccc(-c4cc(C#C[C@@H](C)O)cn5ncc(C#N)c45)cn2)C3)cn1]

6-((R)-3-hydroxybut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (S)-but-3-yn-2-ol as raw materials with reference to step 2 of embodiment 96.

MS m/z (ESI): 506.2 $[M+H]^+$.

$^1$H NMR (400 MHz, Methanol-$d_4$) δ 8.85 (d, J=1.4 Hz, 1H), 8.47 (s, 1H), 8.35 (d, J=2.5 Hz, 1H), 8.09 (s, 1H), 7.84 (dd, J=8.8, 2.5 Hz, 1H), 7.72 (dd, J=8.5, 2.5 Hz, 1H), 7.42 (d, J=1.4 Hz, 1H), 6.88 (d, J=8.9 Hz, 1H), 6.78 (d, J=8.5 Hz, 1H), 4.75-4.70 (m, 1H), 3.92-3.85 (m, 5H), 3.84-3.75 (m, 2H), 3.68-3.58 (m, 4H), 2.74-2.67 (m, 1H), 1.71 (d, J=9.0 Hz, 1H), 1.51 (d, J=6.7 Hz, 3H).

Embodiment 100

N-(1-(5-(6-(3-amino-3-methylbut-1-yn-1-yl)-3-cyanopyrazolo[1,5-a]pyridin-4-yl)pyridin-2-yl)-4-methylpiperidin-4-yl)-3-chloropicolinamide

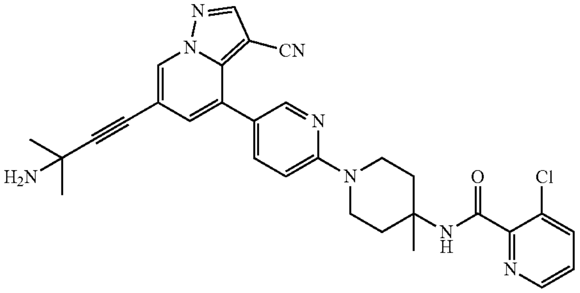

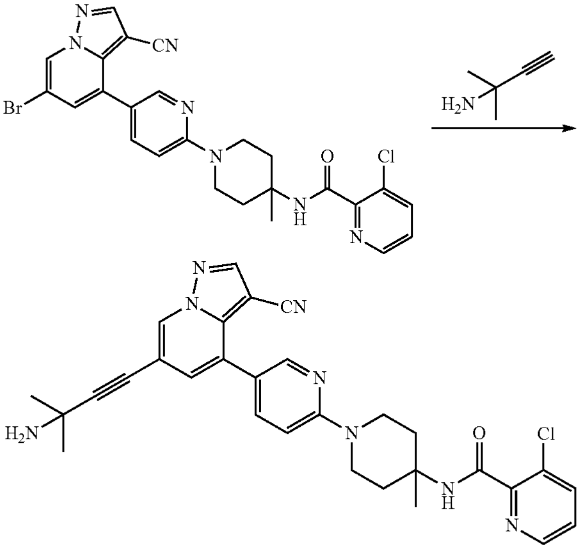

N-(1-(5-(6-(3-amino-3-methylbut-1-yn-1-yl)-3-cyanopyrazolo[1,5-a]pyridin-4-yl)pyridin-2-yl)-4-methylpiperidin-4-yl)-3-chloropicolinamide (white solid) was obtained by using N-(1-(5-(6-bromo-3-cyanopyrazolo[1,5-a]pyridin-4-yl)pyridin-2-yl)-4-methylpiperidin-4-yl)-3-chloropicolinamide and 2-methylbut-3-yn-2-amine as raw materials with reference to step 2 of embodiment 96.

MS m/z (ESI): 553.2 $[M+H]^+$.

$^1$H NMR (400 MHz, Methanol-$d_4$) δ 8.80 (d, J=1.4 Hz, 1H), 8.50 (d, J=4.8 Hz, 1H), 8.45 (s, 1H), 8.28 (d, J=2.5 Hz, 1H), 7.99-7.94 (m, 1H), 7.78-7.73 (m, 1H), 7.51-7.46 (m, 1H), 7.38 (s, 1H), 6.98 (d, J=8.8 Hz, 1H), 4.15-4.05 (m, 2H), 3.50-3.45 (m, 2H), 2.44-2.38 (m, 2H), 1.78-1.72 (m, 2H), 1.56 (s, 3H), 1.52 (s, 6H).

Embodiment 101

6-(3-Amino-3-methylbut-1-yn-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

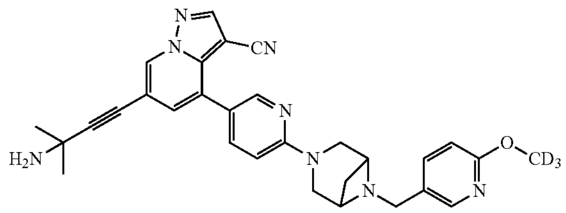 [SMILES: [2H]C([2H])([2H])Oc1ccc(CN2C3CC2CN(c2ccc(-c4cc(C#CC(C)(C)N)cn5ncc(C#N)c45)cn2)C3)cn1]

Step 1: Preparation of 6-bromo-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

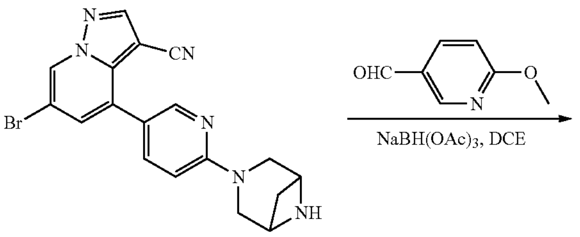

-continued

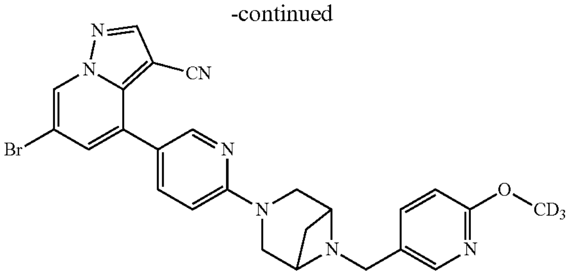

6-Bromo-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile (yellow solid) was obtained by using 4-(6-(3,6-diazabicyclo[3.1.1]heptan-3-yl)pyridin-3-yl)-6-bromopyrazolo[1,5-a]pyridine-3-carbonitrile as raw material with reference to step 6 of embodiment 1. MS m/z (ESI): 519.1 $[M+H]^+$.

Step 2: Preparation of 6-(3-amino-3-methylbut-1-yn-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

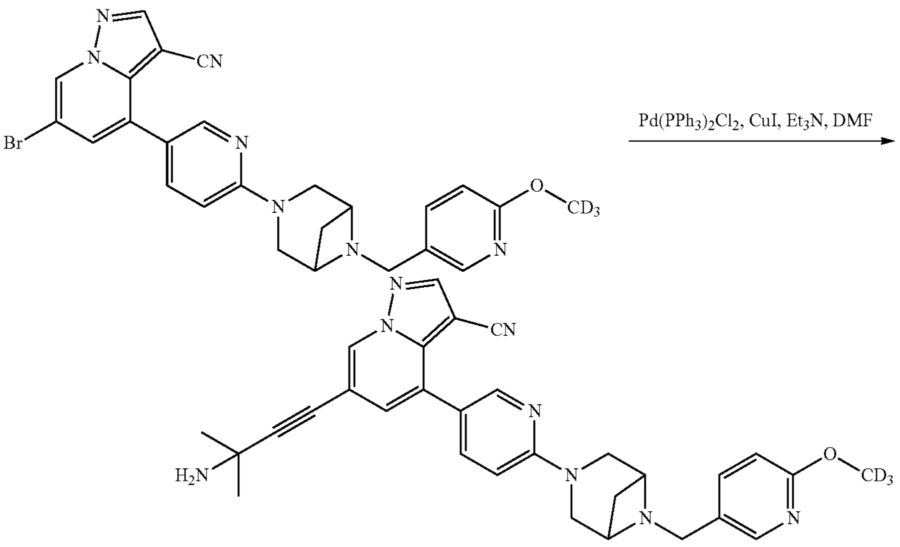

6-(3-Amino-3-methylbut-1-yn-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile as raw material with reference to step 2 of embodiment 96.

MS m/z (ESI): 522.2 $[M+H]^+$.

Embodiment 102

6-(3-Amino-3-methylbut-1-yn-1-yl)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

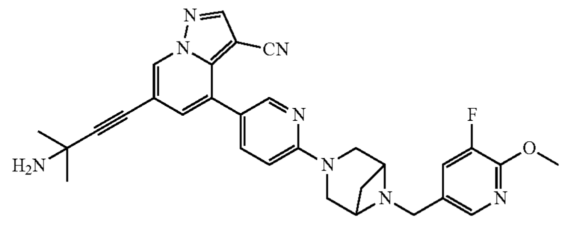 [SMILES: COc1ncc(CN2C3CC2CN(c2ccc(-c4cc(C#CC(C)(C)N)cn5ncc(C#N)c45)cn2)C3)cc1F]

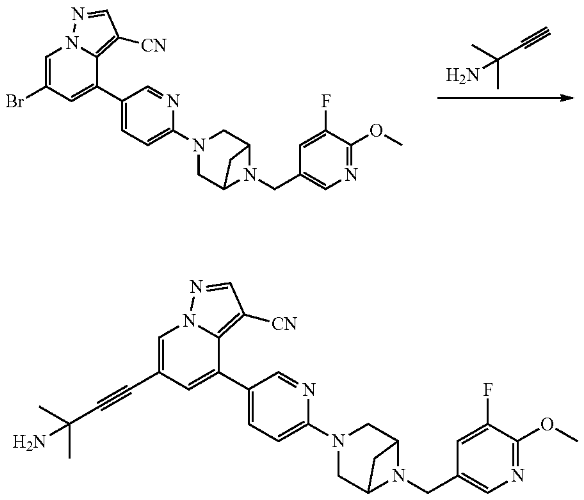

6-(3-Amino-3-methylbut-1-yn-1-yl)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile and 2-methylbut-3-yn-2-amine as raw material with reference to step 2 of embodiment 96.

MS m/z (ESI): 537.2 $[M+H]^+$.

Embodiment 103

N-(1-(5-(6-(3-amino-3-methylbut-1-yn-1-yl)-3-cyanopyrazolo[1,5-a]pyridin-4-yl)pyridin-2-yl)-4-methylpiperidin-4-yl)-5-fluoro-2-methylbenzamide

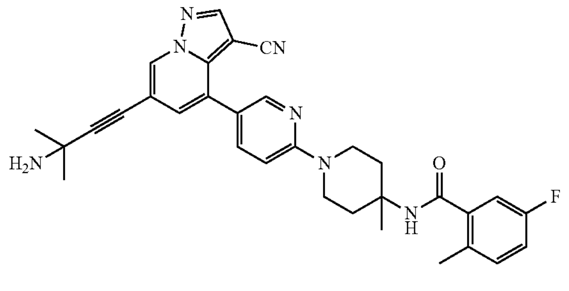 [SMILES: Cc1ccc(F)cc1C(=O)NC1(C)CCN(c2ccc(-c3cc(C#CC(C)(C)N)cn4ncc(C#N)c34)cn2)CC1]

Step 1: N-(1-(5-(6-bromo-3-cyanopyrazolo[1,5-a]pyridin-4-yl)pyridin-2-yl)-4-methylpiperidin-4-yl)-5-fluoro-2-methylbenzamide

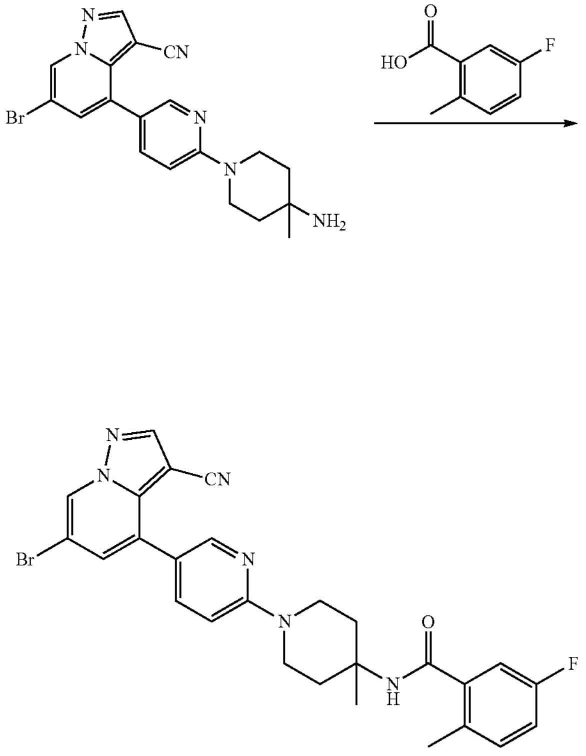

N-(1-(5-(6-bromo-3-cyanopyrazolo[1,5-a]pyridin-4-yl)pyridin-2-yl)-4-methylpiperidin-4-yl)-5-fluoro-2-methylbenzamide (white solid) was obtained by using 4-(6-(4-amino-4-methylpiperidin-1-yl)pyridin-3-yl)-6-bromopyrazolo[1,5-a]pyridine-3-carbonitrile and 5-fluoro-2-methylbenzoic acid as raw material with reference to step 2 of embodiment 96.

MS m/z (ESI): 547.1 $[M+H]^+$.

Step 2: N-(1-(5-(6-(3-amino-3-methylbut-1-yn-1-yl)-3-cyanopyrazolo[1,5-a]pyridin-4-yl)pyridin-2-yl)-4-methylpiperidin-4-yl)-5-fluoro-2-methylbenzamide

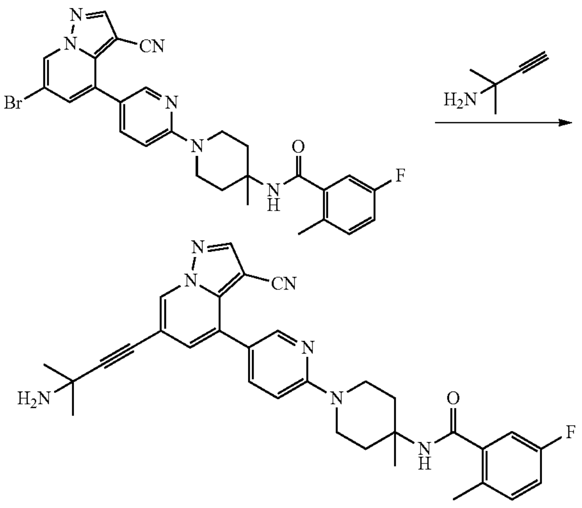

N-(1-(5-(6-(3-amino-3-methylbut-1-yn-1-yl)-3-cyanopyrazolo[1,5-a]pyridin-4-yl)pyridin-2-yl)-4-methylpiperidin-4-yl)-5-fluoro-2-methylbenzamide (white solid) was obtained by using N-(1-(5-(6-bromo-3-cyanopyrazolo[1,5-a]pyridin-4-yl)pyridin-2-yl)-4-methylpiperidin-4-yl)-5-fluoro-2-methylbenzamide and 2-methylbut-3-yn-2-amine as raw materials with reference to step 2 of embodiment 96.

MS m/z (ESI): 550.2 $[M+H]^+$.

$^1$H NMR (400 MHz, Methanol-$d_4$) δ 8.80 (d, J=1.3 Hz, 1H), 8.45 (s, 1H), 8.28 (d, J=2.6 Hz, 1H), 7.76 (dd, J=8.9, 2.6 Hz, 1H), 7.38 (d, J=1.2 Hz, 1H), 7.28-7.21 (m, 1H), 7.11-7.02 (m, 2H), 6.98 (d, J=8.9 Hz, 1H), 4.08-4.00 (m, 2H), 3.43-3.38 (m, 2H), 2.46-2.39 (m, 2H), 2.38 (s, 3H), 1.75-1.69 (m, 2H), 1.54 (s, 3H), 1.52 (s, 6H).

Embodiment 104

6-(3-Hydroxy-3-methylbut-1-yn-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

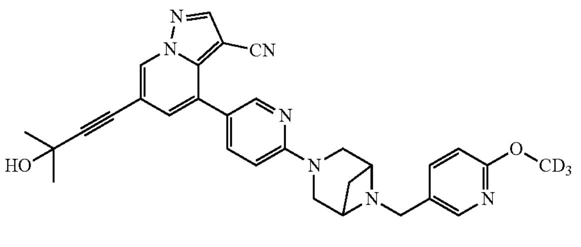 [SMILES: [2H]C([2H])([2H])Oc1ccc(CN2C3CC2CN(c2ccc(-c4cc(C#CC(C)(C)O)cn5ncc(C#N)c45)cn2)C3)cn1]

6-(3-Hydroxy-3-methylbut-1-yn-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile as raw material with reference to step 2 of embodiment 96.

MS m/z (ESI): 523.3 $[M+H]^+$.

Embodiment 105

4-(6-(6-((6-cyclopropoxypyridin-3-yl)methyl)-3,6-diazabicyclo[3.1.1]heptan-3-yl)pyridin-3-yl)-6-(3-hydroxy-3-methylbut-1-yn-1-yl)pyrazolo[1,5-a]pyridine-3-carbonitrile

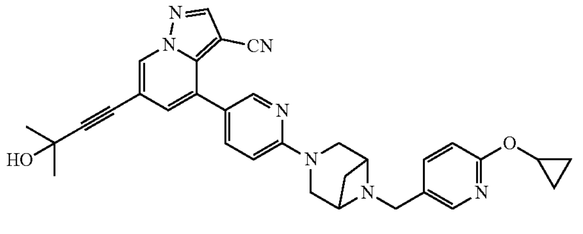 [SMILES: CC(C)(O)C#Cc1cc(-c2ccc(N3CC4CC(C3)N4Cc3ccc(OC4CC4)nc3)nc2)c2c(C#N)cnn2c1]

Step 1: 5-(chloromethyl)-2-cyclopropoxypyridine

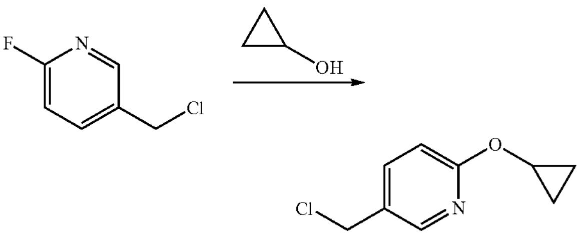

5-(Chloromethyl)-2-fluoropyridine (900 mg, 6.2 mmol) was dissolved in 30 mL of THF, and cyclopropanol (539 mg, 9.3 mmol) was added thereto. Tert-butyl potassium (1.04 g, 9.3 mmol) was slowly added to the reaction mixture in batches. The reaction was stirred at room temperature for 4 hours. Water was added to the reaction mixture to quench the reaction, and then the mixture was extracted with ethyl acetate. The organic phase was dried and evaporated to dryness. The crude product was purified by column chromatography to obtain 5-(chloromethyl)-2-cyclopropoxypyridine (0.6 g, yield: 52%).

MS m/z (ESI): 184.2 $[M+H]^+$.

Step 2: 6-Bromo-4-(6-(6-((6-cyclopropoxypyridin-3-yl)methyl)-3,6-diazabicyclo[3.1.1]heptan-3-yl)pyridin-3-yl)pyrazolo[1,5-a]pyridine-3-carbonitrile

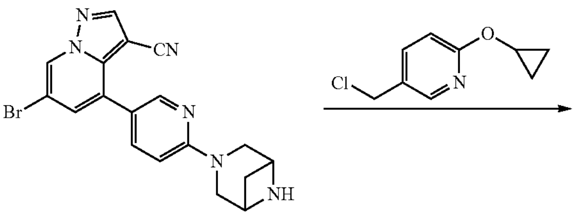

-continued

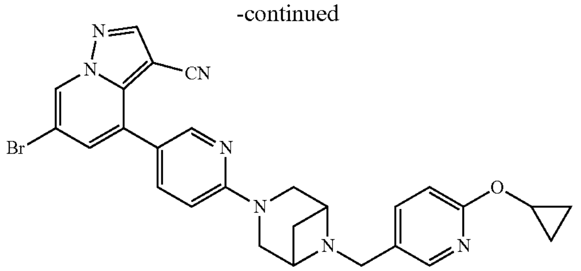

4-(6-(3,6-Diazabicyclo[3.1.1]heptan-3-yl)pyridin-3-yl)-6-bromopyrazolo[1,5-a]pyridine-3-carbonitrile (500 mg, 1.26 mmol) was dissolved in DMAc (15 mL), then 5-(chloromethyl)-2-cyclopropoxypyridine (279 mg, 1.52 mmol) and potassium tert-butoxide (284 mg, 2.53 mmol) were added thereto. The reaction mixture was stirred at 90° C. for 4 hours. Water was added to quench the reaction, and then the mixture was extracted with ethyl acetate. The organic phase was dried and evaporated to dryness. The crude product was purified by column chromatography to obtain 6-bromo-4-(6-(6-((6-cyclopropoxypyridin-3-yl)methyl)-3,6-diazabicyclo[3.1.1]heptan-3-yl)pyridin-3-yl)pyrazolo[1,5-a]pyridine-3-carbonitrile (300 mg, yield was 44%).

MS m/z (ESI): 542.2 [M+H]+.

Step 3: 4-(6-(6-((6-cyclopropoxypyridin-3-yl)methyl)-3,6-diazabicyclo[3.1.1]heptan-3-yl)pyridin-3-yl)-6-(3-hydroxy-3-methylbut-1-yn-1-yl)pyrazolo[1,5-a]pyridine-3-carbonitrile

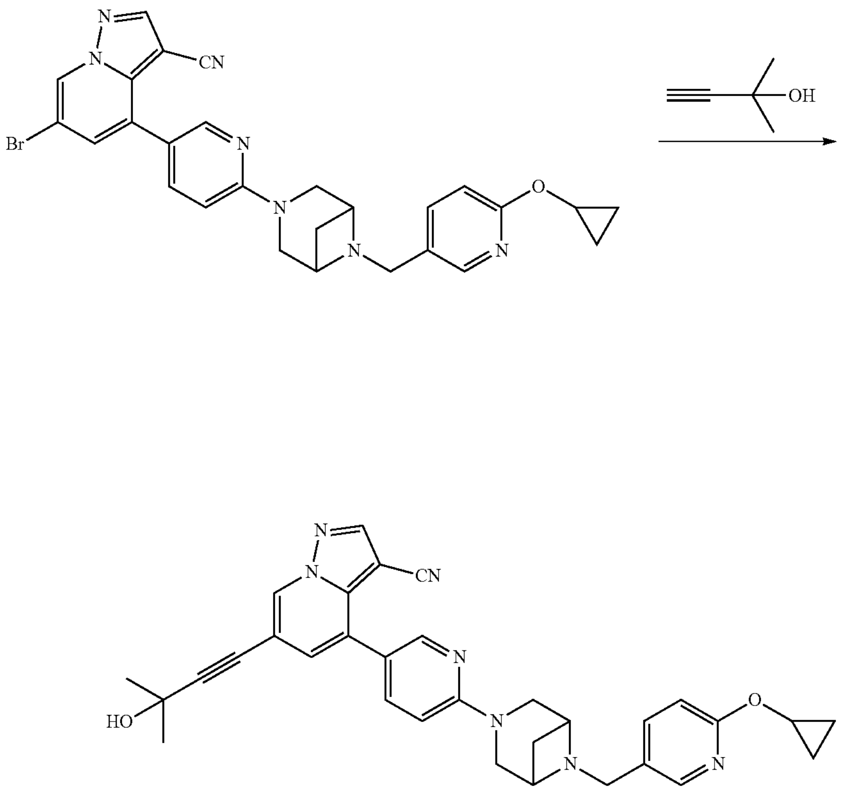

4-(6-(6-((6-Cyclopropoxypyridin-3-yl)methyl)-3,6-diazabicyclo[3.1.1]heptan-3-yl)pyridin-3-yl)-6-(3-hydroxy-3-methylbut-1-yn-1-yl)pyrazolo[1,5-a]pyridine-3-carbonitrile was obtained by using 2-methylbut-3-yn-2-ol and 6-bromo-4-(6-(6-((6-cyclopropoxypyridin-3-yl)methyl)-3,6-diazabicyclo[3.1.1]heptan-3-yl)pyridin-3-yl)pyrazolo[1,5-a]pyridine-3-carbonitrile as raw material with reference to embodiment 31.

MS m/z (ESI): 546.2 [M+H]+.

Embodiment 106

6-((1-Cyanocyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

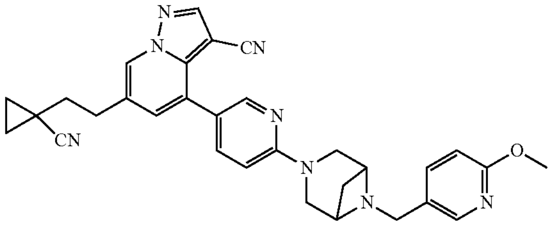 [SMILES: COc1ccc(CN2C3CC2CN(c2ccc(-c4cc(CCC5(C#N)CC5)cn5ncc(C#N)c45)cn2)C3)cn1]

Step 1: 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

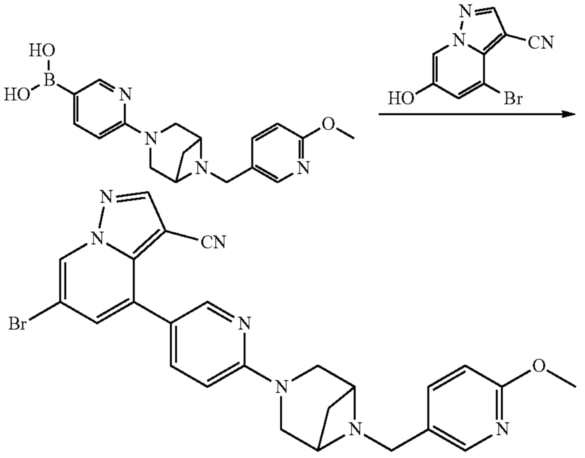

6-Hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using (6-(6-((6-methoxypyridin-3-yl)methyl)-3,6-diazabicyclo[3.1.1]heptan-3-yl)pyridin-3-yl)boronic acid and 4-bromo-6-hydroxypyrazolo[1,5-a]pyridine-3-carbonitrile as raw material with reference to step 8 of embodiment 1 (500 mg, white solid, yield was 80%).

MS m/z (ESI): 454.1 $[M+H]^+$.

Step 2: 6-((1-Cyanocyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

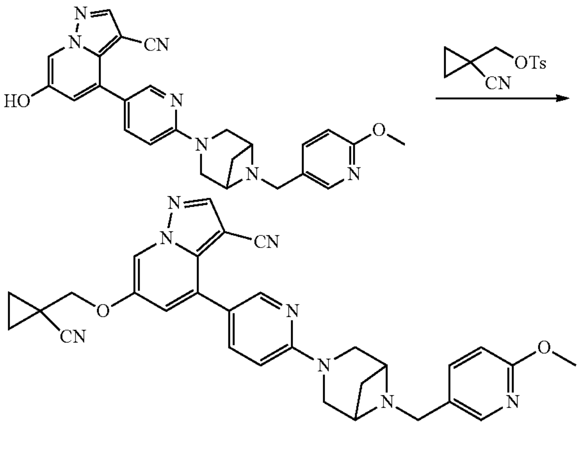

6-Hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (50 mg, 0.11 mmol) was dissolved in 2 mL of DMF; (1-cyanocyclopropyl)methyl 4-methylbenzenesulfonate (28 mg, 0.11 mmol) and potassium carbonate (42 mg, 0.3 mmol) were added thereto, and the mixture was stirred overnight at 90° C. 10 mL of water was added, and the mixture was extracted with ethyl acetate (2 mL*3). The organic phase was washed with saturated saline, dried over anhydrous sodium sulfate. The residue was filtered, evaporated to dryness, and the crude product was purified by prep-HPLC to obtain 6-((1-cyanocyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (23 mg, white solid, yield: 39%).

MS m/z (ESI): 533.2 $[M+H]^+$.

$^1H$ NMR (400 MHz, Methanol-$d_4$) δ 8.47 (d, J=2.1 Hz, 1H), 8.39-8.33 (m, 2H), 8.09 (s, 1H), 7.86 (dd, J=8.8, 2.5 Hz, 1H), 7.72 (dd, J=8.5, 2.5 Hz, 1H), 7.35 (d, J=2.1 Hz, 1H), 6.88 (d, J=8.9 Hz, 1H), 6.78 (d, J=8.5 Hz, 1H), 4.15 (s, 2H), 3.93-3.87 (m, 5H), 3.82-3.77 (m, 2H), 3.69-3.60 (m, 4H), 2.74-2.65 (m, 1H), 1.75-1.66 (m, 1H), 1.47-1.40 (m, 2H), 1.28-1.24 (m, 2H).

Embodiment 107

6-((1-Cyanocyclopropyl)methoxy)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

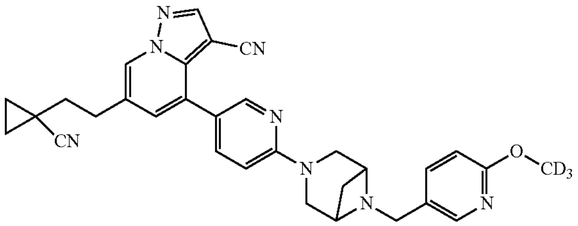 [SMILES: [2H]C([2H])([2H])Oc1ccc(CN2C3CC2CN(c2ccc(-c4cc(CCC5(C#N)CC5)cn5ncc(C#N)c45)cn2)C3)cn1]

Step 1: 3-(5-bromopyridin-2-yl)-6-((6-(methoxy-d3)pyridin-3-yl)methyl)-3,6-diazabicyclo[3.1.1]heptane

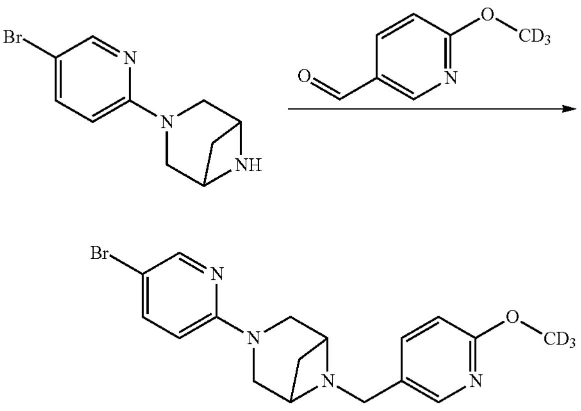

3-(5-Bromopyridin-2-yl)-6-((6-(methoxy-d3)pyridin-3-yl)methyl)-3,6-diazabicyclo[3.1.1]heptane was obtained by using 3-(5-bromopyridin-2-yl)-3,6-diazabicyclo[3.1.1]heptane and 6-(methoxy-d3)nicotinaldehyde as raw material with reference to step 6 of embodiment 1.

MS m/z (ESI): 378.0 $[M+H]^+$.

Step 2: 6-((6-(methoxy-d3)pyridin-3-yl)methyl)-3-(5-(4,4,5,5-tetramethyl-1,3,2-dioxaborolan-2-yl)pyridin-2-yl)-3,6-diazabicyclo[3.1.1]heptane

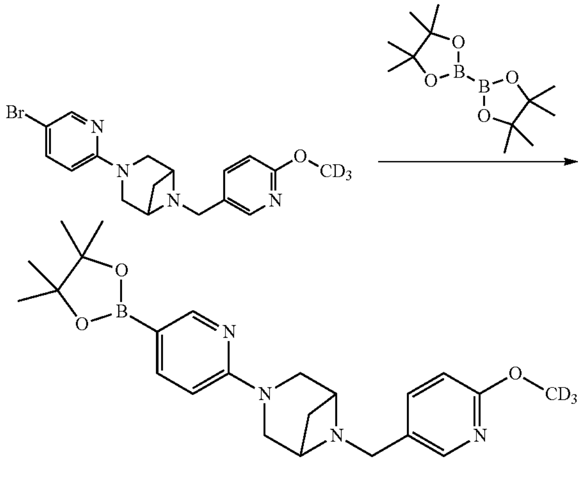

6-((6-(Methoxy-d3)pyridin-3-yl)methyl)-3-(5-(4,4,5,5-tetramethyl-1,3,2-dioxaborolan-2-yl)pyridin-2-yl)-3,6-diazabicyclo[3.1.1]heptane was obtained by using 3-(5-bromopyridin-2-yl)-6-((6-(methoxy-d3)pyridin-3-yl)methyl)-3,6-diazabicyclo[3.1.1]heptane as raw material with reference to step 7 of embodiment 1.

MS m/z (ESI): 426.2 $[M+H]^+$.

Step 3: 6-hydroxy-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

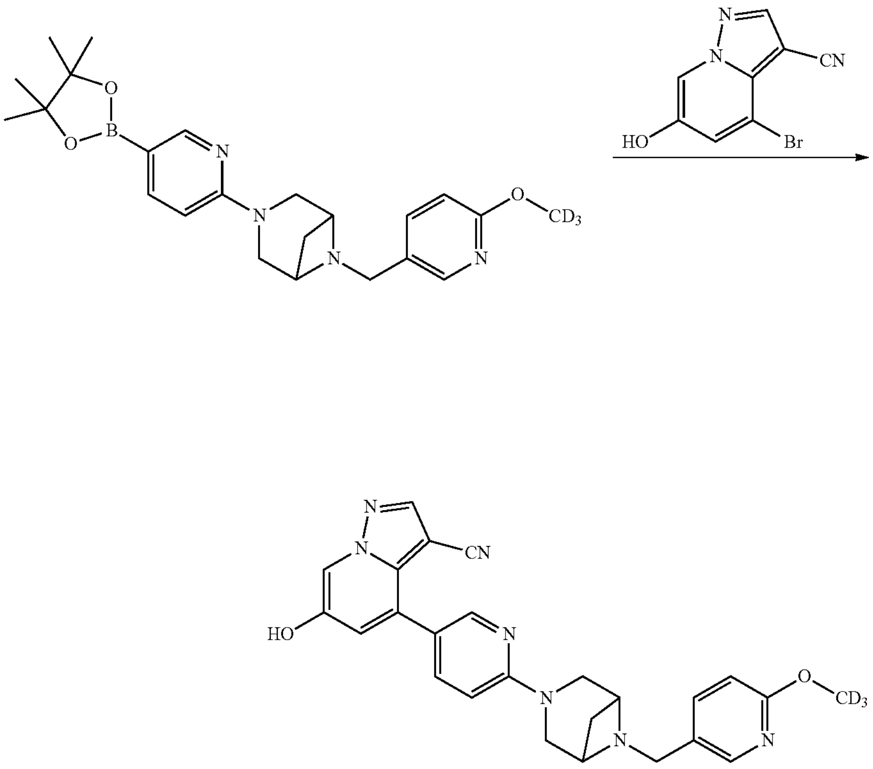

6-Hydroxy-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile was obtained by using 6-((6-(methoxy-d3)pyridin-3-yl)methyl)-3-(5-(4,4,5,5-tetramethyl-1,3,2-dioxaborolan-2-yl)pyridin-2-yl)-3,6-diazabicyclo[3.1.1]heptane and 4-bromo-6-hydroxypyrazolo[1,5-a]pyridine-3-carbonitrile as raw material with reference to step 8 of embodiment 1.

MS m/z (ESI): 457.2 $[M+H]^+$.

Step 4: 6-((1-cyanocyclopropyl)methoxy)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

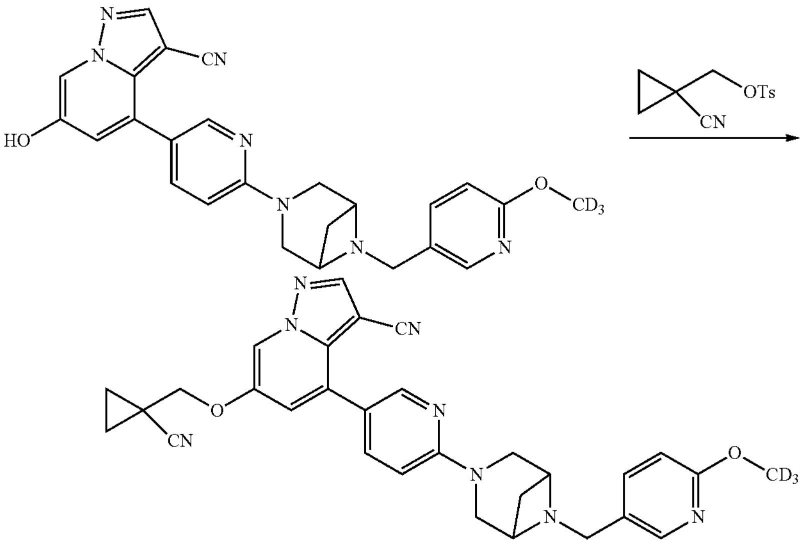

6-((1-Cyanocyclopropyl)methoxy)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile and (1-cyanocyclopropyl)methyl 4-methylbenzenesulfonate as raw material with reference to step 2 of embodiment 106.

MS m/z (ESI): 536.2 $[M+H]^+$.

$^1$H NMR (400 MHz, Chloroform-d) δ 8.42 (d, J=2.5 Hz, 1H), 8.23 (s, 1H), 8.13 (d, J=2.2 Hz, 1H), 8.11 (d, J=2.1 Hz, 1H), 7.91-7.74 (m, 2H), 7.19 (d, J=2.1 Hz, 1H), 6.76 (d, J=8.6 Hz, 1H), 6.71 (d, J=8.8 Hz, 1H), 4.09-3.99 (m, 4H), 3.98-3.89 (m, 2H), 3.84-3.64 (m, 4H), 2.05-1.97 (m, 1H), 1.79-1.71 (m, 1H), 1.53-1.48 (m, 2H), 1.21-1.15 (m, 2H).

Embodiment 108

6-((1-Hydroxycyclopropyl)ethynyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

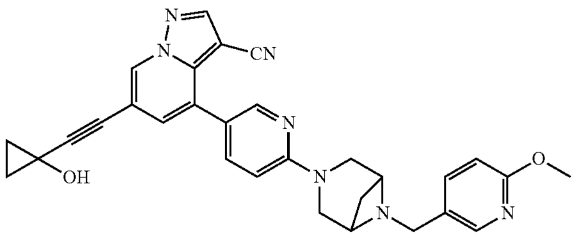

-continued

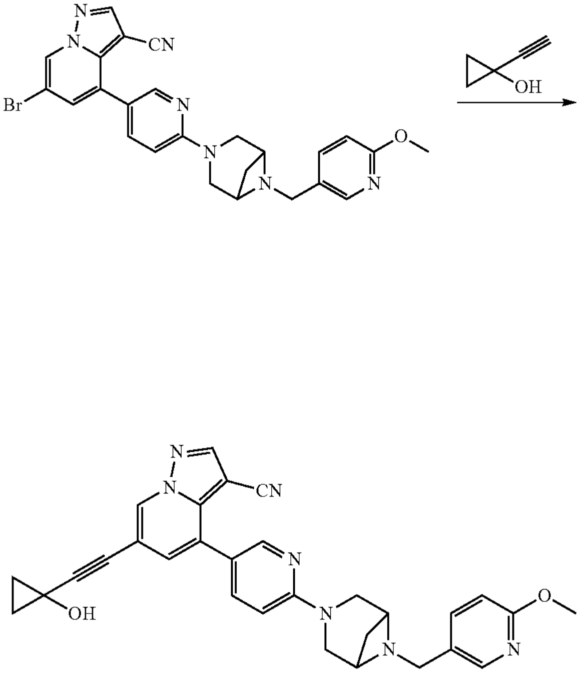

6-((1-Hydroxycyclopropyl)ethynyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and 1-ethynylcyclopropan-1-ol as raw material with reference to step 2 of embodiment 96.

MS m/z (ESI): 518.2 $[M+H]^+$.

Embodiment 109

6-(4-Fluoro-3-(fluoromethyl)-3-hydroxybut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

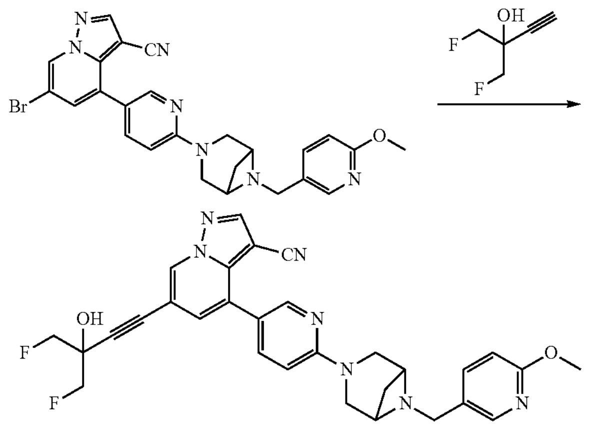

109

6-(4-Fluoro-3-(fluoromethyl)-3-hydroxybut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained by using 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and 1-fluoro-2-(fluoromethyl)but-3-yn-2-ol as raw material with reference to step 2 of embodiment 96.

MS m/z (ESI): 556.2 $[M+H]^+$.

Embodiment 110

4-(6-(6-((5-Fluoro-6-methoxypyridin-3-yl)methyl)-3,6-diazabicyclo[3.1.1]heptan-3-yl)pyridin-3-yl)-6-(3-(2-hydroxypropan-2-yl)azetidin-1-yl)pyrazolo[1,5-a]pyridine-3-carbonitrile

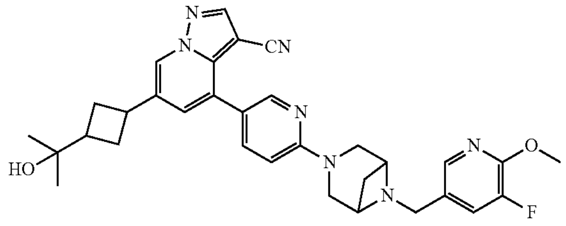 [SMILES: COc1ncc(CN2C3CC2CN(c2ccc(-c4cc(C5CC(C(C)(C)O)C5)cn5ncc(C#N)c45)cn2)C3)cc1F]

Step 1: 4-(6-(6-((5-fluoro-6-methoxypyridin-3-yl)methyl)-3,6-diazabicyclo[3.1.1]heptan-3-yl)pyridin-3-yl)-6-(3-(2-hydroxypropan-2-yl)azetidin-1-yl)pyrazolo[1,5-a]pyridine-3-carbonitrile

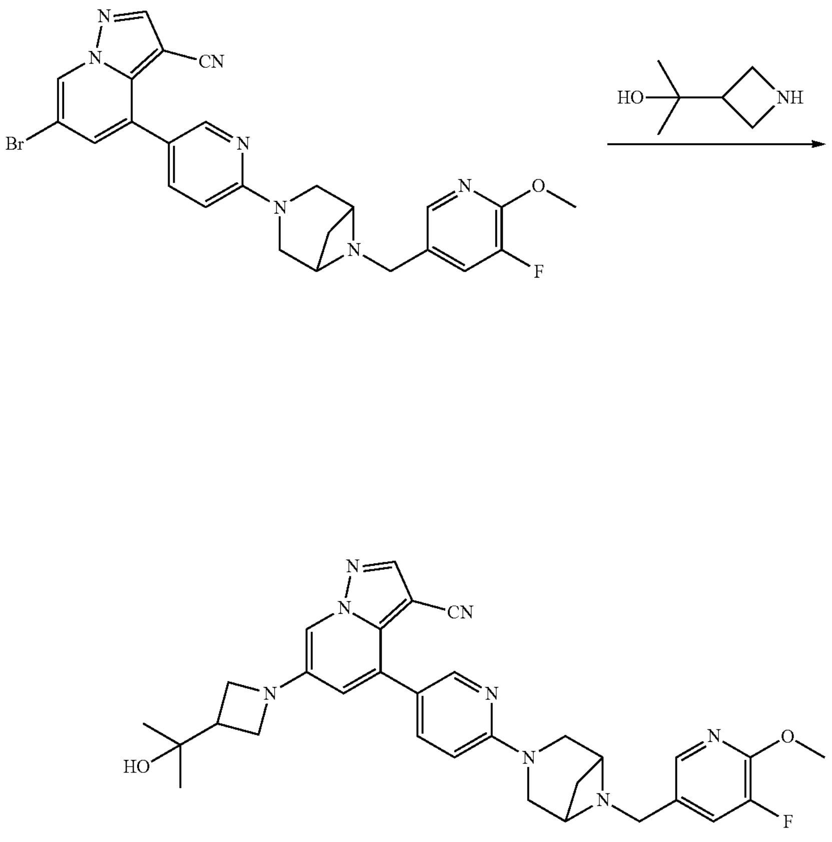

Tris(dibenzylideneacetone)dipalladium (5 mg, 0.005 mmol) and 4,5-bis(diphenylphosphino)-9,9-dimethylxanthene (3 mg, 0.005 mmol) was added to a mixed solution of 6-bromo-4-(6-(6-((5-fluoro-6-methoxypyridin-3-yl) methyl)-3,6-diazabicyclo[3.1.1]heptan-3-yl)pyridin-3-yl) pyrazolo[1,5-a]pyridine-3-carbonitrile (50 mg, 0.094 mmol), 2-(azetidin-3-yl)propan-2-ol (16 mg, 0.14 mmol), cesium carbonate (122 mg, 0.376 mmol) and toluene (3 mL); and the mixture was replaced with nitrogen and stirred at 130° C. for 2 hours under microwave; and after the reaction was completed, the mixture was cooled and filtered; then the filtrate was concentrated under reduced pressure to dryness and separated by preparative chromatography to obtain white solid 4-(6-(6-((5-fluoro-6-methoxypyridin-3-yl)methyl)-3,6-diazabicyclo[3.1.1]heptan-3-yl)pyridin-3-yl)-6-(3-(2-hydroxypropan-2-yl)azetidin-1-yl)pyrazolo[1,5-a]pyridine-3-carbonitrile (15 mg, yield was 28%).

MS m/z (ESI): 569.3 $[M+H]^+$.

$^1$H NMR (400 MHz, $CDCl_3$) δ 8.39 (d, J=2.1 Hz, 1H), 8.14 (s, 1H), 7.88 (s, 1H), 7.79 (dd, J=8.8, 2.3 Hz, 1H), 7.72 (d, J=1.6 Hz, 1H), 7.57 (s, 1H), 6.75 (d, J=1.7 Hz, 1H), 6.69 (d, J=8.7 Hz, 1H), 4.01 (s, 3H), 3.99-3.93 (m, 2H), 3.91-3.83 (m, 4H), 3.66 (s, 4H), 2.91-2.79 (m, 2H), 1.25 (s, 6H).

Embodiment 111

3-Chloro-N-(1-(5-(3-cyano-6-(3-(2-hydroxypropan-2-yl)azetidin-1-yl)pyrazolo[1,5-a]pyridin-4-yl)pyridin-2-yl)-4-methylpiperidin-4-yl)picolinamide

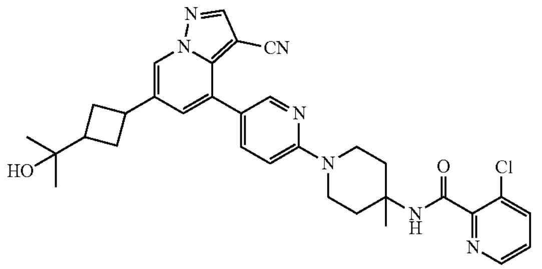 [SMILES: CC1(NC(=O)c2ncccc2Cl)CCN(c2ccc(-c3cc(C4CC(C(C)(C)O)C4)cn4ncc(C#N)c34)cn2)CC1]

3-Chloro-N-(1-(5-(3-cyano-6-(3-(2-hydroxypropan-2-yl) azetidin-1-yl)pyrazolo[1,5-a]pyridin-4-yl)pyridin-2-yl)-4-methylpiperidin-4-yl)picolinamide was obtained by using 2-(azetidin-3-yl)propan-2-ol and N-(1-(5-(6-bromo-3-cyanopyrazolo[1,5-a]pyridin-4-yl)pyridin-2-yl)-4-methylpiperidin-4-yl)-3-chloromethylpyridinamide as raw material with reference to step 1 of embodiment 110.

MS m/z (ESI): 585.2 $[M+H]^+$.

$^1$H NMR (400 MHz, $CDCl_3$) δ 8.46 (d, J=3.9 Hz, 1H), 8.34 (s, 1H), 8.13 (s, 1H), 7.94 (s, 1H), 7.83 (d, J=8.1 Hz, 2H), 7.71 (s, 1H), 7.38 (dd, J=8.1, 4.5 Hz, 1H), 6.77 (s, 1H), 4.14 (s, 2H), 3.96 (t, J=7.6 Hz, 2H), 3.85 (t, J=6.6 Hz, 2H), 3.48 (s, 2H), 2.48 (s, 2H), 1.89-1.80 (m, 2H), 1.25 (s, 3H), 1.24 (s, 6H).

Embodiment 112

6-(6-Hydroxy-6-methyl-2-azaspiro[3.3]heptan-2-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

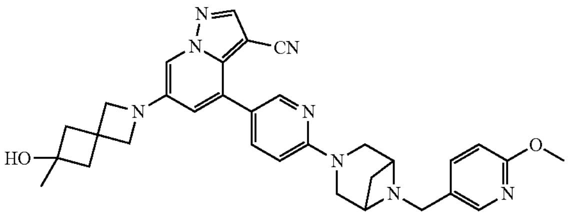 [SMILES: COc1ccc(CN2C3CC2CN(c2ccc(-c4cc(N5CC6(C5)CC(C)(O)C6)cn5ncc(C#N)c45)cn2)C3)cn1]

Step 1: 6-bromo-4-(6-(6-((6-methoxypyridin-3-yl) methyl)-3,6-diazabicyclo[3.1.1]heptan-3-yl)pyridin-3-yl)pyrazolo[1,5-a]pyridine-3-carbonitrile

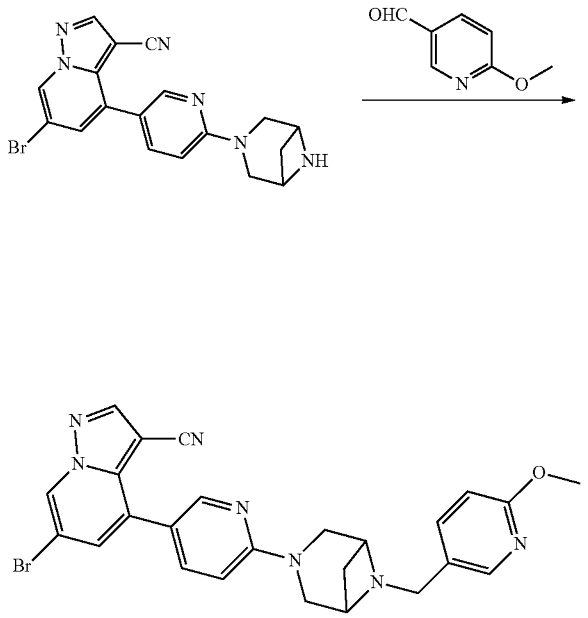

6-Bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 4-(6-(3,6-diazabicyclo[3.1.1]heptan-3-yl)pyridin-3-yl)-6-bromopyrazolo[1,5-a]pyridine-3-carbonitrile and 6-methoxynicotinaldehyde as raw materials with reference to step 9 of embodiment 11.

MS m/z (ESI): 516.1 $[M+H]^+$.

Step 2: 6-(6-hydroxy-6-methyl-2-azaspiro[3.3]heptan-2-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

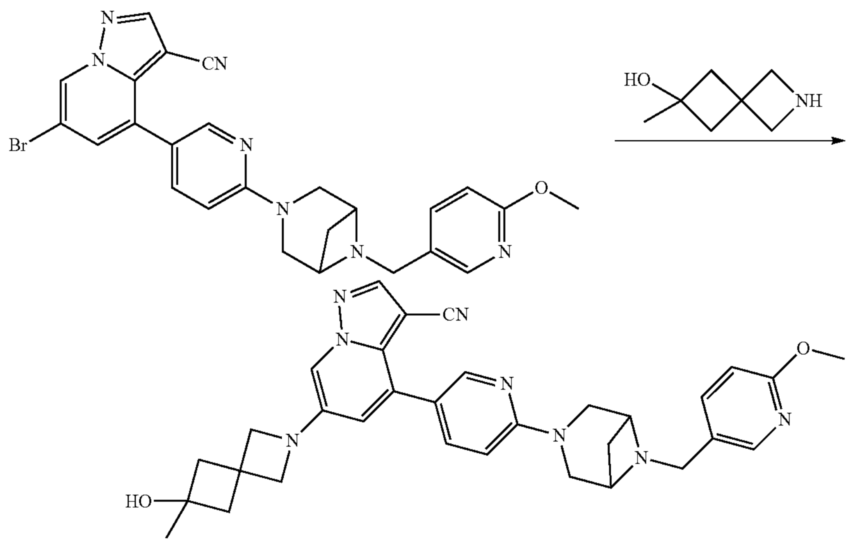

6-(6-Hydroxy-6-methyl-2-azaspiro[3.3]heptan-2-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-methyl-2-azaspiro[3.3]heptan-6-ol as raw material with reference to step 1 of embodiment 110.

MS m/z (ESI): 563.3 $[M+H]^+$.

$^1H$ NMR (400 MHz, $CDCl_3$) δ 8.38 (d, J=2.1 Hz, 1H), 8.14 (d, J=6.8 Hz, 2H), 7.89 (s, 1H), 7.80 (dd, J=8.7, 2.3 Hz, 1H), 7.68 (d, J=1.6 Hz, 1H), 6.76 (d, J=8.5 Hz, 1H), 6.71 (t, J=5.9 Hz, 2H), 4.01-3.93 (m, 10H), 3.74 (s, 4H), 2.96 (s, 1H), 2.39 (s, 4H), 1.40 (s, 3H).

Embodiment 113

3-Chloro-N-(1-(5-(3-cyano-6-(6-hydroxy-6-methyl-2-azaspiro[3.3]heptan-2-yl)pyrazolo[1,5-a]pyridin-4-yl)pyridin-2-yl)-4-methylpiperidin-4-yl)picolinamide

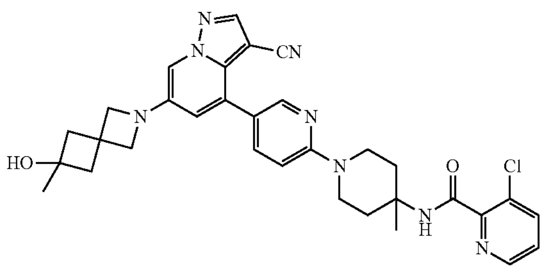 [SMILES: CC1(O)CC2(CN(c3cc(-c4ccc(N5CCC(C)(NC(=O)c6ncccc6Cl)CC5)nc4)c4c(C#N)cnn4c3)C2)C1]

3-Chloro-N-(1-(5-(3-cyano-6-(6-hydroxy-6-methyl-2-azaspiro[3.3]heptan-2-yl)pyrazolo[1,5-a]pyridin-4-yl)pyridin-2-yl)-4-methylpiperidin-4-yl)picolinamide was obtained by using 6-methyl-2-azaspiro[3.3]heptan-6-ol as raw material with reference to step 1 of embodiment 110.

MS m/z (ESI): 597.2 $[M+H]^+$.

$^1H$ NMR (400 MHz, CDCl3) δ 8.47 (s, 1H), 8.32 (s, 1H), 8.13 (s, 1H), 7.94 (s, 1H), 7.83 (d, J=8.6 Hz, 1H), 7.67 (s, 1H), 7.39 (d, J=4.6 Hz, 1H), 6.89 (s, 1H), 6.71 (s, 1H), 4.15 (s, 2H), 3.94 (d, J=5.8 Hz, 4H), 3.47 (s, 2H), 2.48 (s, 2H), 2.38 (s, 4H), 1.84 (s, 2H), 1.39 (s, 3H), 1.25 (s, 3H).

Embodiment 114

6-(3-Hydroxy-3-methylazetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

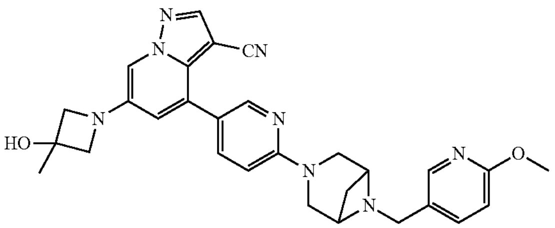 [SMILES: COc1ccc(CN2C3CC2CN(c2ccc(-c4cc(N5CC(C)(O)C5)cn5ncc(C#N)c45)cn2)C3)cn1]

6-(3-Hydroxy-3-methylazetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 3-methylazetidin-3-ol as raw material with reference to step 1 of embodiment 110.

MS m/z (ESI): 523.3 $[M+H]^+$.

$^1H$ NMR (400 MHz, $CDCl_3$) δ 8.40 (s, 1H), 8.15 (s, 3H), 7.82 (d, J=7.4 Hz, 1H), 7.74 (s, 1H), 6.80 (d, J=8.4 Hz, 1H), 6.75 (d, J=1.7 Hz, 1H), 6.72 (d, J=8.8 Hz, 1H), 4.21 (s, 2H), 4.01 (s, 2H), 3.93-3.92 (m, 7H), 3.84 (d, J=7.3 Hz, 4H), 1.68 (s, 3H).

Embodiment 115

6-(3-Hydroxy-3-methylpyrrolidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

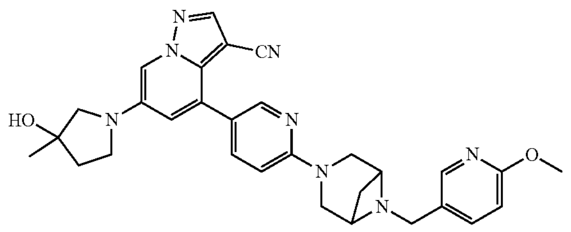 [SMILES: COc1ccc(CN2C3CC2CN(c2ccc(-c4cc(N5CCC(C)(O)C5)cn5ncc(C#N)c45)cn2)C3)cn1]

6-(3-Hydroxy-3-methylpyrrolidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 3-methylpyrrolidin-3-ol as raw material with reference to step 1 of embodiment 110.

MS m/z (ESI): 537.3 $[M+H]^+$.

$^1$H NMR (400 MHz, $CDCl_3$) δ 8.44 (s, 2H), 8.16 (m, 2H), 7.88 (d, J=6.7 Hz, 1H), 7.80 (s, 1H), 6.93 (s, 1H), 6.86 (d, J=8.8 Hz, 1H), 6.76 (d, J=8.6 Hz, 1H), 4.18-4.13 (m, 2H), 4.07-4.03 (m, 2H), 3.93 (s, 3H), 3.65-3.61 (m, 2H), 3.46-3.41 (m, 2H), 2.24-2.12 (m, 3H), 2.0-1.96 (m, 3H), 1.31 (s, 3H).

Embodiment 116

6-(4-Hydroxy-4-methylpiperidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

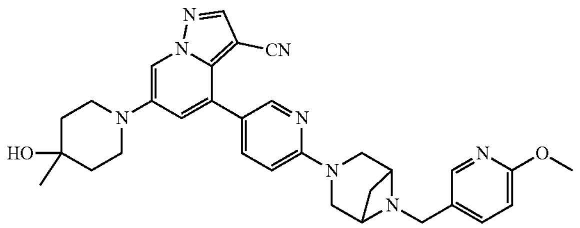 [SMILES: COc1ccc(CN2C3CC2CN(c2ccc(-c4cc(N5CCC(C)(O)CC5)cn5ncc(C#N)c45)cn2)C3)cn1]

6-(4-Hydroxy-4-methylpiperidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 4-methylpiperidin-4-ol as raw material with reference to step 1 of embodiment 110.

MS m/z (ESI): 551.3 $[M+H]^+$.

$^1$H NMR (400 MHz, $CDCl_3$) δ 8.41 (s, 1H), 8.18 (s, 1H), 8.14 (s, 1H), 8.07 (s, 2H), 7.82 (d, J=6.7 Hz, 1H), 7.22 (d, J=1.6 Hz, 1H), 6.79 (d, J=8.6 Hz, 1H), 6.71 (d, J=8.7 Hz, 1H), 3.99 (s, 2H), 3.93 (s, 3H), 3.85 (s, 4H), 3.36-3.32 (m, 2H), 3.23-3.15 (m, 2H), 1.85-1.74 (m, 6H), 1.35 (s, 3H).

Embodiment 117

6-((1-Cyanocyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

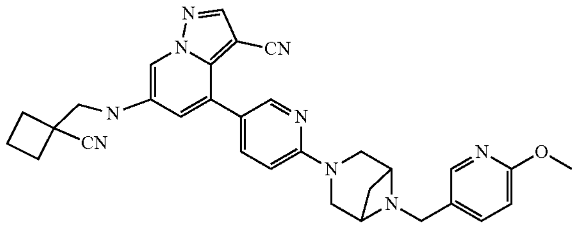 [SMILES: COc1ccc(CN2C3CC2CN(c2ccc(-c4cc(NCC5(C#N)CCC5)cn5ncc(C#N)c45)cn2)C3)cn1]

6-((1-Cyanocyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained with reference to embodiment 106.

MS m/z (ESI): 547.2 $[M+H]^+$.

Embodiment 118

6-((3-Cyanooxetan-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

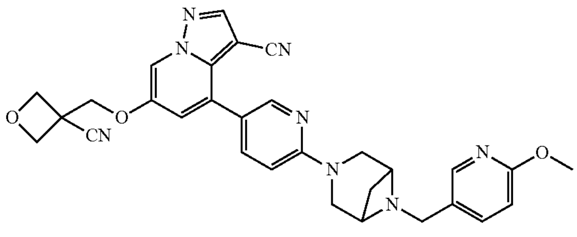 [SMILES: COc1ccc(CN2C3CC2CN(c2ccc(-c4cc(OCC5(C#N)COC5)cn5ncc(C#N)c45)cn2)C3)cn1]

6-((3-Cyanooxetan-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (12 mg, white solid, 29%) was obtained with reference to embodiment 106.

MS m/z (ESI): 549.2 $[M+H]^+$.

H NMR (400 MHz, DMSO) δ 8.83 (d, J=2.0 Hz, 1H), 8.64 (s, 1H), 8.42 (d, J=2.1 Hz, 1H), 8.06 (s, 1H), 7.86 (d, J=8.8 Hz, 1H), 7.68 (d, J=6.9 Hz, 1H), 7.40 (s, 1H), 6.81-6.76 (m, 2H), 4.93 (d, J=6.5 Hz, 2H), 4.70 (s, 2H), 4.68 (d, J=6.5 Hz, 2H), 3.82 (s, 3H), 3.67 (d, J=5.3 Hz, 2H), 3.53-3.47 (m, 6H), 2.01-1.99 (m, 2H).

Embodiment 119

6-(((1-Hydroxycyclopropyl)methyl)(methyl)amino)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

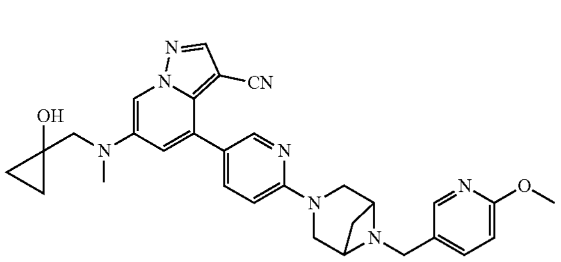 [SMILES: COc1ccc(CN2C3CC2CN(c2ccc(-c4cc(N(C)CC5(O)CC5)cn5ncc(C#N)c45)cn2)C3)cn1]

6-(((1-Hydroxycyclopropyl)methyl)(methyl)amino)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 1-((methylamino)methyl)cyclopropan-1-ol as raw material with reference to step 1 of embodiment 110.

MS m/z (ESI): 537.3 $[M+H]^+$.

Embodiment 120

6-(((1-Cyanocyclopropyl)methyl)amino)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

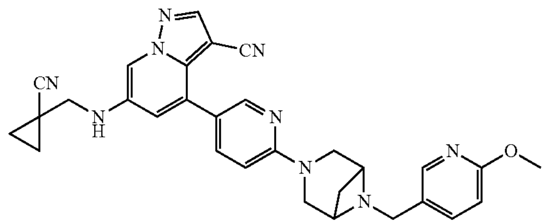 [SMILES: COc1ccc(CN2C3CC2CN(c2ccc(-c4cc(NCC5(C#N)CC5)cn5ncc(C#N)c45)cn2)C3)cn1]

6-(((1-Cyanocyclopropyl)methyl)amino)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 1-(aminomethyl)cyclopropane-1-carbonitrile as raw material with reference to step 1 of embodiment 110.

MS m/z (ESI): 532.3 $[M+H]^+$.

Embodiment 121

4-(6-(6-((6-Cyclopropoxypyridin-3-yl)methyl)-3,6-diazabicyclo[3.1.1]heptan-3-yl)pyridin-3-yl)-6-(3-(2-hydroxypropan-2-yl)azetidin-1-yl)pyrazolo[1,5-a]pyridine-3-carbonitrile

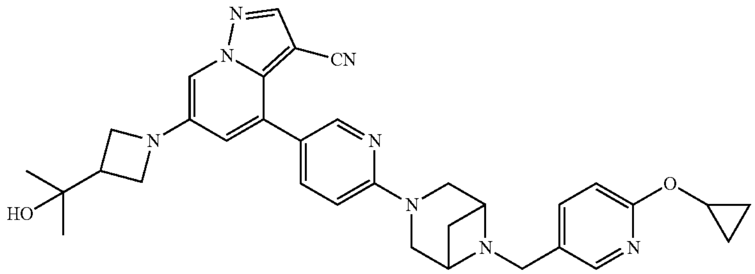

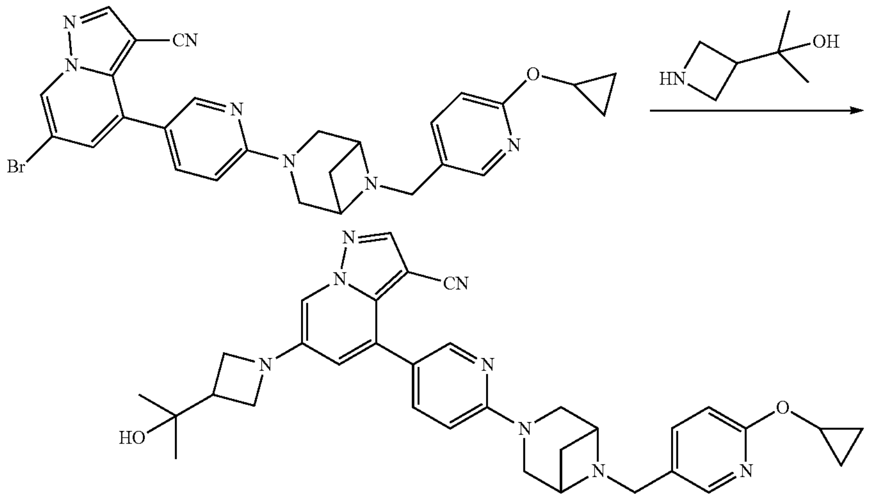

4-(6-(6-((6-Cyclopropoxypyridin-3-yl)methyl)-3,6-diazabicyclo[3.1.1]heptan-3-yl)pyridin-3-yl)-6-(3-(2-hydroxypropan-2-yl)azetidin-1-yl)pyrazolo[1,5-a]pyridine-3-carbonitrile was obtained by using 6-bromo-4-(6-(6-((6-cyclopropoxypyridin-3-yl)methyl)-3,6-diazabicyclo[3.1.1]heptan-3-yl)pyridin-3-yl)pyrazolo[1,5-a]pyridine-3-carbonitrile as raw materials with reference to step 2 of embodiment 110.

MS m/z (ESI): 577.2[M+H]+.

Embodiment 122

6-(3-(2-Hydroxypropan-2-yl)azetidin-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

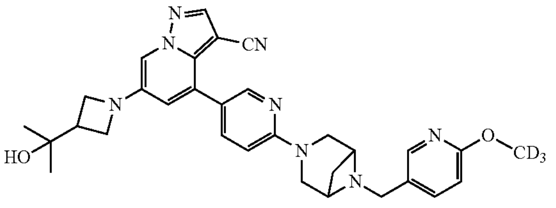 [SMILES: [2H]C([2H])([2H])Oc1ccc(CN2C3CC2CN(c2ccc(-c4cc(N5CC(C(C)(C)O)C5)cn5ncc(C#N)c45)cn2)C3)cn1]

6-(3-(2-Hydroxypropan-2-yl)azetidin-1-yl)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile (20 mg, yellow solid, 30%) was obtained by using 6-bromo-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile as raw material with reference to step 1 of embodiment 110.

MS m/z (ESI): 554.3 [M+H]+.

$^1$H NMR (400 MHz, MeOD) δ 8.32 (d, J=2.1 Hz, 1H), 8.24 (s, 1H), 8.08 (d, J=2.0 Hz, 1H), 7.84 (d, J=1.6 Hz, 1H), 7.82 (dd, J=8.8, 2.4 Hz, 1H), 7.71 (dd, J=8.6, 2.3 Hz, 1H), 6.92 (d, J=1.7 Hz, 1H), 6.87 (d, J=8.8 Hz, 1H), 6.78 (d, J=8.6 Hz, 1H), 3.97 (t, J=7.8 Hz, 2H), 3.91-3.85 (m, 4H), 3.79 (d, J=5.7 Hz, 2H), 3.65 (s, 1H), 3.62 (s, 3H), 2.92-2.84 (m, 1H), 2.71 (s, 1H), 1.70 (d, J=8.9 Hz, 1H), 1.21 (s, 6H).

Embodiment 123

N-(3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)-2-hydroxy-2-methylpropanamide

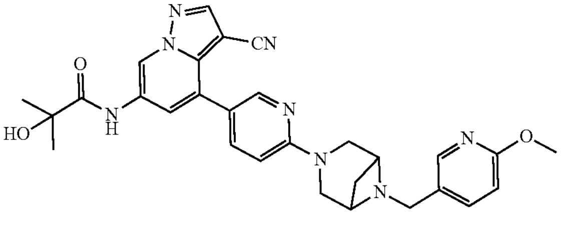 [SMILES: COc1ccc(CN2C3CC2CN(c2ccc(-c4cc(NC(=O)C(C)(C)O)cn5ncc(C#N)c45)cn2)C3)cn1]

Step 1: tert-butyl (3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)carbamate

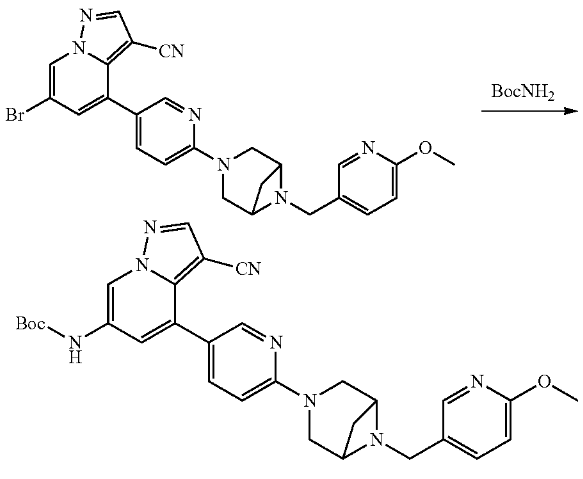

Tert-butyl (3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)carbamate was obtained by using tert-butyl carbamate as raw material with reference to step 1 of embodiment 110.

MS m/z (ESI): 553.3 [M+H]+.

Step 2: 6-amino-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

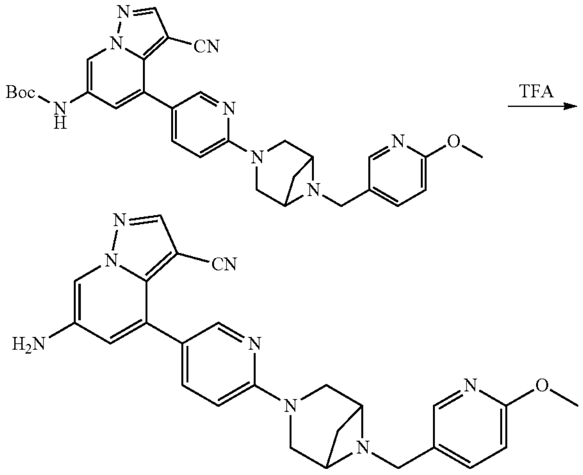

6-Amino-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using tert-butyl (3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)carbamate as raw material with reference to step 1 of embodiment 110.

MS m/z (ESI): 453.3 [M+H]+.

Step 3: N-(3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)-2-hydroxy-2-methylpropanamide

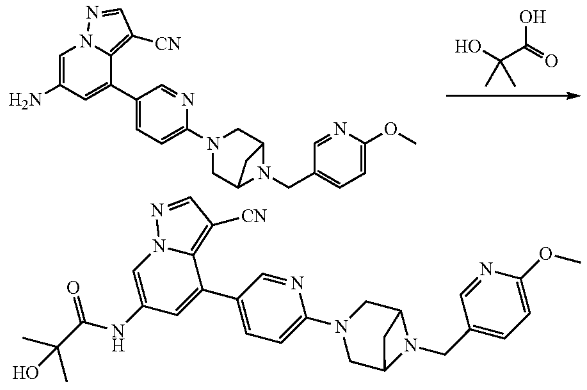

N-(3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)-2-hydroxy-2-methylpropanamide was obtained by using 2-hydroxy-2-methylpropanoic acid as raw material with reference to step 4 of embodiment 28.

MS m/z (ESI): 539.2 $[M+H]^+$.

Embodiment 124

6-((1-Aminocyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

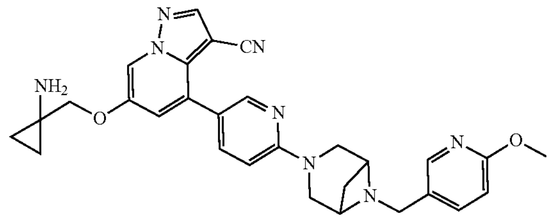 [SMILES: COc1ccc(CN2C3CC2CN(c2ccc(-c4cc(OCC5(N)CC5)cn5ncc(C#N)c45)cn2)C3)cn1]

Step 1: Preparation of tert-butyl (1-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxo methyl cyclopropyl)carbamate

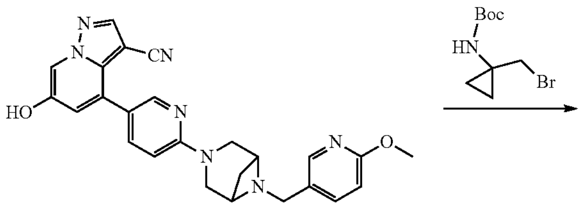

-continued

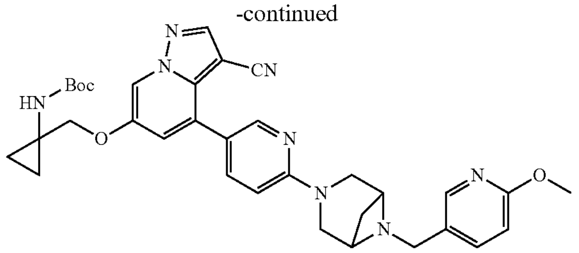

tert-butyl (1-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)cyclopropyl)carbamate was obtained by using tert-butyl (1-(bromomethyl)cyclopropyl)carbamate and 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile as raw materials with reference to step 5 of embodiment 37.

MS m/z (ESI): 623.3 $[M+H]^+$.

Step 2: Preparation of 6-((1-aminocyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

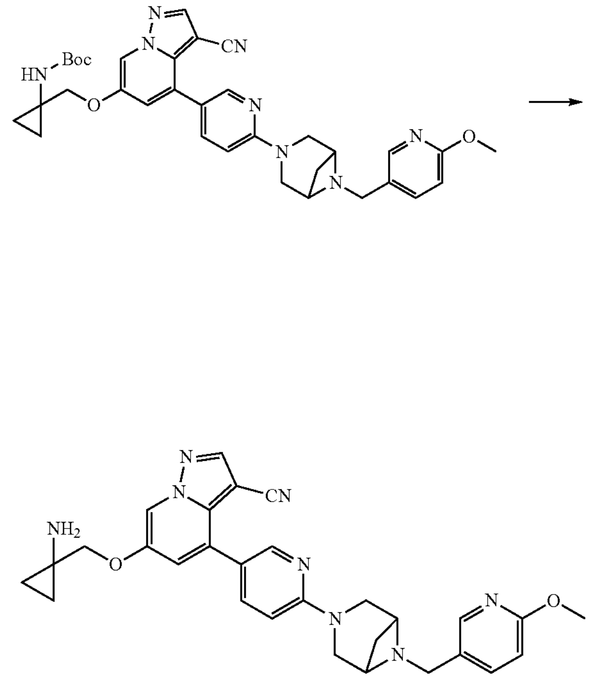

6-((1-Aminocyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using tert-butyl (1-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxo)methyl)cyclopropyl)carbamate as raw material with reference to step 4 of embodiment 43.

MS m/z (ESI): 523.3 $[M+H]^+$.

Embodiment 125

6-((Cis-3-hydroxy-3-methylcyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

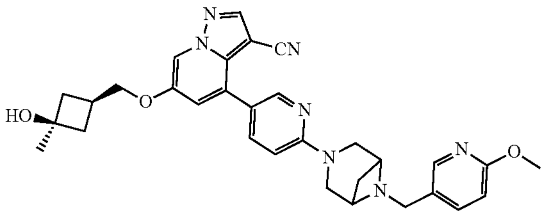 [SMILES: COc1ccc(CN2C3CC2CN(c2ccc(-c4cc(OC[C@H]5C[C@@](C)(O)C5)cn5ncc(C#N)c45)cn2)C3)cn1]

Step 1: cis-3-(hydroxymethyl)-1-methylcyclobutan-1-ol

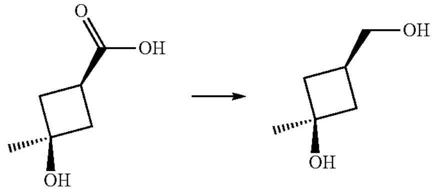

Borane-tetrahydrofuran solution (7.5 mL, 15 mmol, 2 M) was added dropwise to a solution of cis-3-hydroxy-3-methylcyclobutane-1-carboxylic acid (1 g, 7.68 mmol) in tetrahydrofuran (10 mL) at 0° C., then the mixture was stirred at room temperature for 2 hours; and after the reaction was completed, the reaction mixture was quenched with methanol, then extracted with ethyl acetate; the organic phase was combined, washed with saturated saline, dried over anhydrous sodium sulfate, filtered and concentrated under reduced pressure to dryness to obtain colorless oil cis-3-(hydroxymethyl)-1-methylcyclobutan-1-ol (600 mg, crude product).

Step 2: (cis-3-hydroxy-3-methylcyclobutyl)methyl 4-methylbenzenesulfonate

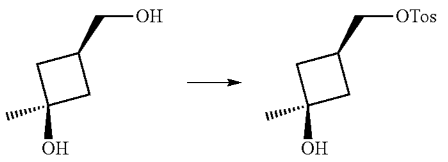

P-toluenesulfonyl chloride (987 mg, 5.17 mmol) was added to a mixed solution of cis-3-(hydroxymethyl)-1-methylcyclobutan-1-ol (600 mg, 5.17 mmol), triethylamine (1.04 g, 10.34 mmol) and dichloromethane (10 mL), and then the mixture was stirred at room temperature for 16 hours; after the reaction was completed, the reaction mixture was quenched with water, and then extracted with ethyl acetate; the organic phase was combined, washed with saturated saline, dried over anhydrous sodium sulfate, filtered, concentrated under reduced pressure to dryness, and then separated by column chromatography to obtain colorless oil (cis-3-hydroxy-3-methylcyclobutyl)methyl 4-methylbenzenesulfonate (800 mg, yield was 57%).

Step 3: 6-((cis-3-hydroxy-3-methylcyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

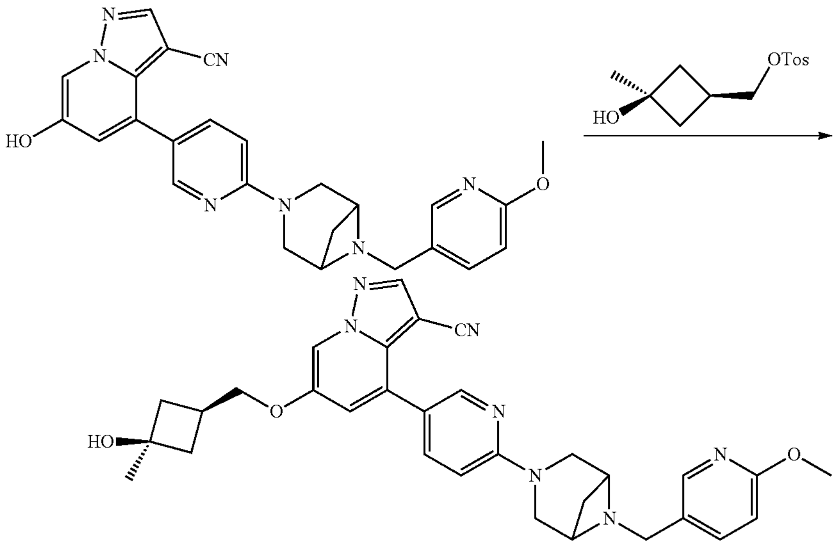

6-((Cis-3-hydroxy-3-methylcyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (cis-3-hydroxy-3-methylcyclobutyl)methyl 4-methylbenzenesulfonate as raw materials with reference to step 2 of embodiment 106.

MS m/z (ESI): 552.3[M+H]$^+$.

$^1$H NMR (400 MHz, $CDCl_3$) δ 8.41 (d, J=1.9 Hz, 1H), 8.21 (s, 1H), 8.13 (s, 2H), 7.87-7.73 (m, 2H), 7.13 (d, J=1.6 Hz, 1H), 6.75 (d, J=8.5 Hz, 1H), 6.70 (d, J=8.8 Hz, 1H), 4.03 (d, J=5.8 Hz, 2H), 3.92 (s, 7H), 3.70 (s, 4H), 2.89 (s, 1H), 2.41-2.36 (m, 1H), 2.32-2.27 (m, 2H), 2.05-2.00 (m, 3H), 1.45 (s, 3H).

Embodiment 126

6-((3-(Hydroxymethyl)bicyclo[1.1.1]pentan-1-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

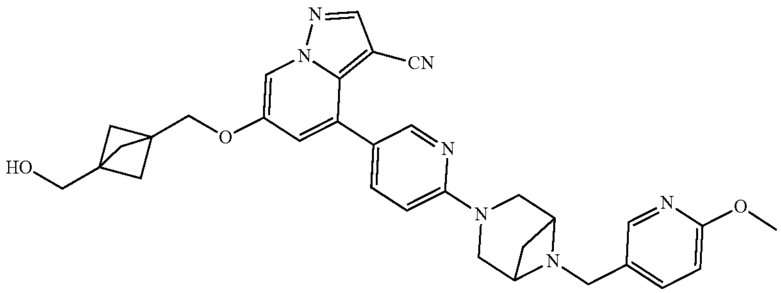 [SMILES: COc1ccc(CN2C3CC2CN(c2ccc(-c4cc(OCC56CC(CO)(C5)C6)cn5ncc(C#N)c45)cn2)C3)cn1]

Step 1: bicyclo[1.1.1]pentane-1,3-diyldimethanol

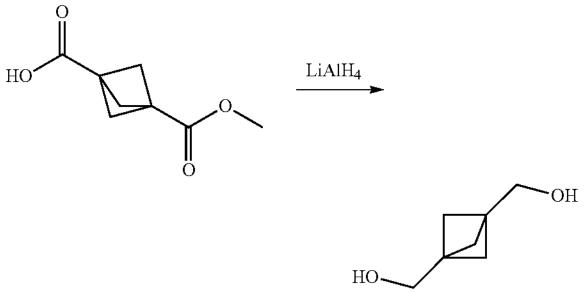

Lithium aluminum hydride (670 mg, 17.63 mmol) was added to a solution of 3-(methyl ester <methoxycarbonyl>) bicyclo[1.1.1]pentane-1-carboxylic acid (1 g, 5.88 mmol) in tetrahydrofuran (10 mL) at 0° C., then the mixture was warmed to room temperature and stirred for 16 hours; after the reaction was completed, the reaction mixture was quenched with sodium sulfate decahydrate, filtered, and the filtrate was concentrated under reduced pressure to dryness to obtain colorless oil bicyclo[1.1.1]pentane-1,3-diyldimethanol (640 mg, 85%).

$^1$H NMR (400 MHz, DMSO) δ 4.39 (t, J=5.5 Hz, 2H), 3.35 (d, J=5.5 Hz, 4H), 1.45 (s, 6H).

Step 2: (3-(hydroxymethyl)bicyclo[1.1.1]pentan-1-yl)methyl 4-methylbenzenesulfonate

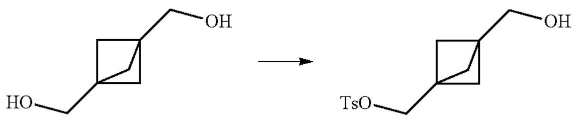 [SMILES: OCC12CC(CO)(C1)C2 ; Cc1ccc(S(=O)(=O)OCC23CC(CO)(C2)C3)cc1]

(3-(Hydroxymethyl)bicyclo[1.1.1]pentan-1-yl)methyl 4-methylbenzenesulfonate was obtained by using bicyclo[1.1.1]pentane-1,3-diyldimethanol as raw material with reference to step 2 of embodiment 125.

Step 3: 6-((3-(hydroxymethyl)bicyclo[1.1.1]pentan-1-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (E)-6-(3-hydroxy-3-methylbut-1-en-1-yl)-4-(6-(6-((6-methoxy-d3)pyridin-3-yl)methyl)-3,6-diazabicyclo[3.1.1]heptan-3-yl)pyridin-3-yl)pyrazolo[1,5-a]pyridine-3-carbonitrile (10 mg, white solid, 30%) was obtained by using 6-bromo-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile and (E)-2-methyl-4-(4,4,5,5-tetramethyl-1,3,2-dioxaborolan-2-yl)but-3-en-2-ol as raw materials with reference to step 8 of embodiment 1.

MS m/z (ESI): 522.3 [M+H]$^+$.

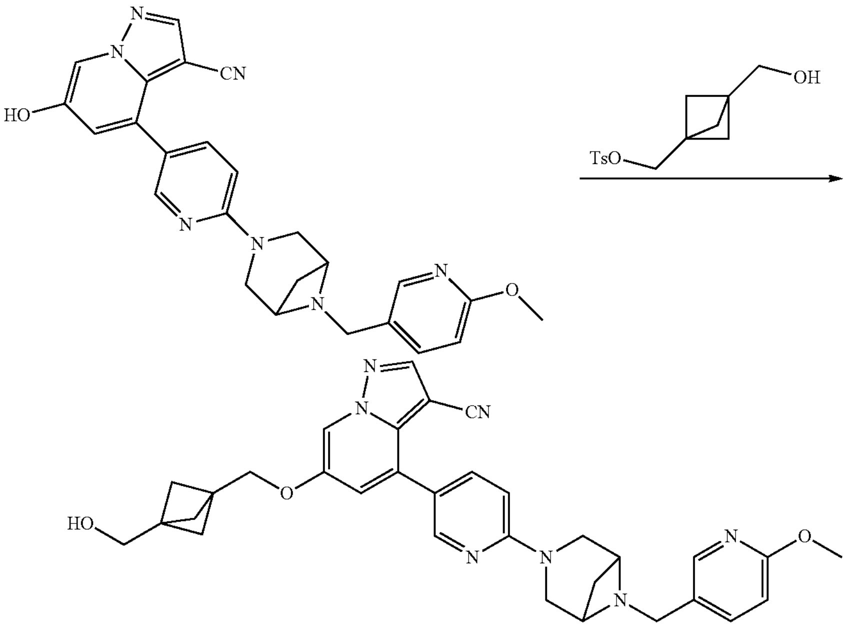

6-((3-(Hydroxymethyl)bicyclo[1.1.1]pentan-1-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (3-(hydroxymethyl)bicyclo[1.1.1]pentan-1-yl)methyl 4-methylbenzenesulfonate as raw materials with reference to step 2 of embodiment 106.

MS m/z (ESI): 564.3[M+H]$^+$.

$^1$H NMR (400 MHz, MeOD) δ 8.71 (s, 1H), 8.40 (s, 1H), 8.36 (d, J=2.1 Hz, 1H), 8.09 (s, 1H), 7.86 (dd, J=8.8, 2.3 Hz, 1H), 7.72 (dd, J=8.5, 2.3 Hz, 1H), 7.64 (s, 1H), 6.89 (d, J=8.9 Hz, 1H), 6.78 (d, J=8.6 Hz, 1H), 6.65 (q, J=16.1 Hz, 2H), 3.91 (s, 1H), 3.88 (s, 4H), 3.79 (d, J=5.5 Hz, 2H), 3.67-3.62 (m, 4H), 2.71 (s, 1H), 1.71 (d, J=9.0 Hz, 1H), 1.40 (s, 6H).

Embodiment 127

(E)-6-(3-hydroxy-3-methylbut-1-en-1-yl)-4-(6-(6-((6-methoxy-d3)pyridin-3-yl)methyl)-3,6-diazabicyclo[3.1.1]heptan-3-yl)pyridin-3-yl)pyrazolo[1,5-a]pyridine-3-carbonitrile

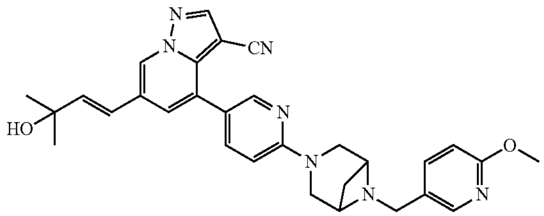 [SMILES: COc1ccc(CN2C3CC2CN(c2ccc(-c4cc(/C=C/C(C)(C)O)cn5ncc(C#N)c45)cn2)C3)cn1]

Embodiment 128

6-((3-Hydroxybicyclo[1.1.1]pentan-1-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

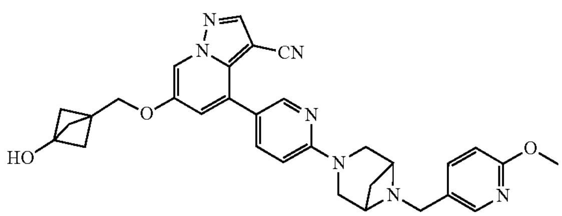 [SMILES: COc1ccc(CN2C3CC2CN(c2ccc(-c4cc(OCC56CC(O)(C5)C6)cn5ncc(C#N)c45)cn2)C3)cn1]

Step 1: 6-((3-hydroxybicyclo[1.1.1]pentan-1-yl) methoxy)-4-(6-(6-((6-methoxypyridin-3-yl)methyl)-3,6-diazabicyclo[3.1.1]heptan-3-yl)pyridin-3-yl) pyrazolo[1,5-a]pyridine-3-carbonitrile

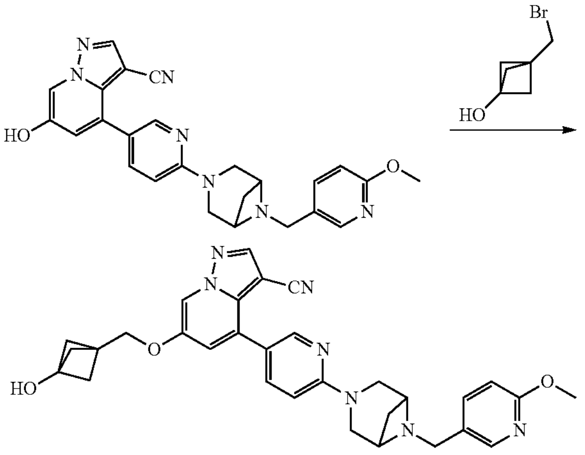

A mixture of 6-hydroxy-4-(6-(6-((6-methoxypyridin-3-yl)methyl)-3,6-diazabicyclo[3.1.1]heptan-3-yl)pyridin-3-yl) pyrazolo[1,5-a]pyridine-3-carbonitrile (50 mg, 0.11 mmol), 3-(bromomethyl)bicyclo[1.1.1]pentan-1-ol (29 mg, 0.17 mmol), potassium carbonate (46 mg, 0.33 mmol) and acetonitrile (5 mL) was stirred at 70° C. for 2 hour, then the mixture was cooled to room temperature and filtered, and the filtrate was concentrated under reduced pressure to dryness and separated by preparative chromatography to obtain 6-((3-hydroxybicyclo[1.1.1]pentan-1-yl)methoxy)-4-(6-(6-((6-methoxypyridin-3-yl)methyl)-3,6-diazabicyclo[3.1.1] heptan-3-yl)pyridin-3-yl)pyrazolo[1,5-a]pyridine-3-carbonitrile (10 mg, yield was 17%).

MS m/z (ESI): 550.2 $[M+H]^+$.

$^1H$ NMR (400 MHz, $CDCl_3$) δ 8.45 (s, 1H), 8.25-8.15 (m, 3H), 7.85 (d, J=4.0 Hz, 1H), 7.17 (s, 1H), 6.84 (d, J=9.2 Hz, 1H), 6.74 (d, J=7.8 Hz, 2H), 4.09 (s, 2H), 4.02 (s, 2H), 3.94 (s, 3H), 3.24-3.19 (m, 2H), 2.93-2.88 (m, 2H), 2.24-2.20 (m, 2H), 1.58 (s, 6H).

Embodiment 129

6-(4-Hydroxy-4-methylpent-1-yn-1-yl)-4-(6-(6-((6-methoxypyridin-3-yl)methyl)-3,6-diazahicyclo [3.1.1]heptan-3-yl)pyridin-3-yl)pyrazol[1,5-a]pyridine-3-carbonitrile

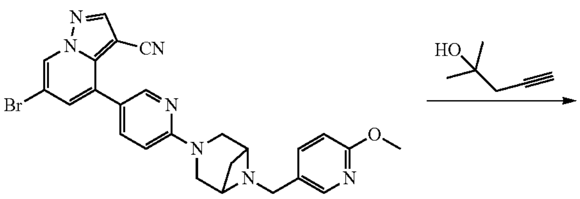

-continued

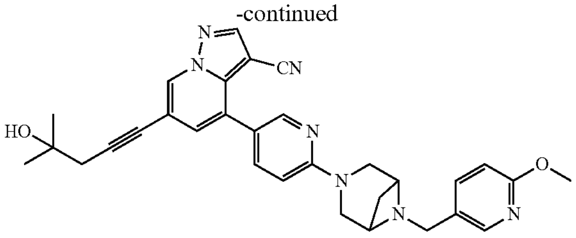

6-(4-Hydroxy-4-methylpent-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 2-methylpent-4-yn-2-ol as raw material with reference to step 2 of embodiment 31.

MS m/z (ESI): 534.3 $[M+H]^+$.

$^1H$ NMR (400 MHz, $CDCl_3$) δ 8.62 (s, 1H), 8.41 (d, J=2.1 Hz, 1H), 8.30 (s, 1H), 8.13 (s, 1H), 7.78 (dd, J=8.8, 2.4 Hz, 2H), 7.31 (s, 1H), 6.75 (d, J=8.6 Hz, 1H), 6.70 (d, J=8.8 Hz, 1H), 3.98-3.93 (m, 7H), 3.72 (s, 4H), 2.66 (s, 2H), 1.41 (s, 6H).

Embodiment 130

6-((1-Aminocyclopropyl)ethynyl)-4-(6-(6-((6-methoxypyridin-3-yl)methyl)-3,6-diazabicyclo [3.1.1]heptan-3-yl)pyridin-3-yl)pyrazolo[1,5-a]pyridine-3-carbonitrile

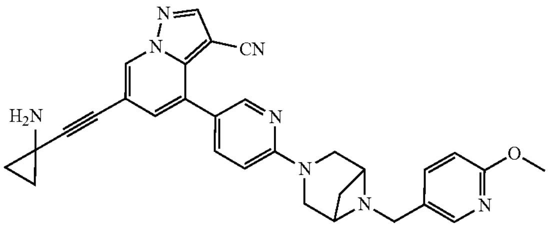 [SMILES: COc1ccc(CN2C3CC2CN(c2ccc(-c4cc(C#CC5(N)CC5)cn5ncc(C#N)c45)cn2)C3)cn1]

6-((1-Aminocyclopropyl)ethynyl)-4-(6-(6-((6-methoxypyridin-3-yl)methyl)-3,6-diazabicyclo[3.1.1]heptan-3-yl) pyridin-3-yl)pyrazolo[1,5-a]pyridine-3-carbonitrile was obtained by using 1-ethynylcyclopropane-1-amine as raw material with reference to step 2 of embodiment 31.

MS m/z (ESI): 517.2 $[M+H]^+$.

Embodiment 131

6-(3-Hydroxy-3-methylbut-1-yn-1-yl)-4-(6-((3S, 5R)-4-((6-methoxypyridin-3-yl)methyl)-3,5-dimethylpiperazin-1-yl)pyridin-3-yl)pyrazolo[1,5-a]pyridine-3-carbonitrile

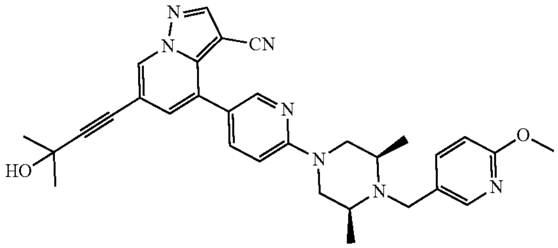 [SMILES: COc1ccc(CN2[C@H](C)CN(c3ccc(-c4cc(C#CC(C)(C)O)cn5ncc(C#N)c45)cn3)C[C@@H]2C)cn1]

Step 1: tert-butyl (3S,5R)-4-((6-methoxypyridin-3-yl)methyl)-3,5-dimethylpiperazine-1-carboxylate

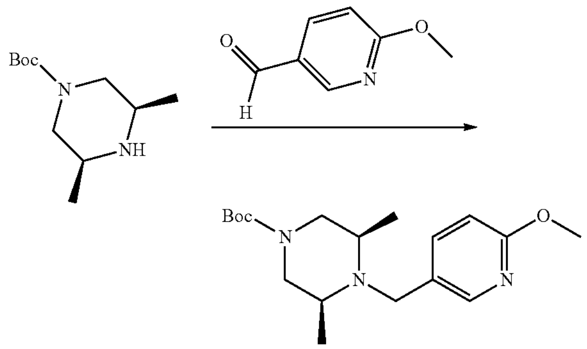

Tert-butyl (3S,5R)-4-((6-methoxypyridin-3-yl)methyl)-3,5-dimethylpiperazine-1-carboxylate was obtained by using tert-butyl (3S,5R)-3,5-dimethylpiperazine-1-carboxylate and 6-methoxynicotinaldehyde as raw materials with reference to step 9 of embodiment 11.

MS m/z (ESI): 336.2[M+H]$^+$.

Step 2: (2S,6R)-1-((6-methoxypyridin-3-yl)methyl)-2,6-dimethylpiperazine

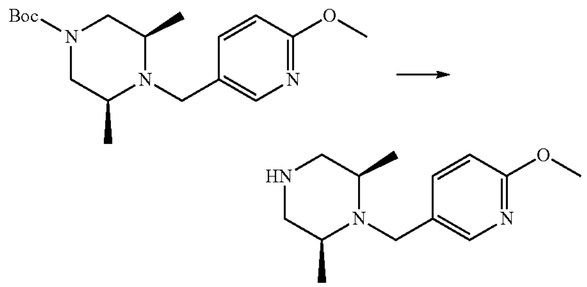

(2S,6R)-1-((6-methoxypyridin-3-yl)methyl)-2,6-dimethylpiperazine was obtain by using tert-butyl (3S,5R)-4-((6-methoxypyridin-3-yl)methyl)-3,5-dimethylpiperazine-1-carboxylate as raw material with reference to step 8 of embodiment 11.

MS m/z (ESI): 236.2[M+H]$^+$.

Step 3: 6-bromo-4-(6-((3S,5R)-4-((6-methoxypyridin-3-yl)methyl)-3,5-dimethylpiperazin-1-yl)pyridin-3-yl)pyrazolo[1,5-a]pyridine-3-carbonitrile

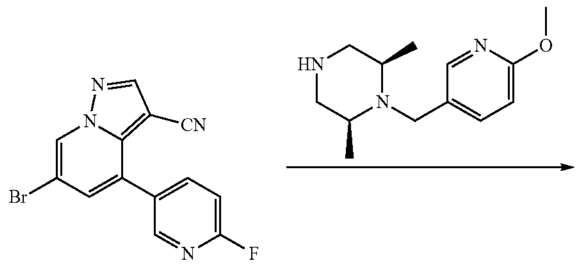

-continued

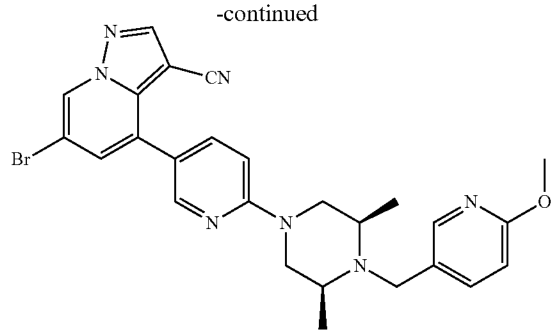

6-Bromo-4-(6-((3S,5R)-4-((6-methoxypyridin-3-yl)methyl)-3,5-dimethylpiperazin-1-yl)pyridin-3-yl)pyrazolo[1,5-a]pyridine-3-carbonitrile was obtained by using 6-bromo-4-(6-fluoropyridin-3-yl)pyrazolo[1,5-a]pyridine-3-carbonitrile and (2R,6S)-1-((6-methoxypyridin-3-yl)methyl)-2,6-dimethylpiperazine as raw materials with reference to step 7 of embodiment 11

MS m/z (ESI): 532.1[M+H]$^+$.

Step 4: 6-(3-hydroxy-3-methylbut-1-yn-1-yl)-4-(6-((3S,5R)-4-((6-methoxypyridin-3-yl)methyl)-3,5-dimethylpiperazin-1-yl)pyridin-3-yl)pyrazolo[1,5-a]pyridine-3-carbonitrile

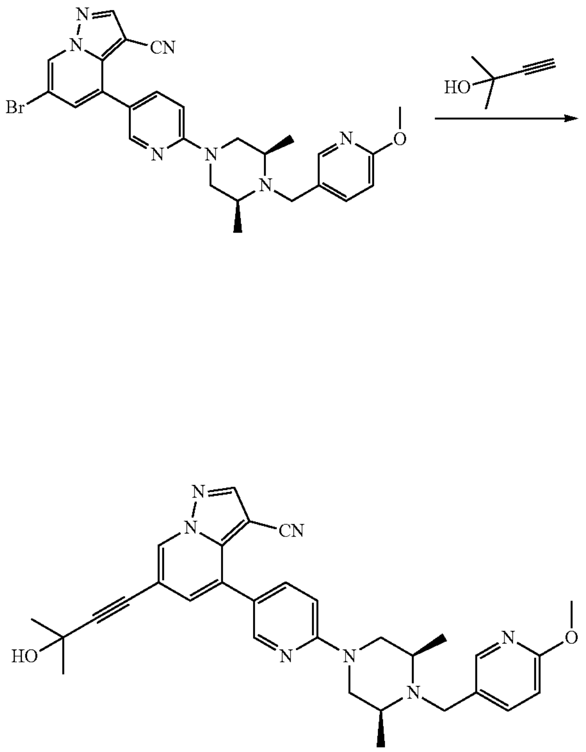

6-(3-Hydroxy-3-methylbut-1-yn-1-yl)-4-(6-((3S,5R)-4-((6-methoxypyridin-3-yl)methyl)-3,5-dimethylpiperazin-1-yl)pyridin-3-yl)pyrazolo[1,5-a]pyridine-3-carbonitrile (white solid) was obtained by using 6-bromo-4-(6-((3S,5R)-4-((6-methoxypyridin-3-yl)methyl)-3,5-dimethylpiperazin-1-yl)pyridin-3-yl)pyrazolo[1,5-a]pyridine-3-carbonitrile as raw material with reference to step 2 of embodiment 31.

MS m/z (ESI): 536.3[M+H]$^+$.

Embodiment 132

6-(3-hydroxy-3-methylbut-1-yn-1-yl)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile

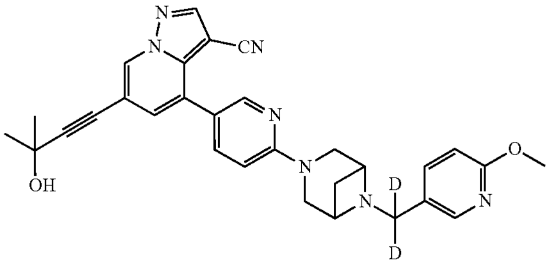 [SMILES: [2H]C([2H])(c1ccc(OC)nc1)N1C2CC1CN(c1ccc(-c3cc(C#CC(C)(C)O)cn4ncc(C#N)c34)cn1)C2]

Step 1: (6-methoxypyridin-3-yl)methan-d2-ol

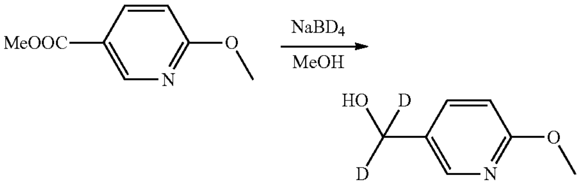

Methyl 6-methoxynicotinate (500 mg, 3 mmol) was dissolved in 10 mL of MeOH, and sodium boron deuteride (187 mg, 4.5 mmol) was added at 0° C., and the mixture was stirred at room temperature for 3 hours. 10 mL of water was added, and the mixture was extracted with ethyl acetate (20 mL*3). The organic phase was washed with saturated saline, dried over anhydrous sodium sulfate. The residue was filtered, evaporated to dryness; and the crude product was separated by column chromatography (eluted with petroleum ether/ethyl acetate=10/1) to obtain (6-methoxypyridin-3-yl)methan-d2-ol (330 mg, yield was 78%).

MS m/z (ESI): 142.2 [M+H]+.

Step 2: 5-(bromomethyl-d2)-2-methoxypyridine

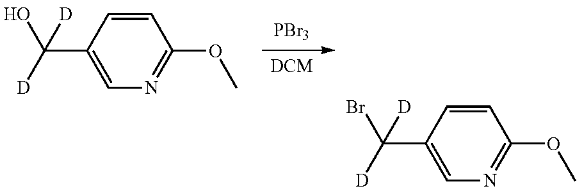

(6-Methoxypyridin-3-yl)methan-d2-ol (330 mg, 2.3 mmol) was dissolved in 10 mL of DCM, and $Pbr3_3$ (824 mg, 3 mmol) was added at 0° C. under the protection of nitrogen, and the mixture was stirred at room temperature for 3 hours. 10 mL of water was added, and the mixture was extracted with ethyl acetate (20 mL*3). The organic phase was washed with saturated saline, dried over anhydrous sodium sulfate. The residue was filtered, evaporated to dryness; and the crude product was separated by column chromatography (eluted with petroleum ether/ethyl acetate=10/1) to obtain 5-(bromomethyl-d2)-2-methoxypyridine (375 mg, yield was 80%).

MS m/z (ESI): 204.0 [M+H]+.

Step 3: 6-bromo-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile

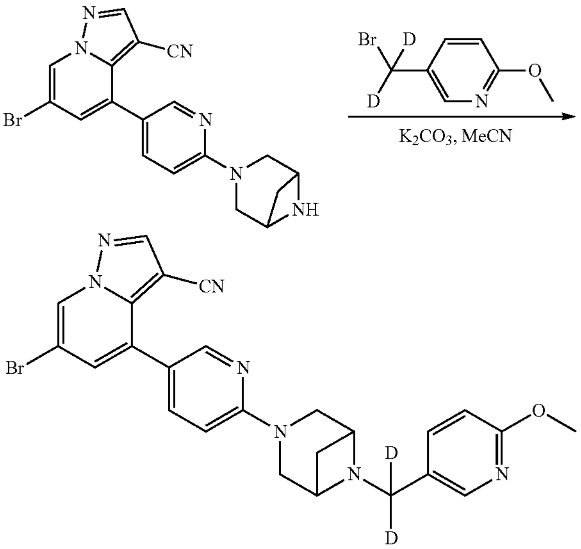

5-(Bromomethyl-d2)-2-methoxypyridine (370 mg, 1.8 mmol), 4-(6-(3,6-diazabicyclo[3.1.1]heptan-3-yl)pyridin-3-yl)-6-bromopyrazolo[1,5-a]pyridine-3-carbonitrile (605 mg, 1.5 mmol), potassium carbonate (621 mg, 4.5 mmol) were dissolved in 20 mL, and the reaction was carried out at 80° C. for 3 hours under the protection of nitrogen. 10 mL of water was added, and the mixture was extracted with ethyl acetate (20 mL*3). The organic phase was washed with saturated saline, dried over anhydrous sodium sulfate. The residue was filtered and evaporated to dryness, and the crude product was separated by column chromatography (eluted with dichloromethane/methanol=10/1) to obtain 6-bromo-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile (426 mg, yield was 55%).

MS m/z (ESI): 518.1 [M+H]+.

Step 4: 6-(3-hydroxy-3-methylbut-1-yn-1-yl)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile

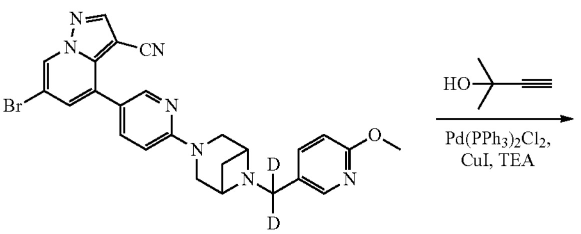

-continued

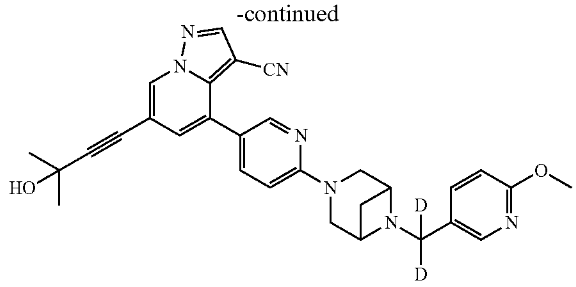

6-(3-Hydroxy-3-methylbut-1-yn-1-yl)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile (14 mg, white solid, yield was 26%) was obtained with reference to step 2 of embodiment 31.

MS m/z (ESI): 522.2 [M+H]$^+$.

Embodiment 133

4-(6-(6-((6-Cyclopropoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile

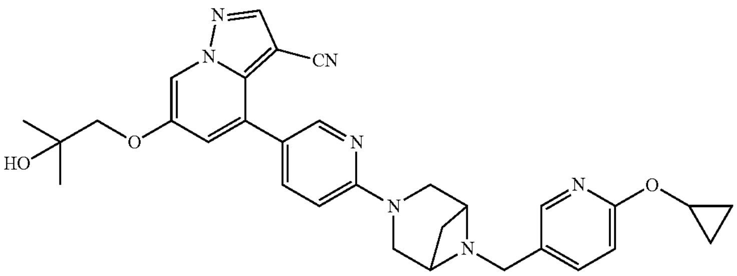

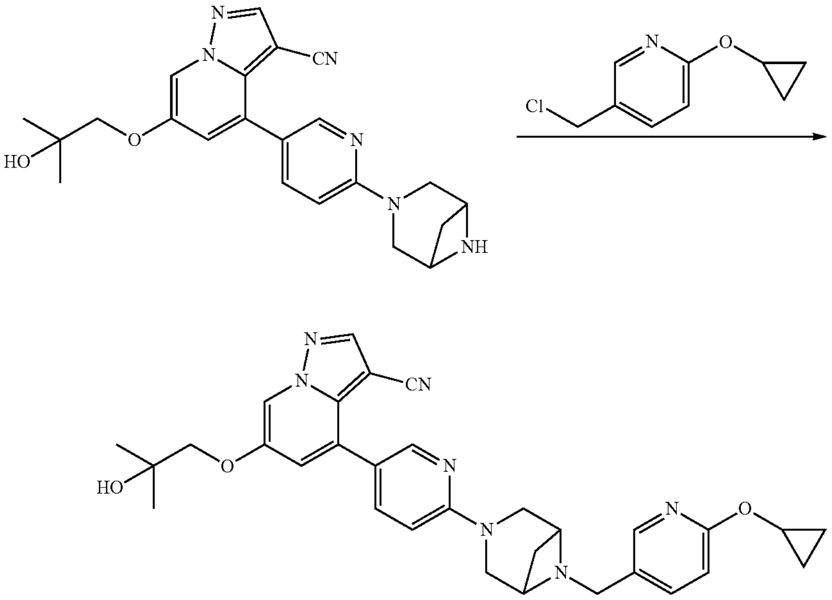

5-(Chloromethyl)-2-cyclopropoxypyridine (91 mg, 0.495 mmol) and 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (200 mg, 0.495 mmol) were dissolved in DMSO (15 mL), and cesium carbonate (322 mg, 0.989 mmol) was added thereto. The reaction was stirred at 90° C. for 2 hours. Water was added to the reaction mixture, and then the mixture was extracted with ethyl acetate. The organic phase was dried and evaporated to dryness. The crude product was purified by prep-HPLC to obtain 4-(6-(6-((6-cyclopropoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (33.6 mg, yield was 12%).

MS m/z (ESI): 552.2 [M+H]$^+$.

$^1$H NMR (400 MHz, DMSO-d6) δ 8.68 (d, J=2.0 Hz, 1H), 8.59 (s, 1H), 8.41 (d, J=2.5 Hz, 1H), 8.10 (d, J=2.4 Hz, 1H), 7.85 (dd, J=8.8, 2.6 Hz, 1H), 7.70 (dd, J=8.5, 2.4 Hz, 1H), 7.31 (d, J=2.1 Hz, 1H), 6.80 (dd, J=8.7, 3.9 Hz, 2H), 4.72 (s, 1H), 4.21-4.11 (m, 1H), 3.88 (s, 2H), 3.80-3.64 (m, 4H), 3.62-3.47 (m, 4H), 2.55-2.53 (m, 1H), 1.59 (d, J=8.4 Hz, 1H), 1.23 (s, 6H), 0.79-0.71 (m, 2H), 0.68-0.59 (m, 2H).

Embodiment 134

6-((1-Hydroxycyclopropyl)ethynyl)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile

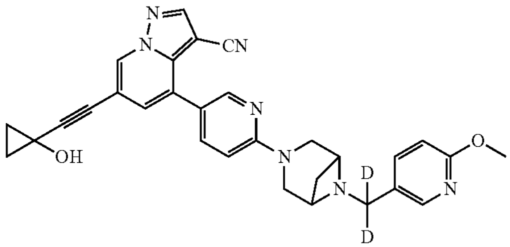

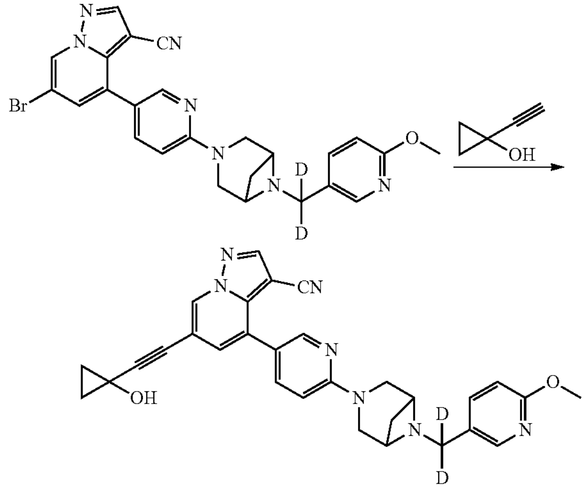

6-((1-Hydroxycyclopropyl)ethynyl)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile was obtained by using 6-bromo-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile and 1-ethynylcyclopropan-1-ol as raw materials with reference to embodiment 95.

MS m/z (ESI): 520.2 $[M+H]^+$.

Embodiment 135

6-((3-Hydroxybicyclo[1.1.1]pentan-1-yl)methoxy)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile

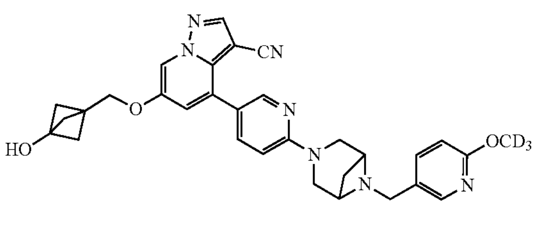

6-((3-Hydroxybicyclo[1.1.1]pentan-1-yl)methoxy)-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-(methoxy-d3)pyridin-3-yl)methyl)-3,6-diazabicyclo[3.1.1]heptan-3-yl)pyridin-3-yl)pyrazolo[1,5-a]pyridine-3-carbonitrile and 3-(bromomethyl)bicyclo[1.1.1]pentan-1-ol as raw materials with reference to step 1 of embodiment 131.

MS m/z (ESI): 553.3 $[M+H]^+$.

Embodiment 136

6-((1-Cyanocyclopropyl)methoxy)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile

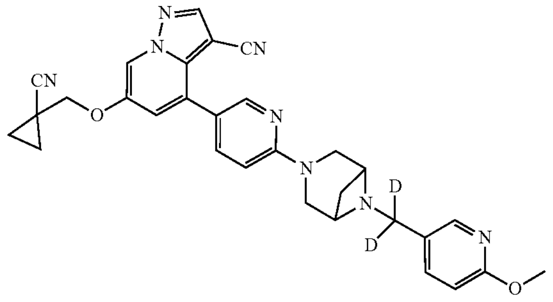 [SMILES: [2H]C([2H])(c1ccc(OC)nc1)N1C2CC1CN(c1ccc(-c3cc(OCC4(C#N)CC4)cn4ncc(C#N)c34)cn1)C2]

Step 1: 3-(5-bromopyridin-2-yl)-6-((6-methoxypyridin-3-yl)methyl-d2)-3,6-diazabicyclo[3.1.1]heptane

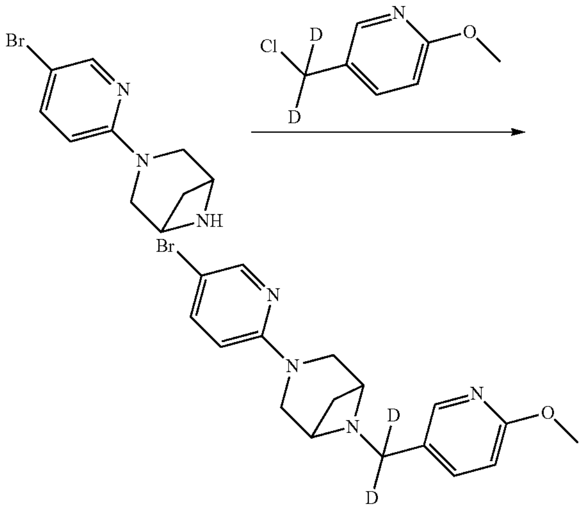

3-(5-Bromopyridin-2-yl)-6-((6-methoxypyridin-3-yl)methyl-d2)-3,6-diazabicyclo[3.1.1]heptane was obtained by using 3-(5-bromopyridin-2-yl)-3,6-diazabicyclo[3.1.1]heptane and 5-(chloromethyl-d2)-2-methoxypyridine as raw materials with reference to step 1 of embodiment 132.

MS m/z (ESI): 377.0 $[M+H]^+$.

Step 2: 6-hydroxy-4-(6-(6-((6-methoxypyridin-3-yl) methyl-d2)-3,6-diazabicyclo[3.1.1]heptan-3-yl)pyridin-3-yl)pyrazolo[1,5-a]pyridine-3-carbonitrile

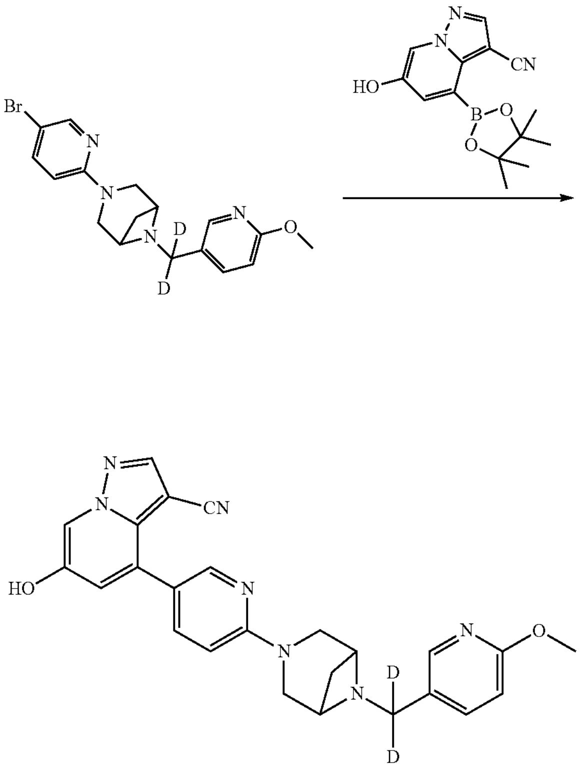

6-Hydroxy-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile was obtained by using 3-(5-bromopyridin-2-yl)-6-((6-methoxypyridin-3-yl)methyl-d2)-3,6-diazabicyclo[3.1.1]heptane and 6-hydroxy-4-(4,4,5,5-tetramethyl-1,3,2-dioxaborolan-2-yl)pyrazolo[1,5-a]pyridine-3-carbonitrile as raw materials with reference to step 8 of embodiment 1.

MS m/z (ESI): 456.2 [M+H]$^+$.

Step 3: 6-((1-cyanocyclopropyl)methoxy)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile

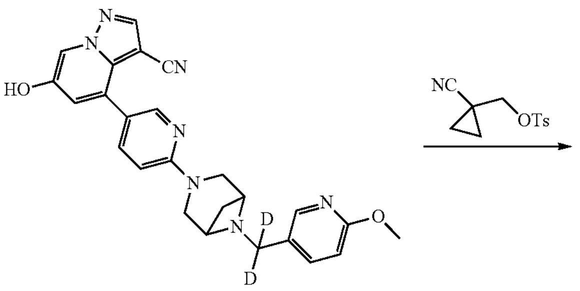

-continued

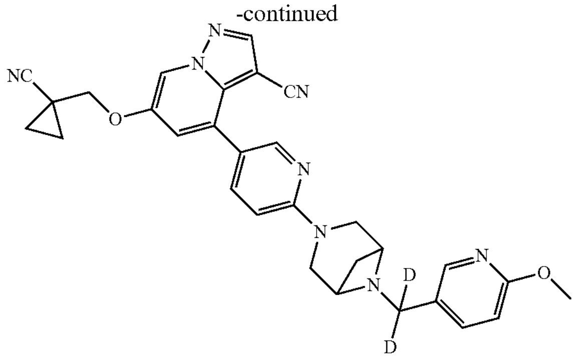

6-((1-Cyanocyclopropyl)methoxy)-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-methoxypyridin-3-yl)methyl-d2)-3,6-diazabicyclo[3.1.1]heptan-3-yl)pyridin-3-yl)pyrazolo[1,5-a]pyridine-3-carbonitrile as raw material with reference to step 2 of embodiment 106.

MS m/z (ESI): 535.2 [M+H]$^+$.

Embodiment 137

6-((3-Cyano-3-methylcyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

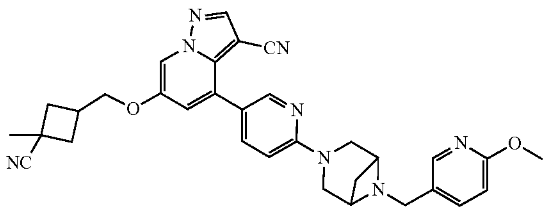

6-((3-Cyano-3-methylcyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (3-cyano-3-methylcyclobutyl)methyl 4-methylbenzenesulfonate as raw materials with reference to step 2 of embodiment 106.

MS m/z (ESI): 561.2 [M+H]$^+$.

Embodiment 138

6-((3-Cyanobicyclo[1.1.1]pentan-1-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

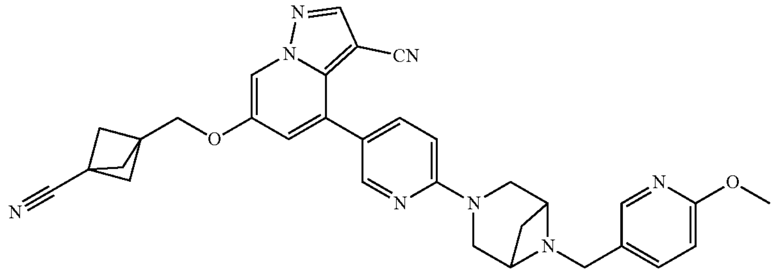 [SMILES: COc1ccc(CN2C3CC2CN(c2ccc(-c4cc(OCC56CC(C#N)(C5)C6)cn5ncc(C#N)c45)cn2)C3)cn1]

6-((3-Cyanobicyclo[1.1.1]pentan-1-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using (3-cyanobicyclo[1.1.1]pentan-1-yl)methyl 4-methylbenzenesulfonate as raw material with reference to step 2 of embodiment 106.

MS m/z (ESI): 559.3. $[M+H]^+$.

Embodiment 139

N-(1-(5-(6-((1-aminocyclopropyl)ethynyl)-3-cyanopyrazolo[1,5-a]pyridin-4-yl)pyridin-2-yl)-4-methylpiperidin-4-yl)-3-chloropicolinamide

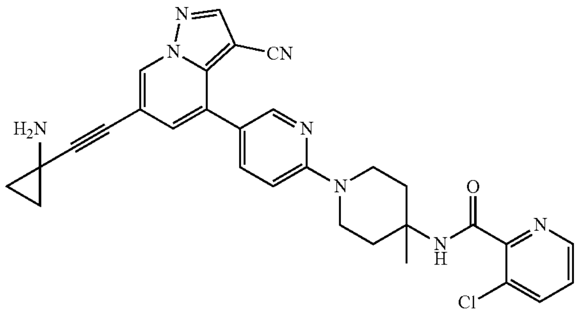 [SMILES: CC1(NC(=O)c2ncccc2Cl)CCN(c2ccc(-c3cc(C#CC4(N)CC4)cn4ncc(C#N)c34)cn2)CC1]

N-(1-(5-(6-((1-aminocyclopropyl)ethynyl)-3-cyanopyrazolo[1,5-a]pyridin-4-yl)pyridin-2-yl)-4-methylpiperidin-4-yl)-3-chloropicolinamide was obtained by using 1-ethynylcyclopropan-1-amine as raw material with reference to step 2 of embodiment 31.

MS m/z (ESI): $551.2[M+H]^+$.

Embodiment 140

N-(1-(5-(6-((1-aminocyclopropyl)methoxy)-3-cyanopyrazolo[1,5-a]pyridin-4-yl)pyridin-2-yl)-4-methylpiperidin-4-yl)-3-chloropicolinamide

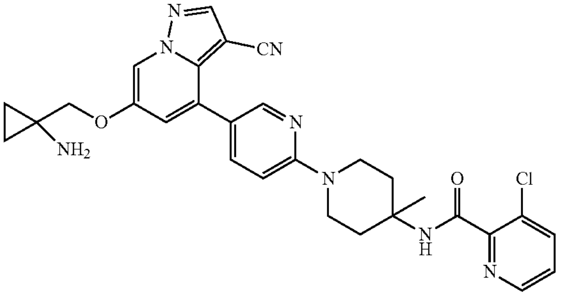 [SMILES: CC1(NC(=O)c2ncccc2Cl)CCN(c2ccc(-c3cc(OCC4(N)CC4)cn4ncc(C#N)c34)cn2)CC1]

Step 1: tert-butyl (1-(((4-(6-(4-(3-chloropicolinamido)-4-methylpiperidin-1-yl)pyridin-3-yl)-3-cyanopyrazolo[1,5-a]pyridin-6-yl)oxo)methyl)cyclopropyl)carbamate

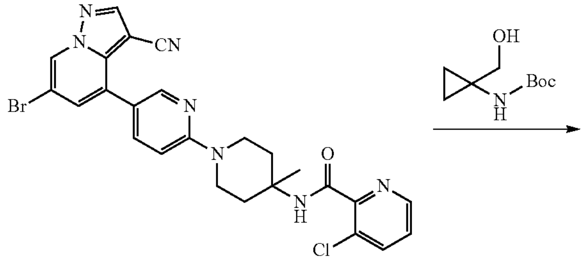

-continued

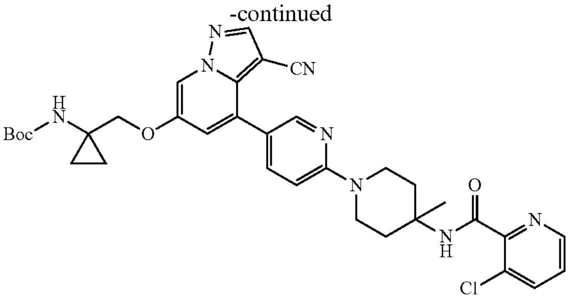

N-(1-(5-(6-bromo-3-cyanopyrazolo[1,5-a]pyridin-4-yl)pyridin-2-yl)-4-methylpiperidin-4-yl)-3-chloropicolinamide (100 mg, 0.182 mmol) was dissolved in NMP (2 mL), and tert-butyl (1-(hydroxy)cyclopropyl)carbamate (51 mg, 0.272 mmol) and cesium carbonate (177 mg, 0.545 mmol) were added thereto. The reaction was stirred at 160° C. for 1 hour under microwave, and then directly prepared to obtain tert-butyl (1-(((4-(6-(4-(3-chloropicolinamido)-4-methylpiperidin-1-yl)pyridin-3-yl)-3-cyanopyrazolo[1,5-a]pyridin-6-yl)oxy)methyl)cyclopropyl)carbamate.

MS m/z (ESI): 657.2 [M+H]$^+$.

Step 2: N-(1-(5-(6-((1-aminocyclopropyl)methoxy)-3-cyanopyrazolo[1,5-a]pyridin-4-yl)pyridin-2-yl)-4-methylpiperidin-4-yl)-3-chloropicolinamide

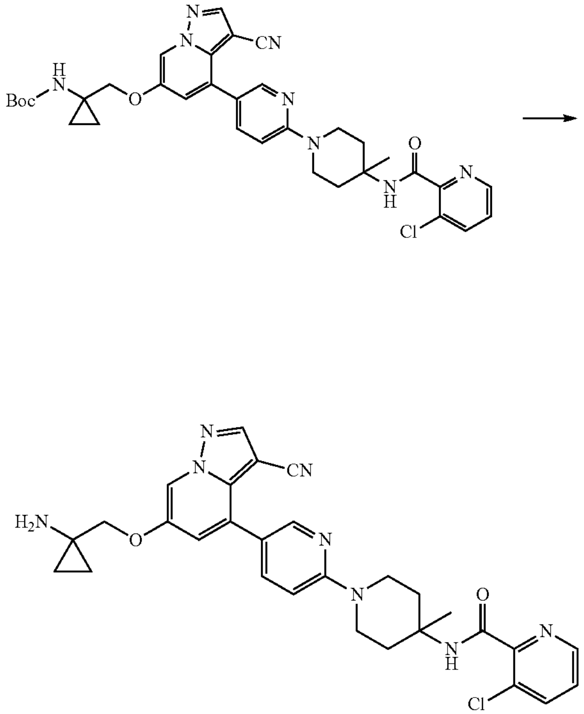 [SMILES: CC1(NC(=O)c2ncccc2Cl)CCN(c2ccc(-c3cc(OCC4(NC(=O)OC(C)(C)C)CC4)cn4ncc(C#N)c34)cn2)CC1 ; CC1(NC(=O)c2ncccc2Cl)CCN(c2ccc(-c3cc(OCC4(N)CC4)cn4ncc(C#N)c34)cn2)CC1]

N-(1-(5-(6-((1-aminocyclopropyl)methoxy)-3-cyanopyrazolo[1,5-a]pyridin-4-yl)pyridin-2-yl)-4-methylpiperidin-4-yl)-3-chloropicolinamide was obtained by using tert-butyl (1-(((4-(6-(4-(3-chloropicolinamido)-4-methylpiperidin-1-yl)pyridin-3-yl)-3-cyanopyrazolo[1,5-a]pyridin-6-yl)oxo)methyl)cyclopropyl)carbamate as raw material with reference to step 5 of embodiment 1.

MS m/z (ESI): 557.2 [M+H]$^+$.

Embodiment 141

6-((1-Imino-1-hydroxyhexahydro-1l6-thiopyran-4-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

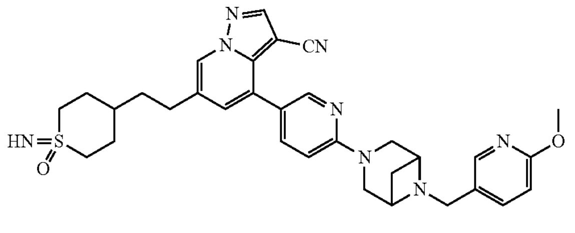 [SMILES: COc1ccc(CN2C3CC2CN(c2ccc(-c4cc(CCC5CCS(=N)(=O)CC5)cn5ncc(C#N)c45)cn2)C3)cn1]

6-((1-Imino-1-hydroxyhexahydro-1l6-thiopyran-4-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using (tetrahydro-2H-thiopyran-4-yl)methanol as raw material with reference to embodiment 90.

$^1$H NMR (400 MHz, DMSO-d6) δ 8.70 (d, J=2.1 Hz, 1H), 8.60 (s, 1H), 8.41 (d, J=2.5 Hz, 1H), 8.07 (d, J=2.4 Hz, 1H), 7.84 (dd, J=8.8, 2.5 Hz, 1H), 7.68 (dd, J=8.5, 2.4 Hz, 1H), 7.32 (d, J=2.1 Hz, 1H), 6.78 (t, J=8.5 Hz, 2H), 4.16 (t, J=6.5 Hz, 1H), 4.09-3.98 (m, 1H), 3.89 (d, J=17.8 Hz, 1H), 3.82 (s, 3H), 3.77-3.64 (m, 4H), 3.60-3.45 (m, 4H), 3.32-3.26 (m, 1H), 3.20-3.09 (m, 1H), 3.08-2.97 (m, 1H), 2.79 (q, J=11.3 Hz, 1H), 2.65-2.53 (m, 1H), 2.38-2.25 (m, 1H), 2.19-2.05 (m, 1H), 2.02-1.93 (m, 1H), 1.92-1.73 (m, 1H), 1.58 (d, J=8.4 Hz, 1H).

MS m/z (ESI): 599.2 [M+H]$^+$.

Embodiment 142

6-((1-Cyanocyclopropyl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

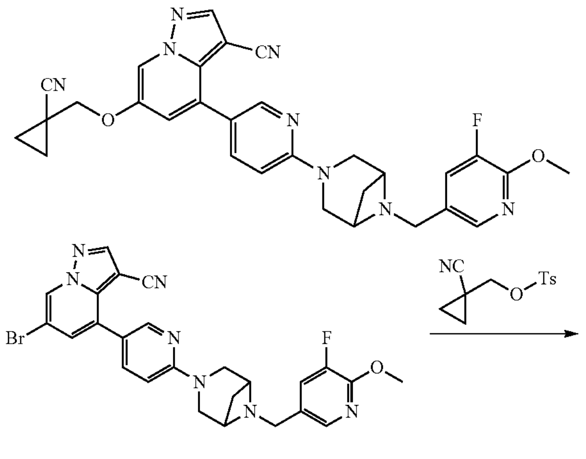

-continued

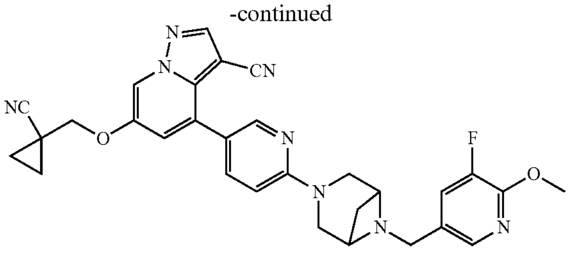

142

6-((1-Cyanocyclopropyl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile and (1-cyanocyclopropyl)methyl 4-methylbenzenesulfonate as raw material with reference to step 2 of embodiment 106.

MS m/z (ESI): 551.2 $[M+H]^+$.

$^1$H NMR (400 MHz, DMSO-$d_6$) δ 8.67 (d, J=2.1 Hz, 1H), 8.62 (s, 1H), 8.42 (d, J=2.5 Hz, 1H), 7.92 (d, J=1.8 Hz, 1H), 7.86 (dd, J=8.8, 2.6 Hz, 1H), 7.64 (dd, J=11.6, 1.9 Hz, 1H), 7.39 (d, J=2.1 Hz, 1H), 6.79 (d, J=8.8 Hz, 1H), 4.21 (s, 2H), 3.92 (s, 3H), 3.84-3.65 (m, 4H), 3.63-3.48 (m, 4H), 2.61-2.53 (m, 1H), 1.59 (d, J=8.4 Hz, 1H), 1.51-1.33 (m, 2H), 1.31-1.16 (m, 2H).

Embodiment 143

4-(6-(6-((5-Fluoro-6-methoxypyridin-3-yl)methyl)-3,6-diazabicyclo[3.1.1]heptan-3-yl)pyridin-3-yl)-6-((3-hydroxybicyclo[1.1.1]pentan-1-yl)methoxy)pyrazolo[1,5-a]pyridine-3-carbonitrile

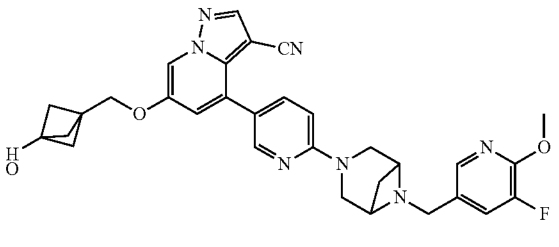 [SMILES: COc1ncc(CN2C3CC2CN(c2ccc(-c4cc(OCC56CC(O)(C5)C6)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((3-hydroxybicyclo[1.1.1]pentan-1-yl)methoxy)pyrazolo[1,5-a]pyridine-3-carbonitrile was obtained by using 3-(bromomethyl)bicyclo[1.1.1]pentan-1-ol and 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw material with reference to step 1 of embodiment 128.

MS m/z (ESI): 568.2 $[M+H]^+$.

Embodiment 144

6-((1-Cyano-3,3-difluorocyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

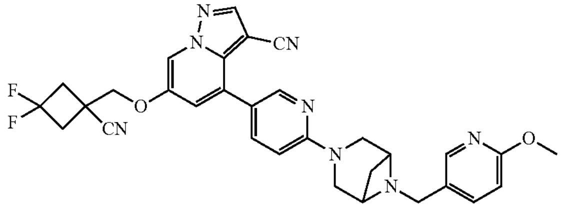 [SMILES: COc1ccc(CN2C3CC2CN(c2ccc(-c4cc(OCC5(C#N)CC(F)(F)C5)cn5ncc(C#N)c45)cn2)C3)cn1]

Step 1: 1-(chloromethyl)-3,3-difluorocyclobutane-1-carbonitrile

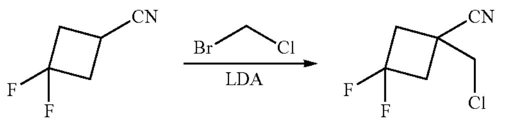

3,3-Difluorocyclobutane-1-carbonitrile (200 mg, 1.7 mmol) was dissolved in 10 mL of THF, LDA (1 mL, 2 M) was added at −78° C., and the mixture was stirred at −78° C. for 1 hour. Bromochloromethane (441 mg, 3.4 mmol) was added thereto at −78° C., and the mixture was stirred at −78° C. to room temperature for 3 hours. Water (20 mL) was added to the reaction mixture, and then the mixture was extracted with ethyl acetate (20 mL*3). The organic phase was dried and evaporated to dryness to obtain crude product 1-(chloromethyl)-3,3-difluorocyclobutane-1-carbonitrile (280 mg, yield: 99%).

Step 2: 6-((1-Cyano-3,3-difluorocyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

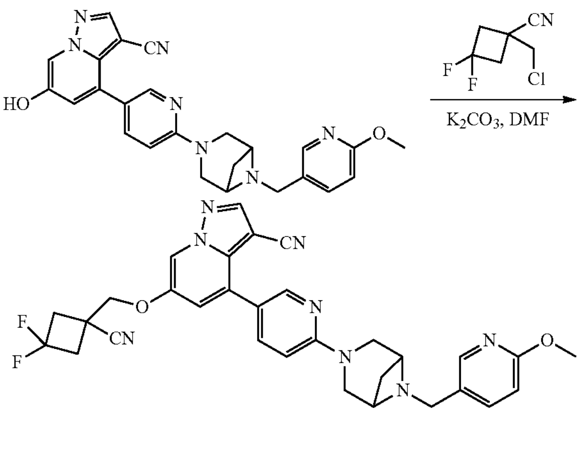

6-Hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (50 mg, 0.13 mmol) was dissolved in 5 mL of DMF; and 1-(chloromethyl)-3,3-difluorocyclobutane-1-carbonitrile (280 mg), potassium carbonate (55 mg, 0.4 mmol) were added thereto, and the mixture was stirred at 80° C. for 5 hours. The residue was evaporated to dryness, and the crude product was purified by prep-HPLC to obtain product 6-((1-cyano-3,3-difluorocyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (3.4 mg, yield. 4.5%).

MS m/z (ESI): 583.2[M+H]$^+$.

$^1$H NMR (400 MHz, $CDCl_3$) δ 8.45 (d, J=2.4 Hz, 1H), 8.26 (s, 1H), 8.23 (d, J=1.3 Hz, 1H), 8.18 (s, 1H), 8.01 (s, 1H), 7.86 (d, J=4.5 Hz, 1H), 7.22-7.19 (m, 1H), 6.90-6.83 (m, 1H), 6.77 (s, 1H), 4.28 (s, 2H), 3.94 (s, 3H), 3.34-3.22 (m, 3H), 3.07-2.97 (m, 3H), 2.96-2.88 (m, 2H), 2.25-2.19 (m, 2H), 2.06-1.93 (m, 4H).

Embodiment 145

6-((3-Cyanooxetan-3-yl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

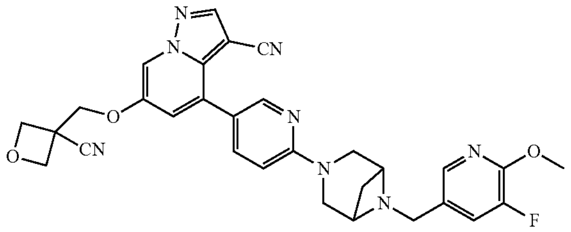 [SMILES: COc1ncc(CN2C3CC2CN(c2ccc(-c4cc(OCC5(C#N)COC5)cn5ncc(C#N)c45)cn2)C3)cc1F]

6-((3-Cyanooxetan-3-yl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw material with reference to embodiment 106.

MS m/z (ESI): 567.2 [M+H]$^+$.

Embodiment 146

3-Chloro-N-(1-(5-(3-cyano-6-((1-cyanocyclopropyl)methoxy)pyrazolo[1,5-a]pyridin-4-yl)pyridin-2-yl)-4-methylpiperidin-4-yl)picolinamide

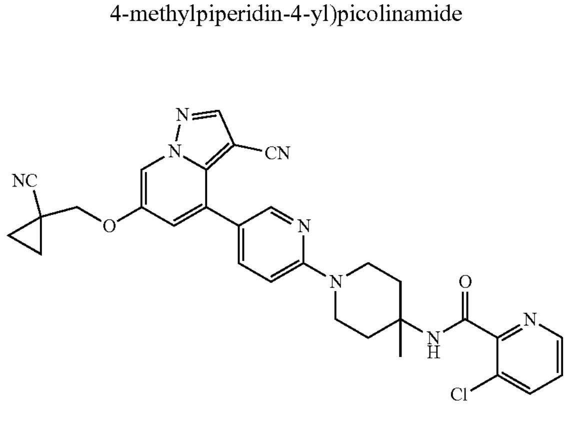

Step 1: 3-chloro-N-(1-(5-(3-cyano-6-hydroxypyrazolo[1,5-a]pyridin-4-yl)pyridin-2-yl)-4-methylpiperidin-4-yl)picolinamide

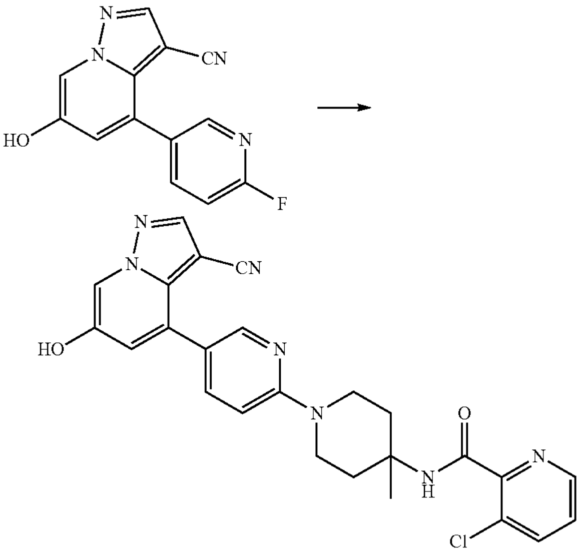

3-Chloro-N-(1-(5-(3-cyano-6-hydroxypyrazolo[1,5-a]pyridin-4-yl)pyridin-2-yl)-4-methylpiperidin-4-yl)picolinamide was obtained by using 4-(6-fluoropyridin-3-yl)-6-hydroxypyrazolo[1,5-a]pyridine-3-carbonitrile as raw material with reference to step 1 to step 3 of embodiment 97.

MS m/z (ESI): 488.1 [M+H]$^+$.

Step 2: 3-chloro-N-(1-(5-(3-cyano-6-((1-cyanocyclopropyl)methoxy)pyrazolo[1,5-a]pyridin-4-yl)pyridin-2-yl)-4-methylpiperidin-4-yl)picolinamide

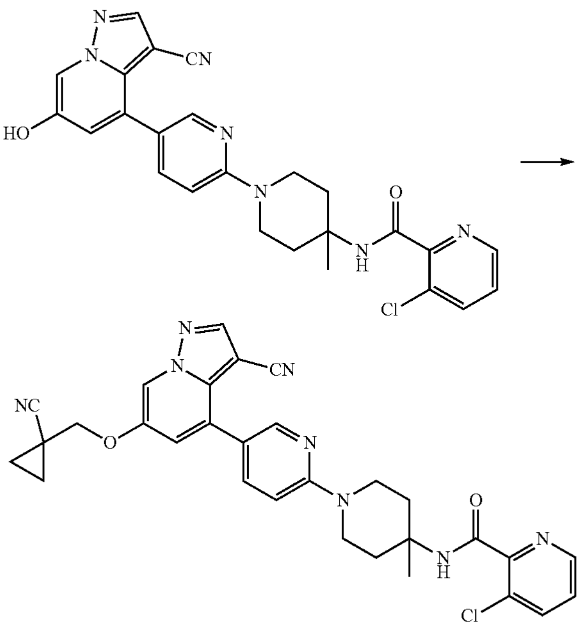

3-Chloro-N-(1-(5-(3-cyano-6-((1-cyanocyclopropyl)methoxy)pyrazolo[1,5-a]pyridin-4-yl)pyridin-2-yl)-4-methylpiperidin-4-yl)picolinamide was obtained by using 3-chloro-N-(1-(5-(3-cyano-6-hydroxypyrazolo[1,5-a]pyridin-4-yl)pyridin-2-yl)-4-methylpiperidin-4-yl)picolinamide as raw material with reference to step 2 of embodiment 106.

MS m/z (ESI): 567.1 $[M+H]^+$.

$^1H$ NMR (400 MHz, DMSO-$d_6$) δ 8.66 (d, J=2.3 Hz, 1H), 8.60 (s, 1H), 8.53 (d, J=4.7 Hz, 1H), 8.34 (d, J=2.5 Hz, 1H), 8.28 (s, 1H), 8.03-7.98 (m, 1H), 7.82-7.74 (m, 1H), 7.52-7.48 (m, 1H), 7.39 (d, J=1.9 Hz, 1H), 6.99 (d, J=8.7 Hz, 1H), 4.20 (s, 2H), 4.10-4.01 (m, 2H), 3.40-3.34 (m, 2H), 2.34-2.30 (m, 2H), 1.63-1.54 (m, 2H), 1.45 (s, 3H), 1.44-1.39 (m, 2H), 1.22-1.16 (m, 2H).

Embodiment 147

N-(1-(5-(3-cyano-6-((1-cyanocyclopropyl)methoxy)pyrazolo[1,5-a]pyridin-4-yl)pyridin-2-yl)-4-methylpiperidin-4-yl)-3-fluoropicolinamide

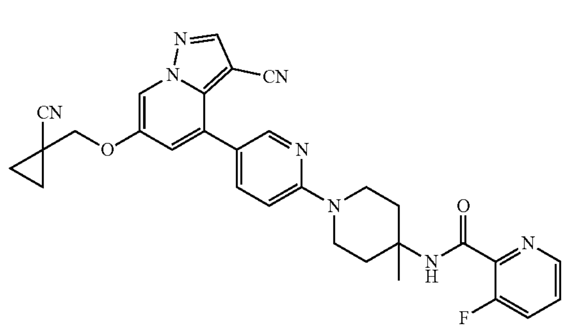 [SMILES: CC1(NC(=O)c2ncccc2F)CCN(c2ccc(-c3cc(OCC4(C#N)CC4)cn4ncc(C#N)c34)cn2)CC1]

Step 1: N-(1-(5-(3-cyano-6-hydroxypyrazolo[1,5-a]pyridin-4-yl)pyridin-2-yl)-4-methylpiperidin-4-yl)-3-fluoropicolinamide

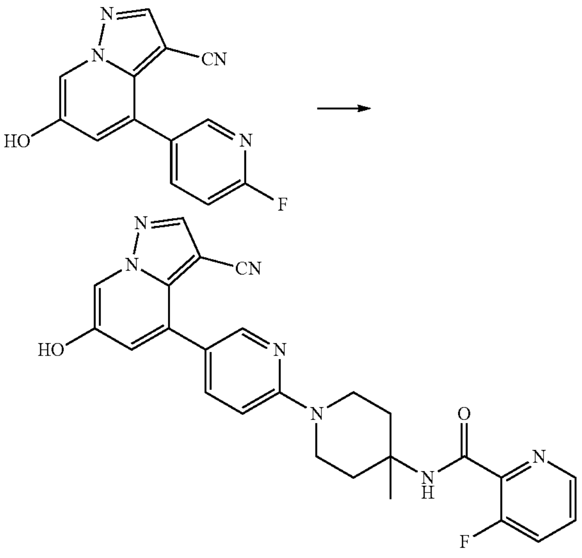

N-(1-(5-(3-cyano-6-hydroxypyrazolo[1,5-a]pyridin-4-yl)pyridin-2-yl)-4-methylpiperidin-4-yl)-3-fluoropicolinamide was obtained by using 4-(6-fluoropyridin-3-yl)-6-hydroxypyrazolo[1,5-a]pyridine-3-carbonitrile as raw material with reference to step 1 to step 3 of embodiment 97.

MS m/z (ESI): 472.1 $[M+H]^+$.

Step 2: N-(1-(5-(3-cyano-6-((1-cyanocyclopropyl)methoxy)pyrazolo[1,5-a]pyridin-4-yl)pyridin-2-yl)-4-methylpiperidin-4-yl)-3-fluoropicolinamide

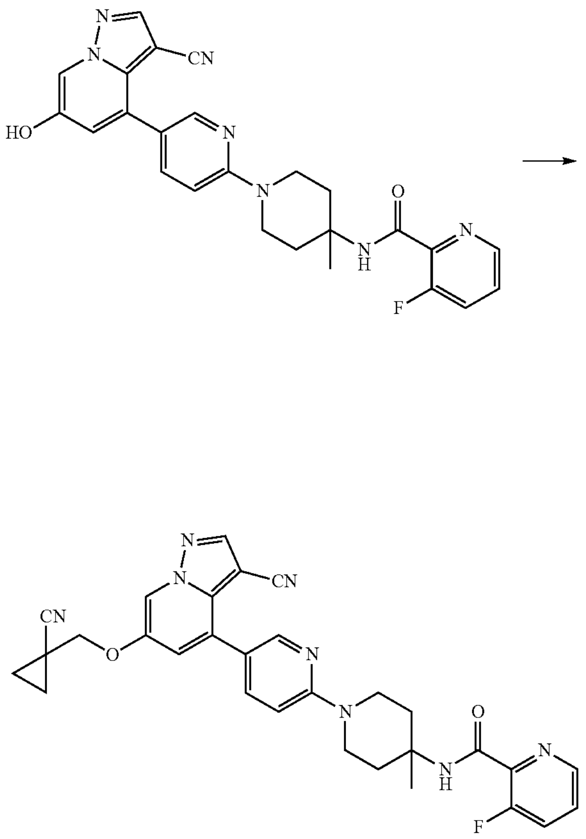

N-(1-(5-(3-cyano-6-((1-cyanocyclopropyl)methoxy)pyrazolo[1,5-a]pyridin-4-yl)pyridin-2-yl)-4-methylpiperidin-4-yl)-3-fluoropicolinamide was obtained by using N-(1-(5-(3-cyano-6-hydroxypyrazolo[1,5-a]pyridin-4-yl)pyridin-2-yl)-4-methylpiperidin-4-yl)-3-fluoropicolinamide as raw material with reference to step 2 of embodiment 106.

MS m/z (ESI): 551.2 $[M+H]^+$.

$^1H$ NMR (400 MHz, DMSO-$d_6$) δ 8.66 (d, J=2.1 Hz, 1H), 8.60 (s, 1H), 8.51-8.43 (m, 1H), 8.35 (d, J=2.5 Hz, 1H), 8.21 (s, 1H), 7.89-7.81 (m, 1H), 7.78 (dd, J=8.8, 2.6 Hz, 1H), 7.68-7.58 (m, 1H), 7.39 (d, J=2.1 Hz, 1H), 6.99 (d, J=8.9 Hz, 1H), 4.20 (s, 2H), 4.10-3.98 (m, 2H), 3.31-3.24 (m, 2H), 2.40-2.27 (m, 2H), 1.69-1.56 (m, 2H), 1.46 (s, 3H), 1.45-1.40 (m, 2H), 1.24-1.16 (m, 2H).

Embodiment 148

6-((4-Cyanotetrahydro-2H-pyran-4-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

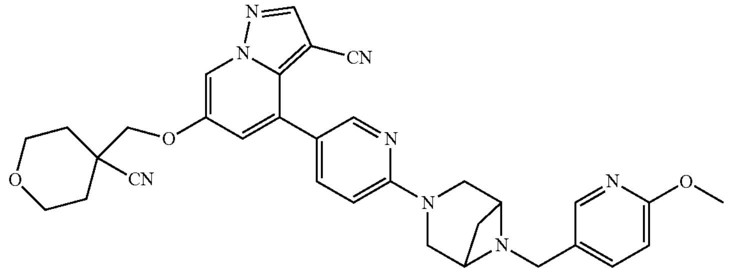

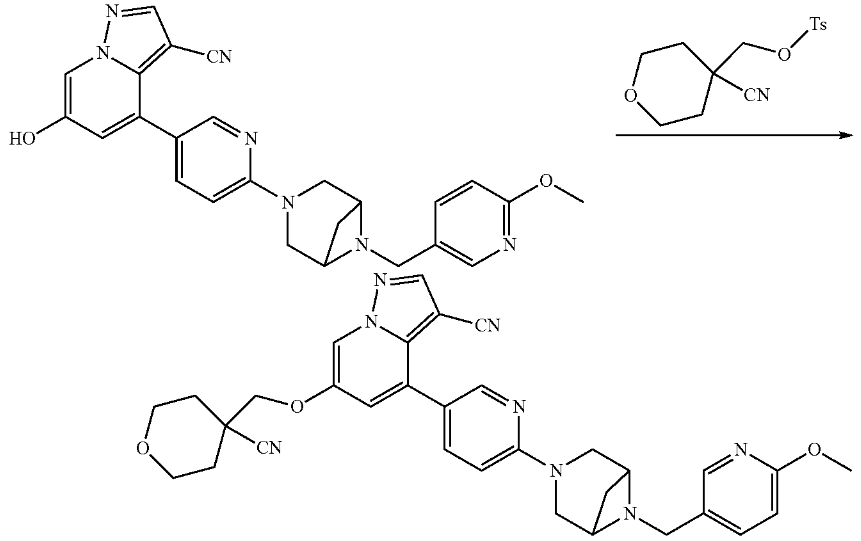

6-((4-Cyanotetrahydro-2H-pyran-4-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and (4-cyanotetrahydro-2H-pyran-4-yl)methyl 4-methylbenzenesulfonate as raw materials with reference to step 2 of embodiment 106.

MS m/z (ESI): 577.2 $[M+H]^+$.

$^1$H NMR (400 MHz, Chloroform-d) δ 8.42 (d, J=2.5 Hz, 1H), 8.24 (s, 1H), 8.17 (d, J=2.1 Hz, 1H), 8.13 (d, J=2.4 Hz, 1H), 7.90-7.78 (m, 2H), 7.18 (d, J=2.1 Hz, 1H), 6.76 (d, J=8.5 Hz, 1H), 6.71 (d, J=8.8 Hz, 1H), 4.14-4.02 (m, 4H), 3.99-3.88 (m, 6H), 3.86-3.61 (m, 6H), 2.12-2.05 (m, 2H), 1.90-1.78 (m, 3H), 1.78-1.64 (m, 2H).

Embodiment 149

6-((4-Cyanotetrahydro-2H-pyran-4-yl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

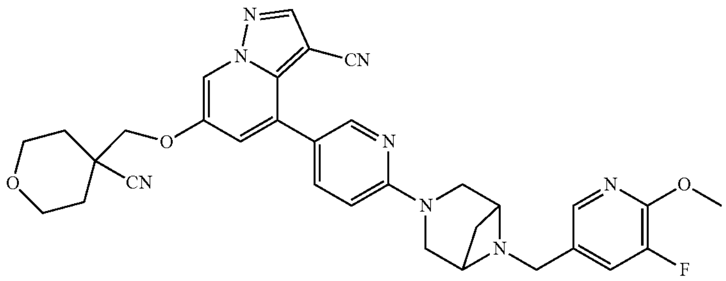

-continued

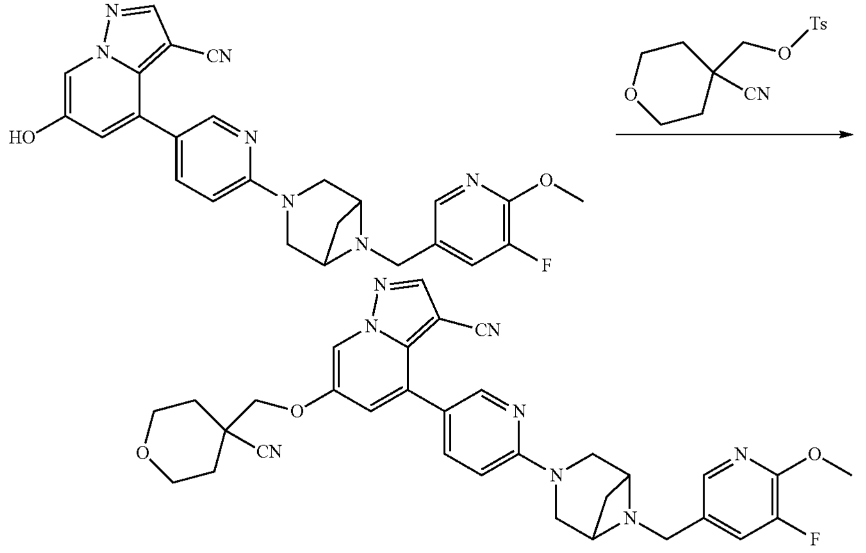

6-((4-Cyanotetrahydro-2H-pyran-4-yl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile and (4-cyanotetrahydro-2H-pyran-4-yl)methyl 4-methylbenzenesulfonate as raw materials with reference to step 2 of embodiment 106.

MS m/z (ESI): 595.2 $[M+H]^+$.

$^1H$ NMR 1H NMR (400 MHz, Chloroform-d) δ 8.42 (d, J=2.5 Hz, 1H), 8.24 (s, 1H), 8.17 (d, J=2.1 Hz, 1H), 7.88 (s, 1H), 7.79 (dd, J=8.8, 2.6 Hz, 1H), 7.55 (d, J=19.9 Hz, 1H), 7.17 (d, J=2.1 Hz, 1H), 6.70 (d, J=8.8 Hz, 1H), 4.09 (d, J=4.0 Hz, 1H), 4.06 (s, 3H), 4.01 (s, 3H), 3.91-3.78 (m, 6H), 3.70-3.62 (m, 3H), 2.90-2.73 (m, 1H), 2.11-2.05 (m, 2H), 1.89-1.77 (m, 3H), 1.73-1.69 (m, 1H).

Embodiment 150

3-Chloro-N-(1-(5-(3-cyano-6-((3-cyanooxetan-3-yl)methoxy)pyrazolo[1,5-a]pyridin-4-yl)pyridin-2-yl)-4-methylpiperidin-4-yl)picolinamide

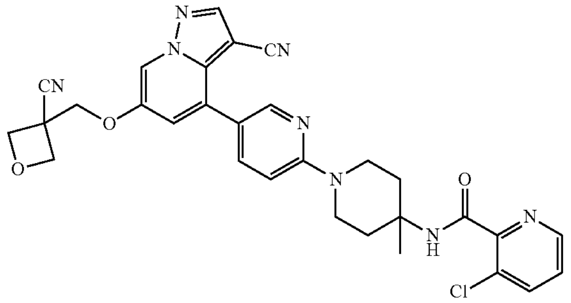 [SMILES: CC1(NC(=O)c2ncccc2Cl)CCN(c2ccc(-c3cc(OCC4(C#N)COC4)cn4ncc(C#N)c34)cn2)CC1]

3-Chloro-N-(1-(5-(3-cyano-6-((3-cyanooxetan-3-yl)methoxy)pyrazolo[1,5-a]pyridin-4-yl)pyridin-2-yl)-4-methylpiperidin-4-yl)picolinamide was obtained by using 3-chloro-N-(1-(5-(3-cyano-6-hydroxypyrazolo[1,5-a]pyridin-4-yl)pyridin-2-yl)-4-methylpiperidin-4-yl)methylpyridinamide as raw material with reference to embodiment 106.

MS m/z (ESI): 583.2 $[M+H]^+$.

Embodiment 151

4-(6-(6-((5-Fluoro-6-methoxypyridin-3-yl)methyl)-3,6-diazabicyclo[3.1.1]heptan-3-yl)pyridin-3-yl)-6-(3-hydroxy-4-methoxy-3-methylbut-1-yn-1-yl)pyrazolo[1,5-a]pyridine-3-carbonitrile

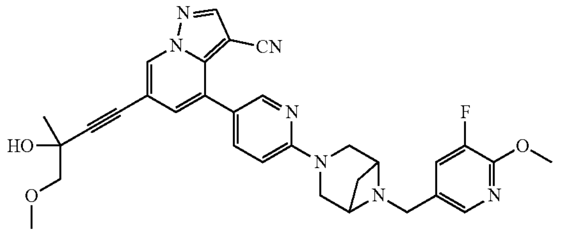 [SMILES: COCC(C)(O)C#Cc1cc(-c2ccc(N3CC4CC(C3)N4Cc3cnc(OC)c(F)c3)nc2)c2c(C#N)cnn2c1]

4-(6-(6-((5-Fluoro-6-methoxypyridin-3-yl)methyl)-3,6-diazabicyclo[3.1.1]heptan-3-yl)pyridin-3-yl)-6-(3-hydroxy-4-methoxy-3-methylbut-1-yn-1-yl)pyrazolo[1,5-a]pyridine-3-carbonitrile was obtained by using 6-bromo-4-(6-(6-((5-fluoro-6-methoxypyridin-3-yl)methyl)-3,6-diazabicyclo[3.1.1]heptan-3-yl)pyridine-3-yl)pyrazolo[1,5-a]pyridine-3-carbonitrile and 1-methoxy-2-methylbut-3-yn-2-ol as raw materials with reference to step 2 of embodiment 31.

MS m/z (ESI): 568.2 $[M+H]^+$.

$^1H$ NMR (400 MHz, $CDCl_3$) δ 8.64 (s, 1H), 8.40 (d, J=2.1 Hz, 1H), 8.31 (s, 1H), 7.90 (s, 1H), 7.78 (dd, J=8.8, 2.4 Hz, 1H), 7.67 (dd, J=11.8, 7.1 Hz, 1H), 7.32 (s, 1H), 6.70 (d, J=8.7 Hz, 1H), 4.02 (s, 3H), 3.89 (s, 3H), 3.72 (s, 5H), 3.60 (d, J=9.1 Hz, 1H), 3.52 (s, 3H), 3.45 (d, J=9.1 Hz, 1H), 2.97 (m, 2H), 1.58 (s, 3H).

Embodiment 152A 6-((2-Hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

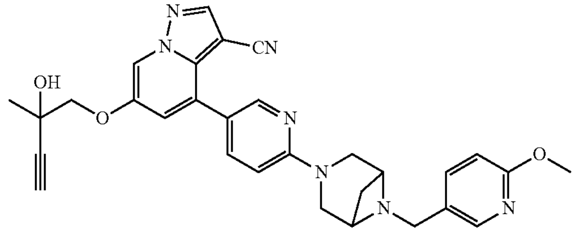 [SMILES: C#CC(C)(O)COc1cc(-c2ccc(N3CC4CC(C3)N4Cc3ccc(OC)nc3)nc2)c2c(C#N)cnn2c1]

Step 1: 4-(6-(6-((6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile

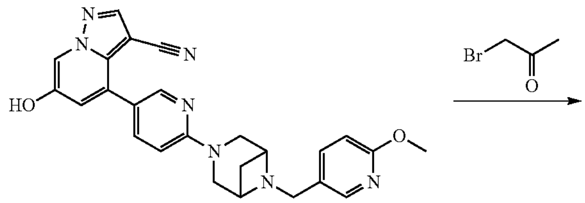

-continued

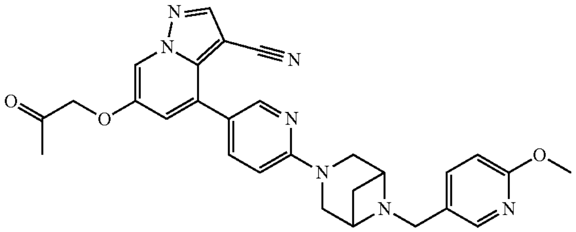

6-Hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (200 mg, 0.441 mmol) was dissolved in DMF (20 mL), and bromoacetone (121 mg, 0.882 mmol), cesium carbonate (431 mg, 1.32 mmol) and sodium iodide (66 mg, 0.441 mmol) were added thereto, respectively. The reaction was stirred at room temperature overnight. Water was added to the reaction mixture, and then the mixture was extracted with ethyl acetate. The organic phase was dried and evaporated to dryness. The crude product was purified by column chromatography to obtain 4-(6-(6-((6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile (160 mg, yield: 71%).

MS m/z (ESI): 510.1 $[M+H]^+$.

Step 2: 6-((2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

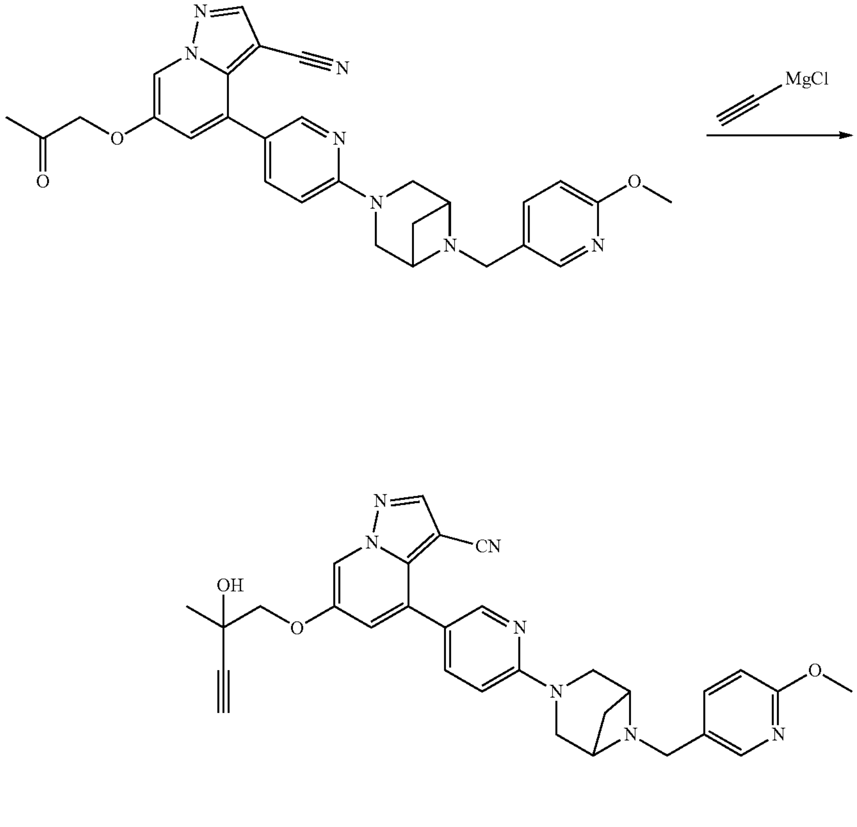

4-(6-(6-((6-Methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile (160 mg, 0.314 mmol) was dissolved in anhydrous tetrahydrofuran (15 mL), and then ethynylmagnesium chloride (6.28 mL, 3.14 mmol, 0.5 M) was slowly added thereto. After the addition was completed, the reaction mixture was stirred for 3 hours. Ammonium chloride aqueous solution was added to quench the reaction, and then the mixture was extracted with ethyl acetate. The organic phase was dried and evaporated to dryness. The crude product was purified by column chromatography to obtain 6-((2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (48 mg, yield was 28%).

MS m/z (ESI): 536.1 $[M+H]^+$.

$^1$H NMR (400 MHz, DMSO-d6) δ 8.74 (d, J=2.1 Hz, 1H), 8.60 (s, 1H), 8.42 (d, J=2.5 Hz, 1H), 8.07 (d, J=2.4 Hz, 1H), 7.85 (dd, J=8.8, 2.6 Hz, 1H), 7.68 (dd, J=8.5, 2.4 Hz, 1H), 7.33 (d, J=2.1 Hz, 1H), 6.78 (dd, J=10.8, 8.6 Hz, 2H), 5.84 (s, 1H), 4.08 (s, 2H), 3.82 (s, 3H), 3.78-3.70 (m, 2H), 3.70-3.65 (m, 2H), 3.61-3.52 (m, 2H), 3.50 (s, 2H), 3.40 (s, 1H), 2.57-2.53 (m, 1H), 1.59 (d, J=8.5 Hz, 1H), 1.49 (s, 3H).

Embodiment 152

6-(((R)-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

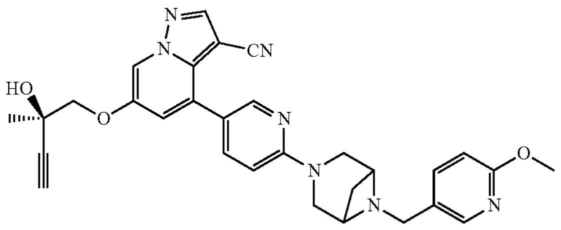 [SMILES: C#C[C@@](C)(O)COc1cc(-c2ccc(N3CC4CC(C3)N4Cc3ccc(OC)nc3)nc2)c2c(C#N)cnn2c1]

Step 1: 4-(6-(6-((6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile

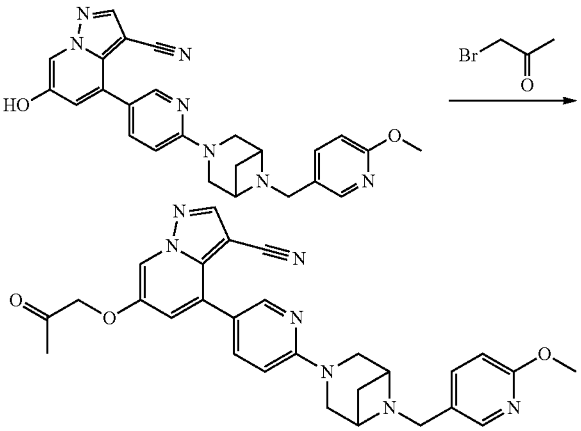

6-Hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (200 mg, 0.441 mmol) was dissolved in DMF (20 mL), and bromoacetone (121 mg, 0.882 mmol), cesium carbonate (431 mg, 1.32 mmol) and sodium iodide (66 mg, 0.441 mmol) were added thereto, respectively. The reaction was stirred at room temperature overnight. Water was added to the reaction mixture, and then the mixture was extracted with ethyl acetate. The organic phase was dried and evaporated to dryness. The crude product was purified by column chromatography to obtain 4-(6-(6-((6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile (160 mg, yield: 71%).

MS m/z (ESI): 510.1 $[M+H]^+$.

Step 2: 6-((2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

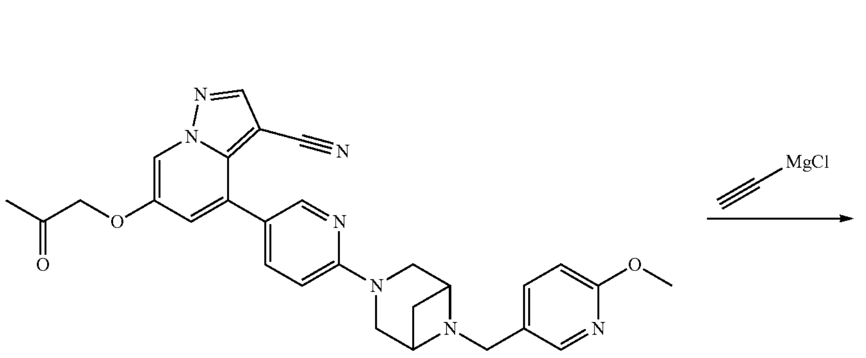

-continued

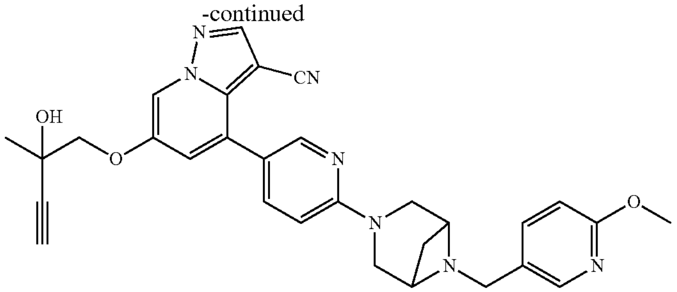

4-(6-(6-((6-Methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile (160 mg, 0.314 mmol) was dissolved in anhydrous tetrahydrofuran (15 mL), and then ethynylmagnesium chloride (6.28 mL, 3.14 mmol, 0.5 M) was slowly added thereto. After the addition was completed, the reaction mixture was stirred for 3 hours. Ammonium chloride aqueous solution was added to quench the reaction, and then the mixture was extracted with ethyl acetate. The organic phase was dried and evaporated to dryness. The crude product was purified by column chromatography to obtain 6-((2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (48 mg, yield was 28%).

MS m/z (ESI): 536.1 $[M+H]^+$.

Step 3: 6-(((R)-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

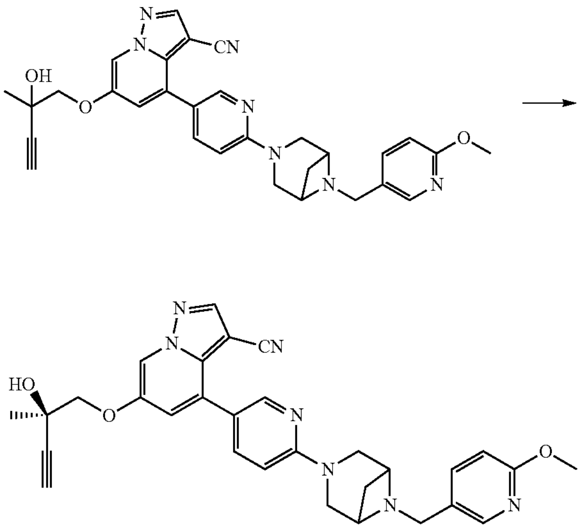

6-(((R)-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (16 mg) was obtained by chiral resolution from 6-((-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (48.2 mg, 0.09 mmol).

Chiral resolution conditions:

TABLE 1

| Instrument | CHIRALPAK IBN |
|---|---|
| Column type | 5.0 cm I.D. × 25 cm L, 10 μm |
| Mobile phase | Hexane/EtOH/DCM = 60/30/10 (V/V/V) |
| Flow rate | 60 mL/min |
| Detection wavelength | UV 254 nm |
| Column temperature | 35° C. |

$t_R$=90.002 min

MS m/z (ESI): 536.1 $[M+H]^+$.

$^1$H NMR (400 MHz, DMSO-$d_6$) δ 8.74 (d, J=2.1 Hz, 1H), 8.60 (s, 1H), 8.42 (d, J=2.5 Hz, 1H), 8.07 (d, J=2.4 Hz, 1H), 7.85 (dd, J=8.8, 2.6 Hz, 1H), 7.68 (dd, J=8.5, 2.4 Hz, 1H), 7.33 (d, J=2.1 Hz, 1H), 6.78 (m, 2H), 5.84 (s, 1H), 4.08 (s, 2H), 3.82 (s, 3H), 3.78-3.63 (m, 4H), 3.61-3.46 (m, 4H), 3.40 (s, 1H), 2.57-2.53 (m, 1H), 1.59 (d, J=8.5 Hz, 1H), 1.49 (s, 3H).

Embodiment 153

6-(((S)-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

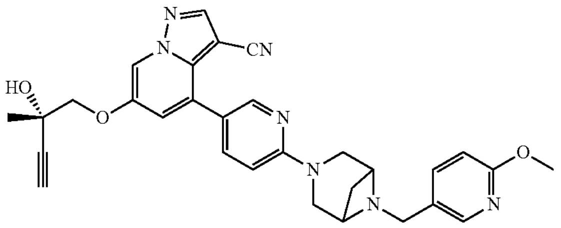 [SMILES: C#C[C@](C)(O)COc1cc(-c2ccc(N3CC4CC(C3)N4Cc3ccc(OC)nc3)nc2)c2c(C#N)cnn2c1]

Step 1: 6-(((S)-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

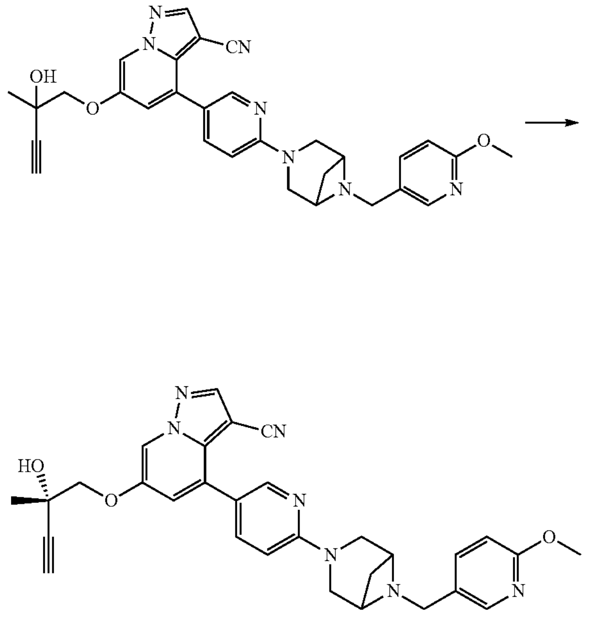

6-(((S)-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (18 mg) was obtained by chiral resolution from 6-((-2-hydroxy-2-methylbut-3-yn-1-yl)oxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (48.2 mg, 0.09 mmol).

Chiral resolution conditions:

TABLE 2

| Instrument | CHIRALPAK IBN |
|---|---|
| Column type | 5.0 cm I.D. × 25 cm L, 10 μm |
| Mobile Phase | Hexane/EtOH/DCM = 60/30/10 (V/V/V) |
| Flow rate | 60 ml/min |
| Detection wavelength | UV 254 nm |
| Column temperature | 35° C. |

$t_R$=70.431 min

MS m/z (ESI): 536.1 $[M+H]^+$.

$^1$H NMR (400 MHz, DMSO-$d_6$) δ 8.74 (d, J=2.1 Hz, 1H), 8.60 (s, 1H), 8.42 (d, J=2.5 Hz, 1H), 8.07 (d, J=2.4 Hz, 1H), 7.85 (dd, J=8.8, 2.6 Hz, 1H), 7.68 (dd, J=8.5, 2.4 Hz, 1H), 7.33 (d, J=2.1 Hz, 1H), 6.78 (m, 2H), 5.84 (s, 1H), 4.08 (s, 2H), 3.82 (s, 3H), 3.78-3.63 (m, 4H), 3.61-3.46 (m, 4H), 3.40 (s, 1H), 2.57-2.53 (m, 1H), 1.59 (d, J=8.5 Hz, 1H), 1.49 (s, 3H).

Embodiment 154

4-(6-(6-((5-Fluoro-6-methoxypyridin-3-yl)methyl)-3,6-diazabicyclo[3.1.1]heptan-3-yl)pyridin-3-yl)-6-(((S)-2-hydroxy-2-methylbut-3-yn-1-yl)oxy)pyrazolo[1,5-a]pyridine-3-carbonitrile

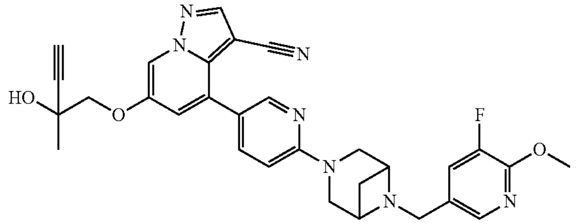 [SMILES: C#CC(C)(O)COc1cc(-c2ccc(N3CC4CC(C3)N4Cc3cnc(OC)c(F)c3)nc2)c2c(C#N)cnn2c1]

Step 1: 4-(6-(6-((5-fluoro-6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile

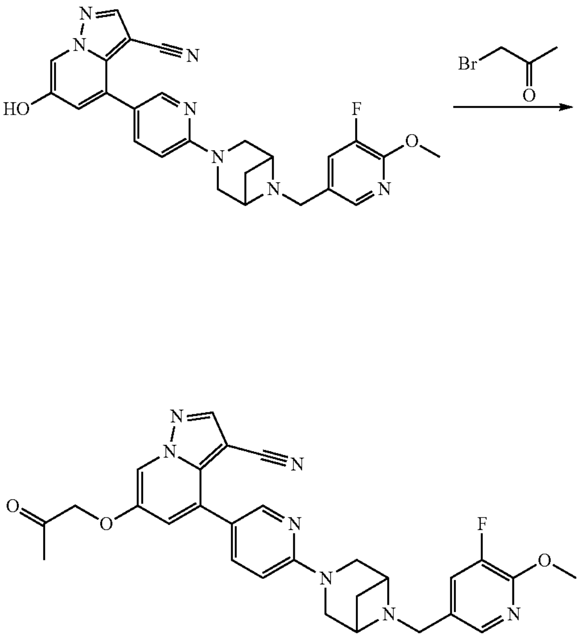

4-(6-(6-((5-Fluoro-6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile (190 mg, yield was 84%) was obtained by using 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw material with reference to step 1 of embodiment 152.

MS m/z (ESI): 528.1 $[M+H]^+$.

Step 2: 4-(6-(6-((5-fluoro-6-methoxypyridin-3-yl)methyl)-3,6-diazabicyclo[3.1.1]heptan-3-yl)pyridin-3-yl)-6-(((S)-2-hydroxy-2-methylbut-3-yn-1-yl)oxy)pyrazolo[1,5-a]pyridine-3-carbonitrile

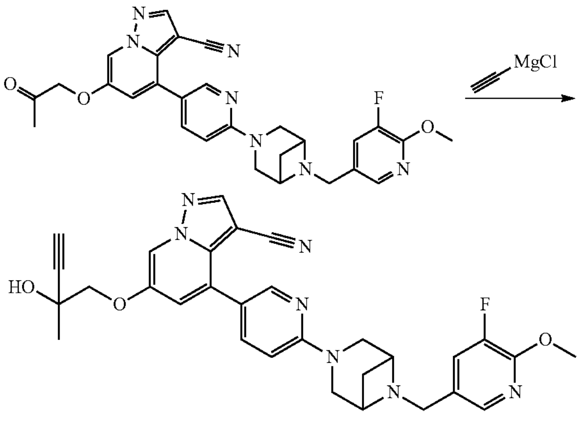

4-(6-(6-((5-Fluoro-6-methoxypyridin-3-yl)methyl)-3,6-diazabicyclo[3.1.1]heptan-3-yl)pyridin-3-yl)-6-(((S)-2-hydroxy-2-methylbut-3-yn-1-yl)oxy)pyrazolo[1,5-a]pyridine-3-carbonitrile (40 mg, yield was 22%) was obtained by using 4-(6-(6-((5-fluoro-6-methoxypyridin-3-yl)methyl)-3,6-diazabicyclo[3.1.1]heptan-3-yl)pyridin-3-yl)-6-(2-oxopropoxy)pyrazolo[1,5-a]pyridine-3-carbonitrile as raw material with reference to step 2 of embodiment 152.

MS m/z (ESI): 554.3 $[M+H]^+$.

$^1$H NMR (400 MHz, DMSO-$d_6$) δ 8.74 (d, J=2.1 Hz, 1H), 8.60 (s, 1H), 8.42 (d, J=2.5 Hz, 1H), 7.92 (d, J=1.9 Hz, 1H), 7.85 (dd, J=8.8, 2.6 Hz, 1H), 7.64 (dd, J=11.5, 1.9 Hz, 1H), 7.33 (d, J=2.1 Hz, 1H), 6.79 (d, J=8.8 Hz, 1H), 5.84 (s, 1H), 4.08 (s, 2H), 3.92 (s, 3H), 3.81-3.65 (m, 4H), 3.64-3.48 (m, 4H), 3.40 (s, 1H), 2.59-2.53 (m, 1H), 1.59 (d, J=8.4 Hz, 1H), 1.49 (s, 3H).

Embodiment 155

3-(((3-Cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxo)methyl)bicyclo[1.1.1]pentane-1-carboxamide

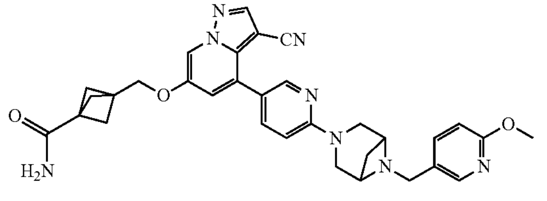 [SMILES: COc1ccc(CN2C3CC2CN(c2ccc(-c4cc(OCC56CC(C(N)=O)(C5)C6)cn5ncc(C#N)c45)cn2)C3)cn1]

3-(((3-Cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)bicyclo[1.1.1]pentane-1-carboxamide was obtained by using (3-carbamoylbicyclo[1.1.1]pentan-1-yl)methyl 4-methylbenzenesulfonate and 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile as raw materials with reference to step 2 of embodiment 106.

MS m/z (ESI): 577.3 $[M+H]^+$.

$^1$H NMR (400 MHz, $CDCl_3$) δ 9.70-9.62 (m, 1H), 8.41 (d, J=2.1 Hz, 1H), 8.21 (s, 1H), 8.16-8.08 (m, 2H), 7.93-7.77 (m, 2H), 7.13 (d, J=1.9 Hz, 1H), 6.73 (dd, J=22.6, 8.7 Hz, 2H), 5.52 (s, 1H), 5.39 (s, 1H), 4.07 (s, 2H), 3.93 (s, 5H), 3.72 (s, 4H), 2.96 (s, 1H), 2.88 (s, 1H), 2.15 (s, 6H).

Embodiment 156

3-(((3-Cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxo)methyl)-N-methylbicyclo[1.1.1]pentane-1-carboxamide

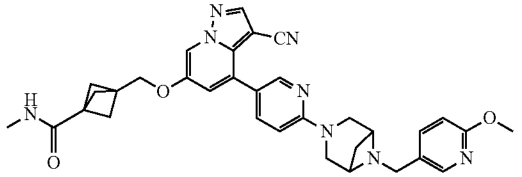

3-(((3-Cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)-N-methylbicyclo[1.1.1]pentane-1-carboxamide was obtained by using (3-(methylcarbamoyl)bicyclo[1.1.1]pentan-1-yl)methyl 4-methylbenzenesulfonate and 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile as raw materials with reference to step 2 of embodiment 106.

MS m/z (ESI): 591.3 $[M+H]^+$.

$^1$H NMR (400 MHz, $CDCl_3$) δ 8.40 (d, J=2.2 Hz, 1H), 8.21 (s, 1H), 8.14-8.05 (m, 2H), 7.78 (dd, J=8.8, 2.4 Hz, 1H), 7.67 (d, J=7.5 Hz, 1H), 7.12 (d, J=1.9 Hz, 1H), 6.70 (dd, J=15.4, 8.7 Hz, 2H), 5.58 (d, J=4.5 Hz, 1H), 4.05 (s, 2H), 3.92 (s, 3H), 3.83 (dd, J=17.6, 8.8 Hz, 4H), 3.60 (s, 4H), 2.83 (d, J=4.9 Hz, 3H), 2.72 (d, J=5.8 Hz, 1H), 2.11 (s, 6H), 1.67 (d, J=8.7 Hz, 1H).

Embodiment 157

4-(6-(6-((5-Fluoro-6-methoxypyridin-3-yl)methyl)-3,6-diazabicyclo[3.1.1]heptan-3-yl)pyridin-3-yl)-6-((R)-3-hydroxybut-1-yn-1-yl)pyrazolo[1,5-a]pyridine-3-carbonitrile

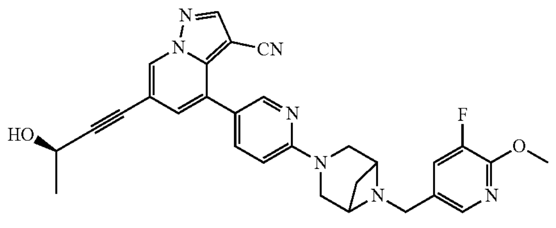 [SMILES: COc1ncc(CN2C3CC2CN(c2ccc(-c4cc(C#C[C@@H](C)O)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((R)-3-hydroxybut-1-yn-1-yl)pyrazolo[1,5-a]pyridine-3-carbonitrile was obtained by using from (R)-but-3-yn-2-ol and 6-bromo-4-(6-(6-((5-fluoro-6-methoxypyridin-3-yl)methyl)-3,6-diazabicyclo[3.1.1]heptan-3-yl)pyrazolo[1,5-a]pyridine-3-carbonitrile as raw materials with reference to step 2 of embodiment 31.

MS m/z (ESI): 524.2 [M+H]$^+$.

$^1$H NMR (400 MHz, $CDCl_3$) δ 8.62 (d, J=1.0 Hz, 1H), 8.40 (d, J=2.2 Hz, 1H), 8.31 (s, 1H), 7.89 (s, 1H), 7.78 (dd, J=8.8, 2.4 Hz, 1H), 7.62 (s, 1H), 7.30 (d, J=1.2 Hz, 1H), 6.70 (d, J=8.8 Hz, 1H), 4.80 (q, J=6.6 Hz, 1H), 4.01 (s, 3H), 3.97-3.82 (m, 3H), 3.71 (s, 4H), 2.87 (s, 2H), 1.74 (d, J=8.2 Hz, 1H), 1.59 (d, J=6.6 Hz, 3H).

Embodiment 158

6-((3-Cyanobicyclo[1.1.1]pentan-1-yl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

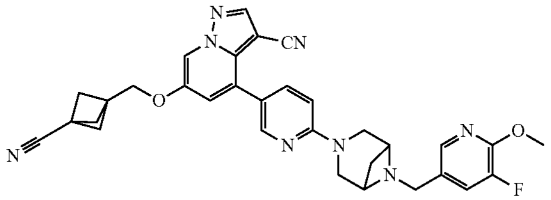 [SMILES: COc1ncc(CN2C3CC2CN(c2ccc(-c4cc(OCC56CC(C#N)(C5)C6)cn5ncc(C#N)c45)cn2)C3)cc1F]

6-((3-Cyanobicyclo[1.1.1]pentan-1-yl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using (3-cyanobicyclo[1.1.1]pentan-1-yl)methyl 4-methylbenzenesulfonate and 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw materials with reference to step 2 of embodiment 106.

MS m/z (ESI): 577.2 [M+H]$^+$.

$^1$H NMR (400 MHz, $CDCl_3$) δ 8.40 (d, J=1.9 Hz, 1H), 8.22 (s, 1H), 8.07 (s, 1H), 7.88 (s, 1H), 7.79 (dd, J=8.7, 2.0 Hz, 1H), 7.60 (s, 1H), 7.11 (s, 1H), 6.70 (d, J=8.8 Hz, 1H), 4.01 (s, 5H), 3.88 (m, 4H), 3.68 (s, 4H), 2.85 (s, 1H), 2.37 (s, 6H), 1.76-1.69 (m, 1H).

Embodiment 159

6-((3-Cyano-3-methylcyclobutyl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

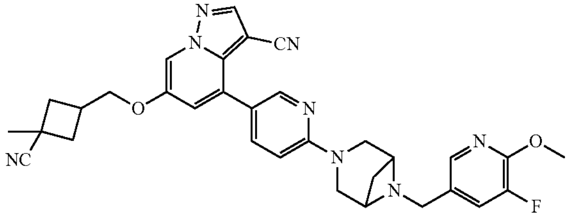

6-((3-Cyano-3-methylcyclobutyl)methoxy)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using (3-cyano-3-methylcyclobutyl)methyl 4-methylbenzenesulfonate and 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw materials with reference to step 2 of embodiment 106.

MS m/z (ESI): 579.3 [M+H]$^+$.

Embodiment 160

4-(6-(6-((5-Fluoro-6-methoxypyridin-3-yl)methyl)-3,6-diazabicyclo[3.1.1]heptan-3-yl)pyridin-3-yl)-6-((3-(hydroxymethyl)bicyclo[1.1.1]pentan-1-yl)methoxy)pyrazolo[1,5-a]pyridine-3-carbonitrile

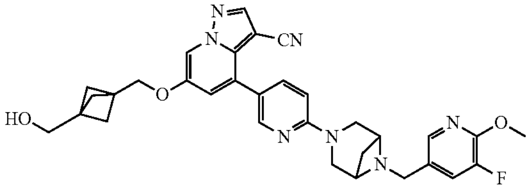 [SMILES: COc1ncc(CN2C3CC2CN(c2ccc(-c4cc(OCC56CC(CO)(C5)C6)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((3-(hydroxymethyl)bicyclo[1.1.1]pentan-1-yl)methoxy)pyrazolo[1,5-a]pyridine-3-carbonitrile was obtained by using (3-(hydroxymethyl)bicyclo[1.1.1]pentan-1-yl)methyl 4-methylbenzenesulfonate and 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw materials with reference to step 2 of embodiment 106.

MS m/z (ESI): 582.3 [M+H]$^+$.

$^1$H NMR (400 MHz, $CDCl_3$) δ 8.41 (d, J=2.1 Hz, 1H), 8.21 (s, 1H), 8.11 (d, J=1.9 Hz, 1H), 7.88 (s, 1H), 7.79 (dd, J=8.8, 2.4 Hz, 1H), 7.54 (d, J=10.8 Hz, 1H), 7.14 (d, J=1.9 Hz, 1H), 6.69 (d, J=8.8 Hz, 1H), 4.05 (s, 2H), 4.01 (s, 3H), 3.85 (d, J=11.3 Hz, 4H), 3.66 (s, 6H), 2.79 (s, 1H), 1.82 (s, 6H), 1.70 (d, J=8.8 Hz, 1H).

Embodiment 161

4-(6-(6-((5-Fluoro-6-methoxypyridin-3-yl)methyl)-3,6-diazabicyclo[3.1.1]heptan-3-yl)pyridin-3-yl)-6-((cis-3-hydroxy-3-methylcyclobutyl)methoxy)pyrazolo[1,5-a]pyridine-3-carbonitrile

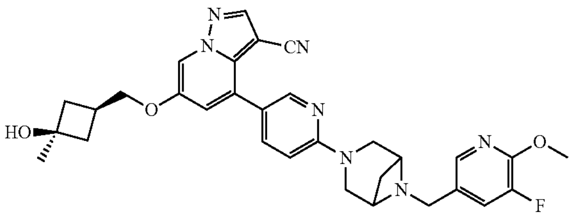 [SMILES: COc1ncc(CN2C3CC2CN(c2ccc(-c4cc(OC[C@H]5C[C@@](C)(O)C5)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((cis-3-hydroxy-3-methylcyclobutyl)methoxy)pyrazolo[1,5-a]pyridine-3-carbonitrile was obtained by using (cis-3-hydroxy-3-methylcyclobutyl)methyl 4-methylbenzenesulfonate and 4-(6-(6-((5-fluoro-6-methoxypyridin-3-yl)methyl)-3,6-diazabicyclo[3.1.1]heptan-3-yl)pyridin-3-yl)-6-hydroxypyrazolo[1,5-a]pyridine-3-carbonitrile as raw materials with reference to step 2 of embodiment 106.

MS m/z (ESI): 570.3 $[M+H]^+$.

$^1H$ NMR (400 MHz, $CDCl_3$) δ 8.42 (d, J=2.1 Hz, 1H), 8.21 (s, 1H), 8.13 (d, J=1.9 Hz, 1H), 7.92 (s, 1H), 7.81 (dd, J=8.7, 2.2 Hz, 1H), 7.75 (s, 1H), 7.14 (d, J=1.9 Hz, 1H), 6.71 (d, J=8.8 Hz, 1H), 4.14-3.99 (m, 7H), 3.93 (s, 2H), 3.77 (s, 4H), 3.00 (s, 1H), 2.38 (dd, J=15.0, 7.6 Hz, 1H), 2.29 (dd, J=12.5, 7.4 Hz, 2H), 2.02 (t, J=10.2 Hz, 2H), 1.78 (s, 2H), 1.45 (s, 3H).

Embodiment 162

3-Chloro-N-(1-(5-(3-cyano-6-(3-hydroxy-3-methylazetidin-1-yl)pyrazolo[1,5-a]pyridin-4-yl)pyridin-2-yl)-4-methylpiperidin-4-yl)picolinamide

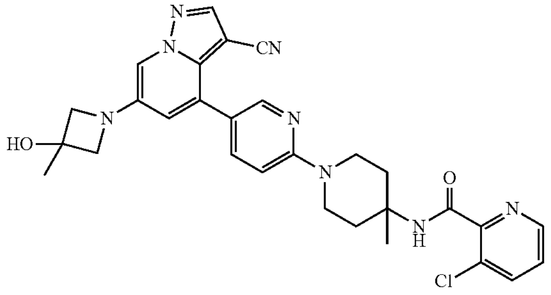 [SMILES: CC1(O)CN(c2cc(-c3ccc(N4CCC(C)(NC(=O)c5ncccc5Cl)CC4)nc3)c3c(C#N)cnn3c2)C1]

3-Chloro-N-(1-(5-(3-cyano-6-(3-hydroxy-3-methylazetidin-1-yl)pyrazolo[1,5-a]pyridin-4-yl)pyridin-2-yl)-4-methylpiperidin-4-yl)picolinamide was obtained by using 3-methylazetidin-3-ol and N-(1-(5-(6-bromo-3-cyanopyrazolo[1,5-a]pyridin-4-yl)pyridin-2-yl)-4-methylpiperidin-4-yl)-3-chloromethylpyridinamide as raw materials with reference to step 1 of embodiment 110.

MS m/z (ESI): 557.2 $[M+H]^+$.

$^1H$ NMR (400 MHz, $CDCl_3$) δ 8.46 (d, J=3.7 Hz, 1H), 8.33 (s, 1H), 8.14 (s, 1H), 7.94 (s, 1H), 7.83 (d, J=8.6 Hz, 1H), 7.72 (s, 1H), 7.38 (dd, J=8.1, 4.5 Hz, 1H), 6.92 (d, J=9.6 Hz, 1H), 6.75 (s, 1H), 4.15 (s, 2H), 3.91 (d, J=7.3 Hz, 2H), 3.82 (d, J=7.2 Hz, 2H), 3.49 (s, 2H), 2.49 (s, 2H), 2.24-2.18 (m, 1H), 1.88-1.80 (m, 2H), 1.68-1.65 (m, 3H), 1.25 (s, 3H).

Embodiment 163

3-Chloro-N-(1-(5-(3-cyano-6-(3-cyano-3-methylazetidin-1-yl)pyrazolo[1,5-a]pyridin-4-yl)pyridin-2-yl)-4-methylpiperidin-4-yl)picolinamide

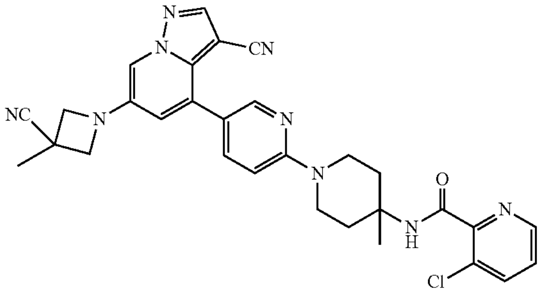 [SMILES: CC1(C#N)CN(c2cc(-c3ccc(N4CCC(C)(NC(=O)c5ncccc5Cl)CC4)nc3)c3c(C#N)cnn3c2)C1]

3-Chloro-N-(1-(5-(3-cyano-6-(3-cyano-3-methylazetidin-1-yl)pyrazolo[1,5-a]pyridin-4-yl)pyridin-2-yl)-4-methylpiperidin-4-yl)picolinamide was obtained by using 3-methylazetidin-3-carbonitrile and N-(1-(5-(6-bromo-3-cyanopyrazolo[1,5-a]pyridin-4-yl)pyridin-2-yl)-4-methylpiperidin-4-yl)-3-chloromethylpyridinamide as raw materials with reference to step 1 of embodiment 110.

MS m/z (ESI): 566.2 $[M+H]^+$.

$^1H$ NMR (400 MHz, $CDCl_3$) δ 8.46 (dd, J=4.5, 1.3 Hz, 1H), 8.31 (d, J=2.3 Hz, 1H), 8.16 (s, 1H), 7.91 (s, 1H), 7.83 (dd, J=8.1, 1.3 Hz, 1H), 7.71 (d, J=1.9 Hz, 1H), 7.37 (dd, J=8.1, 4.5 Hz, 1H), 6.82 (d, J=8.9 Hz, 1H), 6.67 (d, J=1.9 Hz, 1H), 4.28 (d, J=7.0 Hz, 2H), 4.09 (d, J=13.6 Hz, 2H), 3.88 (d, J=7.0 Hz, 2H), 3.39 (t, J=11.1 Hz, 2H), 2.43 (d, J=13.8 Hz, 2H), 1.84 (d, J=4.3 Hz, 1H), 1.82 (s, 3H), 1.78 (d, J=4.1 Hz, 1H), 1.60 (s, 3H).

Embodiment 164

4-(6-(6-((5-Fluoro-6-methoxypyridin-3-yl)methyl)-3,6-diazabicyclo[3.1.1]heptan-3-yl)pyridin-3-yl)-6-(3-hydroxy-3-methylazetidin-1-yl)pyrazolo[1,5-a]pyridine-3-carbonitrile

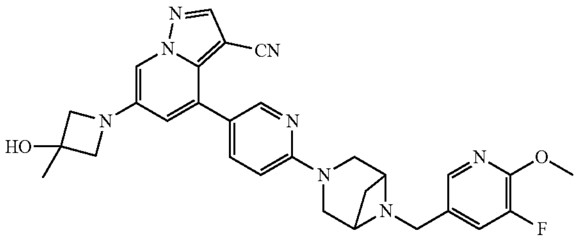 [SMILES: COc1ncc(CN2C3CC2CN(c2ccc(-c4cc(N5CC(C)(O)C5)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-(3-hydroxy-3-methylazetidin-1-yl)pyrazolo[1,5-a]pyridine-3-carbonitrile was obtained by using 3-methylazetidin-3-ol and 6-bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile as raw materials with reference to step 1 of embodiment 110.

MS m/z (ESI): 541.2 $[M+H]^+$.

$^1H$ NMR (400 MHz, $CDCl_3$) δ 8.40 (s, 1H), 8.15 (s, 1H), 7.95 (s, 2H), 7.82 (d, J=8.2 Hz, 1H), 7.74 (d, J=1.6 Hz, 1H), 6.74 (dd, J=11.8, 5.2 Hz, 2H), 4.25 (s, 2H), 4.02 (s, 3H), 3.88 (dd, J=36.0, 7.4 Hz, 7H), 3.22 (s, 1H), 2.25-2.18 (m, 1H), 2.01 (s, 1H), 1.85 (s, 2H), 1.68 (s, 3H).

Embodiment 165

1-Cyano-N-(3-cyano-4-(6-(6-((6-methoxypyridin-3-yl)methyl)-3,6-diazabicyclo[3.1.1]heptan-3-yl)pyridinpyridin-3-yl)pyrazolo[1,5-a]pyridin-6-yl)cyclopropane-1-carboxamide

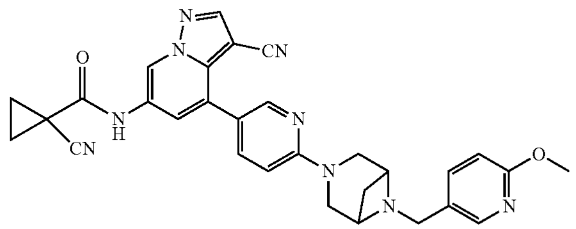 [SMILES: COc1ccc(CN2C3CC2CN(c2ccc(-c4cc(NC(=O)C5(C#N)CC5)cn5ncc(C#N)c45)cn2)C3)cn1]

Step 1: 1-cyano-N-(3-cyano-4-(6-(6-((6-methoxypyridin-3-yl)methyl)-3,6-diazabicyclo[3.1.1]heptan-3-yl)pyridinpyridin-3-yl)pyrazolo[1,5-a]pyridin-6-yl)cyclopropane-1-carboxamide

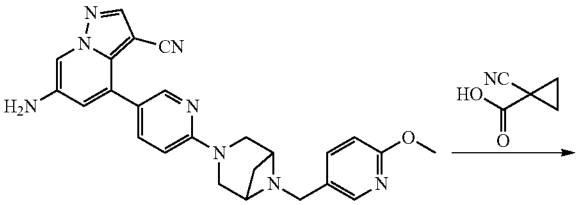

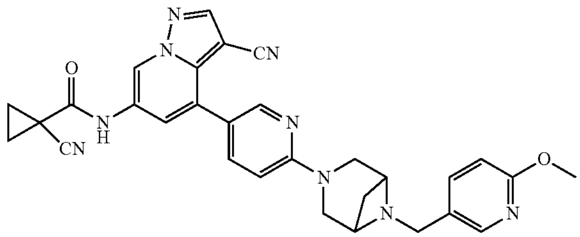

1-Cyano-N-(3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)cyclopropane-1-carboxamide (off-white solid) was obtained by using 6-amino-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and 1-cyanocyclopropane-1-carboxylic acid as raw materials with reference to step 3 of embodiment 40.

MS m/z (ESI): 546.1 $[M+H]^+$.

$^1$H NMR (400 MHz, DMSO-$d_6$) δ 10.43 (br., s, 1H), 9.26 (d, J=1.7 Hz, 1H), 8.65 (s, 1H), 8.40 (d, J=2.6 Hz, 1H), 8.07 (d, J=2.3 Hz, 1H), 7.83 (dd, J=8.8, 2.6 Hz, 1H), 7.74-7.64 (m, 2H), 6.82 (d, J=8.8 Hz, 1H), 6.77 (d, J=8.5 Hz, 1H), 3.82 (s, 3H), 3.80-3.65 (m, 4H), 3.61-3.49 (m, 4H), 1.79-1.70 (m, 3H), 1.59 (d, J=8.4 Hz, 1H), 1.26-1.13 (m, 2H).

Embodiment 166

6-(3-Hydroxy-4-methoxy-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

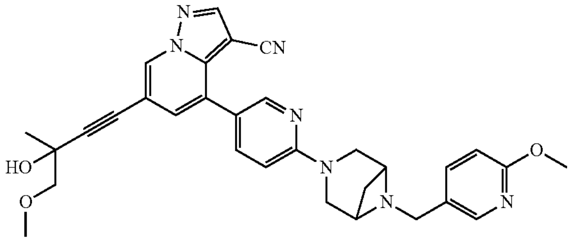 [SMILES: COCC(C)(O)C#Cc1cc(-c2ccc(N3CC4CC(C3)N4Cc3ccc(OC)nc3)nc2)c2c(C#N)cnn2c1]

6-(3-Hydroxy-4-methoxy-3-methylbut-1-yn-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (white solid) was obtained from 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and 1-methoxy-2-methylbut-3-yn-2-ol.

MS m/z (ESI): 550.3 $[M+H]^+$.

$^1$H NMR (400 MHz, DMSO) δ 9.09 (s, 1H), 8.76 (s, 1H), 8.42 (s, 1H), 8.09 (s, 1H), 7.86 (s, 1H), 7.70 (s, 1H), 7.40 (s, 1H), 6.80 (s, 1H), 5.72 (s, 1H), 3.79 (m, 14H), 3.15-2.98 (m, 4H), 1.47 (s, 3H).

Embodiment 167

6-(3-Cyano-3-methylazetidin-1-yl)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile

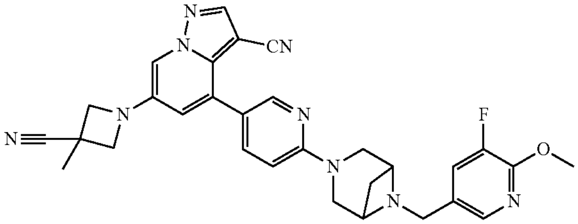 [SMILES: COc1ncc(CN2C3CC2CN(c2ccc(-c4cc(N5CC(C)(C#N)C5)cn5ncc(C#N)c45)cn2)C3)cc1F]

6-(3-Cyano-3-methylazetidin-1-yl)-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-bromo-4-(6-(6-(5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile and 3-methylazetidin-3-carbonitrile as raw materials with reference to step 1 of embodiment 110.

MS m/z (ESI): 550.2 $[M+H]^+$.

$^1$H NMR (400 MHz, $CDCl_3$) δ 8.38 (d, J=2.2 Hz, 1H), 8.18 (s, 1H), 7.87 (s, 1H), 7.79 (dd, J=8.8, 2.4 Hz, 1H), 7.73 (d, J=1.7 Hz, 1H), 7.54 (d, J=10.5 Hz, 1H), 6.70 (dd, J=5.2, 3.4 Hz, 2H), 4.29 (d, J=7.0 Hz, 2H), 4.01 (s, 3H), 3.91-3.85 (m, 6H), 3.67-3.64 (m, 4H), 2.80 (s, 1H), 1.83 (s, 3H), 1.70 (d, J=8.7 Hz, 1H).

Embodiment 168

6-(3-Cyano-3-methylazetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

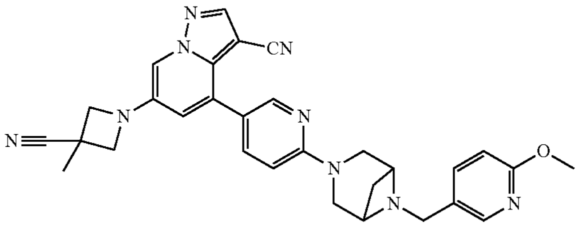 [SMILES: COc1ccc(CN2C3CC2CN(c2ccc(-c4cc(N5CC(C)(C#N)C5)cn5ncc(C#N)c45)cn2)C3)cn1]

Step 1: Preparation of 6-(3-cyano-3-methylazetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

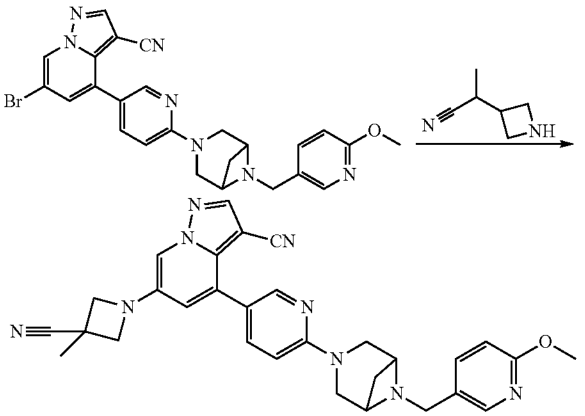

A mixture of 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (100 mg, 0.19 mmol), tris(dibenzylideneacetone)dipalladium (9 mg, 0.0095 mmol), 2-dicyclohexylphospho-2',4',6'-triisopropylbiphenyl (5 mg, 0.011 mmol), cesium carbonate (123 mg, 0.38 mmol), 3-methylazetidin-3-carbonitrile (28 mg, 0.29 mmol) and toluene (5 mL) was replaced with nitrogen, stirred at 130° C. under microwave conditions for 2 hours. After the reaction was cooled to room temperature, the reaction mixture was concentrated, dissolved with ethyl acetate and washed with saturated saline, the organic phase was dried over anhydrous sodium sulfate, filtered, evaporated to dryness, and then purified by preparative chromatography to obtain 6-(3-cyano-3-methylazetidin-1-yl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (45 mg, white solid, yield: 45%).

MS m/z (ESI): 532.3 $[M+H]^+$.

$^1$H NMR (400 MHz, DMSO) δ 8.53 (s, 1H), 8.40 (d, J=2.1 Hz, 1H), 8.21 (d, J=1.5 Hz, 1H), 8.07 (s, 1H), 7.83 (d, J=8.7 Hz, 1H), 7.68 (d, J=8.5 Hz, 1H), 7.03 (d, J=1.7 Hz, 1H), 6.78 (t, J=9.3 Hz, 2H), 4.27 (d, J=7.7 Hz, 2H), 3.91 (d, J=7.7 Hz, 2H), 3.82 (s, 3H), 3.76-3.67 (m, 4H), 3.56-3.50 (m, 4H), 2.04-1.93 (m, 1H), 1.67 (s, 3H), 1.59 (d, J=7.9 Hz, 1H).

Embodiment 169

6-((4-Hydroxytetrahydro-2H-pyran-4-yl)ethynyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

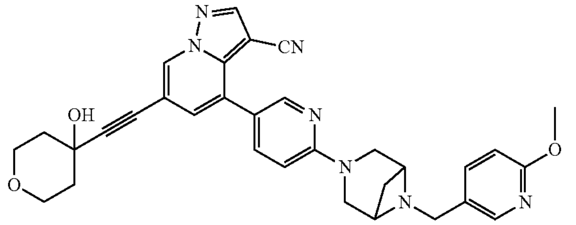 [SMILES: COc1ccc(CN2C3CC2CN(c2ccc(-c4cc(C#CC5(O)CCOCC5)cn5ncc(C#N)c45)cn2)C3)cn1]

6-((4-Hydroxytetrahydro-2H-pyran-4-yl)ethynyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile was obtained by using 6-bromo-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile and 4-ethynyltetrahydro-2H-pyran-4-ol as raw materials with reference to step 2 of embodiment 31.

MS m/z (ESI): 562.3 $[M+H]^+$.

$^1$H NMR (400 MHz, $CDCl_3$) δ 8.66 (s, 1H), 8.42 (d, J=2.0 Hz, 1H), 8.32 (s, 1H), 8.14 (s, 1H), 8.02 (s, 1H), 7.80 (d, J=8.6 Hz, 1H), 7.31 (s, 1H), 6.79 (d, J=8.6 Hz, 1H), 6.72 (d, J=8.9 Hz, 1H), 4.12 (d, J=7.1 Hz, 2H), 4.04-3.90 (m, 7H), 3.88-3.68 (m, 6H), 2.32 (s, 1H), 2.13-2.03 (m, 3H), 1.96-1.90 (m, 2H).

Embodiment 170

4-(6-(6-((5-Fluoro-6-methoxypyridin-3-yl)methyl)-3,6-diazabicyclo[3.1.1]heptan-3-yl)pyridin-3-yl)-6-((4-hydroxytetrahydro-2H-pyran-4-yl)ethynyl)pyrazolo[1,5-a]pyridine-3-carbonitrile

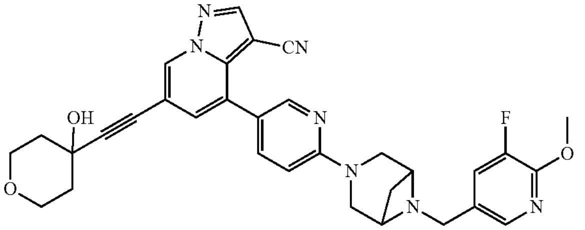 [SMILES: COc1ncc(CN2C3CC2CN(c2ccc(-c4cc(C#CC5(O)CCOCC5)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((4-hydroxytetrahydro-2H-pyran-4-yl)ethynyl)pyrazolo[1,5-a]pyridine-3-carbonitrile was obtained by using 6-bromo-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridine-3-carbonitrile and 4-ethynyltetrahydro-2H-pyran-4-ol as raw materials with reference to step 2 of embodiment 31.

MS m/z (ESI): 580.2 $[M+H]^+$.

$^1H$ NMR (400 MHz, $CDCl_3$) δ 8.66 (s, 1H), 8.42 (s, 1H), 8.32 (s, 1H), 7.97-7.75 (m, 3H), 7.31 (s, 1H), 6.72 (d, J=8.6 Hz, 1H), 4.20-4.08 (m, 2H), 4.05-3.93 (m, 7H), 3.84-3.70 (m, 6H), 2.13-2.03 (m, 3H), 1.97-1.88 (m, 3H).

Embodiment 171

6-((3-Hydroxyoxetan-3-yl)ethynyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

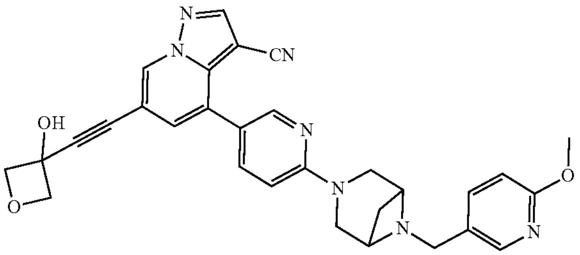 [SMILES: COc1ccc(CN2C3CC2CN(c2ccc(-c4cc(C#CC5(O)COC5)cn5ncc(C#N)c45)cn2)C3)cn1]

6-((3-Hydroxyoxetan-3-yl)ethynyl)-4-(6-(6-((6-methoxy-pyridin-3-yl)methyl)-3,6-diazabicyclo[3.1.1]heptan-3-yl) pyridin-3-yl)pyrazolo[1,5-a]pyridine-3-carbonitrile (white solid)) was obtained with reference to step 2 of embodiment 31.

MS m/z (ESI): 534.2 $[M+H]^+$.

$^1H$ NMR (400 MHz, $CDCl_3$) δ 8.66 (s, 1H), 8.40 (s, 1H), 8.33 (s, 1H), 8.12 (s, 1H), 7.77 (d, J=8.7 Hz, 2H), 7.29 (d, J=10.6 Hz, 1H), 6.72 (dd, J=16.3, 8.5 Hz, 2H), 4.95 (d, J=6.7 Hz, 2H), 4.83 (d, J=6.7 Hz, 2H), 3.92 (s, 3H), 3.89 (s, 4H), 3.67 (s, 4H), 2.82 (s, 1H), 1.72 (d, J=8.2 Hz, 2H).

Embodiment 172

4-(6-(6-((5-Fluoro-6-methoxypyridin-3-yl)methyl)-3,6-diazabicyclo[3.1.1]heptan-3-yl)pyridin-3-yl)-6-((3-hydroxyoxetan-3-yl)ethynyl)pyrazolo[1,5-a]pyridine-3-carbonitrile

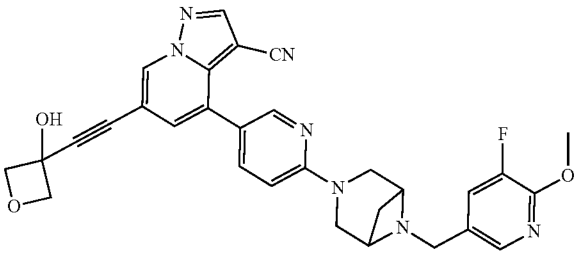 [SMILES: COc1ncc(CN2C3CC2CN(c2ccc(-c4cc(C#CC5(O)COC5)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((3-hydroxyoxetan-3-yl)ethynyl)pyrazolo[1,5-a]pyridine-3-carbonitrile (white solid) was obtained with reference to step 2 of embodiment 31.

MS m/z (ESI): 552.2 $[M+H]^+$.

$^1H$ NMR (400 MHz, $CDCl_3$) δ 8.66 (s, 1H), 8.41 (s, 1H), 8.33 (s, 1H), 7.89 (s, 1H), 7.77 (d, J=8.7 Hz, 1H), 7.54 (s, 1H), 7.30 (s, 1H), 6.70 (d, J=8.7 Hz, 1H), 4.95 (d, J=6.7 Hz, 2H), 4.83 (d, J=6.8 Hz, 2H), 4.01 (s, 3H), 3.88 (s, 4H), 3.66 (s, 4H), 2.81 (s, 1H), 1.71 (d, J=6.8 Hz, 2H).

Embodiment 173

6-((1-Hydroxycyclobutyl)ethynyl)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

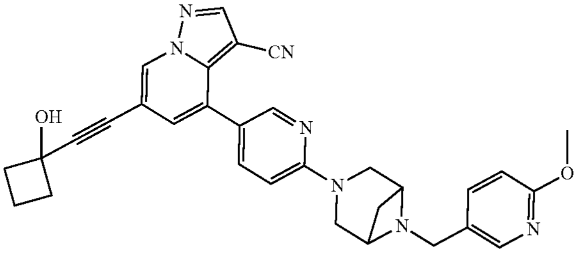 [SMILES: COc1ccc(CN2C3CC2CN(c2ccc(-c4cc(C#CC5(O)CCC5)cn5ncc(C#N)c45)cn2)C3)cn1]

6-((1-Hydroxycyclobutyl)ethynyl)-4-(6-(6-((6-methoxy-pyridin-3-yl)methyl)-3,6-diazabicyclo[3.1.1]heptan-3-yl) pyridin-3-yl)pyrazolo[1,5-a]pyridine-3-carbonitrile was obtained by using 6-bromo-4-(6-(6-((6-methoxypyridin-3-yl)methyl)-3,6-diazabicyclo[3.1.1]heptan-3-yl)pyridin-3-yl) pyrazolo[1,5-a]pyridine-3-carbonitrile and 1-ethynylcyclobutan-1-ol as raw materials with reference to embodiment 31.

MS m/z (ESI): 532.2 $[M+H]^+$.

$^1H$ NMR (400 MHz, DMSO-$d_6$) δ 9.14 (d, J=1.3 Hz, 1H), 8.75 (s, 1H), 8.42 (d, J=2.5 Hz, 1H), 8.07 (d, J=2.3 Hz, 1H), 7.86 (dd, J=8.8, 2.5 Hz, 1H), 7.68 (dd, J=8.5, 2.4 Hz, 1H), 7.46 (d, J=1.4 Hz, 1H), 6.83-6.73 (m, 2H), 6.00 (s, 1H), 3.82 (s, 3H), 3.79-3.67 (m, 4H), 3.60-3.50 (m, 4H), 2.58-2.56 (m, 1H), 2.47-2.39 (m, 2H), 2.29-2.19 (m, 2H), 1.85-1.78 (m, 2H), 1.62-1.57 (m, 1H).

Embodiment 174

4-(6-(6-((5-Fluoro-6-methoxypyridin-3-yl)methyl)-3,6-diazabicyclo[3.1.1]heptan-3-yl)pyridin-3-yl)-6-((1-hydroxycyclobutyl)ethynyl)pyrazolo[1,5-a]pyridine-3-carbonitrile

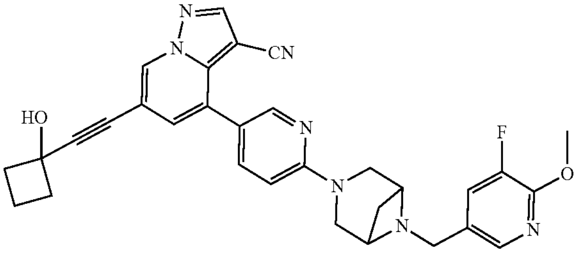 [SMILES: COc1ncc(CN2C3CC2CN(c2ccc(-c4cc(C#CC5(O)CCC5)cn5ncc(C#N)c45)cn2)C3)cc1F]

4-(6-(6-((5-Fluoro-6-methoxypyridin-3-yl)methyl)-3,6-diazabicyclo[3.1.1]heptan-3-yl)pyridin-3-yl)-6-((1-hydroxycyclobutyl)ethynyl)pyrazolo[1,5-a]pyridine-3-carbonitrile was obtained by using 6-bromo-4-(6-(6-((5-fluoro-6-methoxypyridin-3-yl)methyl)-3,6-diazabicyclo[3.1.1] heptan-3-yl)pyridin-3-yl)pyrazolo[1,5-a]pyridine-3-carbonitrile and 1-ethynylcyclobutan-1-ol as raw materials with reference to step 2 of embodiment 31.

MS m/z (ESI): 550.2 [M+H]$^+$.

$^1$H NMR (400 MHz, DMSO-$d_6$) δ 9.14 (s, 1H), 8.75 (s, 1H), 8.42 (s, 1H), 7.91 (s, 1H), 7.86 (dd, J=8.7, 2.6 Hz, 1H), 7.64 (d, J=11.4 Hz, 1H), 7.45 (d, J=1.3 Hz, 1H), 6.80 (d, J=8.8 Hz, 1H), 5.99 (s, 1H), 3.92 (s, 3H), 3.76-3.68 (m, 4H), 3.60-3.51 (m, 4H), 2.58-2.56 (m, 1H), 2.45-2.35 (m, 2H), 2.27-2.23 (m, 2H), 1.83-1.78 (m, 2H), 1.59 (d, J=8.2 Hz, 1H).

Embodiment 175

3-Chloro-N-(1-(5-(3-cyano-6-((3-hydroxyoxetan-3-yl)ethynyl)pyrazolo[1,5-a]pyridin-4-yl)pyridin-2-yl)-4-methylpiperidin-4-yl)picolinamide

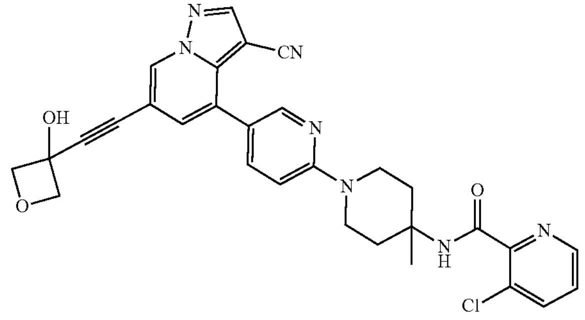 [SMILES: CC1(NC(=O)c2ncccc2Cl)CCN(c2ccc(-c3cc(C#CC4(O)COC4)cn4ncc(C#N)c34)cn2)CC1]

3-Chloro-N-(1-(5-(3-cyano-6-((3-hydroxyoxetan-3-yl) ethynyl)pyrazolo[1,5-a]pyridin-4-yl)pyridin-2-yl)-4-methylpiperidin-4-yl)picolinamide was obtained by using 3-ethynyloxetancyclo-3-ol and N-(1-(5-(6-bromo-3-cyanopyrazolo[1,5-a]pyridin-4-yl)pyridin-2-yl)-4-methylpiperidin-4-yl)-3-chloromethylpyridinamide as raw materials with reference to step 2 of embodiment 31.

MS m/z (ESI): 568.2 [M+H]$^+$.

$^1$H NMR (400 MHz, $CDCl_3$) δ 8.57 (s, 1H), 8.39 (d, J=3.9 Hz, 1H), 8.24 (s, 2H), 7.84 (s, 1H), 7.76 (d, J=8.1 Hz, 1H), 7.67-7.60 (m, 1H), 7.31 (dd, J=7.8, 4.6 Hz, 1H), 7.23 (s, 1H), 6.77 (d, J=9.0 Hz, 1H), 4.87 (d, J=6.6 Hz, 2H), 4.64 (d, J=6.7 Hz, 2H), 3.99 (d, J=13.6 Hz, 2H), 3.34 (t, J=11.0 Hz, 2H), 2.36 (d, J=14.0 Hz, 2H), 1.73 (d, J=3.8 Hz, 2H), 1.53 (s, 3H).

Embodiment 176

1-((8-(6-(6-((6-Methoxypyridin-3-yl)methyl)-3,6-diazabicyclo[3.1.1]heptan-3-yl)pyridin-3-yl)-[1,2,4]triazolo[1,5-a]pyridin-6-yl)oxo)-2-methylpropan-2-ol

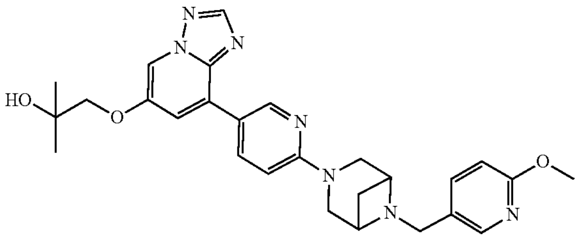 [SMILES: COc1ccc(CN2C3CC2CN(c2ccc(-c4cc(OCC(C)(C)O)cn5ncnc45)cn2)C3)cn1]

1-((8-(6-(6-((6-Methoxypyridin-3-yl)methyl)-3,6-diazabicyclo[3.1.1]heptan-3-yl)pyridin-3-yl)-[1,2,4]triazolo[1,5-a]pyridin-6-yl)oxy)-2-methylpropan-2-ol was obtained by using 8-(6-(6-((6-methoxypyridin-3-yl)methyl)-3,6-diazabicyclo[3.1.1]heptan-3-yl)pyridin-3-yl)-[1,2,4]triazolo[1,5-a]pyridin-6-ol and 1-chloro-2-methyl-2-propanol as raw materials with reference to step 1 of embodiment 152.

MS m/z (ESI): 502.2[M+H]$^+$.

Biological Test Evaluation

The present disclosure is further described below in conjunction with test embodiments to explain the disclosure, but these embodiments are not meant to limit the scope of the disclosure.

I. Testing Enzymology Experiments

Test Embodiment 1: Determination of the Inhibitory Effect of Compounds of the Present Disclosure on the Activity of RET Wild-Type and Mutant Kinases

1. Experimental Purpose

The purpose of this test embodiment is to measure the inhibitory ability of the compounds on the activity of RET wild-type and mutant kinases.

2.1 Experimental Instruments

Centrifuge (Eppendorf 5810R);
Microplate reader (BioTek Synergy H1);
Pipette (Eppendorf & Rainin).

2.2 Experimental Reagents

RET enzyme was purchased from Carna Company, and the article number was 08-159;
RET M918T enzyme was purchased from Carna Company, and the article number was 08-508;
KIF5B-RET was purchased from SignalChem Company, the article number was R02-19FG-05;
CCDC6-RET was purchased from SignalChem Company, the article number was R02-19BG-05;
RET V804M enzyme was purchased from Thermofisher Company, and the article number was PV6223;
RET V804L enzyme was purchased from Thermofisher Company, and the article number was PV4397;
HTRF KinEASE-TK kit was purchased from Cisbio Company, and the article number was 62TKOPEC;
ATP was purchased from Thermofisher Company, and the article number was PV3227;
384-well plate was purchased from PerkinElmer Company, and the article number was 6007290.

2.3 Test Compound

The compound of the embodiment of the present disclosure was self-made.

3. Experimental Methods

In this experiment, the homogeneous time-resolved fluorescence (HTRF) method was used for the detection of compounds on RET kinase activity. The experiments were carried out in 384-well plates, different concentrations of compound solutions were prepared using experimental buffers (25 mM HEPES, 10 mM MgCl2, 0.01% TritonX-100) and was added to 384-well plates, then diluted RET, RET M918T, CCDC6-RET, KIF5B-RET, RET V804M or RET V804L kinase solutions (0.01-2 nM) and substrate TK-substrate biotin (500 nM-1 μM) and Km (0.19-200 μM) concentrations of ATP solution were added thereto respectively, the total reaction system was 10 μL, the mixture was mixed well by centrifugation at 1000 rpm for 1 min; and the reaction was carried out at room temperature for 45 min, 10 μL of Sa-XL665 and TK-ab-Cryptate prepared with the assay solution were added, then the mixture was mixed well by centrifugation at 1000 rpm for 1 minute, and readings at 665 nm and 620 nm were recorded using a BioTek Synergy H1 instrument after 1 hour of reaction at room temperature.

4. Experimental Data Processing Methods

The $IC_{50}$ values were obtained by taking readings with a BioTek Synergy H1 instrument, the readings at 665 nm and 620 nm were recorded, and the ratio (665 nm/620 nm) was calculated, and then the inhibition rate was calculated, and the concentrations and the inhibition rates were fitted to a nonlinear regression curve using Graphpad Prism software.

5. Experimental Results

According to the above test methods, the test data obtained of the compounds of specific embodiments against multiple mutant kinases of RET were shown in Table 3.

TABLE 3

The $IC_{50}$ values of the compounds for inhibiting the activity of multiple mutant kinases of RET

| Embodiment number | RET M918T $IC_{50}$ (nM) | CCDC6-RET $IC_{50}$ (nM) | KIF5B-RET $IC_{50}$ (nM) | RET V804M $IC_{50}$ (nM) | RET V804L $IC_{50}$ (nM) |
|---|---|---|---|---|---|
| 23 | 1.06 | NA | NA | NA | NA |
| 31 | 0.67 | NA | NA | NA | NA |
| 92 | 0.38 | NA | NA | NA | NA |
| 94 | 0.66 | NA | 0.97 | 1.8 | 0.74 |
| 97 | 0.79 | NA | NA | NA | NA |
| 106 | 0.47 | NA | NA | NA | NA |
| 152 | 0.21 | 0.85 | 0.53 | 0.6 | 0.24 |
| 153 | 0.17 | 1.74 | 0.36 | 3.0 | 0.23 |
| 168 | 0.41 | 0.98 | 0.42 | 0.6 | 0.49 |
| 175 | 0.37 | 1.72 | 0.50 | 1.1 | 0.28 |

Note:
"NA" in the table means no test was performed.

According to the above test methods, the test data obtained of the compounds of specific embodiments against wild-type mutant kinases of RET were shown in Table 2.

6. Experimental Conclusion

The compounds of embodiments of the present disclosure show good inhibitory activity against multiple mutant kinases of RET and significant activity in the drug-resistant mutations RET M918T, KIF5B-RET and RET V804L.

Test Embodiment 2: Determination of the Inhibitory Effect of the Compounds of the Present Disclosure on the Activity of KDR Kinase

1. Experimental Purpose

The purpose of this test embodiment was to measure the inhibitory ability of compounds on the activity of KDR kinases.

2.1 Experimental Instruments

Centrifuge (Eppendorf 5810R);
Microplate reader (BioTek Synergy H1);
Pipette (Eppendorf & Rainin)

2.2 Experimental Reagents

KDR kinase was purchased from Carna Company, and the article number was 08-191;
HTRF KinEASE-TK kit was purchased from Cisbio Company, and the article number was 62TKOPEC;
ATP was purchased from Thermofisher Company, and the article number was PV3227;
384-well plate was purchased from PerkinElmer Company, and the article number was 6007290.

2.3 Experimental Compound

The compound of the embodiment of the present disclosure was self-made.

3. Experimental Methods

In this experiment, the homogeneous time-resolved fluorescence (HTRF) method was used for the detection of compounds on KDR kinase activity. The experiments were carried out in 384-well plates, different concentrations of compound solutions were prepared using experimental buffers (25 mM HEPES, 10 mM MgCl2, 0.01% TritonX-100) and were added to 384-well plates, then diluted KDR kinase solutions (0.05 nM) and substrate TK-substrate biotin (500 nM-1 μM) and Km (0.19-200 μM) concentrations of ATP solution were added, the total reaction system was 10 μL, the mixture was mixed well by centrifugation at 1000 rpm for 1 min; and after the reaction was carried out at room temperature for 45 min, 10 μL of Sa-XL665 and TK-ab-Cryptate prepared with the assay solution were added, then the mixture was mixed well by centrifugation at 1000 rpm for 1 minute, and readings at 665 nm and 620 nm were recorded using a BioTek Synergy H1 instrument after 1 hour of reaction at room temperature.

4. Experimental Data Processing Methods

The $IC_{50}$ values were obtained by taking readings with a BioTek Synergy H1 instrument, the readings at 665 nm and 620 nm were recorded, and the ratio (665 nm/620 nm) was calculated, and then the inhibition rate was calculated, and the concentrations and the inhibition rates were fitted to a nonlinear regression curve using Graphpad Prism software.

5. Experimental Results

The test data of specific embodiments obtained through the above test methods were shown in Table 4:

TABLE 4

| Relative IC50 values of compounds inhibiting the activity of RET kinases and KDR kinases | | | |
|---|---|---|---|
| Embodiment number | RET $IC_{50}$ (nM) | KDR $IC_{50}$ (nM) | Ratio (KDR/RET) |
| 1 | 0.47 | 28 | 59 |
| 6 | 0.79 | 27.7 | 35 |
| 23 | 0.69 | 11 | 16 |
| 31 | 0.48 | 16 | 34 |
| 32 | 1.22 | 1.6 | 1.3 |
| 34 | 0.76 | 70.0 | 92 |
| 62 | 1.3 | 17 | 14 |
| 75 | 3.6 | 124 | 35 |
| 85 | 1.3 | 69 | 55 |
| 92 | 0.39 | 8.2 | 21 |
| 94 | 0.31 | 23 | 73 |
| 97 | 0.38 | 46 | 122 |
| 98 | 0.41 | 9.4 | 23 |
| 99 | 0.32 | 24 | 75 |
| 106 | 0.32 | 88 | 280 |
| 110 | 0.75 | 23 | 30 |
| 111 | 1.2 | 61 | 49 |
| 112 | 0.49 | 1.8 | 4 |
| 113 | 1.1 | 8.9 | 8 |
| 114 | 0.4 | 5.6 | 14 |
| 115 | 0.7 | 4.7 | 7 |
| 116 | 0.49 | 6.2 | 13 |
| 117 | 0.83 | 213.3 | 257 |
| 118 | 0.71 | 60.4 | 85 |
| 122 | 0.4 | 11 | 27 |
| 123 | 1.56 | 104.8 | 67 |
| 127 | 0.26 | 6.5 | 25 |
| 128 | 0.40 | 176 | 438 |
| 129 | 0.42 | 13 | 30 |
| 138 | 0.8 | 21.6 | 27 |
| 140 | 1.54 | 204.4 | 133 |
| 141 | 0.34 | 9 | 26 |
| 142 | 0.31 | 37.5 | 121 |
| 144 | 1.1 | 209.3 | 187 |
| 146 | 0.85 | 185.3 | 218 |
| 147 | 1.1 | 150.0 | 136 |
| 148 | 0.58 | 183.9 | 317 |
| 149 | 0.58 | 257.1 | 445 |
| 151 | 0.35 | 11.2 | 32 |
| 152A | 0.48 | 35.24 | 73 |
| 152 | 0.34 | 21.7 | 63 |
| 153 | 0.38 | 44.34 | 118 |
| 154 | 0.33 | 14.5 | 44 |
| 155 | 0.25 | 3.0 | 12 |
| 156 | 0.25 | 4.0 | 16 |
| 157 | 0.44 | 18.9 | 43 |
| 161 | 0.37 | 7.4 | 20 |
| 162 | 1.0 | 24 | 24 |
| 163 | 0.72 | 15.8 | 22 |
| 165 | 1.8 | 246.6 | 137 |
| 168 | 0.37 | 6.90 | 19 |
| 175 | 0.25 | 47.0 | 185 |

6. Experimental Conclusion

The above data show that the compounds of the embodiments shown in the present disclosure have strong inhibitory effect on RET kinase activity and poor inhibitory effect on KDR kinase activity. Comparing the two groups of data, it can be seen that the series of compounds of the present disclosure have high selectivity in inhibiting KDR/RET kinase activity.

II. Testing Cytological Experiments

Test Embodiment 1: Determination of the Inhibitory Effect of Compounds of the Present Disclosure on the Proliferation Activity of TT Cells

1. Experimental Purpose

The purpose of this test embodiment was to measure the inhibitory effect of the compounds on the proliferative activity of TT cells.

2.1 Experimental Instruments

Microplate reader (BioTek Synergy H1);
Pipette (Eppendorf & Rainin).

2.2 Experimental Reagents

TT cells were purchased from the cell bank of the Chinese Academy of Sciences.

Cell Titer-Glo cells were purchased from Promega Company, and the article number was G7573.

2.3 Test Compound

The compound of the embodiment of the present disclosure was self-made.

3. Experimental Methods

When TT cells were cultured to the appropriate fusion level, TT cells were collected, and the cells were adjusted to the appropriate cell concentration using complete medium, and the cell suspension was spread in a 96-well plate, 90 μL per well, and placed in a 37° C., 5% $CO_2$ incubator overnight; and compound solutions of different concentrations were prepared using DMSO and culture medium; and a solvent control was set, the compound solution was added to a 96-well plate, 10 μL per well, at 37° C. in a 5% $CO_2$ incubator for 72 hours; CellTiter-Glo solution was added thereto and the mixture was mixed well by shaking, incubated for 10 min in the dark, and read by BioTek Synergy H1 microplate reader.

4. Experimental Data Processing Methods

The luminescence signal values were used to calculate the inhibition rate, the concentration and the inhibition rate were fitted to a nonlinear regression curve using Graphpad Prism software.

5. Experimental Results

TABLE 5

| Embodiment number | TT (MTC, RET C634W) $IC_{50}$ (nM) |
|---|---|
| 1 | 11.53 |
| 23 | 11.00 |
| 31 | 17.00 |
| 34 | 29.30 |
| 92 | 13.13 |
| 94 | 18.99 |
| 97 | 9.44 |
| 98 | 18.11 |

TABLE 5-continued

| Embodiment number | TT (MTC, RET C634W) $IC_{50}$ (nM) |
|---|---|
| 99 | 20.71 |
| 100 | 14.62 |
| 103 | 23.63 |
| 104 | 14.97 |
| 106 | 18.97 |
| 110 | 6.59 |
| 112 | 2.07 |
| 122 | 9.45 |
| 125 | 12.22 |
| 126 | 9.17 |
| 127 | 5.87 |
| 128 | 13.30 |
| 129 | 19.60 |
| 138 | 24.67 |
| 138 | 25.11 |
| 140 | 29.61 |
| 141 | 9.00 |
| 142 | 28.53 |
| 146 | 27.45 |
| 149 | 28.40 |
| 152 | 14.11 |
| 153 | 27.78 |
| 154 | 12.65 |
| 155 | 5.18 |
| 156 | 6.84 |
| 160 | 8.65 |
| 161 | 13.86 |
| 162 | 15.01 |
| 164 | 5.95 |
| 166 | 24.39 |
| 167 | 3.48 |
| 168 | 4.10 |
| 169 | 13.92 |
| 170 | 10.51 |
| 171 | 17.30 |
| 172 | 13.77 |
| 173 | 17.77 |
| 175 | 18.51 |

6. Experimental Conclusion

The above data show that the compounds of embodiments of the present disclosure have good inhibitory effect on the proliferation of TT cells.

Test Embodiment 2: Determination of the Inhibitory Effect of Compounds of the Present Disclosure on the Proliferation Activity of Ba/F3 KIF5B-RET Cells

1. Experimental Purpose

The inhibitory effect of the compounds on the proliferative activity of Ba/F3 KIF5B-RET cells was measured.

2. Instruments and Reagents

2.1 Experimental Instruments

Microplate reader (BioTek Synergy H1);
Pipette (Eppendorf & Rainin).

2.2 Experimental Reagents

Ba/F3 KIF5B-RET was provided by Kyinno biotechnology Co., Ltd, and the cell number was CVCL_UE86, which can be found on the cell information website https://web-.expasy.org/cellosaurus/, the stably transformed cell line does not need to rely on IL-3 for growth;

Cell Titer-Glo cells were purchased from Promega Company, and the article number was G7573.

2.3 Test Compound

The compound of the embodiment of the present disclosure was self-made.

3. Experimental Methods

When Ba/F3 KIF5B-RET cells were cultured to the appropriate cell density, cells were collected, and the cells were adjusted to the appropriate cell concentration using complete medium, and the cell suspension was spread in a 96-well plate, 90 μL per well, and placed in a 37° C., 5% $CO_2$ incubator for overnight; compound solutions of different concentrations were prepared using DMSO and culture medium; a solvent control was set, and the compound solution was added to a 96-well plate with 10 μL per well at 37° C. in a 5% $CO_2$ incubator for 72 to 144 hours; CellTiter-Glo solution was added thereto and mixed well by shaking, incubated for 10 min in the dark, and read by BioTek Synergy H1 microplate reader.

4. Experimental Data Processing Methods

The luminescence signal values were used to calculate the inhibition rate, the concentrations and the inhibition rates were fitted to a nonlinear regression curve using Graphpad Prism software.

5. Experimental Results

TABLE 6

| Embodiment number | Ba/F3 KIF5B-RET $IC_{50}$ (nM) |
|---|---|
| 1 | 24.62 |
| 23 | 13.00 |
| 31 | 12.00 |
| 34 | 28.88 |
| 94 | 22.62 |
| 95 | 27.83 |
| 99 | 16.94 |
| 100 | 15.42 |
| 103 | 18.55 |
| 104 | 13.54 |
| 106 | 15.90 |
| 125 | 15.30 |
| 126 | 7.06 |
| 138 | 30.64 |
| 142 | 19.61 |
| 146 | 32.10 |
| 148 | 33.97 |
| 149 | 17.96 |
| 151 | 16.77 |
| 152 | 11.05 |
| 153 | 22.56 |
| 154 | 7.03 |
| 155 | 14.84 |
| 156 | 5.33 |
| 157 | 26.30 |
| 160 | 5.59 |
| 161 | 8.59 |
| 162 | 22.46 |
| 164 | 12.04 |
| 166 | 34.73 |
| 167 | 6.04 |
| 168 | 4.79 |
| 169 | 15.62 |
| 170 | 13.66 |

TABLE 6-continued

| Embodiment number | Ba/F3 KIF5B-RET $IC_{50}$ (nM) |
|---|---|
| 171 | 23.93 |
| 172 | 16.79 |
| 173 | 21.93 |
| 175 | 15.49 |

6. Experimental Conclusion

The above data show that the compounds of embodiments of the present disclosure have good inhibitory effect on the proliferation of Ba/F3 KIF5B-RET cells.

Test Example 4. The Inhibitory Effect of the Compound of the Present Disclosure on the Phosphorylation of ERK, a Downstream Signal Factor of TT Cells 1. Experimental Purpose The inhibitory effect of the compound on the phosphorylation level of ERK, a downstream signal factor of TT cells, was detected.

2. Experimental Instruments and Reagents 2.1 Experimental Instruments

Imager (Biorad ChemiDoc™ MP);
Pipette (Eppendorf & Rainin).

2.2 Experimental Reagents pERK antibody was purchased from Cell Signaling Technology Company, the article number was 4370S;
Total ERK antibody was purchased from Cell Signaling Technology Company, the article number was 4696S;
The internal reference GAPDH was purchased from Cell Signaling Technology Company, the article number was 5174S;
The fluorescent secondary antibodies were purchased from LI-COR Company, the article numbers were P/N 925-68071 and P/N 926-32210.

2.3 Test Compound

The compound of the embodiment of the present disclosure was self-made.

3. Experimental Methods

In this experiment, the inhibitory effect of compounds on the phosphorylation level of ERK, a downstream signaling factor in TT cells, was measured by Western Blot method. When TT cells were cultured to the appropriate fusion degree, the cells were collected and adjusted to a suitable cell concentration using complete medium, the cell suspension was spread in a 24-well plate, 1 mL per well, and placed in a 37° C., 5% $CO_2$ incubator overnight, and compound dilutions of different concentrations (3.7 nM, 11.1 nM, 33.3 nM, 100 nM, 300 nM) were added at 37° C. and acted for 2 hours; the cell supernatant was aspirated, washed one time with PBS, and the proteins were collected with lysate; after protein denaturation, Western blot experiments were performed: performing protein electrophoresis at 120V for approximately 75 minutes, followed by 45 minutes of transfer to PVDF membranes at 10V with a semi-dry transfer instrument, enclosing at 5% BSA for 1 hour at room temperature, and then PVDF membranes were cut into strips of appropriate size and incubated with prepared antibody dilutions overnight at 4° C. and washed 6 times with TBST, followed by imaging with goat anti-mouse secondary antibody and sheep anti-rabbit secondary antibody for 1 hour at room temperature, and the membrane was washed 6 times with TBST for imaging in the Biorad ChemiDoc™ MP Imaging System.

4. Experimental Data Processing Methods

The inhibitory effect of compounds on ERK phosphorylation levels in TT cells at different concentrations was determined by detecting protein bands.

5. Experimental Results

Embodiment 152 and embodiment 153 can significantly inhibit the phosphorylation level of ERK in TT cells with a dose-dependent effect. After the compound was incubated with TT cells for 2 hours at 37° C., embodiment 152 almost completely inhibited ERK phosphorylation at 300 nM, 100 nM, 33.3 nM, and 11.1 nM; and at 3.7 nM, it could inhibit about half of the ERK phosphorylation level. Whereas, embodiment 153 can completely inhibit the phosphorylation of ERK at 300 nM and 100 nM, the degree of inhibition was reduced at 33.3 nM, at 11.1 nM, it could inhibit half of the ERK phosphorylation level, and the inhibition level was weaker at 3.7 nM.

6. Experimental Conclusion

According to the above scheme, the compounds shown in the present disclosure show dose-dependent inhibitory effect on the phosphorylation of ERK, the signal factor downstream of TT cells.

III. Determination of Balb/C Mouse Pharmacokinetics

1. Research Purpose

The pharmacokinetic behavior of the following compound embodiments, administered orally at a dose of 5 mg/kg in plasma in mice, was studied using Balb/C mice as test animals.

2. Test Scheme 2.1 Test Drugs

The compound of the embodiment of the present disclosure was self-made.

2.2 Test Animals

Balb/C Mouse 6/embodiment, male, Shanghai Jiesijie Laboratory Animal Co., Ltd, Animal Production License No. (SCXK (Shanghai) 2013-0006 N0.311620400001794).

2.3 Administration

Balb/C mice, males; p.o. after overnight fasting, respectively, at a dose of 5 mg/kg, administered in a volume of 10 mL/kg.

2.4 Sample Preparation 0.5% CMC-Na (1% Tween80) was dissolved by ultrasound, and prepared into clear solution or uniform suspension.

2.5 Sample Collection

Before and after administration, 0.1 mL of blood was collected from mice at 0, 0.5, 1, 2, 4, 6, 8 and 24 hours by orbital collection, placed in $EDTA\text{-}K_2$ tubes, centrifuged at 6000 rpm at 4° C. for 6 min to separate plasma, and stored at −80° C.

2.6 Sample Treatment

40 μL of plasma sample was precipitated by adding 160 μL of acetonitrile, mixed and centrifuged at 3500×g for 5-20 min.

100 μL of the supernatant solution after treatment was taken to analyze the concentration of the test compound by LC/MS/MS.

2.7 Liquid Phase Analysis

Liquid phase conditions: Shimadzu LC-20AD pump

Mass spectrometry conditions: AB Sciex API 4000 mass spectrometer

Chromatographic column: phenomenex Gemiu 5 μM C18 50×4.6 mm

Mobile phase: Liquid A was 0.1% formic acid aqueous solution, liquid B was acetonitrile Flow rate: 0.8 mL/min Elution time: 0-4.0 minutes, the eluent was as follows:

TABLE 7

| Time/minute | Liquid A | Liquid B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Experimental Results and Analysis

The main pharmacokinetic parameters were calculated using WinNonlin 6.1 and the results of the mouse pharmacokinetic experiments were shown in Table 8 below.

TABLE 8

Results of pharmacogenetic experiments in mice

| | Pharmacokinetic experiment (5 mg/kg) | | | | | |
|---|---|---|---|---|---|---|
| Embodiment Number | Peak time $t_{max}$ (ng/mL) | Blood concentration time $C_{max}$ (ng/mL) | Curve area $AUC_{0-t}$ (ng/mL × h) | Curve area $AUC_{0-\infty}$ (ng/mL × h) | Half-life $t_{1/2}$(h) | Average residence time MRT(h) |
| 23 | 0.5 | 3283.3 | 13821.5 | 13830.0 | 2.18 | 3.76 |
| 31 | 0.5 | 3706.7 | 21369.7 | 21511.8 | 3.37 | 4.91 |
| 34 | 0.5 | 1920.0 | 16076.7 | 16389.2 | 4.2 | 5.84 |
| 94 | 0.5 | 2786.7 | 18167.5 | 18230.7 | 2.9 | 4.61 |
| 106 | 0.5 | 3120.0 | 18865.2 | 18904.9 | 2.66 | 4.71 |
| 117 | 0.5 | 1490.0 | 6208.1 | 6220.8 | 2.19 | 3.80 |
| 125 | 0.5 | 1616.7 | 13953.1 | 14019.7 | 3.45 | 5.22 |
| 142 | 2.0 | 1943.3 | 21624.6 | 22084.0 | 4.26 | 6.51 |
| 146 | 0.5 | 9340.0 | 24470.9 | 24473.6 | 1.7 | 2.85 |
| 148 | 0.5 | 1326.7 | 7343.3 | 7369.3 | 2.34 | 4.27 |
| 149 | 0.5 | 3083.0 | 27955.0 | 28150.0 | 3.26 | 5.56 |
| 152A | 0.5 | 2816.7 | 13773.0 | 13789.2 | 2.4 | 4.07 |
| 152 | 1.0 | 2936.7 | 10978.5 | 10981.2 | 1.3 | 2.90 |
| 153 | 1.0 | 3920.0 | 14458.5 | 14460.7 | 1.2 | 2.70 |
| 154 | 2.0 | 2400.0 | 20159.0 | 20251.0 | 3.05 | 5.24 |
| 157 | 0.5 | 1703.3 | 7208.0 | 7218.5 | 1.73 | 3.47 |
| 168 | 0.5 | 4680.0 | 51613.2 | 51946.2 | 3.2 | 6.0 |

4. Experimental Conclusion

It can be seen from the results of mouse pharmacokinetic experiments in the table that the compounds of the embodiments of the present disclosure show good metabolic properties, and both the exposure AUC and the maximum blood drug concentration $C_{max}$ show good performance.

IV. Tumor Suppression Experiment on Ba/F3 KIF51B-RET Transplanted Tumor Model

Experimental Purpose

To evaluate the anti-tumor activity of the tested compounds against the subcutaneously transplanted tumor of Ba/F3 KIF51B-RET cells in nude mice.

2. Experimental Instruments and Reagents 2.1 Instrument

Ultra Clean Bench (BSC-130011 A2, Shanghai Boxun Industrial Co., Ltd. Medical Equipment Factory);

$CO_2$ incubator (311, Thermo);
Centrifuge (Centrifuge 5720R, Eppendorf);
Automatic cell counter (Countess II, life);
Pipette (10-20 μL, Eppendorf);
Microscope (TS100, Nikon);
Vernier caliper (500-196, Sanfeng, Japan);
Cell culture flask (T25/T75/T225, Corning).

2.2 Reagents

RPMI1640 (22400-089, Gibco);
Fetal bovine serum (FBS)(10099-141, Gibco);
Phosphate buffer (PBS)(10010-023, Gibco).

2.3 Test Compound

The compound of the embodiment of the present disclosure was self-made.

3. Experimental Operation

Ba/F3 KIF5B-RET cells were removed from the cell bank, resuscitated and added to RPMI1640 medium (RPMI1640+10% FBS+1% Glu+1% P/S), then cultured in a $CO_2$ incubator (incubator temperature was 37° C., $CO_2$ concentration was 5%), and when the cell number expanded to the required number for in vivo inoculation, Ba/F3 KIF5B-RET cells were collected. The cells were counted with an automatic cell counter, resuspended with PBS according to the count results, made into a cell suspension (density was 2×107/mL), and placed in an ice box for use.

Female BALB/c nude mice aged 6-8 weeks were used, weighing about 18-22 g. Mice were reared in SPF animal house, and were reared in a single cage with 5 mice in each cage. All cages, bedding and water were sterilized at high temperature before use, and all animals can eat and drink freely. Nude mice were labeled with disposable universal ear tags for mice and rats before the start of the experiment, and the skin of the inoculation site was disinfected with 75% medical alcohol before inoculation. 0.1 mL (containing 2*106 cells) of Ba/F3 KIF5B-RET cells were inoculated subcutaneously on the right back of each mouse. When the tumor volume reached 60-200 $mm^3$, it began to be administered in groups, with 5 rats in each group. Each test compound was orally administered twice a day for 14 days. The tumor volume was measured twice a week, the weight of mice was weighed, and the tumor TGI (%) was calculated.

4. Data Processing

The tumor volume ($mm^3$) was calculated as V=0.5*D*d*d, where D and d were the major and minor diameters of the tumor, respectively.

Calculation of TGI (%):

When there was no tumor regression, TGI (%)=[(1−(mean tumor volume at the end of the administration in a treatment group−mean tumor volume at the start of administration in the treatment group))/(mean tumor volume at the end of treatment in the solvent control group−mean tumor volume at the start of treatment in the solvent control group)]×100%.

When there was tumor regression, TGI (%)=[1−(mean tumor volume at the end of dosing in a treatment group−mean tumor volume at the beginning of dosing in the treatment group)/mean tumor volume at the beginning of dosing in the treatment group]×100%.

5. Experimental Results

TABLE 9

| Pharmacodynamic parameters | | | |
|---|---|---|---|
| | Tumor volume ($mm^3$, Mean ± SD) | | TGI (%) |
| Grouping | Day 0 | Day 14 | Day 14 |
| 23 10 mg/kg | 100.80 ± 31.28 (101.24 ± 35.15) | 232.46 ± 133.65 (1,536.07 ± 263.57) | 90.82 |
| 94 30 mg/kg | 132.34 ± 19.40 (133.86 ± 28.86) | 118.64 ± 84.34 (1,366.89 ± 291.81) | 110.35 |
| 146 30 mg/kg | 133.41 ± 18.82 (133.86 ± 28.86) | 98.26 ± 33.71 (1,366.89 ± 291.81) | 126.35 |
| 152A 10 mg/kg | 100.24 ± 27.85 (101.24 ± 35.15) | 247.52 ± 85.65 (1,536.07 ± 263.57) | 89.74 |
| 152 10 mg/kg | 126.13 ± 17.24 (126.52 ± 16.11) | 219.86 ± 64.31 1,882.69 ± 968.48) | 94.66 |
| 153 10 mg/kg | 126.93 ± 16.98 (126.52 ± 16.11) | 330.85 ± 147.00 (1,882.69 ± 968.48) | 88.39 |
| 154 10 mg/kg | 100.40 ± 29.77 (101.24 ± 35.15) | 276.69 ± 106.21 (1,536.07 ± 263.57) | 87.71 |
| 168 10 mg/kg | 101.59 ± 36.86 (101.24 ± 35.15) | 40.84 ± 53.92 (1,536.07 ± 263.57) | 159.80 |

Note:
The data in parentheses indicate that the tumor volume of the embodimencorresponding to the Vehicle QD × 3 w group (i.e., control group) at the corresponding time 6. Experimental Conclusion The above data show that after 14 days of continuous oral administration, the compounds of embodiments of the present disclosure can significantly inhibit the growth of Ba/F3 KIF5B-RET nude mouse transplant tumors.

V. Pharmacodynamic Experiment on Subcutaneous Xenotransplantation Tumor Model of Human Bone Marrow-Like Thyroid Cancer Cell TT 1. Experimental Purpose BALB/c nude mice were used as the test animals, and the TT xenograft tumor model of human myeloid thyroid cancer cells was used for in vivo pharmacodynamic experiments to evaluate the antitumor effects of the test compounds.

2. Experimental Instruments and Reagents 2.1 Instrument $CO_2$ incubator (311, Thermo);
High-speed refrigerated centrifuge (Multifuge X3R, Thermo);
Automatic cell counter (Mini-006-0484, cellometer);
Biosafety cabinet (1300 SERIES A2, Thermo);
Electronic balance (JJ300Y, Changshu Shuangjie);
Vernier caliper (0-150 mm/0.01 mm, Mitutoyo, Japan).

2.2 Reagents

F-12K (21127-022, Gibco);
Fetal bovine serum (FBS)(10099-141, Gibco);
Penicillin dual antibodies (PS) (SV30010, Hyclone).

3 Test Animals

BALB/c nude mice, female, 6-8 weeks old, weighing 18-22 g, provided by Shanghai Lingchang Biotechnology Co., Ltd.

4 Test Compound

The compound of the embodiment of the present disclosure was self-made.

5. Experimental Operation 5.1 Cell Culture

TT cells were cultured in vitro in a monolayer under the following conditions: F-12K medium with 20% heat-inactivated fetal bovine serum and 1% penicillin-streptomycin double antibodies at 37° C. and 5% $CO_2$. Trypsin-EDTA was used twice a week digestion for digestion treatment passaging. When cells were in an exponential growth period, cells were collected, counted and inoculated.

5.2 Tumor Inoculation

TT cells were collected when they were full in a logarithmic growth period, ensuring over 90% of vitality. 0.2 mL cell suspension containing about $1\times10^7$ of TT cells (cells suspended in basic F-12K medium and added with 50% Matrigel) was subcutaneously inoculated into the right back tumor of each mouse when the average volume of the tumor reached about 150-200 $mm^3$.

5.3 Experimental Grouping and Administration

1. The day of grouping was day 0 (D0). The interval of BID administration was 6-8 h/18-16 h. The first dose was given in the afternoon of day D0 and the last dose was given in the morning of day D21.

2. Dosing volume: 10 L/g according to the body weight of nude mice.

Animal husbandry: animals were kept in the experimental environment for 7 days after arrival to start the experiment. Animals were housed in SPF animal rooms in IVC (Independent Ventilation System) cages (5 per cage).

Animal grouping: Before administration, the animals were weighed and the tumor volume was measured. The mice were randomly grouped according to tumor volume (randomized grouping design) with 5 animals per group.

Observation: animals were monitored daily for health status and death, routine checks include observation of the effects of medication on daily behavioral performance such as behavioral activity, food and water intake, changes in body weight (measured twice a week or every other day), physical signs or other abnormalities. The number of animal deaths and side effects within the group were recorded based on the number of animals in each group.

Experimental index: The diameter of tumor was measured by vernier caliper twice a week. The tumor volume was calculated by the formula: $V=a\times b^2/2$, a and b denote the long and short diameter of the tumor, respectively. The tumor suppressive efficacy of the compounds was evaluated by TGI (%). TGI (%)=$(1-(TV_{Treatment/Dx}-TV_{Treatment/D1})/(TV_{Control/Dx}-TV_{Control/D1}))\times100\%$. Tumor suppressive efficacy was measured by TGI=$(1-(TW_{control}-TW_{treatment})/TW_{control}\times100\%$. TGI≥58% indicates that the tested substance can effectively inhibit tumor growth, and TGI≥90% indicates that the tested substance can effectively inhibit tumor growth.

5.4 Data Analysis

T test was used for comparison between two groups. One-way ANOVA was used for comparison among three or more groups. If there were significant differences in F values, multiple comparisons should be made after ANOVA analysis. GraphPadPrism 5.0 was used for all data analysis.

6. Experimental Results

TABLE 10

| Pharmacodynamic parameters | | | |
|---|---|---|---|
| | Tumor volume ($mm^3$, mean ± SEM) | | Tumor inhibition rate TGI |
| Grouping | d 0 | d 22 | d 22 |
| Vehicle | 206.10 ± 22.69 | 1,276.23 ± 161.33 | — |
| 94 30 mg/kg | 199.73 ± 24.07 | 203.56 ± 31.74 | 99.64% |
| 168 10 mg/kg | 205.23 ± 16.57 | 144.14 ± 8.95 | 129.77% |

7. Experimental Conclusion

The above data show that after 21 days of continuous oral administration, the compounds of embodiments of the present disclosure can significantly inhibit the growth of TT nude mouse transplanted tumors of thyroid cancer cells.

Although the above describes specific embodiments of the present disclosure, it should be understood by those skilled in the art that these are merely illustrative embodiments and that a variety of changes or modifications can be made to these embodiments without departing from the principles and substance of the present disclosure. Therefore, the scope of protection of the present disclosure is defined by the appended claims.

The invention claimed is:

1. A compound represented by general formula (IX-B), or a pharmaceutically acceptable salt thereof:

(IX-B)

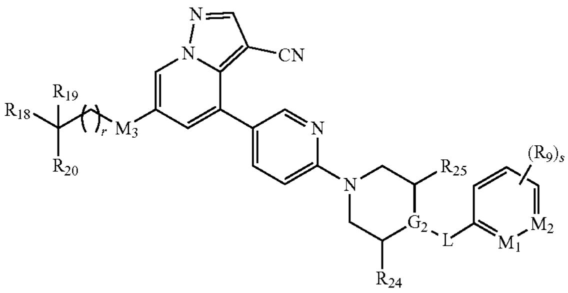

wherein:

$M_3$ is selected from bond, —O—, —S—, —NH— or —$NCH_3$—;

$R_{18}$ and $R_{19}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl or 5-12 membered heteroaryl;

or, $R_{18}$ and $R_{19}$ together with the carbon atoms they are attached to form a $C_{3-8}$ cycloalkyl or a 3-12 membered heterocyclyl;

$R_{20}$ is selected from cyano, or $C_{2-6}$ alkynyl;

or,

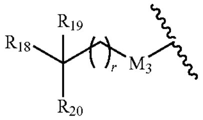

is selected from

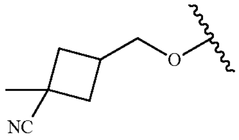

or

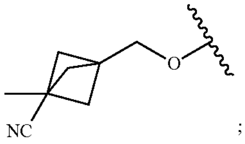

;

$R_{24}$ and $R_{25}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or —$(CH_2)_{n1}OR_{aa}$;

or, $R_{24}$ and $R_{25}$ together with the carbon atoms they are attached to and G2 form a $C_{3-8}$ cycloalkyl or 3-12 membered heterocyclyl;

r is 0, 1 or 2;

L is selected from bond, —$(CH_2)_{n1}CR_{aa}R_{bb}$—, —$(CH_2)_{n1}NR_{aa}C(O)(CH_2)_{n2}$—, —$(CH_2)_{n1}C(O)(CH_2)_{n2}(CR_{aa}R_{bb})_m$—, —$(CH_2)_{n1}C(O)(CR_{aa}R_{bb})_m(CH_2)_{n2}$—, —$(CH_2)_{n1}C(O)NR_{cc}(CR_{aa}R_{bb})_{n2}$—, —$(CH_2)_{n1}(O)(CH_2)_{n2}$— or —$(CH_2)_{n1}NR_{aa}(CH_2)_{n2}$—;

$G_2$ is selected from N or $CR_{aa}$;

$M_1$ is selected from N or $CR_{aa}$;

$M_2$ is selected from N or $CR_{aa}$;

$R_9$ is selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or —$(CH_2)_{n1}OR_{aa}$;

$R_{aa}$, $R_{bb}$ and $R_{cc}$ are each independently selected from hydrogen, deuterium, cyano, amino, $C_{1-6}$ alkyl, $C_{1-6}$ alkoxy, $C_{1-6}$ hydroxyalkyl, hydroxyl, $C_{3-8}$ cycloalkyl, 3-12 membered heterocyclyl or $C_{6-14}$ aryl, wherein the $C_{1-6}$ alkyl, $C_{1-6}$ alkoxy, $C_{1-6}$ hydroxyalkyl, hydroxyl, $C_{3-8}$ cycloalkyl, 3-12 membered heterocylcyl and $C_{6-14}$ aryl are optionally further substituted by one or more substituents selected from hydrogen, halogen, cyano, hydroxyl, oxo, imino, $C_{1-6}$ alkyl or $C_{1-6}$ hydroxyalkyl;

or, any two of $R_{aa}$, $R_{bb}$ and $R_{cc}$ are optionally connected to form a $C_{3-8}$ cycloalkyl or a 3-12 membered heterocyclyl, wherein the $C_{3-8}$ cycloalkyl and 3-12 membered heterocyclyl are optionally further substituted by one or more substituents selected from hydrogen, amino, halogen, cyano, hydroxyl, oxo, imino, $C_{1-6}$ alkyl or $C_{1-6}$ hydroxyalkyl;

n1 is 0, 1 or 2;

n2 is 0, 1 or 2;

m is 0, 1 or 2; and s is 0, 1, 2 or 3.

2. A compound represented by general formula (IX-C), or a pharmaceutically acceptable salt thereof:

(IX-C)

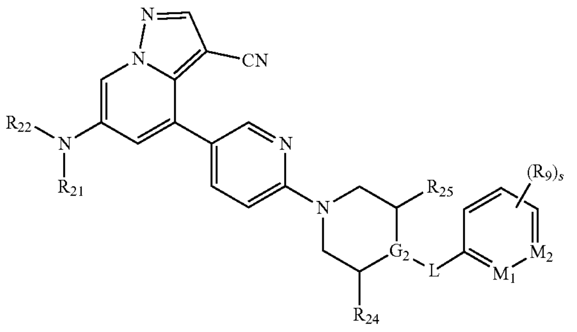

wherein:

$R_{21}$ and $R_{22}$ together with the atoms they are attached to form a azetidinyl or 2-azaspiro[3.3]heptane, wherein the azetidinyl or 2-azaspiro[3.3]heptane are optionally further substituted by one or more substituents selected from hydrogen, amino, halogen, cyano, hydroxyl, oxo, $C_{1-6}$ alkyl or $C_{1-6}$ hydroxyalkyl;

$R_{24}$ and $R_{25}$ are each independently selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or —$(CH_2)_{n1}OR_{aa}$;

or, $R_{24}$ and $R_{25}$ together with the carbon atoms they are attached to and G2 form a $C_{3-8}$ cycloalkyl or 3-12 membered heterocyclyl;

L is selected from bond, —$(CH_2)_{n1}CR_{aa}R_{bb}$—, —$(CH_2)_{n1}NR_{aa}C(O)(CH_2)_{n2}$—, —$(CH_2)_{n1}C(O)(CH_2)_{n2}(CR_{aa}R_{bb})_m$—, —$(CH_2)_{n1}C(O)(CR_{aa}R_{bb})_m(CH_2)_{n2}$—, —$(CH_2)_{n1}C(O)NR_{cc}(CR_{aa}R_{bb})_{n2}$—, —$(CH_2)_{n2}(O)(CH_2)_{n2}$— or —$(CH_2)_{n1}NR_{aa}(CH_2)_{n2}$—;

$G_2$ is selected from N or $CR_{aa}$;

$M_1$ is selected from N or $CR_{aa}$;

$M_2$ is selected from N or $CR_{aa}$;

$R_9$ is selected from hydrogen, deuterium, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, halogen, amino, nitro, hydroxyl, cyano, $C_{2-6}$ alkenyl, $C_{2-6}$ alkynyl, $C_{3-8}$ cycloalkyl, 3-12 membered heterocyclyl, $C_{6-10}$ aryl, 5-12 membered heteroaryl or —$(CH_2)_{n1}OR_{aa}$;

$R_{aa}$, $R_{bb}$ and $R_{cc}$ are each independently selected from hydrogen, deuterium, cyano, amino, $C_{1-6}$ alkyl, $C_{1-6}$ alkoxy, $C_{1-6}$ hydroxyalkyl, hydroxyl, $C_{3-8}$ cycloalkyl, 3-12 membered heterocyclyl or $C_{6-14}$ aryl, wherein the $C_{1-6}$ alkyl, $C_{1-6}$ alkoxy, $C_{1-6}$ hydroxyalkyl, hydroxyl, $C_{3-8}$ cycloalkyl, 3-12 membered heterocylcyl and $C_{6-14}$ aryl are optionally further substituted by one or more substituents selected from hydrogen, halogen, cyano, hydroxyl, oxo, imino, $C_{1-6}$ alkyl or $C_{1-6}$ hydroxyalkyl;

or, any two of $R_{aa}$, $R_{bb}$ and $R_{cc}$ are optionally connected to form a $C_{3-8}$ cycloalkyl or a 3-12 membered heterocyclyl, wherein the $C_{3-8}$ cycloalkyl and 3-12 membered heterocyclyl are optionally further substituted by one or more substituents selected from hydrogen, amino, halogen, cyano, hydroxyl, oxo, imino, $C_{1-6}$ alkyl or $C_{1-6}$ hydroxyalkyl;

n1 is 0, 1 or 2;

n2 is 0, 1 or 2;

m is 0, 1 or 2; and s is 0, 1, 2 or 3.

3. A compound, or a pharmaceutically acceptable salt thereof, wherein, the specific structure of the compound is as follows:

23

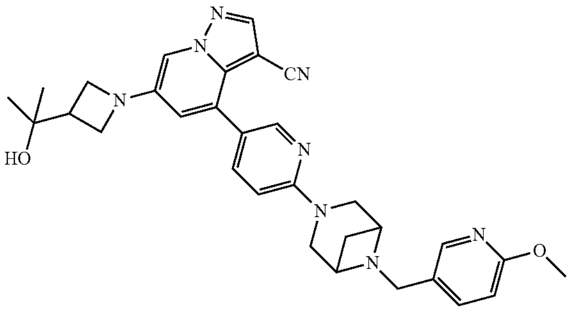

24

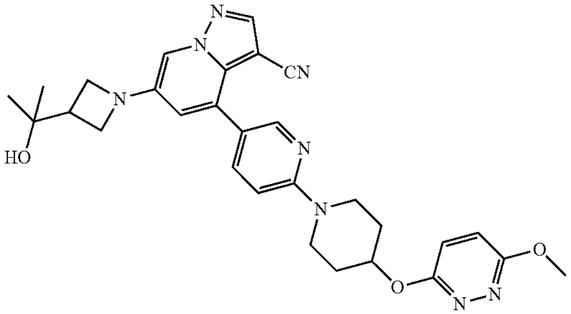

31

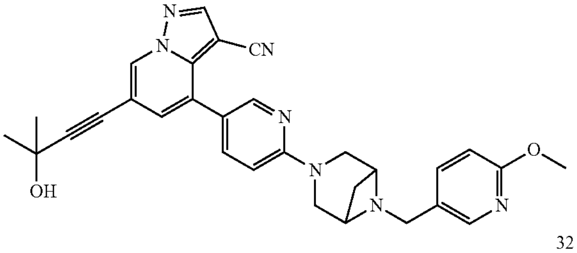

32

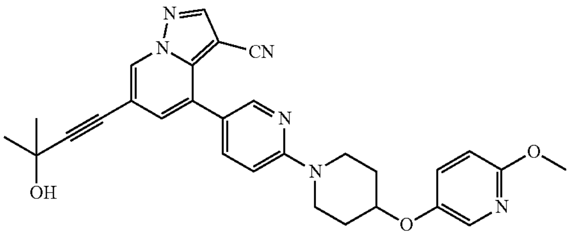

-continued

33

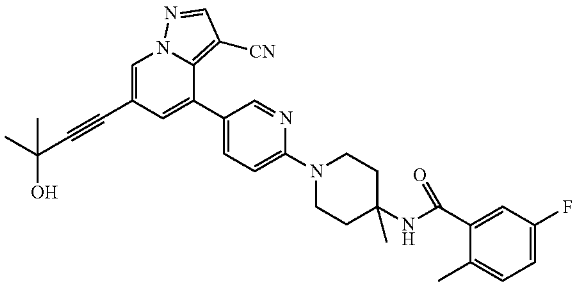

34

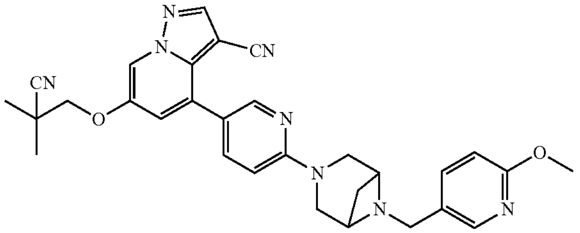

35

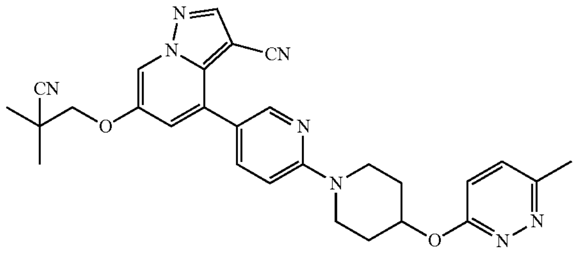

36

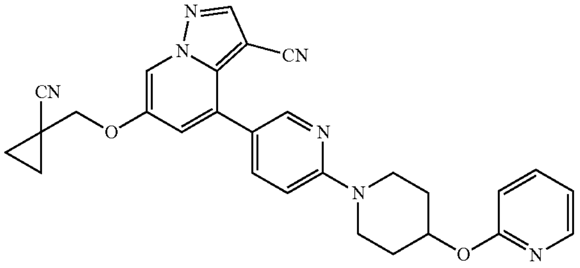

92

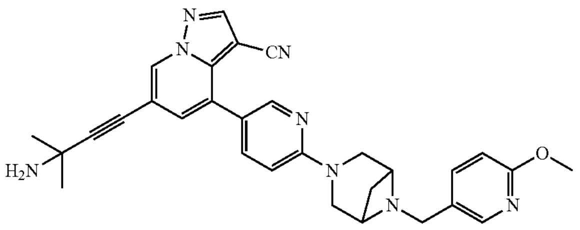

93

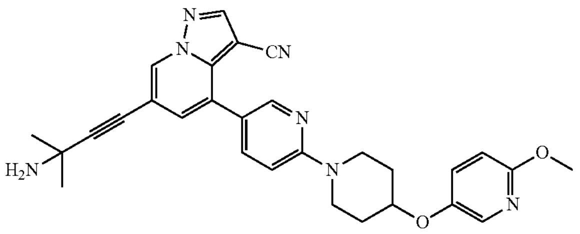

-continued
94
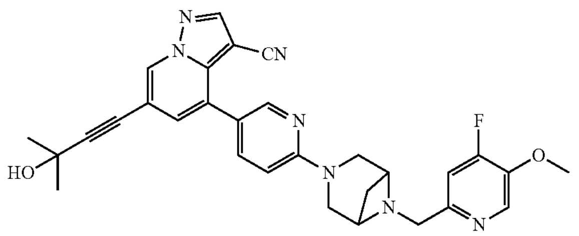
95
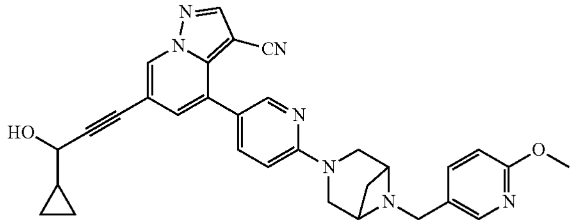
96
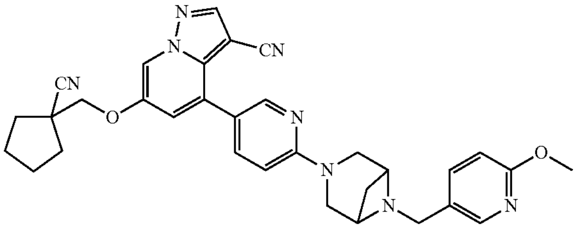
97
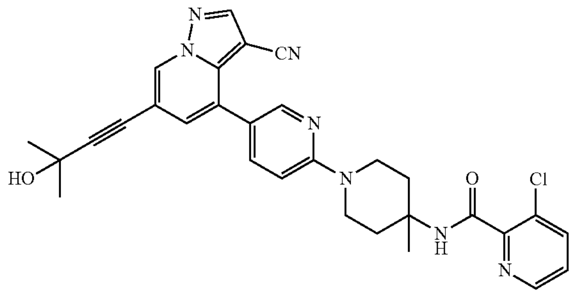
98
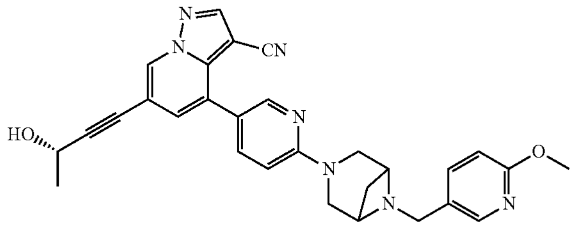
99
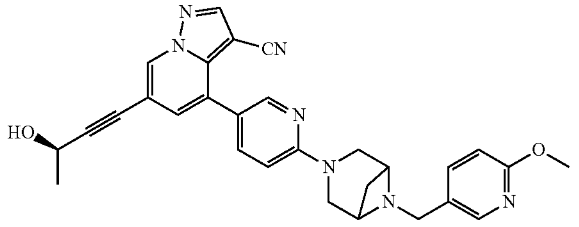
-continued
100
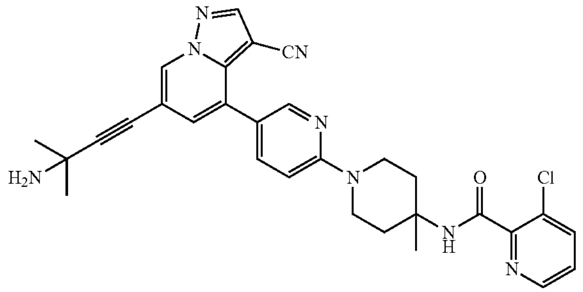
101
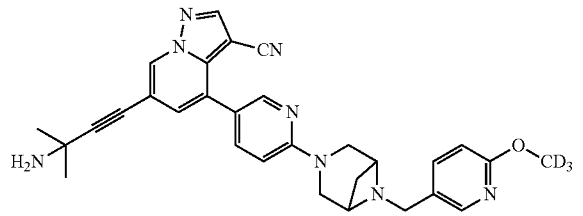
102
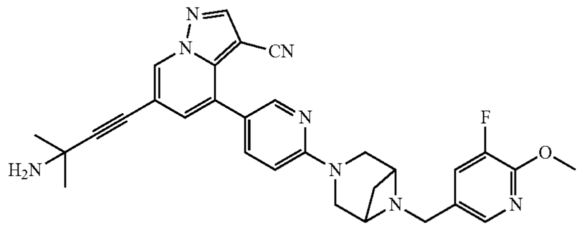
103
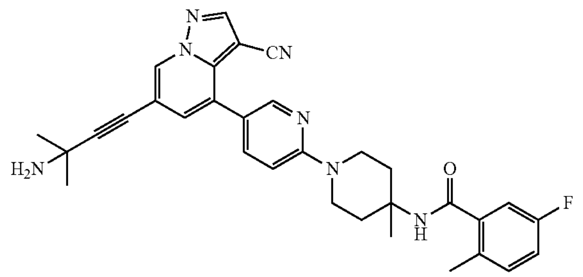
104
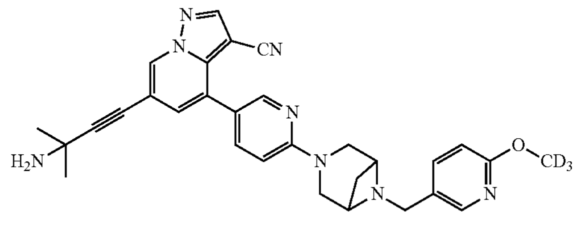
105
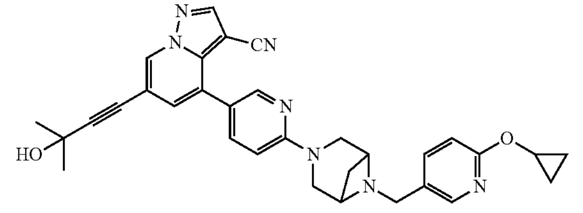

-continued
106
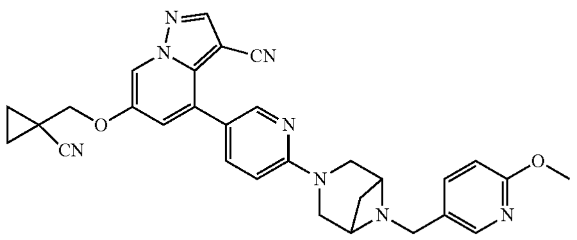
107
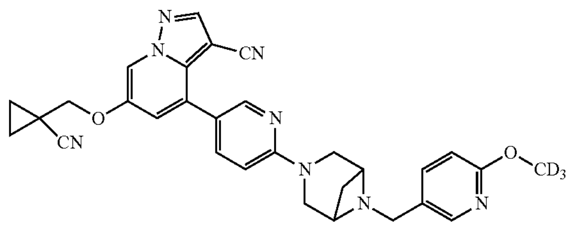
108
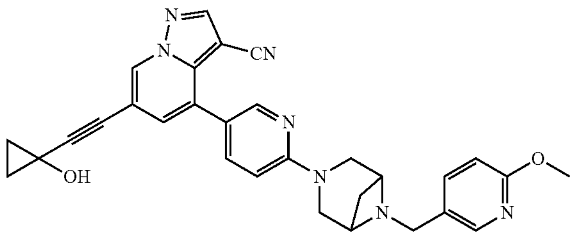
109
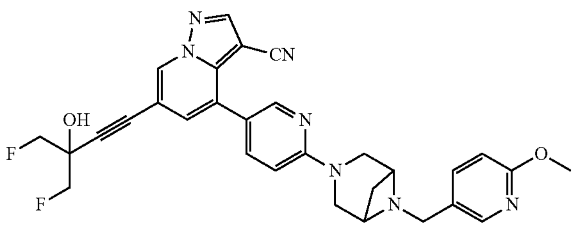
110
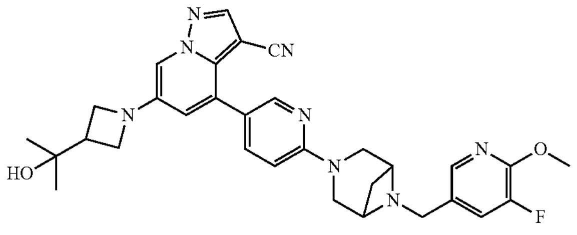
111
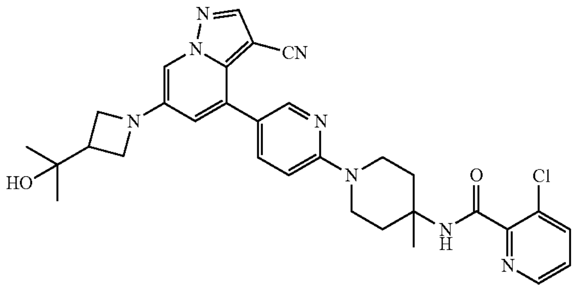
-continued
112
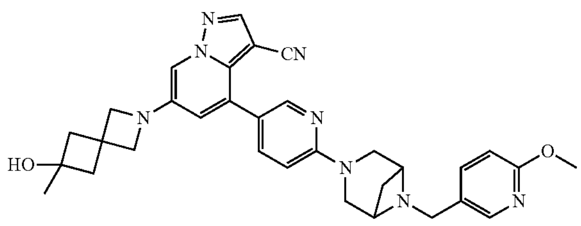
113
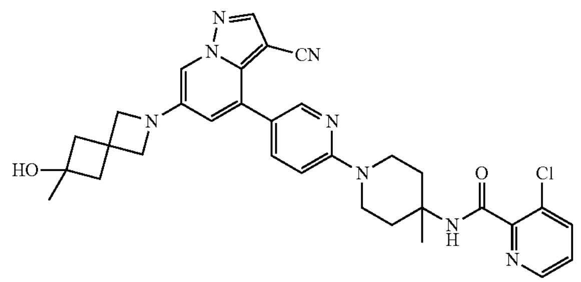
114
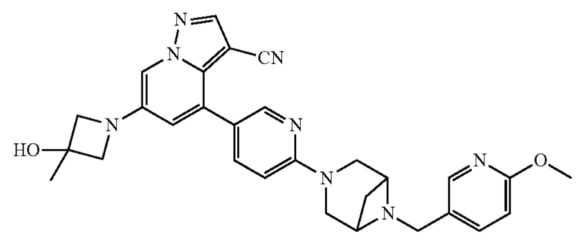
115
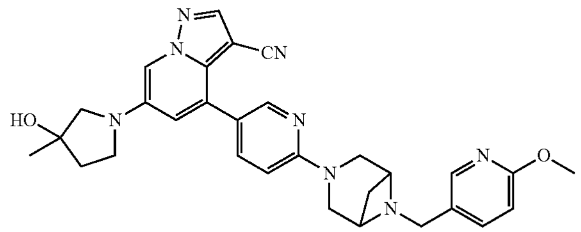
116
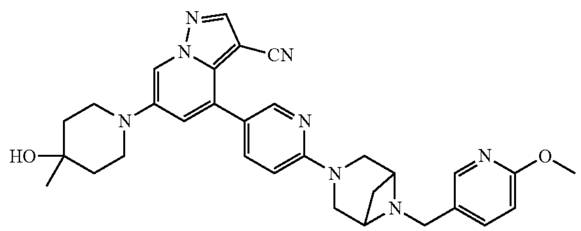
117
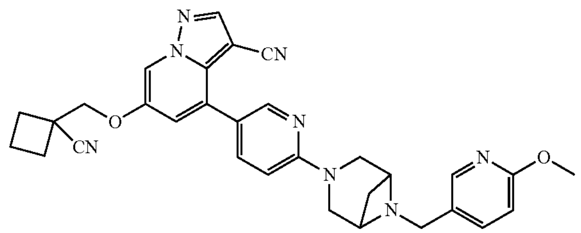

-continued
118
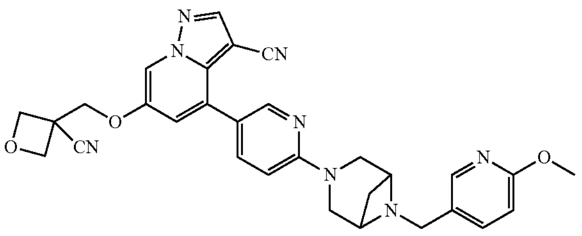
120
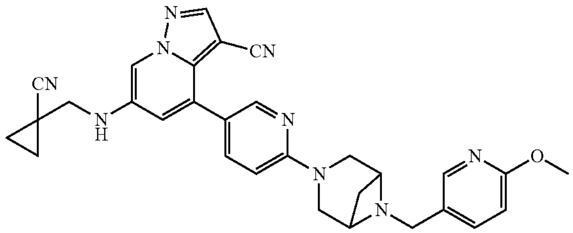
121
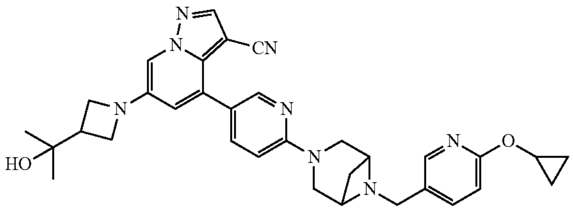
122
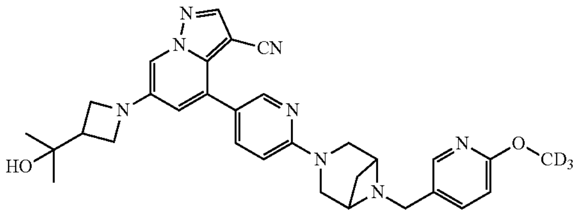
123
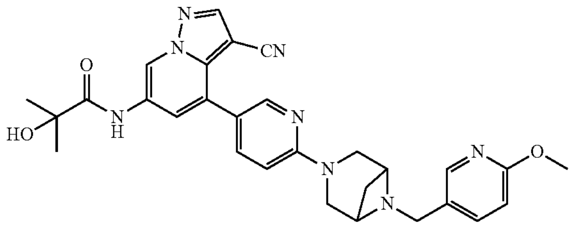
127
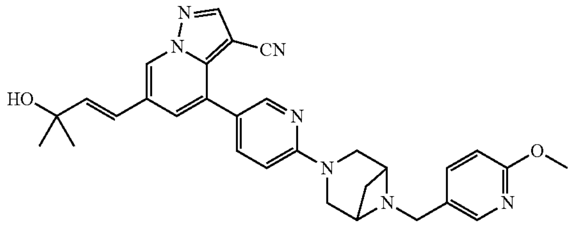
-continued
129
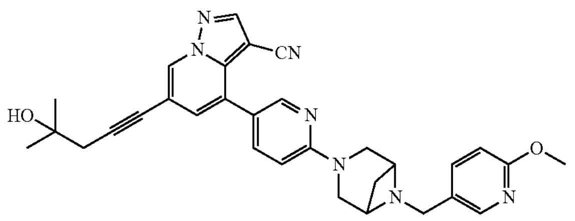
130
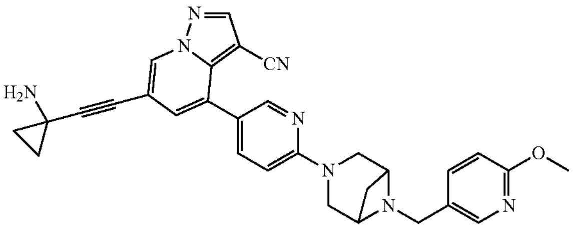
131
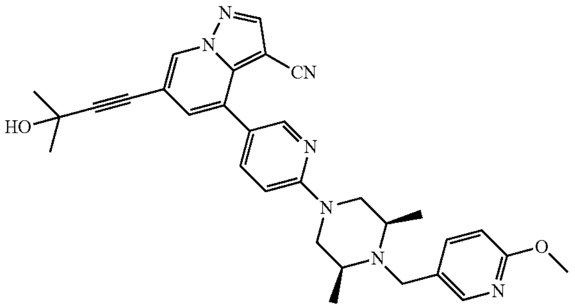
132
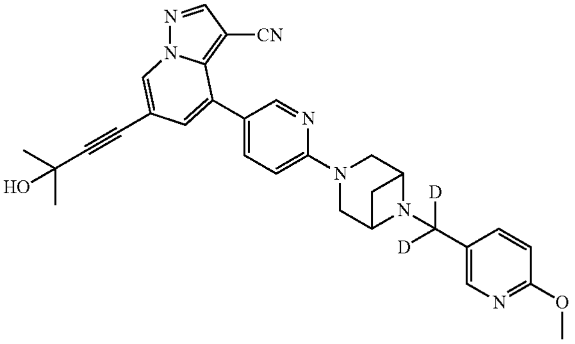
134
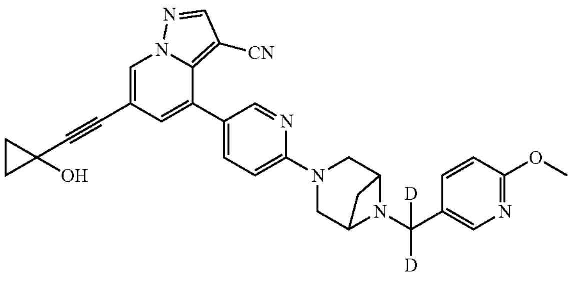

-continued
136
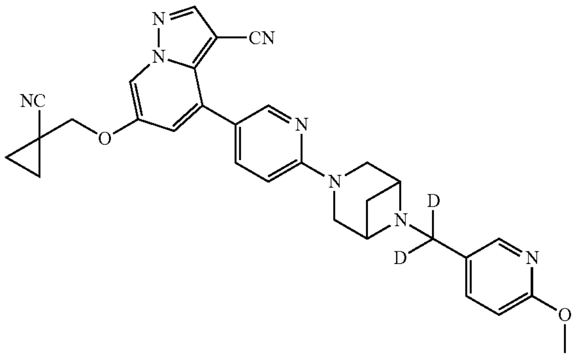
138
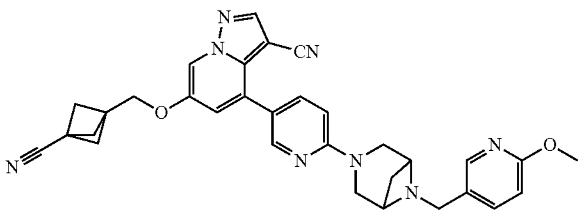
139
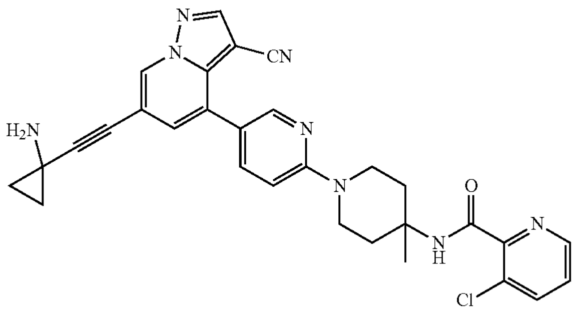
142
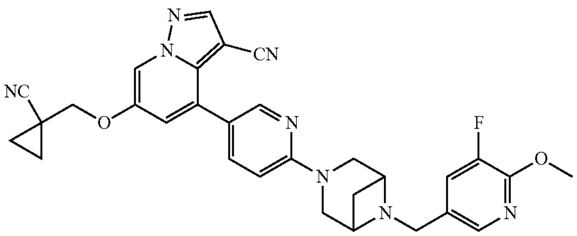
144
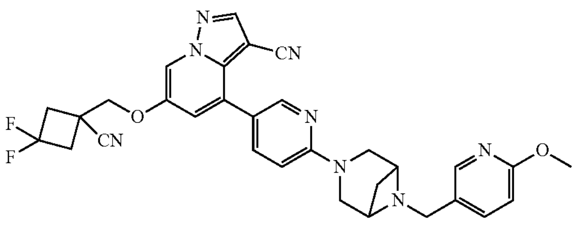
-continued
145
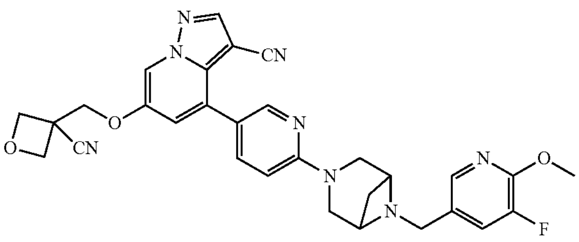
146
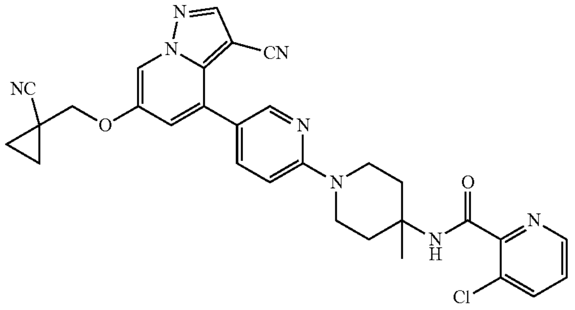
147
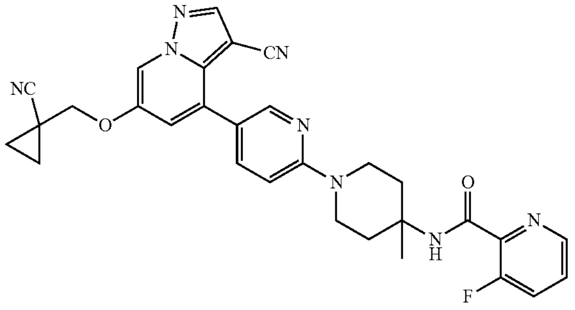
148
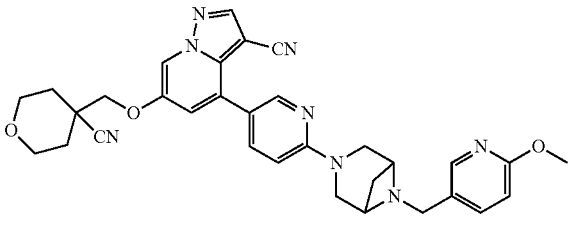
149
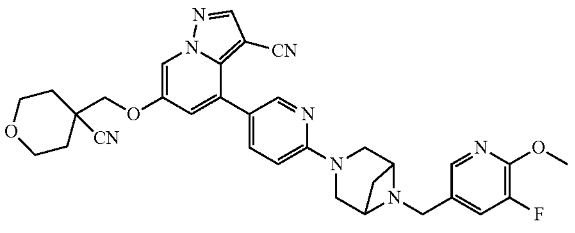

-continued
150
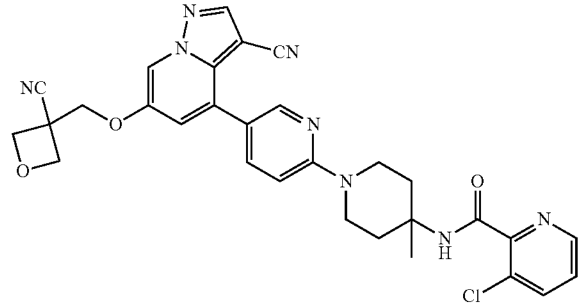
151
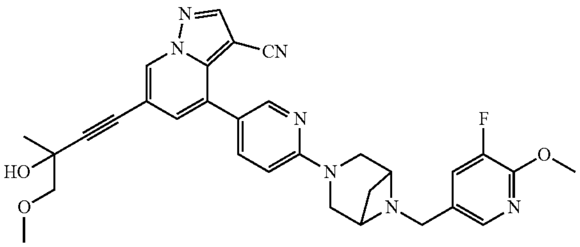
152A
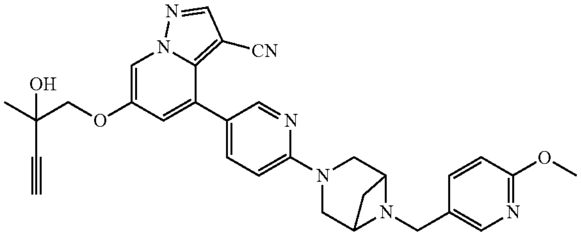
152
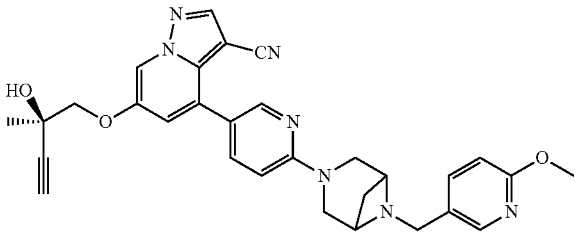
153
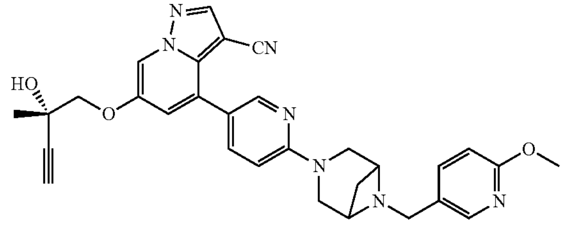
154
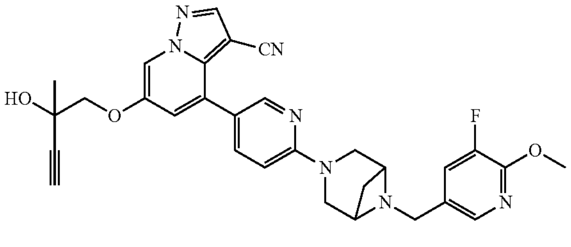
-continued
157
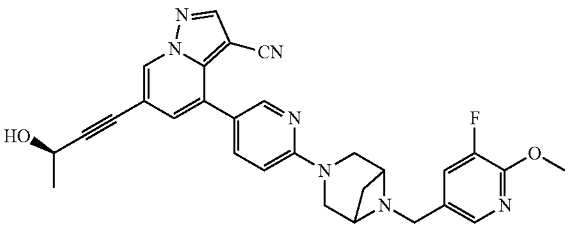
158
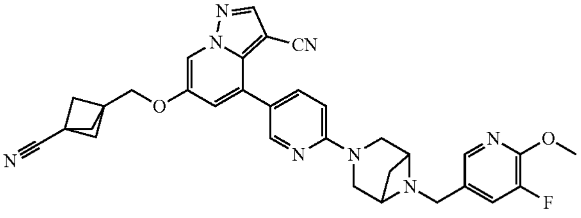
159
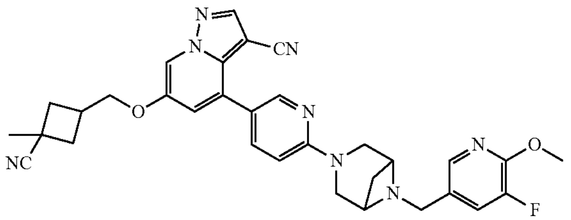
162
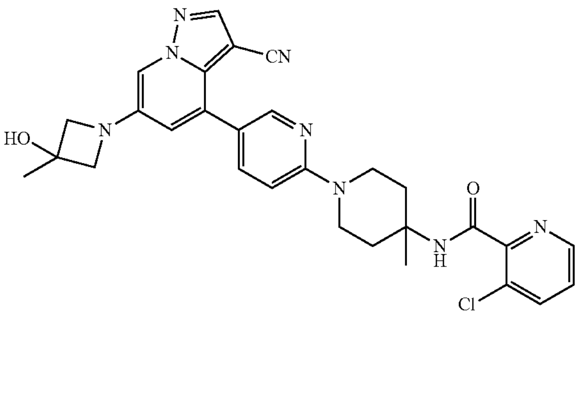
163
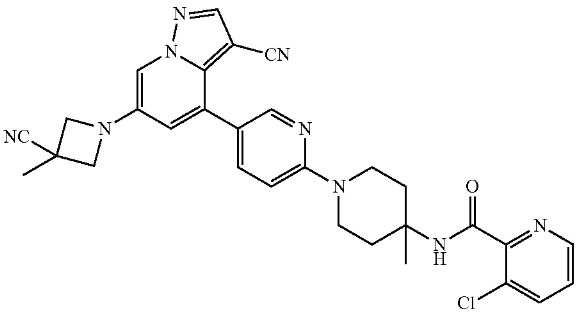

-continued
164
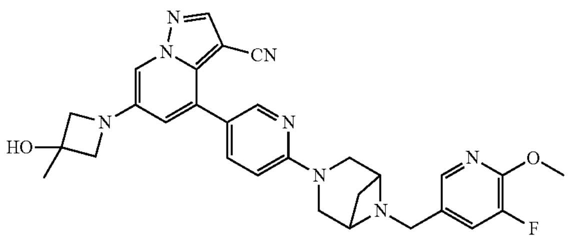
165
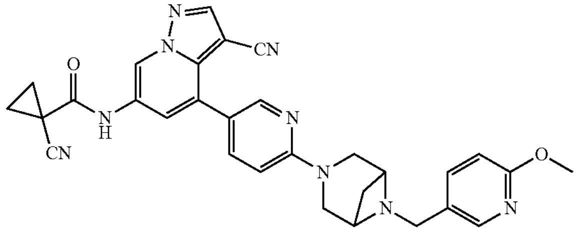
166
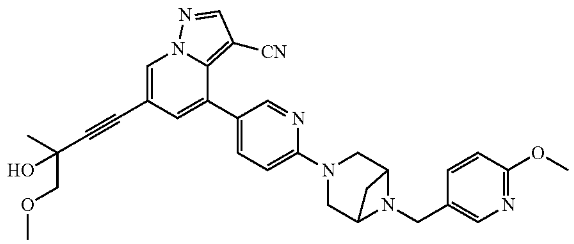
167
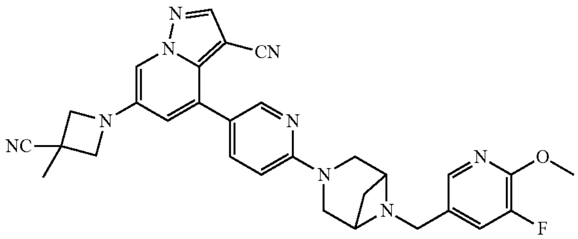
168
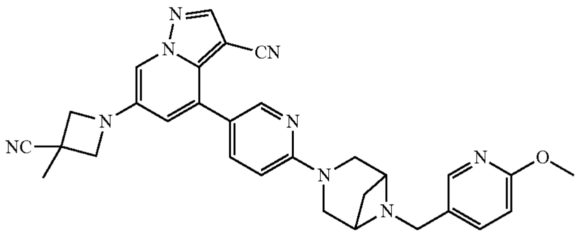
169
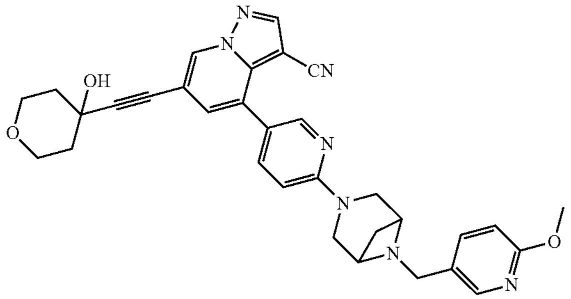
-continued
170
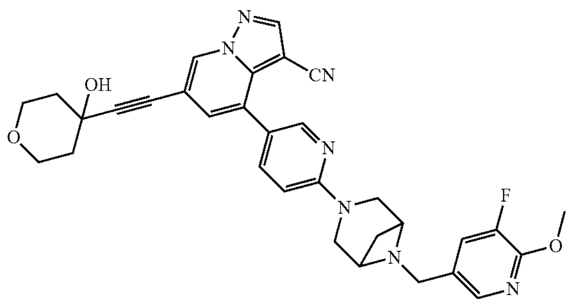
171
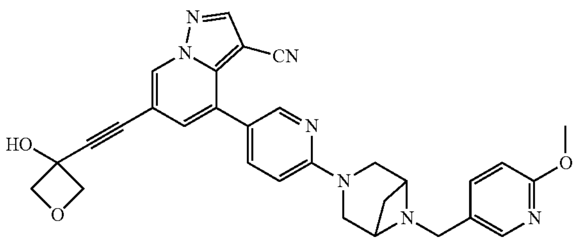
172
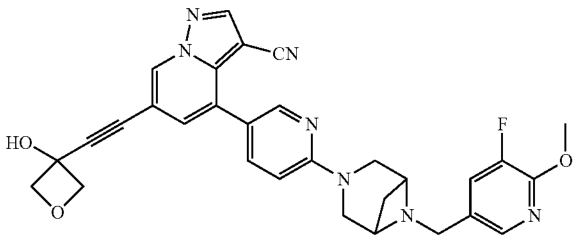
173
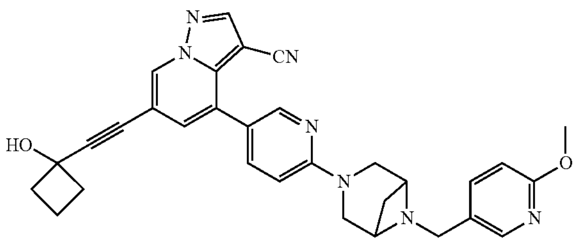
174
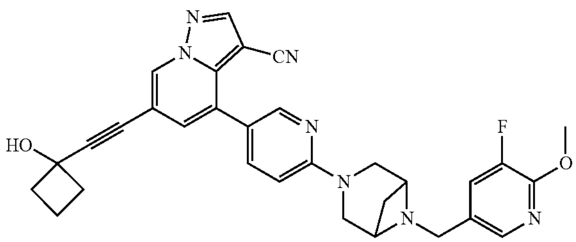
or 175
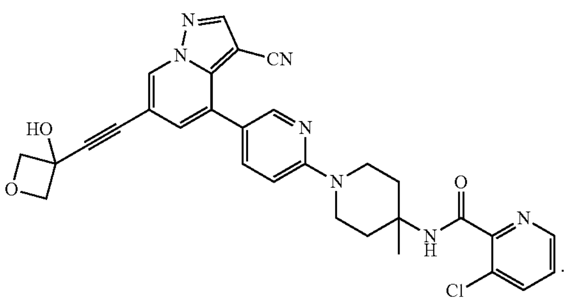
4. The compound as defined in claim 3, or the pharmaceutically acceptable salt thereof, wherein, the specific structure of the compound is as follows:
23
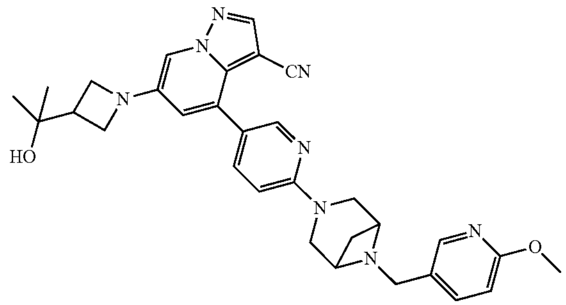
24
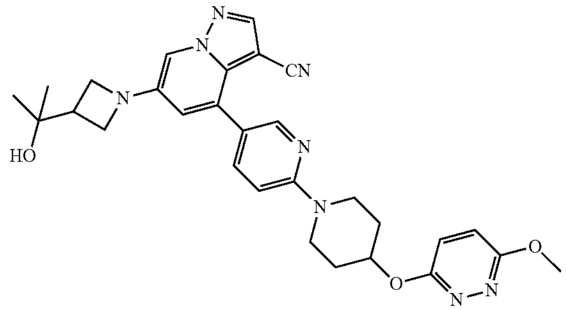
34
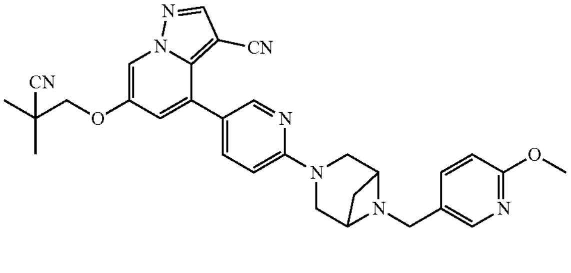
35
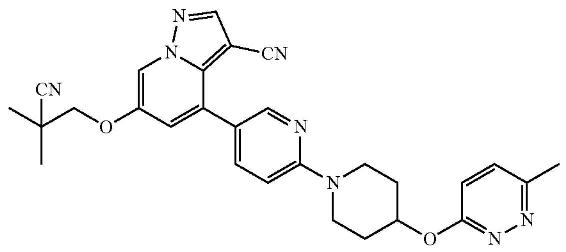
36
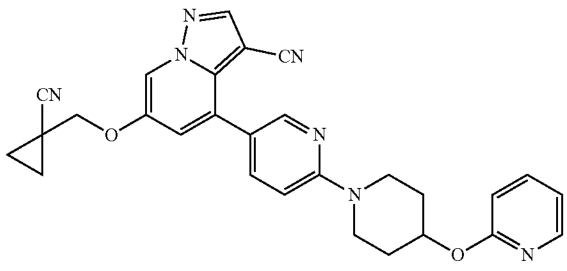
106
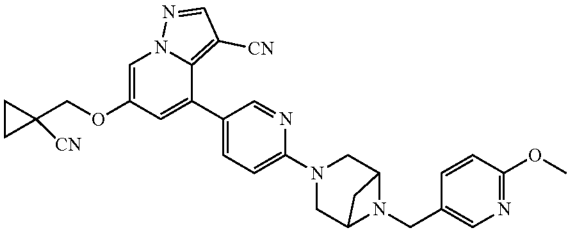
107
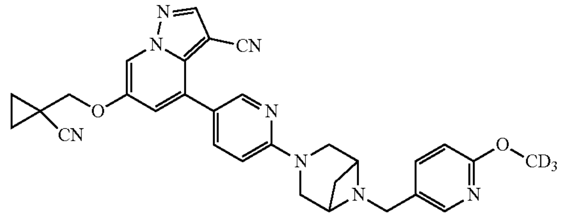
110
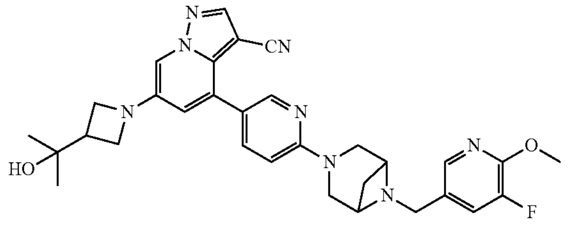
111
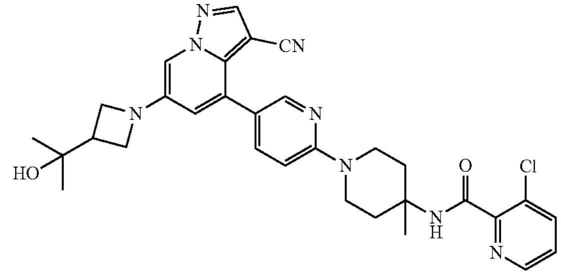

-continued
112
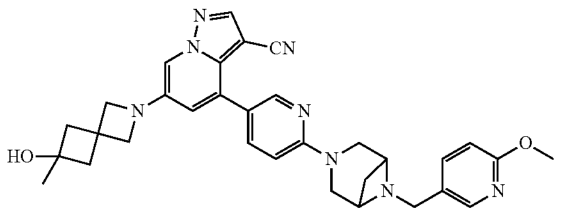
113
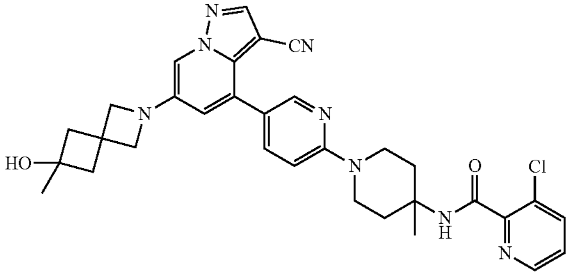
114
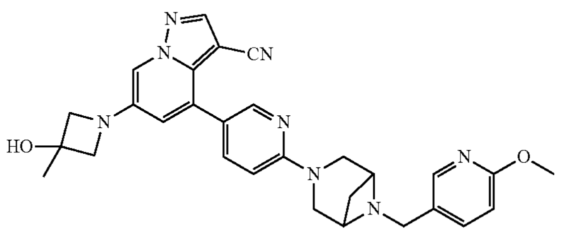
115
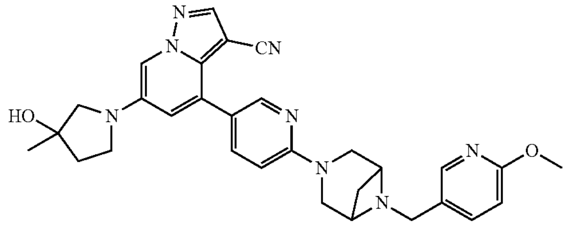
116
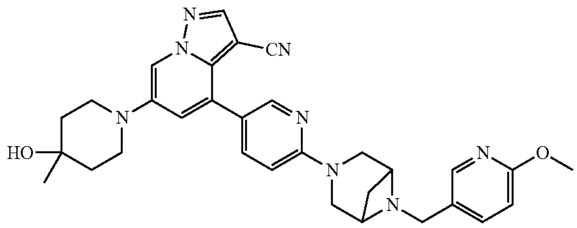
117
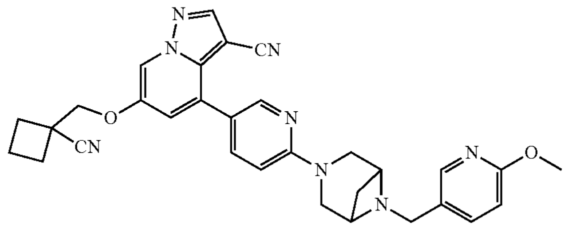
-continued
118
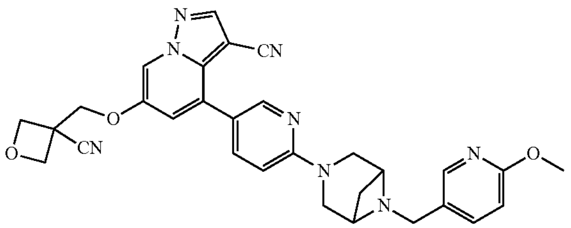
121
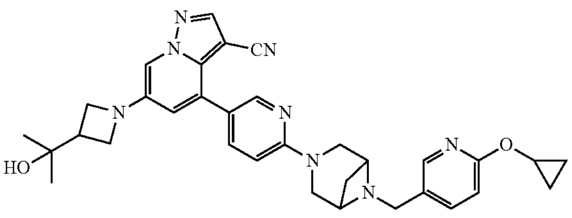
122
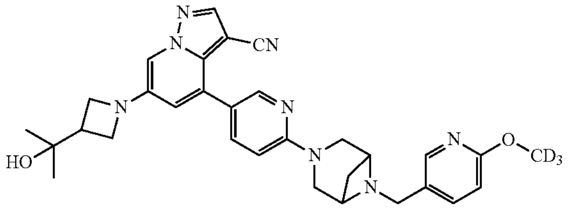
142
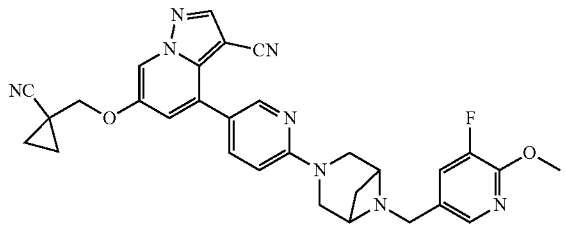
144
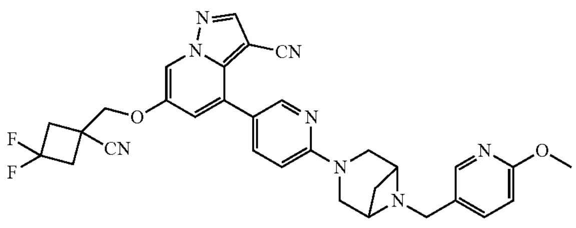
145
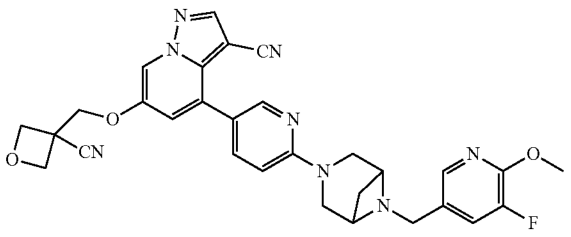

-continued
146
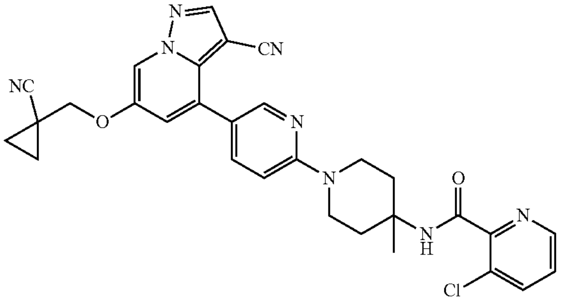
147
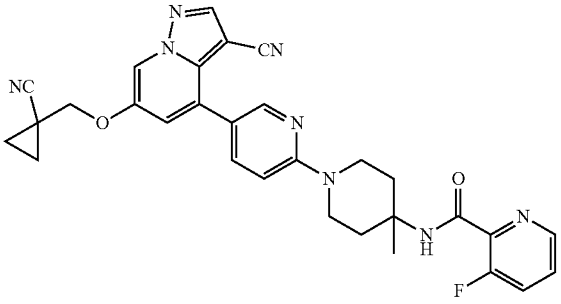
148
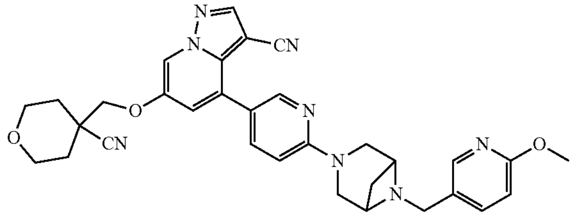
149
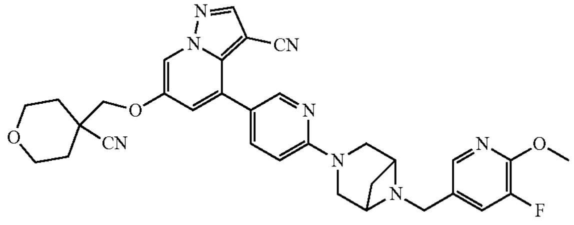
150
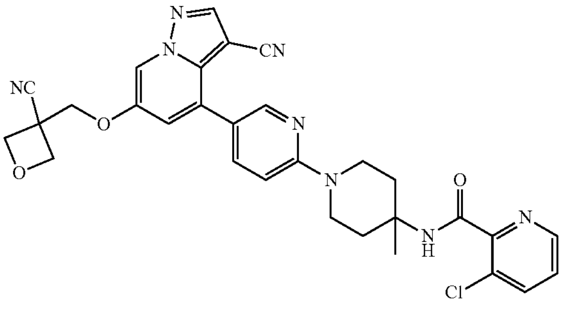
-continued
152A
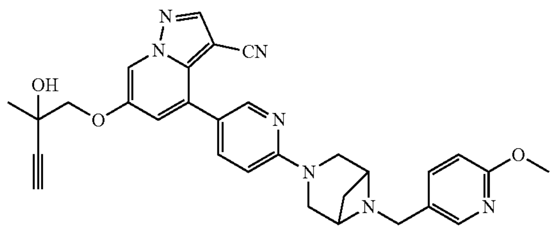
152
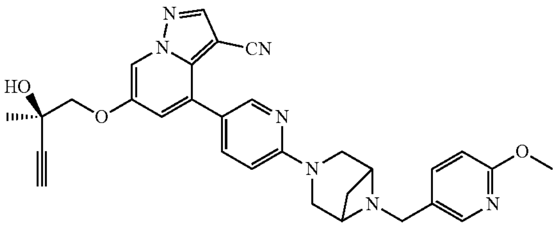
153
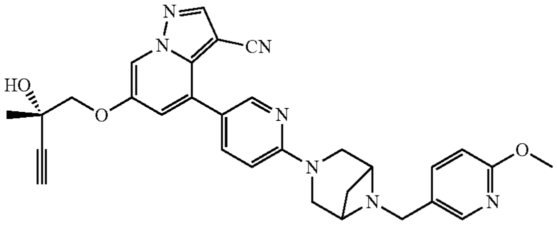
154
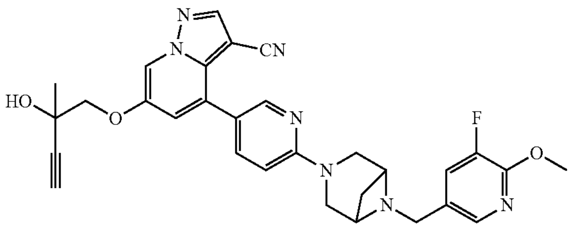
162
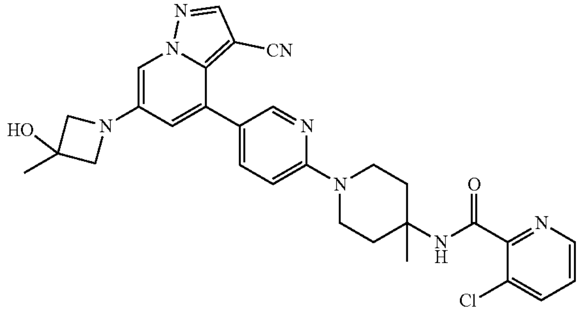

-continued

163

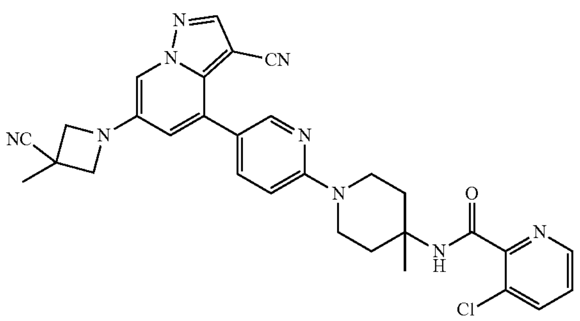

164

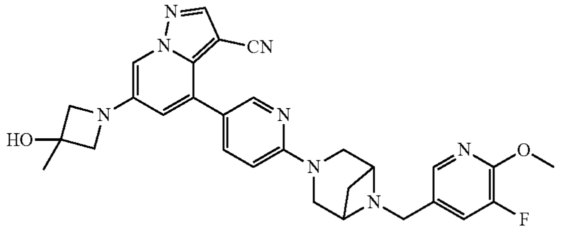

167

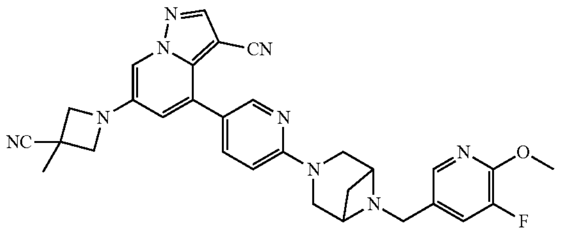

or

168

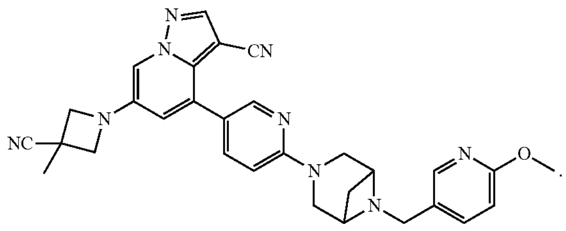

5. A compound represented by general formula (XI) or (XI-A), or a pharmaceutically acceptable salt thereof:

(XI)

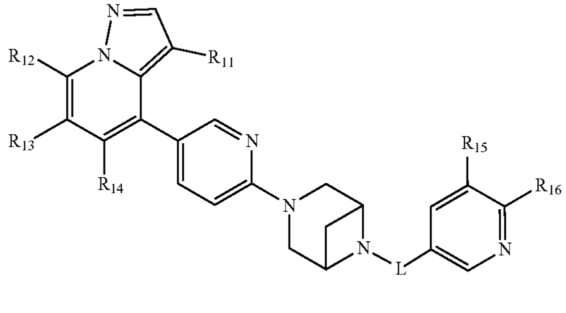

-continued (XI-A)

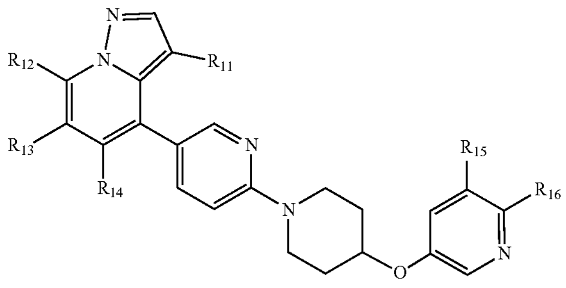

wherein:

$R_{12}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl or heteroaryl;

$R_{13}$ is selected from alkenyl, alkynyl, $—(C≡C)_{n1}(CR_{aa}R_{bb})_mR_{cc}$, $—(C═C)_{n1}(CR_{aa}R_{bb})_mR_{cc}$, $—(CH_2)_{n1}O(CH_2)_{n2}(CR_{aa}R_{bb})_mR_{cc}$, wherein the alkenyl or alkynyl are optionally further substituted by one or more substituents selected from hydrogen, deuterium, substituted or unsubstituted alkyl, substituted or unsubstituted deuterated alkyl, substituted or unsubstituted haloalkyl, substituted or unsubstituted hydroxyalkyl, substituted or unsubstituted cyanoalkyl, substituted or unsubstituted alkoxy, substituted or unsubstituted haloalkoxy, halogen, substituted or unsubstituted amino, nitro, hydroxyl, cyano, oxo, thio, imino, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, $—(CH_2)_{n1}R_{dd}$, $—(CH_2)_{n1}OR_{dd}$, $—(CH_2)_{n1}S(CH_2)_{n2}R_{dd}$, $—(CH_2)_{n1}C(O)R_{dd}$, $—(CH_2)_{n1}C(O)OR_{dd}$, $—(CH_2)_{n1}S(O)R_{dd}$, $—(CH_2)_{n1}S(O)(═NR_{dd})(CH_2)_{n2}R_{ee}$, $—(CH_2)_{n1}NR_{dd}R_{ee}$, $—(CH_2)_{n1}P(O)R_{dd}R_{ee}$, $—(CH_2)_{n1}C(O)NR_{dd}R_{ee}$, $—(CH_2)_{n1}NR_{dd}C(O)R_{ee}$ or $—(CH_2)_{n1}NR_{dd}S(O)_mR_{ee}$;

$R_{14}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl or heteroaryl;

$R_{15}$ and $R_{16}$ are each independently selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl or $—(CH_2)_{n1}OR_{aa}$;

L is selected from bond, $—(CH_2)_{n1}CR_{aa}R_{bb}—$, $—(CH_2)_{n1}NR_{aa}C(O)(CH_2)_{n2}—$, $—(CH_2)_{n1}C(O)(CH_2)_{n2}(CR_{aa}R_{bb})_m—$, $—(CH_2)_{n1}C(O)(CR_{aa}R_{bb})_m(CH_2)_{n2}—$, $—(CH_2)_{n1}C(O)NR_{cc}(CR_{aa}R_{bb})_{n2}—$, $—(CH_2)_{n1}(O)(CH_2)_{n2}—$ or $—(CH_2)_{n1}NR_{aa}(CH_2)_{n2}—$;

$R_{11}$ is selected from hydrogen, deuterium, alkyl, deuterated alkyl, haloalkyl, alkoxy, haloalkoxy, halogen, amino, nitro, hydroxyl, cyano, alkenyl, alkynyl, cycloalkyl, heterocyclyl, aryl, heteroaryl, $—(CH_2)_{n1}R_{aa}$, $—(CH_2)_{n1}OR_{aa}$, $—(CH_2)_{n1}S(CH_2)_{n2}R_{aa}$, $—(CH_2)_{n1}C(O)R_{aa}$, $—(CH_2)_{n1}C(O)OR_{aa}$, $—(CH_2)_{n1}S(O)_mR_{aa}$, $—(CH_2)_{n1}S(O)(═NR_{aa})(CH_2)_{n2}R_{bb}$, $—(CH_2)_{n1}NR_{aa}R_{bb}$, $—(CH_2)_{n1}P(O)R_{aa}R_{bb}$, $—(CH_2)_{n1}C(O)NR_{aa}R_{bb}$, $—(CH_2)_{n1}NR_{aa}C(O)R_{bb}$ or $—(CH_2)_{n1}NR_{aa}S(O)_mR_{bb}$;

$R_{aa}$, $R_{bb}$, $R_{dd}$ and $R_{ee}$ are each independently selected from hydrogen, deuterium, alkyl, deuterated alkyl, haloalkyl, alkoxy, haloalkoxy, halogen, cyano, nitro, hydroxyl, amino, alkenyl, alkynyl, cycloalkyl, heterocyclyl, aryl or heteroaryl, wherein the alkyl, deuterated alkyl, haloalkyl, alkoxy, haloalkoxy, alkenyl, alkynyl, cycloalkyl, heterocyclyl, aryl and heteroaryl are optionally further substituted by one or more substituents selected from hydrogen, deuterium, unsubstituted alkyl, unsubstituted deuterated alkyl, unsubstituted haloalkyl, unsubstituted alkoxy, unsubstituted haloalkoxy, halogen, cyano, nitro, hydroxyl, amino, oxo, imino, unsubstituted alkenyl, unsubstituted alkynyl, unsubstituted cycloalkyl, unsubstituted heterocyclyl, unsubstituted aryl, or unsubstituted heteroaryl;

$R_{cc}$ is selected from cyano or alkynyl; or any two of $R_{aa}$, $R_{bb}$, $R_{dd}$ and $R_{ee}$ are connected to form a cycloalkyl, heterocyclyl, aryl or heteroaryl, wherein the cycloalkyl, heterocyclyl, aryl and heteroaryl are optionally further substituted by one or more substituents selected from hydrogen, deuterium, unsubstituted alkyl, unsubstituted deuterated alkyl, unsubstituted haloalkyl, unsubstituted alkoxy, unsubstituted haloalkoxy, halogen, cyano, nitro, hydroxyl, amino, oxo, imine, unsubstituted alkenyl, unsubstituted alkynyl, unsubstituted cycloalkyl, unsubstituted heterocyclyl, unsubstituted aryl, or unsubstituted heteroaryl;

m is 0, 1 or 2;

n1 is 0, 1, 2 or 3; and n2 is 0, 1, 2 or 3.

6. The compound as defined in claim 1, or the pharmaceutically acceptable salt thereof, wherein, $R_{18}$ and $R_{19}$ in the general formula (IX-B) are each independently selected from hydrogen, methyl, ethynyl, amino, cyano or hydroxyl;

or, $R_{18}$ and $R_{19}$ together with the carbon atoms they are attached to form a $C_{3-6}$ cycloalkyl or 3-7 membered heterocyclyl comprising 1-2 oxygen atoms, nitrogen atoms or sulfur atoms;

$R_{20}$ is ethynyl, or cyano;

$R_{24}$ and $R_{25}$ are each independently selected from hydrogen or methyl;

or, $R_{24}$ and $R_{25}$ together with the carbon atoms they are attached to and G2 form a azetidinyl, L is selected from —$CH_2$—, —$CD_2$-, —O—, —S—, —C(O)NH— or —NHC(O)—;

$G_2$ is selected from —N—, —CH— or —$CCH_3$—;

$M_1$ is selected from —N—, —CH— or —$CCH_3$—;

$M_2$ is selected from —N— or —CH—;

$R_9$ is selected from hydrogen, fluorine, chlorine, methyl, methoxy, deuterated methoxy or cyclopropoxy.

7. The compound as defined in claim 5, or the pharmaceutically acceptable salt thereof, wherein, the general formula (XI) is further represented by general formula (XIII):

(XIII)

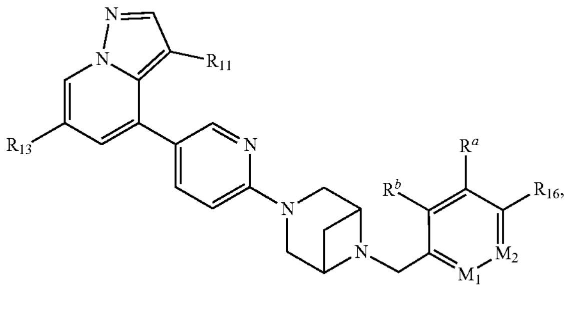

wherein:

$R_{11}$ is selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R_{13}$ is selected from $C_{2-6}$ alkenyl, $C_{2-6}$ alkynyl, or —$O(CH_2)_{n1}(CR_{aa}R_{bb})_mR_{cc}$;

$R_{aa}$ and $R_{bb}$ are each independently selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R_{cc}$ is selected from cyano or $C_{2-6}$ alkynyl;

$M_1$ is —CH—;

$M_2$ is —N—:

$R_{16}$ is selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R^a$ is selected from hydrogen, deuterium, halogen, amino, nitro, hydroxyl, cyano, $C_{1-6}$ alkyl, $C_{1-6}$ deuterated alkyl, $C_{1-6}$ haloalkyl, $C_{1-6}$ alkoxy, $C_{1-6}$ deuterated alkoxy, $C_{1-6}$ haloalkoxy, $C_{2-6}$ alkenyl or $C_{2-6}$ alkynyl;

$R^b$ is hydrogen;

n1 is an integer of 1, 2 or 3;

m is an integer of 1, 2 or 3.

8. The compound as defined in claim 7, or the pharmaceutically acceptable salt thereof, wherein, $R_{11}$ is cyano;

$R_{13}$ is selected from $C_{2-4}$ alkenyl, $C_{2-4}$ alkynyl, —$OCH_2CR_{aa}R_{bb}R_{cc}$;

$R_{aa}$ and $R_{bb}$ are each independently selected from hydrogen, deuterium, halogen, amino, nitro, hydroxyl, cyano, $C_{1-3}$ alkyl, $C_{1-3}$ deuterated alkyl, $C_{1-3}$ haloalkyl, $C_{1-3}$ alkoxy, $C_{1-3}$ deuterated alkoxy, $C_{1-3}$ haloalkoxy, $C_{2-4}$ alkenyl or $C_{2-4}$ alkynyl;

$R_{cc}$ is cyano or $C_{2-6}$ alkynyl;

$M_1$ is —CH—;

$M_2$ is —N—;

$R_{16}$ is selected from hydrogen, deuterium, halogen, amino, nitro, hydroxyl, cyano, $C_{1-3}$ alkyl, $C_{1-3}$ deuterated alkyl, $C_{1-3}$ haloalkyl, $C_{1-3}$ alkoxy, $C_{1-3}$ deuterated alkoxy or $C_{1-3}$ haloalkoxy;

$R^a$ is selected from hydrogen, deuterium or halogen;

$R^b$ is hydrogen.

9. The compound as defined in claim 1, or the pharmaceutically acceptable salt thereof, wherein,

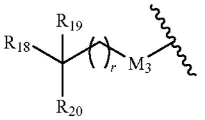

is selected from

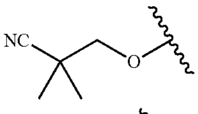
,
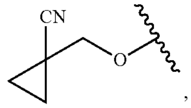
,
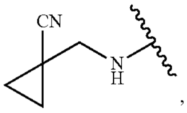
,
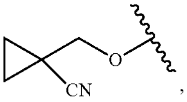
,

-continued

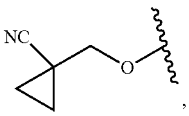
,
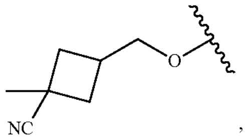
,
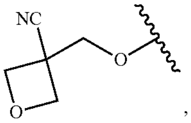
,
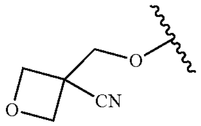
,
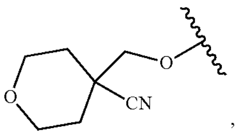
,
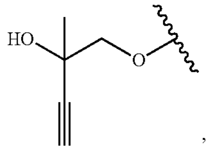
,
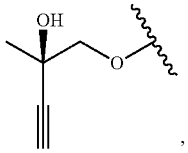
,
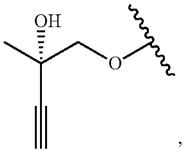
,
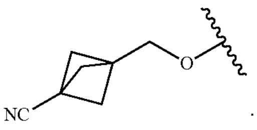
.

10. The compound as defined in claim 2, or the pharmaceutically acceptable salt thereof, wherein, $R_{24}$ and $R_{25}$ are each independently selected from hydrogen or methyl;

or, $R_{24}$ and $R_{25}$ together with the carbon atoms they are attached to and G2 form a azetidiny.

11. A pharmaceutical composition comprising a therapeutically effective amount of the compound as defined in claim 1, or the pharmaceutically acceptable salt thereof, and one or more pharmaceutically acceptable carriers.

12. A pharmaceutical composition comprising a therapeutically effective amount of the compound as defined in claim 2, or the pharmaceutically acceptable salt thereof, and one or more pharmaceutically acceptable carriers.

13. A pharmaceutical composition comprising a therapeutically effective amount of the compound as defined in claim 5, or the pharmaceutically acceptable salt thereof, and one or more pharmaceutically acceptable carriers.

14. A method for preparing the compound represented by general formula (IX-B) as defined in claim 1, or the pharmaceutically acceptable salt thereof, wherein, comprising the following steps:

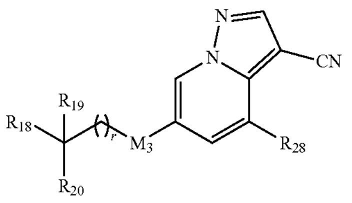
(IX-B1)

+

-continued

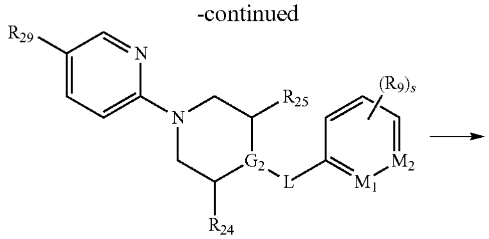
(IX-B2)

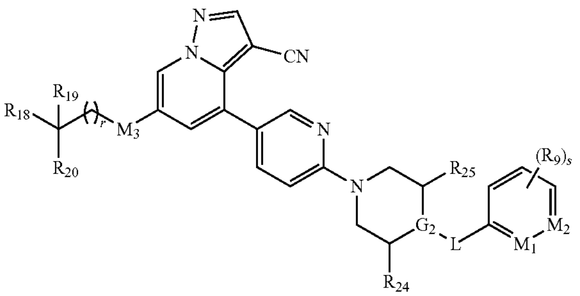
(IX-B)

a reaction is carried out with general formula (IX-B1) and general formula (IX-B2) to obtain the compound represented by general formula (IX-B) or the pharmaceutically acceptable salt thereof;

wherein:

$R_{28}$ is selected from halogen, boric acid or borate ester; preferably fluorine, chlorine, bromine, iodine, —$B(OH)_2$ or

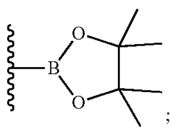 [SMILES: *B1OC(C)(C)C(C)(C)O1]
;

$R_{29}$ is selected from halogen, boric acid or borate ester; preferably fluorine, chlorine, bromine, iodine, —$B(OH)_2$ or

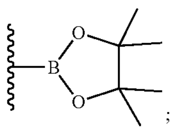 [SMILES: *B1OC(C)(C)C(C)(C)O1]
;

when $R_{28}$ is halogen, $R_{29}$ is selected from boric acid or borate ester;

when $R_{28}$ is selected from boric acid or borate ester, $R_{29}$ is halogen.

15. A method for preparing the compound represented by general formula (IX-C) as defined in claim 2, the stereoisomer thereof or the pharmaceutically acceptable salt thereof, wherein, comprising the following steps:

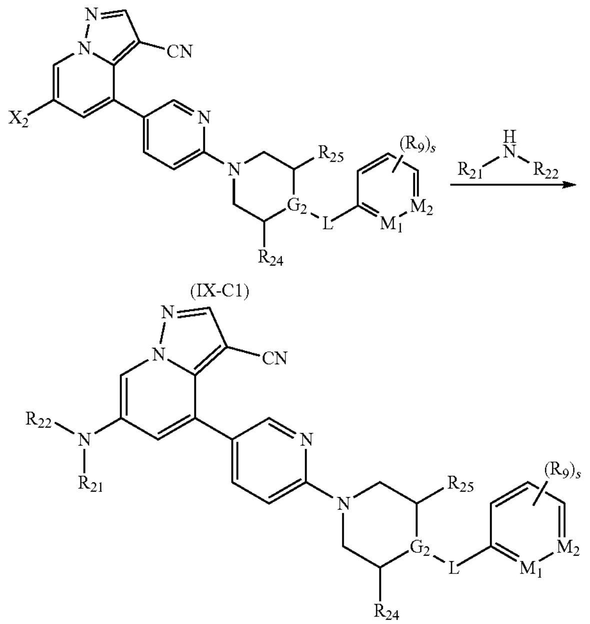

(IX-C1)

(IX-C)

a reaction is carried out with general formula (IX-C1) and general formula (IX-C2) to obtain the compound represented by general formula (IX-C) or the pharmaceutically acceptable salt thereof;

wherein:

$X_2$ is selected from halogen.

16. A method for the treatment of non-small cell lung cancer, medullary thyroid carcinoma, and thyroid papillary tumor, comprising administering to a patient a therapeutically effective dose of the compound as defined in claim 1, or the pharmaceutically acceptable salt thereof.

17. A method for the treatment of non-small cell lung cancer, medullary thyroid carcinoma, and thyroid papillary tumor, comprising administering to a patient a therapeutically effective dose of the compound as defined in claim 2, or the pharmaceutically acceptable salt thereof.

18. A method for the treatment of non-small cell lung cancer, medullary thyroid carcinoma, and thyroid papillary tumor, comprising administering to a patient a therapeutically effective dose of the compound as defined in claim 5, the stereoisomer thereof or the pharmaceutically acceptable salt thereof.

* * * * *